(12) United States Patent
Bebbington et al.

(10) Patent No.: US 7,087,603 B2
(45) Date of Patent: Aug. 8, 2006

(54) PYRAZOLE COMPOUNDS USEFUL AS PROTEIN KINASE INHIBITORS

(75) Inventors: David Bebbington, Newbury (GB); Jean-Damien Charrier, Wantage (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 10/736,426

(22) Filed: Dec. 15, 2003

(65) Prior Publication Data

US 2004/0132781 A1 Jul. 8, 2004

Related U.S. Application Data

(63) Continuation of application No. 10/026,966, filed on Dec. 19, 2001, now abandoned.

(60) Provisional application No. 60/286,949, filed on Apr. 27, 2001, provisional application No. 60/257,887, filed on Dec. 21, 2000.

(51) Int. Cl.
*C07D 401/12* (2006.01)
*C07D 401/14* (2006.01)
*A61K 31/4439* (2006.01)
*A61P 3/10* (2006.01)

(52) U.S. Cl. .................. 514/235.5; 546/119; 546/143; 546/153; 546/159; 546/255; 546/275.4; 546/275.7; 544/124; 544/360; 514/253.01; 514/303; 514/314; 514/333; 514/338; 514/340

(58) Field of Classification Search ............... 546/119, 546/143, 153, 159, 255, 275.4, 275.7; 544/124, 544/360; 514/235.5, 253.01, 303, 314, 333, 514/338, 340
See application file for complete search history.

(56) References Cited

U.S. PATENT DOCUMENTS 3,755,332 A * 8/1973 Wasley et al. .............. 546/160

* cited by examiner

*Primary Examiner*—Kahsay Habte
(74) *Attorney, Agent, or Firm*—Vertex Pharmaceuticals Incorporated

(57) ABSTRACT

This invention describes novel pyrazole compounds of formula IV:

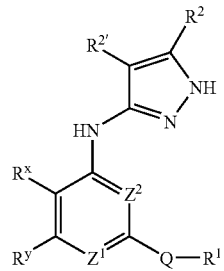

wherein $Z^1$ or $Z^2$ is nitrogen, Q is —S—, —O—, —N($R^4$)—, —C($R^{6'}$)$_2$—, 1,2-cyclopropanediyl, 1,2-cyclobutanediyl, or 1,3-cyclobutanediyl, and $R^1$ is T-Ring D, wherein Ring D is a 5–7 membered monocyclic ring or 8–10 membered bicyclic ring selected from aryl, heteroaryl, heterocyclyl or carbocyclyl; $R^x$ and $R^y$ are independently selected from T—$R^3$ or L—Z—$R^3$, or $R^x$ and $R^y$ are taken together with their intervening atoms to form a fused, unsaturated or partially unsaturated, 5–7 membered ring having 0–3 heteroatoms; and $R^2$ and $R^{2'}$ are as described in the specification. The compounds are useful as protein kinase inhibitors, especially as inhibitors of Aurora-2 and GSK-3, for treating diseases such as cancer, diabetes and Alzheimer's disease.

14 Claims, No Drawings

PYRAZOLE COMPOUNDS USEFUL AS PROTEIN KINASE INHIBITORS

CROSS REFERENCE TO RELATED APPLICATIONS

This application is a continuation of application Ser. No. 10/026,966, filed Dec. 19, 2001, now abandoned, claims priority to U.S. Provisional Patent Application 60/257,887 filed Dec. 21, 2000 and U.S. Provisional Patent Application 60/286,949 filed Apr. 27, 2001, the contents of which are incorporated herein by reference.

FIELD OF THE INVENTION

The present invention is in the field of medicinal chemistry and relates to compounds that are protein kinase inhibitors, compositions containing such compounds and methods of use. More particularly, this invention relates to compounds that are inhibitors of Aurora-2 protein kinase. The invention also relates to methods of treating diseases associated with protein kinases, especially diseases associated with Aurora-2, such as cancer.

BACKGROUND OF THE INVENTION

The search for new therapeutic agents has been greatly aided in recent years by better understanding of the structure of enzymes and other biomolecules associated with target diseases. One important class of enzymes that has been the subject of extensive study is the protein kinases.

Protein kinases mediate intracellular signal transduction. They do this by effecting a phosphoryl transfer from a nucleoside triphosphate to a protein acceptor that is involved in a signaling pathway. There are a number of kinases and pathways through which extracellular and other stimuli cause a variety of cellular responses to occur inside the cell. Examples of such stimuli include environmental and chemical stress signals (e.g. osmotic shock, heat shock, ultraviolet radiation, bacterial endotoxin, $H_2O_2$), cytokines (e.g. interleukin-1 (IL-1) and tumor necrosis factor α (TNF-α)), and growth factors (e.g. granulocyte macrophage-colony-stimulating factor (GM-CSF), and fibroblast growth factor (FGF). An extracellular stimulus may effect one or more cellular responses related to cell growth, migration, differentiation, secretion of hormones, activation of transcription factors, muscle contraction, glucose metabolism, control of protein synthesis and regulation of cell cycle.

Many diseases are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

Aurora-2 is a serine/threonine protein kinase that has been implicated in human cancer, such as colon, breast and other solid tumors. This kinase is believed to be involved in protein phosphorylation events that regulate the cell cycle. Specifically, Aurora-2 may play a role in controlling the accurate segregation of chromosomes during mitosis. Misregulation of the cell cycle can lead to cellular proliferation and other abnormalities. In human colon cancer tissue, the aurora-2 protein has been found to be overexpressed. See Bischoff et al., *EMBO J.*, 1998, 17, 3052–3065; Schumacher et al., *J. Cell Biol.*, 1998, 143, 1635–1646; Kimura et al., *J. Biol. Chem.*, 1997, 272, 13766–13771.

Glycogen synthase kinase-3 (GSK-3) is a serine/threonine protein kinase comprised of α and β isoforms that are each encoded by distinct genes [Coghlan et al., *Chemistry & Biology*, 7, 793–803 (2000); Kim and Kimmel, *Curr. Opinion Genetics Dev.*, 10, 508–514 (2000)]. GSK-3 has been implicated in various diseases including diabetes, Alzheimer's disease, CNS disorders such as manic depressive disorder and neurodegenerative diseases, and cardiomyocete hypertrophy [WO 99/65897; WO 00/38675; and Haq et al., *J. Cell Biol.* (2000) 151, 117]. These diseases may be caused by, or result in, the abnormal operation of certain cell signaling pathways in which GSK-3 plays a role. GSK-3 has been found to phosphorylate and modulate the activity of a number of regulatory proteins. These proteins include glycogen synthase which is the rate limiting enzyme necessary for glycogen synthesis, the microtubule associated protein Tau, the gene transcription factor β-catenin, the translation initiation factor e1F2B, as well as ATP citrate lyase, axin, heat shock factor-1, c-Jun, c-Myc, c-Myb, CREB, and CEPBα. These diverse protein targets implicate GSK-3 in many aspects of cellular metabolism, proliferation, differentiation and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake [Klein et al., *PNAS*, 93, 8455–9 (1996); Cross et al., *Biochem. J.*, 303, 21–26 (1994); Cohen, *Biochem. Soc. Trans.*, 21, 555–567 (1993); Massillon et al., *Biochem J.* 299, 123–128 (1994)]. However, in a diabetic patient where the insulin response is impaired, glycogen synthesis and glucose uptake fail to increase despite the presence of relatively high blood levels of insulin. This leads to abnormally high blood levels of glucose with acute and long term effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [WO 00/38675]. Therapeutic inhibitors of GSK-3 therefore are considered to be useful for treating diabetic patients suffering from an impaired response to insulin.

GSK-3 activity has also been associated with Alzheimer's disease. This disease is characterized by the well-known β-amyloid peptide and the formation of intracellular neurofibrillary tangles. The neurofibrillary tangles contain hyperphosphorylated Tau protein where Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells [Lovestone et al., *Current Biology* 4, 1077–86 (1994); Brownlees et al., *Neuroreport* 8, 3251–55 (1997)]. Therefore, it is believed that GSK-3 activity may promote generation of the neurofibrillary tangles and the progression of Alzheimer's disease.

Another substrate of GSK-3 is β-catenin which is degradated after phosphorylation by GSK-3. Reduced levels of β-catenin have been reported in schizophrenic patients and have also been associated with other diseases related to increase in neuronal cell death [Zhong et al., *Nature*, 395, 698–702 (1998); Takashima et al., *PNAS*, 90, 7789–93 (1993); Pei et al., *J. Neuropathol. Exp*, 56, 70–78 (1997)].

As a result of the biological importance of GSK-3, there is current interest in therapeutically effective GSK-3 inhibitors. Small molecules that inhibit GSK-3 have recently been reported [WO 99/65897 (Chiron) and WO 00/38675 (SmithKline Beecham)].

For many of the aforementioned diseases associated with abnormal GSK-3 activity, other protein kinases have also been targeted for treating the same diseases. However, the various protein kinases often act through different biological pathways. For example, certain quinazoline derivatives have been reported recently as inhibitors of p38 kinase (WO 00/12497 to Scios). The compounds are reported to be useful for treating conditions characterized by enhanced p38-α activity and/or enhanced TGF-β activity. While p38 activity has been implicated in a wide variety of diseases, including diabetes, p38 kinase is not reported to be a constituent of an insulin signaling pathway that regulates glycogen synthesis or glucose uptake. Therefore, unlike GSK-3, p38 inhibition would not be expected to enhance glycogen synthesis and/or glucose uptake.

There is a continued need to find new therapeutic agents to treat human diseases. The protein kinases Aurora-2 and GSK-3 are especially attractive targets for the discovery of new therapeutics due to their important roles in cancer and diabetes, respectively.

DESCRIPTION OF THE INVENTION

It has now been found that compounds of this invention and pharmaceutical compositions thereof are effective as protein kinase inhibitors, particularly as inhibitors of Aurora-2. These compounds have the general formula I:

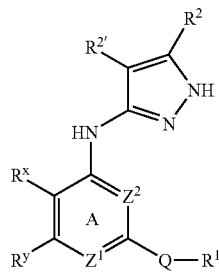

I or a pharmaceutically acceptable derivative or prodrug thereof, wherein:

$Z^1$ is nitrogen or C—$R^8$ and $Z^2$ is nitrogen or CH, wherein at least one of $Z^1$ and $Z^2$ is nitrogen;

$R^x$ and $R^y$ are independently selected from T—$R^3$ or L—Z—$R^3$, or $R^x$ and $R^y$ are taken together with their intervening atoms to form a fused, unsaturated or partially unsaturated, 5–7 membered ring having 0–3 ring heteroatoms selected from oxygen, sulfur, or nitrogen, wherein each substitutable ring carbon of said fused ring formed by $R^x$ and $R^y$ is independently substituted by oxo, T—$R^3$, or L—Z—$R^3$, and each substitutable ring nitrogen of said ring formed by $R^x$ and $R^y$ is independently substituted by $R^4$;

Q is selected from —N($R^4$)—, —O—, —S—, —C($R^{6'}$)$_2$—, 1,2-cyclopropanediyl, 1,2-cyclobutanediyl, or 1,3-cyclobutanediyl;

$R^1$ is T-(Ring D);

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein each substitutable ring carbon of Ring D is independently substituted by oxo, T—$R^5$, or V—Z—$R^5$, and each substitutable ring nitrogen of Ring D is independently substituted by —$R^4$;

T is a valence bond or a $C_{1-4}$ alkylidene chain, wherein when Q is —C($R^{6'}$)$_2$—, a methylene unit of said $C_{1-4}$ alkylidene chain is optionally replaced by —O—, —S—, —N($R^4$)—, —CO—, —CONH—, —NHCO—, —SO$_2$—, —SO$_2$NH—, —NHSO$_2$—, —CO$_2$—, —OC(O)—, —OC(O)NH—, or —NHCO$_2$—;

Z is a $C_{1-4}$ alkylidene chain;

L is —O—, —S—, —SO—, —SO$_2$—, —N($R^6$)SO$_2$—, —SO$_2$N($R^6$)—, —N($R^6$)—, —CO—, —CO$_2$—, —N($R^6$)CO—, —N($R^6$)C(O)O—, —N($R^6$)CON($R^6$)—, —N($R^6$)SO$_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)SO$_2$N($R^6$)—, or —C($R^6$)$_2$N($R^6$)CON($R^6$)—;

$R^2$ and $R^{2'}$ are independently selected from —R, —T—W—$R^6$, or $R^2$ and $R^{2'}$ are taken together with their intervening atoms to form a fused, 5–8 membered, unsaturated or partially unsaturated, ring having 0–3 ring heteroatoms selected from nitrogen, oxygen, or sulfur, wherein each substitutable ring carbon of said fused ring formed by $R^2$ and $R^{2'}$ is independently substituted by halo, oxo, —CN, —NO$_2$, —$R^7$, or —V—$R^6$, and each substitutable ring nitrogen of said ring formed by $R^2$ and $R^{2'}$ is independently substituted by $R^4$;

$R^3$ is selected from —R, -halo, —OR, —C(=O)R, —CO$_2$R, —COCOR, —COCH$_2$COR, —NO$_2$, —CN, —S(O)R, —S(O)$_2$R, —SR, —N($R^4$)$_2$, —CON($R^7$)$_2$, —SO$_2$N($R^7$)$_2$, —OC(=)R, —N($R^7$)COR, —N($R^7$)CO$_2$($C_{1-6}$ aliphatic), —N($R^4$)N($R^4$)$_2$, —C=NN($R^4$)$_2$—, —C=N—OR, —N($R^7$)CON($R^7$)$_2$, —N($R^7$)SO$_2$N($R^7$)$_2$, —N($R^4$)SO$_2$R, or —OC(=O)N($R^7$)$_2$;

each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;

each $R^4$ is independently selected from —$R^7$, —COR$^7$, —CO$_2$(optionally substituted $C_{1-6}$ aliphatic), —CON($R^7$)$_2$, or —SO$_2$R$^7$;

each $R^5$ is independently selected from —R, halo, —OR, —C(=O)R, —CO$_2$R, —COCOR, —NO$_2$, —CN, —S(O)R, —SO$_2$R, —SR, —N($R^4$)$_2$, —CON($R^4$)$_2$, —SO$_2$N($R^4$)$_2$, —OC(=O)R, —N($R^4$)COR, —N($R^4$)CO$_2$(optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)SO$_2$N($R^4$)$_2$, —N($R^4$)SO$_2$R, or —OC(=O)N($R^4$)$_2$;

V is —O—, —S—, —SO—, —SO$_2$—, —N($R^6$)SO$_2$—, —SO$_2$N($R^6$)—, —N($R^6$)—, —CO—, —CO$_2$—, —N($R^6$)CO—, —N($R^6$)C(O)O—, —N($R^6$)CON($R^6$)—, —N($R^6$)SO$_2$N($R^6$)—, N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$ N($R^6$)N($R^6$)—, —C($R^6$)$_2$N($R^6$)SO$_2$N($R^6$)—, or —C($R^6$)$_2$N($R^6$)CON($R^6$)—;

W is —C($R_6$)$_2$O—, —C($R^6$)$_2$S—, —C($R^6$)$_2$SO—, —C($R^6$)$_2$ SO$_2$—, —C($R^6$)$_2$SO$_2$N($R^6$)—, —C($R^6$)$_2$N($R^6$)—,

—CO—, —CO$_2$—, —C(R$^6$)OC(O)—, —C(R$^6$)OC(O)N(R$^6$)—, —C(R$^6$)$_2$N(R$^6$)CO—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, —C(R$^6$)$_2$N(R$^6$)CON(R$^6$)—, or —CON(R$^6$)—;

each R$^6$ is independently selected from hydrogen or an optionally substituted C$_{1-4}$ aliphatic group, or two R$^6$ groups on the same nitrogen atom may be taken together with the nitrogen atom to form a 5–6 membered heterocyclyl or heteroaryl ring;

each R$^{6'}$ is independently selected from hydrogen or a C$_{1-4}$ aliphatic group, or two R$^{6'}$ on the same carbon atom are taken together to form a 3–6 membered carbocyclic ring;

each R$^7$ is independently selected from hydrogen or an optionally substituted C$_{1-6}$ aliphatic group, or two R$^7$ on the same nitrogen are taken together with the nitrogen to form a 5–8 membered heterocyclyl or heteroaryl ring; and R$^8$ is selected from —R, halo, —OR, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$(optionally substituted C$_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$.

As used herein, the following definitions shall apply unless otherwise indicated. The phrase "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

The term "aliphatic" as used herein means straight-chain, branched or cyclic C$_1$–C$_{12}$ hydrocarbons which are completely saturated or which contain one or more units of unsaturation but which are not aromatic. For example, suitable aliphatic groups include substituted or unsubstituted linear, branched or cyclic alkyl, alkenyl, alkynyl groups and hybrids thereof such as (cycloalkyl)alkyl, (cycloalkenyl)alkyl or (cycloalkyl)alkenyl. The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms. The term "cycloalkyl" used alone or as part of a larger moiety shall include cyclic C$_3$–C$_{12}$ hydrocarbons which are completely saturated or which contain one or more units of unsaturation, but which are not aromatic.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0–3 heteroatoms selected from oxygen, sulfur or nitrogen, the nitrogen may be N (as in 3,4-dihydro-2H-pyrrolyl), NH (as in pyrrolidinyl) or NR$^+$ (as in N-substituted pyrrolidinyl).

The terms "carbocycle", "carbocyclyl", "carbocyclo", or "carbocyclic" as used herein means an aliphatic ring system having three to fourteen members. The terms "carbocycle", "carbocyclyl", "carbocyclo", or "carbocyclic" whether saturated or partially unsaturated, also refers to rings that are optionally substituted. The terms "carbocycle", "carbocyclyl" "carbocyclo", or "carbocyclic" also include aliphatic rings that are fused to one or more aromatic or nonaromatic rings, such as in a decahydronaphthyl or tetrahydronaphthyl where the radical or point of attachment is on the aliphatic ring.

The term "aryl" used alone or as part of a larger moiety as in "aralkyl", "aralkoxy", or "aryloxyalkyl", refers to aromatic ring groups having five to fourteen members, such as phenyl, benzyl, phenethyl, 1-naphthyl, 2-naphthyl, 1-anthracyl and 2-anthracyl. The term "aryl" also refers to rings that are optionally substituted. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl, or tetrahydronaphthyl, where the radical or point of attachment is on the aromatic ring.

The term "heterocycle", "heterocyclyl", or "heterocyclic" as used herein includes non-aromatic ring systems having five to fourteen members, preferably five to ten, in which one or more ring carbons, preferably one to four, are each replaced by a heteroatom such as N, O, or S. Examples of heterocyclic rings include 3-1H-benzimidazol-2-one, (1-substituted)-2-oxo-benzimidazol-3-yl, 2-tetrahydrofuranyl, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic"whether saturated or partially unsaturated, also refers to rings that are optionally substituted.

The term "heteroaryl", used alone or as part of a larger moiety as in "heteroaralkyl" or "heteroarylalkoxy", refers to heteroaromatic ring groups having five to fourteen members. Examples of heteroaryl rings include 2-furanyl, 3-furanyl, 3-furazanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 2-pyrazolyl, 3-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, or benzoisoxazolyl. Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" also refers to rings that are optionally substituted. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Examples of suitable substituents on the unsaturated carbon atom of an aryl, heteroaryl, aralkyl, or heteroaralkyl group include a halogen, —R°, —OR°, —SR°, 1,2-methylene-dioxy, 1,2-ethylenedioxy, protected OH (such as acyloxy), phenyl (Ph), substituted Ph, —O(Ph), substituted —O(Ph), —CH$_2$(Ph), substituted —CH$_2$(Ph), —CH$_2$CH$_2$(Ph), substituted —CH$_2$CH$_2$(Ph), —NO$_2$, —CN, —N(R°)$_2$, —NR°C(O)R°, —NR°C(O)N(R°)$_2$, —NR°CO$_2$R°, —NR°NR°C(O)R°, —NR°NR°C(O)N(R°)$_2$, —NR°NR°CO$_2$R°, —C(O)C(O)R°, —C(O)CH$_2$C(O)R°, —CO$_2$R°, —C(O)R°, —C(O)N(R°)$_2$, —OC(O)N(R°)$_2$, —S(O)$_2$R°, —SO$_2$N(R°)$_2$, —S(O)R°, —NR°SO$_2$N(R°)$_2$, —NR°SO$_2$R°, —C(=S)N(R°)$_2$, —C(=NH)—N(R°)$_2$, —(CH$_2$)$_y$NHC(O)R°, —(CH$_2$)$_y$NHC(O)CH(V—R°)(R°); wherein each R° is independently selected from hydrogen, a substituted or unsubstituted aliphatic group, an unsubstituted heteroaryl or heterocyclic ring, phenyl (Ph), substituted Ph, —O(Ph), substituted —O(Ph), —CH$_2$(Ph), or substituted —CH$_2$(Ph); y is 0–6; and V is a linker group. Examples of substituents on the aliphatic group or the phenyl ring of R° include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

An aliphatic group or a non-aromatic heterocyclic ring may contain one or more substituents. Examples of suitable substituents on the saturated carbon of an aliphatic group or of a non-aromatic heterocyclic ring include those listed above for the unsaturated carbon of an aryl or heteroaryl group and the following: =O, =S, =NNHR*, =NN(R*)$_2$, =N—, =NNHC(O)R*, =NNHCO$_2$(alkyl), =NNHSO$_2$(alkyl), or =NR*, where each R* is independently selected from hydrogen, an unsubstituted aliphatic group or a substituted aliphatic group. Examples of substituents on the aliphatic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

Suitable substituents on the nitrogen of a non-aromatic heterocyclic ring include —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, and —NR$^+$SO$_2$R$^+$; wherein each R$^+$ is independently selected from hydrogen, an aliphatic group, a substituted aliphatic group, phenyl (Ph), substituted Ph, —O(Ph), substituted —O(Ph), CH$_2$(Ph), substituted CH$_2$(Ph), or an unsubstituted heteroaryl or heterocyclic ring. Examples of substituents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

The term "linker group" or "linker" means an organic moiety that connects two parts of a compound. Linkers are typically comprised of an atom such as oxygen or sulfur, a unit such as —NH—, —CH$_2$—, —C(O)—, —C(O)NH—, or a chain of atoms, such as an alkylidene chain. The molecular mass of a linker is typically in the range of about 14 to 200, preferably in the range of 14 to 96 with a length of up to about six atoms. Examples of linkers include a saturated or unsaturated C$_{1-6}$ alkylidene chain which is optionally substituted, and wherein one or two saturated carbons of the chain are optionally replaced by —C(O)—, —C(O)C(O)—, —CONH—, —CONHNH—, —CO$_2$—, —OC(O)—, —NHCO$_2$—, —O—, —NHCONH—, —OC(O)NH—, —NHNH—, —NHCO—, —S—, —SO—, —SO$_2$—, —NH—, —SO$_2$NH—, or —NHSO$_2$—.

The term "alkylidene chain" refers to an optionally substituted, straight or branched carbon chain that may be fully saturated or have one or more units of unsaturation. The optional substituents are as described above for an aliphatic group.

A combination of substituents or variables is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

Compounds of formula I or salts thereof may be formulated into compositions. In a preferred embodiment, the composition is a pharmaceutical composition. In one embodiment, the composition comprises an amount of the protein kinase inhibitor effective to inhibit a protein kinase, particularly Aurora-2, in a biological sample or in a patient. Compounds of this invention and pharmaceutical compositions thereof, which comprise an amount of the protein kinase inhibitor effective to treat or prevent an Aurora-2-mediated condition and a pharmaceutically acceptable carrier, adjuvant, or vehicle, may be formulated for administration to a patient.

Another aspect of this invention relates to a method of treating or preventing an Aurora-2-mediated disease with an Aurora-2 inhibitor, which method comprises administering to a patient in need of such a treatment a therapeutically effective amount of a compound of formula I or a pharmaceutical composition thereof.

The term "Aurora-2-mediated disease" or "Aurora-2-mediated condition", as used herein, means any disease or other deleterious condition in which Aurora is known to play a role. The terms "Aurora-2-mediated disease" or "Aurora-2-mediated condition" also mean those diseases or conditions that are alleviated by treatment with an Aurora-2 inhibitor. Such conditions include, without limitation, colon, breast, stomach, and ovarian cancer.

Another aspect of the invention relates to inhibiting Aurora-2 activity in a biological sample, which method comprises contacting the biological sample with the Aurora-2 inhibitor of formula I, or a composition thereof.

Another aspect of this invention relates to a method of inhibiting Aurora-2 activity in a patient, which method comprises administering to the patient a compound of formula I or a composition comprising said compound.

Another aspect of this invention relates to a method of treating or preventing a GSK-3-mediated disease with a GSK-3 inhibitor, which method comprises administering to a patient in need of such a treatment a therapeutically effective amount of a compound of formula I or a pharmaceutical composition thereof.

The terms "GSK-3-mediated disease" or "GSK-3-mediated condition", as used herein, mean any disease or other deleterious condition or state in which GSK-3 is known to play a role. Such diseases or conditions include, without limitation, diabetes, Alzheimer's disease, Huntington's Disease, Parkinson's Disease, AIDS-associated dementia, amyotrophic lateral sclerosis (AML), multiple sclerosis (MS), schizophrenia, cardiomycete hypertrophy, reperfusion/ischemia, and baldness.

One aspect of this invention relates to a method of enhancing glycogen synthesis and/or lowering blood levels of glucose in a patient in need thereof, which method comprises administering to the patient a therapeutically effective amount of a compound of formula I or a pharmaceutical composition thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of β-catenin, which is useful for treating schizophrenia.

Another aspect of the invention relates to inhibiting GSK-3 activity in a biological sample, which method comprises contacting the biological sample with a GSK-3 inhibitor of formula I.

Another aspect of this invention relates to a method of inhibiting GSK-3 activity in a patient, which method comprises administering to the patient a compound of formula I or a composition comprising said compound.

Another aspect of this invention relates to a method of treating or preventing a CDK-2-mediated disease with a CDK-2 inhibitor, which method comprises administering to a patient in need of such a treatment a therapeutically effective amount of a compound of formula I or a pharmaceutical composition thereof.

The terms "CDK-2-mediated disease" or "CDK-2-mediated condition", as used herein, mean any disease or other deleterious condition in which CDK-2 is known to play a role. The terms "CDK-2-mediated disease" or "CDK-2-mediated condition" also mean those diseases or conditions that are alleviated by treatment with a CDK-2 inhibitor. Such conditions include, without limitation, cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis. See Fischer, P. M. and Lane, D. P., *Current Medicinal Chemistry*, 7, 1213–1245 (2000); Mani, S., Wang, C., Wu, K., Francis, R. and Pestell, R., *Exp. Opin. Invest. Drugs*, 9, 1849 (2000); Fry, D. W. and Garrett, M. D., *Current Opinion in Oncologic, Endocrine & Metabolic Investigational Drugs*, 2, 40–59 (2000).

Another aspect of the invention relates to inhibiting CDK-2 activity in a biological sample or a patient, which method comprises administering to the patient a compound of formula I or a composition comprising said compound.

Another aspect of this invention relates to a method of treating or preventing an ERK-2-mediated diseases with an ERK-2 inhibitor, which method comprises administering to a patient in need of such a treatment a, therapeutically effective amount of a compound of formula I or a pharmaceutical composition thereof.

The terms "ERK-mediated disease" or "ERK-mediated condition", as used herein mean any disease or other deleterious condition in which ERK is known to play a role. The terms "ERK-2-mediated disease" or "ERK-2-mediated condition" also mean those diseases or conditions that are alleviated by treatment with a ERK-2 inhibitor. Such conditions include, without limitation, cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases. The term "cancer" includes, but is not limited to the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colonrectum, large intestine, rectum, brain and central nervous system, and leukemia. ERK-2 protein kinase and its implication in various diseases has been described [Bokemeyer et al. 1996, *Kidney Int.* 49, 1187; Anderson et al., 1990, *Nature* 343, 651; Crews et al., 1992, *Science* 258, 478; Bjorbaek et, al., 1995, *J. Biol. Chem.* 270, 18848; Rouse et al., 1994, *Cell* 78, 1027; Raingeaud et al., 1996, *Mol. Cell Biol.* 16, 1247; Raingeaud et al. 1996; Chen et al., 1993 *Proc. Natl. Acad. Sci. USA* 90, 10952; Oliver et al., 1995, *Proc. Soc. Exp. Biol. Med.* 210, 162; Moodie et al., 1993, *Science* 260, 1658; Frey and Mulder, 1997, *Cancer Res.* 57, 628; Sivaraman et al., 1997, *J Clin. Invest.* 99, 1478; Whelchel et al., 1997, *Am. J. Respir. Cell Mol. Biol.* 16, 589].

Another aspect of the invention relates to inhibiting ERK-2 activity in a biological sample or a patient, which method comprises administering to the patient a compound of formula I or a composition comprising said compound.

Another aspect of this invention relates to a method of treating or preventing an AKT-mediated diseases with an AKT inhibitor, which method comprises administering to a patient in need of such a treatment a therapeutically effective amount of a compound of formula I or a pharmaceutical composition thereof.

The terms "AKT-mediated disease" or "AKT-mediated condition", as used herein, mean any disease or other deleterious condition in which AKT is known to play a role. The terms "AKT-mediated disease" or "AKT-mediated condition" also mean those diseases or conditions that are alleviated by treatment with a AKT inhibitor. AKT-mediated diseases or conditions include, but are not limited to, proliferative disorders, cancer, and neurodegenerative disorders. The association of AKT, also known as protein kinase B, with various diseases has been described [Khwaja, A., *Nature*, pp. 33–34, 1990; Zang, Q. Y., et al, *Oncogene*, 19 2000; Kazuhiko, N., et al, *The Journal of Neuroscience*, 20 2000].

Another aspect of the invention relates to inhibiting AKT activity in a biological sample or a patient, which method comprises administering to the patient a compound of formula I or a composition comprising said compound.

Another aspect of this invention relates to a method of treating or preventing a Src-mediated disease with a Src inhibitor, which method comprises administering to a patient in need of such a treatment a therapeutically effective amount of a compound of formula I or a pharmaceutical composition thereof.

The terms "Src-mediated disease" or "Src-mediated condition", as used herein mean any disease or other deleterious condition in which Src is known to play a role. The terms "Src-mediated disease" or "Src-mediated condition" also mean those diseases or conditions that are alleviated by treatment with a Src inhibitor. Such conditions include, without limitation, hypercalcemia, osteoporosis, osteoarthritis, cancer, symptomatic treatment of bone metastasis, and Paget's disease. Src protein kinase and its implication in various diseases has been described [Soriano, *Cell,* 69, 551 (1992); Soriano et al., *Cell,* 64, 693 (1991); Takayanagi, *J. Clin. Invest.,* 104, 137 (1999); Boschelli, *Drugs of the Future* 2000, 25(7), 717, (2000); Talamonti, *J. Clin. Invest.,* 91, 53 (1993); Lutz, *Biochem. Biophys. Res.* 243, 503 (1998); Rosen, *J. Biol. Chem.,* 261, 13754 (1986); Bolen, *Proc. Natl. Acad. Sci. USA,* 84, 2251 (1987); Masaki, *Hepatology,* 27, 1257 (1998); Biscardi, *Adv. Cancer Res.,* 76, 61 (1999); Lynch, *Leukemia,* 7, 1416 (1993); Wiener, *Clin. Cancer Res.,* 5, 2164 (1999); Staley, *Cell Growth Diff.,* 8, 269 (1997)].

Another aspect of the invention relates to inhibiting Src activity in a biological sample or a patient, which method comprises administering to the patient a compound of formula I or a composition comprising said compound.

Another aspect of this invention relates to a method of treating or preventing an Lck-mediated diseases with an Lck inhibitor, which method comprises administering to a patient in need of such a treatment a therapeutically effective amount of a compound of formula I or a pharmaceutical composition thereof.

The terms "Lck-mediated disease" or "Lck-mediated condition", as used herein, mean any disease state or other deleterious condition in which Lck is known to play a role. The terms "Lck-mediated disease" or "Lck-mediated condition" also mean those diseases or conditions that are alleviated by treatment with an Lck inhibitor. Lck-mediated diseases or conditions include, but are not limited to, autoimmune diseases such as transplant rejection, allergies, rheumatoid arthritis, and leukemia. The association of Lck with various diseases has been described [Molina et al., *Nature,* 357, 161 (1992)].

Another aspect of the invention relates to inhibiting Lck activity in a biological sample or a patient, which method comprises administering to the patient a compound of formula I or a composition comprising said compound.

The term "pharmaceutically acceptable carrier, adjuvant, or vehicle" refers to a non-toxic carrier, adjuvant, or vehicle that may be administered to a patient, together with a compound of this invention, and which does not destroy the pharmacological activity thereof.

The term "patient" includes human and veterinary subjects.

The term "biological sample", as used herein, includes, without limitation, cell cultures or extracts thereof; preparations of an enzyme suitable for in vitro assay; biopsied material obtained from a mammal or extracts thereof; and blood, saliva, urine, feces, semen, tears, or other body fluids or extracts thereof.

An amount effective to inhibit protein kinase, for example, Aurora-2 and GSK-3, is an amount that causes measurable inhibition of the kinase activity when compared to the activity of the enzyme in the absence of an inhibitor. Any method may be used to determine inhibition, such as, for example, the Biological Testing Examples described below.

Pharmaceutically acceptable carriers that may be used in these pharmaceutical compositions are generally known in the art. They include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenteral, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical, compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In addition to the compounds of this invention, pharmaceutically acceptable derivatives or prodrugs of the compounds of this invention may also be employed in compositions to treat or prevent the above-identified diseases or disorders.

A "pharmaceutically acceptable derivative or prodrug" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Particularly favored derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, the following derivatives of the present compounds: esters, amino acid esters, phosphate esters, metal salts sulfonate esters, carbamates, and amides.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+$ $(C_{1-4}$ alkyl$)_4$ salts. This invention also envisions the quaternization of any basic nitrogen-containing groups of the compounds disclosed herein. Water or oil-soluble or dispersible products may be obtained by such quaternization.

The amount of the protein kinase inhibitor that may be combined with the carrier materials to produce a single dosage form will vary depending upon the patient treated and the particular mode of administration. Preferably, the compositions should be formulated so that a dosage of between 0.01–100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of the inhibitor will also depend upon the particular compound in the composition.

Depending upon the particular protein kinase-mediated condition to be treated or prevented, additional therapeutic agents, which are normally administered to treat or prevent that condition, may be administered together with the inhibitors of this invention. For example, in the treatment of cancer other chemotherapeutic agents or other anti-proliferative agents may be combined with the present compounds to treat cancer. These agents include, without limitation, adriamycin, dexamethasone, vincristine, cyclophosphamide, fluorouracil, topotecan, taxol, interferons, and platinum derivatives.

Other examples of agents the inhibitors of this invention may also be combined with include, without limitation, agents for treating diabetes such as insulin or insulin analogues, in injectable or inhalation form, glitazones, alpha glucosidase inhibitors, biguanides, insulin sensitizers, and sulfonyl ureas; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferon's, and anti-viral agents; agents for treating blood disorders such as corticosteroids, anti-leukemic agents, and growth factors; and agents for treating immunodeficiency disorders such as gamma globulin.

Those additional agents may be administered separately from the protein kinase inhibitor-containing composition, as part of a multiple dosage regimen. Alternatively, those agents may be part of a single dosage form, mixed together with the protein kinase inhibitor of this invention in a single composition.

Compounds of this invention may exist in alternative tautomeric forms, as in tautomers i and ii shown below. Unless otherwise indicated, the representation of either tautomer is meant to include the other.

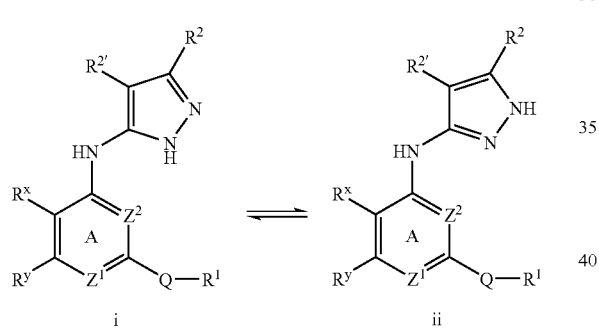

i          ii $R^x$ and $R^y$ may be taken together to form a fused ring, providing a bicyclic ring system containing Ring A. Preferred $R^x/R^y$ rings include a 5-, 6-, or 7-membered unsaturated or partially unsaturated ring having 0–2 heteroatoms, wherein said $R^x/R^y$ ring is optionally substituted. Examples of bicyclic systems containing Ring A are shown below by compounds I-A through I-BB, wherein $Z^1$ is nitrogen or $C(R^8)$ and $Z^2$ is nitrogen or $C(H)$.

I-A

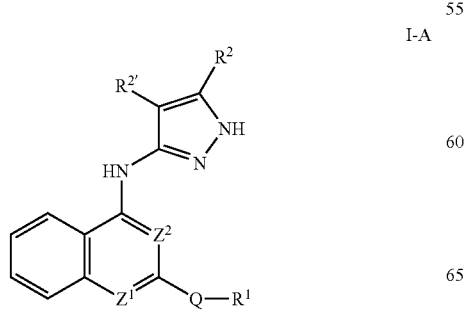

-continued

I-B

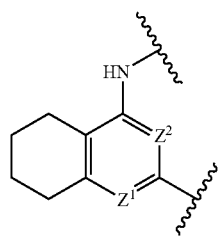

I-C

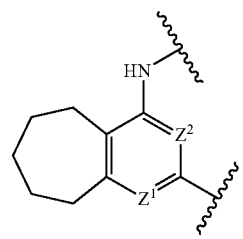

I-D

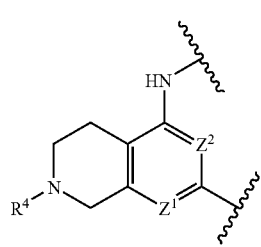

I-E

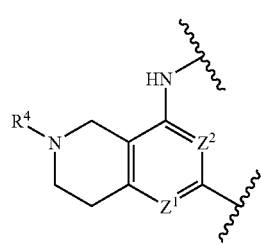

I-F

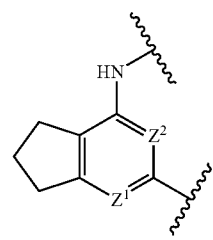

I-G

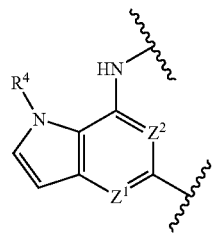

-continued
I-H
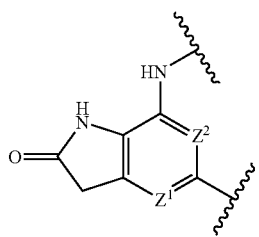
I-I
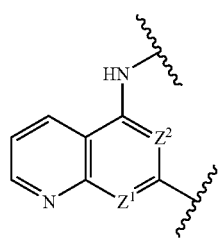
I-J
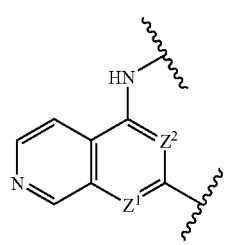
I-K
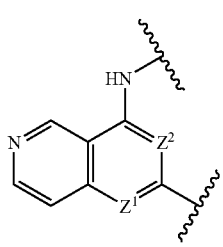
I-L
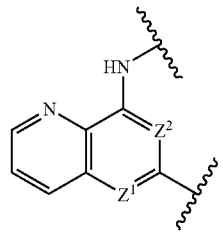
I-M
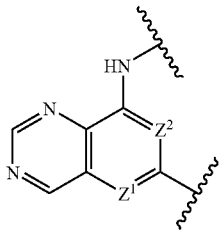
-continued
I-N
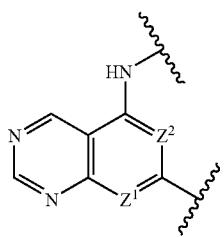
I-O
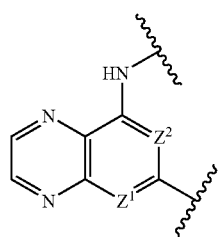
I-P
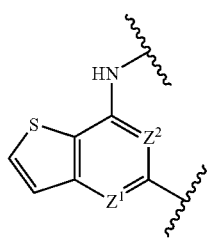
I-Q
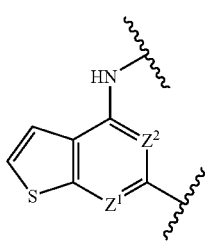
I-R
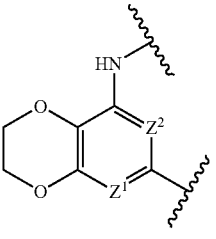
I-S
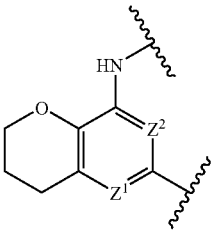

I-T 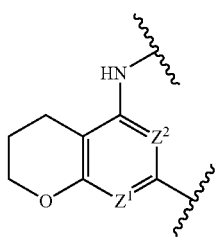

I-U 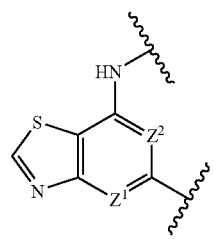

I-V 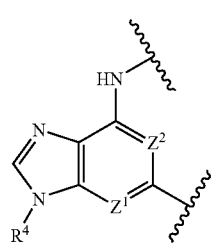

I-W 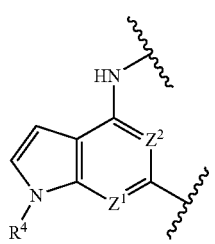

I-X 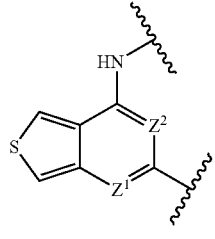

I-Y 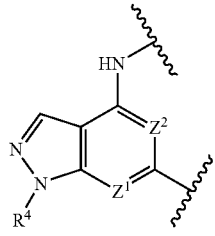

I-Z 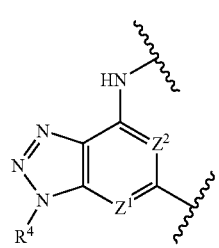

I-AA 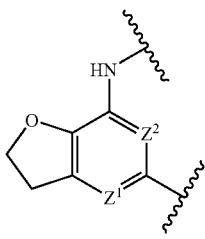

I-BB 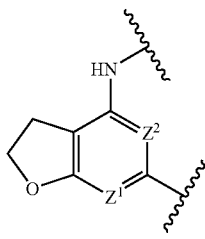

Preferred bicyclic Ring A systems include I-A, I-B, I-C, I-D, I-E, I-F, I-I, I-J, I-K, I-P, I-Q, I-V, and I-U, more preferably I-A, I-B, I-D, I-E, I-J, I-P, and I-V, and most preferably I-A, I-B, I-D, I-E and I-J.

In the monocyclic Ring A system, preferred $R^x$ groups, when present, include hydrogen, alkyl- or dialkylamino, acetamido, or a $C_{1-4}$ aliphatic group such as methyl, ethyl, cyclopropyl, or isopropyl. Preferred $R^y$ groups, when present, include T—$R^3$ or L—Z—$R^3$ wherein T is a valence bond or a methylene, L is —O—, —S—, —C($R^6$)$_2$O—, —CO— or —N($R^4$)—, and $R^3$ is —R, —N($R^4$)$_2$, or —OR. Preferred —$R^y$ groups include 5–6 membered heteroaryl or heterocyclyl rings, such as 2-pyridyl, 4-pyridyl, pyrrolidinyl, piperidinyl, morpholinyl, or piperazinyl; $C_{1-6}$ aliphatic, such as methyl, ethyl, cyclopropyl, isopropyl, or t-butyl; alkoxyalkylamino such as methoxyethylamino;, alkoxyalkyl such as methoxymethyl or methoxyethyl; alkyl- or dialkylamino such as ethylamino or dimethylamino; alkyl- or dialkylaminoalkoxy such as dimethylaminopropyloxy; acetamido; and optionally substituted phenyl such as phenyl or halo-substituted phenyl.

In the bicyclic Ring A system, the ring formed when $R^x$ and $R^y$ are taken together may be substituted or unsubstituted. Suitable substituents include —R, halo, —O(CH$_2$)$_{2-4}$—N(R$^4$)$_2$, —O(CH$_2$)$_{2-4}$—R, —OR, —N(R$^4$)—(CH$_2$)$_{2-4}$—N(R$^4$)$_2$, —N(R$^4$)—(CH$_2$)$_{2-4}$—R, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$(optionally substituted $C_{1-6}$ aliphatic), —N(R$^4$)N(R$^4$)$_2$, —C=NN(R$^4$)$_2$, —C=N—OR, —N(R⁴)CON(R⁴)₂, —N(R⁴)SO₂N(R⁴)₂, —N(R⁴)SO₂R, or —OC(=O)N(R⁴)₂, wherein R and R⁴ arenas defined above. Preferred R^x/R^y ring substituents include -halo, —R, —OR, —COR, —CO₂R, —CON(R⁴)₂, —CN, —O(CH₂)₂₋₄—N(R⁴)₂, —O(CH₂)₂₋₄—R, —NO₂—N(R⁴)₂, —NR⁴COR, —NR⁴SO₂R, —SO₂N(R⁴)₂ wherein R is hydrogen or an optionally substituted C₁₋₆ aliphatic group.

R² and R²' may be taken together to form a fused ring, thus providing a bicyclic ring system containing a pyrazole ring. Preferred fused rings include benzo, pyrido, pyrimido, and a partially unsaturated 6-membered carbocyclo ring, wherein said fused ring is optionally substituted. These are exemplified in the following formula I compounds having a pyrazole-containing bicyclic ring system:

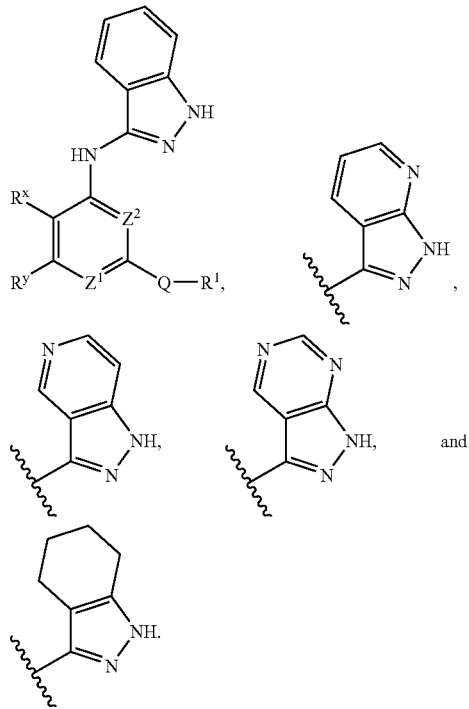

Preferred substituents on the R²/R²' fused ring include one or more of the following: -halo, —N(R⁴)₂, —C₁₋₃ alkyl, —C₁₋₃ haloalkyl, —NO₂, —O(C₁₋₃ alkyl), —CO₂(C₁₋₃ alkyl), —CN, —SO₂(C₁₋₃ alkyl), —SO₂NH₂, —OC(O)NH₂, —NH₂SO₂(C₁₋₃ alkyl), —NC(O)(C₁₋₃ alkyl), —C(O)NH₂, and —CO(C₁₋₃ alkyl), wherein the (C₁₋₃ alkyl) is most preferably methyl.

When the pyrazole ring system is monocyclic, preferred R² groups include hydrogen, C₁₋₄ aliphatic, alkoxycarbonyl, (un)substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocyclyl)carbonyl. Examples of such preferred R² substituents include methyl, cyclopropyl, ethyl, isopropyl, propyl, t-butyl, cyclopentyl, phenyl, CO₂H, CO₂CH₃, CH₂OH, CH₂OCH₃, CH₂CH₂CH₂OH, CH₂CH₂CH₂OCH₃, CH₂CH₂CH₂OCH₂Ph, CH₂CH₂CH₂NH₂, CH₂CH₂CH₂NHCOOC(CH₃)₃, CONHCH(CH₃)₂, CONHCH₂CH=CH₂, CONHCH₂CH₂OCH₃, CONHCH₂Ph, CONH(cyclohexyl), CON(Et)₂, CON(CH₃)CH₂Ph, CONH(n-C₃H₇), CON(Et)CH₂CH₂CH₃, CONHCH₂CH(CH₃)₂, CON(n-C₃H₇)₂, CO(3-methoxymethylpyrrolidin-1-yl), CONH(3-tolyl), CONH(4-tolyl), CONHCH₃, CO(morpholin-1-yl), CO(4-methylpiperazin-1-yl), CONHCH₂CH₂OH, CONH₂, and CO(piperidin-1-yl). A preferred R²' group is hydrogen.

An embodiment that is particularly useful for treating Aurora-2-mediated diseases relates to compounds of formula IIa:

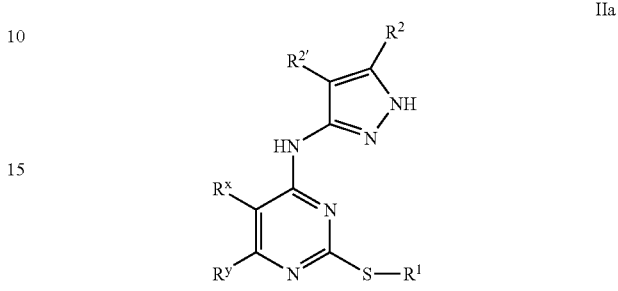

IIa or a pharmaceutically acceptable derivative or prodrug thereof, wherein;

R^x and R^y are taken together with their intervening atoms to form a fused, unsaturated or partially unsaturated, 5–7 membered ring having 0–3 ring heteroatoms selected from oxygen, sulfur, or nitrogen, wherein each substitutable ring carbon of said fused ring formed by R^x and R^y is independently substituted by oxo, T—R³, or L—Z—R³, and each substitutable ring nitrogen of said ring formed by R^x and R^y is independently substituted by R⁴;

R¹ is T-(Ring D);

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein each substitutable ring carbon of Ring D is independently substituted by oxo, T—R⁵, or V—Z—R⁵, and each substitutable ring nitrogen of Ring D is independently substituted by —R⁴;

T is a valence bond or a C₁₋₄ alkylidene chain;

Z is a C₁₋₄ alkylidene chain;

L is —O—, —S—, —SO—, —SO₂—, —N(R⁶)SO₂—, —SO₂N(R⁶)—, —N(R⁶)—, —CO—, —CO₂—, —N(R⁶)CO—, —N(R⁶)C(O)O—, —N(R⁶)CON(R⁶)—, —N(R⁶)SO₂N(R⁶)—, —N(R⁶)N(R⁶)—, —C(O)N(R⁶)—, —OC(O)N(R⁶)—, —C(R⁶)₂O—, —C(R⁶)₂S—, —C(R⁶)₂SO—, —C(R⁶)₂SO₂—, —C(R⁶)₂SO₂N(R⁶)—, —C(R⁶)₂N(R⁶)—, —C(R⁶)₂N(R⁶)C(O)—, —C(R⁶)₂N(R⁶)C(O)O—, —C(R⁶)=NN(R⁶)—, —C(R⁶)=N—O—, —C(R⁶)₂N(R⁶)N(R⁶)—, —C(R⁶)₂N(R⁶)SO₂N(R⁶)—, or —C(R⁶)₂N(R⁶)CON(R⁶)—;

R² and R²' are independently selected from —R, —T—W—R⁶, or R² and R²' are taken together with their intervening atoms to form a fused, 5–8 membered, unsaturated or partially unsaturated, ring having 0–3 ring heteroatoms selected from nitrogen, oxygen, or sulfur, wherein each substitutable ring carbon of said fused ring formed by R² and R²' is independently substituted by halo, oxo, —CN, —NO₂, —R⁷, or —V—R⁶, and each substitutable ring nitrogen of said ring formed by R² and R²' is independently substituted by R⁴;

R³ is selected from —R, -halo, —OR, —C(=O)R, —CO₂R, —COCOR, —COCH₂COR, —NO₂, —CN, —S(O)R, —S(O)₂R, —SR, —N(R⁴)₂, —CON(R⁷)₂, —SO₂N(R⁷)₂, —OC(=)R, —N(R⁷)COR, —N(R⁷)CO₂(C₁₋₆ aliphatic), —N(R⁴)N(R⁴)₂, —C=NN(R⁴)₂, —C=N—OR, —N(R⁷)CON(R⁷)₂, —N(R⁷)SO₂N(R⁷)₂, —N(R⁴)SO₂R, or —OC(=O)N(R⁷)₂;

each R is independently selected from hydrogen or an optionally substituted group selected from C₁₋₆ aliphatic, C₆₋₁₀ aryl, a heteroaryl ring having 5–10 ring atoms, or a heterocyclyl ring having 5–10 ring atoms;

each R⁴ is independently selected from —R⁷, —COR⁷, —CO₂(optionally substituted C₁₋₆ aliphatic), —CON(R⁷)₂, or —SO₂R⁷;

each R⁵ is independently selected from —R, halo, —OR, —C(=O)R, —CO₂R, —COCOR, —NO₂, —CN, —S(O)R, —SO₂R, —SR, —N(R⁴)₂, —CON(R⁴)₂, —SO₂N(R⁴)₂, —OC(=O)R, —N(R⁴)COR, —N(R⁴)CO₂(optionally substituted C₁₋₆ aliphatic), —N(R⁴)N(R⁴)₂, —C=NN(R⁴)₂, —C=N—OR, —N(R⁴)CON(R⁴)₂, —N(R⁴)SO₂N(R⁴)₂, —N(R⁴)SO₂R, or —OC(=O)N(R⁴)₂;

V is —O—, —S—, —SO—, —SO₂—, —N(R⁶)SO₂—, —SO₂N(R⁶)—, —N(R⁶)—, —CO—, —CO₂—, —N(R⁶)CO—, —N(R⁶)C(O)O—, —N(R⁶)CON(R⁶)—, —N(R⁶)SO₂N(R⁶)—, —N(R⁶)N(R⁶)—, —C(O)N(R⁶)—, —OC(O)N(R⁶)—, —C(R⁶)₂O—, —C(R⁶)₂S—, —C(R⁶)₂SO—, —C(R⁶)₂SO₂—, —C(R⁶)₂SO₂N(R⁶)—, —C(R⁶)₂N(R⁶)—, —C(R⁶)₂N(R⁶)C(O)—, —C(R⁶)₂N(R⁶)C(O)O—, —C(R⁶)=NN(R⁶)—, —C(R⁶)=N—O—, —C(R⁶)₂N(R⁶)N(R⁶)—, —C(R⁶)₂N(R⁶)SO₂N(R⁶)—, or —C(R⁶)₂N(R⁶)CON(R⁶)—;

W is —C(R⁶)₂O—, —C(R⁶)₂S—, —C(R⁶)₂SO—, —C(R⁶)₂SO₂—, —C(R⁶)₂SO₂N(R⁶)—, —C(R⁶)₂N(R⁶)—, —CO—, —CO₂—, —C(R⁶)OC(O)—, —C(R⁶)OC(O)N(R⁶)—, —C(R⁶)₂N(R⁶)CO—, —C(R⁶)₂N(R⁶)C(O)O—, —C(R⁶)=NN(R⁶)—, —C(R⁶)=N—O—, —C(R⁶)₂N(R⁶)N(R⁶)—, —C(R⁶)₂N(R⁶)SO₂N(R⁶)—, —C(R⁶)₂N(R⁶)CON(R⁶)—, or —CON(R⁶)—;

each R⁶ is independently selected from hydrogen or an optionally substituted C₁₋₄ aliphatic group, or two R⁶ groups on the same nitrogen atom may be taken together with the nitrogen atom to form a 5–6 membered heterocyclyl or heteroaryl ring; and each R⁷ is independently selected from hydrogen or an optionally substituted C₁₋₆ aliphatic group, or two R⁷ on the same nitrogen are taken together with the nitrogen to form a 5–8 membered heterocyclyl or heteroaryl ring.

Preferred rings formed by R$^x$ and R$^y$ include a 5-, 6-, or 7-membered unsaturated or partially unsaturated ring having 0–2 heteroatoms, wherein said R$^x$/R$^y$ ring is optionally substituted. This provides a bicyclic ring system containing a pyrimidine ring. Examples of preferred pyrimidine ring systems of formula IIa are shown below.

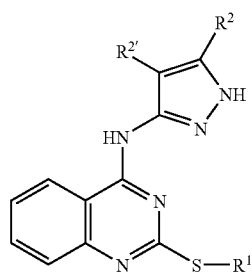
IIa-A

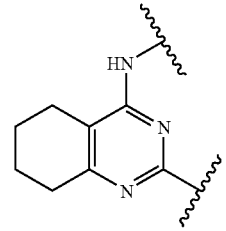
IIa-B

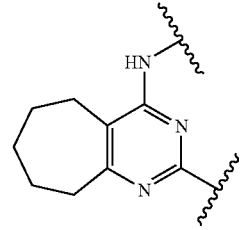
IIa-C

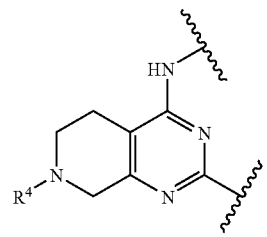
IIa-D

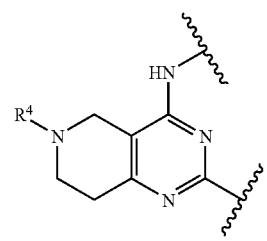
IIa-E

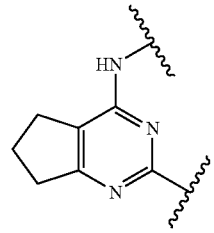
IIa-F

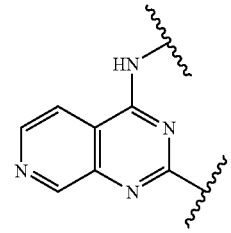
IIa-J

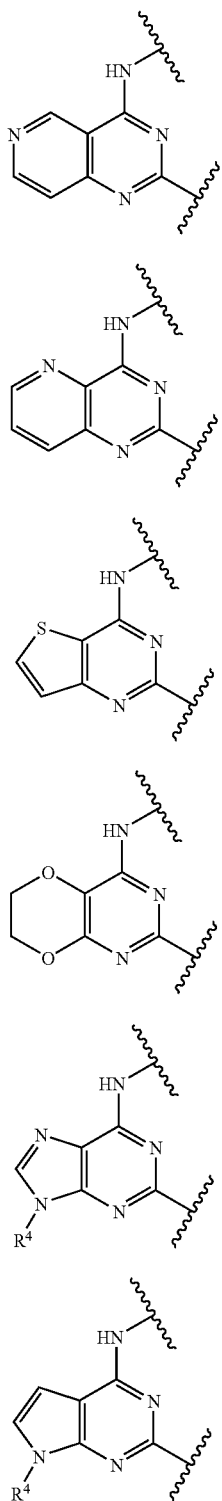

IIa-K

IIa-L

IIa-P

IIa-R

IIa-V

IIa-W

More preferred pyrimidine ring systems of formula IIa include IIa-A, IIa-B, IIa-D, IIa-E, IIa-J, IIa-P, and IIa-V, most preferably IIa-A, IIa-B, IIa-D, IIa-E, and IIa-J.

The ring formed when $R^x$ and $R^y$ are taken together may be substituted or unsubstituted. Suitable substituents include —R, halo, —O(CH$_2$)$_{2-4}$—N(R$^4$)$_2$, —O(CH$_2$)$_{2-4}$—R, —OR, —N(R$^4$)—(CH$_2$)$_{2-4}$—N(R$^4$)$_2$, —N(R$^4$)—(CH$_2$)$_{2-4}$—R, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$(optionally substituted C$_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$, wherein R and R$^4$ are as defined above. Preferred R$^x$/R$^y$ ring substituents include -halo, —R, —OR, —COR, —CO$_2$R, —CON(R$^4$)$_2$, —CN, —O(CH$_2$)$_{2-4}$—N(R$^4$)$_2$, —O(CH$_2$)$_{2-4}$—R, —NO$_2$—N(R$^4$)$_2$, —NR$^4$COR, —NR$^4$SO$_2$R, —SO$_2$N(R$^4$)$_2$ wherein R is hydrogen or an optionally substituted C$_{1-6}$ aliphatic group.

$R^2$ and $R^{2'}$ groups of formula IIa may be taken together to form a fused ring, thus providing a bicyclic ring system containing a pyrazole ring. Preferred fused rings include benzo, pyrido, pyrimido, and a partially unsaturated 6-membered carbocyclo ring. These are exemplified in the following formula IIa compounds having a pyrazole-containing bicyclic ring system:

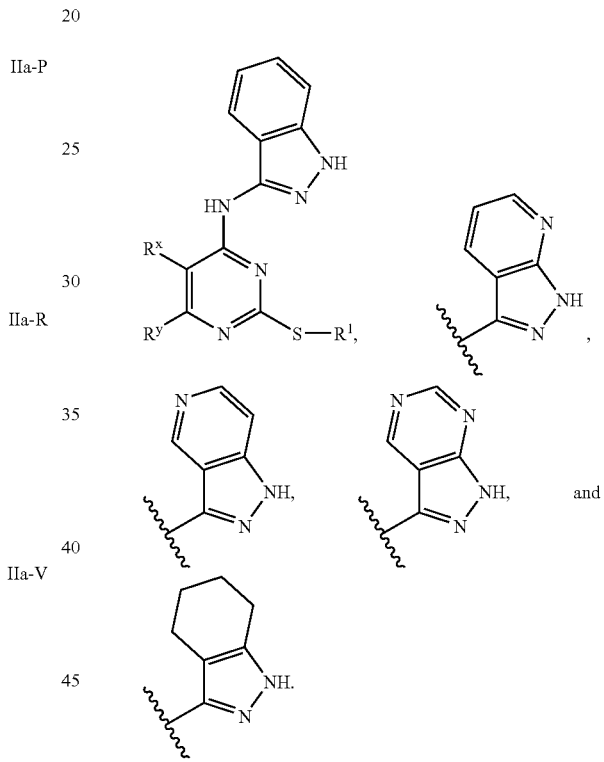

Preferred substituents on the $R^2/R^{2'}$ fused ring of formula IIa include one or more of the following: -halo, —N(R$^4$)$_2$, —C$_{1-4}$ alkyl, —C$_{1-4}$ haloalkyl, —NO$_2$, —O (C$_{1-4}$ alkyl), —CO$_2$(C$_{1-4}$ alkyl), —CN, —SO$_2$(C$_{1-4}$ alkyl), —SO$_2$NH$_2$, —OC(O)NH$_2$, —NH$_2$SO$_2$(C$_{1-4}$ alkyl), —NHC(O)(C$_{1-4}$ alkyl), —C(O)NH$_2$, and —CO(C$_{1-4}$ alkyl), wherein the (C$_{1-4}$ alkyl) is a straight, branched, or cyclic alkyl group. Preferably, the (C$_{1-4}$ alkyl) group is methyl or ethyl.

When the pyrazole ring system of formula IIa is monocyclic, preferred $R^2$ groups include hydrogen or a substituted or unsubstituted group selected from aryl, heteroaryl, or a C$_{1-6}$ aliphatic group. Examples of such preferred $R^2$ groups include H, methyl, ethyl, propyl, cyclopropyl, i-propyl, cyclopentyl, hydroxypropyl, methoxypropyl, and benzyloxypropyl. A preferred $R^{2'}$ group is hydrogen.

When Ring D of formula IIa is monocyclic, preferred Ring D groups include phenyl, pyridyl, pyridazinyl, pyrimidinyl, and pyrazinyl.

When Ring D of formula IIa is bicyclic, preferred bicyclic Ring D groups include naphthyl, tetrahydronaphthyl, indanyl, benzimidazolyl, quinolinyl, indolyl, isoindolyl, indolinyl, benzo[b]furyl, benzo[b]thiophenyl, indazolyl, benzothiazolyl, cinnolinyl, phthalazinyl, quinazolinyl, quinoxazolinyl, 1,8-naphthyridinyl and isoquinolinyl.

On Ring D of formula IIa, preferred T—$R^5$ or V—Z—$R^5$ substituents include -halo, —CN, —$NO_2$, —$N(R^4)_2$, optionally substituted $C_{1-6}$ aliphatic group, —OR, —C(O)R, —$CO_2R$, —$CONH(R^4)$, —$N(R^4)COR$, —$N(R^4)CO_2R$, —$SO_2N(R^4)_2$, —$N(R^4)SO_2R$, —$N(R^6)COCH_2N(R^4)_2$, —$N(R^6)COCH_2CH_2N(R^4)_2$, and —$N(R^6)COCH_2CH_2CH_2N(R^4)_2$, wherein R is selected from hydrogen, $C_{1-6}$ aliphatic, phenyl, a 5–6 membered heteroaryl ring, or a 5–6 membered heterocyclic ring. More preferred $R^5$ substituents include —Cl, —Br, —F, —CN, —$CF_3$, —COOH, —CONHMe, —CONHEt, —$NH_2$, —NHAc, —$NHSO_2Me$, —$NHSO_2Et$, —$NHSO_2$(n-propyl), —$NHSO_2$(isopropyl), —$NHCOEt$, —$NHCOCH_2NHCH_3$, —$NHCOCH_2N(CO_2t$-Bu$)CH_3$, —$NHCOCH_2N(CH_3)_2$, —$NHCOCH_2CH_2N(CH_3)_2$, —$NHCOCH_2CH_2CH_2N(CH_3)_2$, —NHCO(cyclopropyl), —NHCO(isobutyl), —NHCOCH$_2$(morpholin-4-yl), —$NHCOCH_2CH_2$(morpholin-4-yl)), —$NHCOCH_2CH_2CH_2$(morpholin-4-yl), —NHCO(t-butyl), —NH($C_{1-4}$ aliphatic) such as —NHMe, —N($C_{1-4}$ aliphatic)$_2$ such as —$NMe_2$, OH, —O($C_{1-4}$ aliphatic) such as —OMe, $C_{1-4}$ aliphatic such as methyl, ethyl, cyclopropyl, isopropyl, or t-butyl, and —$CO_2(C_{1-4}$ aliphatic).

Preferred formula IIa compounds have one or more, and more preferably all, of the features selected from the group consisting of:

(a) $R^x$ and $R^y$ are taken together with their intervening atoms to form a fused, unsaturated or partially unsaturated, 5–6 membered ring having 0–2 heteroatoms selected from oxygen, sulfur, or nitrogen, wherein each substitutable ring carbon of said fused ring formed by $R^x$ and $R^y$ is independently substituted by oxo, T—$R^3$, or L—Z—$R^3$, and each substitutable ring nitrogen of said ring formed by $R^x$ and $R^y$ is independently substituted by $R^4$;

(b) $R^1$ is T-(Ring D), wherein T is a valence bond or a methylene unit;

(c) Ring D is a 5–7 membered monocyclic ring or an 8–10 membered bicyclic ring selected from an aryl or heteroaryl ring;

(d) $R^2$ is —R or —T—W—$R^6$ and $R^{2'}$ is hydrogen; or $R^2$ and $R^{2'}$ are taken together to form an optionally substituted benzo ring; and (e) $R^3$ is selected from —R, -halo, —OR—, or —$N(R^4)_2$.

More preferred compounds of formula IIa have one or more, and more preferably all, of the features selected from the group consisting of:

(a) $R^x$ and $R^y$ are taken together to form a benzo, pyrido, cyclopento, cyclohexo, cyclohepto, thieno, piperidino, or imidazo ring;

(b) $R^1$ is T-(Ring D), wherein T is a valence bond and Ring D is a 5–6 membered monocyclic ring or an 8–10 membered bicyclic ring selected from an aryl or heteroaryl ring;

(c) $R^2$ is —R and $R^{2'}$ is hydrogen, wherein R is selected from hydrogen, $C_{1-6}$ aliphatic, phenyl, a 5–6 membered heteroaryl ring, or a 5–6 membered heterocyclic ring; and (d) $R^3$ is selected from —R, -halo, —OR, or —$N(R^4)_2$, wherein R is selected from hydrogen, $C_{1-6}$ aliphatic, 5–6 membered heterocyclyl, phenyl, or 5–6 membered heteroaryl, and L is —O—, —S—, or —NH—.

Even more preferred compounds of formula IIa have one or more, and more preferably all, of the features selected from the group consisting of:

(a) $R^x$ and $R^y$ are taken together to form a benzo, pyrido, piperidino, or cyclohexo ring;

(b) $R^1$ is T-Ring D, wherein T is a valence bond and Ring D is a 5–6 membered aryl or heteroaryl ring;

(c) $R^2$is hydrogen or $C_{1-4}$ aliphatic and $R^{2'}$ is hydrogen;

(d) $R^3$ is selected from —R, —OR, or —$N(R^4)_2$, wherein R is selected from hydrogen, $C_{1-6}$ aliphatic, 5–6 membered heterocyclyl, phenyl, or 5–6 membered heteroaryl, and L is —O—, —S—, or —NH—; and (e) Ring D is substituted by up to three substituents selected from -halo, —CN, —$NO_2$, —$N(R^4)_2$, optionally substituted $C_{1-6}$ aliphatic group, —OR, —C(O)R, —$CO_2R$, —$CONH(R^4)$, —$N(R^4)$ COR, —$N(R^4)$ $CO_2R$, —$SO_2N(R^4)_2$, —$N(R^4)SO_2R$, —$N(R^6)COCH_2N(R^4)_2$, —$N(R^6)COCH_2CH_2N(R^4)_2$, or —$N(R^6)COCH_2CH_2CH_2N(R^4)_2$, wherein R is selected from hydrogen, $C_{1-6}$ aliphatic, phenyl, a 5–6 membered heteroaryl ring, or a 5–6 membered heterocyclic ring.

Representative compounds of formula IIa are shown below in Table 1.

TABLE 1

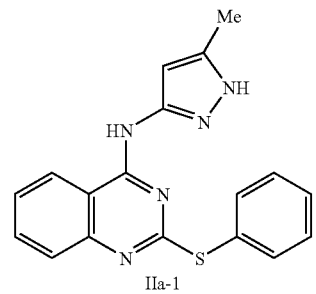

IIa-1

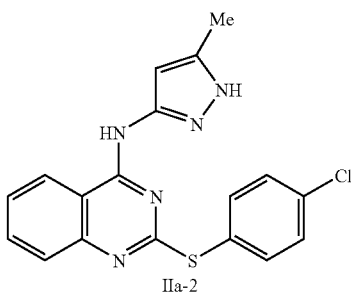

IIa-2

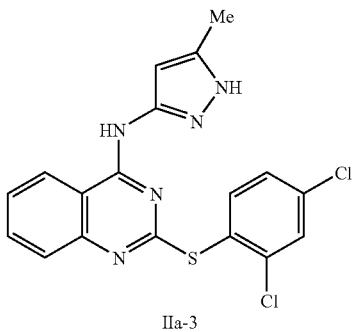

IIa-3

TABLE 1-continued
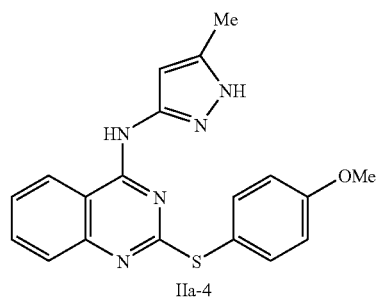
IIa-4
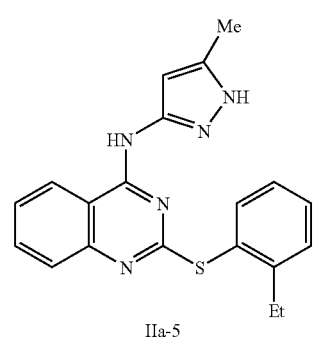
IIa-5
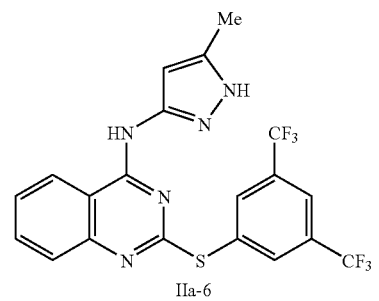
IIa-6
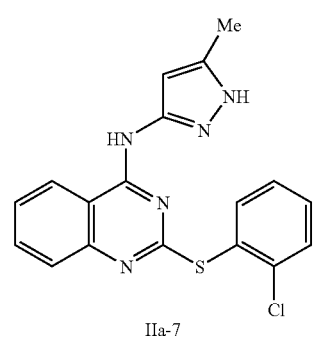
IIa-7
TABLE 1-continued
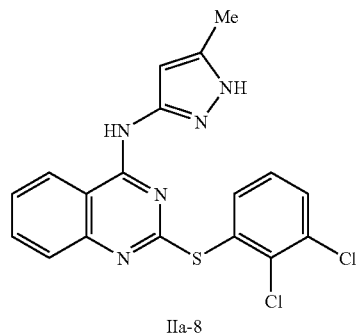
IIa-8
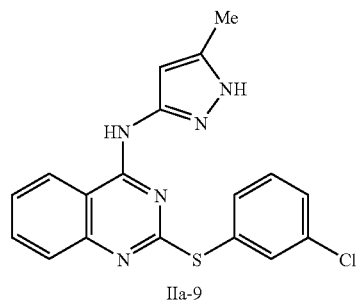
IIa-9
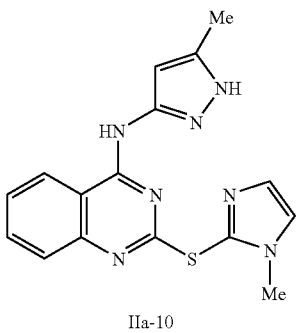
IIa-10
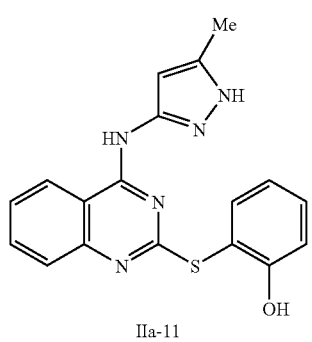
IIa-11

TABLE 1-continued
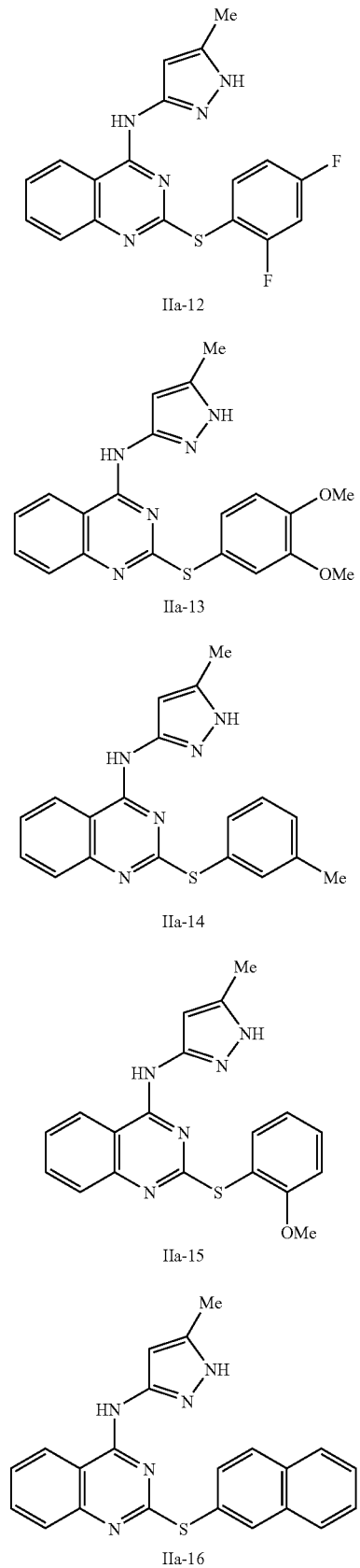
IIa-12
IIa-13
IIa-14
IIa-15
IIa-16
TABLE 1-continued
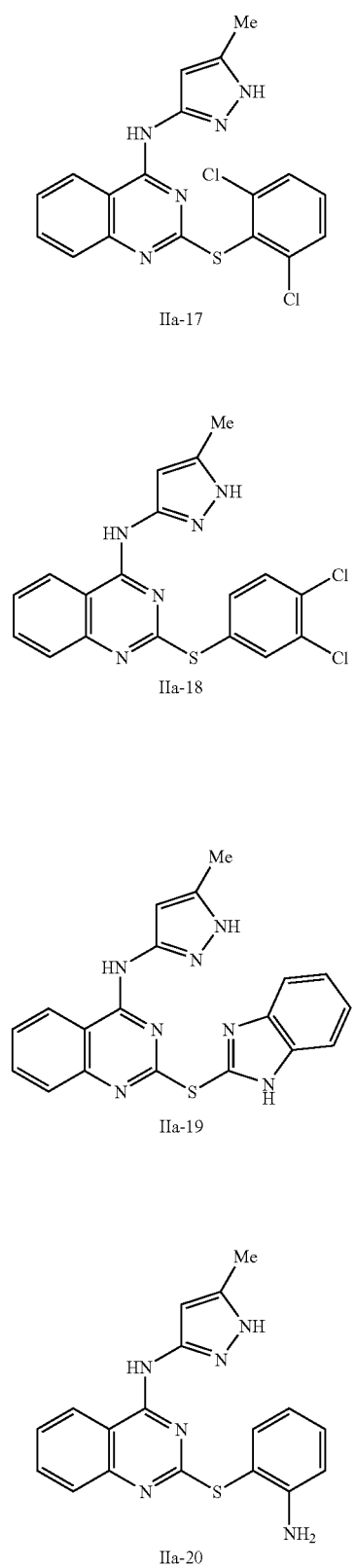
IIa-17
IIa-18
IIa-19
IIa-20

TABLE 1-continued
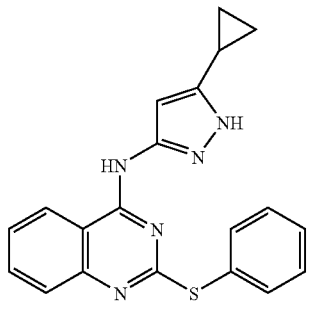
IIa-21
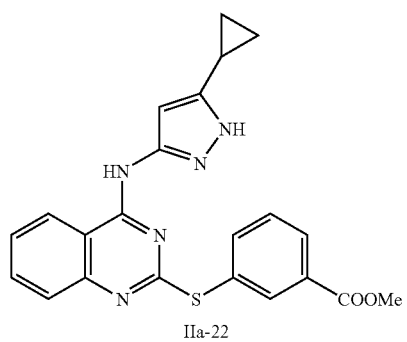
IIa-22
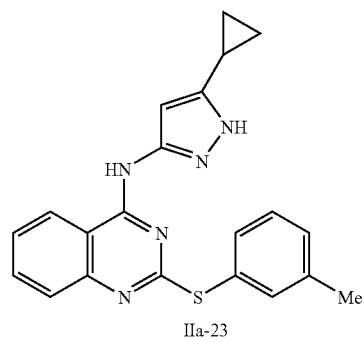
IIa-23
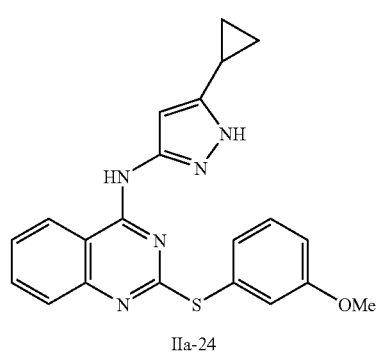
IIa-24
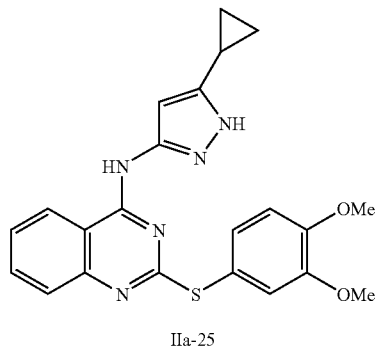
IIa-25
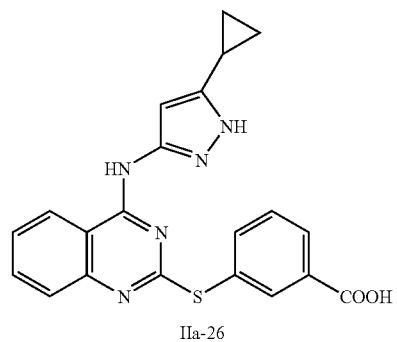
IIa-26
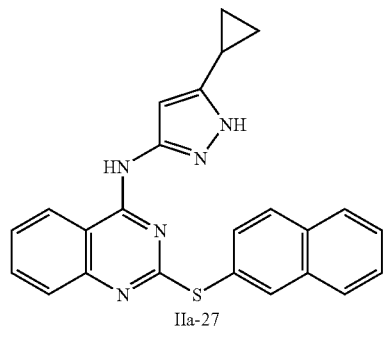
IIa-27
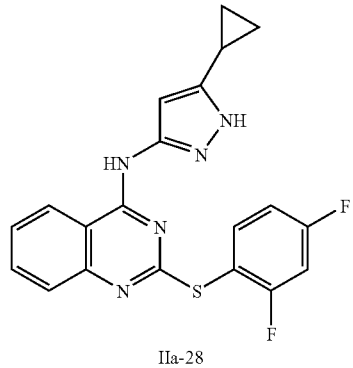
IIa-28

TABLE 1-continued
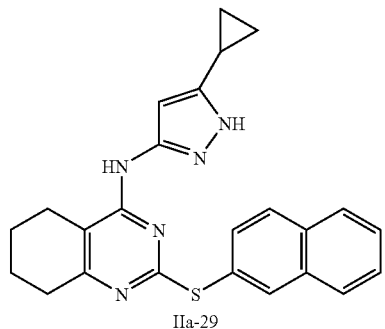
IIa-29
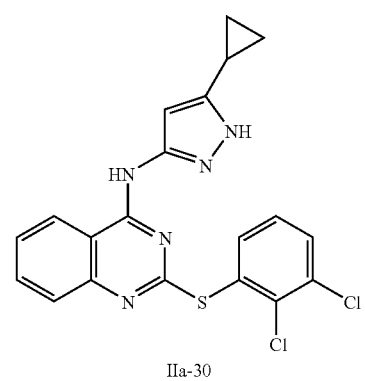
IIa-30
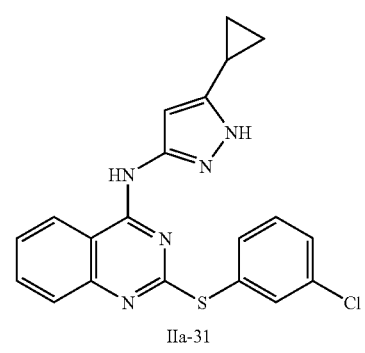
IIa-31
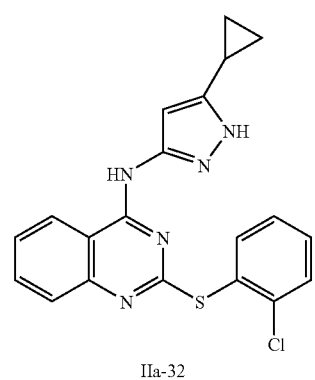
IIa-32
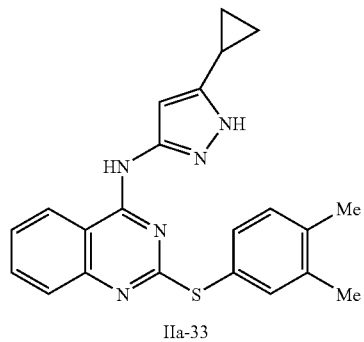
IIa-33
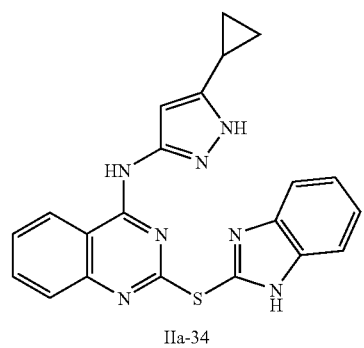
IIa-34
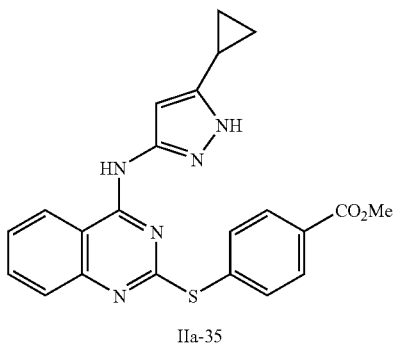
IIa-35
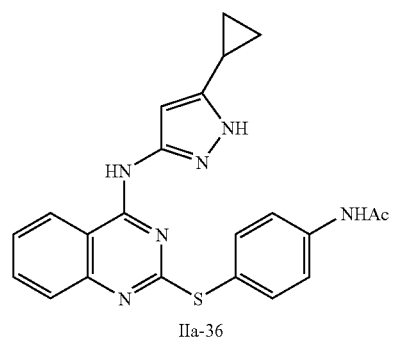
IIa-36

TABLE 1-continued
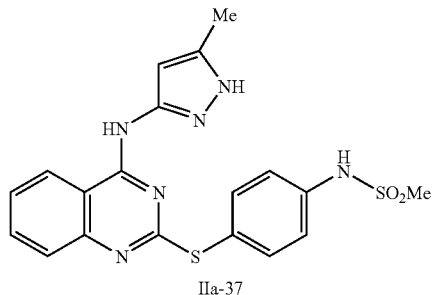
IIa-37
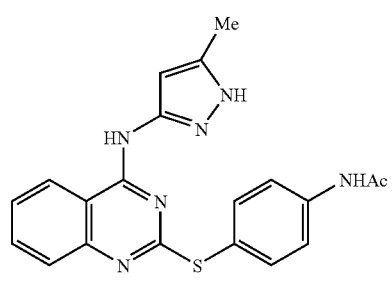
IIa-38
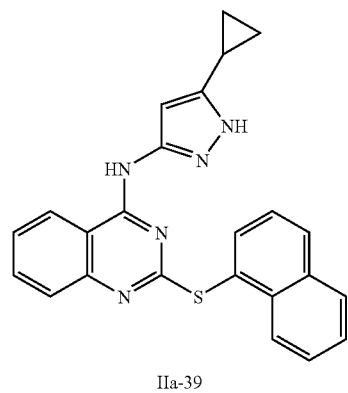
IIa-39
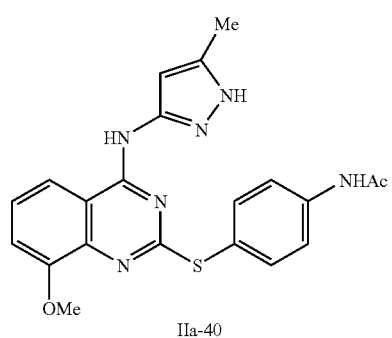
IIa-40
TABLE 1-continued
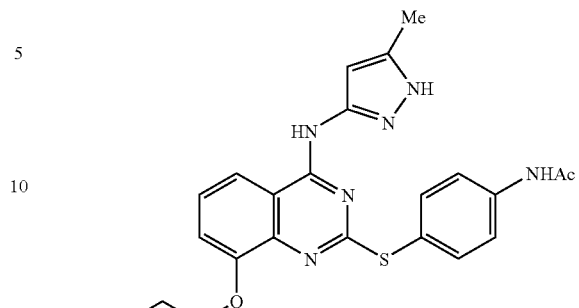
IIa-41
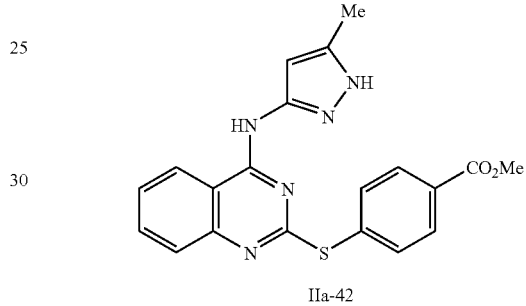
IIa-42
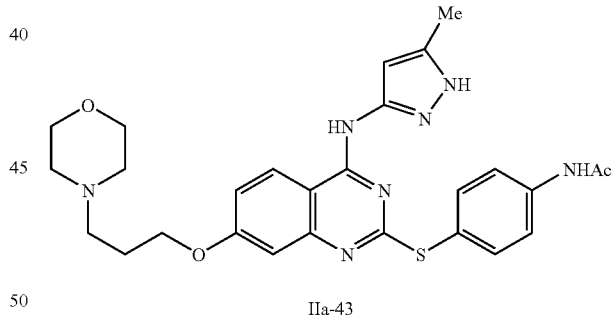
IIa-43
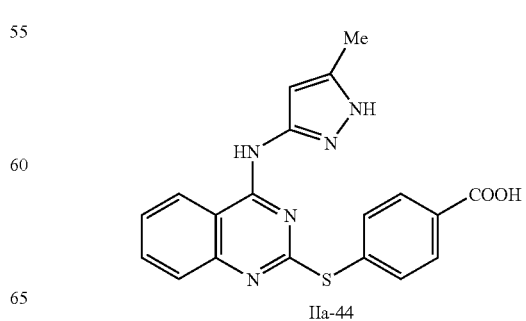
IIa-44

TABLE 1-continued
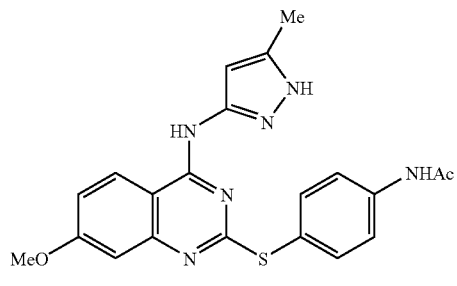
IIa-45
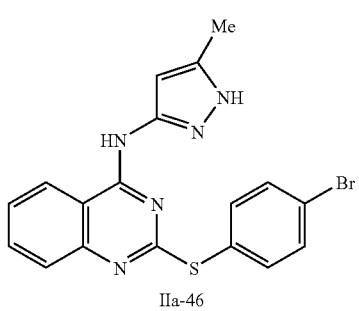
IIa-46
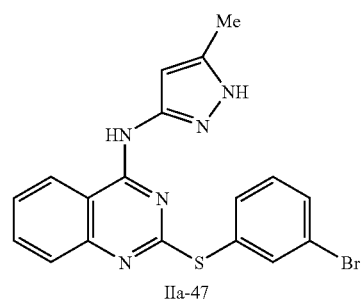
IIa-47
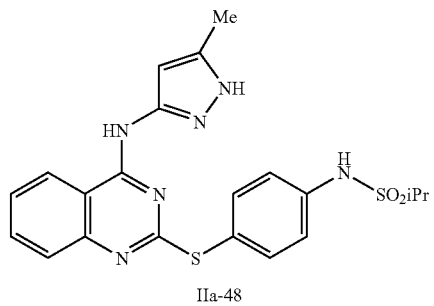
IIa-48
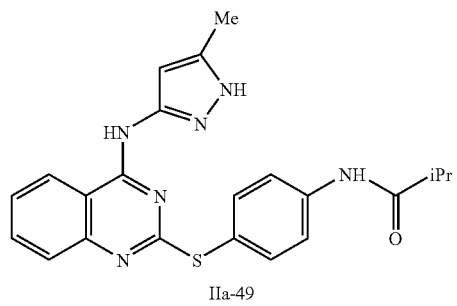
IIa-49
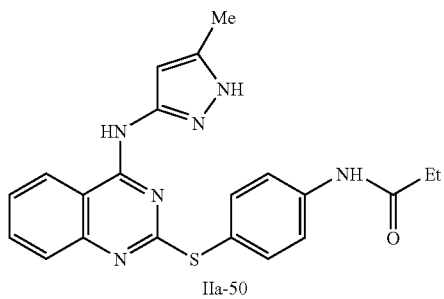
IIa-50
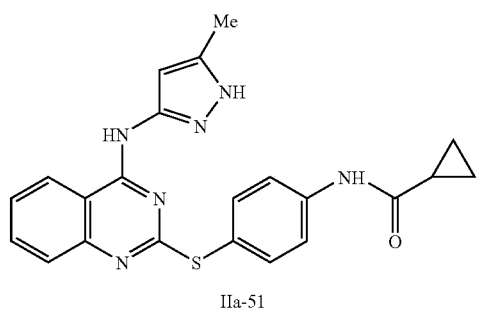
IIa-51
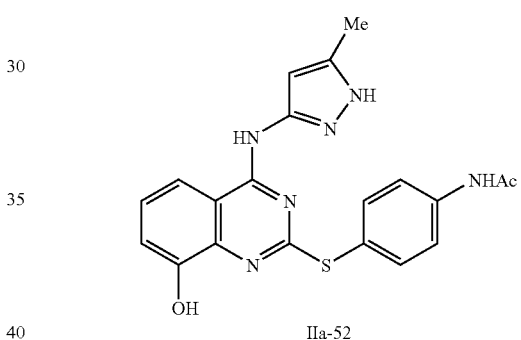
IIa-52
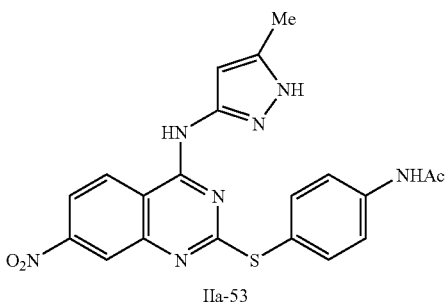
IIa-53
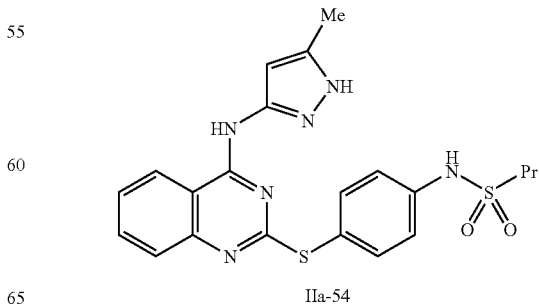
IIa-54

TABLE 1-continued
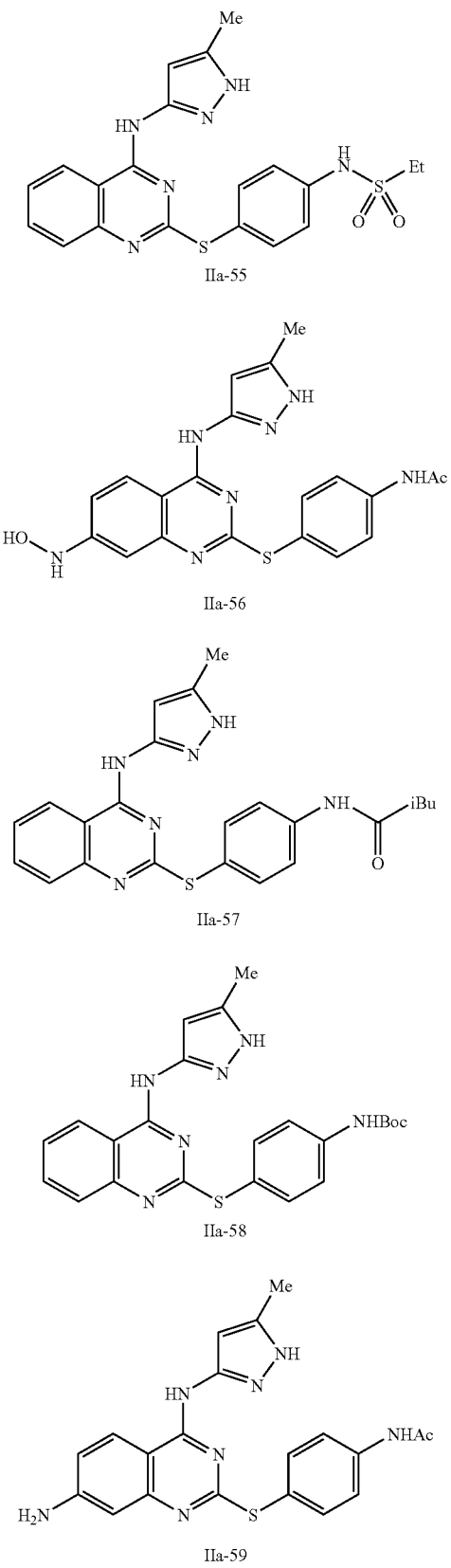
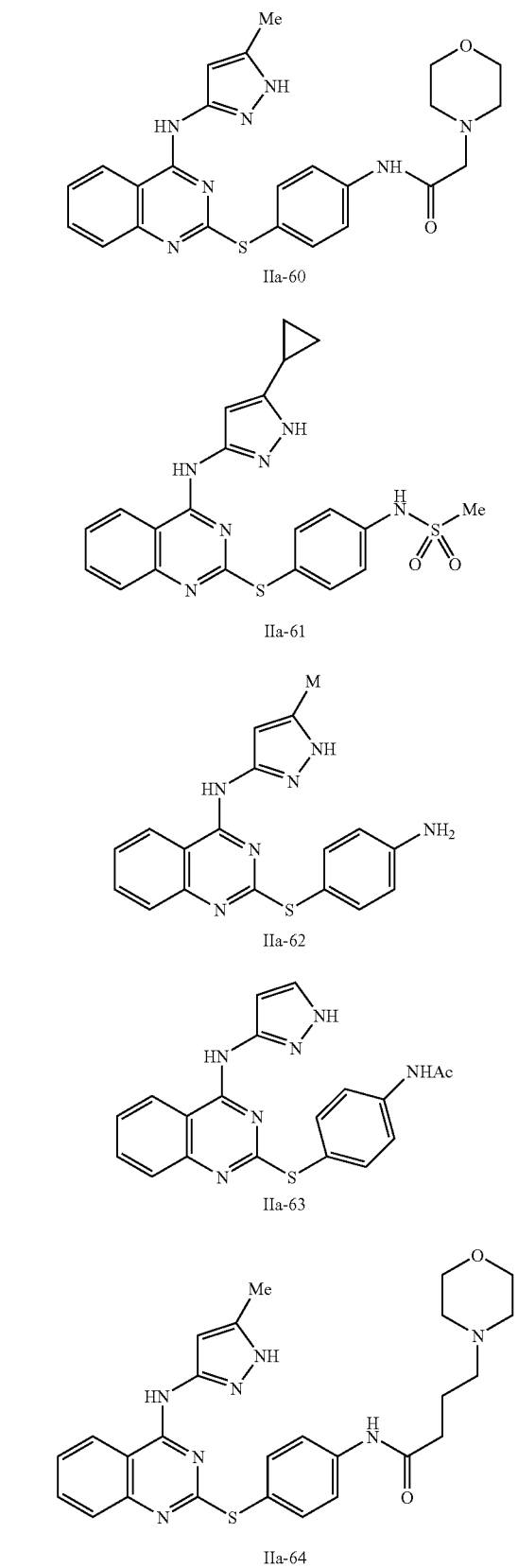

TABLE 1-continued
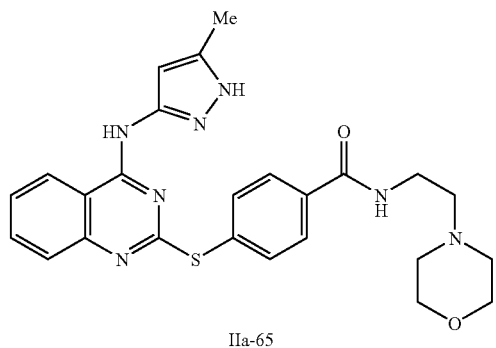
IIa-65
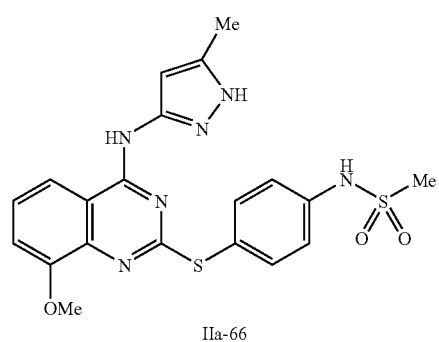
IIa-66
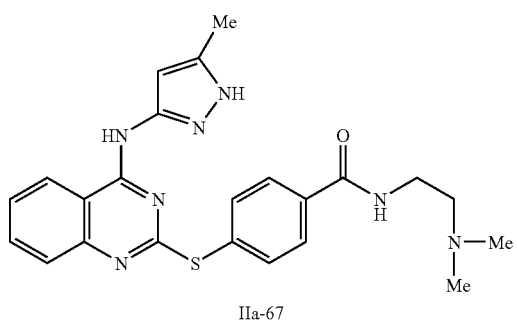
IIa-67
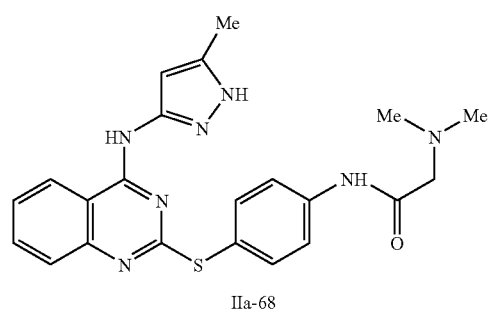
IIa-68
TABLE 1-continued
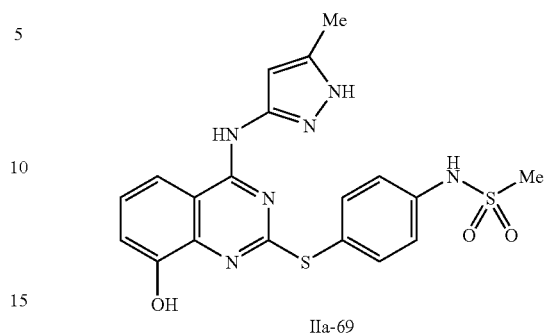
IIa-69
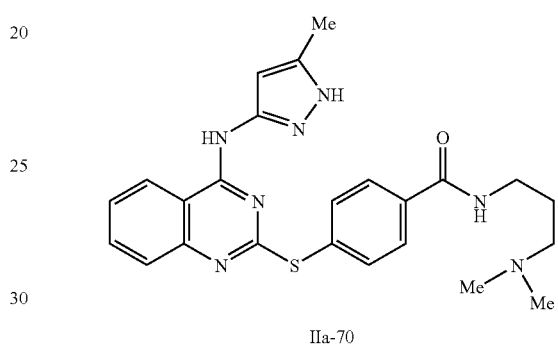
IIa-70
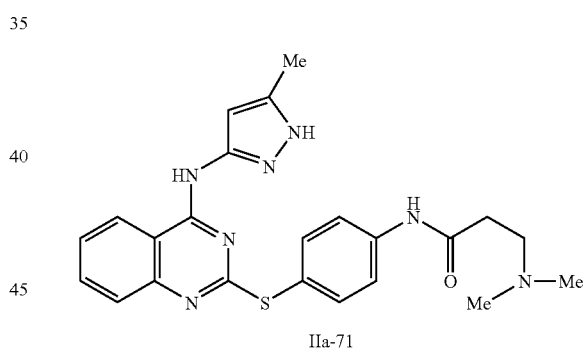
IIa-71
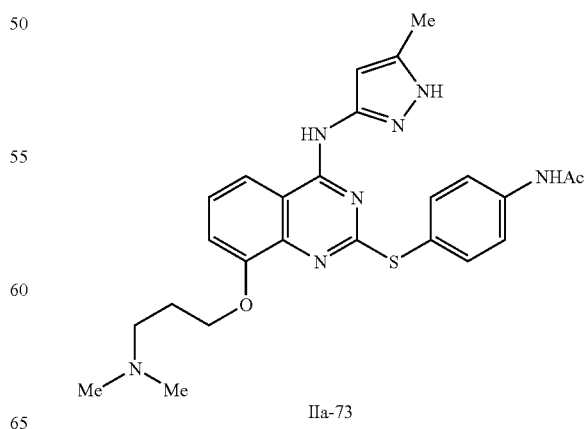
IIa-73

TABLE 1-continued

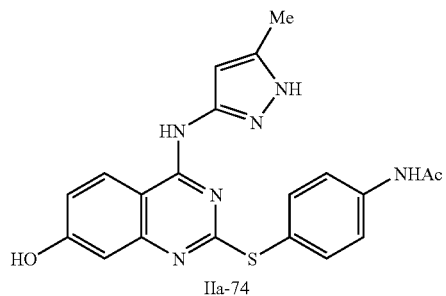

IIa-74

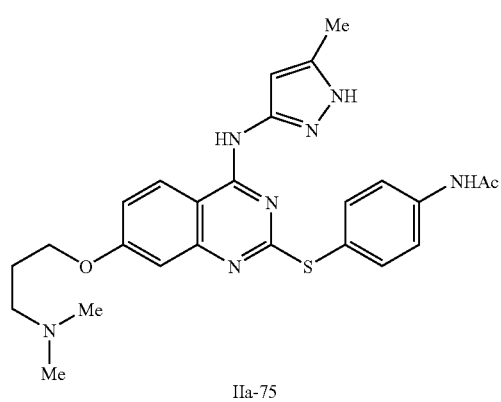

IIa-75

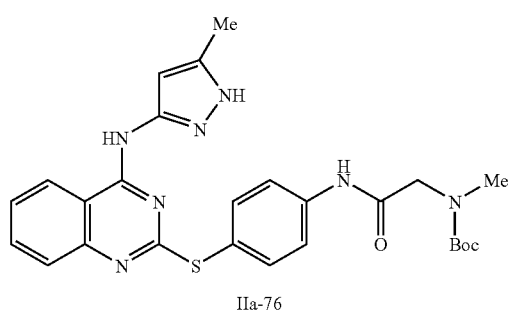

IIa-76

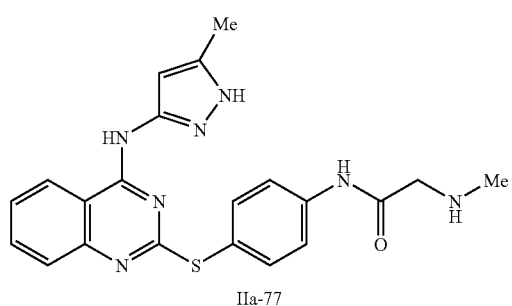

IIa-77

TABLE 1-continued

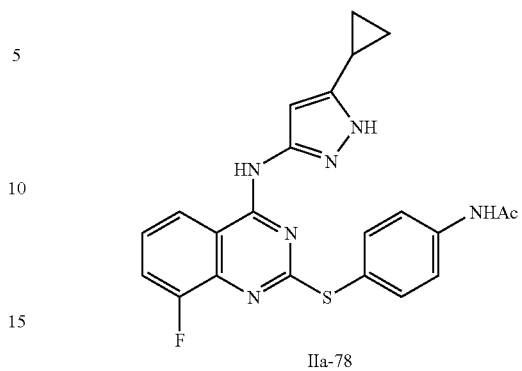

IIa-78

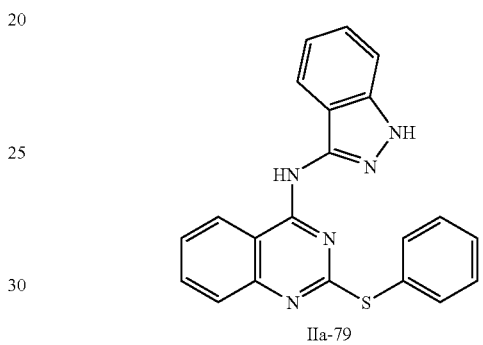

IIa-79

In another embodiment, this invention provides a composition comprising a compound of formula IIa and a pharmaceutically acceptable carrier.

Another aspect of this invention relates to a method of treating or preventing an Aurora-2-mediated disease with an Aurora-2 inhibitor, which method comprises administering to a patient in need of such a treatment a therapeutically effective amount of a compound of formula IIa or a pharmaceutical composition thereof.

Another aspect of this invention relates to a method of inhibiting Aurora-2 activity in a patient, which method comprises administering to the patient a compound of formula IIa or a composition comprising said compound.

Another aspect of this invention relates to a method of treating or preventing a GSK-3-mediated disease with a GSK-3 inhibitor, which method comprises administering to a patient in need of such a treatment a therapeutically effective amount of a compound of formula IIa or a pharmaceutical composition thereof.

One aspect of this invention relates to a method of enhancing glycogen synthesis and/or lowering blood levels of glucose in a patient in need thereof, which method comprises administering to the patient a therapeutically effective amount of a compound of formula IIa or a pharmaceutical composition thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of β-catenin, which is useful for treating schizophrenia.

Another aspect of this invention relates to a method of inhibiting GSK-3 activity in a patient, which method comprises administering to the patient a compound of formula IIa or a composition comprising said compound.

Another aspect of this invention relates to a method of treating or preventing a CDK-2-mediated disease with a CDK-2 inhibitor, which method comprises administering to a patient in need of such a treatment a therapeutically effective amount of a compound of formula IIa or a pharmaceutical composition thereof.

Another aspect of the invention relates to inhibiting CDK-2 activity in a patient, which method comprises administering to the patient a compound of formula IIa or a composition comprising said compound.

Another aspect of this invention relates to a method of treating or preventing a Src-mediated disease with a Src inhibitor, which method comprises administering to a patient in need of such a treatment a therapeutically effective amount of a compound of formula IIa or a pharmaceutical composition thereof.

Another aspect of the invention relates to inhibiting Src activity in a patient, which method comprises administering to the patient a compound of formula IIa or a composition comprising said compound.

Another method relates to inhibiting Aurora-2, GSK-3, CDK2, or Src activity in a biological sample, which method comprises contacting the biological sample with the Aurora-2, GSK-3, CDK2, or Src inhibitor of formula IIa, or a pharmaceutical composition thereof, in an amount effective to inhibit Aurora-2, GSK-3, CDK2, or Src.

Each of the aforementioned methods directed to the inhibition of Aurora-2, GSK-3, CDK2, or Src, or the treatment of a disease alleviated thereby, is preferably carried out with a preferred compound of formula IIa, as described above.

Another embodiment of this invention relates to compounds of formula IIb:

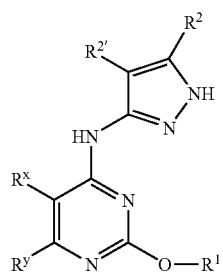

IIb or a pharmaceutically acceptable derivative or prodrug thereof, wherein;

$R^x$ and $R^y$ are taken together with their intervening atoms to form a fused, unsaturated or partially unsaturated, 5–7 membered ring having 0–3 ring heteroatoms selected from oxygen, sulfur, or nitrogen, wherein each substitutable ring carbon of said fused ring formed by $R^x$ and $R^y$ is independently substituted by oxo, T—$R^3$, or L—Z—$R^3$, and each substitutable ring nitrogen of said ring formed by $R^x$ and $R^y$ is independently substituted by $R^4$;

$R^1$ is T-(Ring D);

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein each substitutable ring carbon of Ring D is independently substituted by oxo, T—$R^5$, or V—Z—$R^5$, and each substitutable ring nitrogen of Ring D is independently substituted by —$R^4$;

T is a valence bond or a $C_{1-4}$ alkylidene chain;

Z is a $C_{1-4}$ alkylidene chain;

L is —O—, —S—, —SO—, —SO$_2$—, —N($R^6$)SO$_2$—, —SO$_2$N($R^6$)—, —N($R^6$)—, —CO—, —CO$_2$—, —N($R^6$) CO—, —N($R^6$)C(O)O—, —N($R^6$)CON($R^6$)—, —N($R^6$) SO$_2$N($R^6$)—, —N($R^6$)N($R^6$)—, —C(O)N($R^6$)—, —OC (O)N($R^6$)—, —C($R^6$)$_2$O—, —C($R^6$)$_2$S—, —C($R^6$)$_2$ SO—, —C($R^6$)$_2$SO$_2$—, —C($R^6$)$_2$SO$_2$N($R^6$)—, —C($R^6$)$_2$ N($R^6$)—, —C($R^6$)$_2$N($R^6$)C(O)—, —C($R^6$)$_2$N($R^6$)C(O) O—, —C($R^6$)=NN($R^6$)—, —C($R^6$)=N—O—, —C($R^6$)$_2$N($R^6$)N($R^6$)—, —C($R^6$)$_2$N($R^6$)SO$_2$N($R^6$)—, or —C($R^6$)$_2$N($R^6$)CON($R^6$)—;

$R^2$ and $R^{2'}$ are independently selected from —R, —T—W—$R^6$, or $R^2$ and $R^{2'}$ are taken together with their intervening atoms to form a fused, 5–8 membered, unsaturated or partially unsaturated, ring having 0–3 ring heteroatoms selected from nitrogen, oxygen, or sulfur, wherein each substitutable ring carbon of said fused ring formed by $R^2$ and $R^{2'}$ is independently substituted by halo, oxo, —CN, —NO$_2$, —$R^7$, or —V—$R^6$, and each substitutable ring nitrogen of said ring formed by $R^2$ and $R^{2'}$ is independently substituted by $R^4$;

$R^3$ is selected from —R, -halo, —OR, —C(=O)R, —CO$_2$R, —COCOR, —COCH$_2$COR, —NO$_2$, —CN, —S(O)R, —S(O)$_2$R, —SR, —N($R^4$)$_2$, —CON($R^7$)$_2$, —SO$_2$N($R^7$)$_2$, —OC(=)R, —N($R^7$)COR, —N($R^7$)CO$_2$($C_{1-6}$ aliphatic), —N($R^4$)N($R^4$)$_2$, —C=NN($R^4$)$_2$, —C=N—OR, —N($R^7$)CON($R^7$)$_2$, —N($R^7$)SO$_2$N($R^7$)$_2$, —N($R^4$)SO$_2$R, or —OC(=O)N($R^7$)$_2$;

each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;

each $R^4$ is independently selected from —$R^7$, —COR$^7$, —CO$_2$(optionally substituted $C_{1-6}$ aliphatic), —CON($R^7$)$_2$, or —SO$_2R^7$;

each $R^5$ is independently selected from —R, halo, —OR, —C(=O)R, —CO$_2$R, —COCOR, —NO$_2$, —CN, —S(O)R, —SO$_2$R, —SR, —N($R^4$)$_2$, —CON($R^4$)$_2$, —SO$_2$N($R^4$)$_2$, —OC(=O)R, —N($R^4$)COR, —N($R^4$) CO$_2$(optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)SO$_2$N($R^4$)$_2$, —N($R^4$)SO$_2$R, or —OC(=O)N($R^4$)$_2$;

V is —O—, —S—, —SO—, —SO$_2$—, —N($R^6$)SO$_2$—, —SO$_2$N($R^6$)—, —N($R^6$)—, —CO—, —CO$_2$—, —N($R^6$) CO—, —N($R^6$)C(O)O—, —N($R^6$)CON($R^6$)—, —N($R^6$) SO$_2$N($R^6$)—, —N($R^6$)N($R^6$)—, —C(O)N($R^6$)—, —OC (O)N($R^6$)—, —C($R^6$)$_2$O—, —C($R^6$)$_2$S—, —C($R^6$)$_2$ SO—, —C($R^6$)$_2$SO$_2$—, —C($R^6$)$_2$SO$_2$N($R^6$)—, —C($R^6$)$_2$ N($R^6$)—, —C($R^6$)$_2$N($R^6$)C(O)—, —C($R^6$)$_2$N($R^6$)C(O) O—, —C($R^6$)=NN($R^6$)—, —C($R^6$)=N—O—, —C($R^6$)$_2$ N($R^6$)N($R^6$)—, —C($R^6$)$_2$N($R^6$)SO$_2$N($R^6$)—, or —C($R^6$)$_2$N($R^6$)CON($R^6$)—;

W is —C($R_6$)$_2$O—, —C($R^6$)$_2$S—, —C($R^6$)$_2$SO—, —C($R^6$)$_2$ SO$_2$—, —C($R^6$)$_2$SO$_2$N($R^6$)—, —C($R^6$)$_2$N ($R^6$)—, —CO—, —CO$_2$—, —C($R^6$)OC(O)—, —C($R^6$) OC(O)N($R^6$)—, —C($R^6$)$_2$N($R^6$)CO—, —C($R^6$)$_2$N($R^6$)C (O)O—, —C($R^6$)=NN($R^6$)—, —C($R^6$)=N—O—,

—C(R⁶)₂N(R⁶)N(R⁶)—, —C(R⁶)₂N(R⁶)SO₂N(R⁶)—, —C(R⁶)₂N(R⁶)CON(R⁶)—, or —CON(R⁶)—;

each R⁶ is independently selected from hydrogen or an optionally substituted C₁₋₄ aliphatic group, or two R⁶ groups on the same nitrogen atom may be taken together with the nitrogen atom to form a 5–6 membered heterocyclyl or heteroaryl ring; and each R⁷ is independently selected from hydrogen or an optionally substituted C₁₋₆ aliphatic group, or two R⁷ on the same nitrogen are taken together with the nitrogen to form a 5–8 membered heterocyclyl or heteroaryl ring.

Preferred rings formed by R$^x$ and R$^y$ include a 5-, 6-, or 7-membered unsaturated or partially unsaturated ring having 0–2 heteroatoms, wherein said R$^x$/R$^y$ ring is optionally substituted. This provides a bicyclic ring system containing a pyrimidine ring. Examples of preferred pyrimidine ring systems of formula IIb are shown below.

IIb-A

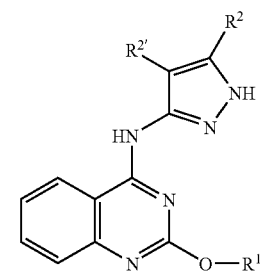

IIb-B

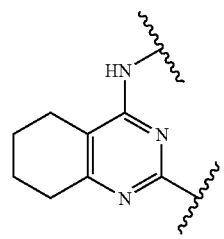

IIb-C

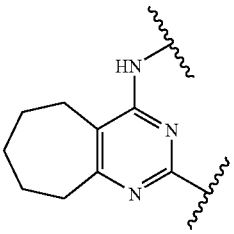

IIb-D

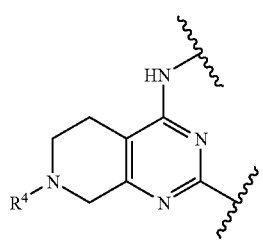

-continued

IIb-E

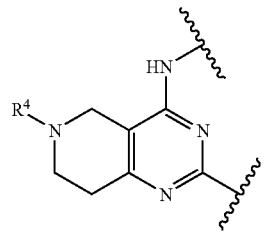

IIb-F

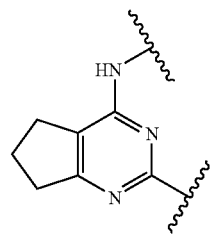

IIb-J

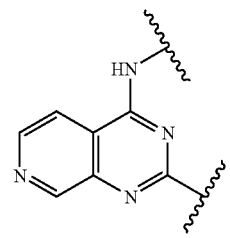

IIb-K

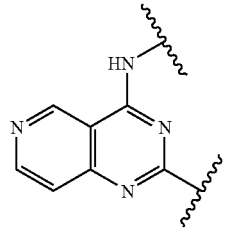

IIb-L

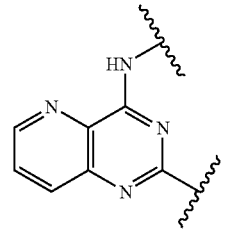

IIb-P

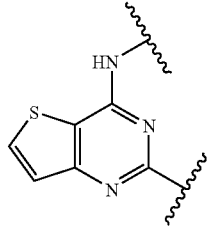

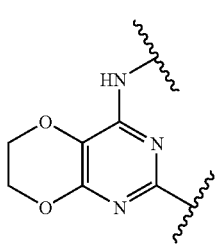
IIb-R

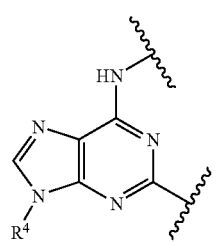
IIb-V

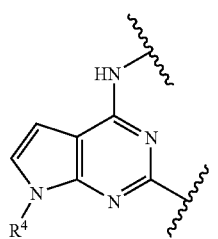
IIb-W

More preferred pyrimidine ring systems of formula IIb include IIb-A, IIb-B, IIb-D, IIb-E, IIb-J, IIb-P, and IIb-V, most preferably, IIb-A, IIb-B, IIb-D, IIb-E, and IIb-J.

The ring formed when $R^x$ and $R^y$ are taken together may be substituted or unsubstituted. Suitable substituents include —R, halo, —O(CH$_2$)$_{2-4}$—N(R$^4$)$_2$, —O(CH$_2$)$_{2-4}$—R, —OR, —N(R$^4$)—(CH$_2$)$_{2-4}$—N(R$^4$)$_2$, —N(R$^4$)—(CH$_2$)$_{2-4}$—R, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$(optionally substituted C$_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$, R and R$^4$ are as defined above. Preferred $R^x$/$R^y$ ring substituents include -halo, —R, —OR, —COR, —CO$_2$R, —CON(R$^4$)$_2$, —CN, —O(CH$_2$)$_{2-4}$—N(R$^6$)$_2$, —O(CH$_2$)$_{2-4}$—R, —NO$_2$ —N(R$^4$)$_2$, —NR$^4$COR, —NR$^4$SO$_2$R, —SO$_2$N(R$^4$)$_2$ wherein R is hydrogen or an optionally substituted C$_{1-6}$ aliphatic group.

$R^2$ and $R^{2'}$ groups of formula IIa may be taken together to form a fused ring, thus providing a bicyclic ring system containing a pyrazole ring. Preferred fused rings include benzo, pyrido, pyrimido, and a partially unsaturated 6-membered carbocyclo ring. These are exemplified in the following formula IIa compounds having a pyrazole-containing bicyclic ring system:

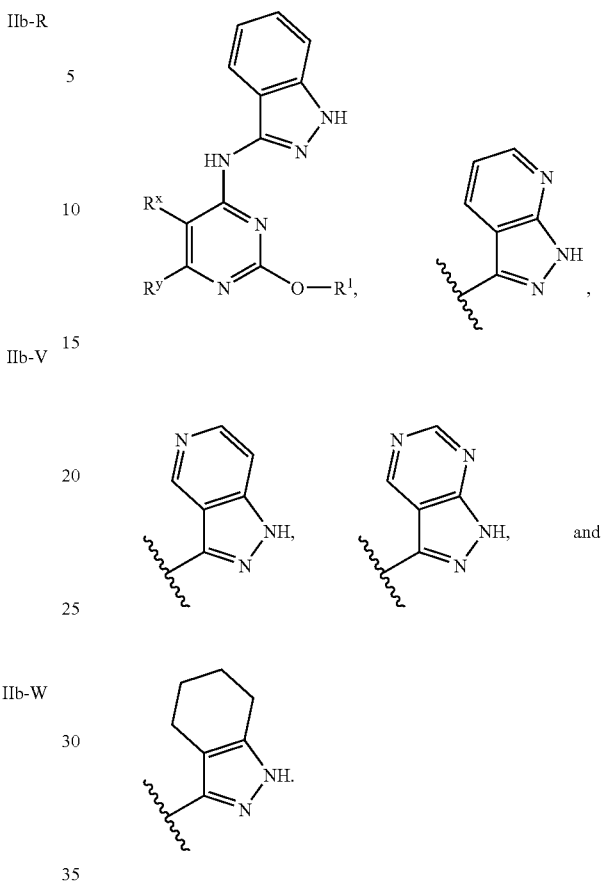

Preferred substituents on the $R^2$/$R^{2'}$ fused ring of formula IIb include one or more of the following: -halo, —N(R$^4$)$_2$, —C$_{1-4}$ alkyl, —C$_{1-4}$ haloalkyl, —NO$_2$, —O(C$_{1-4}$ alkyl), —CO$_2$(C$_{1-4}$ alkyl), —CN, SO$_2$(C$_{1-4}$ alkyl), —SO$_2$NH$_2$, —OC(O)NH$_2$, —NH$_2$SO$_2$(C$_{1-4}$ alkyl), —NHC(O)(C$_{1-4}$ alkyl), —C(O)NH$_2$, and —CO(C$_{1-4}$ alkyl), wherein the (C$_{1-4}$ alkyl) is a straight, branched, or cyclic alkyl group. Preferably, the (C$_{1-4}$ alkyl) group is methyl or ethyl.

When the pyrazole ring system of formula IIb is monocyclic, preferred $R^2$ groups include hydrogen or a substituted or unsubstituted group selected from aryl, heteroaryl, or a C$_{1-6}$ aliphatic group. Examples of such preferred $R^2$ groups include H, methyl, ethyl, propyl, cyclopropyl, i-propyl, cyclopentyl, hydroxypropyl, methoxypropyl, and benzyloxypropyl. A preferred $R^{2'}$ group is hydrogen.

When Ring D of formula IIb is monocyclic, preferred Ring D groups include phenyl, pyridyl, pyridazinyl, pyrimidinyl, and pyrazinyl.

When Ring D of formula IIb is bicyclic, preferred bicyclic Ring D groups include naphthyl, tetrahydronaphthyl, indanyl, benzimidazolyl, quinolinyl, indolyl, isoindolyl, indolinyl, benzo[b]furyl, benzo[b]thiophenyl, indazolyl, benzothiazolyl, cinnolinyl, phthalazinyl, quinazolinyl, quinoxazolinyl, 1,8-naphthyridinyl and isoquinolinyl.

On Ring D of formula IIb, preferred T—R$^5$ or V—Z—R$^5$ substituents include -halo, —CN, —NO$_2$; —N(R$^4$)$_2$, optionally substituted C$_{1-6}$ aliphatic group, —OR, —C(O)R, —CO$_2$R, —CONH(R$^4$), —N(R$^4$)COR, —N(R$^4$)CO$_2$R, —SO$_2$N(R$^4$)$_2$, —N(R$^4$)SO$_2$R, —N(R$^6$)COCH$_2$N(R$^4$)$_2$, —N(R$^6$)COCH$_2$CH$_2$N(R$^4$)$_2$, and —N(R$^6$)

COCH₂CH₂CH₂N(R⁴)₂, wherein R is selected from hydrogen, C₁₋₆ aliphatic, phenyl, a 5–6 membered heteroaryl ring, or a 5–6 membered heterocyclic ring. More preferred R⁵ substituents include —Cl, —Br, —F, —CN, —CF₃, —COOH, —CONHMe, —CONHEt, —NH₂, —NHAc, —NHSO₂Me, —NHSO₂Et, —NHSO₂(n-propyl), —NHSO₂(isopropyl), —NHCOEt, —NHCOCH₂NHCH₃, —NHCOCH₂N(CO₂t-Bu)CH₃, —NHCOCH₂N(CH₃)₂, —NHCOCH₂CH₂N(CH₃)₂, —NHCOCH₂CH₂CH₂N(CH₃)₂, —NHCO(cyclopropyl), —NHCO(isobutyl), —NHCOCH₂(morpholin-4-yl), —NHCOCH₂CH₂(morpholin-4-yl), —NHCOCH₂CH₂CH₂(morpholin-4-yl), —NHCO₂(t-butyl), —NH(C₁₋₄ aliphatic) such as —NHMe, —N(C₁₋₄ aliphatic)₂ such as —NMe₂, OH, —O(C₁₋₄ aliphatic) such as —OMe, C₁₋₄ aliphatic such as methyl, ethyl, cyclopropyl, isopropyl, or t-butyl, and —CO₂(C₁₋₄ aliphatic).

Preferred formula IIb compounds have one or more, and more preferably all, of the features selected from the group consisting of:

(a) R$^x$ and R$^y$ are taken together with their intervening atoms to form a fused, unsaturated or partially unsaturated, 5–6 membered ring having 0–2 heteroatoms selected from oxygen, sulfur, or nitrogen, wherein each substitutable ring carbon of said fused ring formed by R$^x$ and R$^y$ is independently substituted by oxo, T—R³, or L—Z—R³, and each substitutable ring nitrogen of said ring formed by R$^x$ and R$^y$ is independently substituted by R⁴;

(b) R¹ is T-(Ring D), wherein T is a valence bond or a methylene unit;

(c) Ring D is a 5–7 membered monocyclic ring or an 8–10 membered bicyclic ring selected from an aryl or heteroaryl ring;

(d) R² is —R or —T—W—R⁶ and R²' is hydrogen; or R² and R²' are taken together to form an optionally substituted benzo ring; and (e) R³ is selected from —R, -halo, —OR, or —N(R⁴)₂.

More preferred compounds of formula IIb have one or more, and more preferably all, of the features selected from the group consisting of:

(a) R$^x$ and R$^y$ are taken together to form a benzo, pyrido, cyclopento, cyclohexo, cyclohepto, thieno, piperidino, or imidazo ring;

(b) R¹ is T-(Ring D), wherein T is a valence bond and Ring D is a 5–6 membered monocyclic ring or an 8–10 membered bicyclic ring selected from an aryl or heteroaryl ring;

(c) R² is —R and R²' is hydrogen, wherein R is selected from hydrogen, C₁₋₆ aliphatic, phenyl, a 5–6 membered heteroaryl ring, or a 5–6 membered heterocyclic ring; and (d) R³ is selected from —R, -halo, —OR, or —N(R⁴)₂, wherein R is selected from hydrogen, C₁₋₆ aliphatic, or 5–6 membered heterocyclyl, phenyl, or 5–6 membered heteroaryl, and L is —O—, —S—, or —N(R⁴)—.

Even more preferred compounds of formula IIb have one or more, and more preferably all, of the features selected from the group consisting of:

(a) R$^x$ and R$^y$ are taken together to form a benzo, pyrido, piperidino, or cyclohexo ring;

(b) R¹ is T-Ring D, wherein T is a valence bond and Ring D is a 5–6 membered aryl or heteroaryl ring;

(c) R² is hydrogen or C₁₋₄ aliphatic and R²' is hydrogen;

(d) R³ is selected from —R, —OR, or —N(R⁴)₂, wherein R is selected from hydrogen, C₁₋₆ aliphatic, 5–6 membered heterocyclyl, phenyl, or 5–6 membered heteroaryl, and L is —O—, —S—, or —NH—; and (e) Ring D is substituted by up to three substituents selected from -halo, —CN, —NO₂, —N(R⁴)₂, optionally substituted C₁₋₆ aliphatic group, —OR, —C(O)R, —CO₂R, —CONH(R⁴), —N(R⁴)COR, —N(R⁴)CO₂R, —SO₂N(R⁴)₂, —N(R⁴)SO₂R, —N(R⁶)COCH₂N(R⁴)₂, —N(R⁶)COCH₂CH₂N(R⁴)₂, or —N(R⁶)COCH₂CH₂CH₂N(R⁴)₂, wherein R is selected from hydrogen, C₁₋₆ aliphatic, phenyl, a 5–6 membered heteroaryl ring, or a 5–6 membered heterocyclic ring.

Representative compounds of formula IIb are shown below in Table 2.

TABLE 2

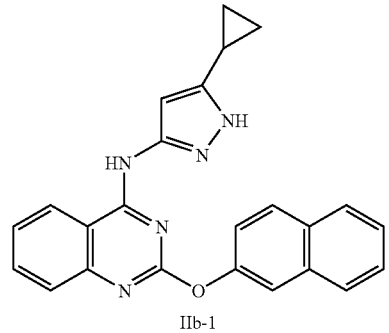

IIb-1

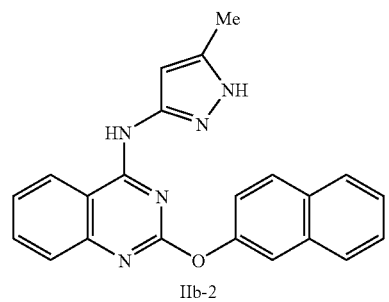

IIb-2

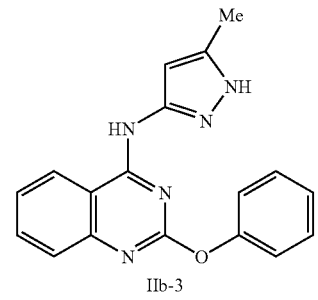

IIb-3

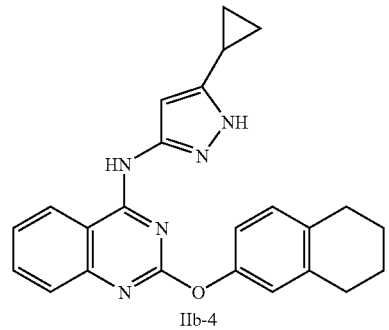

IIb-4

TABLE 2-continued

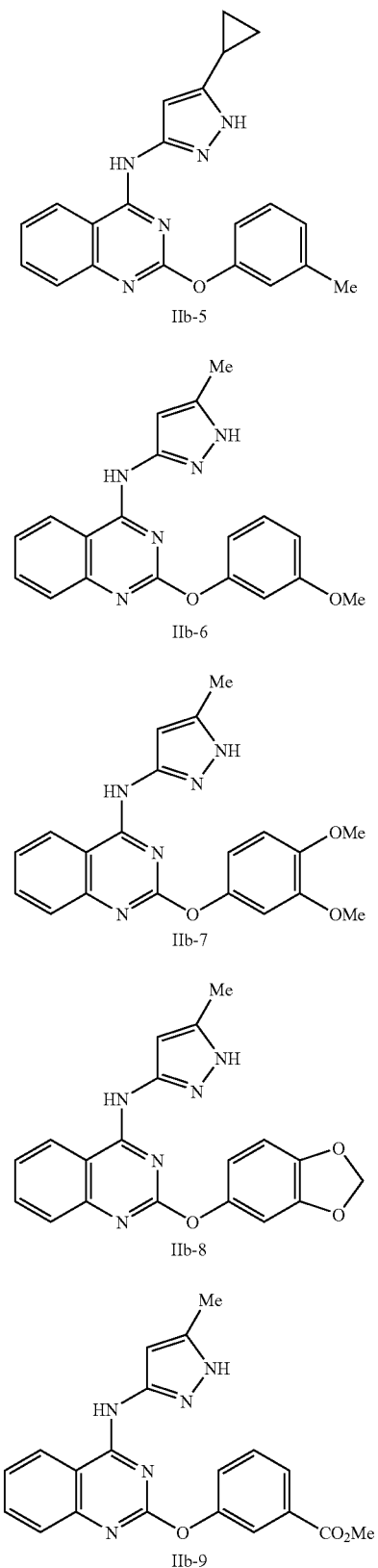

In another embodiment, this invention provides a composition comprising a compound of formula IIb and a pharmaceutically acceptable carrier.

Another aspect of this invention relates to a method of treating or preventing an Aurora-2-mediated disease with an Aurora-2 inhibitor, which method comprises administering to a patient in need of such a treatment a therapeutically effective amount of a compound of formula IIb or a pharmaceutical composition thereof.

Another aspect of this invention relates to a method of inhibiting Aurora-2 activity in a patient, which method comprises administering to the patient a compound of formula IIb or a composition comprising said compound.

Another aspect of this invention relates to a method of treating or preventing a GSK-3-mediated disease with a GSK-3 inhibitor, which method comprises administering to a patient in need of such a treatment a therapeutically effective amount of a compound of formula IIb or a pharmaceutical composition thereof.

One aspect of this invention relates to a method of enhancing glycogen synthesis and/or lowering blood levels of glucose in a patient in need thereof, which method comprises administering to the patient a therapeutically effective amount of a compound of formula IIb or a pharmaceutical composition thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of β-catenin, which is useful for treating schizophrenia.

Another aspect of this invention relates to a method of inhibiting GSK-3 activity in a patient, which method comprises administering to the patient a compound of formula IIb or a composition comprising said compound.

Another method relates to inhibiting Aurora-2 or GSK-3 activity in a biological sample, which method comprises contacting the biological sample with the Aurora-2 or GSK-3 inhibitor of formula IIb, or a pharmaceutical composition thereof, in an amount effective to inhibit Aurora-2 or GSK-3.

Each of the aforementioned methods directed to the inhibition of Aurora-2 or GSK-3, or the treatment of a disease alleviated thereby, is preferably carried out with a preferred compound of formula IIb, as described above.

Another embodiment of this invention relates to compounds of formula IIc:

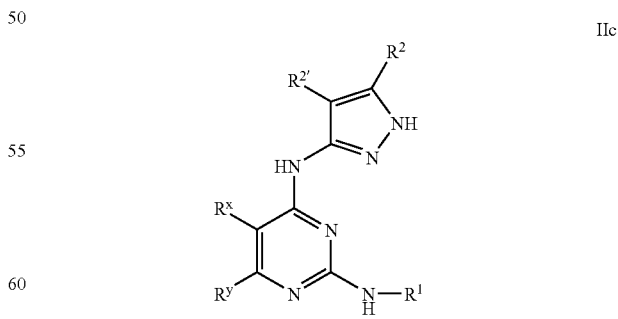

IIc or a pharmaceutically acceptable derivative or prodrug thereof, wherein;

$R^x$ and $R^y$ are taken together with their intervening atoms to form a fused, unsaturated or partially unsaturated, 5–7 membered ring having 0–3 ring heteroatoms selected from oxygen, sulfur, or nitrogen, wherein each substitutable ring carbon of said fused ring formed by $R^x$ and $R^y$ is independently substituted by oxo, T—$R^3$, or L—Z—$R^3$, and each substitutable ring nitrogen of said ring formed by $R^x$ and $R^y$ is independently substituted by $R^4$;

$R^1$ is T-(Ring D);

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein each substitutable ring carbon of Ring D is independently substituted by oxo, T—$R^5$, or V—Z—$R^5$, and each substitutable ring nitrogen of Ring D is independently substituted by —$R^4$;

T is a valence bond or a $C_{1-4}$ alkylidene chain;

Z is a $C_{1-4}$ alkylidene chain;

L is —O—, —S—, —SO—, —SO$_2$—, —N($R^6$)SO$_2$—, —SO$_2$N($R^6$)—, —N($R^6$)—, —CO—, —CO$_2$—, —N($R^6$)CO—, —N($R^6$)C(O)O—, —N($R^6$)CON($R^6$)—, —N($R^6$)SO$_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)SO$_2$N($R^6$)—, or —C($R^6$)$_2$N($R^6$)CON($R^6$)—;

$R^2$ and $R^{2'}$ are independently selected from —R, —T—W—$R^6$, or $R^2$ and $R^{2'}$ are taken together with their intervening atoms to form a fused, 5–8 membered, unsaturated or partially unsaturated, ring having 0–3 ring heteroatoms selected from nitrogen, oxygen, or sulfur, wherein each substitutable ring carbon of said fused ring formed by $R^2$ and $R^{2'}$ is independently substituted by halo, oxo, —CN, —NO$_2$, —$R^7$, or —V—$R^6$, and each substitutable ring nitrogen of said ring formed by $R^2$ and $R^{2'}$ is independently substituted by $R^4$;

$R^3$ is selected from —R, -halo, —OR, —C(=O)R, —CO$_2$R, —COCOR, —COCH$_2$COR, —NO$_2$, —CN, —S(O)R, —S(O)$_2$R, —SR, —N($R^4$)$_2$, —CON($R^7$)$_2$, —SO$_2$N($R^7$)$_2$, —OC(=O)R, —N($R^7$)COR, —N($R^7$)CO$_2$($C_{1-6}$ aliphatic), —N($R^4$)N($R^4$)$_2$, —C=NN($R^4$)$_2$, —C=N—OR, —N($R^7$)CON($R^7$)$_2$, —N($R^7$)SO$_2$N($R^7$)$_2$, —N($R^4$)SO$_2$R, or —OC(=O)N($R^7$)$_2$;

each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;

each $R^4$ is independently selected from —$R^7$, —COR$^7$, —CO$_2$(optionally substituted $C_{1-6}$ aliphatic), —CON($R^7$)$_2$, or —SO$_2R^7$;

each $R^5$ is independently selected from —R, halo, —OR, —C(=O)R, —CO$_2$R, —COCOR, —NO$_2$, —CN, —S(O)R, —SO$_2$R, —SR, —N($R^4$)$_2$, —CON($R^4$)$_2$, —SO$_2$N($R^4$)$_2$, —OC(=O)R, —N($R^4$)COR, —N($R^4$)CO$_2$(optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)SO$_2$N($R^4$)$_2$, —N($R^4$)SO$_2$R, or —OC(=O)N($R^4$)$_2$;

V is —O—, —S—, —SO—, —SO$_2$—, —N($R^6$)SO$_2$—, —SO$_2$N($R^6$)—, —N($R^6$)—, —CO—, —CO$_2$—, —N($R^6$)CO—, —N($R^6$)C(O)O—, —N($R^6$)CON($R^6$)—, —N($R^6$) SO$_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)SO$_2$N($R^6$)—, or —C($R^6$)$_2$N($R^6$)CON($R^6$)—;

W is —C(R$_6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N($R^6$)—, —CO—, —CO$_2$—, —C($R^6$)OC(O)—, —C($R^6$)OC(O)N($R^6$)—, —C($R^6$)$_2$N($R^6$)CO—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)SO$_2$N($R^6$)—, —C($R^6$)$_2$N($R^6$)CON($R^6$)—, or —CON($R^6$)—;

each $R^6$ is independently selected from hydrogen or an optionally substituted $C_{1-4}$ aliphatic group, or two $R^6$ groups on the same nitrogen atom may be taken together with the nitrogen atom to form a 5–6 membered heterocyclyl or heteroaryl ring; and each $R^7$ is independently selected from hydrogen or an optionally substituted $C_{1-6}$ aliphatic group, or two $R^7$ on the same nitrogen are taken together with the nitrogen to form a 5–8 membered heterocyclyl or heteroaryl ring.

Preferred rings formed by $R^x$ and $R^y$ include a 5-, 6-, or 7-membered unsaturated or partially unsaturated ring having 0–2 heteroatoms, wherein said $R^x/R^y$ ring is optionally substituted. This provides a bicyclic ring system containing a pyrimidine ring. Examples of preferred pyrimidine ring systems of formula IIc are shown below.

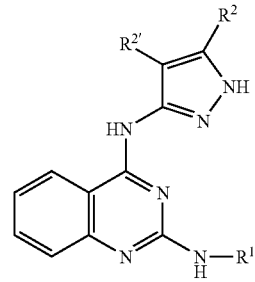

IIc-A

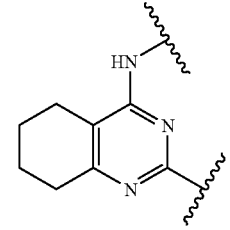

IIc-B

IIc-C 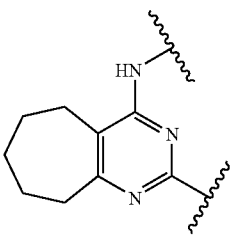

IIc-D 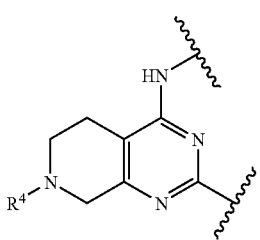

IIc-E 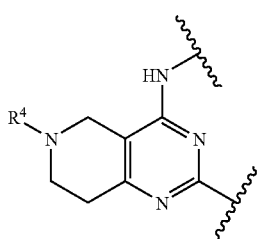

IIc-F 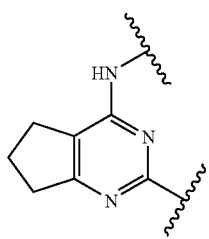

IIc-J 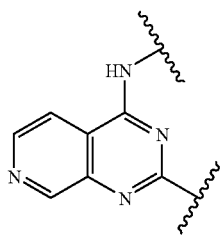

IIc-K 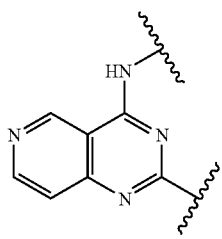

IIc-L 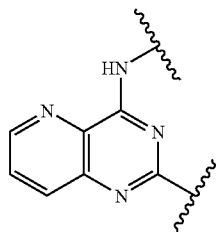

IIc-P 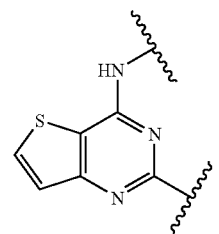

IIc-R 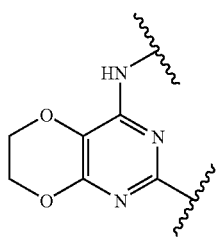

IIc-V 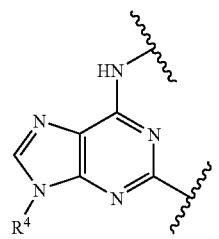

IIc-W 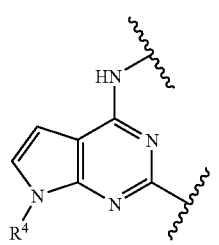

More preferred pyrimidine ring systems of formula IIc include IIc-A, IIc-B, IIc-D, IIc-E, IIc-J, IIc-P, and IIc-V, most preferably IIc-A, IIc-B, IIc-D, IIc-E, and IIc-J.

The ring formed when $R^x$ and $R^y$ of formula IIc are taken together may be substituted or unsubstituted. Suitable substituents include —R, halo, —O(CH$_2$)$_{2-4}$—N(R$^4$)$_2$, —O(CH$_2$)$_{2-4}$—R, —OR, —N(R$^4$)—(CH$_2$)$_{2-4}$—N(R$^4$)$_2$, —N(R$^4$)—(CH$_2$)$_{2-4}$—R, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$(optionally substituted C$_{1-6}$ aliphatic), —N(R$^4$)

N(R⁴)₂, —C=NN(R⁴)₂, —C=N—OR, —N(R⁴)CON(R⁴)₂, —N(R⁴)SO₂N(R⁴)₂, —N(R⁴)SO₂R, or —OC(=O)N(R⁴)₂, R and R⁴ are as defined above. Preferred R$^x$/R$^y$ ring substituents include -halo, —R, —OR, —COR, —CO₂R, —CON(R⁴)₂, —CN, —O(CH₂)₂₋₄—N(R⁴)₂, —O(CH₂)₂₋₄—R, —NO₂, —N(R⁴)₂, —NR⁴COR, —NR⁴SO₂R, —SO₂N(R⁴)₂ wherein R is hydrogen or an optionally substituted C₁₋₆ aliphatic group.

R² and R²' groups of formula IIa may be taken together to form a fused ring, thus providing a bicyclic ring system containing a pyrazole ring. Preferred fused rings include benzo, pyrido, pyrimido, and a partially unsaturated 6-membered carbocyclo ring. These are exemplified in the following formula IIa compounds having a pyrazole-containing bicyclic ring system:

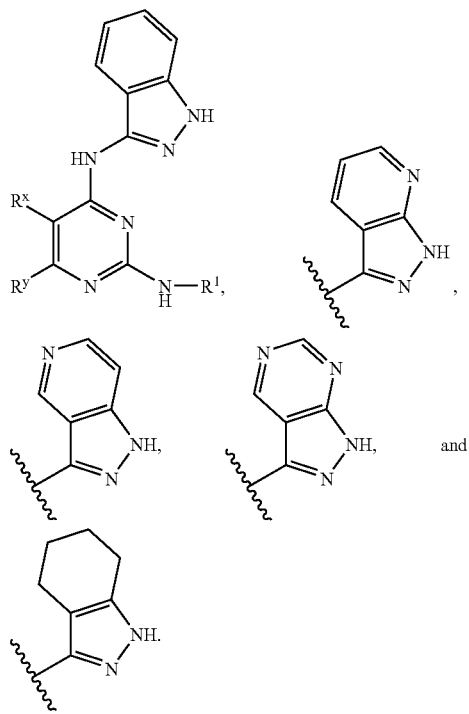

Preferred substituents on the R²/R²' fused ring of formula IIc include one or more of the following: -halo, —N(R⁴)₂, —C₁₋₄ alkyl, —C₁₋₄ haloalkyl, —NO₂, —O(C₁₋₄ alkyl), —CO₂(C₁₋₄ alkyl), —CN, —SO₂(C₁₋₄ alkyl), —SO₂NH₂, —OC(O)NH₂, —NH₂SO₂(C₁₋₄ alkyl), —NHC(O)(C₁₋₄ alkyl), —C(O)NH₂, and —CO(C₁₋₄ alkyl), wherein the (C₁₋₄ alkyl) is a straight, branched, or cyclic alkyl group. Preferably, the (C₁₋₄ alkyl) group is methyl.

When the pyrazole ring system of formula IIc is monocyclic, preferred R² groups include hydrogen or a substituted or unsubstituted group selected from aryl, heteroaryl, or a C₁₋₆ aliphatic group. Examples of such preferred R² groups include H, methyl, ethyl, propyl, cyclopropyl, i-propyl, cyclopentyl, hydroxypropyl, methoxypropyl, and benzyloxypropyl. A preferred R²' group is hydrogen.

When Ring D of formula IIc is monocyclic, preferred Ring D groups include phenyl, pyridyl, pyridazinyl, pyrimidinyl, and pyrazinyl.

When Ring D of formula IIc is bicyclic, preferred bicyclic Ring D groups include naphthyl, tetrahydronaphthyl, indanyl, benzimidazolyl, quinolinyl, indolyl, isoindolyl, indolinyl, benzo[b]furyl, benzo[b]thiophenyl, indazolyl, benzothiazolyl, cinnolinyl, phthalazinyl, quinazolinyl, quinoxazolinyl, 1,8-naphthyridinyl and isoquinolinyl.

On Ring D of formula IIc, preferred T—R⁵ or V—Z—R⁵ substituents include -halo, —CN, —NO₂, —N(R⁴)₂, optionally substituted C₁₋₆ aliphatic group, —OR, —C(O)R, —CO₂R, —CONH(R⁴), —N(R⁴)COR, —N(R⁴)CO₂R, —SO₂N(R⁴)₂, —N(R⁴)SO₂R, —N(R⁶)COCH₂N(R⁴)₂, —N(R⁶)COCH₂CH₂N(R⁴)₂, and —N(R⁶)COCH₂CH₂CH₂N(R⁴)₂, wherein R is selected from hydrogen, C₁₋₆ aliphatic, phenyl, a 5–6 membered heteroaryl ring, or a 5–6 membered heterocyclic ring. More preferred R⁵ substituents include —Cl, —Br, —F, —CN, —CF₃, —COOH, —CONHMe, —CONHEt, —NH₂, —NHAc, —NHSO₂Me, —NHSO₂Et, —NHSO₂(n-propyl), —NHSO₂(isopropyl), —NHCOEt, —NHCOCH₂NHCH₃, —NHCOCH₂N(CO₂t-Bu)CH₃, —NHCOCH₂N(CH₃)₂, —NHCOCH₂CH₂N(CH₃)₂, —NHCOCH₂CH₂CH₂N(CH₃)₂, —NHCO(cyclopropyl), —NHCO(isobutyl), —NHCOCH₂(morpholin-4-yl), —NHCOCH₂CH₂(morpholin-4-yl), —NHCOCH₂CH₂CH₂(morpholin-4-yl), —NHCO₂(t-butyl), —NH(C₁₋₄ aliphatic) such as —NHMe, —N(C₁₋₄ aliphatic)₂ such as —NMe₂, OH, —O(C₁₋₄-aliphatic) such as —OMe, C₁₋₄ aliphatic such as methyl, ethyl, cyclopropyl, isopropyl, or t-butyl, and —CO₂(C₁₋₄. aliphatic).

Preferred formula IIc compounds have one or more, and more preferably all, of the features selected from the group consisting of:

(a) R$^x$ and R$^y$ are taken together with their intervening atoms to form a fused, unsaturated or partially unsaturated, 5–6 membered ring having 0–2 heteroatoms selected from oxygen, sulfur, or nitrogen, wherein each substitutable ring carbon of said fused ring formed by R$^x$ and R$^y$ is independently substituted by oxo, T—R³, or L—Z—R³, and each substitutable ring nitrogen of said ring formed by R$^x$ and R$^y$ is independently substituted by R⁴;

(b) R¹ is T-(Ring D), wherein T is a valence bond or a methylene unit;

(c) Ring D is a 5–7 membered monocyclic ring or an 8–10 membered bicyclic ring selected from an aryl or heteroaryl ring;

(d) R² is —R or —T—W—R⁶ and R²' is hydrogen; or R² and R²' are taken together to form an optionally substituted benzo ring; and (e) R³ is selected from —R, -halo, —OR, or —N(R⁴)₂.

More preferred compounds of formula IIc have one or more, and more preferably all, of the features selected from the group consisting of:

(a) R$^x$ and R$^y$ are taken together to form a benzo, pyrido, cyclopento, cyclohexo, cyclohepto, thieno, piperidino, or imidazo ring;

(b) R¹ is T-(Ring D), wherein T is a valence bond and Ring D is a 5–6 membered monocyclic ring or an 8–10 membered bicyclic ring selected from an aryl or heteroaryl ring;

(c) R² is —R and R²' is hydrogen, wherein R is selected from hydrogen, C₁₋₆ aliphatic, phenyl, a 5–6 membered heteroaryl ring, or a 5–6 membered heterocyclic ring; and (d) R³ is selected from —R, -halo, —OR, or —N(R⁴)₂, wherein R is selected from hydrogen, C₁₋₆ aliphatic, or 5–6 membered heterocyclyl, phenyl, or 5–6 membered heteroaryl, and L is —O—, —S—, or —N(R⁴)—.

Even more preferred compounds of formula IIc have one or more, and more preferably all, of the features selected from the group consisting of:
(a) $R^x$ and $R^y$ are taken together to form a benzo, pyrido, piperidino, or cyclohexo ring;
(b) $R^1$ is T-Ring D, wherein T is a valence bond and Ring D is a 5–6 membered aryl or heteroaryl ring;
(c) $R^2$ is hydrogen or $C_{1-4}$ aliphatic and $R^{2'}$ is hydrogen;
(d) $R^3$ is selected from —R, —OR, or —N(R$^4$)$_2$, wherein R is selected from hydrogen, $C_{1-6}$ aliphatic, 5–6 membered heterocyclyl, phenyl, or 5–6 membered heteroaryl, and L is —O—, —S—, or —NH—; and
(e) Ring D is substituted by up to three substituents selected from -halo, —CN, —NO$_2$, —N(R$^4$)$_2$, optionally substituted $C_{1-6}$ aliphatic group, —OR, —C(O)R, —CO$_2$R, —CONH(R$^4$), —N(R$^4$)COR, —N(R$^4$)CO$_2$R, —SO$_2$N(R$^4$)$_2$, —N(R$^4$)SO$_2$R, —N(R$^6$)COCH$_2$N(R$^4$)$_2$, —N(R$^6$)COCH$_2$CH$_2$N(R$_4$)$_2$, or —N(R$^6$)COCH$_2$CH$_2$CH$_2$N(R$^4$)$_2$, wherein R is selected from hydrogen, $C_{1-6}$ aliphatic, phenyl, a 5–6 membered heteroaryl ring, or a 5–6 membered heterocyclic ring.

Preferred compounds of formula IIc include compounds of formula IIc':

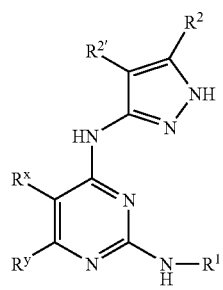

IIc' or a pharmaceutically acceptable derivative or prodrug thereof, wherein;
$R^x$ and $R^y$ are taken together with their intervening atoms to form a fused benzo ring, wherein each substitutable ring carbon of said fused ring formed by $R^x$ and $R^y$ is independently substituted by T—R$^3$, or L—Z—R$^3$;
$R^1$ is T-(Ring D);
Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein each substitutable ring carbon of Ring D is independently substituted by oxo, T—R$^5$, or V—Z—R$^5$, and each substitutable ring nitrogen of Ring D is independently substituted by —R$^4$;
T is a valence bond or a $C_{1-4}$ alkylidene chain;
Z is a $C_{1-4}$ alkylidene chain;
L is —O—, —S—, —SO—, —SO$_2$—, —N(R$^6$)SO$_2$—, —SO$_2$N(R$^6$)—, —N(R$^6$)—,—CO—, —CO$_2$—, —N(R$^6$) CO—, —N(R$^6$)C(O)O—, —N(R$^6$)CON(R$^6$)—, —N(R$^6$) SO$_2$N(R$^6$)—, —N(R$^6$)N(R$^6$)—, —C(O)N(R$^6$)—, —OC (O)N(R$^6$)—, —C(R$^6$)$_2$O—, —C(R$^6$)$_2$S—, —C(R$^6$)$_2$ SO—, —C(R$^6$)$_2$SO$_2$—, —C(R$^6$)$_2$SO$_2$N(R$^6$)—, —C(R$^6$)$_2$ N(R$^6$)—, —C(R$^6$)$_2$N(R$^6$)C(O)—, —C(R$^6$)$_2$N(R$^6$)C(O) O—, —C(R$^6$)=NN(R$^6$)—, —C(R$^6$)=N—O—, —C(R$^6$)$_2$ N(R$^6$)N(R$^6$)—, —C(R$^6$)$_2$N(R$^6$)SO$_2$N(R$^6$)—, or —C(R$^6$)$_2$N(R$^6$)CON(R$^6$)—;

$R^2$ and $R^{2'}$ are independently selected from —R, —T—W—R$^6$, or $R^2$ and $R^{2'}$ are taken together with their intervening atoms to form a fused, 5–8 membered, unsaturated or partially unsaturated, ring having 0–3 ring heteroatoms selected from nitrogen, oxygen, or sulfur, wherein each substitutable ring carbon of said fused ring formed by $R^2$ and $R^{2'}$ is independently substituted by halo, oxo, —CN, —NO$_2$, —R$^7$, or —V—R$^6$, and each substitutable ring nitrogen of said ring formed by $R^2$ and $R^{2'}$ is independently substituted by $R^4$;
$R^3$ is selected from —R, -halo, —OR, —C(=O)R, —CO$_2$R, —COCOR, —COCH$_2$COR, —NO$_2$, —CN, —S(O)R, —S(O)$_2$R, —SR, —N(R$^4$)$_2$, —CON(R$^7$)$_2$, —SO$_2$N(R$^7$)$_2$, —OC(=)R, —N(R$^7$) COR, —N(R$^7$) CO$_2$(C$_{1-6}$ aliphatic), —N(R$^4$)N(R$^4$)$_2$, —C=NN(R$^4$)$_2$, —C=N—OR, —N(R$^7$)CON(R$^7$)$_2$, —N(R$^7$)SO$_2$N(R$^7$)$_2$, —N(R$^4$)SO$_2$R, or —OC(=O)N (R$^7$)$_2$;
each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;
each $R^4$ is independently selected from —R$^7$, —COR$^7$, —CO$_2$(optionally substituted $C_{1-6}$ aliphatic), —CON(R$^7$)$_2$, or —SO$_2$R$^7$;
each $R^5$ is independently selected from —R, halo, —OR, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$) CO$_2$(optionally substituted $C_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$;
V is —O—, —S—, —SO—, —SO$_2$—, —N(R$^6$)SO$_2$—, —SO$_2$N(R$^6$)—, —N(R$^6$)—, —CO—, —CO$_2$—, —N(R$^6$) CO—, —N(R$^6$)C(O)O—, —N(R$^6$)CON(R$^6$)—, —N(R$^6$) SO$_2$N(R$^6$)—, —N(R$^6$)N(R$^6$)—, —C(O)N(R$^6$)—, —OC (O)N(R$^6$)—, —C(R$^6$)$_2$O—, —C(R$^6$)$_2$S—, —C(R$^6$)$_2$ SO—, —C(R$^6$)$_2$SO$_2$—, —C(R$^6$)$_2$SO$_2$N(R$^6$)—, —C(R$^6$)$_2$ N(R$^6$)—, —C(R$^6$)$_2$N(R$^6$)C(O)—, —C(R$^6$)$_2$N(R$^6$)C(O) O—, —C(R$^6$)=NN(R$^6$)—, —C(R$^6$)=N—O—, —C(R$^6$)$_2$ N(R$^6$)N(R$^6$)—, —C(R$^6$)$_2$N(R$^6$)SO$_2$N(R$^6$)—, or —C(R$^6$)$_2$N(R$^6$)CON(R$^6$)—;
W is —C(R$_6$)$_2$O—, —C(R$^6$)$_2$S—, —C(R$^6$)$_2$SO—, —C(R$^6$)$_2$ SO$_2$—, —C(R$^6$)$_2$SO$_2$N(R$^6$)—, —C(R$^6$)$_2$N (R$^6$)—, —CO—, —CO$_2$—, —C(R$^6$)OC(O)—, —C(R$^6$) OC(O)N(R$^6$)—, —C(R$^6$)$_2$N(R$^6$)CO—, —C(R$^6$)$_2$N(R$^6$)C (O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, —C(R$^6$)$_2$N(R$^6$)CON(R$^6$)—, or —CON(R$^6$)—;
each $R^6$ is independently selected from hydrogen or an optionally substituted $C_{1-4}$ aliphatic group, or two $R^6$ groups on the same nitrogen atom may be taken together with the nitrogen atom to form a 5–6 membered heterocyclyl or heteroaryl ring; and
each $R^7$ is independently selected from hydrogen or an optionally substituted $C_{1-6}$ aliphatic group, or two $R^7$ on the same nitrogen are taken together with the nitrogen to form a 5–8 membered heterocyclyl or heteroaryl ring.

The ring formed when $R^x$ and $R^y$ of formula IIc' are taken together may be substituted or unsubstituted. Suitable substituents include —R, halo, —O(CH$_2$)$_{2-4}$—N(R$^4$)$_2$, —O(CH$_2$)$_{2-4}$—R, —OR, —N(R$^4$)—(CH$_2$)$_{2-4}$—N(R$^4$)$_2$, —N(R$^4$)—(CH$_2$)$_{2-4}$—R, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$(optionally substituted $C_{1-6}$ aliphatic), —N(R$^4$)

$N(R^4)_2$, $-C=NN(R^4)_2$, $-C=N-OR$, $-N(R^4)CON(R^4)_2$, $-N(R^4)SO_2N(R^4)_2$, $-N(R^4)SO_2R$, or $-OC(=O)N(R^4)_2$, wherein R and $R^4$ are as defined above. Preferred $R^x/R^y$ ring substituents include -halo, $-R$, $-OR$, $-COR$, $-CO_2R$, $-CON(R^4)_2$, $-CN$, $-O(CH_2)_{2-4}-N(R^6)_2$, $-O(CH_2)_{2-4}-R$, $-NO_2$, $-N(R^4)_2$, $-NR^4COR$, $-NR^4SO_2R$, $-SO_2N(R^4)_2$, wherein R is hydrogen or an optionally substituted $C_{1-6}$ aliphatic group.

$R^2$ and $R^{2'}$ groups of formula IIc' may be taken together to form a fused ring, thus providing a bicyclic ring system containing a pyrazole ring. Preferred fused rings include benzo, pyrido, pyrimido, and a partially unsaturated 6-membered carbocyclo ring. These are exemplified in the following formula IIc' compounds having a pyrazole-containing bicyclic ring system:

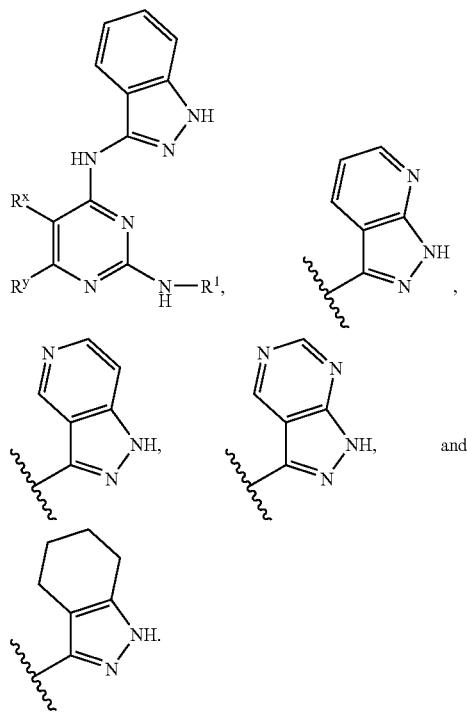

Preferred substituents on the $R^2/R^{2'}$ fused ring of formula IIc' include one or more of the following: -halo, $-N(R^4)_2$, $-C_{1-4}$ alkyl, $-C_{1-4}$ haloalkyl, $-NO_2$, $-O(C_{1-4}$ alkyl), $-CO_2(C_{1-4}$ alkyl), $-CN$, $-SO_2(C_{1-4}$ alkyl), $-SO_2NH_2$, $-OC(O)NH_2$, $-NH_2SO_2(C_{1-4}$ alkyl), $-NHC(O)(C_{1-4}$ alkyl), $-C(O)NH_2$, and $-CO(C_{1-4}$ alkyl), wherein the $(C_{1-4}$ alkyl) is a straight, branched, or cyclic alkyl group. Preferably, the $(C_{1-4}$ alkyl) group is methyl.

When the pyrazole ring system of formula IIc' is monocyclic, preferred $R^2$ groups include hydrogen or a substituted or unsubstituted group selected from aryl, heteroaryl, or a $C_{1-6}$ aliphatic group. Examples of such preferred $R^2$ groups include H, methyl, ethyl, propyl, cyclopropyl, i-propyl, cyclopentyl, hydroxypropyl, methoxypropyl, and benzyloxypropyl. A preferred $R^{2'}$ group is hydrogen.

When Ring D of formula IIc' is monocyclic, preferred Ring D groups include phenyl, pyridyl, pyridazinyl, pyrimidinyl, and pyrazinyl.

When Ring D of formula IIc' is bicyclic, preferred bicyclic Ring D groups include naphthyl, tetrahydronaphthyl, indanyl, benzimidazolyl, quinolinyl, indolyl, isoindolyl, indolinyl, benzo[b]furyl, benzo[b]thiophenyl, indazolyl, benzothiazolyl, cinnolinyl, phthalazinyl, quinazolinyl, quinoxazolinyl, 1,8-naphthyridinyl and isoquinolinyl.

On Ring D of formula IIc', preferred $T-R_5$ or $V-Z-R^5$ substituents include -halo, $-CN$, $-NO_2$, $-N(R^4)_2$, optionally substituted $C_{1-6}$ aliphatic group, $-OR$, $-C(O)R$, $-CO_2R$, $-CONH(R^4)$, $-N(R^4)COR$, $-N(R^4)CO_2R$, $-SO_2N(R^4)_2$, $-N(R^4)SO_2R$, $-N(R^6)COCH_2N(R^4)_2$, $-N(R^6)COCH_2CH_2N(R^4)_2$, and $-N(R^6)COCH_2CH_2CH_2N(R^4)_2$, wherein R is selected from hydrogen, $C_{1-6}$ aliphatic, phenyl, a 5–6 membered heteroaryl ring, or a 5–6 membered heterocyclic ring. More preferred $R^5$ substituents include $-Cl$, $-Br$, $-F$, $-CN$, $-CF_3$, $-COOH$, $-CONHMe$, $-CONHEt$, $-NH_2$, $-NHAc$, $-NHSO_2Me$, $-NHSO_2Et$, $-NHSO_2(n-propyl)$, $-NHSO_2(isopropyl)$, $-NHCOEt$, $-NHCOCH_2NHCH_3$, $-NHCOCH_2N(CO_2t-Bu)CH_3$, $-NHCOCH_2N(CH_3)_2$, $-NHCOCH_2CH_2N(CH_3)_2$, $-NHCOCH_2CH_2CH_2N(CH_3)_2$, $-NHCO(cyclopropyl)$, $-NHCO(isobutyl)$, $-NHCOCH_2(morpholin-4-yl)$, $-NHCOCH_2CH_2(morpholin-4-yl)$, $-NHCOCH_2CH_2CH_2(morpholin-4-yl)$, $-NHCO_2(t-butyl)$, $-NH(C_{1-4}$ aliphatic) such as $-NHMe$, $-N(C_{1-4}$ aliphatic)$_2$ such as $-NMe_2$, OH, $-O(C_{1-4}$ aliphatic) such as $-OMe$, $C_{1-4}$ aliphatic such as methyl, ethyl, cyclopropyl, isopropyl, or t-butyl, and $-CO_2(C_{1-4}$ aliphatic).

Preferred formula IIc' compounds have one or more, and more preferably all, of the features selected from the group consisting of:
(a) $R^1$ is T-(Ring D), wherein T is a valence bond or a methylene unit;
(b) Ring D is a 5–7 membered monocyclic ring or an 8–10 membered bicyclic ring selected from an aryl or heteroaryl ring;
(c) $R^2$ is $-R$ or $-T-W-R^6$ and $R^{2'}$ is hydrogen; or $R^2$ and $R^{2'}$ are taken together to form an optionally substituted benzo ring; and
(d) $R^3$ is selected from $-R$, -halo, $-OR$, or $-N(R^4)_2$.

More preferred compounds of formula IIc' have one or more, and more preferably all, of the features selected from the group consisting of:
(a) $R^1$ is T-(Ring D), wherein T is a valence bond and Ring D is a 5–6 membered monocyclic ring or an 8–10 membered bicyclic ring selected from an aryl or heteroaryl ring;
(b) $R^2$ is $-R$ and $R^{2'}$ is hydrogen, wherein R is selected from hydrogen, $C_{1-6}$ aliphatic, phenyl, a 5–6 membered heteroaryl ring, or a 5–6 membered heterocyclic ring; and
(c) $R^3$ is selected from $-R$, -halo, $-OR$, or $-N(R^4)_2$, wherein R is selected from hydrogen, $C_{1-6}$ aliphatic, or 5–6 membered heterocyclyl, phenyl, or 5–6 membered heteroaryl, and L is $-O-$, $-S-$, or $-N(R^4)-$.

Even more preferred compounds of formula IIc' have one or more, and more preferably all, of the features selected from the group consisting of:
(a) $R^1$ is T-Ring D, wherein T is a valence bond and Ring D is a 5–6 membered aryl or heteroaryl ring;
(b) $R^2$ is hydrogen or $C_{1-4}$ aliphatic and $R^{2'}$ is hydrogen;
(c) $R^3$ is selected from $-R$, $-OR$, or $-N(R^4)_2$, wherein R is selected from hydrogen, $C_{1-6}$ aliphatic, 5–6 membered heterocyclyl, phenyl, or 5–6 membered heteroaryl, and L is $-O-$, $-S-$, or $-NH-$; and
(d) Ring D is substituted by up to three substituents selected from -halo, $-CN$, $-NO_2$, $-N(R^4)_2$, optionally substituted $C_{1-6}$ aliphatic group, $-OR$, $-C(O)R$, $-CO_2R$, $-CONH(R^4)$, $-N(R^4)COR$, $-N(R^4)CO_2R$, —SO$_2$N(R$^4$)$_2$, —N(R$^4$)SO$_2$R, —N(R$^6$)COCH$_2$N(R$^4$)$_2$, —N(R$^6$)COCH$_2$CH$_2$N(R$^4$)$_2$, or —N(R$^6$)COCH$_2$CH$_2$CH$_2$N(R$^4$)$_2$, wherein R is selected from hydrogen, C$_{1-6}$ aliphatic, phenyl, a 5–6 membered heteroaryl ring, or a 5–6 membered heterocyclic ring.

Other preferred compounds of formula IIc include compounds of formula IIc":

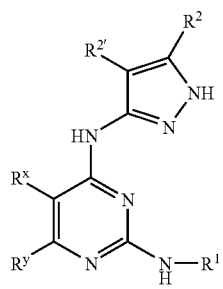

IIc"

or a pharmaceutically acceptable derivative or prodrug thereof, wherein;

R$^x$ and R$^y$ are taken together with their intervening atoms to form a fused, unsaturated or partially unsaturated, 5–7 membered ring having 0–3 ring heteroatoms selected from oxygen, sulfur, or nitrogen, wherein each substitutable ring carbon of said ring formed by R$^x$ and R$^y$ is optionally substituted by oxo, T—R$^3$, or L—Z—R$^3$, and each substitutable ring nitrogen of said ring formed by R$^x$ and R$^y$ is optionally substituted by R$^4$; provided that said fused ring formed by R$^x$ and R$^y$ is other than benzo;

R$^1$ is T-(Ring D);

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein each substitutable ring carbon of Ring D is independently substituted by oxo, T—R$^5$, or V—Z—R$^5$, and each substitutable ring nitrogen of Ring D is independently substituted by —R$^4$;

T is a valence bond or a C$_{1-4}$ alkylidene chain;

Z is a C$_{1-4}$ alkylidene chain;

L is —O—, —S—, —SO—, —SO$_2$—, —N(R$^6$)SO$_2$—, —SO$_2$N(R$^6$)—, —N(R$^6$)—, —CO—, —CO$_2$—, —N(R$^6$)CO—, —N(R$^6$)C(O)O—, —N(R$^6$)CON(R$^6$)—, —N(R$^6$)SO$_2$N(R$^6$)—, —N(R$^6$)N(R$^6$)—, —C(O)N(R$^6$)—, —OC(O)N(R$^6$)—, —C(R$^6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —C(R$^6$)$_2$N(R$^6$)C(O)—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, or —C(R$^6$)$_2$N(R$^6$)CON(R$^6$)—;

R$^2$ and R$^{2'}$ are independently selected from —R, —T—W—R$^6$, or R$^2$ and R$^{2'}$ are taken together with their intervening atoms to form a fused, 5–8 membered, unsaturated or partially unsaturated, ring having 0–3 ring heteroatoms selected from nitrogen, oxygen, or sulfur, wherein each substitutable ring carbon of said fused ring formed by R$^2$ and R$^{2'}$ is independently substituted by halo, oxo, —CN, —NO$_2$, —R$^7$, or —V—R$^6$, and each substitutable ring nitrogen of said ring formed by R$^2$ and R$^{2'}$ is independently substituted by R$^4$;

R$^3$ is selected from —R, -halo, —OR, —C(=O)R, —CO$_2$R, —COCOR, —COCH$_2$COR, —NO$_2$, —CN, —S(O)R, —S(O)$_2$R, —SR, —N(R$^4$)$_2$, —CON(R$^7$)$_2$, —SO$_2$N(R$^7$)$_2$, —OC(=)R, —N(R$^7$)COR, —N(R$^7$)CO$_2$(C$_{1-6}$ aliphatic), —N(R$^4$)N(R$^4$)$_2$, —C=NN(R$^4$)$_2$, —C=N—OR, —N(R$^7$)CON(R$^7$)$_2$, —N(R$^7$)SO$_2$N(R$^7$)$_2$, —N(R$^4$)SO$_2$R, or —OC(=O)N(R$^7$)$_2$;

each R is independently selected from hydrogen or an optionally substituted group selected from C$_{1-6}$ aliphatic, C$_{6-10}$ aryl, a heteroaryl ring having 5–10 ring atoms, or a heterocyclyl ring having 5–10 ring atoms;

each R$^4$ is independently selected from —R$^7$, —COR$^7$, —CO$_2$(optionally substituted C$_{1-6}$ aliphatic), —CON(R$^7$)$_2$, or —SO$_2$R$^7$;

each R$^5$ is independently selected from —R, halo, —OR, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$(optionally substituted C$_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$;

V is —O—, —S—, —SO—, —SO$_2$—, —N(R$^6$)SO$_2$—, —SO$_2$N(R$^6$)—, —N(R$^6$)—, —CO—, —CO$_2$—, —N(R$^6$)CO—, —N(R$^6$)C(O)O—, —N(R$^6$)CON(R$^6$)—, —N(R$^6$)SO$_2$N(R$^6$)—, —N(R$^6$)N(R$^6$)—, —C(O)N(R$^6$)—, —OC(O)N(R$^6$)—, —C(R$^6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —C(R$^6$)$_2$N(R$^6$)C(O)—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, or —C(R$^6$)$_2$N(R$^6$)CON(R$^6$)—;

W is —C(R$_6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —CO—, —CO$_2$—, —C(R$^6$)OC(O)—, —C(R$^6$)OC(O)N(R$^6$)—, —C(R$^6$)$_2$N(R$^6$)CO—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, —C(R$^6$)$_2$N(R$^6$)CON(R$^6$)—, or —CON(R$^6$)—;

each R$^6$ is independently selected from hydrogen or an optionally substituted C$_{1-4}$ aliphatic group, or two R$^6$ groups on the same nitrogen atom may be taken together with the nitrogen atom to form a 5–6 membered heterocyclyl or heteroaryl ring; and each R$^7$ is independently selected from hydrogen or an optionally substituted C$_{1-6}$ aliphatic group, or two R$^7$ on the same nitrogen are taken together with the nitrogen to form a 5–8 membered heterocyclyl or heteroaryl ring.

Preferred rings formed by R$^x$ and R$^y$ of formula IIc" include a 5-, 6-, or 7-membered unsaturated or partially unsaturated ring having 1–2 heteroatoms, or a partially unsaturated carbocyclo ring, wherein said R$^x$/R$^y$ ring is optionally substituted. This provides a bicyclic ring system containing a pyrimidine ring. Examples of preferred pyrimidine ring systems of formula IIc" are shown below.

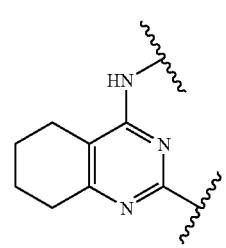

IIc"-B

IIc''-C

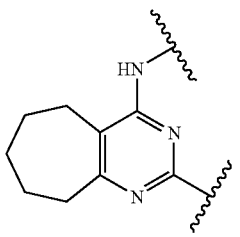

IIc''-D

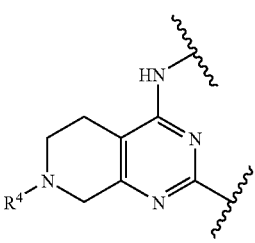

IIc''-E

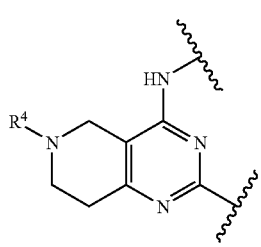

IIc''-F

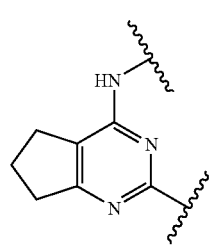

IIc''-J

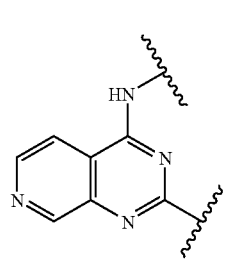

IIc''-K

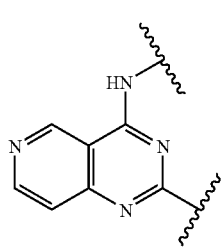

IIc''-L

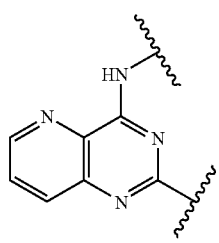

IIc''-P

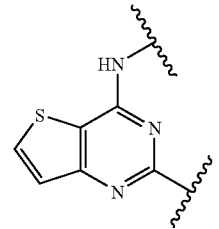

IIc''-R

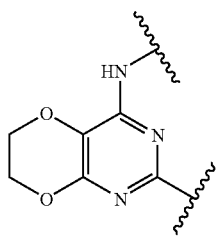

IIc''-V

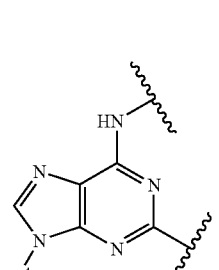

IIc''-W

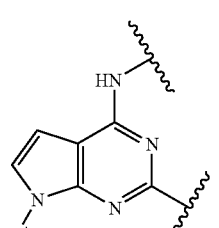

More preferred pyrimidine ring systems of formula IIc'' include IIc''-B, IIc-D, IIc-E, IIc-J, IIc-P, and IIc-V, most preferably IIc-B, IIc-D, IIc-E, and IIc-J.

The ring formed when $R^x$ and $R^y$ of formula IIc'' are taken together may be substituted or unsubstituted. Suitable substituents include —R, halo, —O(CH$_2$)$_{2-4}$—N(R$^4$)$_2$, —O(C$_2$)$_{2-4}$—R, —OR, —N(R$^4$)—(CH$_2$)$_{2-4}$—N(R$^4$)$_2$, —N(R$^4$)—(CH$_2$)$_{2-4}$—R, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$(optionally substituted C$_{1-6}$ aliphatic), —N(R$^4$)N(R$^4$)$_2$, —C=NN(R$^4$)$_2$, —C=N—OR, —N(R⁴)CON(R⁴)₂, —N(R⁴)SO₂N(R⁴)₂, —N(R⁴)SO₂R, or —OC(=O)N(R⁴)₂, wherein R and R⁴ are as defined above. Preferred Rˣ/Rʸ ring substituents include -halo, —R, —OR, —COR, —CO₂R, —CON(R⁴)₂, —CN, —O(CH₂)₂₋₄—N(R⁴)₂, —O(CH₂)₂₋₄—R, —NO₂, —N(R⁴)₂, —NR⁴COR, —NR⁴SO₂R, —SO₂N(R⁴)₂ wherein R is hydrogen or an optionally substituted C₁₋₆ aliphatic group.

R² and R²' groups of formula IIc" may be taken together to form a fused ring, thus providing a bicyclic ring system containing a pyrazole ring. Preferred fused rings include benzo, pyrido, pyrimido, and a partially unsaturated 6-membered carbocyclo ring. These are exemplified in the following formula IIc" compounds having a pyrazole-containing bicyclic ring system:

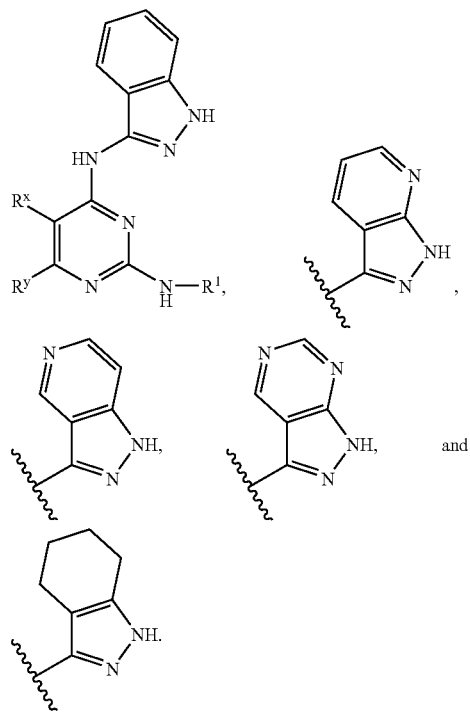

Preferred substituents on the R²/R²' fused ring of formula IIc" include one or more of the following: -halo, —N(R⁴)₂, —C₁₋₄ alkyl, —C₁₋₄ haloalkyl, —NO₂, —O(C₁₋₄ alkyl), CO₂(C₁₋₄ alkyl), —CN, —SO₂(C₁₋₄ alkyl), —SO₂NH₂, —OC(O)NH₂, —NH₂SO₂(C₁₋₄ alkyl), —NHC(O)(C₁₋₄ alkyl), —C(O)NH₂, and —CO(C₁₋₄ alkyl), wherein the (C₁₋₄ alkyl) is a straight, branched, or cyclic alkyl group. Preferably, the (C₁₋₄ alkyl) group is methyl.

When the pyrazole ring system of formula IIc" is monocyclic, preferred R² groups include hydrogen or a substituted or unsubstituted group selected from aryl, heteroaryl, or a C₁₋₆ aliphatic group. Examples of such preferred R² groups include H, methyl, ethyl, propyl, cyclopropyl, i-propyl, cyclopentyl, hydroxypropyl, methoxypropyl, and benzyloxypropyl. A preferred R²' group is hydrogen.

When Ring D of formula IIc" is monocyclic, preferred Ring D groups include phenyl, pyridyl, pyridazinyl, pyrimidinyl, and pyrazinyl.

When Ring D of formula IIc" is bicyclic, preferred bicyclic Ring D groups include naphthyl, tetrahydronaphthyl, indanyl, benzimidazolyl, quinolinyl, indolyl, isoindolyl, indolinyl, benzo[b]furyl, benzo[b]thiophenyl, indazolyl, benzothiazolyl, cinnolinyl, phthalazinyl, quinazolinyl, quinoxazolinyl, 1,8-naphthyridinyl and isoquinolinyl.

On Ring D of formula IIc", preferred T—R⁵ or V—Z—R⁵ substituents include -halo, —CN, —NO₂, —N(R⁴)₂, optionally substituted C₁₋₆ aliphatic group, —OR, —C(O)R, —CO₂R, —CONH(R⁴), —N(R⁴)COR, —N(R⁴)CO₂R, —SO₂N(R⁴)₂, —N(R⁴)SO₂R, —N(R⁶)COCH₂N(R⁴)₂, —N(R⁶)COCH₂CH₂N(R⁴)₂, and —N(R⁶)COCH₂CH₂CH₂N(R⁴)₂, wherein R is selected from hydrogen, C₁₋₆ aliphatic, phenyl, a 5–6 membered heteroaryl ring, or a 5–6 membered heterocyclic ring. More preferred R⁵ substituents include —Cl, —Br, —F, —CN, —CF₃, —COOH, —CONHMe, —CONHEt, —NH₂, —NHAc, —NHSO₂Me, —NHSO₂Et, —NHSO₂(n-propyl), —NHSO₂(isopropyl), —NHCOEt, —NHCOCH₂NHCH₃, —NHCOCH₂N(CO₂t-Bu)CH₃, —NHCOCH₂N(CH₃)₂, —NHCOCH₂CH₂N(CH₃)₂, —NHCOCH₂CH₂CH₂N(CH₃)₂, —NHCO(cyclopropyl), —NHCO(isobutyl), —NHCOCH₂(morpholin-4-yl), —NHCOCH₂CH₂(morpholin-4-yl), —NHCOCH₂CH₂CH₂(morpholin-4-yl), —NHCO₂(t-butyl), —NH(C₁₋₄ aliphatic) such as —NHMe; —N(C₁₋₄ aliphatic)₂ such as —NMe₂, OH, —O(C₁₋₄ aliphatic) such as —OMe, C₁₋₄ aliphatic such as methyl, ethyl, cyclopropyl, isopropyl, or t-butyl, and —CO₂(C₁₋₄ aliphatic).

Preferred formula IIc" compounds have one or more, and more preferably all, of the features selected from the group consisting of:

(a) Rˣ and Rʸ are taken together with their intervening atoms to form a fused, unsaturated or partially unsaturated, 5–6 membered ring having 1–2 heteroatoms selected from oxygen, sulfur, or nitrogen, or a partially unsaturated 6-membered carbocyclo ring, wherein each substitutable ring carbon of said fused ring formed by Rˣ and Rʸ is independently substituted by oxo, T—R³, or L—Z—R³, and each substitutable ring nitrogen of said ring formed by Rˣ and Rʸ is independently substituted by R⁴;

(b) R¹ is T-(Ring D), wherein T is a valence bond or a methylene unit, and Ring D is a 5–7 membered monocyclic or an 8–10 membered bicyclic aryl or heteroaryl ring;

(c) R² is —R or —T—W—R⁶ and R²' is hydrogen; or R² and R²' are taken together to form an optionally substituted benzo ring; and (d) R³ is selected from —R, -halo, —OR, or —N(R⁴)₂.

More preferred compounds of formula IIc" have one or more, and more preferably all, of the features selected from the group consisting of:

(a) Rˣ and Rʸ are taken together to form a benzo, pyrido, cyclopento, cyclohexo, cyclohepto, thieno, piperidino, or imidazo ring, wherein, each substitutable ring carbon of said fused ring formed by Rˣ and Rʸ is independently substituted by oxo, T—R³, or L—Z—R³, and each substitutable ring nitrogen of said ring formed by Rˣ and Rʸ is independently substituted by R⁴;

(b) R¹ is T-(Ring D), wherein T is a valence bond and Ring D is a 5–6 membered monocyclic ring or an 8–10 membered bicyclic ring selected from an aryl or heteroaryl ring;

(c) R² is —R and R²' is hydrogen, wherein R is selected from hydrogen, C₁₋₆ aliphatic, phenyl, a 5–6 membered heteroaryl ring, or a 5–6 membered heterocyclic ring; and (d) R³ is selected from —R, -halo, —OR, or —N(R⁴)₂, wherein R is selected from hydrogen, C₁₋₆ aliphatic, or 5–6 membered heterocyclyl, phenyl, or 5–6 membered heteroaryl, and L is —O—, —S—, or —N(R⁴)—.

Even more preferred compounds of formula IIc" have one or more, and more preferably all, of the features selected from the group consisting of:

(a) $R^x$ and $R^y$ are taken together to form a pyrido, piperidino, or cyclohexo ring, wherein each substitutable ring carbon of said fused ring formed by $R^x$ and $R^y$ is independently substituted by oxo, T—$R^3$, or L—Z—$R^3$, and each substitutable ring nitrogen of said ring formed by $R^x$ and $R^y$ is independently substituted by $R^4$;

(b) $R^1$ is T-Ring D, wherein T is a valence bond and Ring D is a 5–6 membered aryl or heteroaryl ring;

(c) $R^2$ is hydrogen or $C_{1-4}$ aliphatic and $R^{2'}$ is hydrogen;

(d) $R^3$ is selected from —R, —OR, or —N(R⁴)₂, wherein R is selected from hydrogen, $C_{1-6}$ aliphatic, 5–6 membered heterocyclyl, phenyl, or 5–6 membered heteroaryl, and L is —O—, —S—, or —NH—; and (e) Ring D is substituted by up to three substituents selected from -halo, —CN, —NO₂, —N(R⁴)₂, optionally substituted $C_{1-6}$ aliphatic group, —OR, —C(O)R, —CO₂R, —CONH(R⁴), —N(R⁴)COR, —N(R⁴)CO₂R, —SO₂N(R⁴)₂, —N(R⁴)SO₂R, —N(R⁶)COCH₂N(R⁴)₂, —N(R⁶)COCH₂CH₂N(R⁴)₂, or —N(R⁶)COCH₂CH₂CH₂N(R⁴)₂, wherein R is selected from hydrogen, $C_{1-6}$ aliphatic, phenyl, a 5–6 membered heteroaryl ring, or a 5–6 membered heterocyclic ring.

Representative compounds of formula IIc are shown below in Table 3.

TABLE 3

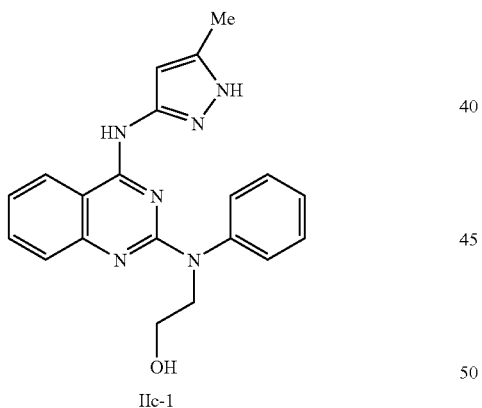

IIc-1

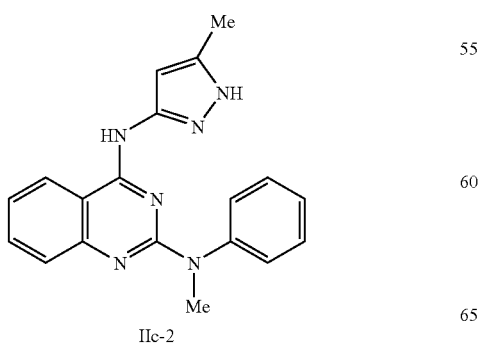

IIc-2

TABLE 3-continued

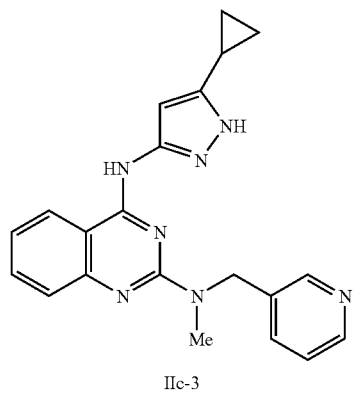

IIc-3

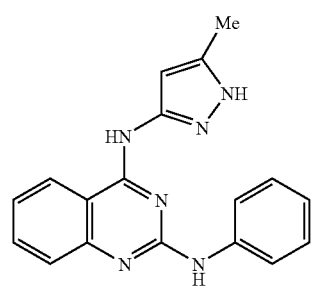

IIc-4

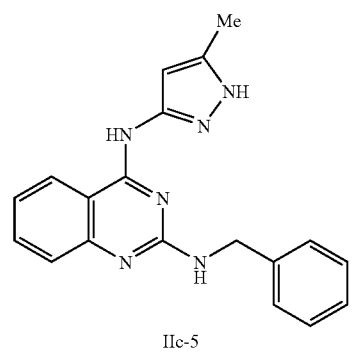

IIc-5

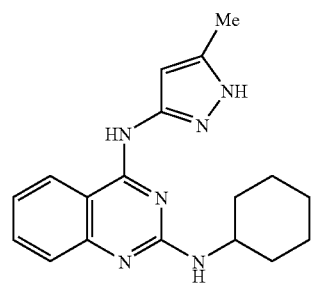

IIc-6

TABLE 3-continued
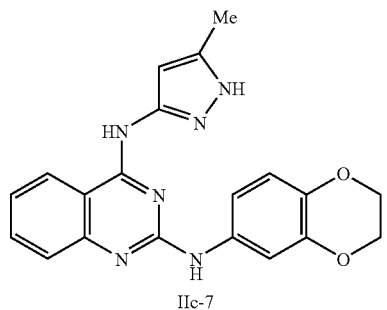
IIc-7
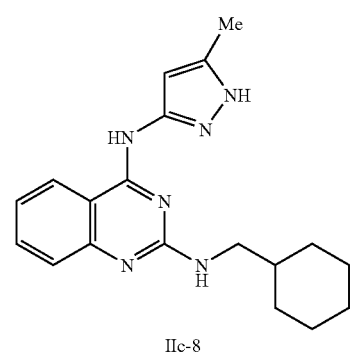
IIc-8
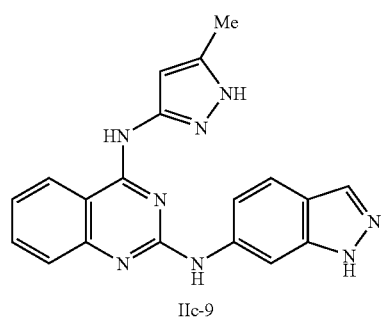
IIc-9
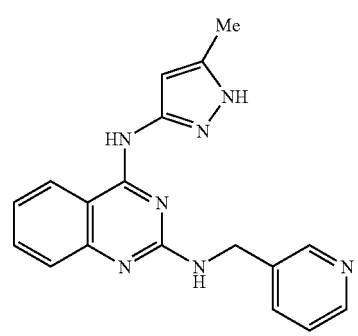
IIc-10
TABLE 3-continued
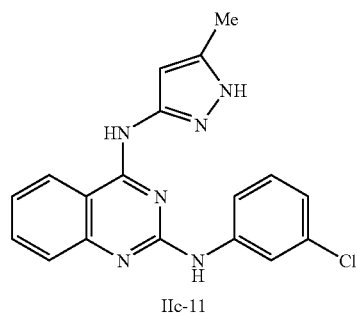
IIc-11
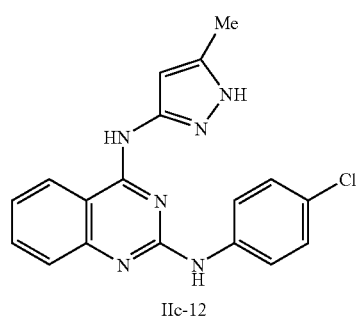
IIc-12
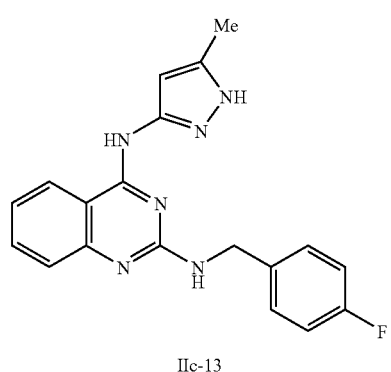
IIc-13
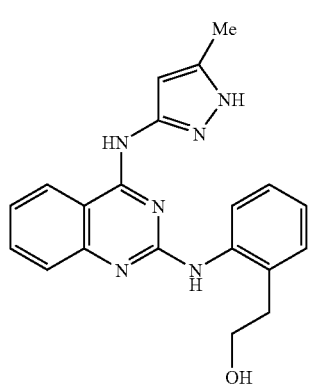
IIc-14

TABLE 3-continued
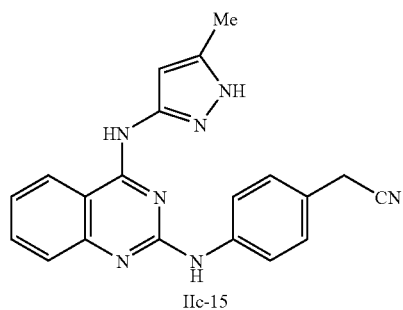
IIc-15
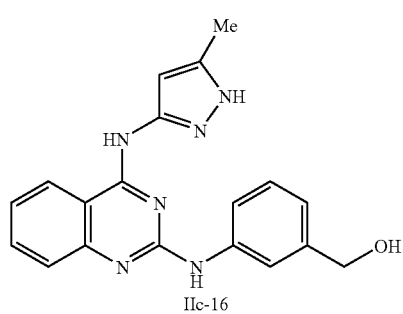
IIc-16
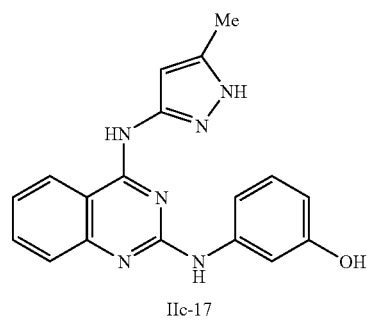
IIc-17
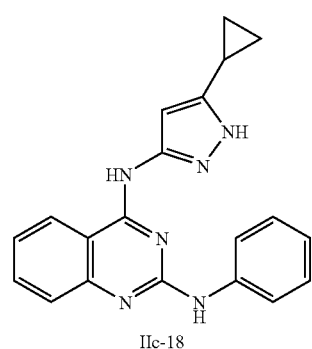
IIc-18
TABLE 3-continued
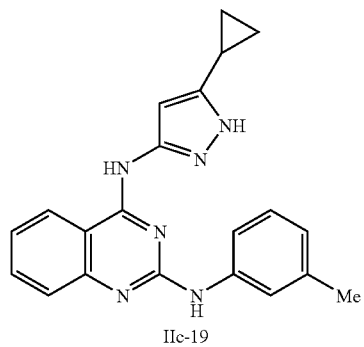
IIc-19
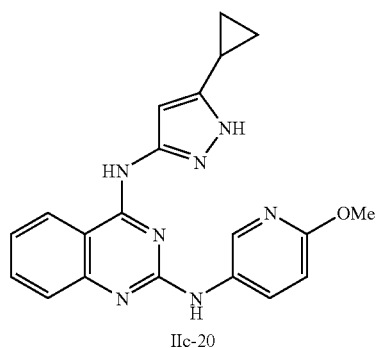
IIc-20
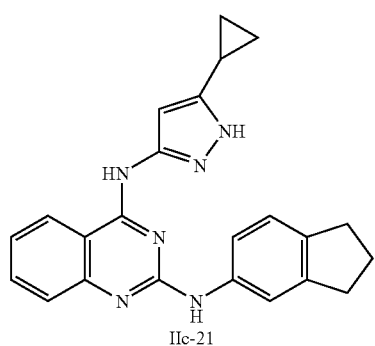
IIc-21
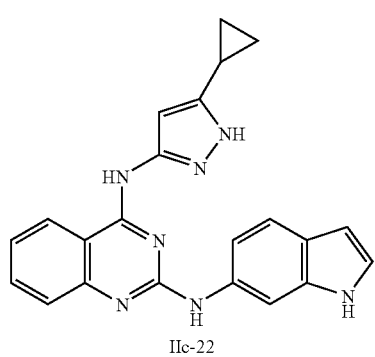
IIc-22

TABLE 3-continued
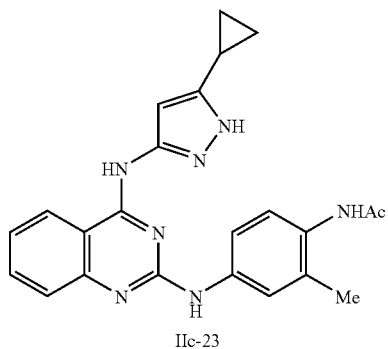
IIc-23
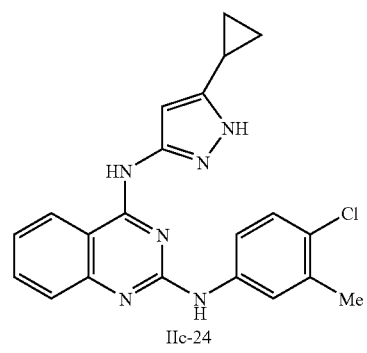
IIc-24
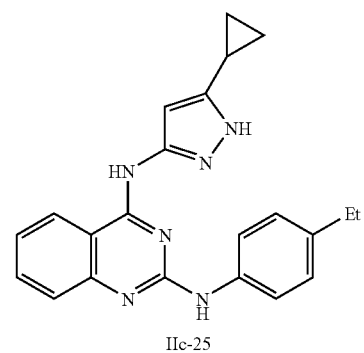
IIc-25
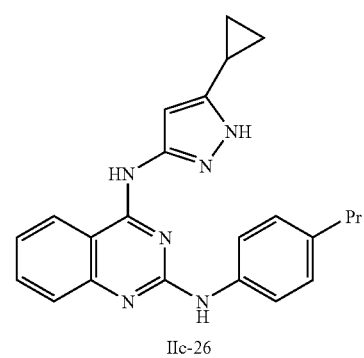
IIc-26
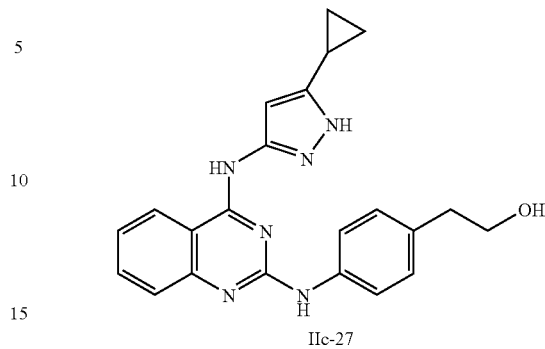
IIc-27
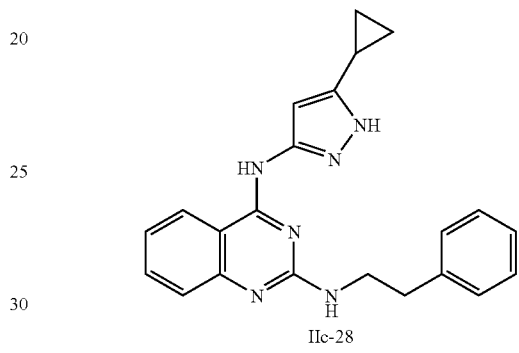
IIc-28
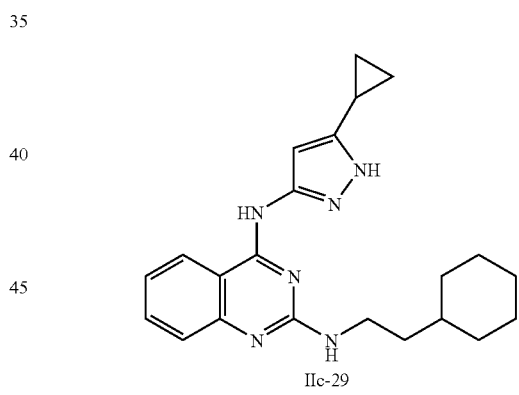
IIc-29
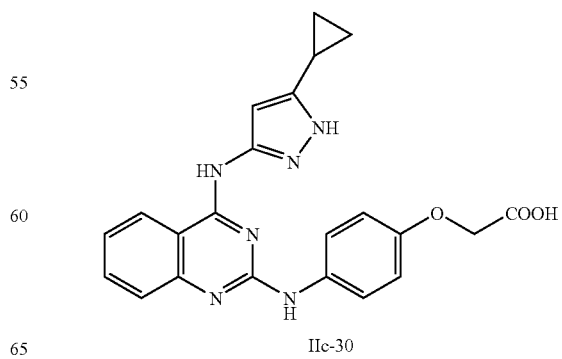
IIc-30

TABLE 3-continued
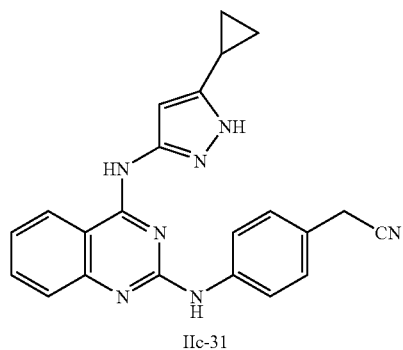
IIc-31
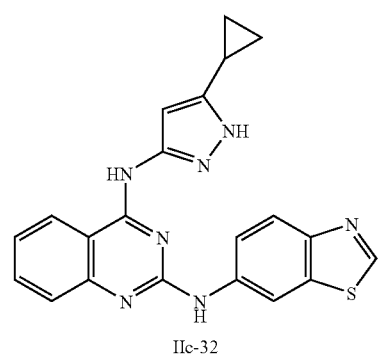
IIc-32
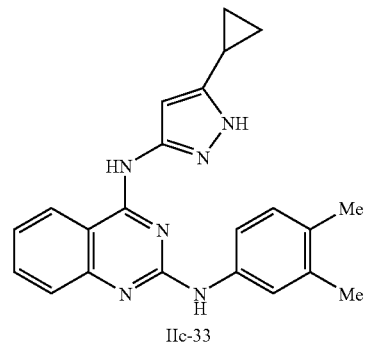
IIc-33
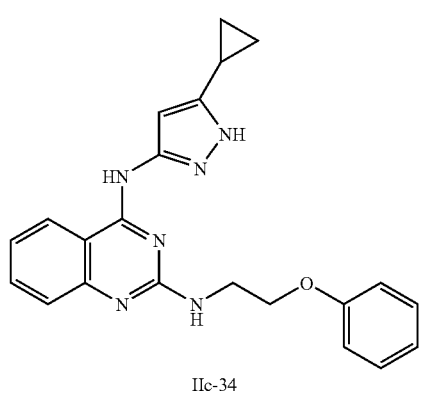
IIc-34
TABLE 3-continued
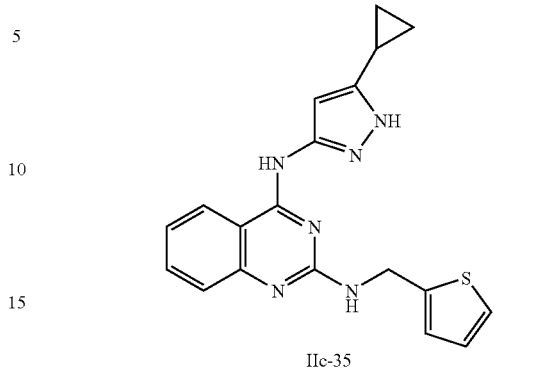
IIc-35
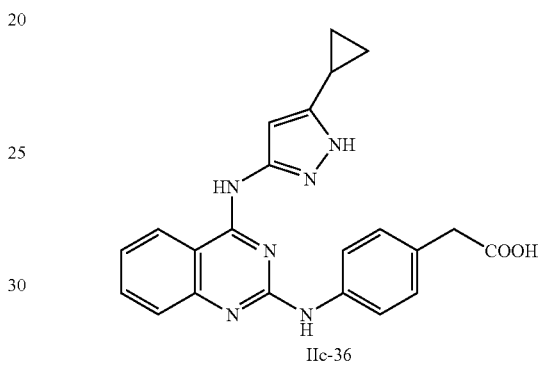
IIc-36
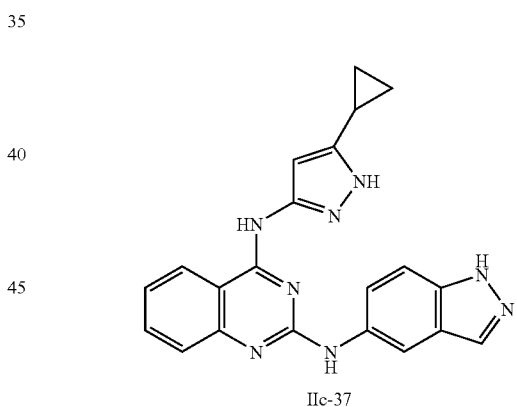
IIc-37
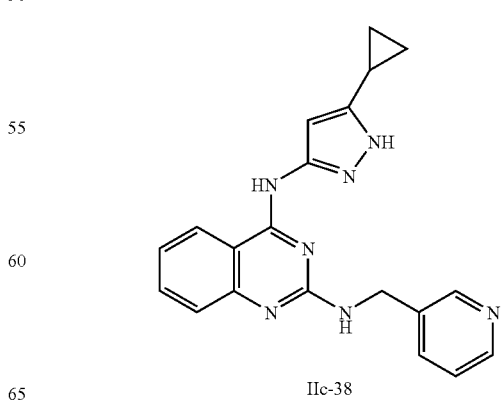
IIc-38

TABLE 3-continued
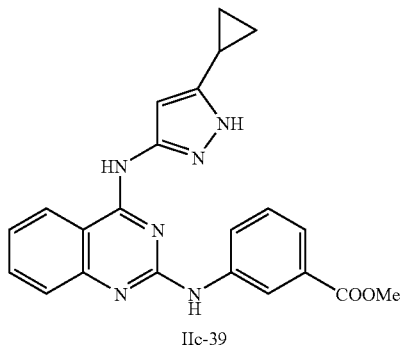
IIc-39
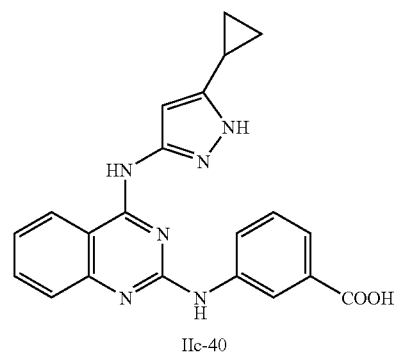
IIc-40
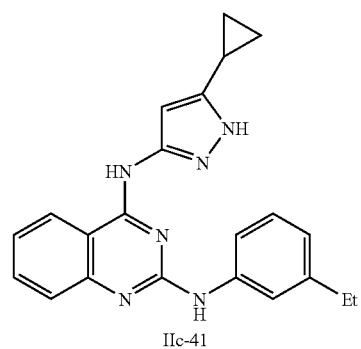
IIc-41
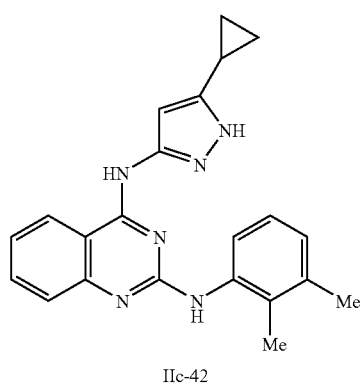
IIc-42
TABLE 3-continued
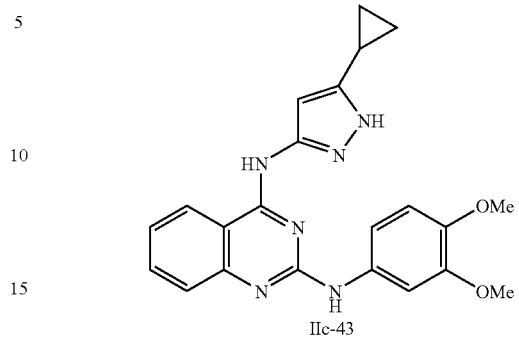
IIc-43
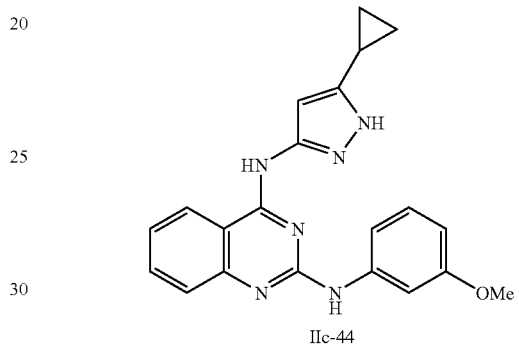
IIc-44
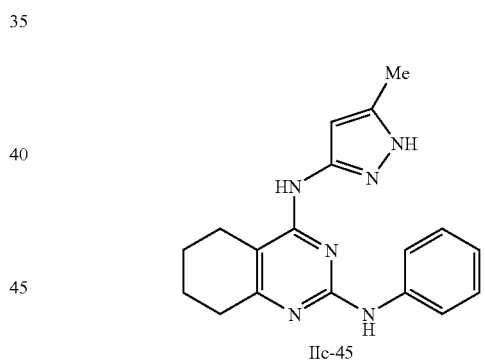
IIc-45
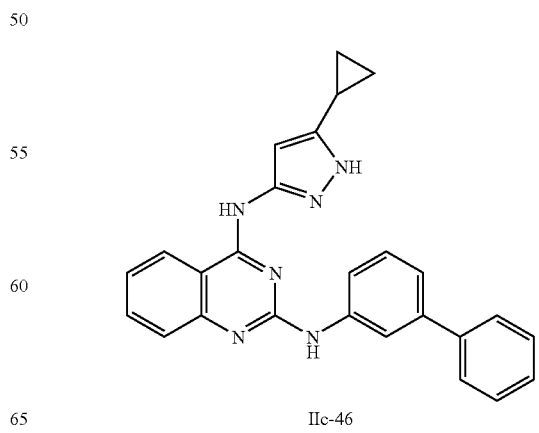
IIc-46

TABLE 3-continued
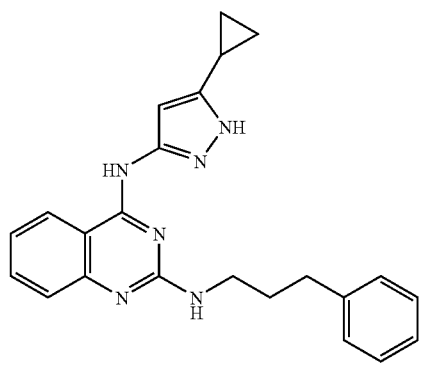
IIc-47
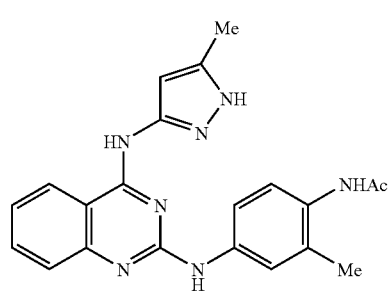
IIc-48
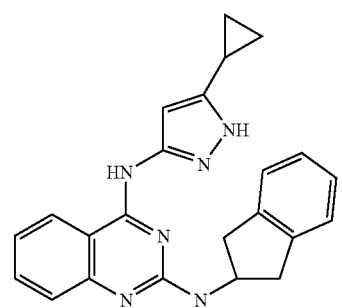
IIc-49
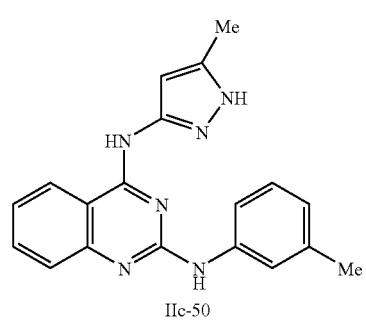
IIc-50
TABLE 3-continued
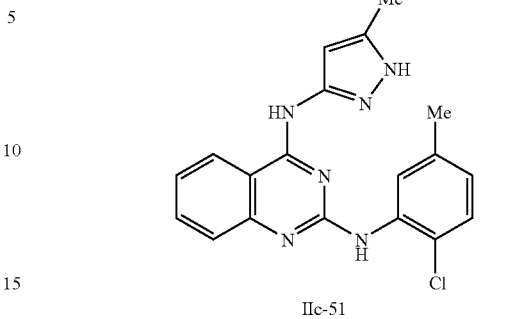
IIc-51
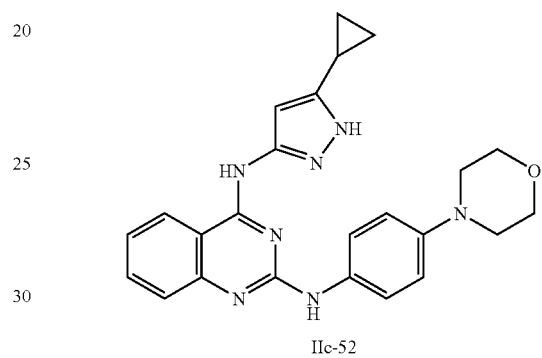
IIc-52
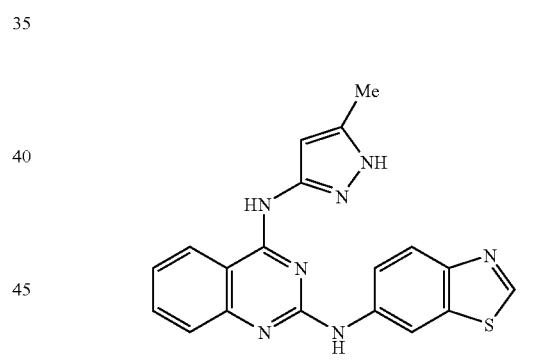
IIc-53
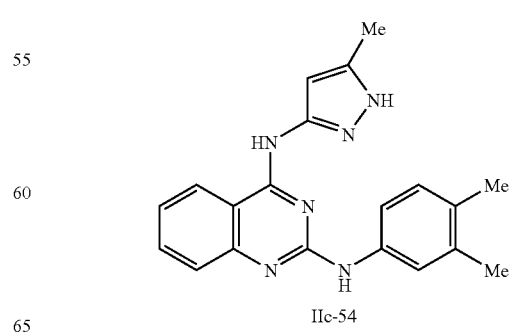
IIc-54

TABLE 3-continued
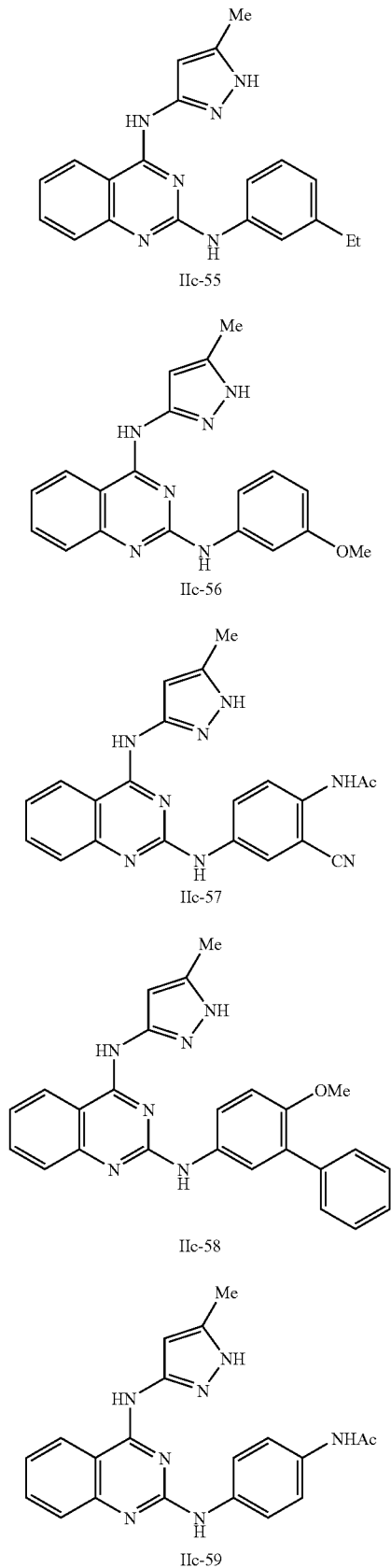
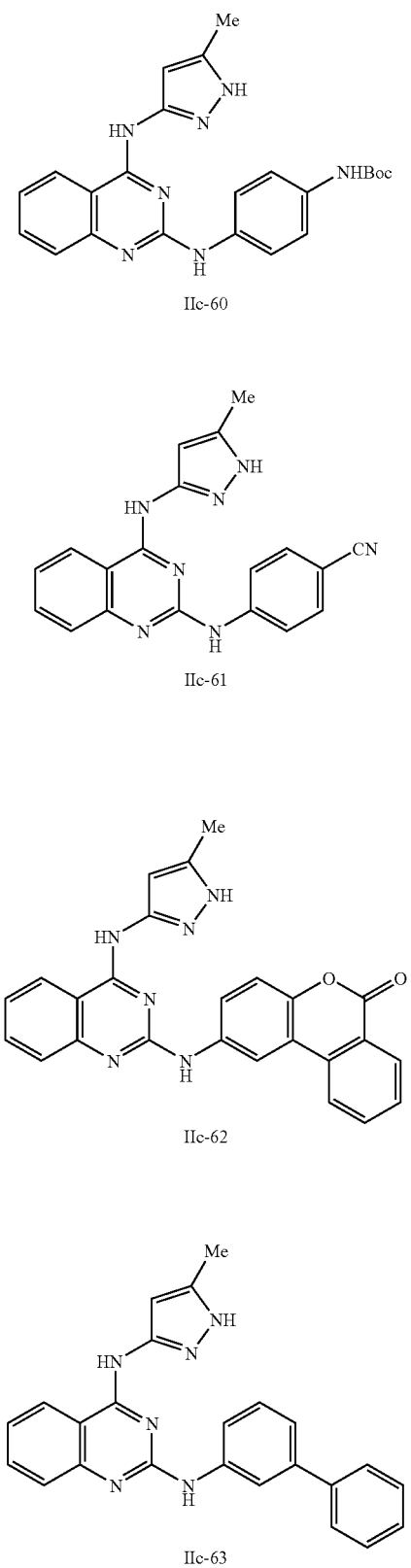

TABLE 3-continued
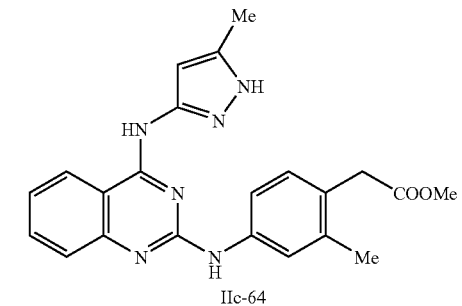
IIc-64
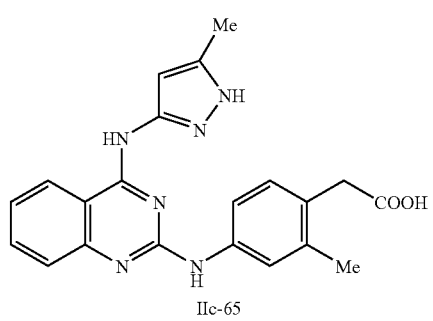
IIc-65
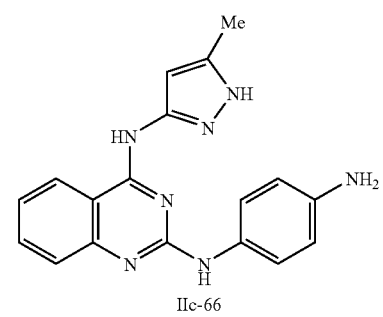
IIc-66
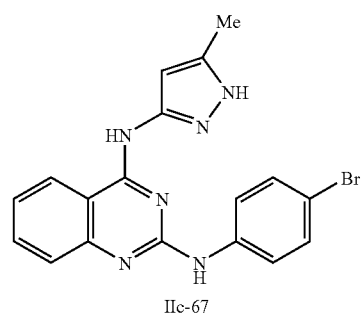
IIc-67
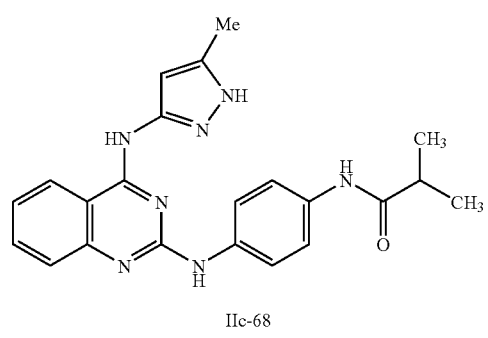
IIc-68
TABLE 3-continued
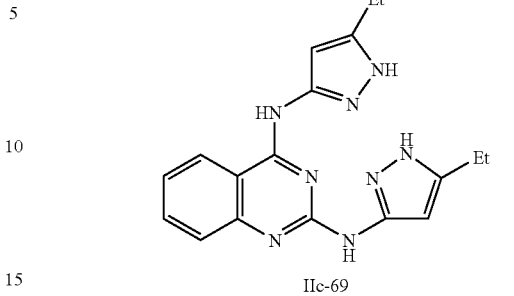
IIc-69
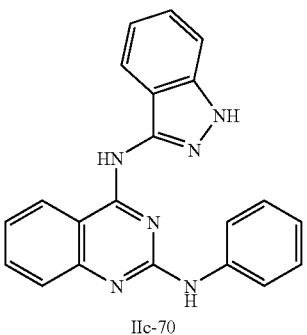
IIc-70
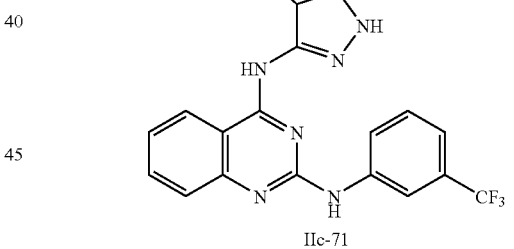
IIc-71
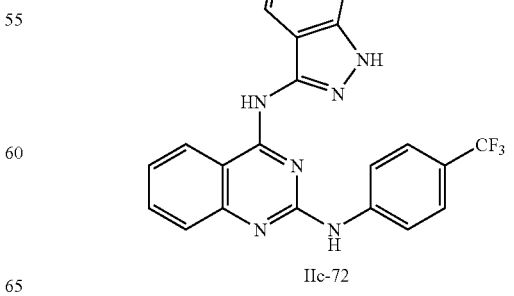
IIc-72

TABLE 3-continued
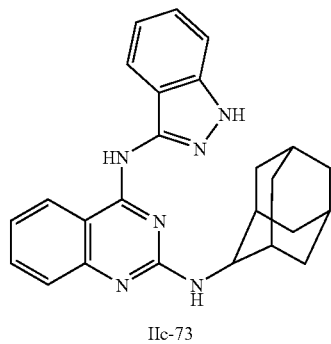
IIc-73
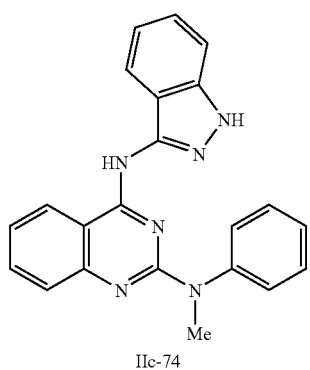
IIc-74
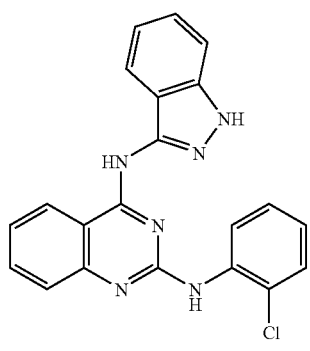
IIc-75
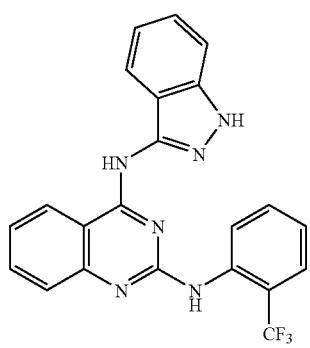
IIc-76
TABLE 3-continued
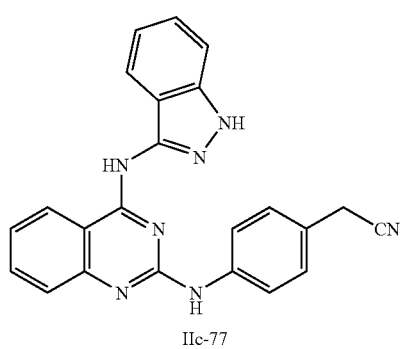
IIc-77
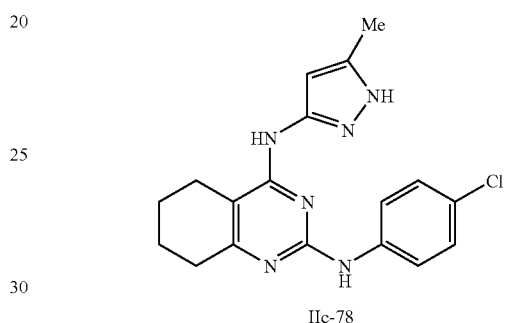
IIc-78
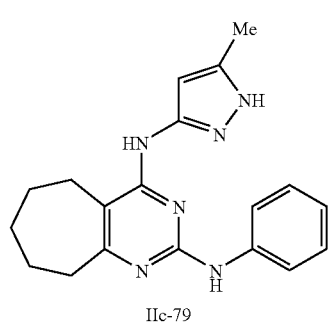
IIc-79
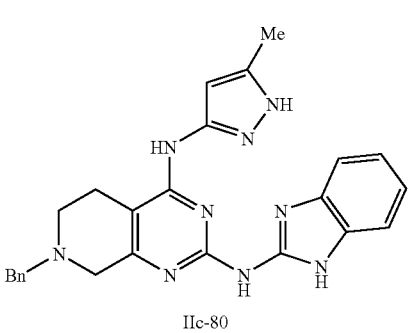
IIc-80

TABLE 3-continued
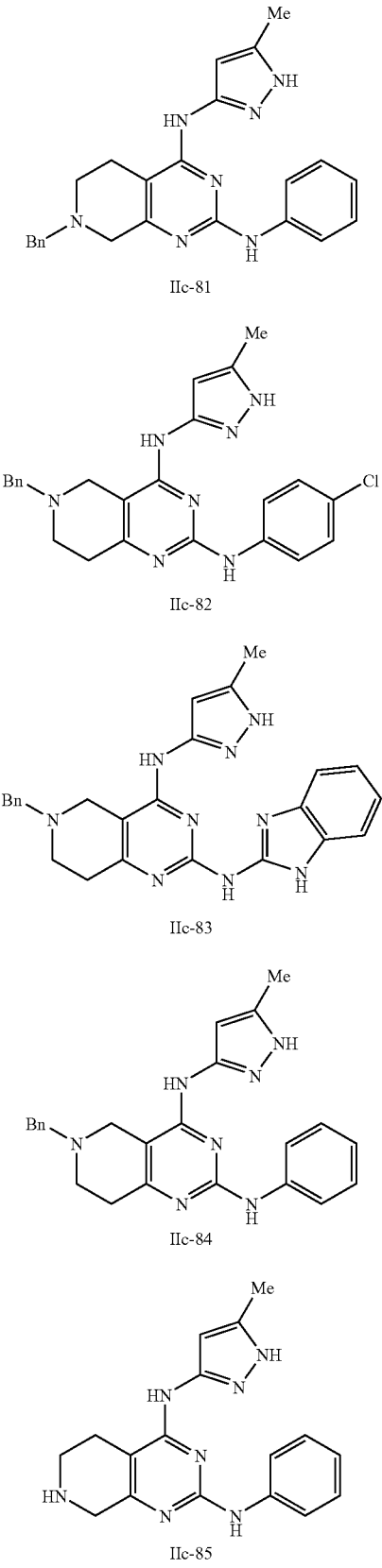
IIc-81
IIc-82
IIc-83
IIc-84
IIc-85
IIc-86
IIc-87
IIc-88
IIc-89

TABLE 3-continued

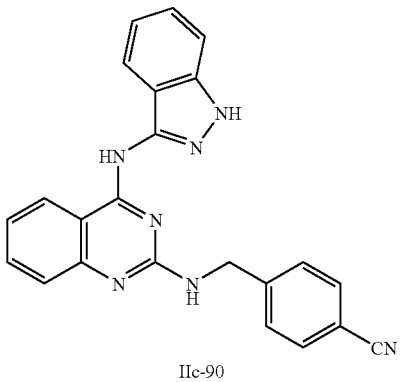

IIc-90

In another embodiment, this invention provides a composition comprising a compound of formula IIc, IIc', or IIc", and a pharmaceutically acceptable carrier.

Another aspect of this invention relates to a method of treating or preventing an Aurora-2-mediated disease with an Aurora-2 inhibitor, which method comprises administering to a patient in need of such a treatment a therapeutically effective amount of a compound of formula IIc, IIc', or IIc", or a pharmaceutical composition thereof.

Another aspect of this invention relates to a method of inhibiting Aurora-2 activity in a patient, which method comprises administering to the patient a compound of formula IIc, IIc', or IIc", or a composition comprising said compound.

Another aspect of this invention relates to a method of treating or preventing a GSK-3-mediated disease with a GSK-3 inhibitor, which method comprises administering to a patient in need of such a treatment a therapeutically effective amount of a compound of formula IIc, IIc', or IIc", or a pharmaceutical composition thereof.

One aspect of this invention relates to a method of enhancing glycogen synthesis and/or lowering blood levels of glucose in a patient in need thereof, which method comprises administering to the patient a therapeutically effective amount of a compound of formula IIc, IIc', or IIc", or a pharmaceutical composition thereof. This method is especially useful for diabetic patients. Another method relates to inhibiting the production of hyperphosphorylated Tau protein; which is useful in halting or slowing the progression of Alzheimer's disease. Another method relates to inhibiting the phosphorylation of β-catenin, which is useful for treating schizophrenia.

Another aspect of this invention relates to a method of inhibiting GSK-3 activity in a patient, which method comprises administering to the patient a compound of formula IIc, IId', or IIc", or a composition comprising said compound.

Another aspect of this invention relates to a method of treating or preventing a Src-mediated disease with a Src inhibitor, which method comprises administering to a patient in need of such a treatment a therapeutically effective amount of a compound of formula IIc, IIc', or IIc", or a pharmaceutical composition thereof.

Another aspect of the invention relates to inhibiting Src activity in a patient, which method comprises administering to the-patient a compound of formula IIc, IIc', or IIc", or a composition comprising said compound.

Another aspect of this invention relates to a method of treating or preventing an ERK-2-mediated diseases with an ERK-2 inhibitor, which method comprises administering to a patient in need of such a treatment a therapeutically effective amount of a compound of formula IIc, IIc', or IIc", or a pharmaceutical composition thereof.

Another aspect of the invention relates to inhibiting ERK-2 activity in a patient, which method comprises administering to the patient a compound of formula IIc, IIc', or IIc", or a composition comprising said compound.

Another aspect of this invention relates to a method of treating or preventing an AKT-mediated diseases with an AKT inhibitor, which method comprises administering to a patient in need of such a treatment a therapeutically effective amount of a compound of formula IIc, IIc', or IIc", or a pharmaceutical composition thereof.

Another aspect of the invention relates to inhibiting AKT activity in a patient, which method comprises administering to the patient a compound of formula IIc, IIc', or IIc", or a composition comprising said compound.

Another method relates to inhibiting Aurora-2, GSK-3, Src, ERK-2, or AKT activity in a biological sample, which method comprises contacting the biological sample with the Aurora-2, GSK-3, Src, ERK-2, or AKT inhibitor of formula IIc, IIc', or IIc", or a pharmaceutical composition thereof, in an amount effective to inhibit Aurora-2, GSK-3, Src, ERK-2, or AKT.

Each of the aforementioned methods directed to the inhibition of Aurora-2, GSK-3, Src, ERK-2, or AKT, or the treatment of a disease alleviated thereby, is preferably carried out with a preferred compound of formula IIc, IIc', or IIc", as described above.

Another embodiment that is particularly useful for treating Aurora-2-mediated diseases relates to compounds of formula IId:

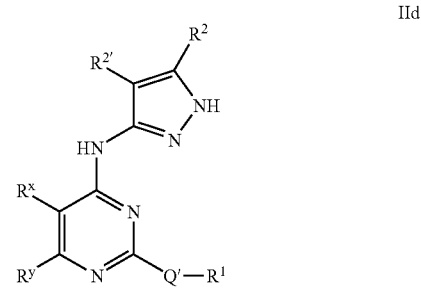

IId or a pharmaceutically acceptable derivative or prodrug thereof, wherein;

Q' is selected from —C($R^6$)$_2$—, 1,2-cyclopropanediyl, 1,2-cyclobutanediyl, or 1,3-cyclobutanediyl;

$R^x$ and $R^y$ are taken together with their intervening atoms to form a fused, unsaturated or partially unsaturated, 5–7 membered ring having 0–3 ring heteroatoms selected from oxygen, sulfur, or nitrogen, wherein each substitutable ring carbon of said fused ring formed by $R^x$ and $R^y$ is independently substituted by oxo, T—$R^3$, or L—Z—$R^3$, and each substitutable ring nitrogen of said ring formed by $R^x$ and $R^y$ is independently substituted by $R^4$;

$R^1$ is T-(Ring D);

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein each substitutable ring carbon of Ring D is independently substituted by oxo, T—$R^5$, or V—Z—$R^5$, and each substitutable ring nitrogen of Ring D is independently substituted by —$R^4$;

T is a valence bond or a $C_{1-4}$ alkylidene chain, wherein when Q' is —$C(R^6)_2$— a methylene group of said $C_{1-4}$ alkylidene chain is optionally replaced by —O—, —S—, —N($R^4$)—, —CO—, —CONH—, —NHCO—, —$SO_2$—, —$SO_2NH$—, —$NHSO_2$—, —$CO_2$—, —OC(O)—, —OC(O)NH—, or —$NHCO_2$—;

Z is a $C_{1-4}$ alkylidene chain;

L is —O—, —S—, —SO—, —$SO_2$—, —$N(R^6)SO_2$—, —$SO_2N(R^6)$—, —$N(R^6)$—, —CO—, —$CO_2$—, —$N(R^6)$CO—, —$N(R^6)C(O)O$—, —$N(R^6)CON(R^6)$—, —$N(R^6)SO_2N(R^6)$—, —$N(R^6)N(R^6)$—, —$C(O)N(R^6)$—, —$OC(O)N(R^6)$—, —$C(R^6)_2O$—, —$C(R^6)_2S$—, —$C(R^6)_2SO$—, —$C(R^6)_2SO_2$—, —$C(R^6)_2SO_2N(R^6)$—, —$C(R^6)_2N(R^6)$—, —$C(R^6)_2N(R^6)C(O)$—, —$C(R^6)_2N(R^6)C(O)O$—, —$C(R^6)=NN(R^6)$—, —$C(R^6)=N$—O—, —$C(R^6)_2N(R^6)N(R^6)$—, —$C(R^6)_2N(R^6)SO_2N(R^6)$—, or —$C(R^6)_2N(R^6)CON(R^6)$—;

$R^2$ and $R^{2'}$ are independently selected from —R, —T—W—$R^6$, or $R^2$ and $R^{2'}$ are taken together with their intervening atoms to form a fused, 5–8 membered, unsaturated or partially unsaturated, ring having 0–3 ring heteroatoms selected from nitrogen, oxygen, or sulfur, wherein each substitutable ring carbon of said fused ring formed by $R^2$ and $R^{2'}$ is independently substituted by halo, oxo, —CN, —$NO_2$, —$R^7$, or —V—$R^6$, and each substitutable ring nitrogen of said ring formed by $R^2$ and $R^{2'}$ is independently substituted by $R^4$;

$R^3$ is selected from —R, -halo, —OR, —C(=O)R, —$CO_2R$, —COCOR, —$COCH_2COR$, —$NO_2$, —CN, —S(O)R, —$S(O)_2R$, —SR, —$N(R^4)_2$, —$CON(R^7)_2$, —$SO_2N(R^7)_2$, —OC(=O)R, —$N(R^7)$ COR, —$N(R^7)CO_2(C_{1-6}$ aliphatic), —$N(R^4)N(R^4)_2$, —C=$NN(R^4)_2$, —C=N—OR, —$N(R^7)CON(R^7)_2$, —$N(R^7)SO_2N(R^7)_2$, —$N(R^4)SO_2R$, or —$OC(=O)N(R^7)_2$;

each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;

each $R^4$ is independently selected from —$R^7$, —$COR^7$, —$CO_2$ (optionally substituted $C_{1-6}$ aliphatic), —$CON(R^7)_2$, or —$SO_2R^7$;

each $R^5$ is independently selected from —R, halo, —OR, —C(=O)R, —$CO_2R$, —COCOR, —$NO_2$, —CN, —S(O)R, —$SO_2R$, —SR, —$N(R^4)_2$, —$CON(R^4)_2$, —$SO_2N(R^4)_2$, —OC(=O)R, —$N(R^4)COR$, —$N(R^4)CO_2$(optionally substituted $C_{1-6}$ aliphatic), —$N(R^4)N(R^4)_2$, —C=$NN(R^4)_2$, —C=N—OR, —$N(R^4)CON(R^4)_2$, —$N(R^4)SO_2N(R^4)_2$, —$N(R^4)SO_2R$, or —$OC(=O)N(R^4)_2$;

V is —O—, —S—, —SO—, —$SO_2$—, —$N(R^6)SO_2$—, —$SO_2N(R^6)$—, —$N(R^6)$—, —CO—, —$CO_2$—, —$N(R^6)$CO—, —$N(R^6)C(O)O$—, —$N(R^6)CON(R^6)$—, —$N(R^6)SO_2N(R^6)$—, —$N(R^6)N(R^6)$—, —$C(O)N(R^6)$—, —$OC(O)N(R^6)$—, —$C(R^6)_2O$—, —$C(R^6)_2S$—, —$C(R^6)_2SO$—, —$C(R^6)_2SO_2$—, —$C(R^6)_2SO_2N(R^6)$—, —$C(R^6)_2N(R^6)$—, —$C(R^6)_2N(R^6)C(O)$—, —$C(R^6)_2N(R^6)C(O)O$—, —$C(R^6)=NN(R^6)$—, —$C(R^6)=N$—O—, —$C(R^6)_2N(R^6)N(R^6)$—, —$C(R^6)_2N(R^6)SO_2N(R^6)$—, or —$C(R^6)_2N(R^6)CON(R^6)$—;

W is —$C(R^6)_2O$—, —$C(R^6)_2S$—, —$C(R^6)_2SO$—, —$C(R^6)_2SO_2$—, —$C(R^6)_2SO_2N(R^6)$—, —$C(R^6)_2N(R^6)$—, —CO—, —$CO_2$—, —$C(R^6)OC(O)$—, —$C(R^6)OC(O)N(R^6)$—, —$C(R^6)_2N(R^6)CO$—, —$C(R^6)_2N(R^6)C(O)O$—, —$C(R^6)=NN(R^6)$—, —$C(R^6)=N$—O—, —$C(R^6)_2N(R^6)N(R^6)$—, —$C(R^6)_2N(R^6)SO_2N(R^6)$—, —$C(R^6)_2N(R^6)CON(R^6)$—, or —$CON(R^6)$—;

each $R^6$ is independently selected from hydrogen or an optionally substituted $C_{1-4}$ aliphatic group, or two $R^6$ groups on the same nitrogen atom are taken together with the nitrogen atom to form a 5–6 membered heterocyclyl or heteroaryl ring;

each $R^{6'}$ is independently selected from hydrogen or a $C_{1-4}$ aliphatic group, or two $R^{6'}$ on the same carbon atom are taken together to form a 3–6 membered carbocyclic ring; and each $R^7$ is independently selected from hydrogen or an optionally substituted $C_{1-6}$ aliphatic group, or two $R^7$ on the same nitrogen are taken together with the nitrogen to form a 5–8 membered heterocyclyl or heteroaryl ring.

Preferred rings formed by $R^x$ and $R^y$ include a 5-, 6-, or 7-membered unsaturated or partially unsaturated ring having 0–2 heteroatoms, wherein said $R^x/R^y$ ring is optionally substituted. This provides a bicyclic ring system containing a pyrimidine ring. Examples of preferred pyrimidine ring systems of formula IId are shown below.

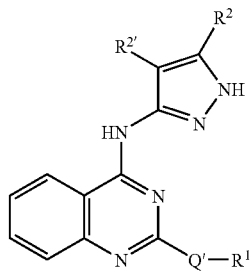

IId-A

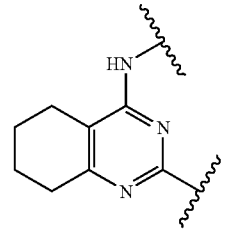

IId-B

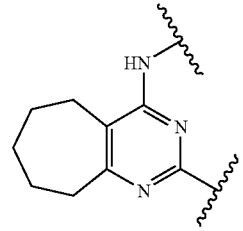

IId-C

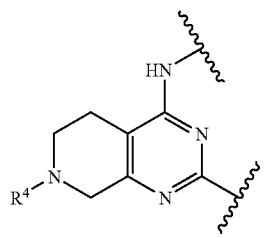

IId-D

IId-E

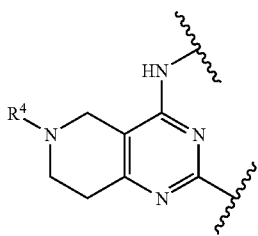

IId-F

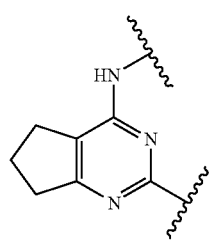

IId-J

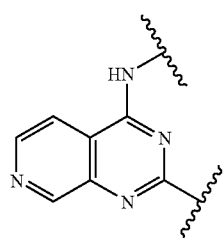

IId-K

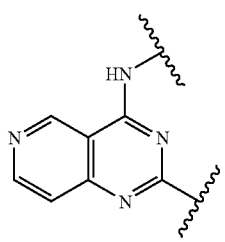

IId-L

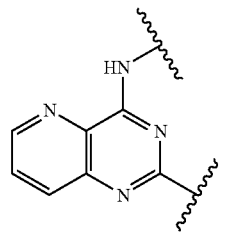

IId-P

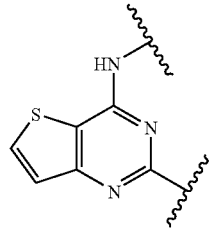

IId-R

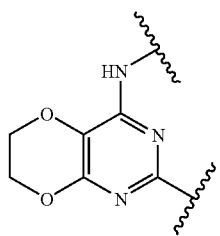

IId-V

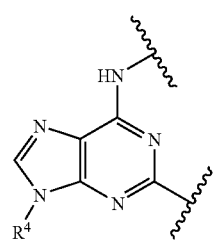

IId-W

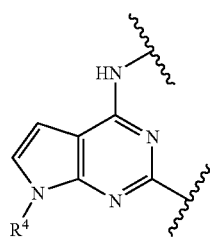

More preferred pyrimidine ring systems of formula IId include IId-A, IId-B, IId-D, IId-E, IId-J, IId-P, and IId-V, most preferably IId-A, IId-B, IId-D, IId-E, and IId-J.

The ring formed when $R^x$ and $R^y$ of formula IId are taken together may be substituted or unsubstituted. Suitable substituents include —R, halo, —O(CH$_2$)$_{2-4}$—N(R$^4$)$_2$, —O(CH$_2$)$_{2-4}$—R, —OR, —N(R$^4$)—(CH$_2$)$_{2-4}$—N(R$^4$)$_2$, —N(R$^4$)—(CH$_2$)$_{2-4}$—R, —C(═O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(═O)R, —N(R$^4$)COR, —N(R$^4$)CO$_2$(optionally substituted C$_{1-6}$ aliphatic), —N(R$^4$)N(R$^4$)$_2$, —C═NN(R$^4$)$_2$, —C═N—OR, —N(R$^4$)CON(R$^4$)$_2$, —N(R$^4$)SO$_2$N(R$^4$)$_2$, —N(R$^4$)SO$_2$R, or —OC(═O)N(R$^4$)$_2$, R and R$^4$ are as defined above. Preferred $R^x/R^y$ ring substituents include -halo, —R, —OR, —COR, —CO$_2$R, —CON(R$^4$)$_2$, —CN, —O(CH$_2$)$_{2-4}$—N(R$^4$)$_2$, —O(CH$_2$)$_{2-4}$—R, —NO$_2$—N(R$^4$)$_2$, —NR$^4$COR, —NR$^4$SO$_2$R, —SO$_2$N(R$^4$)$_2$ wherein R is hydrogen or an optionally substituted C$_{1-6}$ aliphatic group.

The $R^2$ and $R^{2'}$ groups of formula IId may be taken together to form a fused ring, thus providing a bicyclic ring system containing a pyrazole ring. Preferred fused rings include benzo, pyrido, pyrimido, and a partially unsaturated 6-membered carbocyclo ring. These are exemplified in the following formula IId compounds having a pyrazole-containing bicyclic ring system:

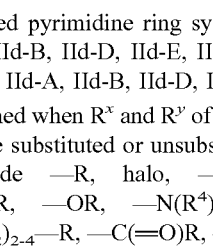

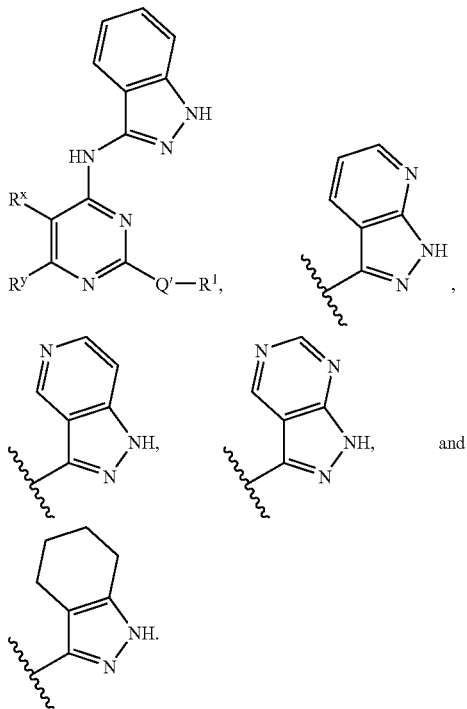

Preferred substituents on the R²/R²' fused ring of formula IId include one or more of the following: -halo, —N(R⁴)₂, —C₁₋₄ alkyl, —C₁₋₄ haloalkyl, —NO₂, —O(C₁₋₄ alkyl), —CO₂(C₁₋₄ alkyl), —CN, —SO₂(C₁₋₄ alkyl), —SO₂NH₂, —OC(O)NH₂, —NH₂SO₂(C₁₋₄ alkyl), —NHC(O)(C₁₋₄ alkyl), —C(O)NH₂, and —CO(C₁₋₄ alkyl), wherein the (C₁₋₄ alkyl) is a straight, branched, or cyclic alkyl group. Preferably, the (C₁₋₄ alkyl) group is methyl.

When the pyrazole ring system of formula IId is monocyclic, preferred R² groups include hydrogen or a substituted or unsubstituted group selected from aryl, heteroaryl, or a C₁₋₆ aliphatic group. Examples of such preferred R² groups include H, methyl, ethyl, propyl, cyclopropyl, i-propyl, cyclopentyl, hydroxypropyl, methoxypropyl, and benzyloxypropyl. A preferred R²' group is hydrogen.

When Ring D of formula IId is monocyclic, preferred Ring D groups include phenyl, pyridyl, pyridazinyl, pyrimidinyl, and pyrazinyl.

When Ring D of formula IId is bicyclic, preferred bicyclic Ring D groups include naphthyl, tetrahydronaphthyl, indanyl, benzimidazolyl, quinolinyl, indolyl, isoindolyl, indolinyl, benzo[b]furyl, benzo[b]thiophenyl, indazolyl, benzothiazolyl, cinnolinyl, phthalazinyl, quinazolinyl, quinoxazolinyl, 1,8-naphthyridinyl and isoquinolinyl.

On Ring D of formula IId, preferred T—R⁵ or V—Z—R⁵ substituents include -halo, —CN, —NO₂, —N(R⁴)₂, optionally substituted C₁₋₆ aliphatic group, —OR, —C(O)R, —CO₂R, —CONH(R⁴), —N(R⁴)COR, —N(R⁴)CO₂R, —SO₂N(R⁴)₂, —N(R⁴)SO₂R, —N(R⁶)COCH₂N(R⁴)₂, —N(R⁶)COCH₂CH₂N(R⁴)₂, and —N(R⁶)COCH₂CH₂CH₂N(R⁴)₂ wherein R is selected from hydrogen, C₁₋₆ aliphatic, phenyl, a 5–6 membered, heteroaryl ring, or a 5–6 membered heterocyclic ring. More preferred R⁵ substituents include —Cl, —Br, —F, —CN, —CF₃, —COOH, —CONHMe, —CONHEt, —NH₂, —NHAc, —NHSO₂Me, —NHSO₂Et, —NHSO₂(n-propyl), —NHSO₂(isopropyl), —NHCOEt, —NHCOCH₂NHCH₃, —NHCOCH₂N(CO₂t-Bu)CH₃, —NHCOCH₂N(CH₃)₂, —NHCOCH₂CH₂N(CH₃)₂, —NHCOCH₂CH₂CH₂N(CH₃)₂, —NHCO(cyclopropyl), —NHCO(isobutyl), —NHCOCH₂(morpholin-4-yl), —NHCOCH₂CH₂(morpholin-4-yl), —NHCOCH₂CH₂CH₂(morpholin-4-yl), —NHCO₂(t-butyl), —NH(C₁₋₄ aliphatic) such as —NHMe, —N(C₁₋₄ aliphatic)₂ such as —NMe₂, OH, —O(C₁₋₄ aliphatic) such as —OMe, C₁₋₄ aliphatic such as methyl, ethyl, cyclopropyl, isopropyl, or t-butyl, and —CO₂(C₁₋₄ aliphatic).

Preferred Q' groups of formula IId include —C(R⁶')₂— or 1,2-cyclopropanediyl, wherein each R⁶' is independently selected from hydrogen or methyl. A more preferred Q' group, is —CH₂—.

Preferred formula IIc compounds have one or more, and more preferably all, of the features selected from the group consisting of:

(a) Rˣ and Rʸ are taken together with their intervening atoms to form a fused, unsaturated or partially unsaturated, 5–6 membered ring having 0–2 heteroatoms selected from oxygen, sulfur, or nitrogen, wherein each substitutable ring carbon of said fused ring formed by Rˣ and Rʸ is independently substituted by oxo, T—R³, or L—Z—R³, and each substitutable ring nitrogen of said ring formed by Rˣ and Rʸ is independently substituted by R⁴;

(b) R¹ is T-(Ring D), wherein T is a valence bond or a methylene unit and wherein said methylene unit is optionally replaced by —O—, —NH—, or —S—;

(c) Ring D is a 5–7 membered monocyclic ring or an 8–10-membered bicyclic ring selected from an aryl or heteroaryl ring;

(d) R² is —R or —T—W—R⁶ and R²' is hydrogen; or R² and R²' are taken together to form an optionally substituted benzo ring; and (e) R³ is selected from —R, -halo, —OR, or —N(R⁴)₂.

More preferred compounds of formula IIc have one or more, and more preferably all, of the features selected from the group consisting of:

(a) Rˣ and Rʸ are taken together to form a benzo, pyrido, cyclopento, cyclohexo, cyclohepto, thieno, piperidino, or imidazo ring;

(b) R¹ is T-(Ring D), wherein T is a valence bond or a methylene unit and wherein said methylene unit is optionally replaced by —O—, and Ring D is a 5–6 membered monocyclic ring or an 8–10 membered bicyclic ring selected from an aryl or heteroaryl ring;

(c) R² is —R and, R²' is hydrogen, wherein R is selected from hydrogen, C₁₋₆ aliphatic, phenyl, a 5–6 membered heteroaryl ring, or a 5–6 membered heterocyclic ring;

(d) R³ is selected from —R, -halo, —OR, or —N(R⁴)₂, wherein R is selected from hydrogen, C₁₋₆ aliphatic, or 5–6 membered heterocyclyl, phenyl, or 5–6 membered heteroaryl, and L is —O—, —S—, or —N(R⁴)—; and (e) Q' is —C(R⁶')₂— or 1,2-cyclopropanediyl, wherein each R⁶' is-independently selected from hydrogen or methyl.

Even more preferred compounds of formula IIc have one or more, and more preferably all, of the features selected from the group consisting of:

(a) Rˣ and Rʸ are taken-together to form a benzo, pyrido, piperidino, or cyclohexo ring;

(b) R¹ is T-Ring D, wherein T is a valence bond and Ring D is a 5–6 membered aryl or heteroaryl ring;

(c) R² is hydrogen or C₁₋₄ aliphatic and R²' is hydrogen;

(d) R³ is selected from —R, —OR, or —N(R⁴)₂, wherein R is selected from hydrogen, C₋₁₋₆ aliphatic, 5–6 membered heterocyclyl, phenyl, or 5–6 membered heteroaryl, and L is —O—, —S—, or —NH—;.

(e) Ring D is substituted by up to three substituents selected from -halo, —CN, —NO₂, —N(R⁴)₂, optionally substituted C₁₋₆ aliphatic group, —OR, —C(O)R, —CO₂R, —CONH(R⁴); —N(R⁴)COR, —N(R⁴)CO₂R, —SO₂N(R⁴)₂, —N(R⁴)SO₂R, —N(R⁶)COCH₂N(R⁴)₂, —N(R⁶)COCH₂CH₂N(R⁴)₂, or —N(R⁶)COCH₂CH₂CH₂N(R⁴)₂, wherein R is selected from hydrogen, C₁₋₆ aliphatic, phenyl, a 5–6 membered heteroaryl ring, or a 5–6 membered heterocyclic, ring; and (f) Q' is —CH₂—.

Representative compounds of formula IId are shown below in Table 4.

TABLE 4

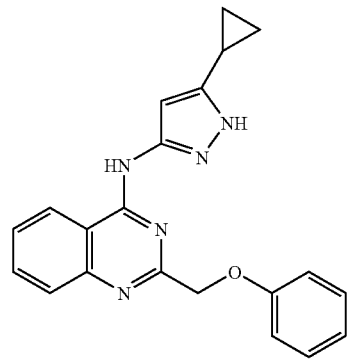

IId-1

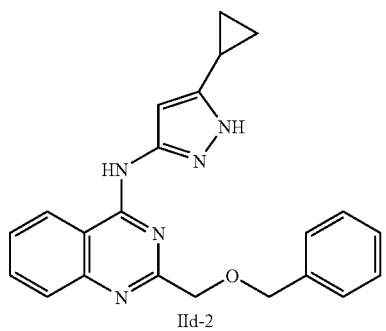

IId-2

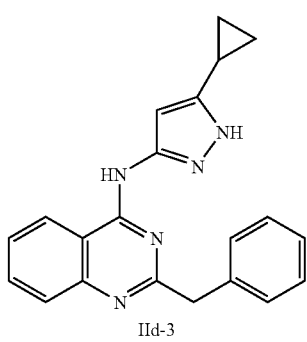

IId-3

TABLE 4-continued

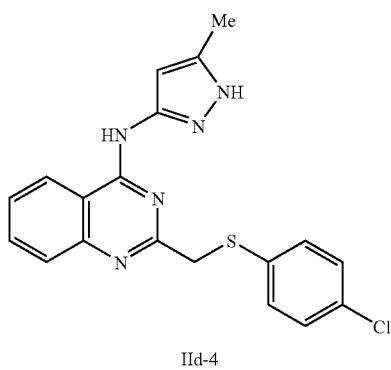

IId-4

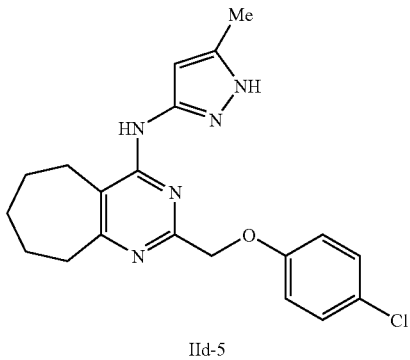

IId-5

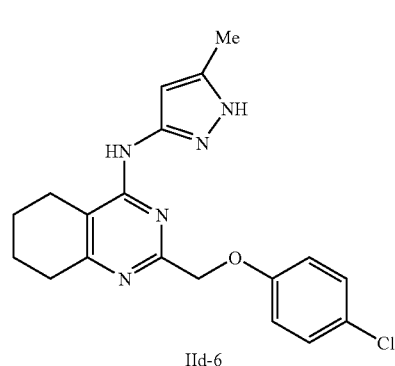

IId-6

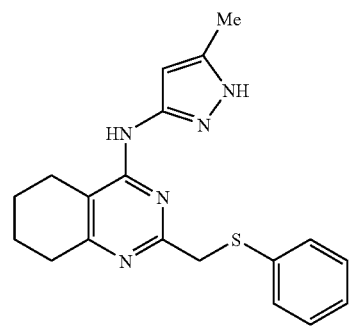

IId-7

TABLE 4-continued
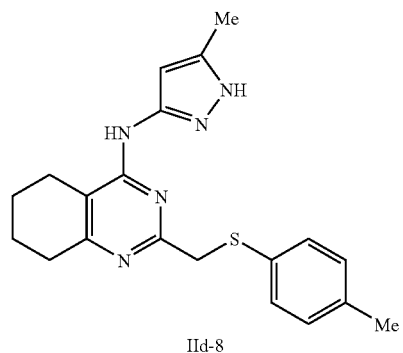
IId-8
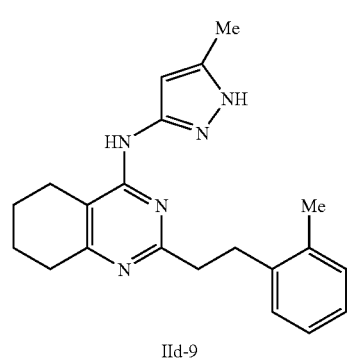
IId-9
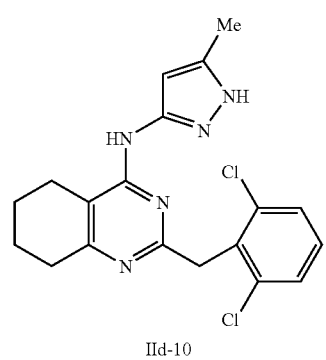
IId-10
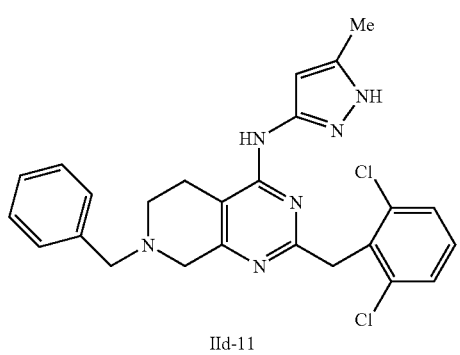
IId-11
TABLE 4-continued
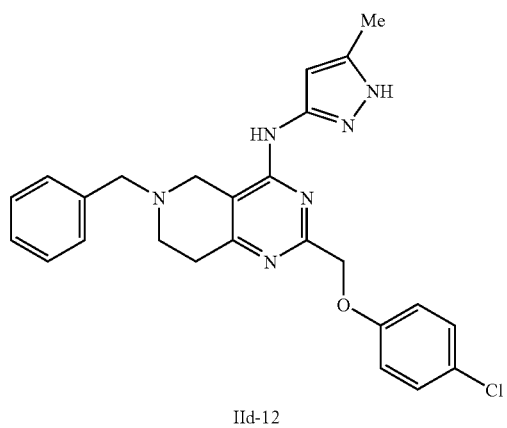
IId-12
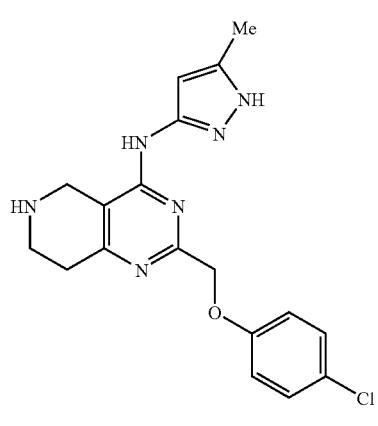
IId-13
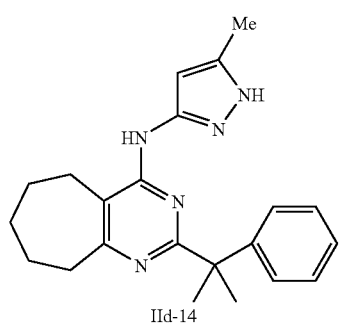
IId-14
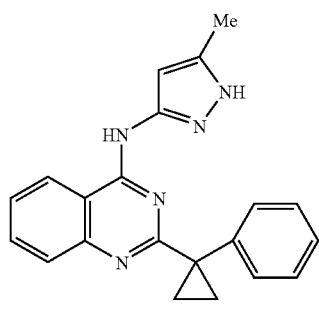
IId-15

TABLE 4-continued

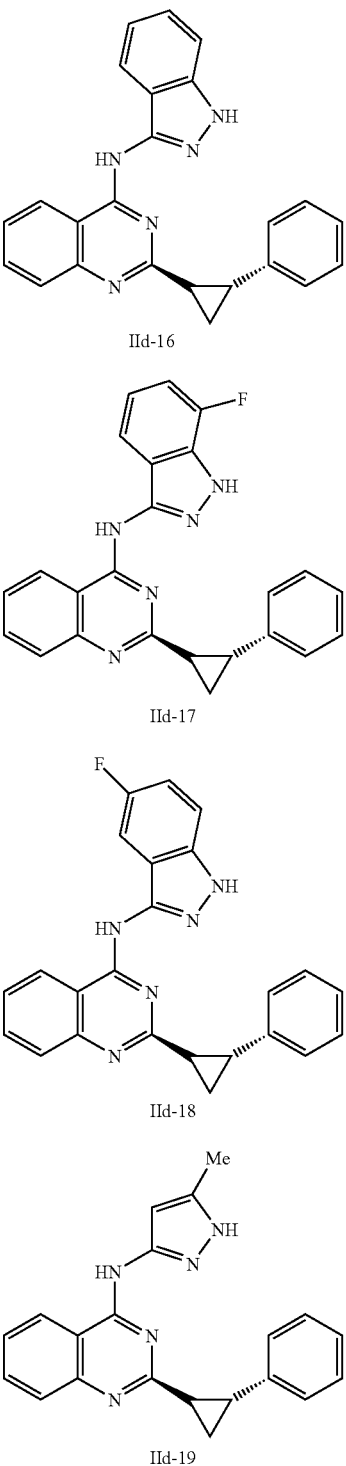

IId-16

IId-17

IId-18

IId-19

In another embodiment, this invention provides a composition comprising a compound of formula IId and a pharmaceutically acceptable carrier.

Another aspect of this invention relates to a method of treating or preventing an Aurora-2-mediated disease with an Aurora-2 inhibitor, which method comprises administering to a patient in need of such a treatment a therapeutically effective amount of a compound of formula IId or a pharmaceutical composition thereof.

Another aspect of this invention relates to a method of inhibiting Aurora-2 activity in a patient, which method comprises administering to the patient a compound of formula IId or a composition comprising said compound.

Another aspect of this invention relates to a method of treating or preventing a GSK-3-mediated disease with a GSK-3 inhibitor, which method comprises administering to a patient in need of such a treatment a therapeutically effective amount of a compound of formula IId or a pharmaceutical composition thereof.

One aspect of this invention relates to a method of enhancing glycogen synthesis and/or lowering blood levels of glucose in a patient in need thereof, which method comprises administering to the patient a therapeutically effective amount of a compound of formula IId or a pharmaceutical composition thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of β-catenin, which is useful for treating schizophrenia.

Another aspect of this invention relates to a method of inhibiting GSK-3 activity in a patient, which method comprises administering to the patient a compound of formula IId or a composition comprising said compound.

Another method relates to inhibiting Aurora-2 or GSK-3 activity in a biological sample, which method comprises contacting the biological sample with the Aurora-2 or GSK-3 inhibitor of formula IId, or a pharmaceutical composition thereof, in an amount effective to inhibit Aurora-2 or GSK-3.

Each of the aforementioned methods directed to the inhibition of Aurora-2 or GSK-3, or the treatment of a disease alleviated thereby, is preferably carried out with a preferred compound of formula IId, as described above.

Another embodiment of this invention relates to compounds of formula IIIa:

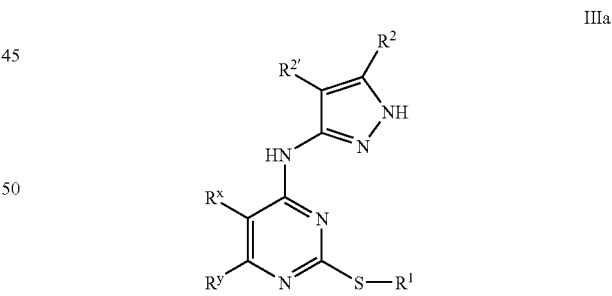

IIIa or a pharmaceutically acceptable derivative or prodrug thereof, wherein:

$R^x$ and $R^y$ are independently selected from T—$R^3$ or L—Z—$R^3$;

$R^1$ is T-(Ring D);

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein each substitutable ring carbon of Ring D is independently substituted by oxo, T—$R^5$, or V—Z—R⁵, and each substitutable ring nitrogen of Ring D is independently substituted by —R⁴;

T is a valence bond or a $C_{1-4}$ alkylidene chain;

Z is a $C_{1-4}$ alkylidene chain;

L is —O—, —S—, —SO—, —SO₂—, —N(R⁶)SO₂—, —SO₂N(R⁶)—, —N(R⁶)—, —CO—, —CO₂—, —N(R⁶)CO—, —N(R⁶)C(O)O—, —N(R⁶)CON(R⁶)—, —N(R⁶)SO₂N(R⁶)—, —N(R⁶)N(R⁶)—, —C(O)N(R⁶)—, —OC(O)N(R⁶)—, —C(R⁶)₂O—, —C(R⁶)₂S—, —C(R⁶)₂SO—, —C(R⁶)₂SO₂—, —C(R⁶)₂SO₂N(R⁶)—, —C(R⁶)₂N(R⁶)—, —C(R⁶)₂N(R⁶)C(O)—, —C(R⁶)₂N(R⁶)C(O)O—, —C(R⁶)=NN(R⁶)—, —C(R⁶)=N—O—, —C(R⁶)₂N(R⁶)N(R⁶)—, —C(R⁶)₂N(R⁶)SO₂N(R⁶)—, or —C(R⁶)₂N(R⁶)CON(R⁶)—;

R² and R²' are independently selected from —R, —T—W—R⁶, or R² and R²' are taken together with their intervening atoms to form a fused, 5–8 membered, unsaturated or partially unsaturated, ring having 0–3 ring heteroatoms selected from nitrogen, oxygen, or sulfur, wherein each substitutable ring carbon of said fused ring formed by R² and R²' is independently substituted by halo, oxo, —CN, —NO₂, —R⁷, or —V—R⁶, and each substitutable ring nitrogen of said ring formed by R² and R²' is independently substituted by R⁴;

R³ is selected from —R, -halo, —OR, —C(=O)R, —CO₂R, —COCOR, —COCH₂COR, —NO₂, —CN, —S(O)R, —S(O)₂R, —SR, —N(R⁴)₂, —CON(R⁷)₂, —SO₂N(R⁷)₂, —OC(=O)R, —N(R⁷)COR, —N(R⁷)CO₂(C₁₋₆ aliphatic), —N(R⁴)N(R⁴)₂, —C=NN(R⁴)₂, —C=N—OR, —N(R⁷)CON(R⁷)₂, —N(R⁷)SO₂N(R⁷)₂, —N(R⁴)SO₂R, or —OC(=O)N(R⁷)₂;

each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;

each R⁴ is independently selected from —R⁷, —COR⁷, —CO₂(optionally substituted $C_{1-6}$ aliphatic), —CON(R⁷)₂, or —SO₂R⁷;

each R⁵ is independently selected from —R, halo, —OR, —C(=O)R, —CO₂R, —COCOR, —NO₂, —CN, —S(O)R, —SO₂R, —SR, —N(R⁴)₂, —CON(R⁴)₂, —SO₂N(R⁴)₂, —OC(=O)R, —N(R⁴)COR, —N(R⁴)CO₂(optionally substituted $C_{1-6}$ aliphatic) —N(R⁴)N(R⁴)₂, —C=NN(R⁴)₂, —C=N—OR, —N(R⁴)CON(R⁴)₂, —N(R⁴)SO₂N(R⁴)₂, —N(R⁴)SO₂R, or —OC(=O)N(R⁴)₂;

V is —O—, —S—, —SO—, —SO₂—, —N(R⁶)SO₂—, —SO₂N(R⁶)—, —N(R⁶)—, —CO—, —CO₂—, —N(R⁶)CO—, —N(R⁶)C(O)O—, —N(R⁶)CON(R⁶)—, —N(R⁶)SO₂N(R⁶)—, —N(R⁶)N(R⁶)—, —C(O)N(R⁶)—, —OC(O)N(R⁶)—, —C(R⁶)₂O—, —C(R⁶)₂S—, —C(R⁶)₂SO—, —C(R⁶)₂SO₂—, —C(R⁶)₂SO₂N(R⁶)—, —C(R⁶)₂N(R⁶)—, —C(R⁶)₂N(R⁶)C(O)—, —C(R⁶)₂N(R⁶)C(O)O—, —C(R⁶)=NN(R⁶)—, —C(R⁶)=N—O—, —C(R⁶)₂N(R⁶)N(R⁶)—, —C(R⁶)₂N(R⁶)SO₂N(R⁶)—, or —C(R⁶)₂N(R⁶)CON(R⁶)—;

W is —C(R⁶)₂O—, —C(R⁶)₂S—, —C(R⁶)₂SO—, —C(R⁶)₂SO₂—, —C(R⁶)₂SO₂N(R⁶)—, —C(R⁶)₂N(R⁶)—, —CO—, —CO₂—, —C(R⁶)OC(O)—, —C(R⁶)OC(O)N(R⁶)—, —C(R⁶)₂N(R⁶)CO—, —C(R⁶)₂N(R⁶)C(O)O—, —C(R⁶)=NN(R⁶)—, —C(R⁶)=N—O—, —C(R⁶)₂N(R⁶)N(R⁶)—, —C(R⁶)₂N(R⁶)SO₂N(R⁶)—, —C(R⁶)₂N(R⁶)CON(R⁶)—, or —CON(R⁶)—;

each R⁶ is independently selected from hydrogen or an optionally substituted $C_{1-4}$ aliphatic group, or two R⁶ groups on the same nitrogen atom are taken together with the nitrogen atom to form a 5–6 membered heterocyclyl or heteroaryl ring; and each R⁷ is independently selected from hydrogen or an optionally substituted $C_{1-6}$ aliphatic group, or two R⁷ on the same nitrogen are taken together with the nitrogen to form a 5–8 membered heterocyclyl or heteroaryl ring.

Preferred $R^x$ groups of formula IIIa include hydrogen, alkyl- or dialkylamino, acetamido, or a $C_{1-4}$ aliphatic group such as methyl, ethyl, cyclopropyl, or isopropyl.

Preferred $R^y$ groups of formula IIIa include T—R³ or L—Z—R³ wherein T is a valence bond or a methylene, L is —O—, —S—, or —N(R⁴)—, C(R⁶)₂O—, —CO— and R³ is —R, —N(R⁴)₂, or —OR. Examples of preferred $R^y$ groups include 2-pyridyl, 4-pyridyl, pyrrolidinyl, piperidinyl, morpholinyl, piperazinyl, methyl, ethyl, cyclopropyl, isopropyl, t-butyl, alkoxyalkylamino such as methoxyethylamino, alkoxyalkyl such as methoxymethyl or methoxyethyl, alkyl- or dialkylamino such as ethylamino or dimethylamino, alkyl- or dialkylaminoalkoxy such as dimethylaminopropyloxy, acetamido, optionally substituted phenyl such as phenyl or halo-substituted phenyl.

The R² and R²' groups of formula IIIa may be taken together to form a fused ring, thus providing a bicyclic ring system containing a pyrazole ring. Preferred fused rings include benzo, pyrido, pyrimido, and a partially unsaturated 6-membered carbocyclo ring. These are exemplified in the following formula IIIa compounds having a pyrazole-containing bicyclic ring system:

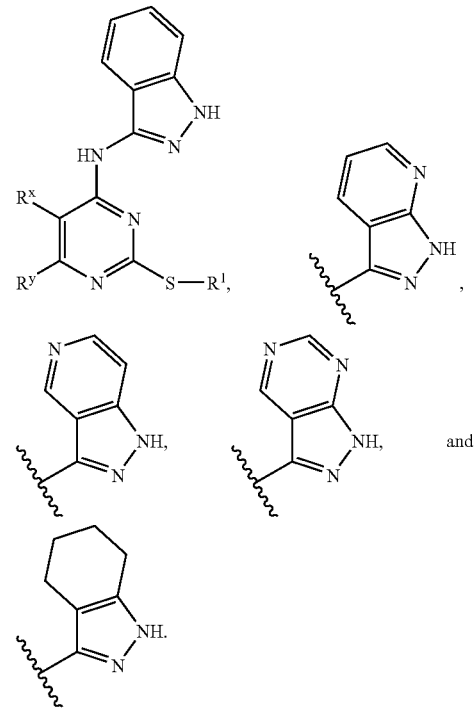

Preferred substituents on the R²/R²' fused ring of formula IIIa include one or more of the following: -halo, —N(R⁴)₂, —$C_{1-4}$ alkyl, —$C_{1-4}$ haloalkyl, —NO₂, —O($C_{1-4}$ alkyl), —CO₂($C_{1-4}$ alkyl), —CN, —SO₂($C_{1-4}$ alkyl), —SO₂NH₂, —OC(O)NH₂, —NH₂SO₂($C_{1-4}$ alkyl), —NHC(O)($C_{1-4}$ alkyl), —C(O)NH₂, and —CO($C_{1-4}$ alkyl), wherein the ($C_{1-4}$ alkyl) is a straight, branched, or cyclic alkyl group. Preferably, the ($C_{1-4}$ alkyl) group is methyl.

When the pyrazole ring system of formula IIIa is monocyclic, preferred $R^2$ groups include hydrogen or a substituted or unsubstituted group selected from aryl, heteroaryl, or a $C_{1-6}$ aliphatic group. Examples of such preferred $R^2$ groups include H, methyl, ethyl, propyl, cyclopropyl, i-propyl, cyclopentyl, hydroxypropyl, methoxypropyl, and benzyloxypropyl. A preferred $R^{2'}$ group is hydrogen.

When Ring D of formula IIIa is monocyclic, preferred Ring D groups include phenyl, pyridyl, pyridazinyl, pyrimidinyl, and pyrazinyl.

When Ring D of formula IIIa is bicyclic, preferred bicyclic Ring D groups include naphthyl, tetrahydronaphthyl, indanyl, benzimidazolyl, quinolinyl, indolyl, isoindolyl, indolinyl, benzo[b]furyl, benzo[b]thiophenyl, indazolyl, benzothiazolyl, cinnolinyl, phthalazinyl, quinazolinyl, quinoxazolinyl, 1,8-naphthyridinyl and isoquinolinyl.

On Ring D of formula IIIa, preferred T—$R^5$ or V—Z—$R^5$ substituents include -halo, —CN, —$NO_2$, —$N(R^4)_2$, optionally substituted $C_{1-6}$ aliphatic group, —OR, —C(O)R, —$CO_2R$, —$CONH(R^4)$, —$N(R^4)COR$, —$N(R^4)CO_2R$, —$SO_2N(R^4)_2$, —$N(R^4)SO_2R$, —$N(R^6)COCH_2N(R^4)_2$, —$N(R^6)COCH_2CH_2N(R^4)_2$, and —$N(R^6)COCH_2CH_2CH_2N(R^4)_2$, wherein R is selected from hydrogen, $C_{1-6}$ aliphatic, phenyl, a 5–6 membered heteroaryl ring, or a 5–6 membered heterocyclic ring. More preferred $R^5$ substituents include —Cl, —Br, —F, —CN, —$CF_3$, —COOH, —CONHMe, —CONHEt, —$NH_2$, —NHAc, —$NHSO_2Me$, —$NHSO_2Et$, —$NHSO_2$(n-propyl), —$NHSO_2$(isopropyl), —NHCOEt, —$NHCOCH_2NHCH_3$, —$NHCOCH_2N(CO_2t$-Bu) $CH_3$, —$NHCOCH_2N(CH_3)_2$, —$NHCOCH_2CH_2N(CH_3)_2$, —$NHCOCH_2CH_2CH_2N(CH_3)_2$, —NHCO(cyclopropyl), —NHCO(isobutyl), —$NHCOCH_2$(morpholin-4-yl), —$NHCOCH_2CH_2$(morpholin-4-yl), —$NHCOCH_2CH_2CH_2$(morpholin-4-yl), —$NHCO_2$(t-butyl), —$NH(C_{1-4}$ aliphatic) such as —NHMe, —$N(C_{1-4}$ aliphatic$)_2$ such as —$NMe_2$, OH, —$O(C_{1-4}$ aliphatic) such as —OMe, $C_{1-4}$ aliphatic such as methyl, ethyl, cyclopropyl, isopropyl, or t-butyl, and —$CO_2(C_{1-4}$ aliphatic).

Preferred formula IIIa compounds have one or more, and more preferably all, of the features selected from the group consisting of:
- (a) $R^x$ is hydrogen, alkyl- or dialkylamino, acetamido, or a $C_{1-4}$ aliphatic group;
- (b) $R^y$ is T—$R^3$ or L—Z—$R^3$, wherein T is a valence bond or a methylene and $R^3$ is —R, —$N(R^4)_2$, or —OR;
- (c) $R^1$ is T-(Ring D), wherein T is a valence bond or a methylene unit;
- (d) Ring D is a 5–7 membered monocyclic or an 8–10 membered bicyclic aryl or heteroaryl ring; and
- (e) $R^2$ is —R or —T—W—$R^6$ and $R^{2'}$ is hydrogen, or $R^2$ and $R^{2'}$ are taken together to form an optionally substituted benzo ring.

More-preferred compounds of formula IIIa have one or more, and more preferably all, of the features selected from the group consisting of:
- (a) $R^y$ is T—$R^3$ or L—Z—$R^3$ wherein T is a valence bond or a methylene and $R^3$ is selected from —R, —OR, or —$N(R^4)_2$, wherein R is selected from hydrogen, $C_{1-6}$ aliphatic, or 5–6 membered heterocyclyl, phenyl, or 5–6 membered heteroaryl;
- (b) $R^1$ is T-(Ring D), wherein T is a valence bond;
- (c) Ring D is a 5–6 membered monocyclic or an 8–10 membered bicyclic aryl or heteroaryl ring;
- (d) $R^2$ is —R and $R^{2'}$ is hydrogen, wherein R is selected from hydrogen, $C_{1-6}$ aliphatic, phenyl, a 5–6 membered heteroaryl ring, or a 5–6 membered heterocyclic ring; and
- (e) L is —O—, —S—, or —$N(R^4)$—.

Even more preferred compounds of formula IIIa have one or more, and more preferably all, of the features selected from the group consisting of:
- (a) $R^x$ is hydrogen methyl, ethyl, propyl, cyclopropyl, isopropyl, methylamino or acetimido;
- (b) $R^y$ is selected from 2-pyridyl, 4-pyridyl, pyrrolidinyl, piperidinyl, morpholinyl, piperazinyl, methyl, ethyl, cyclopropyl, isopropyl, t-butyl, alkoxyalkylamino, alkoxyalkyl, alkyl- or dialkylamino, alkyl- or dialkylaminoalkoxy, acetamido, optionally substituted phenyl, or methoxymethyl;
- (c) $R^1$ is T-(Ring D), wherein T is a valence bond and Ring D is a 5–6 membered aryl or heteroaryl ring, wherein Ring D is optionally substituted with one to two groups selected from -halo, —CN, —$NO_2$, —$N(R^4)_2$, optionally substituted $C_{1-6}$ aliphatic group, —OR, —$CO_2R$, —$CONH(R^4)$, —$N(R^4)COR$, —$N(R^4)SO_2R$, —$N(R^6)COCH_2CH_2N(R^4)_2$, or —$N(R^6)COCH_2CH_2CH_2N(R^4)_2$; and
- (d) $R^2$ is hydrogen or a substituted or unsubstituted $C_{1-6}$ aliphatic, and L is —O—, —S—, or —NH—.

Representative compounds of formula IIIa are shown below in Table 5.

TABLE 5

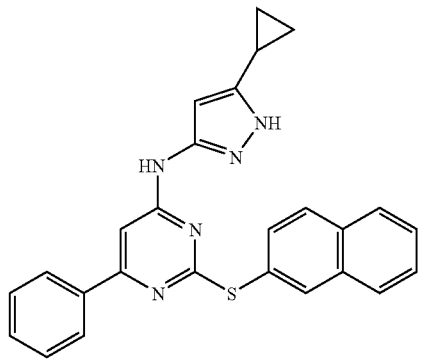

IIIa-1

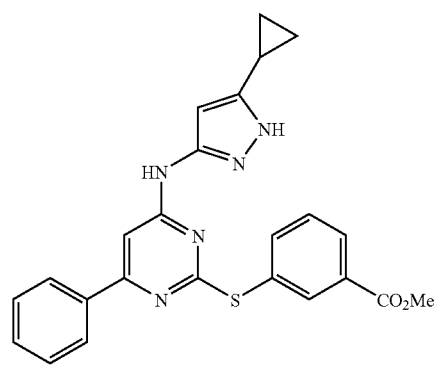

IIIa-2

TABLE 5-continued
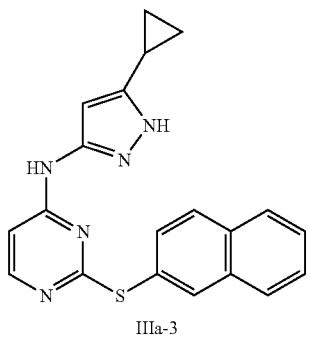
IIIa-3
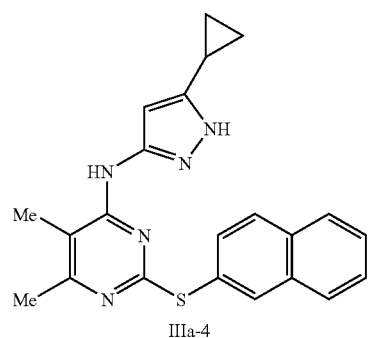
IIIa-4
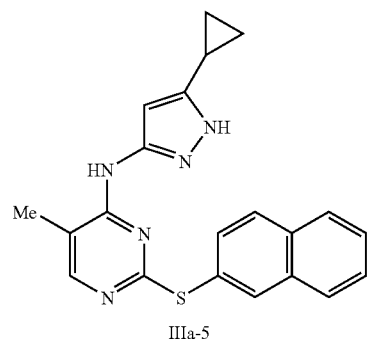
IIIa-5
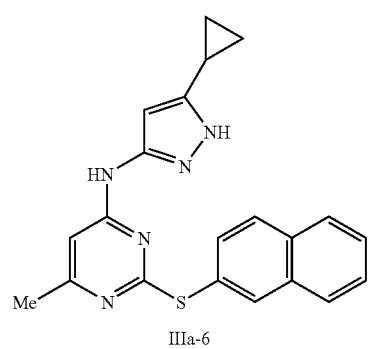
IIIa-6
TABLE 5-continued
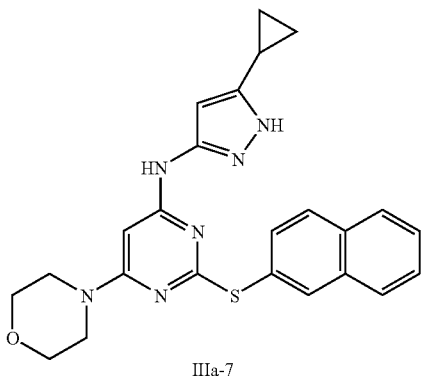
IIIa-7
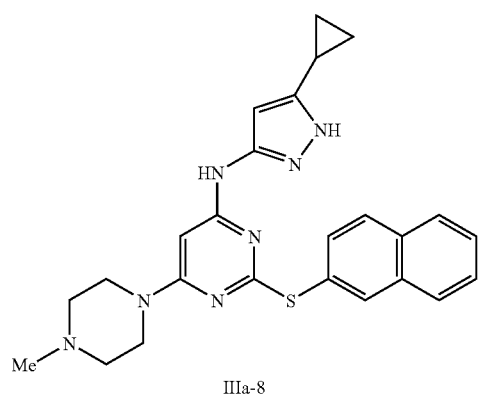
IIIa-8
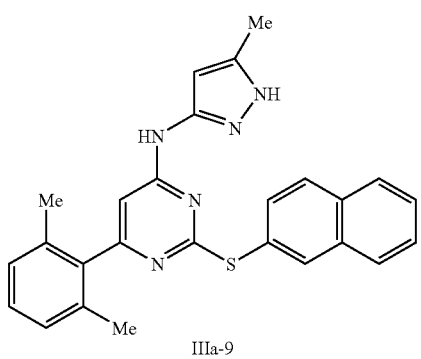
IIIa-9
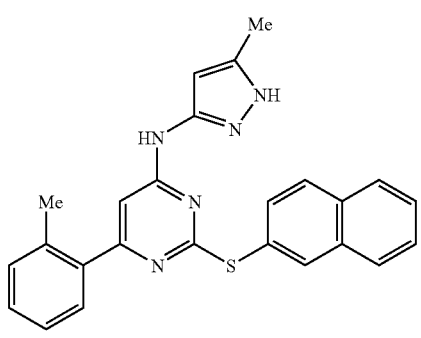
IIIa-10

TABLE 5-continued
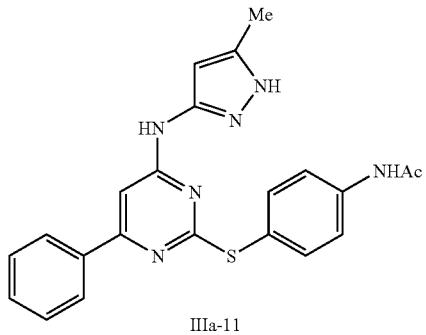
IIIa-11
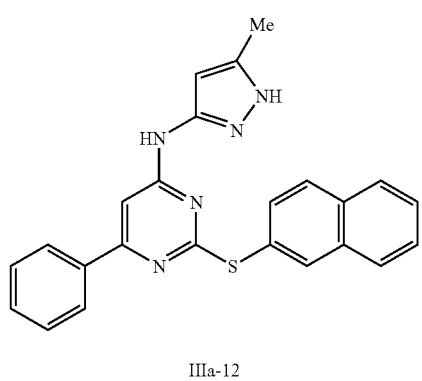
IIIa-12
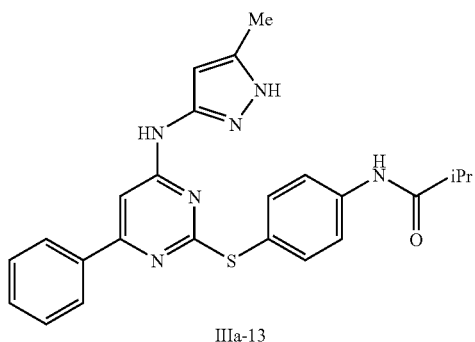
IIIa-13
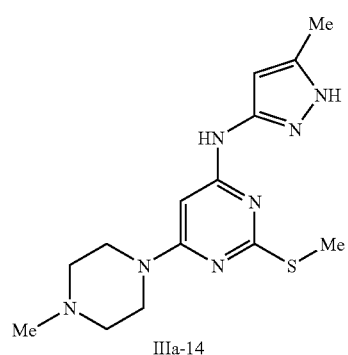
IIIa-14
TABLE 5-continued
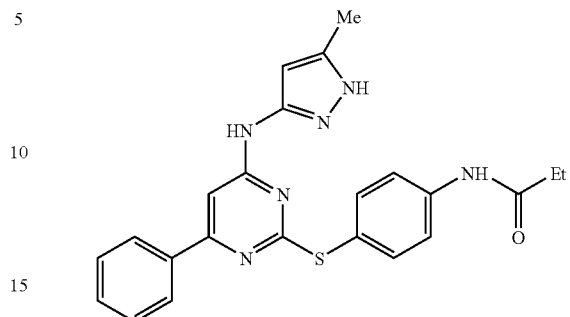
IIIa-15
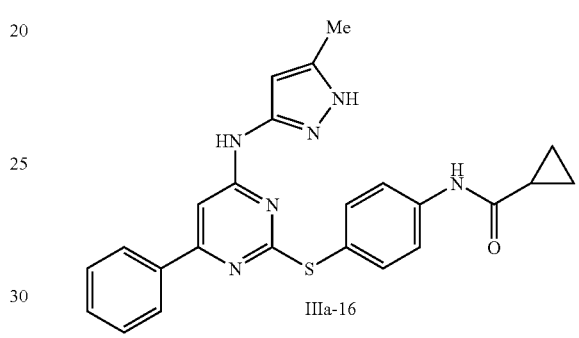
IIIa-16
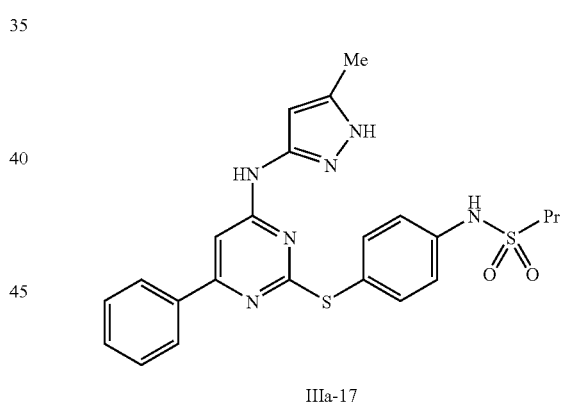
IIIa-17
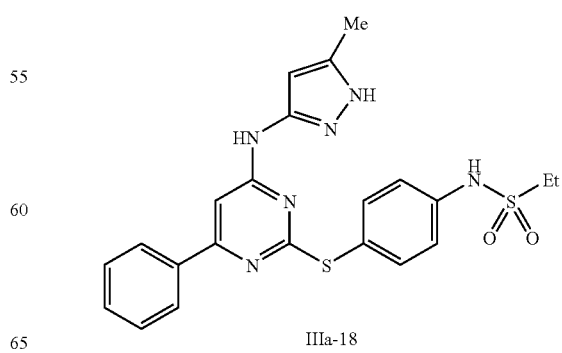
IIIa-18

TABLE 5-continued
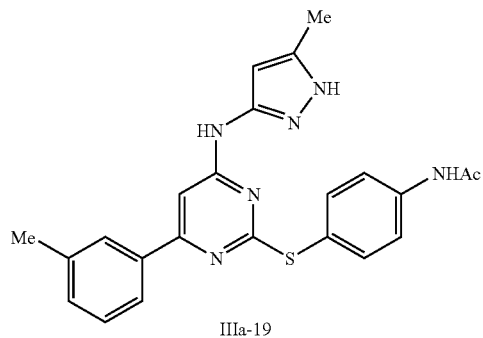
IIIa-19
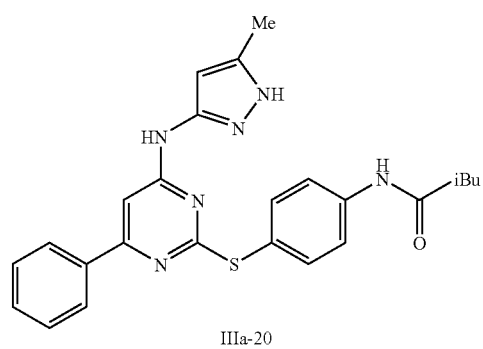
IIIa-20
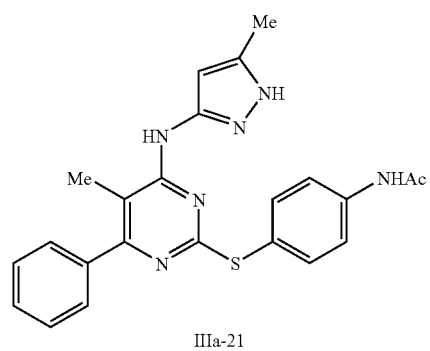
IIIa-21
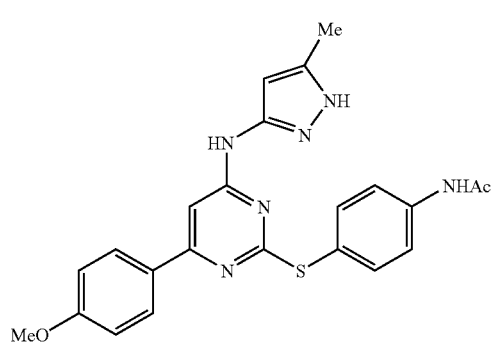
IIIa-22
TABLE 5-continued
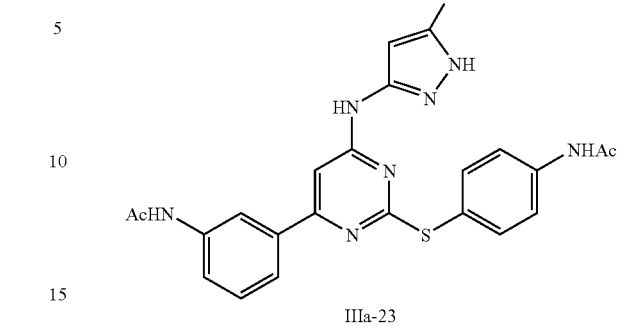
IIIa-23
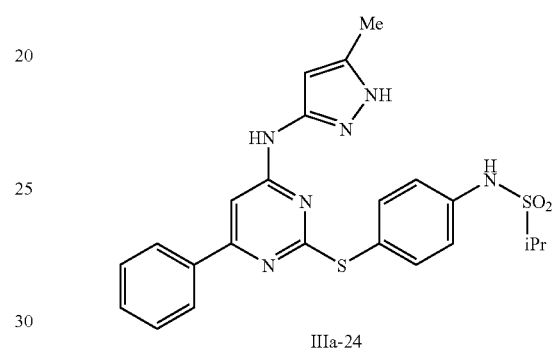
IIIa-24
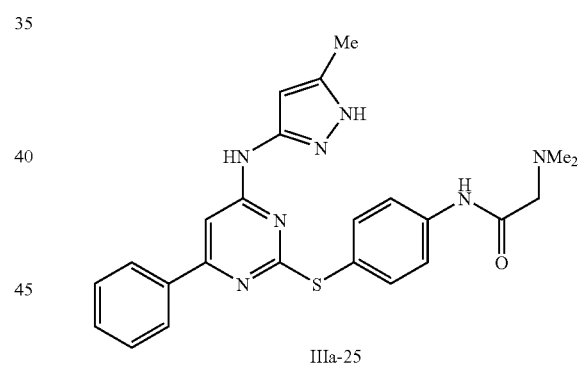
IIIa-25
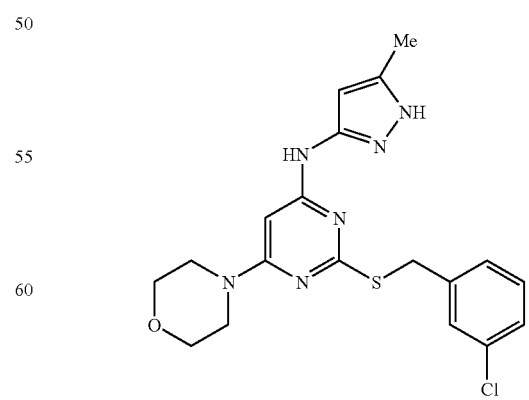
IIIa-26

TABLE 5-continued
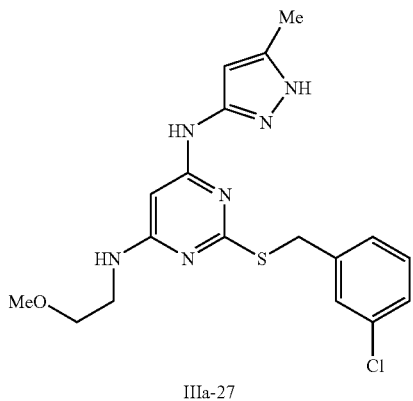
IIIa-27
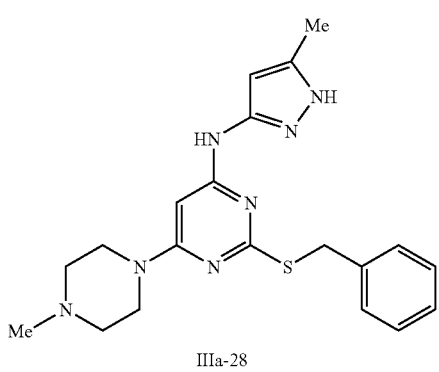
IIIa-28
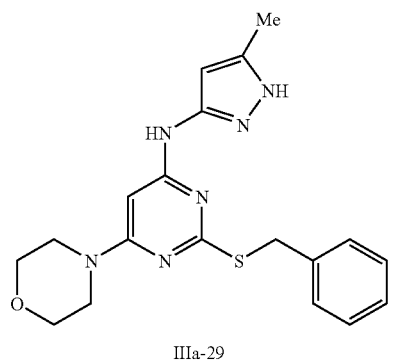
IIIa-29
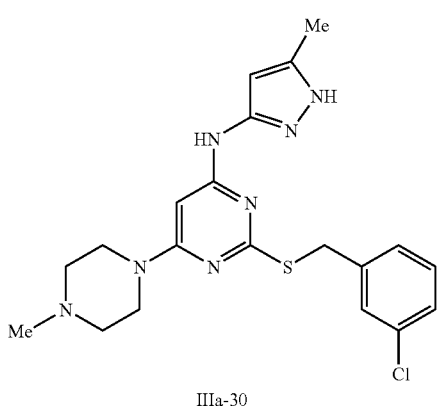
IIIa-30
TABLE 5-continued
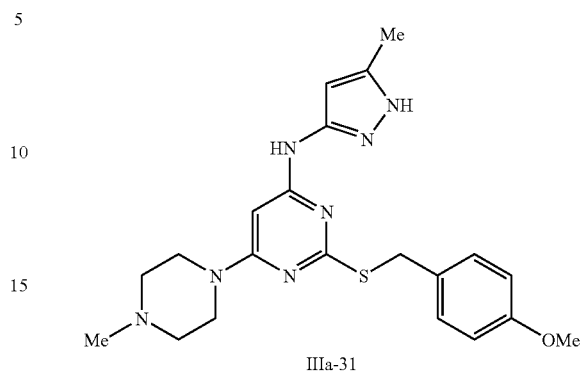
IIIa-31
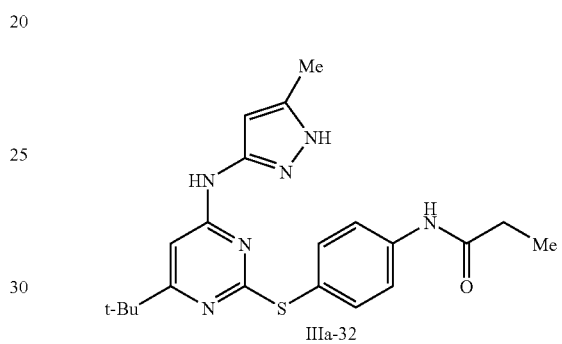
IIIa-32
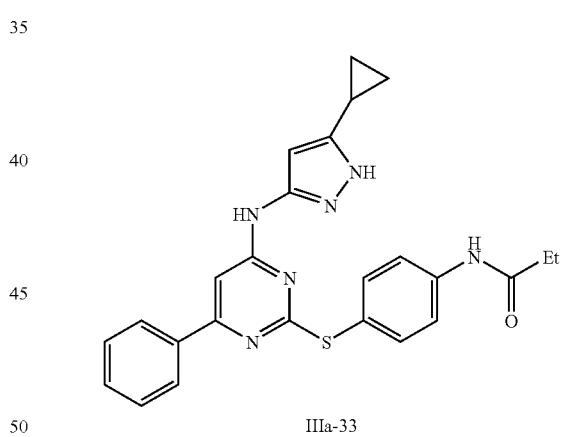
IIIa-33
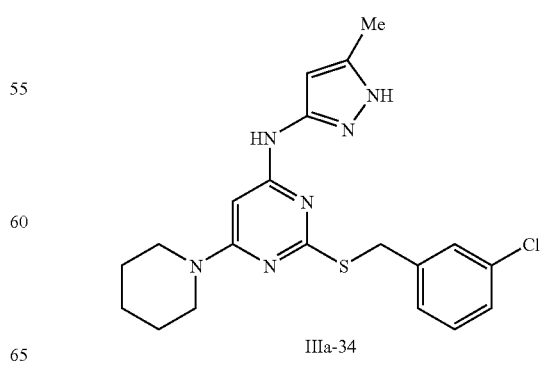
IIIa-34

TABLE 5-continued
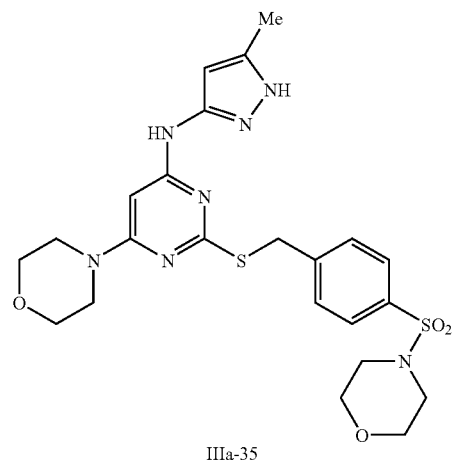
IIIa-35
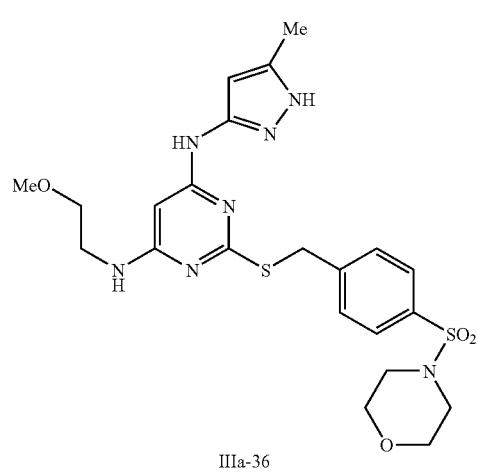
IIIa-36
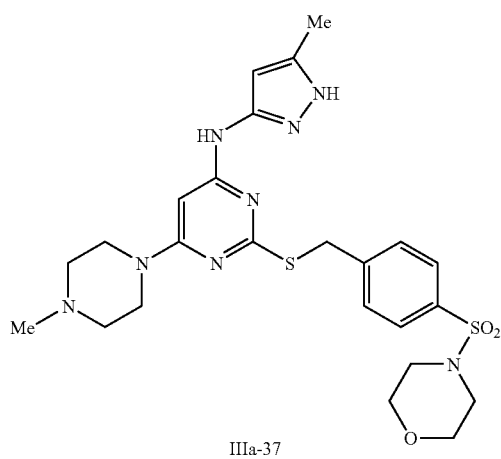
IIIa-37
TABLE 5-continued
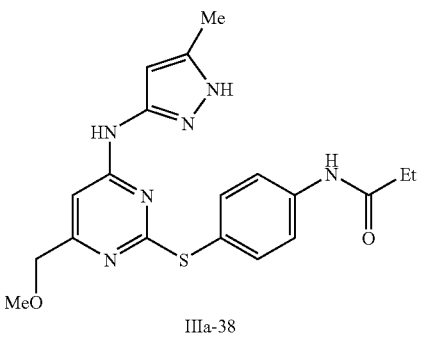
IIIa-38
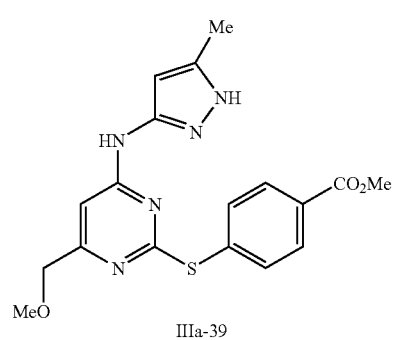
IIIa-39
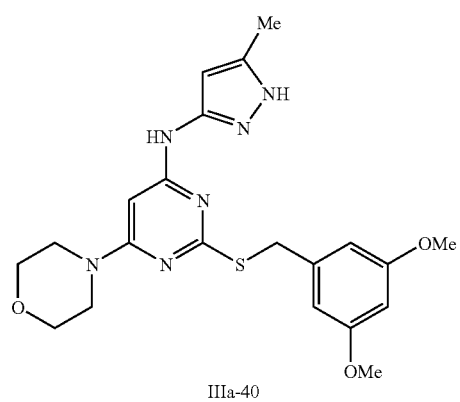
IIIa-40
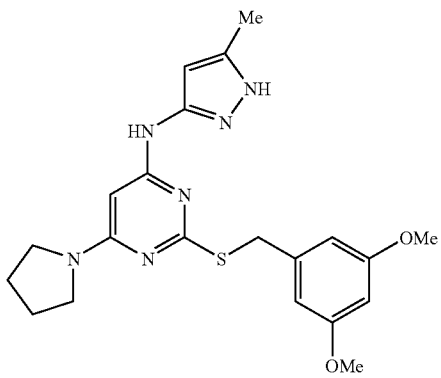
IIIa-41

TABLE 5-continued
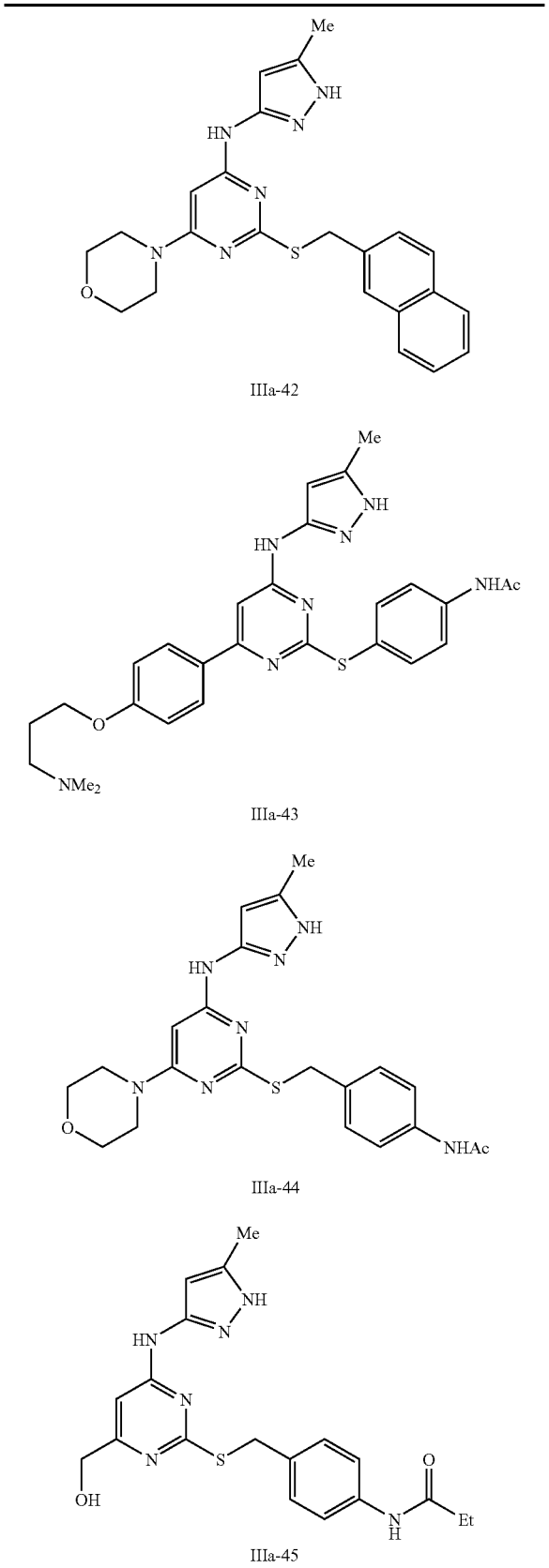
IIIa-42
IIIa-43
IIIa-44
IIIa-45
TABLE 5-continued
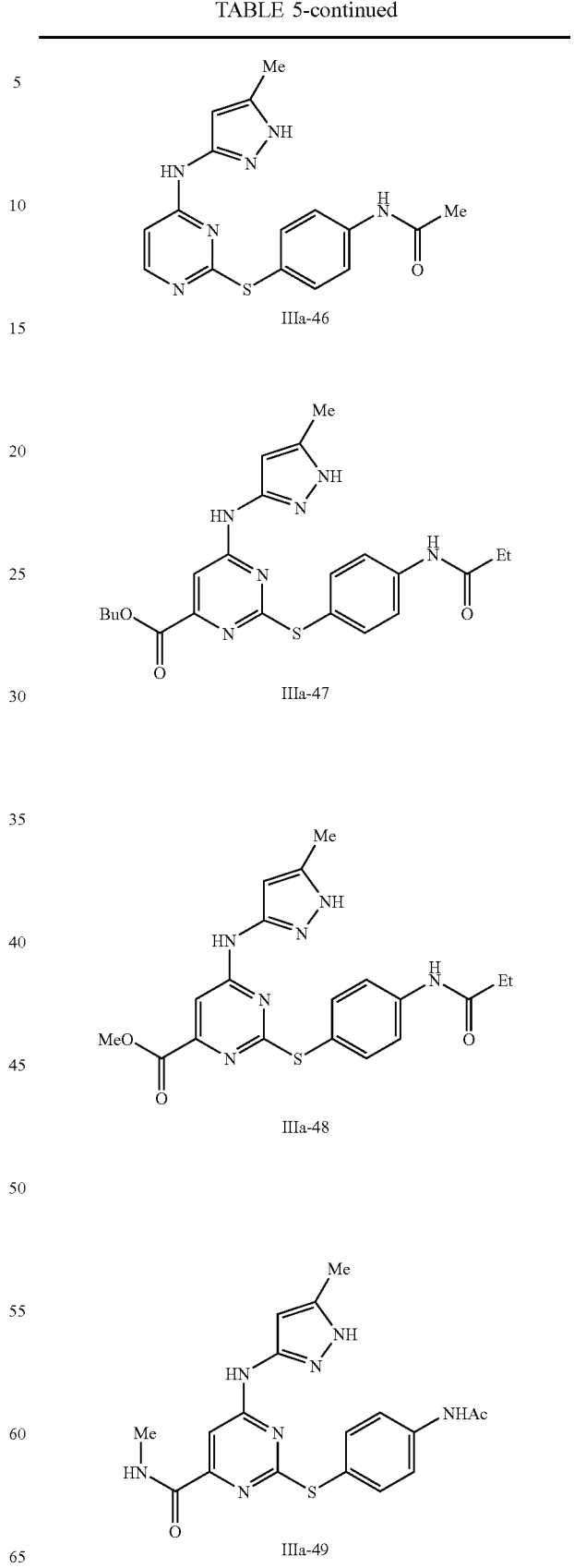
IIIa-46
IIIa-47
IIIa-48
IIIa-49

TABLE 5-continued
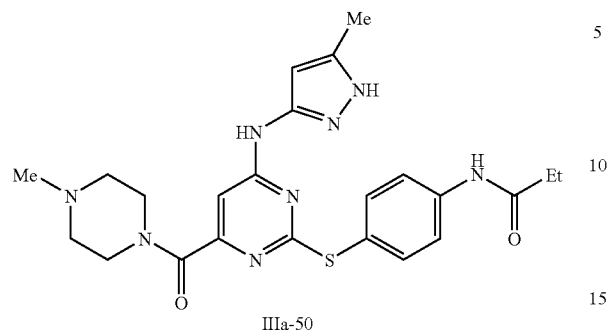
IIIa-50
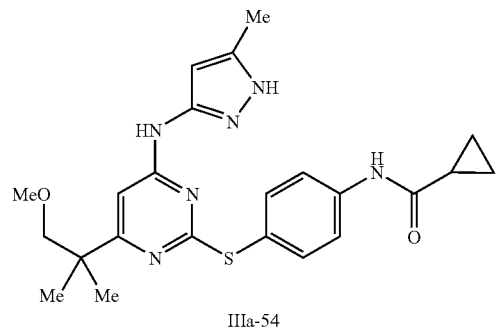
IIIa-54
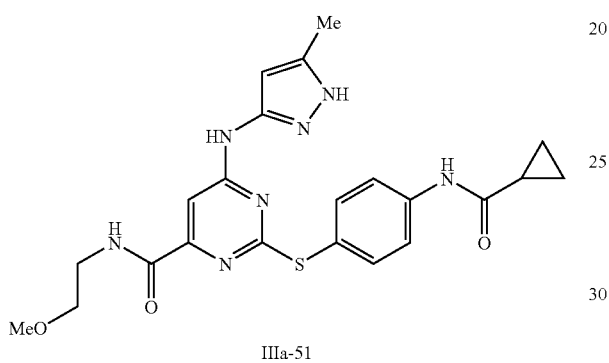
IIIa-51
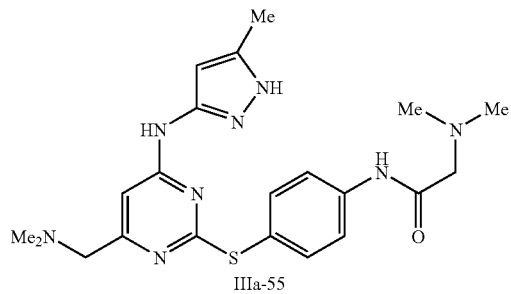
IIIa-55
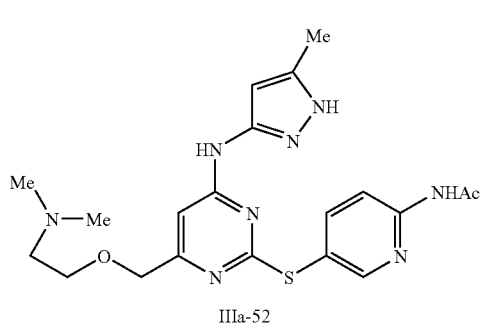
IIIa-52
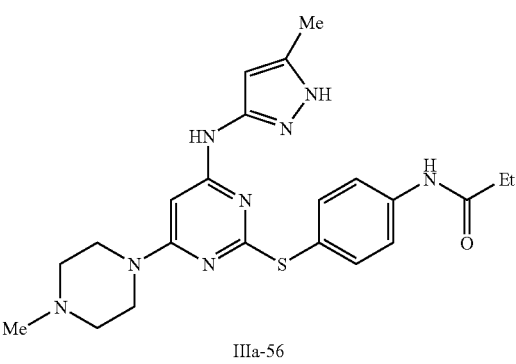
IIIa-56
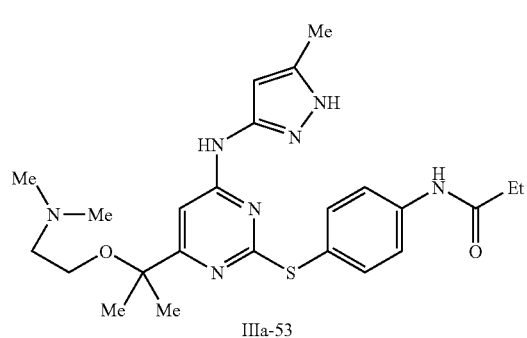
IIIa-53
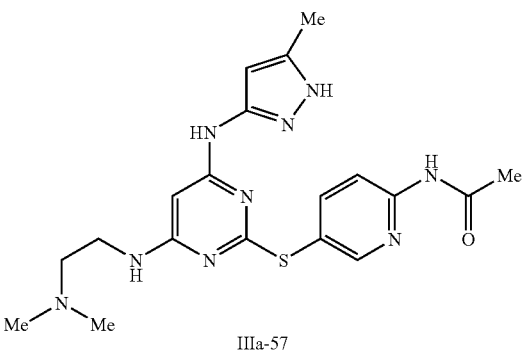
IIIa-57

TABLE 5-continued
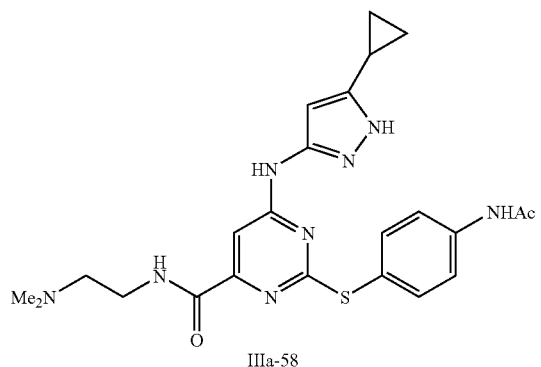
IIIa-58
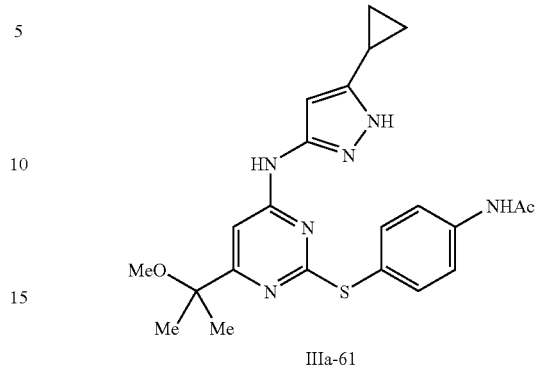
IIIa-61
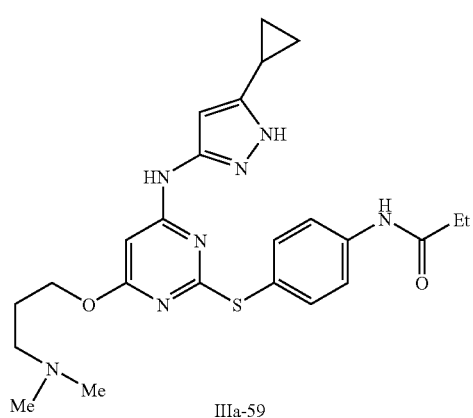
IIIa-59
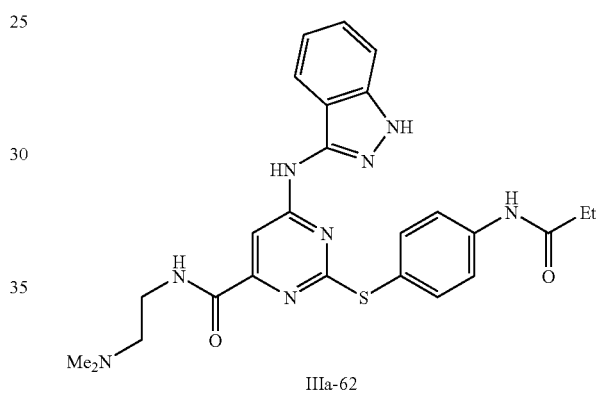
IIIa-62
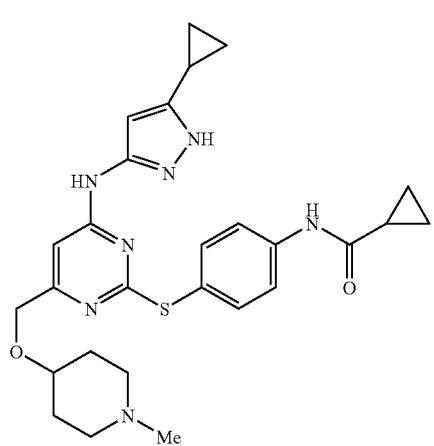
IIIa-60
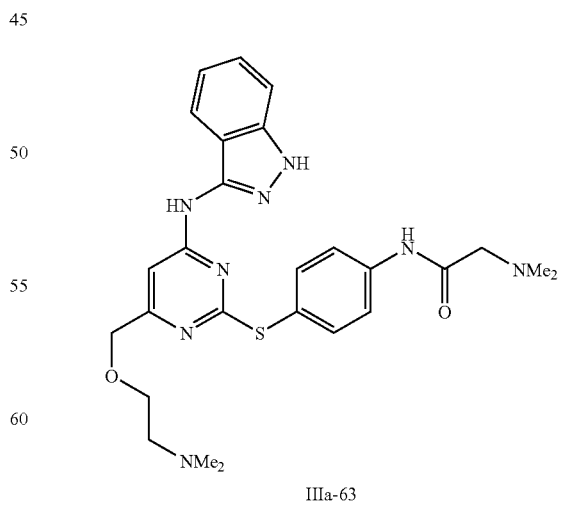
IIIa-63

In another embodiment, this invention provides a composition comprising a compound of formula IIIa and a pharmaceutically acceptable carrier.

Another aspect of this invention relates to a method of treating or preventing an Aurora-2-mediated disease with an Aurora-2 inhibitor, which method comprises administering to a patient in need of such a treatment a therapeutically effective amount of a compound of formula IIIa or a pharmaceutical composition thereof.

Another aspect of this invention relates to a method of inhibiting Aurora-2 activity in a patient, which method comprises administering to the patient a compound of formula IIIa or a composition comprising said compound.

Another aspect of this invention relates to a method of treating or preventing a GSK-3-mediated disease with a GSK-3 inhibitor, which method comprises administering to a patient in need of such a treatment a therapeutically effective amount of a compound of formula IIIa or a pharmaceutical composition thereof.

One aspect of this invention relates to a method of enhancing glycogen synthesis and/or lowering blood levels of glucose in a patient in need thereof, which method comprises administering to the patient a therapeutically effective amount of a compound of formula IIIa or a pharmaceutical composition thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of β-catenin, which is useful for treating schizophrenia.

Another aspect of this invention relates to a method of inhibiting GSK-3 activity in a patient, which method comprises administering to the patient a compound of formula IIIa or a composition comprising said compound.

Another aspect of this invention relates to a method of treating or preventing a Src-mediated disease with a Src inhibitor, which method comprises administering to a patient in need of such a treatment a therapeutically effective amount of a compound of formula IIIa or a pharmaceutical composition thereof.

Another aspect of the invention relates to inhibiting Src activity in a patient, which method comprises administering to the patient a compound of formula IIIa or a composition comprising said compound.

Another method relates to inhibiting Aurora-2, GSK-3, or Src activity in a biological sample, which method comprises contacting the biological sample with the Aurora-2, GSK-3, or Src inhibitor of formula IIIa, or a pharmaceutical composition thereof, in an amount effective to inhibit Aurora-2, GSK-3, or Src.

Each of the aforementioned methods directed to the inhibition of Aurora-2, GSK-3, or Src, or the treatment of a disease alleviated thereby, is preferably carried out with a preferred compound of formula IIIa, as described above.

Another embodiment of this invention relates to compounds of formula IIIb:

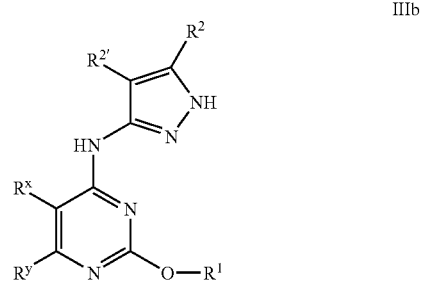

IIIb or a pharmaceutically acceptable derivative or prodrug thereof, wherein:

$R^x$ and $R^y$ are independently selected from T—$R^3$ or L—Z—$R^3$;

$R^1$ is T-(Ring D);

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein each substitutable ring carbon of Ring D is independently substituted by oxo, T—$R^5$, or V—Z—$R^5$, and each substitutable ring nitrogen of Ring D is independently substituted by —$R^4$;

T is a valence bond or a $C_{1-4}$ alkylidene chain;

Z is a $C_{1-4}$ alkylidene chain;

L is —O—, —S—, —SO—, —SO$_2$, —N(R$^6$)SO$_2$—, —SO$_2$N(R$^6$)—, —N(R$^6$)—, —CO—, —CO$_2$—, —N(R$^6$) CO—, —N(R$^6$)C(O)O—, —N(R$^6$)CON(R$^6$)—, —N(R$^6$) SO$_2$N(R$^6$)—, —N(R$^6$)N(R$^6$)—, —C(O)N(R$^6$)—, —OC (O)N(R$^6$)—, —C(R$^6$)$_2$O—, —C(R$^6$)$_2$S—, —C(R$^6$) $_2$SO—, —C(R$^6$)$_2$SO$_2$—, —C(R$^6$)$_2$SO$_2$N(R$^6$)—, —C(R$^6$) $_2$N(R$^6$)—, —C(R$^6$)$_2$N(R$^6$)C(O)—, —C(R$^6$)$_2$N(R$^6$)C(O) O—, —C(R$^6$)=NN(R$^6$)—, —C(R$^6$)=N—O—, —C(R$^6$) $_2$N(R$^6$)N(R$^6$)—, —C(R$^6$)$_2$N(R$^6$)SO$_2$N(R$^6$)—, or —C(R$^6$) $_2$N(R$^6$)CON(R$^6$)—;

$R^2$ and $R^{2'}$ are independently selected from —R, —T—W—R$^6$, or $R^2$ and $R^{2'}$ are taken together with their intervening atoms to form a fused, 5–8 membered, unsaturated or partially unsaturated, ring having 0–3 ring heteroatoms selected from nitrogen, oxygen, or sulfur, wherein each substitutable ring carbon of said fused ring formed by $R^2$ and $R^{2'}$ is independently substituted-by halo, oxo, —CN, —NO$_2$, —R$^7$, or —V—R$^6$, and each substitutable ring nitrogen of said ring formed by $R^2$ and $R^{2'}$ is independently substituted by R$^4$;

$R^3$ is selected from —R, —halo, —OR, —C(=O)R, —CO$_2$R, —COCOR, —COCH$_2$COR, —NO$_2$, —CN, —S(O)R, —S(O)$_2$R, —SR, —N(R$^4$)$_2$, —CON(R$^7$)$_2$, —SO$_2$N(R$^7$)$_2$, —OC(=O)R, —N(R$^7$)COR, —N(R$^7$)CO$_2$ (C$_{1-6}$ aliphatic), —N(R$^4$)N(R$^4$)$_2$, —C=NN(R$^4$)$_2$, —C=N—OR, —N(R$^7$)CON(R$^7$)$_2$, —N(R$^7$)SO$_2$N(R$^7$)$_2$, —N(R$^4$)SO$_2$R, or —OC(=O)N(R$^7$)$_2$;

each R is independently selected from hydrogen or an optionally substituted group selected from C$_{1-6}$ aliphatic, $C_{6-10}$ aryl, a heteroaryl ring having 5–10 ring atoms, or a heterocyclyl ring having 5–10 ring atoms;

each $R^4$ is independently selected from —$R^7$, —$COR^7$, $CO_2$(optionally substituted $C_{1-6}$ aliphatic), —$CON(R^7)_2$, or —$SO_2R^7$;

each $R^5$ is independently selected from —R, halo, —OR, —C(=O)R, —$CO_2R$, —COCOR, —$NO_2$, —CN, —S(O)R, —$SO_2R$, —SR, —$N(R^4)_2$, —$CON(R^4)_2$, —$SO_2N(R^4)_2$, —OC(=O)R, —$N(R^4)COR$, —$N(R^4)CO_2$(optionally substituted $C_{1-6}$ aliphatic), —$N(R^4)N(R^4)_2$, —C=$NN(R^4)_2$, —C=N—OR, —$N(R^4)CON(R^4)_2$, —$N(R^4)SO_2N(R^4)_2$, —$N(R^4)SO_2R$, or —OC(=O)$N(R^4)_2$;

V is —O—, —S—, —SO—, —$SO_2$—, —$N(R^6)SO_2$—, —$SO_2N(R^6)$—, —$N(R^6)$—, —CO—, —$CO_2$—, —$N(R^6)CO$—, —$N(R^6)C(O)O$—, —$N(R^6)CON(R^6)$—, —$N(R^6)SO_2N(R^6)$—, —$N(R^6)N(R^6)$—, —$C(O)N(R^6)$—, —OC(O)$N(R^6)$—, —$C(R^6)_2O$—, —$C(R^6)_2S$—, —$C(R^6)_2SO$—, —$C(R^6)_2SO_2$—, —$C(R^6)_2SO_2N(R^6)$—, —$C(R^6)_2N(R^6)$—, —$C(R^6)_2N(R^6)C(O)$—, —$C(R^6)_2N(R^6)C(O)O$—, —$C(R^6)$=$NN(R^6)$—, —$C(R^6)$=N—O—, —$C(R^6)_2N(R^6)N(R^6)$—, —$C(R^6)_2N(R^6)SO_2N(R^6)$—, or —$C(R^6)_2N(R^6)CON(R^6)$—;

W is —$C(R^6)_2O$—, —$C(R^6)_2S$—, —$C(R^6)_2SO$—, —$C(R^6)_2SO_2$—, —$C(R^6)_2SO_2N(R^6)$—, —$C(R^6)_2N(R^6)$—, —CO—, —$CO_2$—, —$C(R^6)OC(O)$—, —$C(R^6)OC(O))N(R^6)$—, —$C(R^6)_2N(R^6)CO$—, —$C(R^6)_2N(R^6)C(O)O$—, —$C(R^6)$=$NN(R^6)$—, —$C(R^6)$=N—O—, —$C(R^6)_2N(R^6)N(R^6)$—, —$C(R^6)_2N(R^6)SO_2N(R^6)$—, —$C(R^6)_2N(R^6)CON(R^6)$—, or —$CON(R^6)$—;

each $R^6$ is independently selected from hydrogen or an optionally substituted $C_{1-4}$ aliphatic group, or two $R^6$ groups on the same nitrogen atom are taken together with the nitrogen atom to form a 5–6 membered heterocyclyl or heteroaryl ring; and each $R^7$ is independently selected from hydrogen or an optionally substituted $C_{1-6}$ aliphatic group, or two $R^7$ on the same nitrogen are taken together with the nitrogen to form a 5–8 membered heterocyclyl or heteroaryl ring.

Preferred $R^x$ groups of formula IIIb include hydrogen, alkyl- or dialkylamino, acetamido, or a $C_{1-4}$ aliphatic group such as methyl, ethyl, cyclopropyl, or isopropyl.

Preferred $R^y$ groups of formula IIIb include T—$R^3$ or L—Z—$R^3$ wherein T is a valence bond or a methylene, L is —O—, —S—, or —$N(R^4)$—, —$C(R^6)_2O$—, —CO— and $R^3$ is —R, —$N(R^4)_2$, or —OR. Examples of preferred $R^y$ groups include 2-pyridyl, 4-pyridyl, pyrrolidinyl, piperidinyl, morpholinyl, piperazinyl, methyl, ethyl, cyclopropyl, isopropyl, t-butyl, alkoxyalkylamino such as methoxyethylamino, alkoxyalkyl such as methoxymethyl or methoxyethyl, alkyl- or dialkylamino such as ethylamino or dimethylamino, alkyl- or dialkylaminoalkoxy such as dimethylaminopropyloxy, acetamido, optionally substituted phenyl such as phenyl or halo-substituted phenyl.

The $R^2$ and $R^{2'}$ groups of formula IIIb may be taken together to form a fused ring, thus providing a bicyclic ring system containing a pyrazole ring. Preferred fused rings include benzo, pyrido, pyrimido, and a partially unsaturated 6-membered carbocyclo ring. These are exemplified in the following formula IIIb compounds having a pyrazole-containing bicyclic ring system:

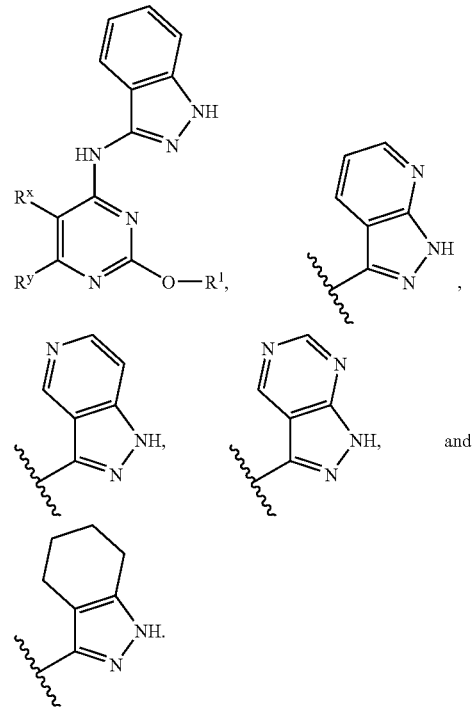

Preferred substituents on the $R^2/R^{2'}$ fused ring of formula IIIb include one or more of the following: -halo, —$N(R^4)_2$, —$C_{1-4}$ alkyl, —$C_{1-4}$ haloalkyl, —$NO_2$, —O($C_{1-4}$ alkyl), —$CO_2(C_{1-4}$ alkyl), —CN, —$SO_2(C_{1-4}$ alkyl), —$SO_2NH_2$, —OC(O)$NH_2$, —$NH_2SO_2(C_{1-4}$alkyl), —NHC(O) ($C_{1-4}$ alkyl), —C(O)$NH_2$, and —CO($C_{1-4}$ alkyl), wherein the ($C_{1-4}$ alkyl) is a straight, branched, or cyclic alkyl group. Preferably, the ($C_{1-4}$alkyl) group is methyl.

When the pyrazole ring system of formula IIIb is monocyclic, preferred $R^2$ groups include hydrogen or a substituted or unsubstituted group selected from aryl, heteroaryl, or a $C_{1-6}$ aliphatic group. Examples of such preferred $R^2$ groups include H, methyl, ethyl, propyl, cyclopropyl, i-propyl, cyclopentyl, hydroxypropyl, methoxypropyl, and benzyloxypropyl. A preferred $R^{2'}$ group is hydrogen.

When Ring D of formula IIIb is monocyclic, preferred Ring D groups include phenyl, pyridyl, pyridazinyl, pyrimidinyl, and pyrazinyl.

When Ring D of formula IIIb is bicyclic, preferred bicyclic Ring D groups include naphthyl, tetrahydronaphthyl, indanyl, benzimidazolyl, quinolinyl, indolyl, isoindolyl, indolinyl, benzo[b]furyl, benzo[b]thiophenyl, indazolyl, benzothiazolyl, cinnolinyl, phthalazinyl, quinazolinyl, quinoxazolinyl, 1,8-naphthyridinyl and isoquinolinyl.

On Ring D of formula IIIb, preferred T—$R^5$ or V—Z—$R^5$ substituents include -halo, —CN, —$NO_2$, —$N(R^4)_2$, optionally substituted $C_{1-6}$ aliphatic group, —OR, —C(O)R, —$CO_2R$, —CONH($R^4$), —$N(R^4)COR$, —$N(R^4)CO_2R$, —$SO_2N(R^4)_2$, —$N(R^4) SO_2R$, —$N(R^6)COCH_2N(R^4)_2$, —$N(R^6)COCH_2CH_2N(R^4)_2$, and —$N(R^6)COCH_2CH_2CH_2N(R^4)_2$, wherein R is selected from hydrogen, $C_{1-6}$ aliphatic, phenyl, a 5–6-membered heteroaryl ring, or a 5–6 membered heterocyclic ring. More preferred $R^5$ substituents include —Cl, —Br, —F, —CN, —$CF_3$, —COOH, —CONHMe; —CONHEt, —$NH_2$, —NHAC, —$NHSO_2Me$, —$NHSO_2Et$, —NHSO (n-propyl), —$NHSO_2$ (isopropyl), —NHCOEt, —NHCOCH$_2$NHCH$_3$, —NHCOCH$_2$N(CO$_2$t-Bu)CH$_3$, —NHCOCH$_2$N(CH$_3$)$_2$, —NHCOCH$_2$CH$_2$N(CH$_3$)$_2$, —NHCOCH$_2$CH$_2$CH$_2$N(CH$_3$)$_2$, —NHCO(cyclopropyl), —NHCO(isobutyl), —NHCOCH$_2$(morpholin-4-yl), —NHCOCH$_2$CH$_2$(morpholin-4-yl), —NHCOCH$_2$CH$_2$CH$_2$(morpholin-4-yl), —NHCO$_2$(t-butyl), —NH(C$_{1-4}$ aliphatic) such as —NHMe, —N(C$_{1-4}$ aliphatic)$_2$ such as —NMe$_2$, OH, —O(C$_{1-4}$ aliphatic) such as —OMe, C$_{1-4}$ aliphatic such as methyl, ethyl, cyclopropyl, isopropyl, or t-butyl, and —CO$_2$(C$_{1-4}$ aliphatic).

Preferred formula IIIb compounds have one or more, and more preferably all, of the features selected from the group consisting of:
(a) R$^x$ is hydrogen, alkyl- or dialkylamino, acetamido, or a C$_{1-4}$ aliphatic group;
(b) R$^y$ is T—R$^3$ or L—Z—R$^3$, wherein T is a valence bond or a methylene and R$^3$ is —R, —N(R$^4$)$_2$, or —OR;
(c) R$^1$ is T-(Ring D), wherein T is a valence bond or a methylene unit;
(d) Ring D is a 5–7 membered monocyclic or an 8–10 membered bicyclic aryl or heteroaryl ring; and
(e) R$^2$ is —R or —T—W—R$^6$ and R$^{2'}$ is hydrogen, or R$^2$ and R$^{2'}$ are taken together to form an optionally substituted benzo ring.

More preferred compounds of formula IIIb have one or more, and more preferably all, of the features selected from the group consisting of:
(a) R$^y$ is T—R$^3$ or L—Z—R$^3$ wherein T is a valence bond or a methylene and R$^3$ is selected from —R, —OR, or —N(R$^4$)$_2$, wherein R is selected from hydrogen, C$_{1-6}$ aliphatic, or 5–6 membered heterocyclyl, phenyl, or 5–6 membered heteroaryl;
(b) R$^1$ is T-(Ring D), wherein T is a valence bond;
(c) Ring D is a 5–6 membered monocyclic or an 8–10 membered bicyclic aryl-or heteroaryl ring;
(d) R$^2$ is —R and R$^{2'}$ is hydrogen, wherein R is selected from hydrogen C, C$_{1-6}$ aliphatic, phenyl, a 5–6 membered heteroaryl ring, or a 5–6 membered heterocyclic ring; and
(e) L is —O—, —S—, or —N(R$^4$)—.

Even more preferred compounds of formula IIIb have one or more, and more preferably all, of the features selected from the group consisting of:
(a) R$^x$ is hydrogen methyl, ethyl, propyl, cyclopropyl, isopropyl, methylamino or acetimido;
(b) R$^y$ is selected from 2-pyridyl, 4-pyridyl, pyrrolidinyl, piperidinyl, morpholinyl, piperazinyl, methyl, ethyl, cyclopropyl, isopropyl, t-butyl, alkoxyalkylamino, alkoxyalkyl, alkyl- or dialkylamino, alkyl- or dialkylaminoalkoxy, acetamido, optionally substituted phenyl, or methoxymethyl;
(c) R$^1$ is T-(Ring D), wherein T is a valence bond and Ring D is a 5–6 membered aryl or heteroaryl ring, wherein Ring D is optionally substituted with one to two groups selected from -halo, —CN, —NO$_2$, —N(R$^4$)$_2$, optionally substituted C$_{1-6}$ aliphatic group, —OR, —CO$_2$R, —CONH(R$^4$), —N(R$^4$)COR, —N(R$^4$)SO$_2$R, —N(R$^6$)COCH$_2$CH$_2$N(R$^4$)$_2$, or —N(R$^6$)COCH$_2$CH$_2$CH$_2$N(R$^4$)$_2$; and
(d) R$^2$ is hydrogen or a substituted or unsubstituted C$_{1-6}$ aliphatic, and L is —O—, —S—, or —NH—.

Representative compounds of formula IIIb are shown below in Table 6.

TABLE 6

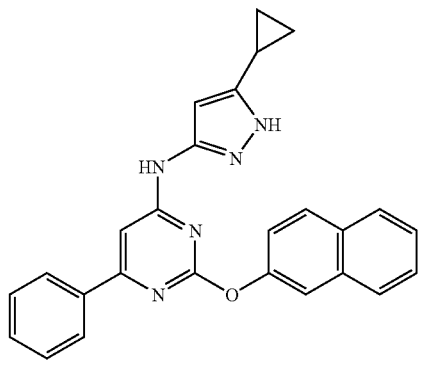

IIIb-1

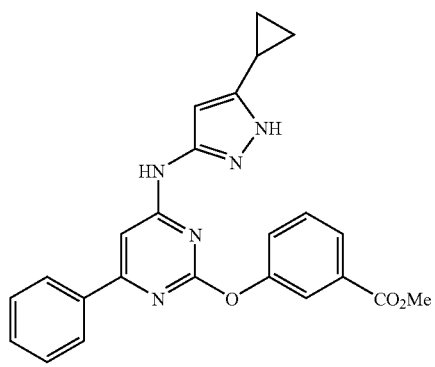

IIIb-2

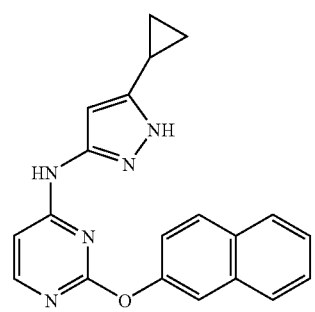

IIIb-3

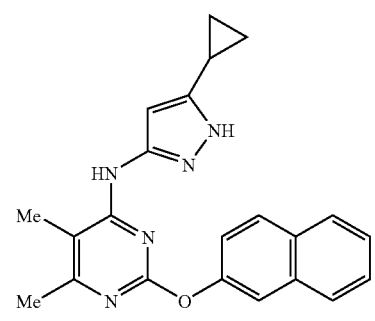

IIIb-4

TABLE 6-continued
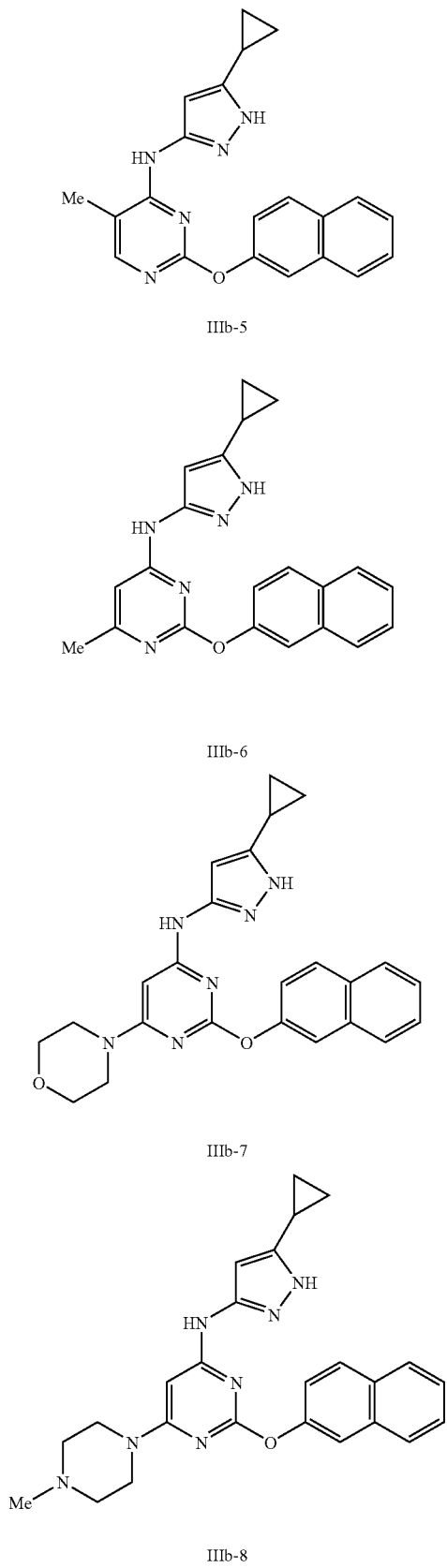
IIIb-5
IIIb-6
IIIb-7
IIIb-8
TABLE 6-continued
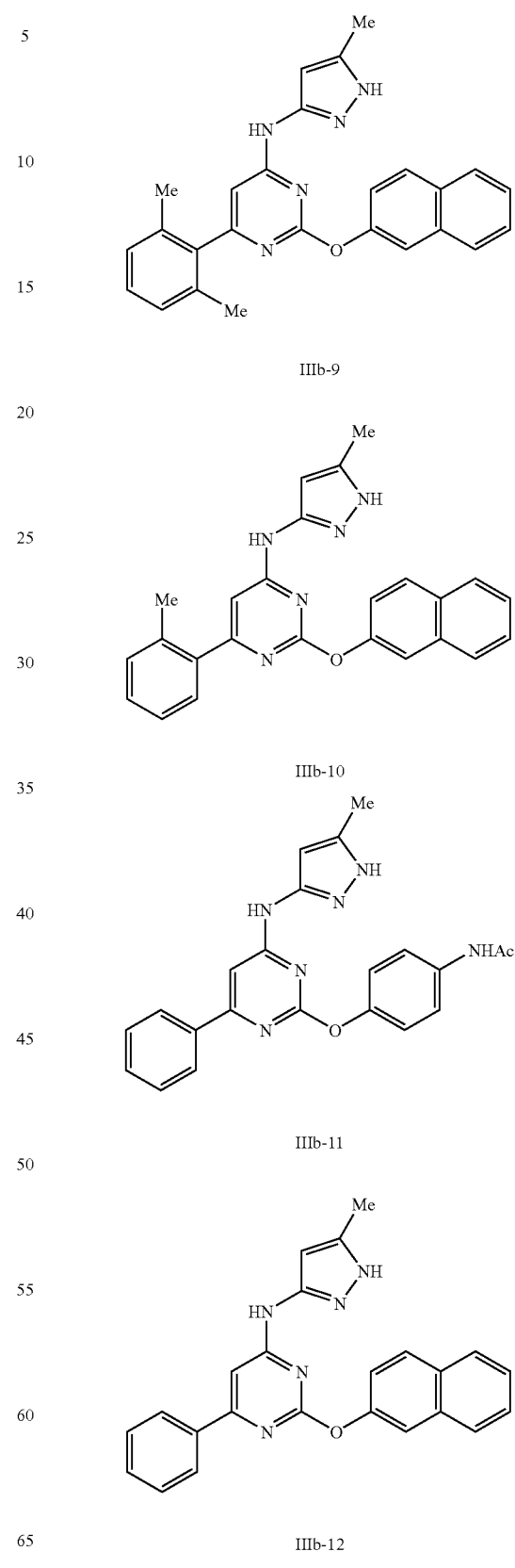
IIIb-9
IIIb-10
IIIb-11
IIIb-12

TABLE 6-continued
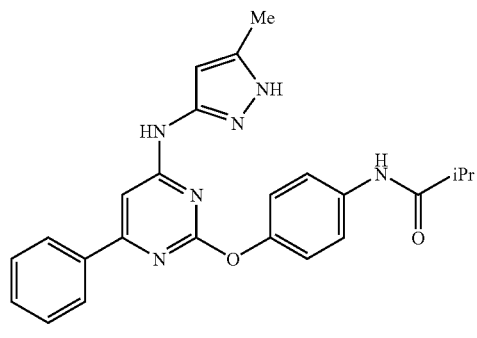
IIIb-13
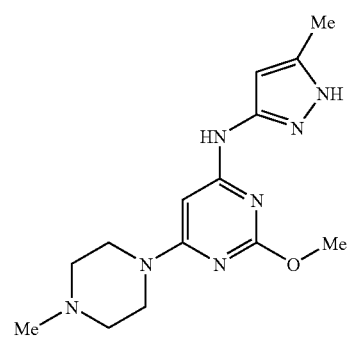
IIIb-14
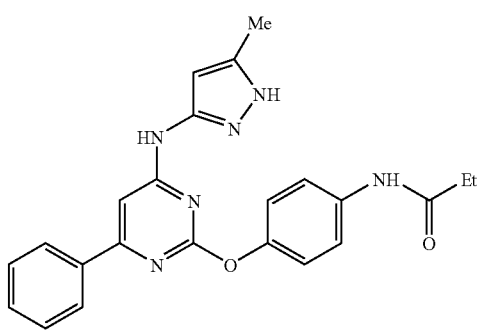
IIIb-15
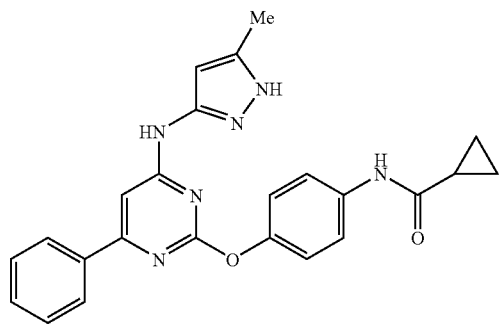
IIIb-16
TABLE 6-continued
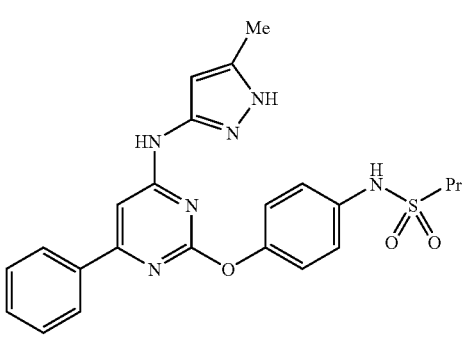
IIIb-17
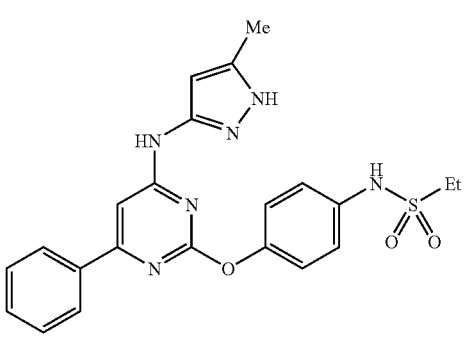
IIIb-18
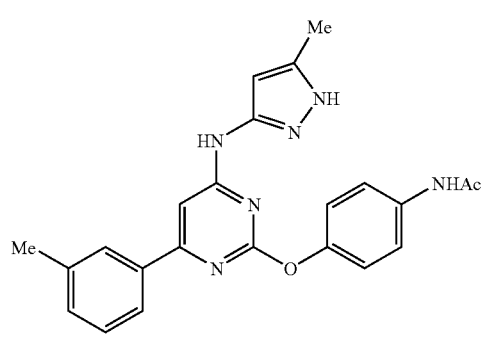
IIIb-19
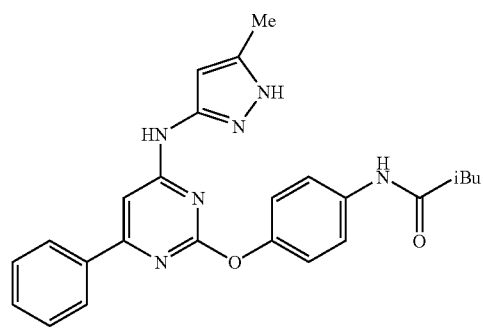
IIIb-20

TABLE 6-continued
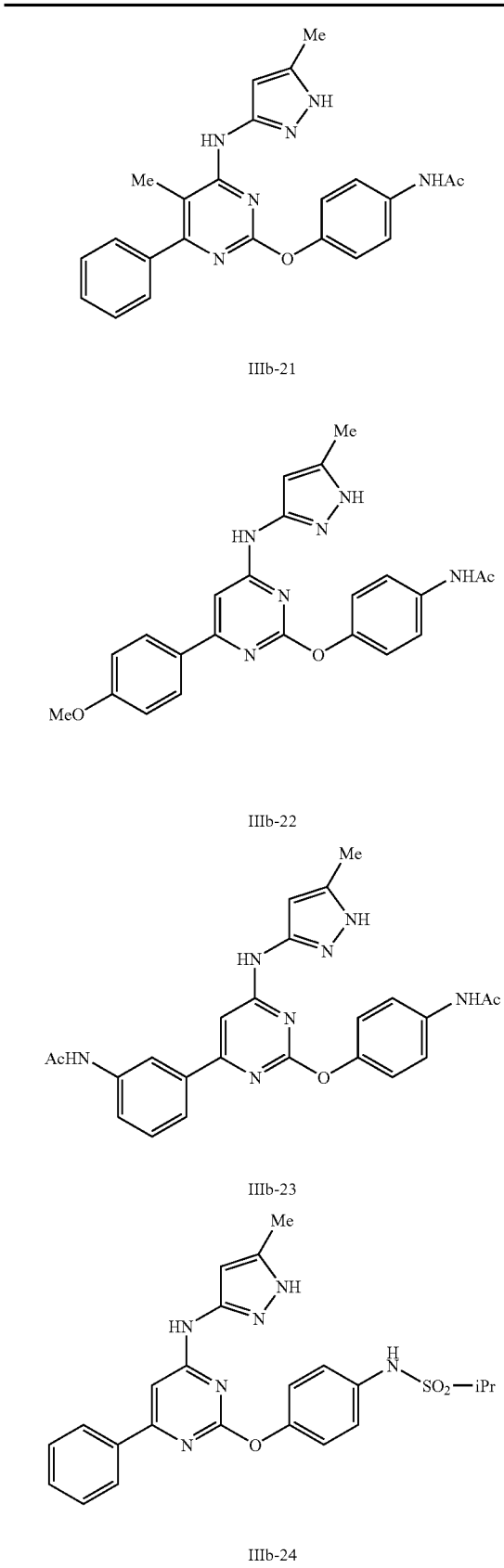
IIIb-21
IIIb-22
IIIb-23
IIIb-24
TABLE 6-continued
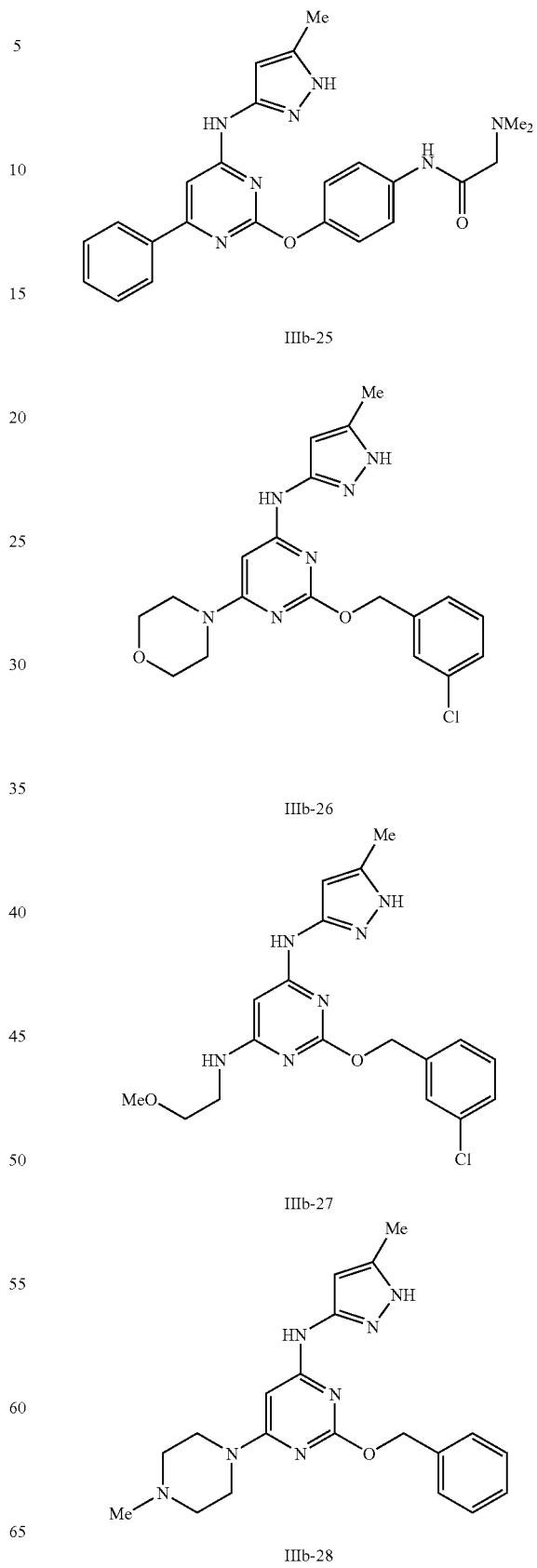
IIIb-25
IIIb-26
IIIb-27
IIIb-28

TABLE 6-continued

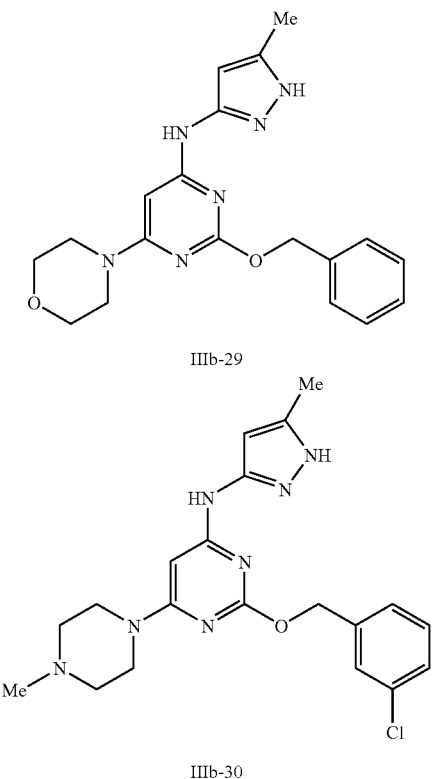

IIIb-29

IIIb-30

In another embodiment, this invention provides a composition comprising a compound of formula IIIb and a pharmaceutically acceptable carrier.

Another aspect of this invention relates to a method of treating or preventing an Aurora-2-mediated disease with an Aurora-2 inhibitor, which method comprises administering to a patient in need of such a treatment a therapeutically effective amount of a compound of formula IIIb or a pharmaceutical composition thereof.

Another aspect of this invention relates to a method of inhibiting Aurora-2 activity in a patient, which method comprises administering to the patient a compound of formula IIIb or a composition comprising said compound.

Another aspect of this invention relates to a method of treating or preventing a GSK-3-mediated disease with a GSK-3 inhibitor, which-method comprises administering to a patient in need of such a treatment a therapeutically effective-amount of a compound of formula IIIb or a pharmaceutical composition thereof.

One aspect of this invention relates to a method of enhancing glycogen synthesis and/or lowering blood levels of glucose in a patient in need thereof, which method comprises administering to the patient a therapeutically effective amount of a compound of formula IIIb or a pharmaceutical composition thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of β-catenin, which is useful for treating schizophrenia.

Another aspect of this invention relates to a method of inhibiting GSK-3 activity in a patient, which method comprises administering to the patient a compound of formula IIIb or a composition comprising said compound.

Another method relates to inhibiting Aurora-2 or GSK-3 activity in a biological sample,.which method comprises contacting the biological sample with the Aurora-2 or-GSK-3 inhibitor of formula IIIb, or a pharmaceutical composition thereof, in an amount effective to inhibit Aurora-2 or GSK-3.

Each of the aforementioned methods directed to the inhibition of Aurora-2 or GSK-3, or the treatment of a disease alleviated thereby, is preferably carried out with a preferred compound of formula IIIb, as described above.

Another-embodiment of this invention relates to compounds of formula IIIc:

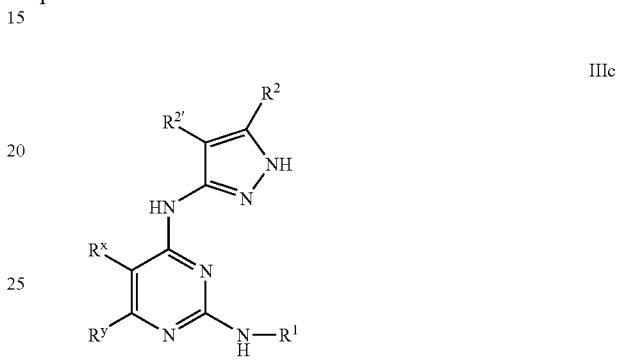

IIIc or a pharmaceutically acceptable derivative or prodrug thereof, wherein:

$R^x$ and $R^y$ are independently selected from T—$R^3$ or L—Z—$R^3$;

$R^1$ is T-(Ring D);

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein each substitutable ring carbon of Ring D is independently substituted by oxo, T—$R^5$, or V—Z—$R^5$, and each substitutable ring nitrogen of Ring D is independently substituted by —$R^4$;

T is a valence bond or a $C_{1-4}$ alkylidene chain;

Z is a $C_{1-4}$ alkylidene chain;

L is —O—, —S—, —SO—, —SO$_2$—, —N(R$^6$)SO$_2$—, —SO$_2$N(R$^6$)—, —N(R$^6$)—, —CO—, —CO$_2$—, —N(R$^6$) CO—, —N(R$^6$)C(O)O—, —N(R$^6$)CON(R$^6$)—, —N(R$^6$) SO$_2$N(R$^6$)—, —N(R$^6$)N(R$^6$)—, —C(O)N(R$^6$)—, —OC (O)N(R$^6$)—, —C(R$^6$)$_2$O—, —C(R$^6$)$_2$S—, —C(R$^6$)$_2$ SO—, —C(R$^6$)$_2$SO$_2$—, —C(R$^6$)$_2$SO$_2$N(R$^6$)—, —C(R$^6$)$_2$ N(R$^6$)—, —C(R$^6$)$_2$N(R$^6$)C(O)—, —C(R$^6$)$_2$N(R$^6$)C(O) O—, —C(R$^6$)=NN(R$^6$)—, —C(R$^6$)=N—O—, —C(R$^6$)$_2$ N(R$^6$)N(R$^6$)—, —C(R$^6$)$_2$N(R$^6$)SO$_2$N(R$^6$)—, or —C(R$^6$)$_2$N(R$^6$)CON(R$^6$)—;

$R^2$ and $R^{2'}$ are independently selected from —R, —T—W—$R^6$, or $R^2$ and $R^{2'}$ are taken together with their intervening atoms to form a fused, 5–8 membered, unsaturated or partially unsaturated, ring having 0–3 ring heteroatoms selected from nitrogen, oxygen, or sulfur, wherein each substitutable ring carbon of said fused ring formed by $R^2$ and $R^{2'}$ is independently substituted by halo, oxo, —CN, —NO$_2$, —$R^7$, or —V—$R^6$, and each substitutable ring nitrogen of said ring formed by $R^2$ and $R^{2'}$ is independently substituted by $R^4$;

$R^3$ is selected from —R, -halo, —OR, —C(=O)R, —CO$_2$R, —COCOR, —COCH$_2$COR, —NO$_2$, —CN, —S(O)R, —S(O)₂R, —SR, —N(R⁴)₂, —CON(R⁷)₂, —SO₂N(R⁷)₂, —OC(=O)R, —N(R⁷)COR, —N(R⁷)CO₂(C₁₋₆ aliphatic), —N(R⁴)N(R⁴)₂, —C=NN(R⁴)₂, —C=N—OR, —N(R⁷)CON(R⁷)₂, —N(R⁷)SO₂N(R⁷)₂, —N(R⁴)SO₂R, or —OC(=O)N(R⁷)₂;

each R is independently selected from hydrogen or an optionally substituted group selected from C₁₋₆ aliphatic, C₆₋₁₀ aryl, a heteroaryl ring having 5–10 ring atoms, or a heterocyclyl ring having 5–10 ring atoms;

each R⁴ is independently selected from —R⁷, —COR⁷, —CO₂(optionally substituted C₁₋₆ aliphatic), —CON(R⁷)₂, or —SO₂R⁷;

each R⁵ is independently selected from —R, halo, —OR, —C(=O)R, —CO₂R, —COCOR, —NO₂, —CN, —S(O)R, —SO₂R, —SR, —N(R⁴)₂, —CON(R⁴)₂, —SO₂N(R⁴)₂, —OC(=O)R, —N(R⁴)COR, —N(R⁴)CO₂(optionally substituted C₁₋₆ aliphatic), —N(R⁴)N(R⁴)₂, —C=NN(R⁴)₂, —C=N—OR, —N(R⁴)CON(R⁴)₂, —N(R⁴)SO₂N(R⁴)₂, —N(R⁴)SO₂R, or —OC(=O)N(R⁴)₂;

V is —O—, —S—, —SO—, —SO₂—, —N(R⁶)SO₂—, —SO₂N(R⁶)—, —N(R⁶)—, —CO—, —CO₂—, —N(R⁶)CO—, —N(R⁶)C(O)O—, —N(R⁶)CON(R⁶)—, —N(R⁶)SO₂N(R⁶)—, —N(R⁶)N(R⁶)—, —C(O)N(R⁶)—, —OC(O)N(R⁶)—, —C(R⁶)₂O—, —C(R⁶)₂S—, —C(R⁶)₂SO—, —C(R⁶)₂SO₂—, —C(R⁶)₂SO₂N(R⁶)—, —C(R⁶)₂N(R⁶)—, —C(R⁶)₂N(R⁶)C(O)—, —C(R⁶)₂N(R⁶)C(O)O—, —C(R⁶)=NN(R⁶)—, —C(R⁶)=N—O—, —C(R⁶)₂N(R⁶)N(R⁶)—, —C(R⁶)₂N(R⁶)SO₂N(R⁶)—, or —C(R⁶)₂N(R⁶)CON(R⁶)—;

W is —C(R⁶)₂O—, —C(R⁶)₂S—, —C(R⁶)₂SO—, —C(R⁶)₂SO₂—, —C(R⁶)₂SO₂N(R⁶)—, —C(R⁶)₂N(R⁶)—, —CO—, —CO₂—, —C(R⁶)OC(O)—, —C(R⁶)OC(O)N(R⁶)—, —C(R⁶)₂N(R⁶)CO—, —C(R⁶)₂N(R⁶)C(O)O—, —C(R⁶)=NN(R⁶)—, —C(R⁶)=N—O—, —C(R⁶)₂N(R⁶)N(R⁶)—, —C(R⁶)₂N(R⁶)SO₂N(R⁶)—, —C(R⁶)₂N(R⁶)CON(R⁶)—, or —CON(R⁶)—;

each R⁶ is independently selected from hydrogen or an optionally substituted C₁₋₄ aliphatic group, or two R⁶ groups on the same nitrogen atom are taken together with the nitrogen atom to form a 5–6 membered heterocyclyl or heteroaryl ring; and each R⁷ is independently selected from hydrogen or an optionally substituted C₁₋₆ aliphatic group, or two R⁷ on the same nitrogen are taken together with the nitrogen to form a 5–8 membered heterocyclyl or heteroaryl ring.

Preferred Rˣ groups of formula IIIc include hydrogen, alkyl- or dialkylamino, acetamido, or a C₁₋₄ aliphatic group such as methyl, ethyl, cyclopropyl, or isopropyl.

Preferred Rʸ groups of formula IIIc include T—R³ or L—Z—R³ wherein T is a valence bond or a methylene, L is —O—, —S—, or —N(R⁴)—, —C(R⁶)₂O—, —CO— and R³ is —R, —N(R⁴)₂, or —OR. Examples of preferred Rʸ groups include 2-pyridyl, 4-pyridyl, pyrrolidinyl, piperidinyl, morpholinyl, piperazinyl, methyl, ethyl, cyclopropyl, isopropyl, t-butyl, alkoxyalkylamino such as methoxyethylamino, alkoxyalkyl such as methoxymethyl or methoxyethyl, alkyl- or dialkylamino such as ethylamino or dimethylamino, alkyl- or dialkylaminoalkoxy such as dimethylaminopropyloxy, acetamido, optionally substituted phenyl such as phenyl or halo-substituted phenyl.

The R² and R²' groups of formula IIIc may be taken together to form a fused ring, thus providing a bicyclic ring system containing a pyrazole ring. Preferred fused rings include benzo, pyrido, pyrimido, and a partially unsaturated 6-membered carbocyclo ring. These are exemplified in the following formula IIIc compounds having a pyrazole-containing bicyclic ring system:

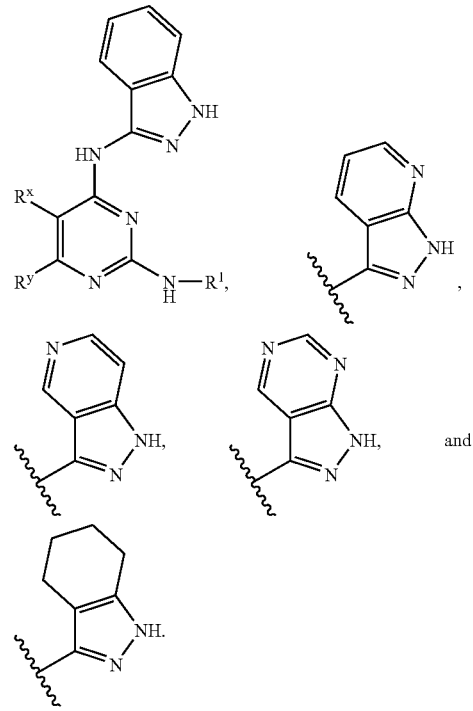

Preferred substituents on the R²/R²' fused ring of formula IIIc include one or more of the following: -halo, —N(R⁴)₂, —C₁₋₄ alkyl, —C₁₋₄ haloalkyl, —NO₂, —O(C₁₋₄ alkyl), —CO₂(C₁₋₄ alkyl), —CN, —SO₂(C₁₋₄ alkyl), —SO₂ NH₂, —OC(O)NH₂, —NH₂SO₂(C₁₋₄ alkyl), —NHC(O)(C₁₋₄ alkyl), —C(O)NH₂, and —CO(C₁₋₄ alkyl), wherein the (C₁₋₄ alkyl) is a straight, branched, or cyclic alkyl group. Preferably, the (C₁₋₄ alkyl) group is methyl.

When the pyrazole ring system of formula IIIc is monocyclic, preferred R² groups include hydrogen or a substituted or unsubstituted group selected from aryl, heteroaryl, or a C₁₋₆ aliphatic group. Examples of such preferred R² groups include H, methyl, ethyl, propyl, cyclopropyl, i-propyl, cyclopentyl, hydroxypropyl, methoxypropyl, and benzyloxypropyl. A preferred R²' group is hydrogen.

When Ring D of formula IIIc is monocyclic, preferred Ring D groups include phenyl, pyridyl, pyridazinyl, pyrimidinyl, and pyrazinyl.

When Ring D of formula IIIc is bicyclic, preferred bicyclic Ring D groups include naphthyl, tetrahydronaphthyl, indanyl, benzimidazolyl, quinolinyl, indolyl, isoindolyl, indolinyl, benzo[b]furyl, benzo[b]thiophenyl, indazolyl, benzothiazolyl, cinnolinyl, phthalazinyl, quinazolinyl, quinoxazolinyl, 1,8-naphthyridinyl and isoquinolinyl.

On Ring D of formula IIIc, preferred T—R⁵ or V—Z—R⁵ substituents include -halo, —CN, —NO₂, —N(R⁴)₂, optionally substituted C₁₋₆ aliphatic group, —OR, —C(O)R, —CO₂R, —CONH(R⁴), —N(R⁴)COR, —N(R⁴)CO₂R, —SO₂N(R⁴)₂, —N(R⁴)SO₂R, —N(R⁶) COCH₂N(R⁴)₂, —N(R⁶) COCH₂CH₂N(R⁴)₂, and —N(R⁶) COCH₂CH₂CH₂N(R⁴)₂, wherein R is selected from hydrogen, C₁₋₆ aliphatic, phenyl, a 5–6 membered heteroaryl ring, or a 5–6 membered heterocyclic ring. More preferred R⁵ substituents include —Cl, —Br, —F, —CN, —CF$_3$; —COOH, —CONHMe, —CONHEt, —NH$_2$, —NHAc, —NHSO$_2$Me, —NHSO$_2$Et, —NHSO$_2$(n-propyl), —NHSO$_2$(isopropyl), —NHCOEt, —NHCOCH$_2$NHCH$_3$, —NHCOCH$_2$N(CO$_2$t-Bu)CH$_3$, —NHCOCH$_2$N(CH$_3$)$_2$, —NHCOCH$_2$CH$_2$N(CH$_3$)$_2$, —NHCOCH$_2$CH$_2$CH$_2$N(CH$_3$)$_2$, —NHCO(cyclopropyl), —NHCO(isobutyl), —NHCOCH$_2$(morpholin-4-yl), —NHCOCH$_2$CH$_2$(morpholin-4-yl), —NHCOCH$_2$CH$_2$CH$_2$(morpholin-4-yl), —NHCO$_2$(t-butyl), —NH(C$_{1-4}$ aliphatic) such as —NHMe, —N(C$_{1-4}$ aliphatic)$_2$ such as —NMe$_2$, OH, —O(C$_{1-4}$ aliphatic) such as —OMe, C$_{1-4}$ aliphatic such as methyl, ethyl, cyclopropyl, isopropyl, or t-butyl, and —CO$_2$(C$_{1-4}$ aliphatic).

Preferred formula IIIc compounds have one or more, and more preferably all, of the features selected from the group consisting of:
(a) R$^x$ is hydrogen, alkyl- or dialkylamino, acetamido, or a C$_{1-4}$ aliphatic group;
(b) R$^y$ is T—R$^3$ or L—Z—R$^3$, wherein T is a valence bond or a methylene and R$^3$ is —R, —N(R$^4$)$_2$, or —OR;
(c) R$^1$ is T-(Ring D), wherein T is a valence bond or a methylene unit;
(d) Ring D is a 5–7 membered monocyclic or an 8–10 membered bicyclic aryl or heteroaryl ring; and
(e) R$^2$ is —R or —T—W—R$^6$ and R$^{2'}$ is hydrogen, or R$^2$ and R$^{2'}$ are taken together to form an optionally substituted benzo ring.

More preferred compounds of formula IIIc have one or more, and more preferably all, of the features selected from the group consisting of:
(a) R$^y$ is T—R$^3$ or L—Z—R$^3$ wherein T is a valence bond or a methylene and R$^3$ is selected from —R, —OR, or —N(R$^4$)$_2$, wherein R is selected from C$_{1-6}$ aliphatic, or 5–6 membered heterocyclyl, phenyl, or 5–6 membered heteroaryl;
(b) R$^1$ is T-(Ring D), wherein T is a valence bond;
(c) Ring D is a 5–6 membered monocyclic or an 8–10 membered bicyclic aryl or heteroaryl ring;
(d) R$^2$ is —R and R$^{2'}$ is hydrogen, wherein R is selected from hydrogen, C$_{1-6}$ aliphatic, phenyl, a 5–6 membered heteroaryl ring, or a 5–6 membered heterocyclic ring; and
(e) L is —O—, —S—, or —N(R$^4$)—.

Even more preferred compounds of formula IIIc have one or more, and more preferably all, of the features selected from the group consisting of:
(a) R$^x$ is hydrogen methyl, ethyl, propyl, cyclopropyl, isopropyl, methylamino or acetimido;
(b) R$^y$ is selected from 2-pyridyl, 4-pyridyl, pyrrolidinyl, piperidinyl, morpholinyl, piperazinyl, methyl, ethyl, cyclopropyl, isopropyl, t-butyl, alkoxyalkylamino, alkoxyalkyl, alkyl- or dialkylamino, alkyl- or dialkylaminoalkoxy, acetamido, optionally, substituted phenyl, or methoxymethyl;
(c) R$^1$ is T-(Ring D), wherein T is a valence bond and Ring D is a 5–6 membered aryl or heteroaryl ring, wherein Ring D is optionally substituted with one to two groups selected from -halo, —CN, —NO$_2$, —N(R$^4$)$_2$, optionally substituted C$_{1-6}$ aliphatic group, —OR, —CO$_2$R, —CONH(R$^4$), —N(R$^4$)COR, —N(R$^4$)SO$_2$R, —N(R$^6$)COCH$_2$CH$_2$N(R$^4$)$_2$, or —N(R$^6$)COCH$_2$CH$_2$CH$_2$N(R$^4$)$_2$; and
(d) R$^2$ is hydrogen or a substituted or unsubstituted C$_{1-6}$aliphatic, and L is —O—, —S—, or —NH—.

Representative compounds of formula IIIc are shown below in Table 7.

TABLE 7

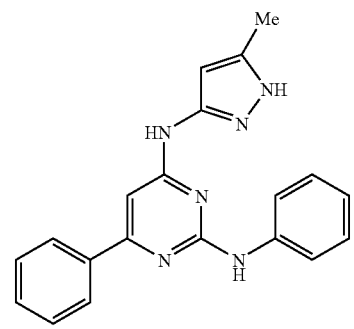

IIIc-1

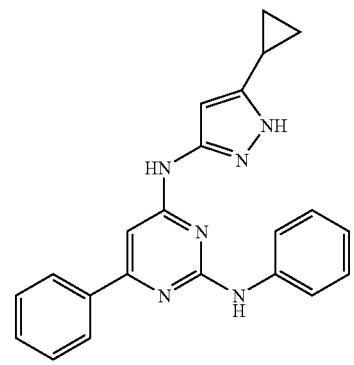

IIIc-2

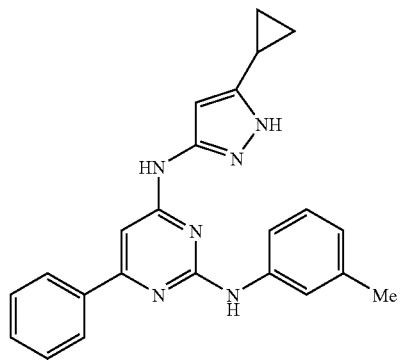

IIIc-3

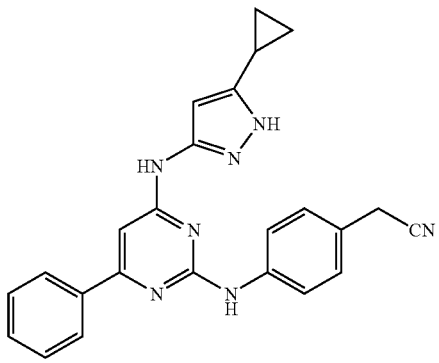

IIIc-4

TABLE 7-continued
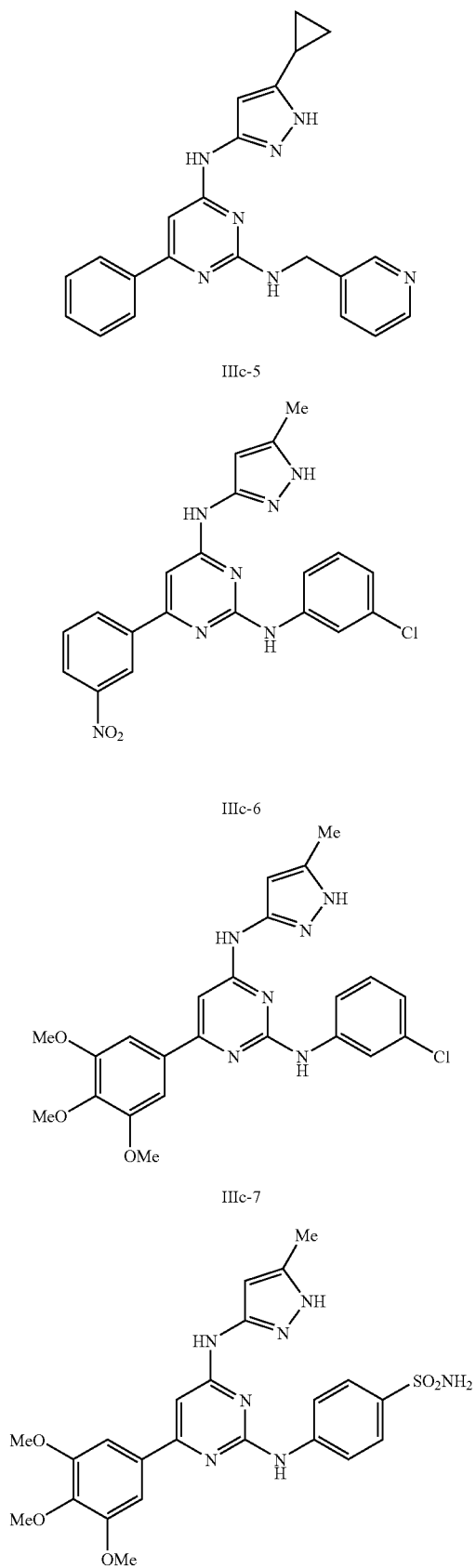
IIIc-5
IIIc-6
IIIc-7
TABLE 7-continued
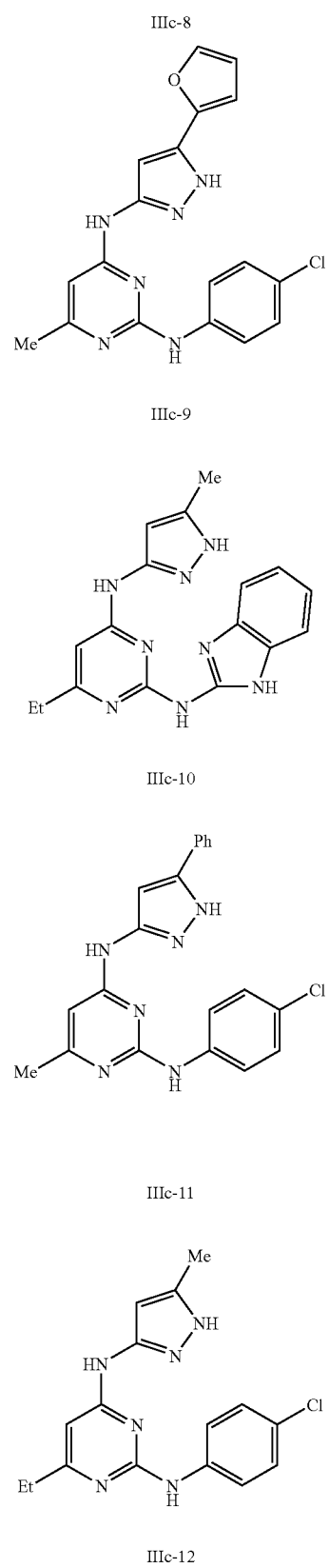
IIIc-8
IIIc-9
IIIc-10
IIIc-11
IIIc-12

TABLE 7-continued
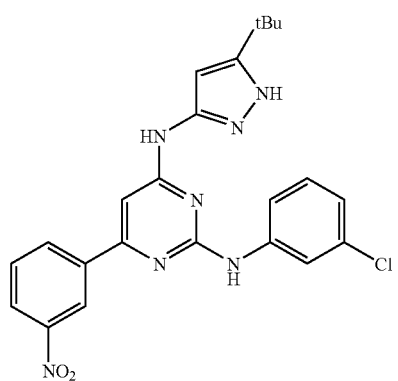
IIIc-13
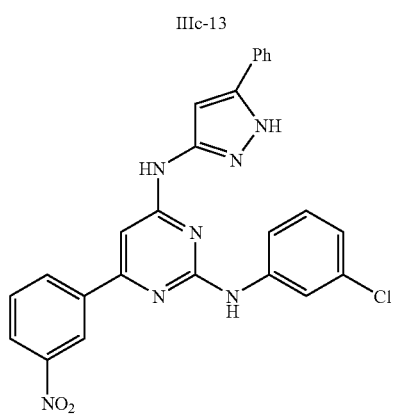
IIIc-14
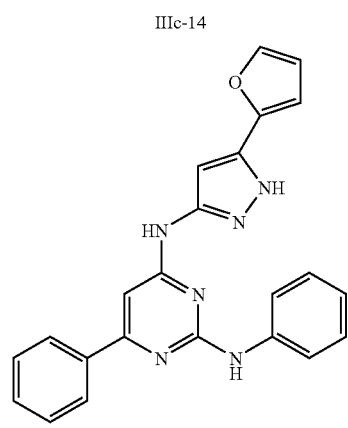
IIIc-15
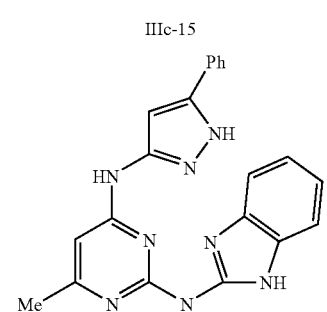
IIIc-16
TABLE 7-continued
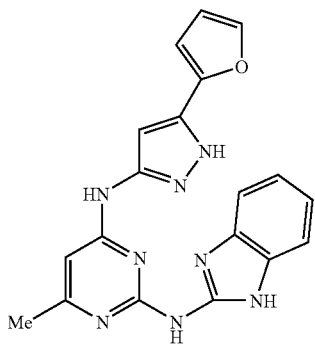
IIIc-17
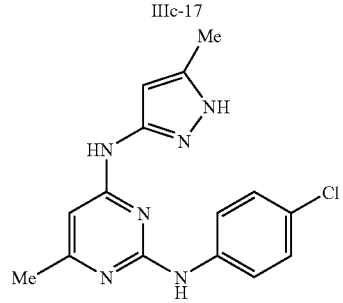
IIIc-18
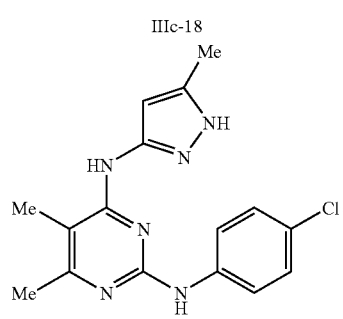
IIIc-19
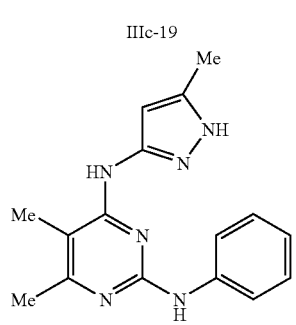
IIIc-20
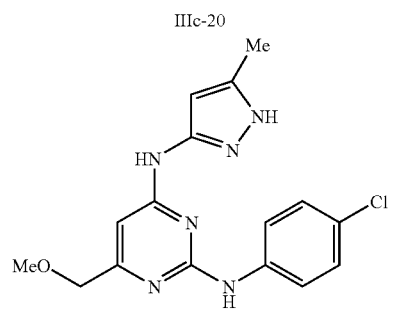
IIIc-21

TABLE 7-continued

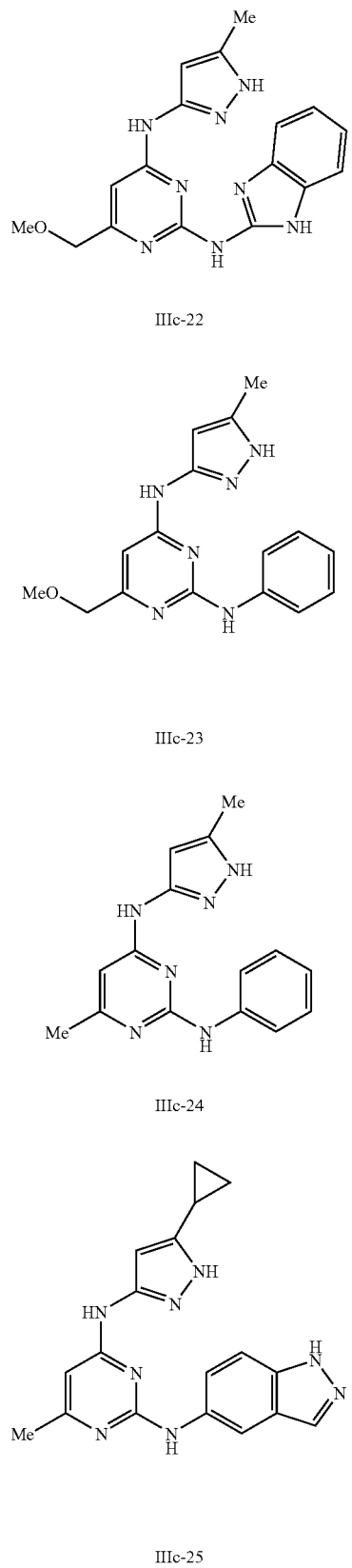

IIIc-22

IIIc-23

IIIc-24

IIIc-25

TABLE 7-continued

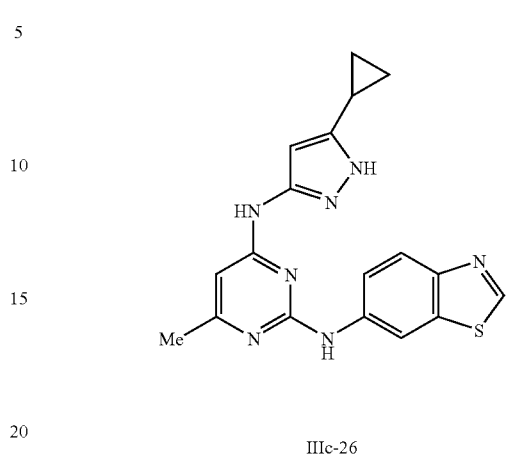

IIIc-26

In another embodiment, this invention provides a composition comprising a compound of formula IIIc and a pharmaceutically acceptable carrier.

Another aspect of this invention relates to a method of treating or preventing an Aurora-2-mediated disease with an Aurora-2 inhibitor, which method comprises administering to a patient in need of such a treatment a therapeutically effective amount of a compound of formula IIIc or a pharmaceutical composition thereof.

Another aspect of this invention relates to a method of inhibiting Aurora-2 activity in a patient, which method comprises administering to the patient a compound of formula IIIc or a composition comprising said compound.

Another aspect of this invention relates to a method of treating or preventing a GSK-3-mediated disease with a GSK-3 inhibitor, which method comprises administering to a patient in need of such a treatment a therapeutically effective amount of a compound of formula IIIc or a pharmaceutical composition thereof.

One aspect of this invention relates to a method of enhancing glycogen synthesis and/or lowering blood levels of glucose in a patient in need thereof, which method comprises administering to the patient a therapeutically effective amount of a compound of formula IIIc or a pharmaceutical composition thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of β-catenin, which is useful for treating schizophrenia.

Another aspect of this invention relates to a method of inhibiting GSK-3 activity in a patient, which method comprises administering to the patient a compound of formula IIIc or a composition comprising said compound.

Another aspect of this invention relates to a method of treating or preventing a Src-mediated disease with a Src inhibitor, which method comprises administering to a patient in need of such a treatment a therapeutically effective amount of a compound of formula IIIc or a pharmaceutical composition thereof.

Another aspect of the invention relates to inhibiting Src activity in a patient, which method comprises administering to the patient a compound of formula IIIc or a composition comprising said compound.

Another method relates to inhibiting Aurora-2, GSK-3, or Src activity in a biological sample, which method comprises contacting the biological sample with the Aurora-2, GSK-3, or Src inhibitor of formula IIIc, or a pharmaceutical composition thereof, in an amount effective to Aurora-2, GSK-3, or Src.

Each of the aforementioned methods directed to the inhibition of Aurora-2, GSK-3, or Src, or the treatment of a disease alleviated thereby, is preferably carried out with a preferred compound of formula IIIc, as described above.

Another embodiment of this invention relates to compounds of formula IIId:

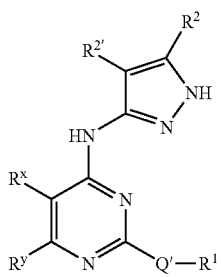

IIId or a pharmaceutically acceptable derivative or prodrug thereof, wherein:

Q' is selected from —C($R^{6'}$)$_2$—, 1,2-cyclopropanediyl, 1,2-cyclobutanediyl, or 1,3-cyclobutanediyl;

$R^x$ and $R^y$ are independently selected from T—$R^3$ or L—Z—$R^3$;

$R^1$ is T-(Ring D);

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein each substitutable ring carbon of Ring D is independently substituted by oxo, T—$R^5$, or V—Z—$R^5$, and each substitutable ring nitrogen of Ring D is independently substituted by —$R^4$;

T is a valence bond or a $C_{1-4}$ alkylidene chain, wherein when Q' is —C($R^{6'}$)$_2$— a methylene group of said $C_{1-4}$ alkylidene chain is optionally replaced by —O—, —S—, —N($R^4$)—, —CO—, —CONH—, —NHCO—, —SO$_2$—, —SO$_2$NH—, —NHSO$_2$—, —CO$_2$—, —OC(O)—, —OC(O)NH—, or —NHCO$_2$—;

Z is a $C_{1-4}$ alkylidene chain;

L is —O—, —S—, —SO—, —SO$_2$—, —N($R^6$)SO$_2$—, —SO$_2$N($R^6$)—, —N($R^6$)—, —CO—, —CO$_2$—, —N($R^6$)CO—, —N($R^6$)C(O)O—, —N($R^6$)CON($R^6$)—, —N($R^6$)SO$_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)SO$_2$N($R^6$)—, or —C($R^6$)$_2$N($R^6$)CON($R^6$)—;

$R^2$ and $R^{2'}$ are independently selected from —R, —T—W—$R^6$, or $R^2$ and $R^{2'}$ are taken together with their intervening atoms to form a fused, 5–8 membered, unsaturated or partially unsaturated, ring having 0–3 ring heteroatoms selected from nitrogen, oxygen, or sulfur, wherein each substitutable ring carbon of said fused ring formed by $R^2$ and $R^{2'}$ is independently substituted by halo, oxo, —CN, —NO$_2$, —$R^7$, or —V—$R^6$, and each substitutable ring nitrogen of said ring formed by $R^2$ and $R^{2'}$ is independently substituted by $R^4$;

$R^3$ is selected from —R, -halo, —OR, —C(=O)R, —CO$_2$R, —COCOR, —COCH$_2$COR, —NO$_2$, —CN, —S(O)R, —S(O)$_2$R, —SR, —N($R^4$)$_2$, —CON($R^7$)$_2$, —SO$_2$N($R^7$)$_2$, —OC(=O)R, —N($R^7$)COR, —N($R^7$)CO$_2$(C$_{1-6}$ aliphatic), —N($R^4$)N($R^4$)$_2$, —C=NN($R^4$)$_2$, —C=N—OR, —N($R^7$)CON($R^7$)$_2$, —N($R^7$)SO$_2$N($R^7$)$_2$, —N($R^4$)SO$_2$R, or —OC(=O)N($R^7$)$_2$;

each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;

each $R^4$ is independently selected from —$R^7$, —COR$^7$, —CO$_2$(optionally substituted $C_{1-6}$ aliphatic), —CON($R^7$)$_2$, or —SO$_2$R$^7$;

each $R^5$ is independently selected from —R, halo, —OR, —C(=O)R, —CO$_2$R, —COCOR, —NO$_2$, —CN, —S(O)R, —SO$_2$R, —SR, —N($R^4$)$_2$, —CON($R^4$)$_2$, —SO$_2$N($R^4$)$_2$, —OC(=O)R, —N($R^4$)COR, —N($R^4$)CO$_2$(optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)SO$_2$N($R^4$)$_2$, —N($R^4$)SO$_2$R, or —OC(=O)N($R^4$)$_2$;

V is —O—, —S—, —SO—, —SO$_2$—, —N($R^6$)SO$_2$—, —SO$_2$N($R^6$)—, —N($R^6$)—, —CO—, —CO$_2$—, —N($R^6$)CO—, —N($R^6$)C(O)O—, —N($R^6$)CON($R^6$)—, —N($R^6$)SO$_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)SO$_2$N($R^6$)—, or —C($R^6$)$_2$N($R^6$)CON($R^6$)—;

W is —C($R^6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N($R^6$)—, —CO—, —CO$_2$—, —C($R^6$)OC(O)—, —C($R^6$)OC(O)N($R^6$)—, —C($R^6$)$_2$N($R^6$)CO—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)SO$_2$N($R^6$)—, —C($R^6$)$_2$N($R^6$)CON($R^6$)—, or —CON($R^6$)—;

each $R^6$ is independently selected from hydrogen or an optionally substituted $C_{1-4}$ aliphatic group, or two $R^6$ groups on the same nitrogen atom are taken together with the nitrogen atom to form a 5–6 membered heterocyclyl or heteroaryl ring;

each $R^{6'}$ is independently selected from hydrogen or a $C_{1-4}$ aliphatic group, or two $R^{6'}$ on the same carbon atom are taken together to form a 3–6 membered carbocyclic ring; and each $R^7$ is independently selected from hydrogen or an optionally substituted $C_{1-6}$ aliphatic group, or two $R^7$ on the same nitrogen are taken together with the nitrogen to form a 5–8 membered heterocyclyl or heteroaryl ring.

Preferred $R^x$ groups of formula IIId include hydrogen, alkyl- or dialkylamino, acetamido, or a $C_{1-4}$ aliphatic group such as methyl, ethyl, cyclopropyl, or isopropyl.

Preferred $R^y$ groups of formula IIId include T—$R^3$ or L—Z—$R^3$ wherein T is a valence bond or a methylene, L is —O—, —S—, or —N($R^4$)—, —C($R^6$)$_2$ O—, —CO— and $R^3$ is —R, —N($R^4$)$_2$, or —OR. Examples of preferred $R^y$ groups include 2-pyridyl, 4-pyridyl, pyrrolidinyl, piperidinyl, morpholinyl, piperazinyl, methyl, ethyl, cyclopropyl, isopropyl, t-butyl, alkoxyalkylamino such as methoxyethylamino, alkoxyalkyl such as methoxymethyl or methoxyethyl, alkyl- or dialkylamino such as ethylamino or dimethylamino, alkyl- or dialkylaminoalkoxy such as dimethylaminopropyloxy, acetamido, optionally substituted phenyl such as phenyl or halo-substituted phenyl.

The $R^2$ and $R^{2'}$ groups of formula IIId may be taken together to form a fused ring, thus providing a bicyclic ring system containing a pyrazole ring. Preferred fused rings include benzo, pyrido, pyrimido, and a partially unsaturated 6-membered carbocyclo ring. These are exemplified in the following formula IIId compounds having a pyrazole-containing bicyclic ring system:

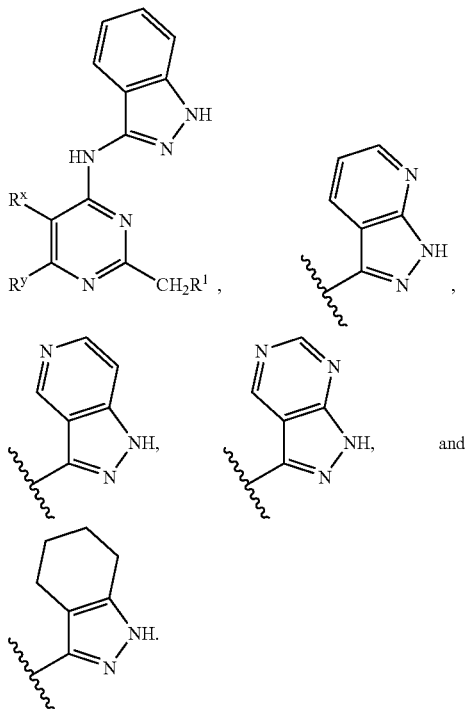

Preferred substituents on the $R^2/R^{2'}$ fused ring of formula IIId include one or more of the following: -halo, $-N(R^4)_2$, $-C_{1-4}$ alkyl, $-C_{1-4}$ haloalkyl, $-NO_2$, $-O(C_{1-4}$ alkyl), $-CO_2(C_{1-4}$ alkyl), $-CN$, $-SO_2(C_{1-4}$ alkyl), $-SO_2NH_2$, $-OC(O)NH_2$, $-NH_2SO_2(C_{1-4}$ alkyl), $-NHC(O)(C_{1-4}$ alkyl), $-C(O)NH_2$, and $-CO(C_{1-4}$ alkyl), wherein the $(C_{1-4}$ alkyl) is a straight, branched, or cyclic alkyl group. Preferably, the $(C_{1-4}$ alkyl) group is methyl.

When the pyrazole-ring system of formula IIId is monocyclic, preferred $R^2$ groups include hydrogen or a substituted or unsubstituted group selected from aryl, heteroaryl, or a $C_{1-6}$ aliphatic group. Examples of such preferred $R^2$ groups include H, methyl, ethyl, propyl, cyclopropyl, i-propyl, cyclopentyl, hydroxypropyl, methoxypropyl, and benzyloxypropyl. A preferred $R^{2'}$ group is hydrogen.

When Ring D of formula IIId is mono cyclic, preferred Ring D groups include phenyl, pyridyl, pyridazinyl, pyrimidinyl, and pyrazinyl.

When Ring D of formula IIId is bicyclic, preferred bicyclic Ring D groups include naphthyl, tetrahydronaphthyl, indanyl, benzimidazolyl, quinolinyl, indolyl, isoindolyl, indolinyl, benzo[b]furyl, benzo[b]thiophenyl, indazolyl, benzothiazolyl, cinnolinyl, phthalazinyl, quinazolinyl, quinoxazolinyl, 1,8-naphthyridinyl and isoquinolinyl.

On Ring D of formula IIId, preferred $T-R^5$ or $V-Z-R^5$ substituents include -halo, $-CN$, $-NO^2$, $-N(R^4)_2$, optionally substituted $C_{1-6}$ aliphatic group, $-OR$, $-C(O)R$, $-CO_2R$, $-CONH(R^4)$, $-N(R^4)COR$, $-N(R^4)CO_2R$, $-SO_2N(R^4)_2$, $-N(R^4)SO_2R$, $-N(R^6)COCH_2N(R^4)_2$, $-N(R^6)COCH_2CH_2N(R^4)_2$, and $-N(R^6)COCH_2CH_2CH_2N(R^4)_2$, wherein R is selected from hydrogen, $C_{1-6}$ aliphatic, phenyl, a 5–6 membered heteroaryl ring, or a 5–6 membered heterocyclic ring. More preferred $R^5$ substituents include $-Cl$, $-Br$, $-F$, $-CN$, $-CF_3$, $-COOH$, $-CONMe$, $-CONHEt$, $-NH_2$, $-NHAc$, $-NHSO_2Me$, $-NHSO_2Et$, $-NHSO_2(n\text{-propyl})$, $-NHSO_2(\text{isopropyl})$, $-NHCOEt$, $-NHCOCH_2NHCH_3$, $-NHCOCH_2N(CO_2t\text{-Bu})CH_3$, $-NHCOCH_2N(CH_3)_2$, $-NHCOCH_2CH_2N(CH_3)_2$, $-NHCOCH_2CH_2CH_2N(CH_3)_2$, $-NHCO(\text{cyclopropyl})$, $-NHCO(\text{isobutyl})$, $-NHCOCH_2$ (morpholin-4-yl), $-NHCOCH_2CH_2(\text{morpholin-4-yl})$, $-NHCOCH_2CH_2CH_2$ (morpholin-4-yl), $-NHCO_2(\text{t-butyl})$, $-NH(C_{1-4}$ aliphatic) such as $-NHMe$, $-N(C_{1-4}$ aliphatic)$_2$ such as $-NMe_2$, OH, $-O(C_{1-4}$ aliphatic) such as $-OMe$, $C_{1-4}$ aliphatic such as methyl, ethyl, cyclopropyl, isopropyl, or t-butyl, and $-CO_2(C_{1-4}$ aliphatic).

Preferred Q' groups of formula IIId include. $-C(R^{6'})_2-$ or 1,2-cyclopropanediyl, wherein each $R^{6'}$ is independently selected from hydrogen or methyl. A more preferred Q' group is $-CH_2-$.

Preferred formula IIId compounds have one or more, and more preferably all, of the features selected from the group consisting of:

(a) $R^x$ is hydrogen, alkyl- or dialkylamino, acetamido, or a $C_{1-4}$ aliphatic group;
(b) $R^x$ is $T-R^3$ or $L-Z-R^3$, wherein T is a valence bond or a methylene and $R^3$ is $-R$, $-N(R^4)_2$, or $-OR$;
(c) $R^1$ is T (Ring D), wherein T is a valence bond or a methylene unit and wherein said methylene unit is optionally replaced by $-O-$, $-NH-$, or $-S-$;
(d) Ring D is a 5–7 membered monocyclic or an 8–10 membered bicyclic aryl or heteroaryl ring; and
(e) $R^2$ is $-R$ or $-T-W-R^6$ and $R^{2'}$ is hydrogen, or $R^2$ and $R^{2'}$ are taken together to form an optionally. substituted benzo ring.

More preferred compounds of formula IIId have one or more, and more preferably all, of the features selected from the group consisting of:

(a) $R^y$ is $T-R^3$ or $L-Z-R^3$ wherein T is a valence bond or a methylene and $R^3$ is selected from $-R$, $-OR$, or $-N(R^4)_2$, wherein R is selected from hydrogen, $C_{1-6}$ aliphatic, or 5–6 membered heterocyclyl, phenyl, or 5–6 membered heteroaryl;
(b) $R^1$ is T-(Ring D), wherein T is a valence bond;
(c) Ring D is a 5–6 membered monocyclic or an 8–10 membered bicyclic aryl or heteroaryl ring;
(d) $R^2$ is $-R$ and $R^{2'}$ is hydrogen, wherein R is selected from hydrogen, $C_{1-6}$ aliphatic, phenyl, a 5–6 membered heteroaryl ring, or a 5–6 membered heterocyclic ring;
(e) L is $-O-$, $-S-$, or $-N(R^4)-$; and
(f) Q' is $-C(R^{6'})_2-$ or 1,2-cyclopropanediyl, wherein each $R^{6'}$ is independently selected from hydrogen or methyl.

Even more preferred compounds of formula IIId have one or more, and more preferably all, of the features selected from thee group consisting of:

(a) $R^x$ is hydrogen methyl, ethyl, propyl, cyclopropyl, isopropyl, methylamino or acetimido;

(b) $R^y$ is selected from 2-pyridyl, 4-pyridyl, pyrrolidinyl, piperidinyl, morpholinyl, piperazinyl, methyl, ethyl, cyclopropyl, isopropyl, t-butyl, alkoxyalkylamino, alkoxyalkyl, alkyl- or dialkylamino, alkyl- or dialkylaminoamido, acetamido, optionally substituted phenyl, or methoxymethyl;

(c) $R^1$ is T-(Ring D), wherein T is a valence bond and Ring D is a 5–6 membered aryl or heteroaryl ring, wherein Ring D is optionally substituted with one to two groups selected from -halo, —CN, —NO$_2$, —N(R$^4$)$_2$, optionally substituted C$_{1-6}$ aliphatic group, —OR, —CO$_2$R, —CONH(R$^4$), —N(R$^4$)COR, —N(R$^4$)SO$_2$R, —N(R$^6$)COCH$_2$CH$_2$N(R$^4$)$_2$, or —N(R$^6$)COCH$_2$CH$_2$CH$_2$N(R$^4$)$_2$;

(d) $R^2$ is hydrogen or a substituted or unsubstituted C$_{1-6}$ aliphatic; and L is —O—, —S—, or —NH—; and (e) Q' is —CH$_2$—.

Representative compounds of formula IIId are shown below in Table 8.

TABLE 8

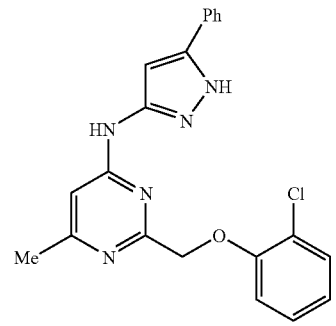

IIId-1

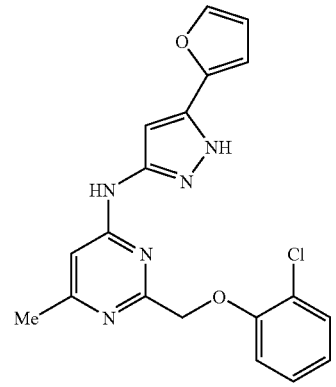

IIId-2

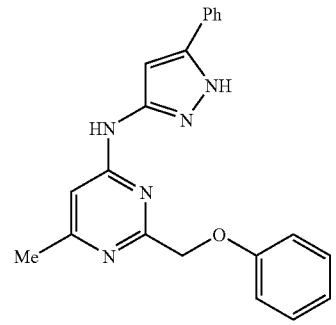

IIId-3

TABLE 8-continued

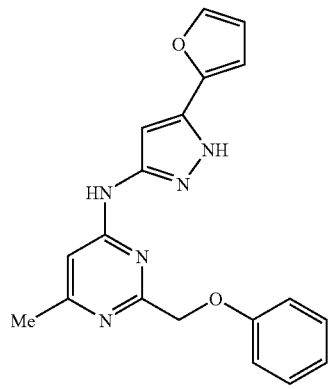

IIId-4

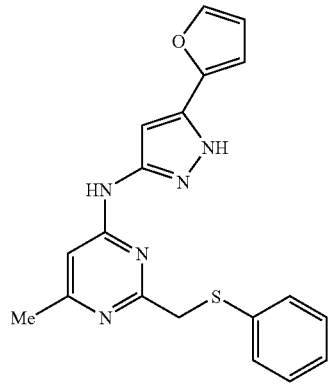

IIId-5

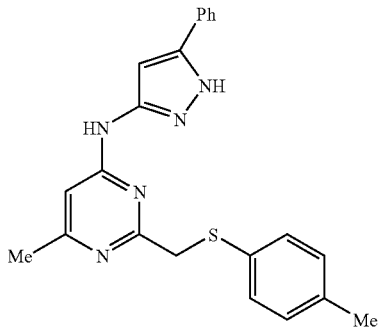

IIId-6

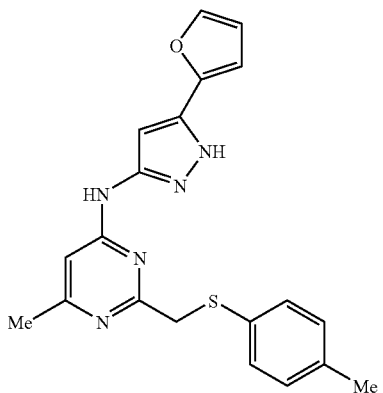

IIId-7

TABLE 8-continued
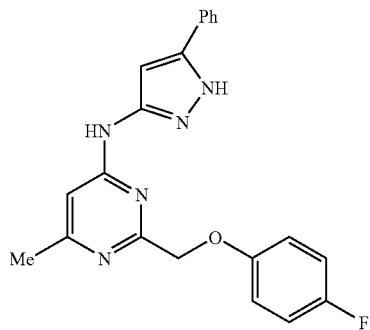
IIId-8
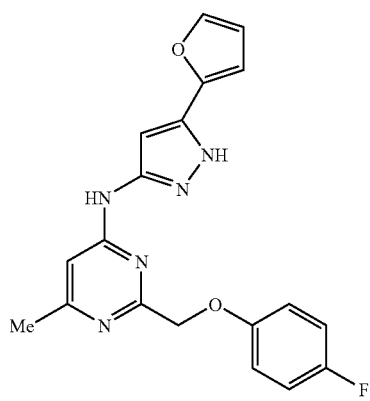
IIId-9
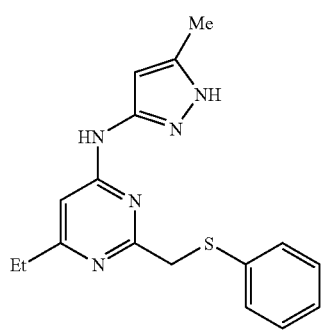
IIId-10
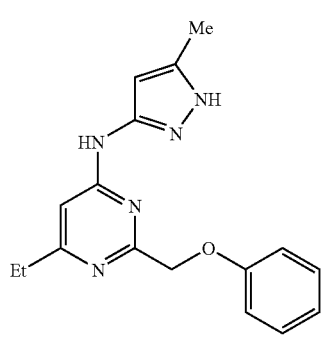
IIId-11
TABLE 8-continued
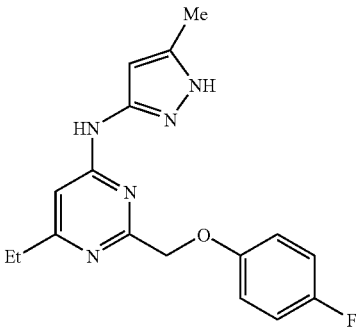
IIId-12
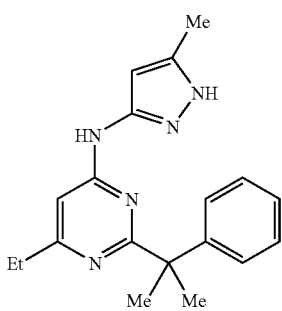
IIId-13
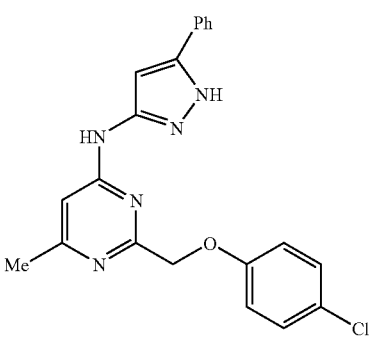
IIId-14
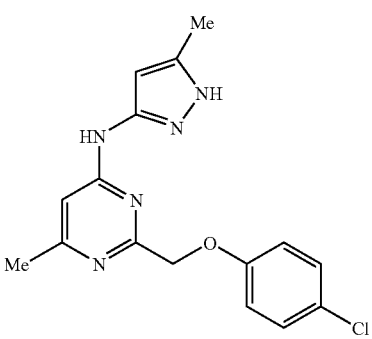
IIId-15

TABLE 8-continued
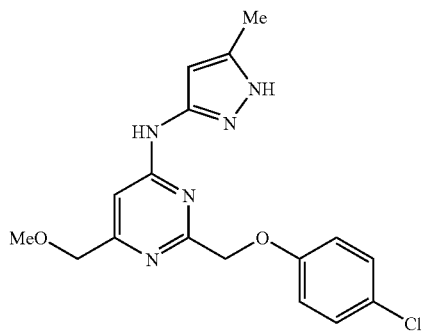
IIId-16
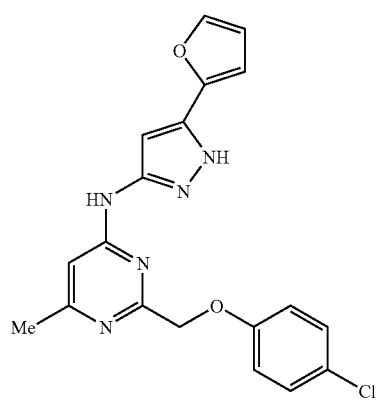
IIId-17
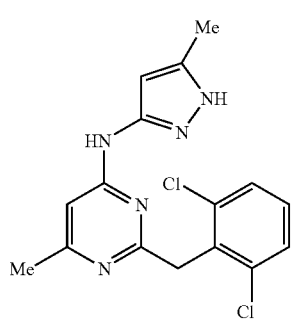
IIId-18
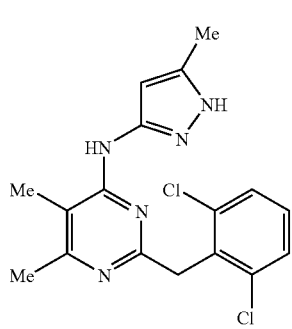
IIId-19
TABLE 8-continued
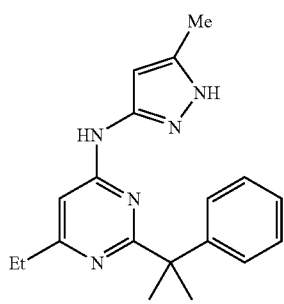
IIId-20
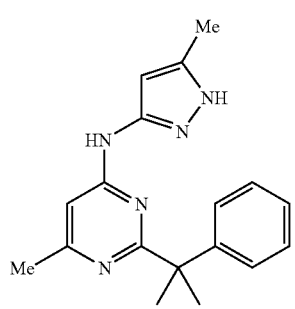
IIId-21
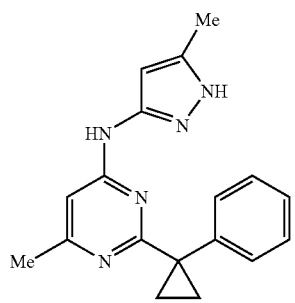
IIId-22
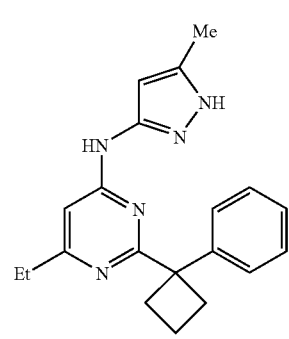
IIId-23

TABLE 8-continued

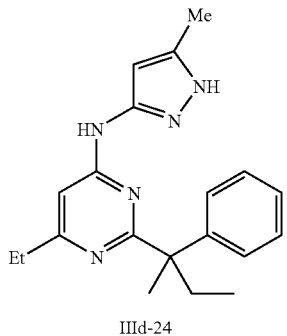

IIId-24

In another-embodiment, this invention provides a composition comprising a compound of formula IIId and a pharmaceutically acceptable carrier.

Another aspect of this invention relates to a method of treating or preventing an Aurora-2-mediated disease with an Aurora-2 inhibitor, which .method comprises administering to a patient in need of such a treatment a therapeutically effective amount of a compound of formula IIId or a pharmaceutical composition thereof.

Another aspect of this invention relates to a method of inhibiting Aurora-2 activity in a patient, which method comprises administering to the patient a compound of formula IIId or a composition comprising said compound.

Another aspect of this invention relates to a method of treating or preventing a GSK-3-mediated disease with a GSK-3 inhibitor, which method comprises administering to a patient in need of such a treatment a therapeutically effective amount of a compound of formula IIId or a pharmaceutical composition thereof.

One aspect of this invention relates to a method of enhancing glycogen synthesis and/or lowering blood levels of glucose in a patient in need thereof, which method comprises administering to the patient a therapeutically effective amount of a compound of formula IIId or a pharmaceutical composition thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of β-catenin, which is useful for treating schizophrenia.

Another aspect of this invention relates to a method of inhibiting GSK-3 activity in a patient, which method comprises administering to the patient a compound of formula IIId or a composition comprising said compound.

Another method relates to inhibiting Aurora-2 or GSK-3 activity in a biological sample, which method comprises contacting the biological sample with the Aurora-2 or GSK-3 inhibitor of formula IIId, or a pharmaceutical composition thereof, in an amount effective to inhibit Aurora-2 or GSK-3.

Each of the aforementioned methods directed to the inhibition of Aurora-2 or GSK-3, or the treatment of a disease alleviated thereby, is preferably carried out with a preferred compound of formula IIId, as described above.

Another embodiment of this invention relates to compounds of formula IVa:

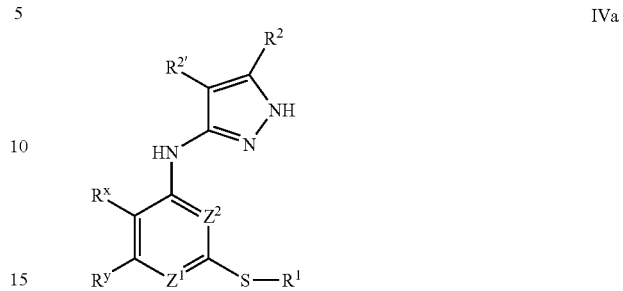

IVa or a pharmaceutically acceptable derivative or prodrug thereof, wherein:

$Z^1$ is nitrogen or C—$R^8$ and $Z^2$ is nitrogen or CH, wherein one of $Z^1$ or $Z^2$ is nitrogen;

$R^x$ and $R^y$ are independently selected from T—$R^3$ or L—Z—$R^3$, or $R^x$ and $R^y$ are taken together with their intervening atoms to form a fused, unsaturated or partially unsaturated, 5–7 membered ring having 0–3 ring heteroatoms selected from oxygen, sulfur, or nitrogeno, wherein each substitutable ring carbon of said fused ring formed by $R^x$ and $R^y$ is independently substituted by oxo, T—$R^3$, or L—Z—$R^3$, and each substitutable ring nitrogen of said ring formed by $R^x$ and $R^y$ is independently substituted by $R^4$;

$R^1$ is T-(Ring D);

Ring D is a 5–7-membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein each substitutable ring carbon of Ring D is independently substituted by oxo, T—$R^5$, or V—Z—$R^5$, and each substitutable ring nitrogen of Ring D is independently substituted by —$R^4$;

T is a valence bond or a $C_{1-4}$ alkylidene chain;

Z is a $C_{1-4}$ alkylidene chain;

L is —O—, —S—, —SO—, —SO$_2$—, —N($R^6$)SO$_2$—, SO$_2$N($R^6$)—, —N($R^6$)—, —CO—, —CO$_2$—, —N($R^6$) CO—, —N($R^6$)C(O)O—, —N($R^6$)CON($R^6$)—, —N($R^6$) SO$_2$N($R^6$)—, —N($R^6$)N($R^6$)—, —C(O)N($R^6$)—, —OC (O)N($R^6$)—, —C($R^6$)$_2$O—, —C($R^6$)$_2$S—, —C($R^6$)$_2$ SO—, —C($R^6$)$_2$SO$_2$—, —C($R^6$)$_2$SO$_2$N($R^6$)—, —C($R^6$)$_2$ N($R^6$)—, —C($R^6$)$_2$N($R^6$)C(O)—, —C($R^6$)$_2$N($R^6$)C(O) O—, —C($R^6$)=NN($R^6$)—, —C($R^6$)=N—O—, —C($R^6$)$_2$ N($R^6$)N($R^6$)—, —C($R^6$)$_2$N($R^6$)SO$_2$N($R^6$)—, or —C($R^6$)$_2$N($R^6$)CON($R^6$)—;

$R^2$ and $R^{2'}$ are independently selected from —R, —T—W—$R^6$, or $R^2$ and $R^{2'}$ are taken together with their intervening atoms to form a fused, 5–8 membered, unsaturated or partially unsaturated, ring having 0–3 ring heteroatoms selected from nitrogen, oxygen, or sulfur, wherein each substitutable ring carbon of said fused ring formed by $R^2$ and $R^{2'}$ independently substituted by halo, oxo, —CN, —NO$_2$, —$R^7$, or —V—$R^6$; and each substitutable ring nitrogen of said ring formed by $R^2$ and $R^{2'}$ is independently substituted by $R^4$;

$R^3$ is selected from —R, -halo, —OR, —C(=O)R, —CO$_2$R, —COCOR, —COCH$_2$COR, —NO$_2$, —CN, —S(O)R, —S(O)$_2$R, —SR, —N($R^4$)$_2$, —CON($R^7$)$_2$, —SO$_2$N($R^7$)$_2$, —OC(=O)R, —N($R^7$)COR, —N($R^7$)CO$_2$($C_{1-6}$ aliphatic), —N(R⁴)N(R⁴)₂, —C=NN(R⁴)₂, —C=N—OR, —N(R⁷)CON(R⁷)₂, —N(R⁷)SO₂N(R⁷)₂, —N(R⁴)SO₂R, or —OC(=O)N(R⁷)₂;

each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;

each $R^4$ is independently selected from —R⁷, —COR⁷, —CO₂(optionally substituted $C_{1-6}$ aliphatic), —CON(R⁷)₂, or —SO₂R⁷;

each $R^5$ is independently selected from —R, halo, —OR, —C(=O)R, —CO₂R, —COCOR, —NO₂, —CN, —S(O)R, —SO₂R, —SR, —N(R⁴)₂, —CON(R⁴)₂, —SO₂N(R⁴)₂, —OC(=O)R, —N(R⁴)COR, —N(R⁴)CO₂(optionally substituted $C_{1-6}$ aliphatic), —N(R⁴)N(R⁴)₂, —C=NN(R⁴)₂, —C=N—OR, —N(R⁴)CON(R⁴)₂, —N(R⁴)SO₂N(R⁴)₂, —N(R⁴)SO₂R, or —OC(=O)N(R⁴)₂;

V is —O—, —S—, —SO—, —SO₂—, —N(R⁶)SO₂—, —SO₂N(R⁶)—, —N(R⁶)—, —CO—, —CO₂—, —N(R⁶)CO—, —N(R⁶)C(O)O—, —N(R⁶)CON(R⁶)—, —N(R⁶)SO₂N(R⁶)—, —N(R⁶)N(R⁶)—, —C(O)N(R⁶)—, —OC(O)N(R⁶)—, —C(R⁶)₂O—, —C(R⁶)₂S—, —C(R⁶)₂SO—, —C(R⁶)₂SO₂—, —C(R⁶)₂SO₂N(R⁶)—, —C(R⁶)₂N(R⁶)—, —C(R⁶)₂N(R⁶)C(O)—, —C(R⁶)₂N(R⁶)C(O)O—, —C(R⁶)=NN(R⁶)—, —C(R⁶)=N—O—, —C(R⁶)₂N(R⁶)N(R⁶)—, —C(R⁶)₂N(R⁶)SO₂N(R⁶)—, or —C(R⁶)₂N(R⁶)CON(R⁶)—;

W is —C(R⁶)₂O—, —C(R⁶)₂S—, —C(R⁶)₂SO—, —C(R⁶)₂SO₂—, —C(R⁶)₂SO₂N(R⁶)—, —C(R⁶)₂N(R⁶)—, —CO—, —CO₂—, —C(R⁶)OC(O)—, —C(R⁶)OC(O)N(R⁶)—, —C(R⁶)₂N(R⁶)CO—, —C(R⁶)₂N(R⁶)C(O)O—, —C(R⁶)=NN(R⁶)—, —C(R⁶)=N—O—, —C(R⁶)₂N(R⁶)N(R⁶)—, —C(R⁶)₂N(R⁶)SO₂N(R⁶)—, —C(R⁶)₂N(R⁶)CON(R⁶)—, or —CON(R⁶)—;

each $R^6$ is independently selected from hydrogen or an optionally substituted $C_{1-4}$ aliphatic group, or two $R^6$ groups on the same nitrogen atom are taken together with the nitrogen atom to form a 5–6 membered heterocyclyl or heteroaryl ring;

each $R^7$ is independently selected from hydrogen or an optionally substituted $C_{1-6}$ aliphatic group, or two $R^7$ on the same nitrogen are taken together with the nitrogen to form a 5–8 membered heterocyclyl or heteroaryl ring; and $R^8$ is selected from —R, halo, —OR, —C(=O)R, —CO₂R, —COCOR, —NO₂, —CN, —S(O)R, —SO₂R, —SR, —N(R⁴)₂, —CON(R⁴)₂, —SO₂N(R⁴)₂, —OC(=O)R, —N(R⁴)COR, —N(R⁴)CO₂(optionally substituted $C_{1-6}$ aliphatic), —N(R⁴)N(R⁴)₂, —C=NN(R⁴)₂, —C=N—OR, —N(R⁴)CON(R⁴)₂, —N(R⁴)SO₂N(R⁴)₂, —N(R⁴)SO₂R, or —OC(=O)N(R⁴)₂.

Preferred rings formed by $R^x$ and $R^y$ of formula IVa include a 5-, 6-, or 7-membered unsaturated or partially unsaturated ring having 0–2 heteroatoms, wherein said $R^x/R^y$ ring is optionally substituted. This provides a bicyclic ring system containing a pyridine ring. Preferred pyridine ring systems of formula IVa are shown below.

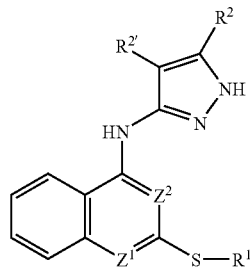

IVa-A

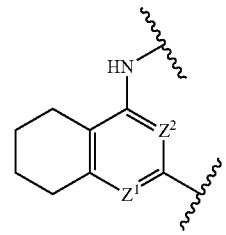

IVa-B

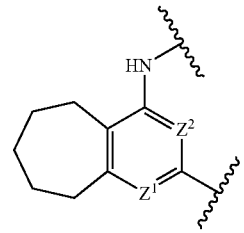

IVa-C

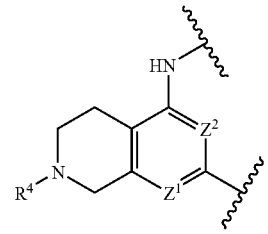

IVa-D

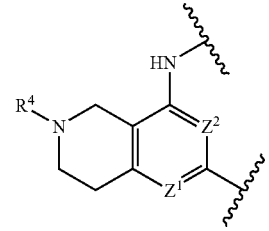

IVa-E

IVa-F

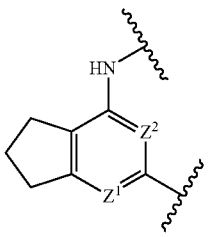

IVa-J

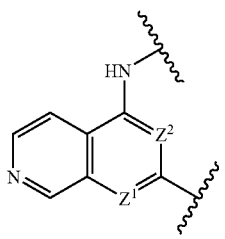

IVa-K

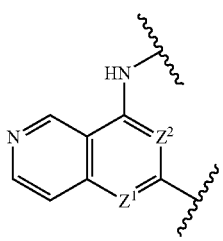

IVa-L

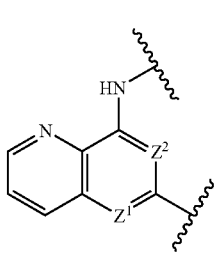

IVa-P

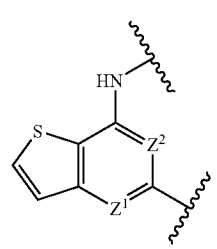

IVa-R

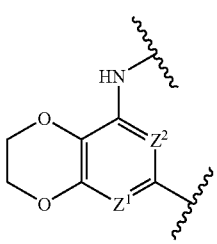

IVa-V

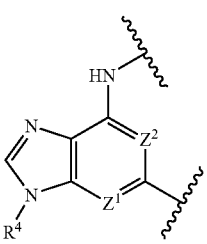

IVa-W

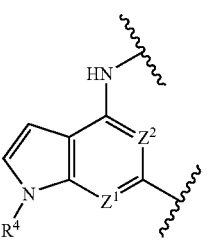

More preferred pyridine ring systems of formula IVa include IVa-A, IVa-B, IVa-D, IVa-E, IVa-J, IVa-P, and IVa-V, most preferably IVa-A, IVa-B, IVa-D, IVa-E, and IVa-J. Even more preferred pyridine ring-systems of formula IVa are those described above, wherein $Z^1$ is nitrogen and $Z^2$ is CH.

Preferred $R^x$ groups of formula IVa include hydrogen, alkyl- or dialkylamino, acetamido, or a $C_{1-4}$ aliphatic group such as methyl, ethyl, cyclopropyl, or isopropyl.

Preferred $R^y$ groups of formula IVa include T—$R^3$ or L—Z—$R^3$ wherein T is a valence bond or a methylene, L is —O—, —S—, or —N($R^4$)—, —C($R^6$)$_2$O—, —CO— and $R^3$ is —R, —N($R^4$)$_2$, or —OR. Examples of preferred $R^y$ groups include 2-pyridyl, 4-pyridyl, pyrrolidinyl, piperidinyl morpholinyls piperazinyl, methyl, ethyl, cyclopropyl, isopropyl, t-butyl, alkoxyalkylamino such as methoxyethylamino, alkoxyalkyl such as methoxymethyl or methoxyethyl, alkyl- or dialkylamino such as a ethylamino or dimethylamino, alkyl- or dialkylaminoalkoxy such as dimethylaminopropyloxy, acetamido, optionally substituted phenyl such as phenyl or halo-substituted phenyl.

The ring formed when the $R^x$ and $R^y$ groups of formula IVa are taken together may be substituted or unsubstituted. Suitable substituents include —R, halo, —O(CH$_2$)$_{2-4}$—N(R$^4$)$_2$, —O(CH$_2$)$_{2-4}$—R, —OR, —N(R$^4$)—(CH$_2$)$_{2-4}$—N(R$^4$)$_2$, —N(R$^4$)—(CH$_2$)$_{2-4}$—R, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$(optionally substituted C$_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$, R and R$^4$ are as defined above. Preferred $R^x$/$R^y$ ring substituents include -halo, —R, —OR, —COR, —CO$_2$R, —CON(R$^4$)$_2$, —CN, —O(CH$_2$)$_{2-4}$—N(R$^4$)$_2$, —O(CH$_2$)$_{2-4}$—R, —NO$_2$—N(R$^4$)$_2$, —NR$^4$COR, —NR$^4$SO$_2$R, —SO$_2$N(R$^4$)$_2$ wherein R is hydrogen or an optionally substituted C$_{1-6}$ aliphatic group.

The $R^2$ and $R^{2'}$ groups of formula IVa may be taken together to form a fused ring, thus providing a bicyclic ring system containing a pyrazole ring. Preferred fused rings include benzo, pyrido, pyrimido, and a partially unsaturated 6-membered carbocyclo ring. These are exemplified in the following formula IVa compounds having a pyrazole containing bicyclic ring system:

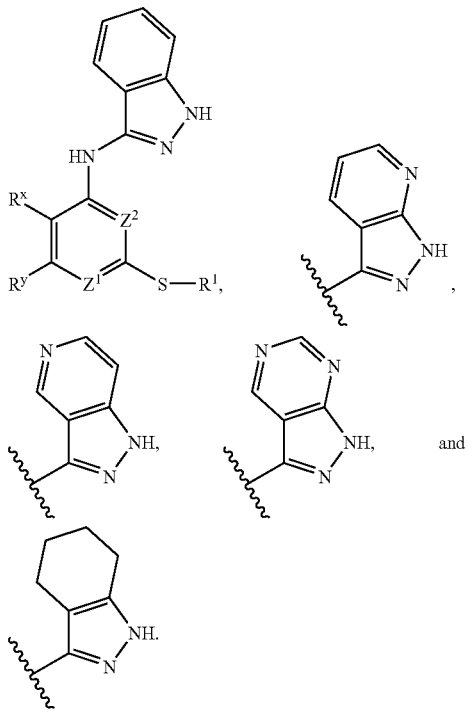

Preferred substituents on the R²/R²' fused ring of formula IVa include one or more of the following: -halo, —N(R⁴)₂, —C₁₋₄ alkyl, —C₁₋₄ haloalkyl, —NO₂, —O(C₁₋₄ alkyl), —CO₂(C₁₋₄ alkyl), —CN, —SO₂(C₁₋₄ alkyl), —SO₂ NH₂, —OC(O)NH₂, —NH₂SO₂(C₁₋₄ alkyl), —NHC(O)(C₁₋₄ alkyl), —C(O)NH₂, and —CO(C₁₋₄ alkyl), wherein the (C₁₋₄ alkyl) is a straight, branched, or cyclic alkyl group. Preferably, the (C₁₋₄ alkyl) group is methyl.

When the pyrazole ring system of formula IVa is monocyclic, preferred R² groups include hydrogen or a substituted or unsubstituted group selected from aryl, heteroaryl, or a C₁₋₆ aliphatic group. Examples of such preferred R² groups include H, methyl, ethyl, propyl, cyclopropyl, i-propyl, cyclopentyl, hydroxypropyl, methoxypropyl, and benzyloxypropyl. A preferred R²' group is hydrogen.

When Ring D of formula IVa is monocyclic, preferred Ring D groups include phenyl, pyridyl, pyridazinyl, pyrimidinyl, and pyrazinyl.

When Ring D of formula IVa is bicyclic, preferred bicyclic Ring D groups include naphthyl, tetrahydronaphthyl, indanyl, benzimidazolyl, quinolinyl, indolyl, isoindolyl, indolinyl, benzo[b]furyl, benzo[b]thiophenyl, indazolyl, benzothiazolyl, cinnolinyl, phthalazinyl, quinazolinyl, quinoxazolinyl, naphthyridinyl and isoquinolinyl.

On Ring D of formula IVa, preferred T—R⁵ or V—Z—R⁵ substituents include -halo, —CN, —NO₂, —N(R⁴)₂, optionally substituted C₁₋₆ aliphatic group, —OR, —C(O)R, —CO₂R, —CONH(R⁴), —N(R⁴)COR, —N(R⁴)CO₂R, —SO₂N(R⁴)₂, —N(R⁴)SO₂R, —N(R⁶)COCH₂N(R⁴)₂, —N(R⁶)COCH₂CH₂N(R⁴)₂, and —N(R⁶)COCH₂CH₂CH₂N(R⁴)₂, wherein R is selected from hydrogen, C₁₋₆ aliphatic, phenyl, a 5–6 membered heteroaryl ring, or a 5–6 membered heterocyclic ring. More preferred R⁵ substituents include —Cl, —Br, —F, —CN, —CF₃, —COOH, —CONHMe, —CONHEt, —NH₂, —NHAc, —NHSO₂Me, —NHSO₂Et, —NHSO₂(n-propyl), —NHSO₂(isopropyl), —NHCOEt, —NHCOCH₂NHCH₃, —NHCOCH₂N(CO₂t-Bu)CH₃, —NHCOCH₂N(CH₃)₂, —NHCOCH₂CH₂N(CH₃)₂, —NHCOCH₂CH₂N(CH₃)₂, —NHCO(cyclopropyl), —NHCO(isobutyl), —NHCOCH₂ (morpholin-4-yl), —NHCOCH₂CH₂(morpholin-4-yl), —NHCOCH₂CH₂CH₂ (morpholin-4-yl), —NHCO₂(t-butyl), —NH(C₁₋₄ aliphatic) such as —NHMe, —N(C₁₋₄ aliphatic)₂ such as —NMe₂, OH, —O(C₁₋₄ aliphatic) such as —OMe, C₁₋₄ aliphatic such as methyl, ethyl, cyclopropyl, isopropyl, or t-butyl, and —CO₂(C₁₋₄ aliphatic).

Preferred R⁸ groups of formula IVa, when present, include R, OR, and N(R⁴)₂. Examples of preferred R⁸ include methyl, ethyl, NH₂, NH₂CH₂CH₂NH, N(CH₃)₂ CH₂CH₂NH, N(CH₃)₂CH₂CH₂O, (piperidin-1-yl) CH₂CH₂O, and NH₂CH₂CH₂O.

Preferred formula IVa compounds have one or more, and more preferably all, of the features selected from the group consisting of:

(a) R^x is hydrogen, alkyl- or dialkylamino, acetamido, or a C₁₋₄ aliphatic group and R^y is T—R³ or L—Z—R³, wherein T is a valence bond or a methylene and R³ is —R; —N(R⁴)₂, or —OR; or R^x and R^y are taken together with their intervening atoms to form a fused, unsaturated or partially unsaturated, 5–6 membered ring having 0–2 heteroatoms selected from oxygen, sulfur, or nitrogen, wherein each substitutable ring carbon of said fused ring formed by R^x and R^y is independently substituted by oxo, T—R³, or L—Z—R³, and each substitutable ring nitrogen of said ring formed by R^x and R^y is independently substituted by R⁴;

(b) R¹ is T-(Ring D), wherein T is a valence bond or a methylene-unit;

(c) Ring D is a 5–7 membered monocyclic or an 8–10 membered bicyclic aryl or heteroaryl ring; and (d) R² is —R or —T—W—R⁶ and R²' is hydrogen, or R² and R²' are taken together to form an optionally substituted benzo ring.

More preferred compounds of formula IVa have one or more, and more preferably all, of the features selected from the group consisting of:

(a) R^y is T—R³ or L—Z—R³ wherein T is a valence bond or a methylene and R³ is selected from —R, —OR, or —N(R⁴)₂, wherein R is selected from hydrogen, C₁₋₆ aliphatic, or 5–6 membered heterocyclyl, phenyl, or 5–6 membered heteroaryl; or R^x and R^y are taken together with their intervening atoms to form a benzo, pyrido, cyclopento, cyclohexo, cyclohepto, thieno, piperidino, or imidazo ring, wherein each substitutable ring carbon of said fused ring formed by R^x and R^y is independently substituted by oxo, T—R³, or L—Z—R³, and each substitutable ring nitrogen of said ring formed by R^x and R^y is independently substituted by R⁴;

(b) R¹ is T-(Ring D), wherein T is a valence bond, and Ring D is a 5–6 membered monocyclic or an 8–10 membered bicyclic aryl or heteroaryl ring;

(c) R² is —R and R²' is hydrogen, wherein R is selected from hydrogen, C₁₋₆ aliphatic, phenyl, a 5–6 membered heteroaryl ring, or a 5–6 membered heterocyclic ring; and (d) R³ is selected from —R, -halo, —OR, or —N(R⁴)₂, wherein R is selected from hydrogen, C₁₋₆ aliphatic, or 5–6 membered-heterocyclyl, phenyl, or 5–6 membered heteroaryl, and L is —O—, —S—, or —N(R⁴)—.

Even more preferred compounds of formula IVa have one or more, and more preferably all, of the features selected from the group consisting of:

(a) $R^x$ is hydrogen methyl, ethyl, propyl, cyclopropyl, isopropyl, methylamino or acetamido and $R^y$ is selected from 2-pyridyl, 4-pyridyl, pyrrolidinyl, piperidinyl, morpholinyl, piperazinyl, methyl, ethyl, cyclopropyl, isopropyl, t-butyl, alkoxyalkylamino, alkoxyalkyl, alkyl- or dialkylamino, alkyl- or dialkylaminoalkoxy, acetamido, optionally substituted phenyl, or methoxymethyl; or $R^x$ and $R^y$ are taken together with their intervening atoms to form a benzo, pyrido, piperidino, or cyclohexo ring, wherein said ring is optionally substituted with -halo, —R, —OR, —COR, —CO$_2$R, —CON(R$^4$)$_2$, —CN, —O(CH$_2$)$_{2-4}$—N(R$^4$)$_2$, —O(CH$_2$)$_{2-4}$—R, —NO$_2$, —N(R$^4$)$_2$, —NR$^4$COR, —NR$^4$SO$_2$R, or —SO$_2$N(R$^4$)$_2$, wherein R is hydrogen or an optionally substituted C$_{1-6}$ aliphatic group;

(b) $R^1$ is T-(Ring D), wherein T is a valence bond and Ring D is a 5–6 membered aryl or heteroaryl ring optionally substituted with one or two groups selected from -halo, —CN, —NO$_2$, —N(R$^4$)$_2$, optionally substituted C$_{1-6}$ aliphatic, —OR, —C(O)R, —CO$_2$R, —CONH(R$^4$), —N(R$^4$)COR, —N(R$^4$)CO$_2$R, —SO$_2$N(R$^4$)$_2$, —N(R$^4$) SO$_2$R, —N(R$^6$)COCH$_2$N(R$^4$)$_2$, —N(R$^6$)COCH$_2$CH$_2$N (R$^4$)$_2$, or —N(R$^6$)COCH$_2$CH$_2$CH$_2$N(R$^4$)$_2$;

(c) $R^2$ is hydrogen or a substituted or unsubstituted group selected from aryl, heteroaryl, or a C$_{1-6}$ aliphatic group, and $R^{2'}$ is hydrogen; and (d) $R^3$ is selected from —R, —OR, or —N(R$^4$)$_2$, wherein R is selected from hydrogen, C$_{1-6}$aliphatic, 5–6 membered heterocyclyl, phenyl, or 5–6 membered heteroaryl, and L is —O—, —S—, or —NH—; and (e) Ring D is substituted by up to three substituents selected from -halo, —CN, —NO$_2$, —N(R$^4$)$_2$, optionally substituted C$_{1-6}$ aliphatic group, —OR, —C(O)R, —CO$_2$R, —CONH(R$^4$), —N(R$^4$)COR, —N(R$^4$)CO$_2$R, —SO$_2$N(R$^4$)$_2$, —N(R$^4$)SO$_2$R, —N(R$^6$)COCH$_2$N(R$^4$)$_2$, —N(R$^6$)COCH$_2$CH$_2$N(R$^4$)$_2$, or —N(R$^6$) COCH$_2$CH$_2$CH$_2$N(R$^4$)$_2$, wherein R is selected from hydrogen, C$_{1-6}$ aliphatic, phenyl, a 5–6 membered heteroaryl ring, or a 5–6 membered heterocyclic ring.

Representative compounds of formula IVa are shown below in Table 9.

TABLE 9

IVa-1

TABLE 9-continued

IVa-2

IVa-3

IVa-4

IVa-5

TABLE 9-continued

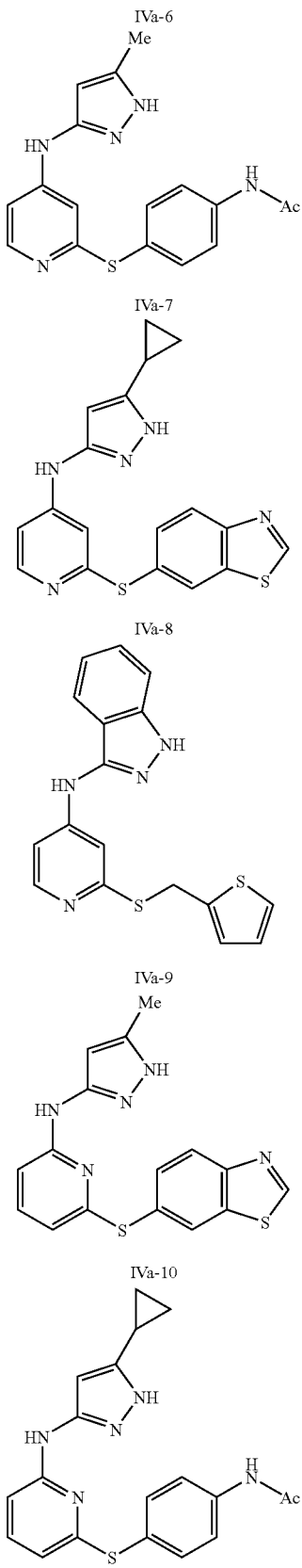

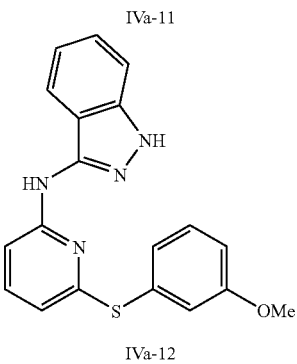

In another embodiment, this invention provides a composition comprising a compound of formula IVa and a pharmaceutically acceptable carrier.

Another aspect of this invention relates to a method of treating or preventing an Aurora-2-mediated disease with an Aurora-2 inhibitor, which method comprises administering to a patient in need of such a treatment a therapeutically effective amount of a compound of formula IVa or a pharmaceutical composition thereof.

Another aspect of this invention relates toga method of inhibiting Aurora-2 activity in a patient, which-method comprises administering to the patient a compound of formula IVa or a composition comprising said compound.

Another aspect of this invention relates to a method of treating or preventing a GSK-3-mediated disease with a GSK-3 inhibitor, which method comprises administering to a patient in need of such a treatment a therapeutically effective amount of a compound of formula IVa or a pharmaceutical composition thereof.

One aspect of this invention relates to a method of enhancing glycogen synthesis and/or lowering blood levels of glucose in a patient in need thereof, which method comprises administering to the patient a therapeutically effective amount of a compound of formula IVa or a pharmaceutical composition thereof. This method is especially useful for diabetic patients. Another method relates to inhibiting the production of hyperphosphorylated Tau protein, which is useful in halting or slowing the progression of Alzheimer's disease Another method relates to inhibiting the phosphorylation of β-catenin, which is useful for treating schizophrenia.

Another aspect of this invention relates to a method of inhibiting GSK-3 activity in a patient, which method comprises administering to the patient a compound of formula IVa or a composition comprising said compound.

Another method relates to inhibiting Aurora-2 or GSK-3 activity in a biological sample, which method comprises contacting the biological sample with the Aurora-2 or GSK-3 inhibitor of formula IVa, or a pharmaceutical composition thereof, in an amount, effective to inhibit Aurora-2 or GSK-3.

Each of the aforementioned methods directed to the inhibition of Aurora-2 or GSK-3, or the treatment of a disease alleviated thereby, is preferably carried out with a preferred compound of formula IVa, as described above.

Another embodiment of this invention relates to compounds of formula IVb:

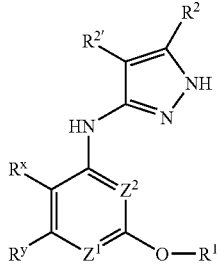

IVb or a pharmaceutically acceptable derivative or prodrug thereof, wherein:

$Z^1$ is nitrogen or C—$R^8$ and $Z^2$ is nitrogen or CH, wherein one of $Z^1$ or $Z^2$ is nitrogen;

$R^x$ and $R^y$ are independently selected from T—$R^3$ or L—Z—$R^3$, or $R^x$ and $R^y$ are taken together with their intervening atoms to form a fused, unsaturated or partially unsaturated, 5–7 membered ring having 0–3 ring heteroatoms selected from oxygen, sulfur, or nitrogen, wherein each substitutable ring carbon of said fused ring formed by $R^x$ and $R^y$ is independently substituted by oxo, T—$R^3$, or L—Z—$R^3$, and each substitutable ring nitrogen of said ring formed by $R^x$ and $R^y$ is independently substituted by $R^4$;

$R^1$ is T-(Ring D);

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein each substitutable ring carbon of Ring D is independently substituted by oxo, T—$R^5$, or V—Z—$R^5$, and each substitutable ring nitrogen of Ring D is independently substituted by —$R^4$;

T is a valence bond or a $C_{1-4}$ alkylidene chain;

Z is a $C_{1-4}$ alkylidene chain;

L is —O—, —S—, —SO—, —SO$_2$—, —N($R^6$)SO$_2$—, —SO$_2$N($R^6$)—, —N($R^6$)—, —CO—, —CO$_2$—, —N($R^6$)CO—, —N($R^6$)C(O)O—, —N($R^6$)CON($R^6$)—, —N($R^6$)SO$_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$ N($R^6$)N($R^6$)—, —C($R^6$)$_2$N($R^6$)SO$_2$N($R^6$)—, or —C($R^6$)N($R^6$)CON($R^6$)—;

$R^2$ and $R^{2'}$ are independently selected from —R, —T—W—$R^6$, or $R^2$ and $R^{2'}$ are taken together with their intervening atoms to form a fused, 5–8 membered, unsaturated or partially unsaturated, ring having 0–3 ring heteroatoms selected from nitrogen, oxygen, or sulfur, wherein each substitutable ring carbon of said fused ring formed by $R^2$ and $R^{2'}$ independently substituted by halo, oxo, —CN, —NO$_2$, —$R^7$, or —V—$R^6$, and each substitutable ring nitrogen of said ring formed by $R^2$ and $R^{2'}$ is independently substituted by $R^4$;

$R^3$ is selected from —R, -halo, —OR, —C(=O)R, —CO$_2$R, —COCOR, —COCH$_2$COR, —NO$_2$, —CN, —S(O)R, —S(O)$_2$R, —SR, —N($R^4$)$_2$, —CON($R^7$)$_2$, —SO$_2$N($R^7$)$_2$, —OC(=O)R, —N($R^7$)COR, —N($R^7$)CO$_2$($C_{1-6}$ aliphatic), —N($R^4$)N($R^4$)$_2$, —C=NN($R^4$)$_2$, —C=N—OR, —N($R^7$)CON($R^7$)$_2$, —N($R^7$)SO$_2$N($R^7$)$_2$, —N($R^4$)SO$_2$R, or —OC(=O)N($R^7$)$_2$;

each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;

each $R^4$ is independently selected from —$R^7$, —COR$^7$, —CO$_2$(optionally substituted $C_{1-6}$ aliphatic), —CON($R^7$)$_2$, or —SO$_2$R$^7$;

each $R^5$ is independently selected from —R, halo, —OR, —C(=O)R, —CO$_2$R, —COCOR, —NO$_2$, —CN, —S(O)R, —SO$_2$R, —SR, —N($R^4$)$_2$, —CON($R^4$)$_2$, —SO$_2$N($R^4$)$_2$, —OC(=O)R, —N($R^4$)COR, —N($R^4$)CO$_2$(optionally substituted $C_{1-6}$ aliphatic), —N($R^4$)—N($R^4$)$_2$, —C=NN($R^4$)$_2$, —C=N—OR, —N($R^4$)CON($R^4$)$_2$, —N($R^4$)SO$_2$N($R^4$)$_2$, —N($R^4$)SO$_2$R, or —OC(=O)N($R^4$)$_2$;

V is —O—, —S—, —SO—, —SO$_2$—, —N($R^6$)SO$_2$—, —SO$_2$N($R^6$)—, —N($R^6$)—, —CO—, —CO$_2$—, —N($R^6$)CO—, —N($R^6$)C(O)O—, —N($R^6$)CON($R^6$)—, —N($R^6$)SO$_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$ N($R^6$)N($R^6$)—, —C($R^6$)$_2$N($R^6$)SO$_2$N($R^6$)—, or —C($R^6$)$_2$N($R^6$)CON($R^6$)—;

W is —C($R^6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N($R^6$)—, —CO—, —CO$_2$—, —C($R^6$)OC(O)R—, —C($R^6$)OC(O)N($R^6$)—, —C($R^6$)$_2$N($R^6$)CO—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)SO$_2$N($R^6$)—, —C($R^6$)$_2$N($R^6$)CON($R^6$)—, or CON($R^6$)—;

each $R^6$ is independently selected from hydrogen or an optionally substituted $C_{1-4}$ aliphatic group, or two $R^6$ groups on the same nitrogen atom are taken together with the nitrogen atom to form a 5–6 membered heterocyclyl or heteroaryl ring;

each $R^7$ is independently selected from hydrogen or an optionally substituted $C_{1-6}$ aliphatic group, or two $R^7$ on the same nitrogen are taken together with the nitrogen to form a 5–8 membered heterocyclyl or heteroaryl ring; and $R^8$ is selected from —R, halo, —OR, —C(=O)R, —CO$_2$R, —COCOR, —NO$_2$, —CN, —S(O)R, —SO$_2$R, —SR, —N($R^4$)$_2$, —CON($R^4$)$_2$, —SO$_2$N($R^4$)$_2$, —OC(=O)R, —N($R^4$)COR, —N($R^4$)CO$_2$(optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)SO$_2$N($R^4$)$_2$, —N($R^4$)SO$_2$R, or —OC(=O)N($R^4$)$_2$.

Preferred rings formed by $R^x$ and $R^y$ of formula IVb include a 5-, 6-, or 7-membered unsaturated or partially unsaturated ring having 0–2 heteroatoms, wherein said $R^x$/$R^y$ ring is optionally substituted. This provides a bicyclic ring system containing a pyrimidine ring. Preferred pyrimidine-ring systems of formula IVd are shown below.

IVb-A 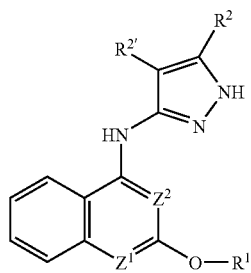
IVb-B 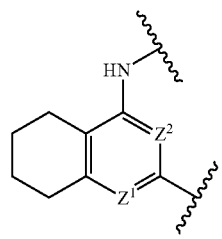
IVb-C 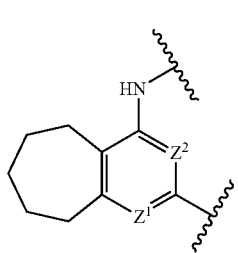
IVb-D 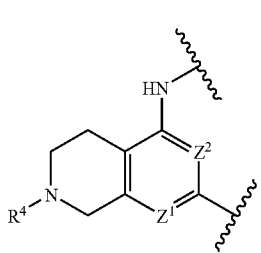
IVb-E 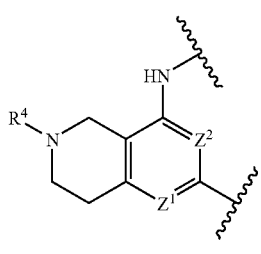
IVb-F 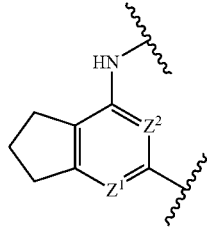
-continued
IVb-J 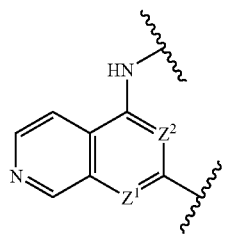
IVb-K 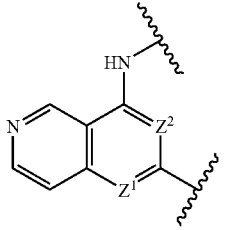
IVb-L 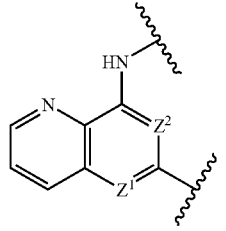
IVb-P 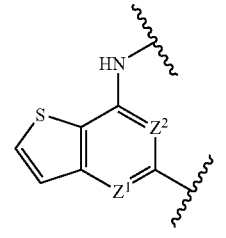
IVb-R 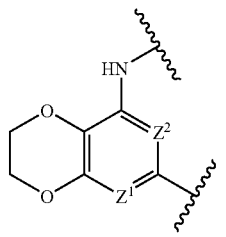
IVb-V 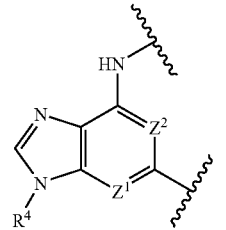

-continued

IVb-W

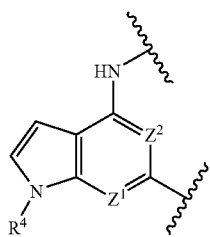

More preferred pyrimidine ring systems of formula IVb include IVb-A, IVb-B, IVb-D, IVb-E, IVb-J, IVb-P, and IVb-V, most preferably IVb-A, IVb-B, IVb-D, IVb-E, and IVb-J. Even more preferred pyridine ring systems of formula IVb are those described above, wherein $Z^1$ is nitrogen and $Z^2$ is CH.

Preferred $R^x$ groups of formula IVb include hydrogen, alkyl- or dialkylamino, acetamido, or a $C_{1-4}$ aliphatic group such as methyl, ethyl, cyclopropyl, or isopropyl.

Preferred $R^y$ groups of formula IVb include T—$R^3$ or L—Z—$R^3$ wherein T is a valence bond or a methylene, L is —O—, —S—, or —N($R^4$)—, —C($R^6$)$_2$O—, —CO— and $R^3$ is —R, —N($R^4$)$_2$, or —OR. Examples of preferred $R^y$ groups include 2-pyridyl, 4-pyridyl, pyrrolidinyl, piperidinyl, morpholinyl, piperazinyl, methyl, ethyl, cyclopropyl, isopropyl, t-butyl, alkoxyalkylamino such as methoxyethylamino, alkoxyalkyl such as methoxymethyl or methoxyethyl, alkyl- or dialkylamino such as ethylamino or dimethylamino, alkyl- or dialkylaminoalkoxy such as dimethylaminopropyloxy, acetamido, optionally substituted phenyl such as phenyl or halo-substituted phenyl.

The ring formed when the $R^x$ and $R^y$ groups of formula IVba are taken together may be substituted or unsubstituted. Suitable substituents include —R, halo, —O(CH$_2$)$_{2-4}$—N(R$^4$)$_2$, —O(CH$_2$)$_{2-4}$—R, —OR, —N(R$^4$)—(CH$_2$)$_{2-4}$—N(R$^4$)$_2$, —N(R$^4$)—(CH$_2$)$_{2-4}$—R, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$(optionally substituted $C_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$, R and $R^4$ are as defined above. Preferred $R^x$/$R^y$ ring substituents include -halo, —R, —OR, —COR, —CO$_2$R, —CON(R$^4$)$_2$, —CN, —O(CH$_2$)$_{2-4}$—N(R$^4$)$_2$, —O(CH$_2$)$_{2-4}$—R, —NO$_2$—N(R$^4$)$_2$, —NR$^4$COR, —NR$^4$SO$_2$R, —SO$_2$N(R$^4$)$_2$ wherein R is hydrogen or an optionally substituted $C_{1-6}$ aliphatic group.

The $R^2$ and $R^{2'}$ groups of formula IVb may be taken together to form a fused ring, thus providing a bicyclic ring system containing a pyrazole ring. Preferred fused rings include benzo, pyrido, pyrimido, and a partially unsaturated 6-membered carbocyclo ring. These are exemplified in the following formula IVb compounds having a pyrazole containing bicyclic ring system:

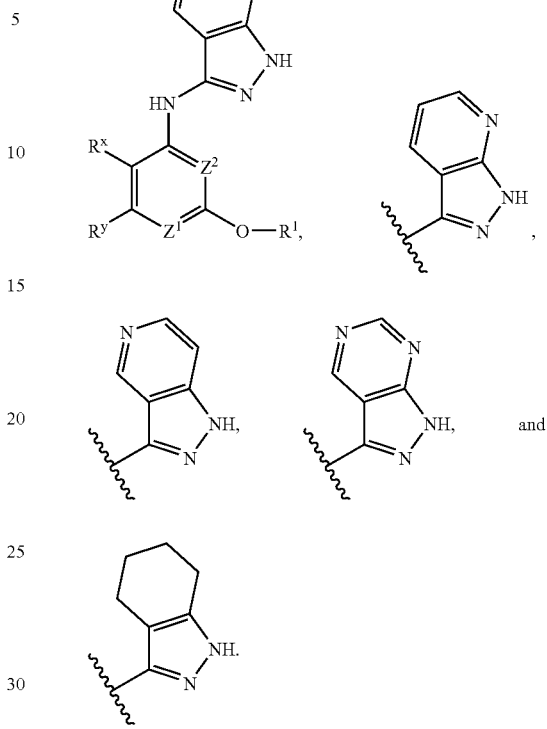

Preferred substituents on the $R^2$/$R^{2'}$ fused ring of formula IVb include one or more of the following: -halo, —N(R$^4$)$_2$, —C$_{1-4}$ alkyl, —C$_{1-4}$ haloalkyl, —NO$_2$, —O(C$_{1-4}$ alkyl), —CO$_2$(C$_{1-4}$ alkyl), —CN, —SO$_2$(C$_{1-4}$ alkyl), —SO$_2$NH$_2$, —OC(O)NH$_2$—, —NH$_2$SO$_2$(C$_{1-4}$ alkyl), —NHC(O)(C$_{1-4}$ alkyl), —C(O)NH$_2$, and —CO(C$_{1-4}$ alkyl), wherein the (C$_{1-4}$ alkyl) is a straight, branched, or cyclic alkyl group. Preferably, the (C$_{1-4}$ alkyl) group is methyl.

When the pyrazole ring system of formula IVb is monocyclic, preferred $R^2$ groups include hydrogen or a substituted or unsubstituted group selected from aryl heteroaryl, or a $C_{1-6}$ aliphatic group. Examples of such preferred $R^2$ groups include hydrogen, methyl, ethyl, propyl, cyclopropyl, i-propyl, cyclopentyl, hydroxypropyl, methoxypropyl, and benzyloxypropyl. A preferred $R^{2'}$ group is hydrogen.

When Ring D of formula IVb is monocyclic, preferred Ring D groups include phenyl, pyridyl, pyridazinyl, pyrimidinyl, and pyrazinyl.

When Ring D of formula IVb is bicyclic, preferred bicyclic Ring D groups include naphthyl, tetrahydronaphthyl, indanyl, benzimidazolyl, quinolinyl, indolyl, isoindolyl, indolinyl, benzo[b]furyl, benzo[b]thiophenyl indazolyl, benzothiazolyl, cinnolinyl, phthalazinyl, quinazolinyl, quinoxazolinyl, 1,8-naphthyridinyl and isoquinolinyl.

On Ring D of formula IVb, preferred T—$R^5$ or V—Z—$R^5$ substituents include -halo, —CN, —NO$_2$, —N(R$^4$)$_2$, optionally substituted $C_{1-6}$ aliphatic group, —OR, —C(O)R, —CO$_2$R, —CONH(R$^4$), —N(R$^4$)COR, —N(R$^4$)CO$_2$R, —SO$_2$N(R$^4$)$_2$, —N(R$^4$)SO$_2$R, —N(R$^6$)COCH$_2$N(R$^4$)$_2$, —N(R$^6$) COCH$_2$CH$_2$N(R$^4$)$_2$, and —N(R$^6$)

COCH$_2$CH$_2$CH$_2$N(R$^4$)$_2$, wherein R is selected from hydrogen, C$_{1-6}$ aliphatic, phenyl, a 5–6 membered heteroaryl ring, or a 5–6 membered heterocyclic ring. More preferred R$^5$ substituents include —Cl, —Br, —F, —CN, —CF$_3$, —COOH, —CONHMe, —CONHEt, —NH$_2$, —NHAc, —NHSO$_2$Me, —NHSO$_2$Et, —NHSO$_2$(n-propyl), —NHSO$_2$(isopropyl), —NHCOEt, —NHCOCH$_2$NHCH$_3$, —NHCOCH$_2$N(CO$_2$t -Bu)CH$_3$, —NHCOCH$_2$N(CH$_3$)$_2$, —NHCOCH$_2$CH$_2$N(CH$_3$)$_2$, —NHCOCH$_2$CH$_2$CH$_2$N(CH$_3$)$_2$, —NHCO(cyclopropyl), —NHCO(isobutyl), —NHCOCH$_2$(morpholin-4-yl), —NHCOCH$_2$CH$_2$(morpholin-4-yl), —NHCOCH$_2$CH$_2$CH$_2$(morpholin-4-yl), —NHCO$_2$(t-butyl), —NH(C$_{1-4}$ aliphatic) such as —NHMe, —N(C$_{1-4}$ aliphatic)$_2$ such as —NMe$_2$, OH, —O(C$_{1-4}$ aliphatic) such as —OMe, C$_{1-4}$ aliphatic such as methyl, ethyl, cyclopropyl, isopropyl, or t-butyl, and —CO$_2$(C$_{1-4}$ aliphatic).

Preferred R$^8$ groups of formula IVb, when present, include R, OR, and N(R$^4$)$_2$. Examples of preferred R$^8$ include methyl, ethyl, NH$_2$, NH$_2$CH$_2$CH$_2$NH, N(CH$_3$)$_2$CH$_2$CH$_2$NH, N(CH$_3$)$_2$CH$_2$CH$_2$O, (piperidin-1-yl)CH$_2$CH$_2$O, and NH$_2$CH$_2$CH$_2$O.

Preferred formula IVb compounds have one or more, and more preferably all, of the features selected from the group consisting of:
(a) R$^x$ is hydrogen, alkyl- or dialkylamino, acetamido, or a C$_{1-4}$ aliphatic group and R$^y$ is T—R$^3$ or L—Z—R$^3$, wherein T is a valence bond or a methylene and R$^3$ is —R, —N(R$^4$)$_2$, or —OR; or R$^x$ and R$^y$ are taken together with their intervening atoms to form a fused, unsaturated or partially unsaturated, 5–6 membered ring having 0–2 heteroatoms selected from oxygen, sulfur, or nitrogen, wherein each substitutable ring carbon of said fused ring formed by R$^x$ and R$^y$ is independently substituted by oxo, T—R$^3$, or L—Z—R$^3$, and each substitutable ring nitrogen of said ring formed by R$^x$ and R$^y$ is independently substituted by R$^4$;
(b) R$^1$ is T-(Ring D), wherein T is a valence bond or a methylene unit;
(c) Ring D is a 5–7 membered monocyclic or an 8–10 membered bicyclic aryl or heteroaryl ring; and
(d) R$^1$ is —R or —T—W—R$^6$ and R$^{2'}$ is hydrogen, or R$^2$ and R$^{2'}$ are taken together to form an optionally is substituted benzo ring.

More preferred compounds of formula IVb have one or more, and more preferably all, of the features selected from the group consisting of:
(a) R$^y$ is T—R$^3$ or L—Z—R$^3$ wherein T is a valence bond or a methylene and R$^3$ is selected from —R, —OR, or —N(R$^4$)$_2$, wherein R is selected from hydrogen, C$_{1-2}$ aliphatic, or 5–6 membered heterocyclyl, phenyl, or 5–6 membered heteroaryl; or R$^x$ and R$^y$ are taken together with their intervening atoms to form a benzo, pyrido cyclopento, cyclohexo, cyclohepto, thieno, piperidino or imidazo ring, wherein each substitutable ring carbon of said fused ring formed by R$^x$ and R$^y$ is independently substituted by oxo, T—R$^3$, or L—Z—R$^3$, and each substitutable ring nitrogen of said ring formed by R$^x$ and R$^y$ is independently substituted by R$^4$;
(b) R$^1$ is T-(Ring D), wherein T is a valence bond, and Ring D is a 5–6 membered monocyclic or an 8–10 membered bicyclic aryl or heteroaryl ring;
(c) R$^2$ is —R and R$^{2'}$ is hydrogen, wherein R is selected from hydrogen, C$_{1-6}$ aliphatic, phenyl, a 5–6 membered heteroaryl ring, or a 5–6 membered heterocyclic ring; and
(d) R$^3$ is selected from —R, -halo, —OR, or —N(R$^4$)$_2$, wherein R is selected from-hydrogen, C$_{1-6}$ aliphatic, or 5–6 membered heterocyclyl, phenyl, or 5–6 membered heteroaryl, and L is —O—, —S—, or —N(R$^4$).

Even more preferred compounds of formula IVb have one or more, and more preferably all, of the features selected from the group consisting of:
(a) R$^x$ is hydrogen methyl, ethyl, propyl, cyclopropyl, isopropyl, methylamino or acetamido and R$^y$ is selected from 2-pyridyl, 4-pyridyl, pyrrolidinyl, piperidinyl, morpholinyl, piperazinyl, methyl, ethyl, cyclopropyl, isopropyl, t-butyl, alkoxyalkylamino, alkoxyalkyl, alkyl- or dialkylamino, alkyl- or dialkylaminoalkoxy, acetamido, optionally substituted phenyl, or methoxymethyl; or R$^x$ and R$^y$ are taken together with their intervening atoms to form a benzo, pyrido, piperidino, or cyclohexo ring, wherein said ring is optionally substituted with -halo, —R, —OR, —COR, —CO$_2$R, —CON(R$^4$)$_2$, —CN, —O(CH$_2$)$_{2-4}$—N(R$^4$)$_2$, —O(CH$_2$)$_{2-4}$—R, —NO$_2$—N(R$^4$)$_2$, —NR$^4$COR, —NR$^4$SO$_2$R, or —SO$_2$N(R$^4$)$_2$, wherein R is hydrogen or an optionally substituted C$_{1-6}$ aliphatic group;
(b) R$^1$ is T-(Ring D), wherein T is a valence bond and Ring D is a 5–6 membered aryl or heteroaryl ring optionally substituted with one or two groups selected from -halo, —CN, —NO$_2$, —N(R$^4$)$_2$, optionally substituted C$_{1-6}$ aliphatic, —OR, —C(O)R, —CO$_2$R, —CONH(R$^4$), —N(R$^4$)COR, —N(R$^4$)CO$_2$R, —SO$_2$N(R$^4$)$_2$, —N(R$^4$)SO$_2$R, —N(R$^6$)COCH$_2$N(R$^4$)$_2$, —N(R$^6$)COCH$_2$CH$_2$N(R$^4$)$_2$, or —N(R$^6$)COCH$_2$CH$_2$CH$_2$N(R$^4$)$_2$;
(c) R$^2$ is hydrogen or a substituted or unsubstituted group selected from aryl, heteroaryl, or a C$_{1-6}$ aliphatic group, and R$^{2'}$ is hydrogen; and
(d) R$^3$ is selected from —R, —OR, or —N(R$^4$)$_2$, wherein R is selected from hydrogen, C$_{1-6}$ aliphatic, 5–6 membered heterocyclyl, phenyl, or 5–6 membered heteroaryl, and L is —O—, —S—, or —NH—; and
(e) Ring D is substituted by up to three substituents selected from -halo, —CN, —NO$_2$, —N(R$^4$)$_2$, optionally substituted C$_{1-6}$ aliphatic group, —OR, —C(O)R, —CO$_2$R, —CONH(R$^4$), —N(R$^4$)COR, —N(R$^4$)CO$_2$R, —SO$_2$N(R$^4$)$_2$, —N(R$^4$)SO$_2$R, —N(R$^6$)COCH$_2$N—(R$^4$)$_2$, —N(R$^6$)COCH$_2$CH$_2$N(R$^4$)$_2$, or —N(R$^6$)COCH$_2$CH$_2$CH$_2$N(R$^4$)$_2$, wherein R is selected from hydrogen, C$_{1-6}$ aliphatic, phenyl, a 5–6 membered heteroaryl ring, or a 5–6 membered heterocyclic ring.

Representative compounds of formula IVb are shown below in Table 10.

TABLE 10

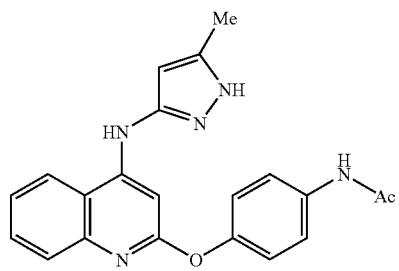

TABLE 10-continued
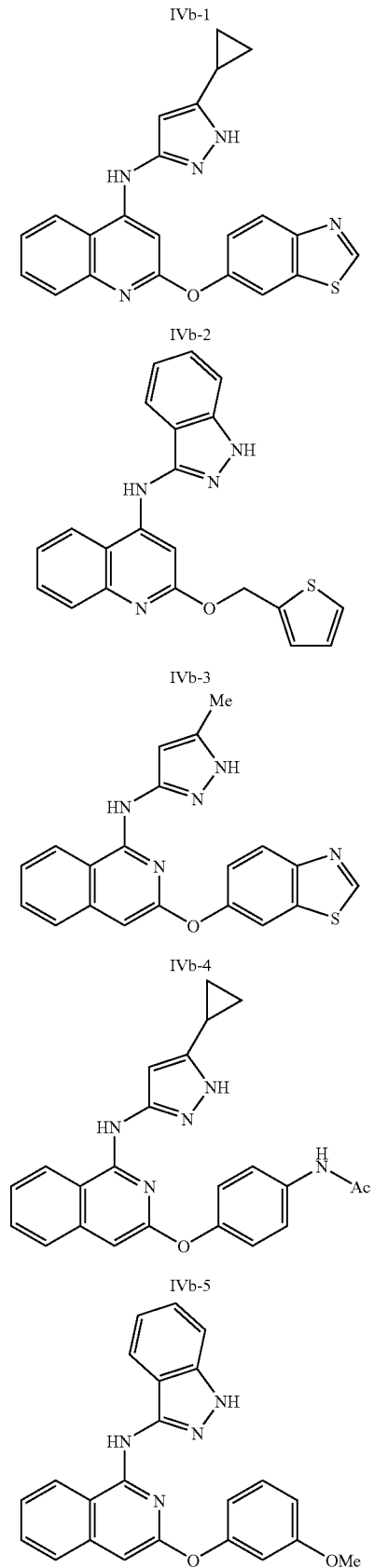
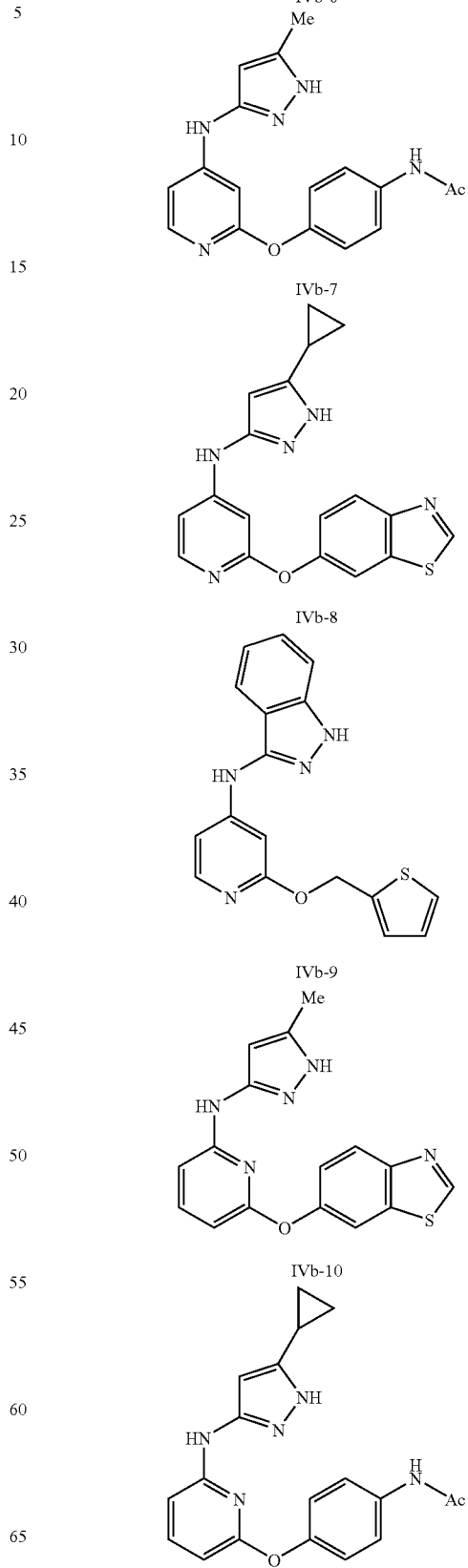

TABLE 10-continued

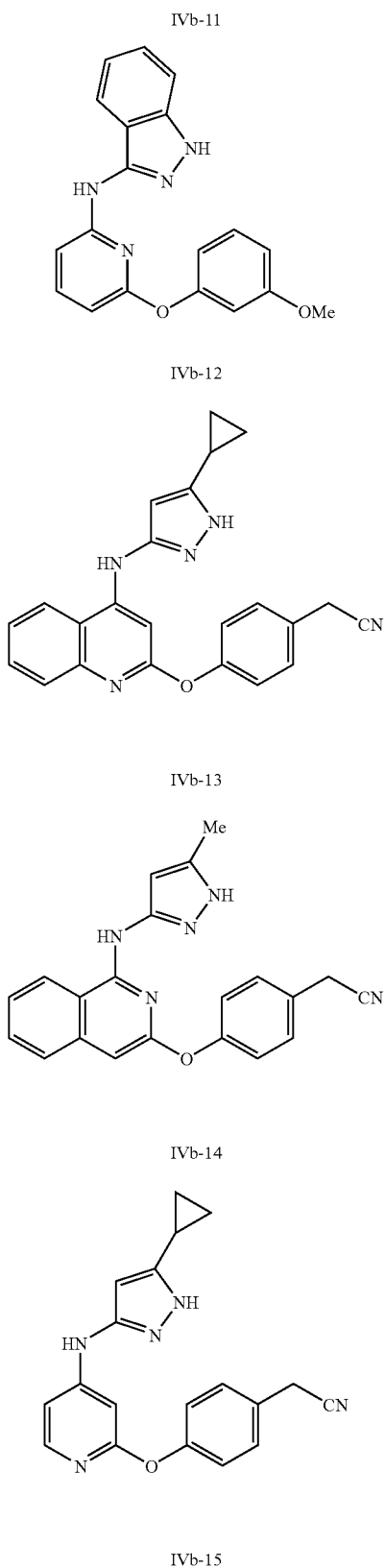

IVb-11

IVb-12

IVb-13

IVb-14

IVb-15

TABLE 10-continued

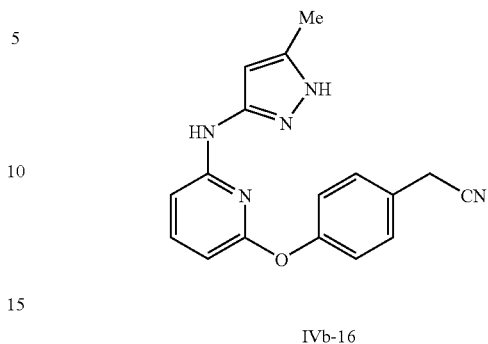

IVb-16

In another embodiment, this invention provides a composition comprising a compound of formula IVb and a pharmaceutically acceptable carrier.

Another aspect of this invention relates to a method of treating or preventing an Aurora-2-mediated disease with an Aurora-2 inhibitor, which method comprises administering to a patient in need of such a treatment a therapeutically effective amount of a compound of formula IVb or a pharmaceutical composition thereof.

Another aspect of this invention relates to a method of inhibiting Aurora-2 activity in a patient, which method comprises administering to the patient a compound of formula IVb or a composition comprising said compound.

Another aspect of this invention relates to a method of treating or preventing a GSK-3-mediated disease with a GSK-3 inhibitor, which method comprises administering to a patient in need of such a treatment a therapeutically effective amount of a compound of formula IVb or a pharmaceutical composition thereof.

One aspect of this invention relates to a method of enhancing glycogen synthesis and/or lowering blood levels of glucose in a patient in need thereof, which method comprises administering to the patient a therapeutically effective amount of a compound of formula IVb or a pharmaceutical composition thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of β-catenin, which is useful for treating schizophrenia.

Another aspect of this invention relates to a method of inhibiting GSK-3 activity in a patient, which method comprises administering to the patient a compound of formula IVb or a composition comprising said compound.

Another method relates to inhibiting Aurora-2 or GSK-3 activity in a biological sample, which method comprises contacting the biological sample with the Aurora-2 or GSK-3 inhibitor of formula IVb, or a pharmaceutical composition thereof, in an amount effective to inhibit Aurora-2 or GSK-3.

Each of the aforementioned methods directed to the inhibition of Aurora-2 or GSK-3, or the treatment of a disease alleviated thereby, is preferably carried out with a preferred compound of formula IVb, as described above.

Another embodiment of this invention relates to compounds of formula IVc:

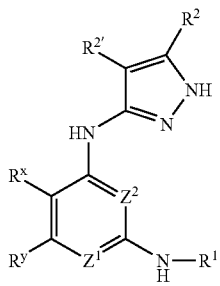

IVc or a pharmaceutically acceptable derivative or prodrug thereof, wherein:

$Z^1$ is nitrogen or C—$R^8$ and $Z^2$ is nitrogen or CH, wherein one of $Z^1$ or $Z^2$ is nitrogen;

$R^x$ and $R^y$ are independently selected from T—$R^3$ or L—Z—$R^3$, or $R^x$ and $R^y$ are taken together with their intervening atoms to form a fused, unsaturated or partially unsaturated, 5–7 membered ring having 0–3 ring heteroatoms selected from oxygen, sulfur, or nitrogen, wherein each substitutable ring carbon of said fused ring formed by $R^x$ and $R^y$ is independently substituted by oxo, T—$R^3$, or L—Z—$R^3$, and each substitutable ring nitrogen of said ring formed by $R^x$ and $R^y$ is independently substituted by $R^4$;

$R^1$ is T-(Ring D);

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein each substitutable ring carbon of Ring D is independently substituted by oxo, T—$R^5$, or V—Z—$R^5$, and each substitutable ring nitrogen of Ring D is independently substituted by —$R^4$;

T is a valence bond or a $C_{1-4}$ alkylidene chain;

Z is a $C_{1-4}$ alkylidene chain;

L is —O—, —S—, —SO—, —$SO_2$—, —N($R^6$)$SO_2$—, —$SO_2$N($R^6$)—, —N($R^6$)—, —CO—, —$CO_2$—, —N($R^6$)CO—, —N($R^6$)C(O)O—, —N($R^6$)CON($R^6$)—, —N($R^6$)$SO_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$$SO_2$—, —C($R^6$)$_2$$SO_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)$SO_2$N($R^6$)—, or —C($R^6$)$_2$N($R^6$)CON($R^6$)—;

$R^2$ and $R^{2'}$ are independently selected from —R, —T—W—$R^6$, or $R^2$ and $R^{2'}$ are taken together with their intervening atoms to form a fused, 5–8 membered, unsaturated or partially unsaturated, ring having 0–3 ring heteroatoms selected from nitrogen, oxygen, or sulfur, wherein each substitutable ring carbon of said fused ring formed by $R^2$ and $R^{2'}$ is independently substituted by halo, oxo, —CN, —$NO_2$, —$R^7$, or —V—$R^6$, and each substitutable ring nitrogen of said ring formed by $R^2$ and $R^{2'}$ is independently substituted by $R^4$;

$R^3$ is selected from —R, -halo, —OR, —C(=O)R, —$CO_2$R, —COCOR, —COCH$_2$COR, —$NO_2$, —CN, —S(O)R, —S(O)$_2$R, —SR, —N($R^4$)$_2$, —CON($R^7$)$_2$, —$SO_2$N($R^7$)$_2$, —OC(=O)R, —N($R^7$)COR, —N($R^7$)$CO_2$($C_{1-6}$ aliphatic), —N($R^4$)N($R^4$)$_2$, —C=NN($R^4$)$_2$, —C=N—OR, —N($R^7$)CON($R^7$)$_2$, —N($R^7$)$SO_2$N($R^7$)$_2$, —N($R^4$)$SO_2$R, or —OC(=O)N($R^7$)$_2$;

each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;

each $R^4$ is independently selected from —$R^7$, —COR$^7$, —$CO_2$(optionally substituted $C_{1-6}$ aliphatic), —CON($R^7$)$_2$, or —$SO_2$$R^7$;

each $R^5$ is independently selected from —R, halo, —OR, —C(=O)R, —$CO_2$R, —COCOR, —$NO_2$, —CN, —S(O)R, —$SO_2$R, —SR, —N($R^4$)$_2$, —CON($R^4$)$_2$, —$SO_2$N($R^4$)$_2$, —OC(=O)R, —N($R^4$)COR, —N($R^4$)$CO_2$(optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)$SO_2$N($R^4$)$_2$, —N($R^4$)$SO_2$R, or —OC(=O)N($R^4$)$_2$;

V is —O—, —S—, —SO—, —$SO_2$—, —N($R^6$)$SO_2$—, —$SO_2$N($R^6$)—, —N($R^6$)—, —CO—, —$CO_2$—, —N($R^6$)CO—, —N($R^6$)C(O)O—, —N($R^6$)CON($R^6$)—, —N($R^6$)$SO_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$$SO_2$—, —C($R^6$)$_2$$SO_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)$SO_2$N($R^6$)—, or —C($R^6$)$_2$N($R^6$)CON($R^6$)—;

W is —C($R^6$)$_2$O—, —C($R^6$)$S$—, —C($R^6$)$_2$SO—, —C($R^6$)$_2$$SO_2$—, —C($R^6$)$_2$$SO_2$N($R^6$)—, —C($R^6$)$_2$N($R^6$)—, —CO—, —$CO_2$—, —C($R^6$)OC(O)—, —C($R^6$)OC(O)N($R^6$)—, —C($R^6$)$_2$N($R^6$)CO—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)$SO_2$N($R^6$)—, —C($R^6$)$_2$N($R^6$)CON($R^6$)—, or —CON($R^6$)—;

each $R^6$ is independently selected from hydrogen or an optionally substituted $C_{1-4}$ aliphatic group, or two $R^6$ groups on the same nitrogen atom are taken together with the nitrogen atom to form a 5–6 membered heterocyclyl or heteroaryl ring;

each $R^7$ is independently selected from hydrogen or an optionally substituted $C_{1-6}$ aliphatic group, or two $R^7$ on the same nitrogen are taken together with the nitrogen to form a 5–8 membered heterocyclyl or heteroaryl ring; and $R^8$ is selected from —R, halo, —OR, —C(=O)R, —$CO_2$R, —COCOR, —$NO_2$, —CN, —S(O)R, —$SO_2$R, —SR, —N($R^4$)$_2$, —CON($R^4$)$_2$, —$SO_2$N($R^4$)$_2$, —OC(=O)R, —N($R^4$)COR, —N($R^4$)$CO_2$(optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)$SO_2$N($R^4$)$_2$, —N($R^4$)$SO_2$R, or —OC(=O)N($R^4$)$_2$.

Preferred rings formed by $R^x$ and $R^y$ of formula IVc include a 5-, 6-, or 7-membered unsaturated or partially unsaturated ring having 0–2 heteroatoms, wherein said $R^x$/$R^y$ ring is optionally substituted. This provides a bicyclic ring system containing a pyridine ring. Preferred pyridine ring systems of formula IVc are shown below.

IVc-A
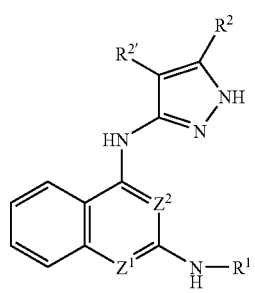
IVc-B
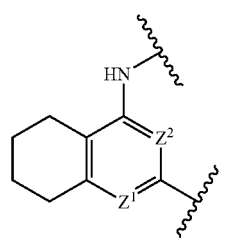
IVc-C
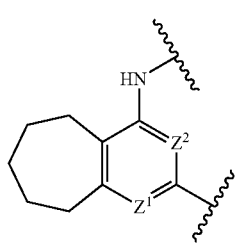
IVc-D
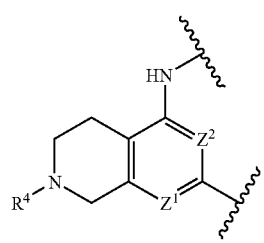
IVc-E
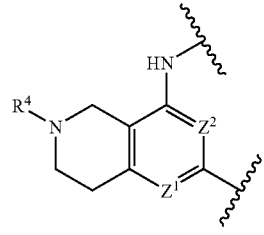
IVc-F
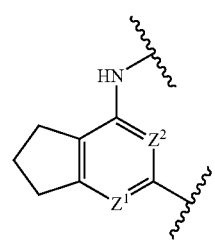
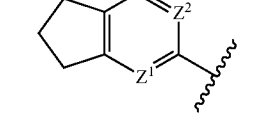
-continued
IVc-J
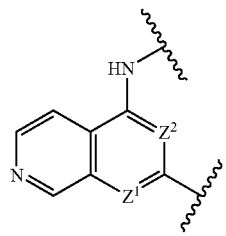
IVc-K
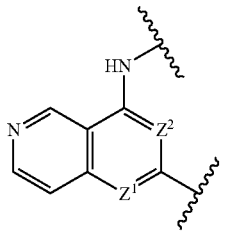
IVc-L
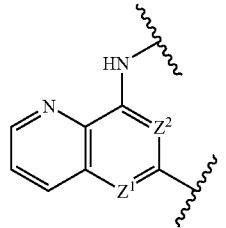
IVc-P
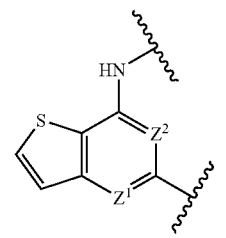
IVc-R
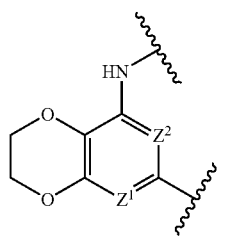
IVc-V
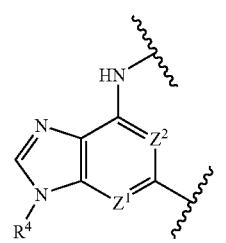

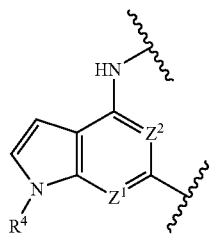

IVc-W

More preferred pyridine ring systems of formula IVc include IVc-A, IVc-B, IVc-D, IVc-E, IVc-J, IVc-P, and IVc-V, most preferably IVc-A, IVc-B, IVc-D, IVc-E, and IVc-J. Even more preferred pyridine-ring systems of formula IVc are those described above, wherein $Z^1$ is nitrogen and $Z^2$ is CH.

Preferred $R^x$ groups of formula IVc include hydrogen, alkyl- or dialkylamino, acetamido, or a $C_{1-4}$ aliphatic group such as methyl, ethyl, cyclopropyl, or isopropyl.

Preferred $R^y$ groups of formula IVc include T—$R^3$ or L—Z—$R^3$ wherein T is a valence bond or a methylene, L is —O—, —S—, or —N($R^4$)—, —C($R^6$)$_2$O—, —CO— and $R^3$ is —R, —N($R^4$)$_2$, or —OR. Examples of preferred $R^y$ groups include 2-pyridyl, 4-pyridyl, pyrrolidinyl, piperidinyl, morpholinyl, piperazinyl, methyl, ethyl, cyclopropyl, isopropyl, t-butyl, alkoxyalkylamino such as methoxyethylamino, alkoxyalkyl such as methoxymethyl or methoxyethyl, alkyl- or dialkylamino such as ethylamino or dimethylamino, alkyl- or dialkylaminoalkoxy such as dimethylaminopropyloxy, acetamido, optionally substituted phenyl such as phenyl or halo-substituted phenyl.

The ring formed when the $R^x$ and $R^y$ groups of formula IVc are taken together may be substituted or unsubstituted. Suitable substituents include —R, halo, —O(CH$_2$)$_{2-4}$—N(R$^4$)$_2$, —O(CH$_2$)$_{2-4}$—R, —OR, —N(R$^4$)—(CH$_2$)$_{2-4}$—N(R$^4$)$_2$, —N(R$^4$)—(CH$_2$)$_{2-4}$—R, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$(optionally substituted $C_{1-6}$ aliphatic), —N(R$^4$)N(R$^4$)$_2$, —C=NN(R$^4$ )$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$, R and $R^4$ are as defined above. Preferred $R^x/R^y$ ring substituents include -halo, —R, —OR, —COR, —CO$_2$R, —CON(R$^4$)$_2$, —CN, —O(CH$_2$)$_{2-4}$—N(R$^4$)$_2$, —O(CH$_2$)$_{2-4}$—R, —NO$_2$—N(R$^4$)$_2$, —NR$^4$COR, —NR$^4$SO$_2$R, —SO$_2$N(R$^4$)$_2$ wherein R is hydrogen or an optionally substituted $C_{1-6}$ aliphatic group.

The $R^2$ and $R^{2'}$ groups of formula IVc may be taken together to form a fused ring, thus providing a bicyclic ring system containing a pyrazole ring. Preferred fused rings include benzo, pyrido, pyrimido, and a partially unsaturated 6-membered-carbocyclo ring. These are exemplified in the following formula IVc compounds having a pyrazole-containing bicyclic ring system:

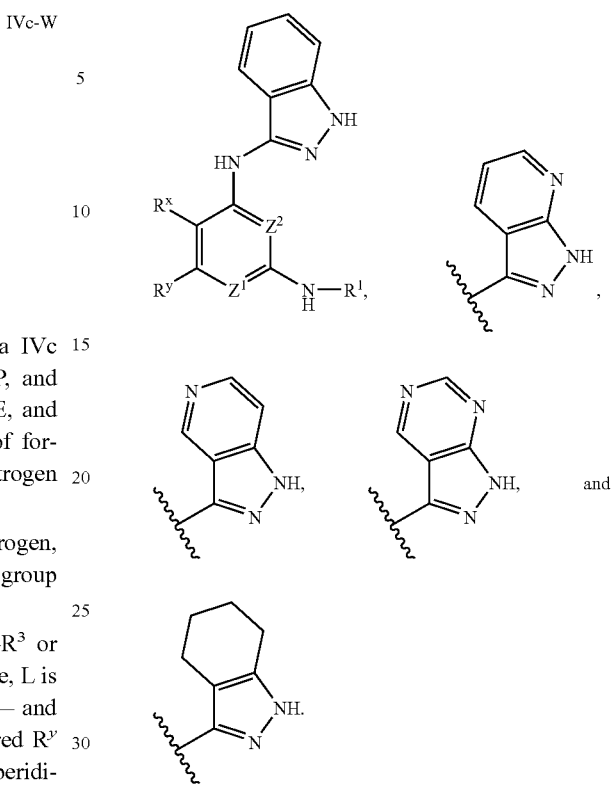

Preferred substituents on:the $R^2/R^{2'}$ fused ring of formula IVc include one or more of the following: -halo, —N(R$^4$)$_2$, —C$_{1-4}$ alkyl, —C$_{1-4}$ haloalkyl, —NO$_2$, —O(C$_{1-4}$ alkyl), —CO$_2$(C$_{1-4}$ alkyl), —CN, —SO$_2$(C$_{1-4}$ alkyl), —SO$_2$NH$_2$, —OC(O)NH$_2$, —NH$_2$SO$_2$(C$_{1-4}$ alkyl), —NHC(O)(C$_{1-4}$ alkyl), —C(O)NH$_2$, and —CO(C$_{1-4}$ alkyl), wherein the (C$_{1-4}$ alkyl) is a straight, branched, or cyclic alkyl group. Preferably, the (C$_{1-4}$ alkyl) group is methyl.

When the pyrazole ring system of formula IVc is monocyclic, preferred $R^2$ groups include hydrogen or a substituted or unsubstituted group selected from aryl, heteroaryl, or a $C_{1-6}$ aliphatic group. Examples of such preferred $R^2$ groups include H, methyl, ethyl, propyl, cyclopropyl, i-propyl, cyclopentyl, hydroxypropyl, methoxypropyl, and benzyloxypropyl. A preferred $R^{2'}$ group is hydrogen.

When Ring D of formula IVc is monocyclic, preferred Ring D groups include phenyl, pyridyl, pyridazinyl, pyrimidinyl, and pyrazinyl.

When Ring D of formula IVc is bicyclic, preferred bicyclic Ring D groups include naphthyl, tetrahydronaphthyl, indanyl, benzimidazolyl, quinolinyl, indolyl, isoindolyl, indolinyl, benzo[b]furyl, benzo[b]thiophenyl, indazolyl, benzothiazolyl, cinnolinyl, phthalazinyl, quinazolinyl, quinoxazolinyl, 1,8-naphthyridinyl and isoquinolinyl.

On Ring D of formula IVc, preferred T—$R^5$ or V—Z—$R^5$ substituents include -halo, —CN, —NO$_2$, —N(R$^4$)$_2$, optionally substituted $C_{1-6}$ aliphatic group, —OR, —C(O)R, —CO$_2$R, —CONH(R$^4$), —N(R$^4$)COR, —N(R$^4$)CO$_2$R, —SO$_2$N(R$^4$)$_2$, —N(R$^4$)SO$_2$R, —N(R$^6$)COCH$_2$N(R$^4$)$_2$, —N(R$^6$)COCH$_2$CH$_2$N(R$^4$)$_2$, and —N(R$^6$) COCH$_2$CH$_2$CH$_2$N(R$^4$)$_2$, wherein R is selected from hydrogen, $C_{1-6}$ aliphatic, phenyl, a 5–6 membered heteroaryl ring, or a 5–6 membered heterocyclic ring. More preferred $R^5$ substituents include —Cl, —Br, —F, —CN, —$CF_3$, —COOH, —CONHMe, —CONHEt, —$NH_2$, —NHAc, —$NHSO_2Me$, —$NHSO_2Et$, —$NHSO_2$(n-propyl), —$NHSO_2$(isopropyl), —NHCOEt, —$NHCOCH_2NHCH_3$, —$NHCOCH_2N(CO_2\text{-}t\text{-Bu})CH_3$, —$NHCOCH_2N(CH_3)_2$, —$NHCOCH_2CH_2N(CH_3)_2$, —$NHCOCH_2CH_2CH_2N(CH_3)_2$, —NHCO(cyclopropyl), —NHCO(isobutyl), —$NHCOCH_2$(morpholin-4-yl), —$NHCOCH_2CH_2$(morpholin-4-yl), —$NHCOCH_2CH_2CH_2$(morpholin-4-yl), —$NHCO$(t-butyl), —$NH(C_{1-4}$ aliphatic) such as —NHMe, —$N(C_{1-4}$ aliphatic)$_2$ such as —$NMe_2$, OH, —$O(C_{1-4}$ aliphatic) such as —OMe, $C_{1-4}$ aliphatic such as methyl, ethyl, cyclopropyl, isopropyl, or t-butyl, and —$CO_2(C_{1-4}$ aliphatic).

Preferred $R^8$ groups of formula IVc, when present, include R, OR, and $N(R^4)_2$. Examples of preferred $R^8$ include methyl, ethyl, $NH_2$, $NH_2CH_2CH_2NH$, $N(CH_3)_2CH_2CH_2NH$, $N(CH_3)_2CH_2CH_2O$, (piperidin-1-yl)$CH_2CH_2O$, and $NH_2CH_2CH_2O$.

Preferred formula IVc compounds have one or more, and more preferably all, of the features selected from the group consisting of:

(a) $R^x$ is hydrogen, alkyl- or dialkylamino, acetamido, or a $C_{1-4}$ aliphatic group and $R^y$ is T—R or L—Z—$R^3$, wherein T is a valence bond or a methylene and $R^3$ is —R, —$N(R^4)_2$, or —OR; or $R^x$ and $R^y$ are taken together-with their intervening atoms to form a fused, unsaturated or partially unsaturated, 5–6 membered ring having 0–2 heteroatoms selected from oxygen, sulfur, or nitrogen, wherein each substitutable ring carbon of said fused ring formed by $R^x$ and $R^y$ is independently substituted by oxo, T—$R^3$, or L—Z—$R^3$, and each substitutable ring nitrogen of said ring formed by $R^x$ and $R^y$ is independently substituted by $R^4$;

(b) $R^1$ is T-(Ring D), wherein T is a valence bond or a methylene unit;

(c) Ring D is a 5–7 membered monocyclic or an 8–10 membered bicyclic aryl or heteroaryl ring; and (d) $R^2$ is —R or —T—W—$R^6$ and $R^{2'}$ is hydrogen, or $R^2$ and $R^{2'}$ are taken together to form an optionally substituted benzo ring.

More preferred compounds of formula IVc have one or more, and more preferably all, of the features selected from the group consisting of:

(a) $R^y$ is T—$R^3$ or L—Z—$R^3$ wherein T is a valence bond or a methylene and. $R^3$ is selected from —R, —OR, or —$N(R^4)_2$, wherein R is selected from hydrogen, $C_{1-6}$ aliphatic, or 5–6 membered heterocyclyl, phenyl, or 5–6 membered-heteroaryl; or $R^x$ and $R^y$ are taken together with their intervening atoms to form a benzo, pyrido, cyclopento, cyclohexo, cyclohepto, thieno, piperidino, or imidazo ring, wherein each substitutable ring carbon of said fused ring formed by $R^x$ and $R^y$ is independently substituted by oxo, T—$R^3$, or L—Z—$R^3$, and each substitutable ring nitrogen of said ring formed by $R^x$ and $R^y$ is independently substituted by $R^4$;

(b) $R^1$ is T-(Ring D), wherein T is a valence bond, and Ring D is a 5–6 membered monocyclic or an 8–10 membered bicyclic aryl or heteroaryl ring;

(c) $R^2$ is —R and $R^{2'}$ is hydrogen, wherein R is selected from hydrogen, $C_{1-6}$ aliphatic, phenyl, a 5–6 membered heteroaryl ring, or a 5–6 membered heterocyclic ring; and (d) $R^3$ is selected from —R, -halo, —OR, or —$N(R^4)_2$, wherein R is selected from-hydrogen, $C_{1-6}$ aliphatic, or 5–6 membered heterocyclyl, phenyl, or 5–6 membered heteroaryl, and L is —O—, —S—, or —$N(R^4)$—.

Even more preferred compounds of formula IVc have one or more, and more preferably all, of the features selected from the group consisting of:

(a) $R^x$ is hydrogen methyl, ethyl, propyl, cyclopropyl, isopropyl, methylamino or acetamido and $R^y$ is selected from 2-pyridyl, 4-pyridyl, pyrrolidinyl, piperidinyl, morpholinyl, piperazinyl, methyl, ethyl, cyclopropyl, isopropyl, t-butyl, alkoxyalkylamino, alkoxyalkyl, alkyl- or dialkylamino, alkyl- or dialkylaminoalkoxy, acetamido, optionally substituted phenyl, or methoxymethyl; or $R^x$ and $R^y$ are taken together with their intervening atoms to form a benzo, pyrido, piperidino, or cyclohexo ring, wherein said ring is optionally substituted with -halo, —R, —OR, —COR, —$CO_2R$, —$CON(R^4)_2$, —CN, —$O(CH_2)_{2-4}$—$N(R^4)_2$, —$O(CH_2)_{2-4}$—R, —$NO_2$—$N(R^4)_2$, —$NR^4COR$, —$NR^4SO_2R$, or —$SO_2N(R^4)_2$, wherein R is hydrogen or an optionally substituted $C_{1-6}$ aliphatic group;

(b) $R^1$ is T-(Ring D), wherein T is a valence bond and Ring D is a 5–6 membered aryl or heteroaryl ring optionally substituted with one or two groups selected from -halo, —CN, —$NO_2$, —$N(R^4)_2$, optionally substituted $C_{1-6}$ aliphatic, —OR, —C(O)R, —$CO_2R$, —$CONH(R^4)$, —$N(R^4)COR$, —$N(R^4)CO_2R$, —$SO_2N(R^4)_2$, —$N(R^4)SO_2R$, —$N(R^6)COCH_2N(R^4)_2$, —$N(R^6)COCH_2CH_2N(R^4)_2$, or —$N(R^6)COCH_2CH_2CH_2N(R^4)_2$;

(c) $R^2$ is hydrogen or a substituted or unsubstituted group selected from aryl, heteroaryl, or a $C_{1-6}$ aliphatic group, and $R^{2'}$ is hydrogen; and (d) $R^3$ is selected from —R, —OR, or —$N(R^4)_2$, wherein R is selected from hydrogen, $C_{1-6}$ aliphatic, 5–6 membered heterocyclyl, phenyl, or 5–6 membered heteroaryl, and L is —O—, —S—, or —NH—; and (e) Ring D is substituted by up to three substituents selected from -halo, —CN, —$NO_2$, —$N(R^4)_2$, optionally substituted $C_{1-6}$ aliphatic group, —OR, —C(O)R, —$CO_2R$, —$CONH(R^4)$, —$N(R^4)COR$, —$N(R^4)CO_2R$, —$SO_2N(R^4)_2$, —$N(R^4)SO_2R$, —$N(R^6)COCH_2N(R^4)_2$, —$N(R^6)COCH_2CH_2N(R^4)_{21}$, or —$N(R^6)COCH_2CH_2CH_2N(R^4)_2$, wherein R is selected from hydrogen, $C_{1-6}$ aliphatic, phenyl, a 5–6 membered heteroaryl ring, or a 5–6 membered heterocyclic ring.

Representative compounds of formula IVc are shown below in Table 11.

TABLE 11

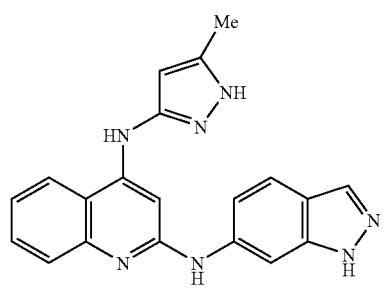

IVc-1

TABLE 11-continued
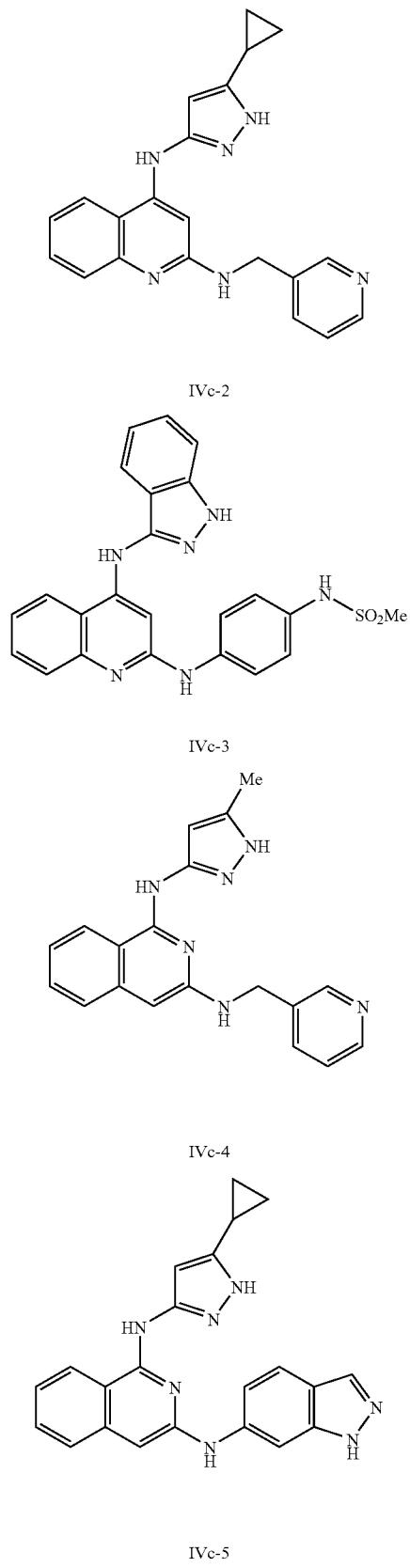
IVc-2
IVc-3
IVc-4
IVc-5
TABLE 11-continued
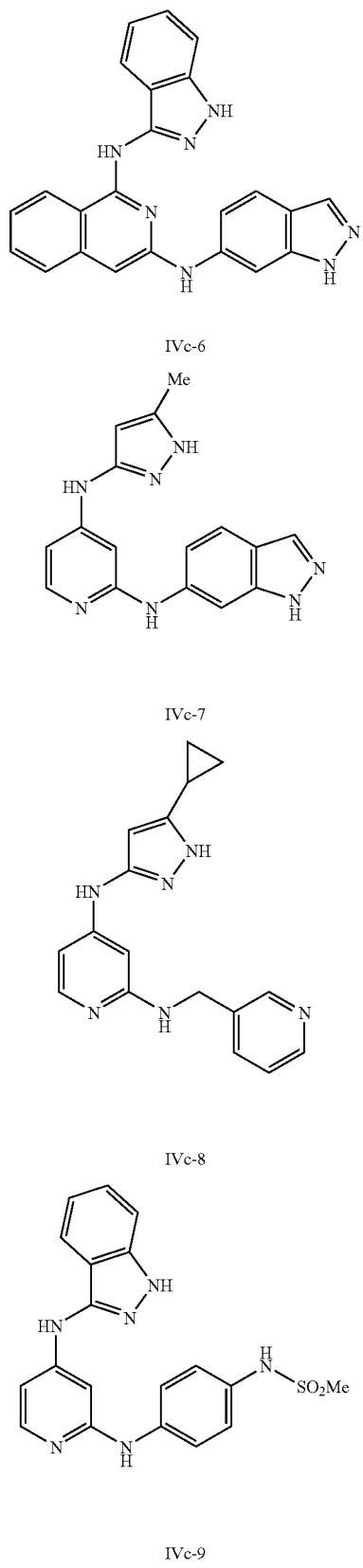
IVc-6
IVc-7
IVc-8
IVc-9

TABLE 11-continued

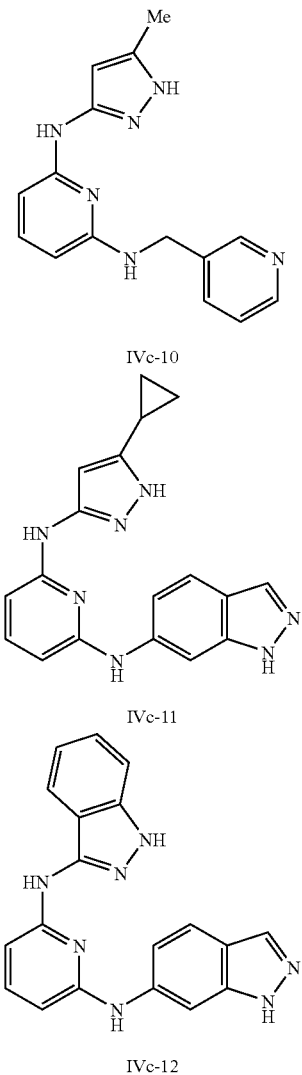

IVc-10

IVc-11

IVc-12

In another embodiment, this invention provides a composition comprising a compound of formula IVc and a pharmaceutically acceptable carrier.

Another aspect of this invention relates to a method-of treating or preventing an Aurora-2-mediated disease with an Aurora-2 inhibitor, which method comprises administering to a patient in need of such a treatment a therapeutically effective amount of a compound of formula IVc or a pharmaceutical composition thereof.

Another aspect of this invention relates to a method of inhibiting Aurora-2 activity in a patient, which method comprises administering to the patient a compound of formula IVc or a composition comprising said compound.

Another aspect of this invention relates to a method of treating or preventing a GSK-3-mediated disease with a GSK-3 inhibitor, which method comprises administering to a patient in need of such a treatment a therapeutically effective amount of a compound of formula IVc or a pharmaceutical composition thereof.

One aspect of this invention relates to a method of enhancing glycogen synthesis and/or lowering blood levels of glucose in a patient in need thereof, which method comprises administering to the patient a therapeutically effective amount of a compound of formula IVc or a pharmaceutical composition thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of β-catenin, which is useful for treating schizophrenia.

Another aspect of this invention relates to a method of inhibiting GSK-3 activity in a patient, which method comprises administering to the patient a compound of formula IVc or a composition comprising said compound.

Another method relates to inhibiting Aurora-2 or GSK-3 activity in a biological sample, which method comprises contacting the biological sample with the Aurora-2 or GSK-3 inhibitor of formula IVc, or a pharmaceutical composition thereof, in an amount effective to inhibit Aurora-2 or GSK-3.

Each of the aforementioned methods directed to the inhibition-of Aurora-2 or GSK-3, or the treatment of a disease alleviated thereby, is preferably carried out with a preferred compound of formula IVc, as described above.

Another embodiment of this invention relates to compounds of formula IVd:

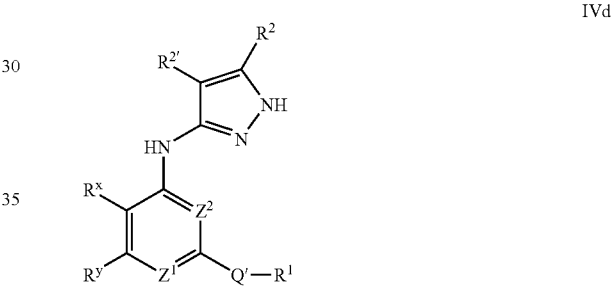

IVd or a pharmaceutically acceptable derivative or prodrug thereof, wherein:

$Z^1$ is nitrogen or C—$R^8$ and $Z^2$ is nitrogen or CH, wherein one of $Z^1$ or $Z^2$ is nitrogen;

Q' is selected from —C($R^{6'}$)$_2$—, 1,2-cyclopropanediyl, 1,2-cyclobutanediyl, or 1,3-cyclobutanediyl;

$R^x$ and $R^y$ are independently selected from T—$R^3$ or L—Z—$R^3$, or $R^x$ and $R^y$ are taken together with their intervening atoms to form a fused, unsaturated or partially unsaturated, 5–7 membered ring having 0–3 ring heteroatoms selected from oxygen, sulfur, or nitrogen, wherein each substitutable ring carbon of said fused ring formed by $R^x$ and $R^y$ is independently substituted by oxo, T—$R^3$, or L—Z—$R^3$, and each substitutable ring nitrogen of said ring formed by $R^x$ and $R^y$ is independently substituted by $R^4$;

$R^1$ is T-(Ring D);

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein each substitutable ring carbon of Ring D is independently substituted by oxo, T—$R^5$, or V—Z—$R^5$, and each substitutable ring nitrogen of Ring D is independently substituted by —$R^4$;

T is a valence bond or a $C_{1-4}$ alkylidene chain, wherein when Q' is —C($R^{6'}$)$_2$— a methylene group of said $C_{1-4}$ alkylidene chain is optionally replaced by —O—, —S—, —N(R⁴)—, —CO—, —CONH—, —NHCO—, —SO₂—, —SO₂NH—, —NHSO₂—, —CO₂—, —OC(O)—, —OC(O)NH—, or —NHCO₂—;

Z is a C₁₋₄ alkylidene chain;

L is —O—, —S—, —SO—, —SO₂—, —N(R⁶)SO₂—, —SO₂N(R⁶)—, —N(R⁶)—, —CO—, —CO₂—, —N(R⁶)CO—, —N(R⁶)C(O)O—, —N(R⁶)CON(R⁶)—, —N(R⁶)SO₂N(R⁶)—, —N(R⁶)N(R⁶)—, —C(O)N(R⁶)—, —OC(O)N(R⁶)—, —C(R⁶)₂O—, —C(R⁶)₂S—, —C(R⁶)SO—, —C(R⁶)₂SO₂—, —C(R⁶)₂SO₂N(R⁶)—, —C(R⁶)₂N(R⁶)—, —C(R⁶)₂N(R⁶)C(O)—, —C(R⁶)₂N(R⁶)C(O)O—, —C(R⁶)=NN(R⁶)—, —C(R⁶)=N—O—, —C(R⁶)₂N(R⁶)N(R⁶)—, —C(R⁶)₂N(R⁶)SO₂N(R⁶)—, or —C(R⁶)₂N(R⁶)CON(R⁶)—;

R² and R²' are independently selected from —R, —T—W—R⁶, or R² and R²' are taken together with their intervening atoms to form a fused, 5–8 membered, unsaturated or partially unsaturated, ring having 0–3 ring heteroatoms selected from nitrogen, oxygen, or sulfur, wherein each substitutable ring carbon of said fused ring formed by R² and R²' is independently substituted by halo, oxo, —CN, —NO₂, —R⁷, or —V—R⁶, and each substitutable ring nitrogen of said ring formed by R² and R²' is independently substituted by R⁴;

R³ is selected from —R, -halo, —OR, —C(=O)R, —CO₂R, —COCOR, —COCH₂COR, —NO₂, —CN, —S(O)R, —S(O)₂R, —SR, —N(R⁴)₂, —CON(R⁷)₂, —SO₂N(R⁷)₂, —OC(=O)R, —N(R⁷)COR, —N(R⁷)CO₂(C₁₋₆ aliphatic), —N(R⁴)N(R⁴)₂, —C=NN(R⁴)₂, —C=N—OR, —N(R⁷)CON(R⁷)₂, —N(R⁷)SO₂N(R⁷)₂, —N(R⁴)SO₂R, or —OC(=O)N(R⁷)₂;

each R is independently selected from hydrogen or an optionally substituted group selected from C₁₋₆ aliphatic, C₆₋₁₀ aryl, a heteroaryl ring having 5–10 ring atoms, or a heterocyclyl ring having 5–10 ring atoms;

each R⁴ is independently selected from —R⁷, —COR⁷, —CO₂(optionally substituted C₁₋₆ aliphatic) —CON(R⁷)₂, or —SO₂R⁷;

each R⁵ is independently selected from —R, halo, —OR, —C(=O)R, —CO₂R, —COCOR, —NO₂, —CN, —S(O)R, —SO₂R, —SR, —N(R⁴)₂, —CON(R⁴)₂, —SO₂N(R⁴)₂, —OC(=O)R, —N(R⁴)COR, —N(R⁴)CO₂(optionally substituted C₁₋₆ aliphatic), —N(R⁴)N(R⁴)₂, —C=NN(R⁴)₂, —C=N—OR, —N(R⁴)CON(R⁴)₂, —N(R⁴)SO₂N(R⁴)₂, —N(R⁴)SO₂R, or —OC(=O)N(R⁴)₂;

V is —O—, —S—, —SO—, —SO₂—, —N(R⁶)SO₂—, —SO₂N(R⁶)—, —N(R⁶)—, —CO—, —CO₂—, —N(R⁶)CO—, —N(R⁶)C(O)O—, —N(R⁶)CON(R⁶)—, —N(R⁶)SO₂N(R⁶)—, —N(R⁶)N(R⁶)—, —C(O)N(R⁶)—, —OC(O)N(R⁶)—, —C(R⁶)₂O—, —C(R⁶)₂S—, —C(R⁶)₂SO—, —C(R⁶)₂SO₂—, —C(R⁶)₂SO₂N(R⁶)—, —C(R⁶)₂N(R⁶)—, —C(R⁶)₂N(R⁶)C(O)—, —C(R⁶)₂N(R⁶)C(O)O—, —C(R⁶)=NN(R⁶)—, —C(R⁶)=N—O—, —C(R⁶)₂N(R⁶)N(R⁶)—, —C(R⁶)₂N(R⁶)SO₂N(R⁶)—, or —C(R⁶)₂N(R⁶)CON(R⁶)—;

W is —C(R⁶)₂O—, —C(R⁶)₂S—, —C(R⁶)₂SO—, —C(R⁶)₂SO₂—, —C(R⁶)₂SO₂N(R⁶)—, —C(R⁶)₂N(R⁶)—, —CO—, —CO₂—, —C(R⁶)OC(O)—, —C(R⁶)OC(O)N(R⁶)—, —C(R⁶)₂N(R⁶)CO—, —C(R⁶)₂N(R⁶)C(O)O—, —C(R⁶)=NN(R⁶)—, —C(R⁶)=N—O—, —C(R⁶)₂N(R⁶)N(R⁶)—, —C(R⁶)N(R⁶)SO₂N(R⁶)—, —C(R⁶)₂N(R⁶)CON(R⁶)—, or —CON(R⁶)—;

each R⁶ is independently selected from hydrogen or an optionally substituted C₁₋₄ aliphatic group, or two R⁶ groups on the same nitrogen atom are taken together with the nitrogen atom to form a 5–6 membered heterocyclyl or heteroaryl ring;

each R⁶' is independently selected from hydrogen or a C₁₋₄ aliphatic group, or two R⁶' on the same carbon atom are taken together to form a 3–6 membered carbocyclic ring;

each R⁷ is independently selected from hydrogen or an optionally substituted C₁₋₆ aliphatic group, or two R⁷ on the same nitrogen are taken together with the nitrogen to form a 5–8 membered heterocyclyl or heteroaryl ring; and R⁸ is selected from —R, halo, —OR, —C(=O)R, —CO₂R, —COCOR, —NO₂, —CN, —S(O)R, —SO₂R, —SR, —N(R⁴)₂, —CON(R⁴)₂, —SO₂N(R⁴)₂, —OC(=O)R, —N(R⁴)COR, —N(R⁴)CO₂(optionally substituted C₁₋₆ aliphatic), —N(R⁴)N(R⁴)₂, —C=NN(R⁴)₂, —C=N—OR, —N(R⁴)CON(R⁴)₂, —N(R⁴)SO₂N(R⁴)₂, —N(R⁴)SO₂R, or —OC(=O)N(R⁴)₂.

Preferred rings formed by Rˣ and Rʸ of formula IVd include a 5-, 6-, or 7-membered unsaturated or partially unsaturated ring having 0–2 heteroatoms, wherein said Rˣ/Rʸ ring is optionally substituted. This provides a bicyclic ring system containing a pyridine ring. Preferred pyridine ring systems of formula IVa are shown below.

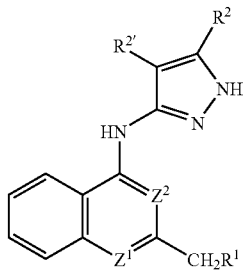

IVd-A

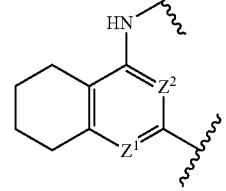

IVd-B

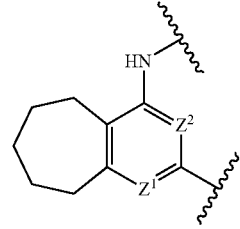

IVd-C

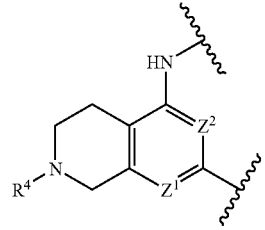

IVd-D

IVd-E
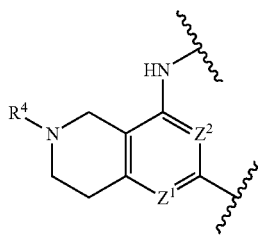

IVd-F
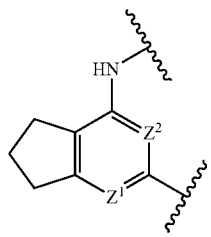

IVd-J
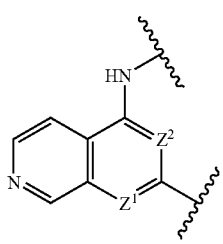

IVd-K
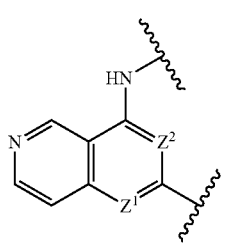

IVd-L
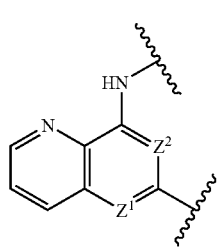

IVd-P
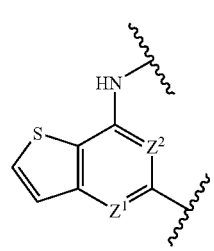

IVd-R
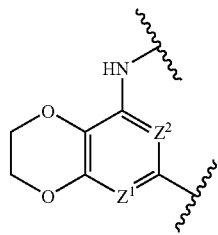

IVd-V
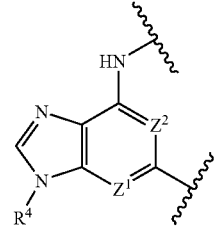

IVd-W
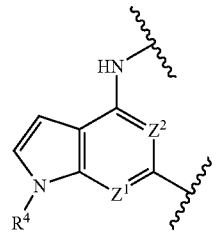

More preferred pyridine ring systems of formula IVd include IVd-A, IVd-B,-IVd-D, IVd-E, IVd-J, IVd-P, and IVd-V, most preferably IVd-A, IVd-B, IVd-D, IVd-E, and IVd-J. Even more preferred pyridine ring systems of formula IVd include those described above, wherein $Z^1$ is nitrogen and $Z^2$ is CH.

Preferred $R^x$ groups of formula IVd include hydrogen, alkyl or dialkylamino, acetamido, or a $C_{1-4}$ aliphatic group such as methyl, ethyl, cyclopropyl, or isopropyl.

Preferred $R^y$ groups of formula IVd include T—$R^3$ or L—Z—$R^3$ wherein T is a valence bond or a methylene, L is —O—, —S—, or —N($R^4$)—, —C($R^6$)$_2$O—, —CO— and $R^3$ is —R, —N($R^4$)$_2$, or —OR. Examples of preferred $R^y$ groups include 2-pyridyl, 4-pyridyl, pyrrolidinyl, piperidinyl, morpholinyl, piperazinyl, methyl, ethyl, cyclopropyl, isopropyl, t-butyl, alkoxyalkylamino such as methoxyethylamino, alkoxyalkyl such as methoxymethyl or methoxyethyl, alkyl- or dialkylamino such as ethylamino or dimethylamino, alkyl- or dialkylaminoalkoxy such as dimethylaminopropyloxy, acetamido, optionally substituted phenyl such as phenyl or halo-substituted phenyl.

The ring formed when the $R^x$ and $R^y$ groups of formula IVd are taken together may be substituted or unsubstituted. Suitable substituents include —R, halo, —O(CH$_2$)$_{2-4}$—N(R$^4$)$_2$, —O(CH$_2$)$_{2-4}$—R, —OR, —N(R$^4$)—(CH$_2$)$_{2-4}$—N(R$^4$)$_2$, —N(R$^4$)—(CH$_2$)$_{2-4}$—R, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$(optionally substituted $C_{1-6}$ aliphatic), —N(R$^4$)N(R$^4$)$_2$, —C=NN(R$^4$)$_2$, —C=N—OR, —N(R⁴)CON(R⁴)₂, —N(R⁴)SO₂N(R⁴)₂, —N(R⁴)SO₂R, or —OC(=O)N(R⁴)₂, R and R⁴ are as defined above. Preferred Rˣ/Rʸ ring substituents include -halo, —R, —OR, —COR, —CO₂R, —CON(R⁴)₂, —CN, —O(CH₂)₂₋₄—N(R⁴)₂, —O(CH₂)₂₋₄—R, —NO₂—N(R⁴)₂, —NR⁴COR, —NR⁴SO₂R, —SO₂N(R⁴)₂ wherein R is hydrogen or an optionally substituted C₁₋₆ aliphatic group.

The R² and R²' groups of formula IVd may be taken together to form a fused ring, thus providing a bicyclic ring system containing a pyrazole ring. Preferred fused rings include benzo, pyrido, pyrimido, and a partially unsaturated 6-membered carbocyclo ring. These are exemplified in the following formula IVd compounds having a pyrazole-containing bicyclic ring system:

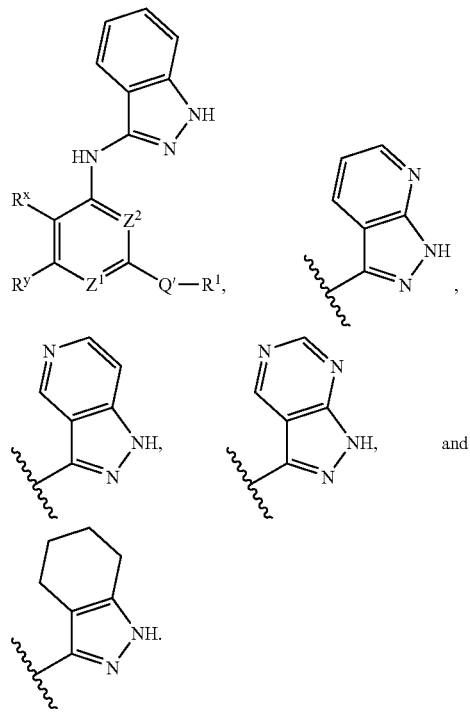

Preferred substituents on the R²/R²' fused ring of formula IVd include one or more of the following: -halo, —N(R⁴)₂, —C₁₋₄ alkyl, —C₁₋₄ haloalkyl, —NO₂, —O(C₁₋₄ alkyl, —CO₂(C₁₋₄ alkyl), —CN, —SO₂(C₁₋₄ alkyl), —SO₂NH₂, —OC(O)NH₂, —NH₂SO₂(C₁₋₄ alkyl), —NHC(O)(C₁₋₄ alkyl), —C(O)NH₂, and —CO(C₁₋₄ alkyl), wherein the (C₁₋₄ alkyl) is a straight, branched, or cyclic alkyl group. Preferably, the (C₁₋₄ alkyl) group is methyl.

When the pyrazole ring system of formula IVd is monocyclic, preferred R² groups include hydrogen or a substituted or unsubstituted group selected from aryl, heteroaryl, or a C₁₋₆ aliphatic group. Examples of such preferred R² groups include H, methyl, ethyl, propyl, cyclopropyl, i-propyl, cyclopentyl, hydroxypropyl, methoxypropyl, and benzyloxypropyl. A preferred R²' group is hydrogen.

When Ring D of formula IVd is monocyclic, preferred Ring D groups include phenyl, pyridyl, pyridazinyl, pyrimidinyl, and pyrazinyl.

When Ring D of formula IVd is bicyclic, preferred bicyclic Ring D groups include naphthyl, tetrahydronaphthyl, indanyl, benzimidazolyl, quinolinyl, indolyl, isoindolyl, indolinyl, benzo[b]furyl, benzo[b]thiophenyl, indazolyl, benzothiazolyl, cinnolinyl, phthalazinyl, quinazolinyl, quinoxazolinyl, 1,8-naphthyridinyl and isoquinolinyl.

On Ring D of formula IVd, preferred T—R⁵ or V—Z—R⁵ substituents include -halo, —CN, —NO₂, —N(R⁴)₂, optionally substituted C₁₋₆ aliphatic group, —OR, —C(O)R, —CO₂R, —CONH(R⁴), —N(R⁴)COR, —N(R⁴)CO₂R, —SO₂N(R⁴)₂, —N(R⁴)SO₂R, —N(R⁶)COCH₂N(R⁴)₂, —N(R⁶)COCH₂CH₂N(R⁴)₂, and —N(R⁶)COCH₂CH₂CH₂N(R⁴)₂, wherein R is selected from hydrogen, C₁₋₆ aliphatic, phenyl, a 5–6 membered heteroaryl ring, or a 5–6 membered heterocyclic ring. More preferred R⁵ substituents include —Cl, —Br, —F, —CN, —CF₃, —COOH, —CONHMe, —CONHEt, —NH₂, —NHAc, —NHSO₂Me, —NHSO₂Et, —NHSO₂(n-propyl), —NHSO₂(isopropyl), —NHCOEt, —NHCOCH₂NHCH₃, —NHCOCH₂N(CO₂t-Bu)CH₃, —NHCOCH₂N(CH₃)₂, —NHCOCH₂CH₂N(CH₃)₂, —NHCOCH₂CH₂CH₂N(CH₃)₂, —NHCO(cyclopropyl), —NHCO(isobutyl), —NHCOCH₂(morpholin-4-yl), —NHCOCH₂(morpholin-4-yl), —NHCOCH₂CH₂CH₂(morpholin-4-yl), —NHCO₂(t-butyl), —NH(C₄₋₁ aliphatic) such as —NHMe, —N(C₁₋₄ aliphatic)₂ such as —NMe₂, OH, —O(C₁₋₄ aliphatic) such as —OMe, C₁₋₄ aliphatic such as methyl, ethyl, cyclopropyl, isopropyl, or t-butyl, and —CO₂(C₁₋₄ aliphatic).

Preferred R⁸ groups of formula IVd, when present, include R, OR, and N(R⁴)₂. Examples of preferred R⁸ include methyl, ethyl, NH₂, NH₂CH₂CH₂NH, N(CH₃)₂CH₂CH₂NH, N(CH₃)₂CH₂CH₂O, (piperidin-1-yl)CH₂CH₂O, and NH₂CH₂CH₂O.

Preferred Q' groups of formula IVd include —C(R⁶')₂— or 1,2-cyclopropanediyl, wherein each R⁶' is independently selected from hydrogen or methyl. A more preferred Q' group is —CH₂—.

Preferred formula IVd compounds have one or more, and more preferably all, of the features selected from the group consisting of:

(a) Rˣ is hydrogen, alkyl- or dialkylamino, acetamido, or a C₁₋₄ aliphatic group and Rʸ is T—R³ or L—Z—R³, wherein T is a valence bond or a methylene and R³ is —R, —N(R⁴)₂, or —OR; or Rˣ and Rʸ are taken together with their intervening atoms to form a fused, unsaturated or partially unsaturated, 5–6 membered ring having 0–2 heteroatoms selected from oxygen, sulfur, or nitrogen, wherein each substitutable ring carbon of said fused ring formed by Rˣ and Rʸ is independently substituted by oxo, T—R³, or L—Z—R³, and each substitutable ring nitrogen of said ring formed by Rˣ and Rʸ is independently substituted by R⁴;

(b) R¹ is T-(Ring D), wherein T is a valence bond or a methylene unit and wherein said methylene unit is optionally replaced by —O—, —NH—, or —SO—;

(c) Ring D is a 5–7 membered monocyclic or an 8–10 membered bicyclic aryl or heteroaryl ring; and (d) R² is —R or —T—W—R⁶ and R²' is hydrogen, or R² and R²' are taken together to form an optionally substituted benzo ring.

More preferred compounds of formula IVd have one or more, and more preferably all, of the features selected from the group consisting of:

(a) Rʸ is T—R³ or L—Z—R³ wherein T is a valence bond or a methylene and R³ is selected from —R, —OR, or —N(R⁴)₂, wherein R is selected from hydrogen, C₁₋₆ aliphatic, or 5–6 membered heterocyclyl, phenyl, or 5–6 membered heteroaryl; or Rˣ and Rʸ are taken together with their intervening atoms to form a benzo, pyrido, cyclopento, cyclohexo, cyclohepto, thieno, piperidino, or imidazo ring, wherein each substitutable ring carbon of said fused ring formed by $R^x$ and $R^y$ is independently substituted by oxo, $T-R^3{}_1$ or $L-Z-R^3$, and each substitutable ring nitrogen of said ring formed by $R^x$ and $R^y$ is independently substituted by $R^4$;

(b) $R^1$ is T-(Ring D), wherein T is a valence bond, and Ring D is a 5–6 membered monocyclic or an 8–10 membered bicyclic aryl or heteroaryl ring;

(c) $R^2$ is —R and $R^{2'}$ is hydrogen, wherein R is selected from hydrogen, $C_{1-6}$ aliphatic, phenyl, a 5–6 membered heteroaryl ring, or a 5–6 membered heterocyclic ring;

(d) $R^3$ is selected from —R, -halo, —OR, or —N($R^4$)$_2$, wherein R is selected from hydrogen, $C_{1-6}$ aliphatic, or 5–6 membered heterocyclyl, phenyl, or 5–6 membered heteroaryl, and L is —O—, —S—, or —N($R^4$)—; and (e) Q' is —C($R^{6'}$)$_2$— or 1,2-cyclopropanediyl, wherein each $R^{6'}$ is independently selected from hydrogen or methyl.

Even more preferred compounds of formula IVd have one or more, and more preferably all, of the features selected from the group consisting of:

(a) $R^x$ is hydrogen methyl, ethyl, propyl, cyclopropyl, isopropyl, methylamino or acetamido and $R^y$ is selected from 2-pyridyl, 4-pyridyl, pyrrolidinyl, piperidinyl, morpholinyl, piperazinyl, methyl, ethyl, cyclopropyl, isopropyl, t-butyl, alkoxyalkylamino, alkoxyalkyl, alkyl- or dialkylamino, alkyl- or dialkylaminoalkoxy, acetamido, optionally substituted phenyl, or methoxymethyl; or $R^x$ and $R^y$ are taken together with their intervening atoms to form a benzo, pyrido, piperidino, or cyclohexo ring, wherein said ring is optionally substituted with -halo, —R, —OR, —COR, —CO$_2$R, —CON($R^4$)$_2$, —CN, —O(CH$_2$)$_{2-4}$—N($R^4$)$_2$, —O(CH$_2$)$_{2-4}$—R, —NO$_2$ —N($R^4$)$_2$, —N$R^4$COR, —N$R^4$SO$_2$R, or —SO$_2$N($R^4$)$_2$, wherein R is hydrogen or an optionally substituted $C_{1-6}$ aliphatic group;

(b) $R^1$ is T-(Ring D), wherein T is a valence bond and Ring D is a 5–6 membered aryl or heteroaryl ring optionally substituted with one or two groups selected from -halo, —CN, —NO$_2$, —N($R^4$)$_2$ optionally substituted $C_{1-6}$ aliphatic, —OR, —C(O)R, —CO$_2$R, —CONH($R^4$), —N($R^4$)COR, —N($R^4$)CO$_2$R, —SO$_2$N($R^4$)$_2$, —N($R^4$)SO$_2$R, —N($R^6$)COCH$_2$N($R^4$)$_2$, —N($R^6$)COCH$_2$CH$_2$N($R^4$)$_2$, or —N($R^6$)COCH$_2$CH$_2$CH$_2$N($R^4$)$_2$;

(c) $R^2$ is hydrogen or a substituted or unsubstituted group selected from aryl, heteroaryl, or a $C_{1-6}$ aliphatic group, and $R^{2'}$ is hydrogen; and (d) $R^3$ is selected from —R, —OR, or —N($R^4$)$_2$, wherein R is selected from hydrogen, $C_{1-6}$ aliphatic, 5–6 membered heterocyclyl, phenyl, or 5–6 membered heteroaryl, and L is —O—, —S—, or —NH—;

(e) Ring D is substituted by up to three substituents selected from -halo, —CN, —NO$_2$, —N($R^4$)$_2$, optionally substituted $C_{1-6}$ aliphatic group, —OR, —C(O)R, —CO$_2$R, —CONH($R^4$), —N($R^4$)COR, —N($R^4$)CO$_2$R, —SO$_2$N($R^4$)$_2$, —N($R^4$)SO$_2$R, —N($R^6$)COCH$_2$N($R^4$)$_2$, —N($R^6$)COCH$_2$CH$_2$N($R^4$)$_2$, or —N($R^6$)COCH$_2$CH$_2$CH$_2$N($R^4$)$_2$, wherein R is selected from hydrogen, $C_{1-6}$ aliphatic, phenyl, a 5–6 membered heteroaryl ring, or a 5–6 membered heterocyclic ring; and (f) Q' is —CH$_2$—.

Representative compounds of formula IVd are shown below in Table 12.

TABLE 12

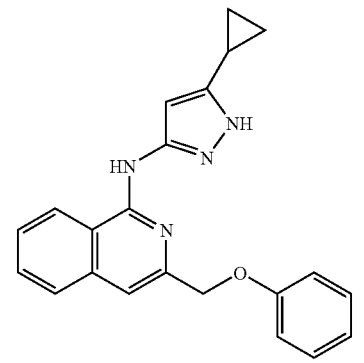

IVd-1

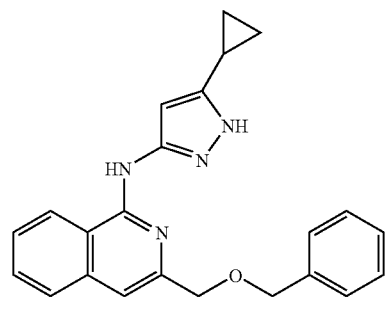

IVd-2

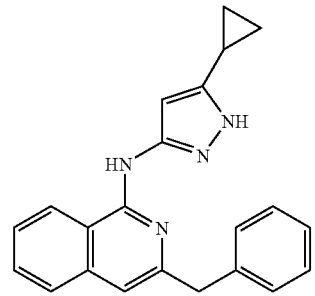

IVd-3

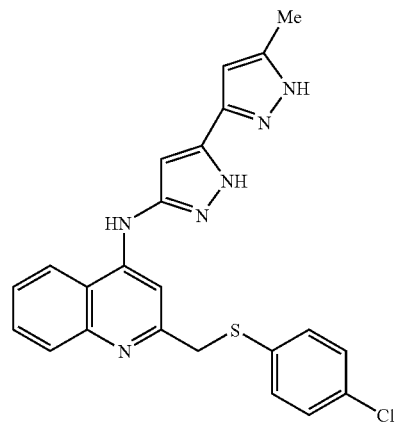

IVd-4

TABLE 12-continued

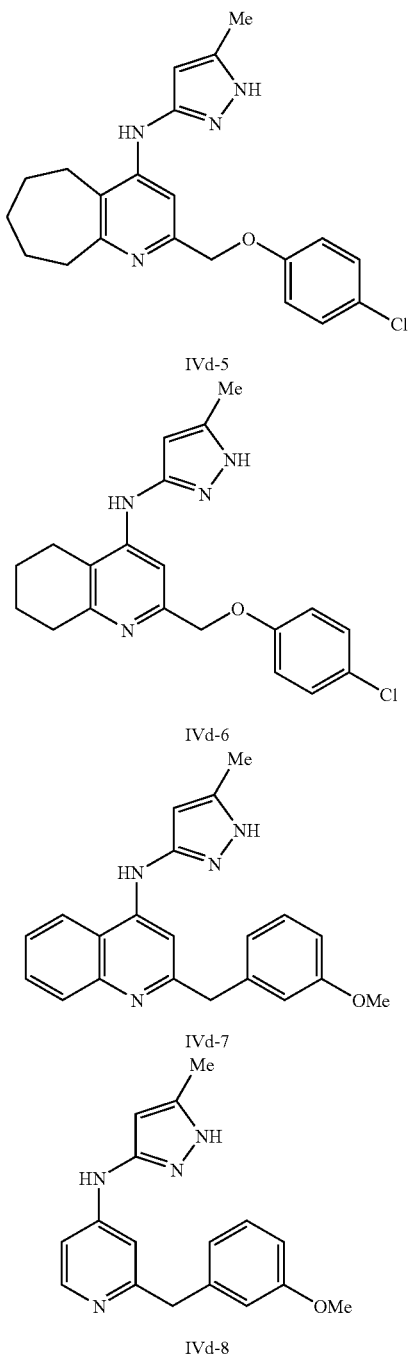

IVd-5

IVd-6

IVd-7

IVd-8

In another embodiment, this invention provides a composition comprising a compound of formula IVd and a pharmaceutically acceptable carrier.

Another aspect of this invention relates to a method of treating or preventing an Aurora-2-mediated disease with an Aurora-2 inhibitor, which method comprises administering to a patient in need of such a treatment a therapeutically effective amount of a compound of formula IVd or a pharmaceutical composition thereof.

Another aspect of this invention relates to a method inhibiting Aurora-2 activity in a patient, which method comprises administering to the patient a compound of formula IVd or a composition comprising said compound.

Another aspect of this invention relates to a method of treating or preventing a GSK-3-mediated disease with a GSK-3 inhibitor, which method comprises administering to a patient in need of such a treatment a therapeutically effective amount of a compound of formula IVd or a pharmaceutical composition thereof.

One aspect of this invention relates to a method of enhancing glycogen synthesis and/or lowering blood levels of glucose in a patient in need thereof, which method comprises administering to the patient a therapeutically effective amount of a compound of formula IVd or a pharmaceutical composition thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of β-catenin, which is useful for treating schizophrenia.

Another aspect of this invention relates to a method of inhibiting GSK-3 activity in a patient, which method comprises administering to the patient a compound of formula IVd or a composition comprising said compound.

Another method relates to inhibiting Aurora-2 or GSK-3 activity in a biological sample which method comprises contacting the biological sample with the Aurora-2 or GSK-3 inhibitor of formula IVd, or a pharmaceutical composition thereof, in an amount effective to inhibit Aurora-2 or GSK-3.

Each of the aforementioned methods directed to the inhibition of Aurora-2 or GSK-3, or the treatment of a disease alleviated thereby, is preferably carried out with a preferred compound of formula IVd, as described above.

The compounds of this invention may be prepared in general by methods known to those skilled in the art for analogous compounds, as illustrated by the general Schemes I–VII, the general-methods that follow, and by the preparative examples below.

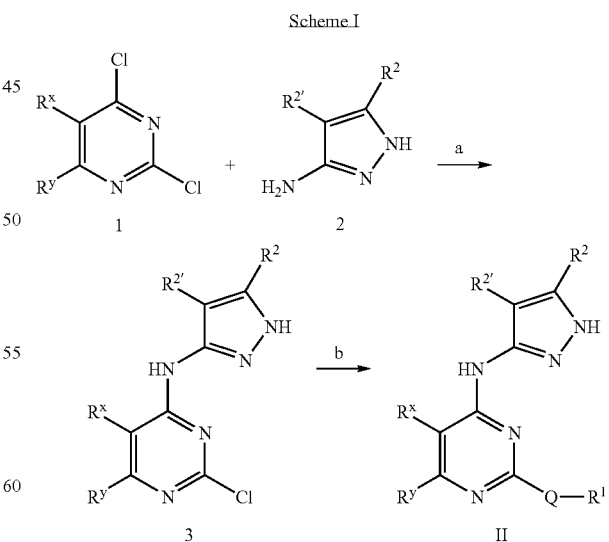

Scheme I

Reagents: (a) EtOH, Et$_3$N, room temperature; (b) R$^1$—QH (Q=S, NH or O) or R$^1$—CH$_2$-M/catalyst (M is Al or Mg or Sn, catalyst=Pd$^o$ or Ni$^o$)

Scheme I above shows a general route for the preparation of the present compounds. The dichlorinated starting material 1 may be prepared using methods similar to the those reported in *J. Indian. Chem. Soc.*, 61, 690–693 (1984) or in *J. Med. Chem.*, 37, 3828–3833; (1994). The reaction of 1 with aminopyrazole (or aminoindazole) 2 in a manner as described in *Bioorg. Med. Chem, Lett*, 10, 11, 1175–1180, (2000) or in *J. Het. Chem*, 21, 1161–1167, (1984) provides the versatile monochloro intermediate 3. Conditions for displacing the chloro group of 3 by $R^1$—Q will depend on the nature of the Q linker moiety and are generally known in the field. See, for example, *J. Med. Chem.* 38, 14, 2763–2773, (1995) (where Q is an N-Link) or *Chem. Pharm. Bull.*, 40, 1, 227–229, (1992) (S-Link), or *J. Het. Chem.*, 21, 1161–1167, (1984) (O-Link) or *Bioorg. Med. Chem. Lett*, 8, 20, 2891–2896, (1998) (C-Link).

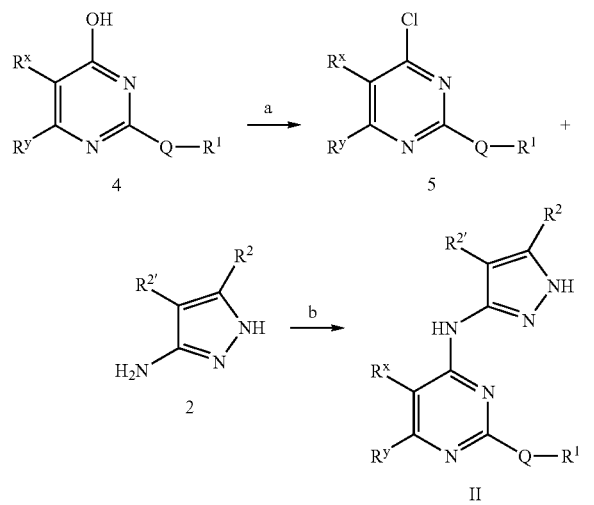

Scheme II

Reagents: (a) POCl$_3$, Pr$_3$N, 110° C.; (b) EtOH, Et$_3$N, room temperature.

Scheme II above shows an alternative route for the preparation of the present compounds. The starting material 4 may be prepared in a manner similar to that described for analogous compounds. See *Chem. Heterocycl. Compd.*, 35, 7, 818–820 (1999) (where Q is an N-Link), *Indian J. Chem. Sect. B.* 22, 1, 37–42 (1983) (N-Link). *Pestic. Sci*, 47, 2, 103–114 (1996) (O-Link), *J. Med. Chem.*, 23, 8, 913–918 (1980) (S-Link), or *Pharmazie*, 43, 7, 475–476 (1988) (C-Link). The chlorination of 4 provides intermediate 5. See *J. Med. Chem.*, 43, 22, 4288–4312 (2000) (Q is an N-Link), *Pestic. Sci*, 47, 2, 103–114 (1996) (L-Link), *J. Med. Chem.*, 41, 20, 3793–3803 (1998) (S-Link ), or *J. Med. Chem.*, 43, 22, 4288–4312 (2000) (C-Link). Displacement of the 4-Cl group in intermediate 5 with aminopyrazole (or aminoindazole) 2 to provide compounds of this invention may be performed according to known methods for analogous compounds. See *J. Med. Chem.*, 38, 14, 2763–2773 (1995) (where Q is an N-Link), *Bioorg. Med. Chem. Lett.*, 7, 4, 421–424 (1997) (O-Link), *Bioorg. Med. Chem. Lett.*, 10, 8, 703–706 (2000) (S-Link), or *J. Med. Chem.*, 41, 21, 4021–4035 (1998) (C-Link).

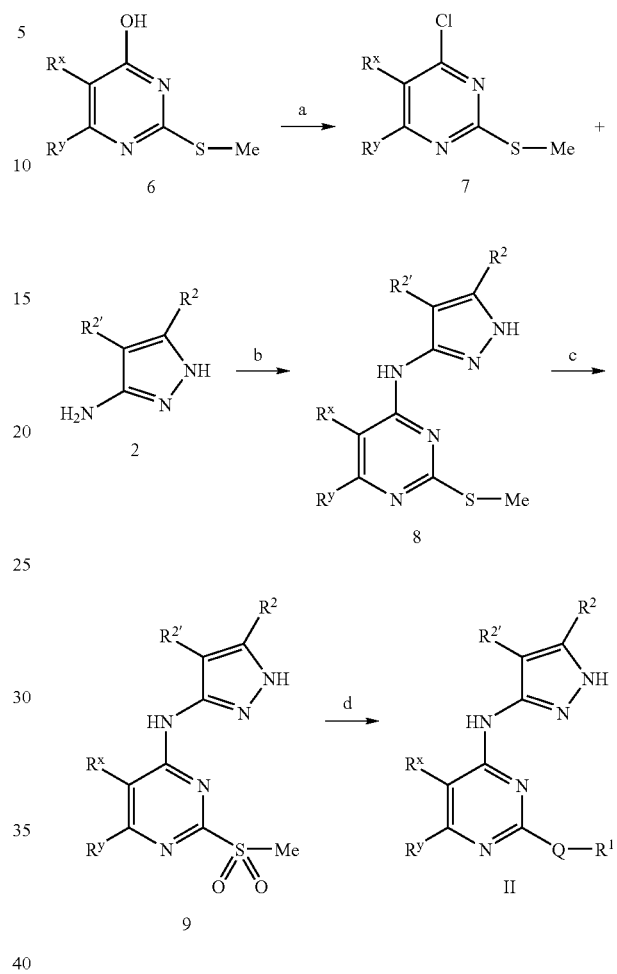

Scheme III

Reagents: (a) POCl$_3$; (b) EtOH, Et$_3$N, room temperature; (c) Oxone; (d) $R^1$—QH (Q=S, NH or O) or $R^1$—CH$_2$—M/ catalyst (M is Al or Mg or Sn, catalyst=Pd° or Ni°)

Scheme III above shows another alternative route for preparing the present compounds. The starting material 6 may be chlorinated to provide intermediate 7. Displacement of the 4-chloro group in 7 with aminopyrazole (or aminoindazole) 2 gives intermediate 8 which, upon oxidation of the methylsulfanyl group, provides the methylsulfone 9. The methylsulfonyl group of 9 may be displaced readily with $R^1$—QH to give the desired product I. See *J. Am. Chem. Soc.*, 81, 5997–6006 (1959) (where Q is an N-Link) or in *Bioorg. Med. Chem. Lett.*, 10, 8, 821–826 (2000) (S-Link).

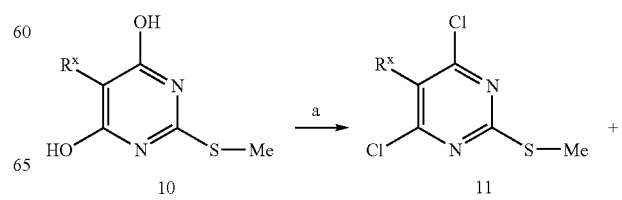

Scheme IV

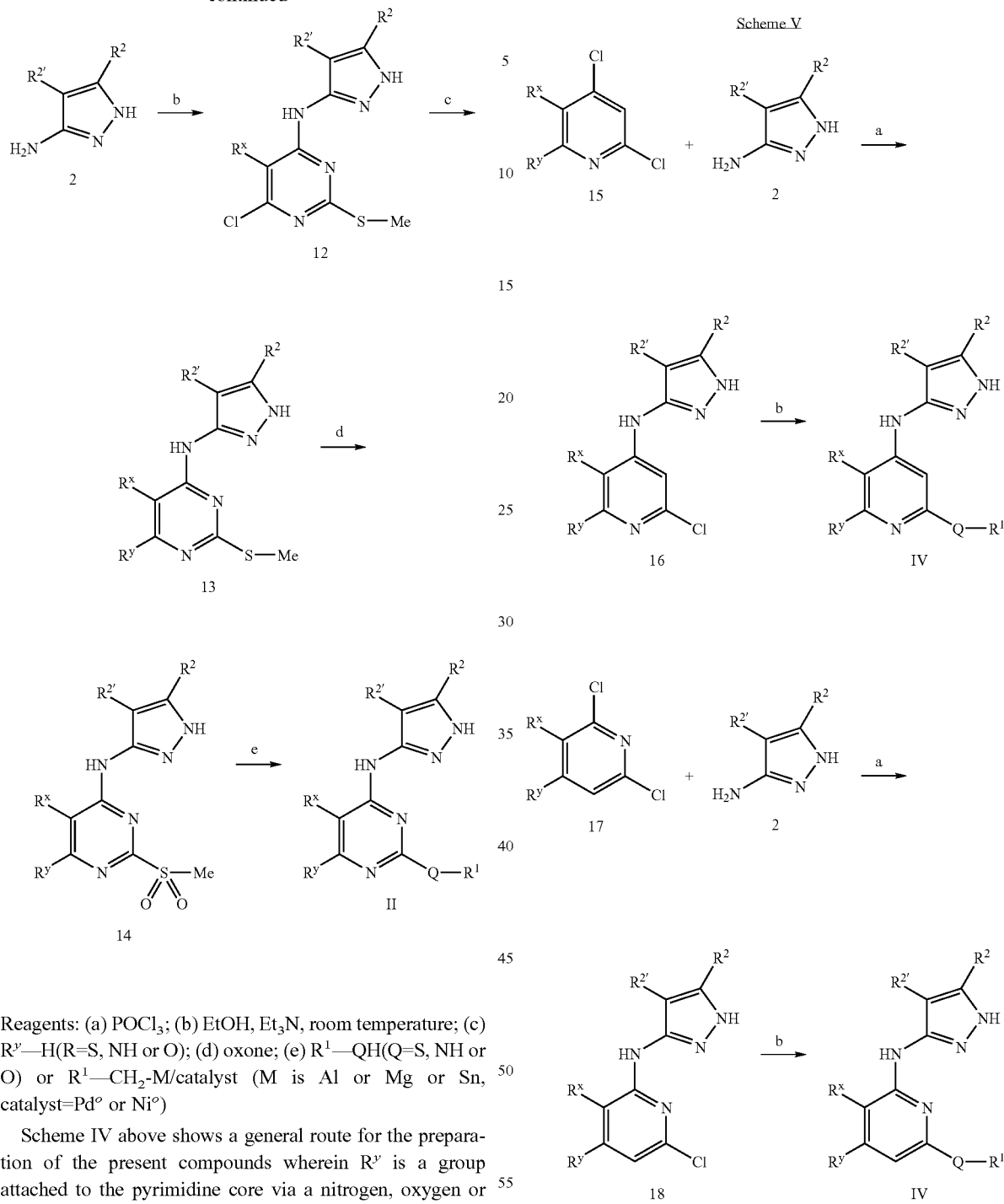

Reagents: (a) POCl$_3$; (b) EtOH, Et$_3$N, room temperature; (c) R$^y$—H(R=S, NH or O); (d) oxone; (e) R$^1$—QH(Q=S, NH or O) or R$^1$—CH$_2$-M/catalyst (M is Al or Mg or Sn, catalyst=Pd° or Ni°)

Scheme IV above shows a general route for the preparation of the present compounds wherein R$^y$ is a group attached to the pyrimidine core via a nitrogen, oxygen or sulfur heteroatom. The starting 4,6-dihydroxy-2-methylsulfanylpyrimidine 10 may be prepared as described in *J. Med. Chem.*, 27, 12, 1621–1629 (1984). The chloro groups of intermediate 11 may be displaced sequentially with aminopyrazole (or aminoindazole) 2 and then with another amine (or alcohol or thiol) following procedures similar to those reported in U.S. Pat. No. 2,585,906 (ICI, 1949). The methylsulfanyl group of 13 may then be oxidized to provide the methylsulfone 14. Displacement of the methylsulfonyl group of 14 gives the desired product II.

Scheme V above shows general routes for the preparation of compounds of formulae IVa, IVb, IVc, and IVd. Steps (a) and (b) are analogous to the corresponding steps described in Scheme I above. See *Indian J. Chem. Sect. B*, 34, 9, 1995, 778–790; *J. Chem. Soc.*, 1947, 899–905; *J. Chem. Soc.*, 34, 9, 1948, 777–782; and *Indian J. Chem.*, 1967, 467–470.

The synthetic transformations shown in Schemes I–IV above are further illustrated by the following methods.

Scheme VI

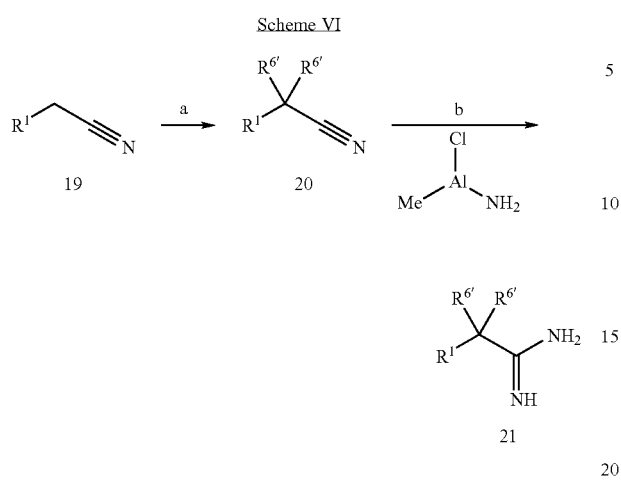

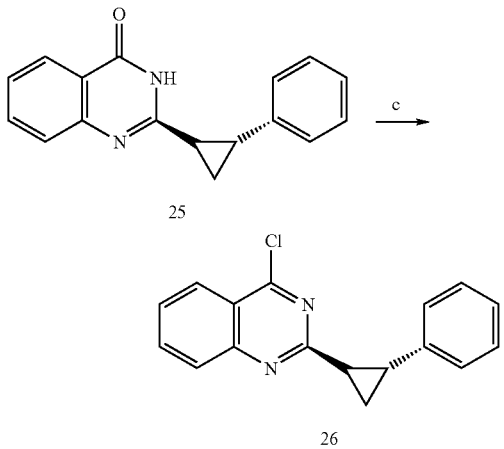

Scheme VI above shows a general route for preparing the aryl guanidine intermediate used to prepare compounds where Q is —C(R$^{6'}$)$_2$—. The mono- or bis-alkylation of 19 at step (a) to prepare compound 20 can be achieved by using methods substantially similar to those described by Jeffery, J. E., et al, J. Chem Soc, Perkin Trans 1, 1996 (21) 2583–2589; Gnecco, D., et al, Org Prep Proced Int, 1996, 28 (4), 478–480; Fedorynski, M. and Jonczyk, A., Org Prep Proced Int, 1995, 27 (3), 355–359; Suzuki, S, et al, Can J Chem, 1994, 71 (2) 357–361; and Prasad, G., et al, J Org Chem, 1991, (25), 7188–7190. The method of step (b) to prepare compound 21 from compound 20 can be achieved by using methods substantially similar to those described by Moss, R., et al, Tetrahedron Lett, 1995, (48), 8761–8764 and Garigipati, R., Tetrahedron Lett, 1990, (14), 1969–1972.

The aryl guanidine intermediates prepared according to Scheme VI may then be used to prepare the compounds of this invention by the methods described in the above Schemes I–V and by methods known to one skilled in the art.

Scheme VII

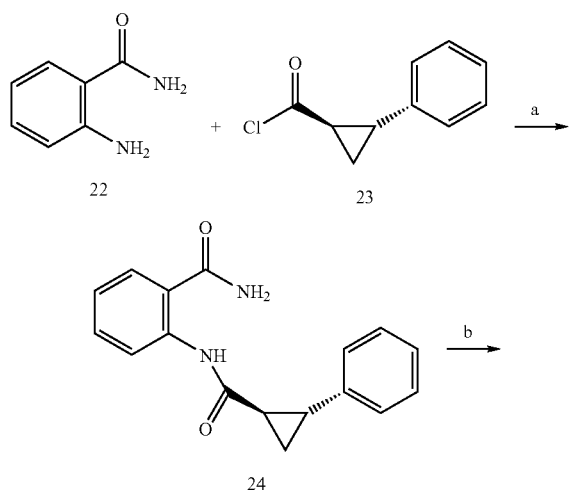

Scheme VII above shows a general method that may be used to prepare compounds of formula II wherein Q is 1,2-cyclopropanediyl. Compound 26 may then be used to prepare the desired amino-pyrazole compounds using the methods described above at Scheme I step (b).

Method A. To a solution of 2,4-dichloroquinazoline (12.69 g, 63 mmol) and 3-amino-5-methylpyrazole (6.18 g, 63 mmol) in ethanol (220 mL) is added triethylamine (8.13 mL, 63 mmol) and the reaction mixture is stirred for 3 hours at room temperature. The pale yellow precipitate is then collected by filtration, washed with cold ethanol and dried under vacuum to give (2-chloroquinazolin-4-yl)-(5-methyl-2H-pyrazol-3-yl)-amine.

The above-prepared (2-chloroquinazolin-4-yl)-(5-methyl-2H-pyrazol-3-yl)-amine (155 mg, 0.6 mmol) and 3-chloroaniline (0.316 mL, 2.99 mmol) are refluxed in tert-butanol (3 mL) over 20 h. The mixture is concentrated in vacuo and the residue is suspended in EtOH/H$_2$O (1 mL/3 mL). K$_2$CO$_3$ (83 mg, 0.6 mmol) is added and the suspension is stirred for 2 h at room temperature. The solid that forms is collected and dried under vacuum to give the product [2-(3-chlorophenylamino)-quinazolin-4-yl]-(5-methyl-2H-pyrazol-3-yl)-amine.

Method B. Sodium hydride (45 mg, 1.12 mmol) in THF (2 mL) is treated with 3-methoxyphenol (0.94 g, 7.6 mmol) and the reaction mixture is stirred until effervescence ceases. The THF is removed in vacuo and the above-prepared (2-chloroquinazolin-4-yl)-(5-methyl-2H-pyrazol-3-yl)-amine (150 mg, 0.51 mmol)) is added. The reaction mixture is stirred at 100° C. for 20 h, then poured into aqueous K$_2$CO$_3$ and stirred for 2 h at room temperature. The solid that forms is collected and re-crystallized from ethanol to give the product [2-(3-methoxyphenoxy)-quinazolin-4-yl]-(5-methyl-2H-pyrazol-3-yl)-amine.

Method C. To a solution of 4-hydroxy-2-phenoxymethylquinazoline (2 g, 7.93 mmol) in phosphorus oxychloride (10 mL) is added tripropylamine (3.02 mL, 15.8 mmol) and the reaction mixture is heated for 30 minutes at 110° C. The excess phosphorus oxychloride is evaporated in vacuo, the residue is poured, on ice cold aqueous NaHCO$_3$ and extracted with ethyl acetate. The organic layer is washed with brine, dried, filtered and evaporated. The resulting residue is purified on flash chromatography (SiO$_2$, hexane/ AcOEt gradient) to give 4-chloro-2-phenoxymethylquinazoline.

To a solution of the above 4-chloro-2-phenoxymethylquinazoline (0.5 g, 1.85 mmol) in THF (30 mL) is added 3-amino-5-cyclopropylpyrazole (0.47 g, 3.69 mmol) and the reaction mixture is heated at 65° C. for 24 hours. Solvent is evaporated and ethanol is added. A white solid forms and is collected by filtration and dried under vacuum to give (5-cCyclopropyl-2H-pyrazol-3-yl)-(2-phenoxymethyl-quinazolin-4-yl)-amine.

Method D. To a solution of the above-prepared (2-chloroquinazolin-4-yl)-(5-cyclopropyl-2H-pyrazol-3-yl)-amine (123 mg, 0.43 mmol) in THF (5 mL) is added NiCl$_2$(dppp) (12 mg, 2.1.10$^{-5}$ mol), followed by 1M benzylmagnesium chloride in THF (2.15 mL, 2.15 mmol). The solution is heated at 50° C. for 20 hours and the reaction mixture is then quenched with aqueous NH$_4$Cl and the product extracted in ethyl acetate. The solvent is evaporated and the residue purified by flash chromatography to yield the desired (2-benzyl-quinazolin-4-yl)-(5-cyclopropyl-2H-pyrazol-3-yl)-amine.

Method E. A solution of (2-chloroquinazolin-4-yl)-(5-methyl-2H-pyrazol-3-yl)-amine (200 mg, 0.77 mmol) and 4-acetamidothiophenol (644 mg, 3.85 mmol) is refluxed in tert-butanol (3 mL) over a 20 hour period. Diethylether (10 mL) is added to the mixture and a solid forms that is collected by filtration. This solid is suspended in EtOH/H$_2$O 1 mL/3 mL), then K$_2$CO$_3$ (110 mg, 0.8 mmol) is added and the suspension is stirred for 2 h at room temperature. A solid forms and is collected and dried under vacuum to give the product [2-(4-acetamidophenylsulfanyl)-quinazolin-4-yl]-(5-methyl-2H-pyrazol-3-yl)-amine.

Method F. To a solution of 2,4-dichloro-5,6,7,8-tetrahydroquinazoline (500 mg, 2.46 mmol) and 3-amino-5-cyclopropylpyrazole (303 mg, 2.46 mmol) in DMF (10 mL) is added triethylamine (0.357 mL, 2.56 mmol) followed by sodium iodide (368 mg, 2.46 mmol) and the reaction mixture is heated at 90° C. for 20 h. The reaction mixture is partitioned between ethyl acetate and aqueous saturated NaHCO$_3$. The organic layer is washed with brine and evaporated in vacuo. The residue is purified by flash chromatography (SiO$_2$, hexane/AcOEt gradient) to give (2-chloro-5,6,7,8-tetrahydroquinazolin-4-yl)-(5-cyclopropyl-2H-pyrazol-3-yl)-amine.

The above-prepared (2-chloro-5,6,7,8-tetrahydroquinazolin-4-yl)-(5-cyclopropyl-2H-pyrazol-3-yl)-amine is reacted with 2-naphthalene mercaptan as described in Method L to yield the desired (5-cyclopropyl-2H-pyrazol-3-yl)-[2-(naphthalen-2-ylsulfanyl)-5,6,7,8-tetrahydroquinazolin-4-yl]-amine.

Method G. A solution of (5-cyclopropyl-2H-pyrazol-3-yl)-[2-(3-methoxycarbonylphenylsulfanyl)-quinazolin-4-yl]-amine (110 mg, 0.26 mmol) in a mixture of THF/water (1/1, 10 mL) is treated with 1M LiOH (0.75 mL, 0.75 mmol). The mixture is stirred for 20 hours at room temperature and then neutralized with 1M HCl (0.75 mL, 0.75 mmol). A solid forms and is collected by filtration to afford the desired [2-(3-carboxyphenylsulfanyl)-quinazolin-4-yl]-(5-cyclopropyl-2H-pyrazol-3-yl)-amine.

Method H. A solution of [2-(4-acetamidophenylsulfanyl)-7-methoxy-quinazolin-4-yl]-(5-methyl-2H-pyrazol-3-yl)-amine (23 mg, 5.54.10$^{-5}$ mol) in dichloromethane (3 mL) is treated with 1M BBr$_3$ in dichloromethane (222 μL, 2.21.10$^{-4}$ mol). The mixture os heated at 80° C. for 4 hours before 1M BBr$_3$ in DCM (222 μL, 2.21.10$^{-4}$ mol) is added. The reaction mixture is heated at 80° C. for a further 3 hours. The solvent is evaporated and methanol is added to the residue to quench residual BBr$_3$. The solvent is evaporated in vacuo and this operation repeated 3 times. 1M HCl (2 mL) is added to the solid residue and the suspension stirred at room temperature for 15 hours. The solid is collected by filtration and suspended in a mixture water/EtOH (3/1, 8 mL). The mixture is neutralized with NaHCO$_3$ and stirred for 2 hours at room temperature. The solid is then collected by filtration, rinsed with water and diethyl ether to give the desired [2-(4-acetamidophenylsulfanyl)-7-hydroxy-quinazolin-4-yl]-(5-methyl-2H-pyrazol-3-yl)-amine.

Method I. To a solution of [2-(4-acetamidophenylsulfanyl)-7-hydroxy-quinazolin-4-yl]-(5-methyl-2H-pyrazol-3-yl)-amine (32 mg, 7.87.10$^{-5}$ mol) in DMF (1 mL) is added potassium carbonate (65 mg, 4.72.10$^{-4}$ mol) and the reaction mixture is heated to 80° C. N-(3-chloropropyl)morpholine (39 mg, 2.36.10$^{-4}$ mol) is then added, and the mixture is stirred at 80° C. for 4 hours, cooled to room temperature and the solvent is evaporated. The resulting residue is purified by flash chromatography to afford the desired [2-(4-acetamidophenylsulfanyl)-7-(3-morpholin-4-yl-propoxy)-quinazolin-4-yl]-(5-methyl-2H-pyrazo-3-yl)-amine.

Method J. To a solution of [2-(4-acetamido-phenylsulfanyl)-7-nitroquinazolin-4-yl]-(5-methyl-2H-pyrazol-3-yl)-amine (147 mg, 3.38.10$^{-4}$ mol) in methanol (5 mL) is added Pd/C 10% (40 mg) and the reaction mixture is treated with hydrogen at balloon pressure at 45° C. for 20 hours. The catalyst is filtered through a pad of celite which is then washed with dilute HCl. The combined yellow filtrate is evaporated and the resulting solid residue is crystallized from methanol to afford the desired [2-(4-acetamido-phenylsulfanyl)-7-hydroxyaminoquinazolin-4-yl]-(5-methyl-2H-pyrazol-3-yl)-amine.

Method K. [2-(4-Acetamido-phenylsulfanyl)-7-nitroquinazolin-4-yl]-(5-methyl-2H-pyrazol-3-yl)-amine (182 mg, 4.18.10$^{-4}$ mol) is dissolved in a mixture EtOH/water/ AcOH(25/10/1, 36 mL) and the reaction is heated at 90° C. Iron powder (93 mg) is added and the mixture is stirred at 90° C. for 4 hours, cooled to room temperature and filtered through a pad of celite. The pad is washed with methanol and the combined filtrate is concentrated in vacuo. The residue is purified by flash chromatography (SiO$_2$, DCM/ MeOH gradient) to give the desired [2-(4-acetamido-phenylsulfanyl)-7-aminoquinazolin-4-yl]-(5-methyl-2H-pyrazol-3-yl)-amine.

Method L. To a solution of 2,4-dichloro-6-phenyl-pyrimidine (3.00 mg, 1.33. mmol) and 3-amino-5-methylpyrazole (129 mg, 1.33 mmol) in DMF (7 mL) is added triethylamine (195 μL, 1.40 mmol) followed by sodium iodide (200 mg, 1.33 mmol) and the reaction mixture is stirred for 15 hours at 90° C. The resulting solution is partitioned between ethyl acetate and water and the organic phase washed with brine, dried over MgSO$_4$ then concentrated in vacuo. The residue is triturated in methanol and the resulting white solid collected by filtration to afford (2-chloro-6-phenyl-pyrimidin-4-yl)-(5-methyl-2H-pyrazol-3-yl)-amine (236 mg, 62%).

The above prepared (2-chloro-6-phenyl-pyrimidin-4-yl)-(5-methyl-2H-pyrazol-3-yl)-amine. (60 mg, 0.21 mmol) is combined with 4-acetamidothiophenol (176 mg, 1.05 mmol) in tert-butanol (5 mL) and the mixture heated at reflux for 20 hours. The reaction mixture is cooled to room temperature and partitioned between ethyl acetate and aqueous NaHCO$_3$. The organic layer is washed with brine, dried over MgSO$_4$ and concentrated in vacuo. The resulting residue is purified by flash chromatography (SiO$_2$, DCM/MeOH gradient) to afford [2-(4-acetamido-phenylsulfanyl)-6-phenyl-pyrimidin-4-yl]-(5-methyl-2H-pyrazol-3-yl)-amine (74 mg, 85%)

Method M. To a suspension of 4,6-dihydroxymercaptopyrimidine (8 g, 55 mmol) in a mixture of EtOH/water (1/1, 140 mL) is added NaOH(2.33 g, 58.3 mmol) followed by 4-methoxybenzyl chloride (7.90 mL, 58.3 mmol). The solution is stirred for 1.5 hours at 60° C. and then at room temperature for a further 6 hours. The resulting white precipitate is collected by filtration to give 4,6-dihydroxy-2-(4-methoxy-benzylsulfanyl)-pyrimidine.

The above-prepared 4,6-dihydroxy-2-(4-methoxy-benzylsulfanyl)-pyrimidine (2.5 g, 9.46 mmol) is suspended in $POCl_3$ (20 mL), and tripropylamine (3.60 mL, 18.9 mmol) is added dropwise to the mixture. The reaction is then heated at 110° C. for 4 hours. The brown solution is cooled to room temperature and the solvent is evaporated. The residue is poured on ice cold $NaHCO_3$ and the product is then extracted with ethyl acetate. The organic phase is dried over $MgSO_4$, concentrated in vacuo and the residue is purified by flash chromatography ($SiO_2$, hexane/AcOEt gradient) to give 4,6-dichloro-2-(4-methoxy-benzylsulfanyl)-pyrimidine.

To a solution of above-prepared 4,6-dichloro-2-(4-methoxy-benzylsulfanyl)-pyrimidine (915 mg, 3.04 mmol) and 3-amino-5-methylpyrazole (310 mg, 3.19 mmol) in BuOH (20 mL) is added diisopropylethylamine (0.56 mL, 3.19 mmol) followed by sodium iodide (455 mg, 3.04 mmol). The reaction mixture is stirred for 15 hours at 120° C. The solvent is removed in vacuo and the residue is purified by flash chromatography ($SiO_2$, hexane/AcOEt gardient) to give [6-chloro-2-(4-methoxy-benzylsulfanyl)-pyrimidin-4-yl]-(5-methyl-2H-pyrazol-3-yl)-amine.

The above-prepared [6-chloro-2-(4-methoxy-benzylsulfanyl)-pyrimidin-4-yl]-(5-methyl-2H-pyrazol-3-yl)-amine (500 mg, 1.38 mmol) in 1-methylpiperazine (10 mL) is heated at 130° C. for 15 hours. The solvent is then removed in vacuo and the residue is purified by flash chromatography ($SiO_2$, dichloromethane/MeOH gradient) to give the desired product [2-(4-methoxy-benzylsulfanyl)-6-(4-methylpiperazin-1-yl)-pyrimidin-4-yl]-(5-methyl-2H-pyrazol-3-yl)-amine.

Method N. A solution of [2-(4-acetamido-phenyl-sulfanyl)-6-(4-methoxyphenyl)-pyrimidin-4-yl]-(5-methyl-2H-pyrazol-3-yl)-amine (100 mg, $2.24.10^{-4}$ mol) in dichloroethane (5 mL) is treated with 1M $BBr_3$ in DCM (896 µL, $8.96.10^{-4}$ mol). The mixture is then heated at 80° C. for 4 hours before 1M $BBr_3$ in DCM (896 µL, $8.96.10^{-4}$ mol) is added. The reaction mixture is then heated at 80° C. for a further 3 hours. The solvent is evaporated and methanol is added to the residue to quench any residual $BBr_3$. The solvent is evaporated in vacuo and this evaporation step is repeated 3 times. 1M HCl(8 mL) is added to the solid residue and the suspension is stirred at room temperature for 15 hours. The solid is collected by filtration and suspended in a mixture of water/EtOH (3/1, 24 mL). The mixture is neutralized with $NaHCO_3$ and stirred for 2 hours at room temperature. The solid is then collected by filtration, rinsed with water and with diethyl ether to give [2-(4-acetamido-phenyl-sulfanyl)-6-(4-hydroxyphenyl)-pyrimidin-4-yl]-(5-methyl-2H-pyrazol-3-yl)-amine.

To a solution of the above-prepared [2-(4-acetamido-phenyl-sulfanyl)-6-(4-hydroxyphenyl)-pyrimidin-4-yl]-(5-methyl-2H-pyrazol-3-yl)-amine (70 mg, $1.62.10^{-4}$ mol) in DMF (3 mL) is added potassium carbonate (134 mg, $9.71.10^{-4}$ mol). The reaction mixture is heated to 80° C. before 1-dimethylamino-3-chloropropane hydrochloride (77 mg, $4.86.10^{-4}$ mol) is added. The mixture is stirred at 80° C. for 4 hours, cooled to room temperature and the solvent is evaporated. The residue is purified by flash chromatography to afford the desired product {2-(4-acetamido-phenyl-sulfanyl)-6-[4-(3-dimethylamino-propoxy)-phenyl]-pyrimidin-4-yl}-(5-methyl-2H-pyrazol-3-yl)-amine.

Method O. To a solution of [6-methoxycarbonyl-2-(4-propionylamino-phenyl-sulfanyl)-pyrimidin-4-yl]-(5-methyl-2H-pyrazol-3-yl)-amine (2 g, 4.85 mmol) in THF (100 mL) is added lithium borohydride (0.32 g, 14.5 mmol). The reaction mixture is stirred at 50° C. for 1.5 hours. The reaction is then quenched with dilute HCl and extracted with ethyl acetate. The organic layer is successively washed with aqueous saturated $NaHCO_3$ and brine, dried over $MgSO_4$ and evaporated. The solid residue is triturated in ethyl acetate and the resulting white solid is collected by filtration to give the desired product [6-hydroxymethyl-2-(4-propionylamino-phenyl-sulfanyl)-pyrimidin-4-yl]-(5-methyl-2H-pyrazol-3-yl)-amine.

Method P. To a solution of 4,6-dichloro-2-methylsulfanyl-pyrimidine (5 g, 25.6 mmol) and 3-amino-5-methylpyrazole 2.61 g, 26.9 mmol) in BuOH (60 mL) is added diisopropylethylamine (4.69 mL, 26.9 mmol) followed by sodium iodide (3.84 g, 25.6 mmol). The reaction mixture is stirred for 15 hours at 120° C. The solvent is then removed in vacuo and the residue is purified by flash chromatography ($SiO_2$, hexane/AcOEt gradient) to give [6-chloro-2-methylsulfanyl-pyrimidin-4-yl)-(5-methyl-2H-pyrazol-3-yl)-amine.

The above-prepared [6-chloro-2-methylsulfanyl-pyrimidin-4-yl)-(5-methyl-2H-pyrazol-3-yl)-amine (2.42 g, 9.46 mmol) is heated in morpholine (10 mL) at 130° C. for 15 hours. The solvent is then removed in vacuo and the solid residue is triturated in EtOH and collected by filtration to give [2-methylsulfanyl-6-(morpholin-4-yl)-pyrimidin-4-yl]-(5-methyl-2H-pyrazol-3-yl)-amine.

To a suspension of the above-prepared [2-methylsulfanyl-6-(morpholin-4-yl)-pyrimidin-4-yl]-(5-methyl-2H-pyrazol-3-yl)-amine (500 mg, 1.63 mmol) in MeOH (10 mL) is added a solution of oxone (3.0 g) in water (10 mL). The reaction mixture is stirred at room temperature for 15 hours and most of the solvent is evaporated. The residue is partitioned between DCM and aqueous saturated $NaHCO_3$. The organic layer is washed with brine, dried, filtered and evaporated. The residue is triturated in MeOH and the resulting white solid is collected by filtration to give [2-methylsulfonyl-6-(morpholin-4-yl)-pyrimidin-4-yl]-(5-methyl-2H-pyrazol-3-yl)-amine.

The above-prepared [2-methylsulfonyl-6-(morpholin-4-yl)-pyrimidin-4-yl]-(5-methyl-2H-pyrazol-3-yl)-amine (178 mg, 0.52 mmol) and 4-acetamidothiophenol (176 mg, 1.05 mmol) are refluxed in tert-butanol (5 mL) over 20 h. The reaction mixture is cooled to room temperature and partitioned between ethyl acetate and aqueous $NaHCO_3$. The organic layer is washed with brine, dried over $MgSO_4$ and concentrated in vacuo. The residue is purified by flash chromatography to give the desired product [2-(4-acetamidophenylsulfanyl)-6-(morpholin-4-yl)-pyrimidin-4-yl]-(5-methyl-2H-pyrazol-3-yl)-amine.

In order that the invention described herein may be more fully understood, the following examples are set forth. It should be understood that these examples are for illustrative purposes only and are not to be construed as limiting this invention in any manner.

SYNTHETIC EXAMPLES

The following HPLC methods were used in the analysis of the compounds as specified in the Synthetic Examples set forth below. As used herein, the term "R_t" refers to the retention time observed for the compound using the HPLC method specified.

HPLC-Method A:
Column: C18, 3 um, 2.1×50 mm, "Lighting" by Jones Chromatography.
Gradient: 100% water (containing 1% acetonitrile, 0.1% TFA) to 100% acetonitrile (containing 0.1% TFA) over 4.0 min, hold at 100% acetonitrile for 1.4 min and return to initial conditions. Total run time 7.0 min. Flow rate: 0.8 mL/min.

HPLC-Method B:
Column: C18, 5 um, 4.6×150 mm "Dynamax" by Rainin
Gradient: 100% water (containing 1% acetonitrile, 0.1% TFA) to 100% acetonitrile (containing 0.1% TFA) over 20 min, hold at 100% acetonitrile for 7.0 min. and return to initial conditions. Total run time 31.5 min. Flow rate: 1.0 mL/min.

HPLC-Method C:
Column: Cyano, 5 um, 4.6×150 mm "Microsorb" by Varian.
Gradient: 99% water (0.1% TFA), 1% acetonitrile (containing. 0.1% TFA) to 50% water (0.1% TFA), 50% acetonitrile (containing 0.1% TFA) over 20 min, hold for 8.0 min and return to initial conditions. Total run time 30 min. Flow rate: 1.0 mL/min.

HPLC-Method D:
Column: Waters (YMC) ODS-AQ 2.0×50 mm, S5, 120A.
Gradient: 90% water (0.2% Formic acid), 10% acetonitrile (containing 0.1% Formic acid) to 10% water (0.1% formic acid), 90% acetonitrile (containing 0.1% formic acid) over 5.0 min, hold for 0.8 min and return to initial conditions. Total run time 7.0 min.
Flow rate: 1.0 mL/min.

HPLC Method E:
Column: 50×2.0 mm Hypersil C18 BDS; 5 μm
Gradient: elution 100% water (0.1% TFA), to 5% water (0.1% TFA), 95% acetonitrile (containing 0.1% TFA) over 2.1 min, returning to initial conditions after 2.3 min.
Flow rate: 1 mL/min.

Example 1

(5-Methyl-2H-pyrazol-3-yl)-(2-phenylsulfanyl-quinazolin-4-yl)-amine (IIa-1): Prepared in a manner similar to the above described Method E to afford a pale yellow solid, mp >300° C. (dec.); $^1$H NMR (DMSO) δ 2.07(3H, s), 5.54(1H, s), 7.38(1H, m), 7.56–7.45(4H, m), 7.65(2H, m), 7.73 (1H, m), 8.55(1H, d), 10.43(1H, s), 12.05(1H, br s); IR (solid) 3259, 3170, 3109, 1618, 1594, 1565, 1525, 1476; MS 334.0 (M+H)$^+$ Example 2

[2-(4-Chlorophenylsulfanyl)-quinazolin-4-yl]-(5-methyl-2H-pyrazol-3-yl)-amine (IIa-2): Prepared in a manner similar to the above described Method E to afford a pale yellow solid, mp 259–260° C.; $^1$H NMR (DMSO) δ 2.12 (3H, s), 5.40 (1H, s), 7.60 (1H, t), 7.64 (2H, d), 7.76 (3H, d), 7.92 (1H, t), 8.70 (1H, d)11.50 (1H, br s); IR (solid) 1627, 1606, 1557, 1484, 1473, 1433, 1400, 1339, 1286, 1219; MS 368.0 (M+H)$^+$ Example 3

[2-(2,4-Dichlorophenylsulfanyl)-quinazolin-4-yl]-(5-methyl-2H-pyrazol-3-yl)-amine (IIa-3): Prepared in a manner similar to the above described Method E to afford a pale yellow solid, mp 258–259° C.; $^1$H NMR (DMSO) δ 2.12 (3H, s), 5.40 (1H, s), 7.54 (1H, t), 7.63 (1H, m), 7.68 (1H, d), 7.86 (1H, t), 7.92 (1H, d), 7.96 (1H, d), 8.66 (1H, d) 11.20 (1H, br s); IR (solid) 1623, 1610, 1551, 1488, 1435, 1410, 1339, 1284, 1217; MS 402.0 (M+H)$^+$ Example 4

[2-(4-Methoxyphenylsulfanyl)-quinazolin-4-yl]-(5-methyl-2H-pyrazol-3-yl)-amine (IIa-4): Prepared in a manner similar to the above described Method E to afford a pale yellow solid, mp 264–268° C.;$^1$H NMR (DMSO) δ 2.04 (3H, s), 3.85 (3H, s), 5.43 (1H, s), 7.12 (2H, d), 7.53 (1H, t), 7.61 (3H, d), 7.84 (3H, t), 8.63 (1H, d), 11.09 (1H, br s), 12.30 (1H, br s); IR (solid) 1622, 1598, 1552, 1492, 1404, 1340, 1292, 1249, 1219, 1171, 1161; MS 364.1 (M+H)$^+$ Example 5

[2-(2-Ethylphenylsulfanyl)-quinazolin-4-yl]-(5-methyl-2H-pyrazol-3-yl)-amine (IIa-5): Prepared in a manner similar to the above described Method E to afford a pale yellow solid, mp 205–208° C.; $^1$H NMR (DMSO) δ 2.05 (3H, s), 5.19 (1H, s), 7.38 (1H, t), 7.52–7.64 (3H, m), 7.68 (2H, d), 7.90 (1H, t), 8.68 (1H, d); IR (solid) 3262, 2967, 1632, 1605, 1558, 1492, 1434, 1403, 1344, 1294, 1224, 1162; MS 362.1 (M+H)$^+$ Example 6

{2-[2,4-Bis(trifluoromethyl)phenylsulfanyl]-quinazolin-4-yl}-(5-methyl-2H-pyrazol-3-yl)-amine (IIa-6): Prepared in a manner similar to the above described Method E to afford a pale yellow solid, mp >300° C.; $^1$H NMR (DMSO) δ 1.98 (3H, s), 5.37 (1H, s), 7.50 (1H, t), 7.59 (2H, d), 7.84 (1H, d), 8.32 (1H, s), 8.40 (2H, s), 8.66 (1H, d), 10.73 (1H, br s); IR (solid) 1628, 1603, 1577, 1548, 1512, 1493, 1448, 1417, 1354, 1275, 1196, 1124; MS 470.1 (M+H)$^+$ Example 7

[2-(2-(3-Chlorophenylsulfanyl)-quinazolin-4-yl]-(5-methyl-2H-pyrazol-3-yl)-amine (IIa-7): Prepared in a manner similar to the above described Method E to afford a pale yellow solid, mp 262–263° C.; $^1$H NMR (DMSO) δ 2.05 (3H, s), 5.35 (1H, s), 7.52 (2H, t), 7.65 (2H, m), 7.74 (1H, d), 7.83 (1H, t), 7.88 (1H, d), 8.62 (1H, d), 10.97 (1H, br s); IR (solid) 1621, 1603, 1569, 1544, 1491, 1448, 1400, 1376, 1336, 1288, 1208; MS 368.0 (M+H)$^+$ Example 8

[2-(2,3-Dichlorophenylsulfanyl)-quinazolin-4-yl]-(5-methyl-2H-pyrazol-3-yl)-amine (IIa-8): Prepared in a manner similar to the above described Method E to afford a pale yellow solid, mp >300° C.; $^1$H NMR (DMSO) δ 2.05 (3H, s), 5.34 (1H, s), 7.50 (2H, m), 7.60 (1H, d), 7.75 (1H, t), 7.88 (2H, m), 8.62 (1H, d), 10.72 (1H, br s); IR (solid) 1632, 1609, 1561, 1532, 1492, 1432, 1400, 1380, 1345, 1298, 1228, 1162, 1125; MS 402.0 (M+H)$^+$ Example 9

[2-(3-Chlorophenylsulfanyl)-quinazolin-4-yl]-(5-methyl-2H-pyrazol-3-yl)-amine (IIa-9): Prepared in a manner similar to the above described Method E to afford a pale yellow solid, mp 248–249° C.; ¹H NMR (DMSO) δ 2.05 (3H, s), 5.42 (1H, 3), 7.55 (2H, m), 7.66 (3H, m), 7.81 (1H, s), 7.85 (1H, t), 8.62 (1H, d), 11.10 (1H, br s); IR (solid) 1628, 1611, 1551, 1487, 1432, 1410, 1341, 1292, 1217, 1165; MS 368.0 (M+H)⁺

Example 10

[2-(1-Methylimidazol-2-ylsulfanyl)-quinazolin-4-yl]-(5-methyl-2H-pyrazol-3-yl)-amine (IIa-10): Prepared in a manner similar to the above described Method E to afford an off white solid, mp 255–256° C.; ¹H NMR (DMSO) δ 2.19 (3H, s), 3.59 (1H, s), 5.51 (1H, s), 7.18 (1H, s), 7.45 (1H, t), 7.57 (1H, s), 7.59 (1H, d), 7.77 (1H, t), 8.57 (1H, d), 10.57 (1H, s), 12.13 (1H, br s ); IR (solid) 1628, 1565, 1550, 1532, 1492, 1430, 1376, 1333, 1292, 1278, 1211; MS 338.2 (M+H)⁺

Example 11

[2-(2-Hydroxyphenylsulfanyl)-quinazolin-4-yl]-(5-methyl-2H-pyrazol-3-yl)-amine (IIa-11): Prepared in a manner similar to the above described Method E to afford a pale yellow solid, mp 273–275° C.; ¹H NMR (DMSO) δ 2.06 (3H, s), 5.4.1 (1H, s), 6.99 (1H, t), 7.07 (1H, d), 7.50 (1H, t), 7.57–7.62 (2H, m), 7.73 (1H, d), 7.94 (1H, t), 8.71 (1H, d), 10.29 (1H, br s), 11.66 (1H, br s); IR (solid) 1623, 1597, 1552, 1485, 1442, 1404, 1354, 1341, 1289, 1221, 1165; MS 350.1 (M+H)⁺

Example 12

[2-(2,4-Difluorophenylsulfanyl)-quinazolin-4-yl]-(5-methyl-2H-pyrazol-3-yl)-amine (IIa-12): Prepared in a manner similar to the above described Method E to afford a pale yellow solid, mp 256–258° C.; ¹H NMR (DMSO) 2.10 (3H, s), 5.41 (1H, s), 7.33 (1H, t), 7.51–7.58 (2H, m), 7.65.(1H, d), 7.82–7.91 (2H, m), 8.63 (1H, d), 11.06 (1H, br s); IR (solid) 1626, 1608, 1556, 1482, 1409, 1341, 1288; 1270, 1219, 1162, 1140; MS 370.1 (M+H)⁺

Example 13

[2-(3,4-Dimethoxyphenylsulfanyl)-quinazolin-4-yl]-(5-methyl-2H-pyrazol-3-yl)-amine (IIa-13): Prepared in a manner similar to the above described Method E to afford a pale yellow solid, mp 229–232° C.; ¹H NMR (DMSO) δ 2.05 (3H, s), 3.70 (3H, s), 3.85 (3H, s), 5.39 (1H, s), 6.95 (1H, d), 7.30 (2H, d), 7.60 (1H, t), 7.77 (1H, d), 7.94 (1H, t), 8.72 (1H, d), 11.66 (1H, br s); IR (solid) 1625, 1607, 1551, 1503, 1436, 1404, 1342, 1290, 1254, 1237, 1218, 1161, 1137, MS 394.1 (M+H)⁺

Example 14

[2-(3-Methylphenylsulfanyl)-quinazolin-4-yl]-(5-methyl-2H-pyrazol-3-yl)-amine (IIa-14): Prepared in a manner similar to the above described Method E to afford a pale yellow solid, mp 249–250° C.; ¹H NMR (DMSO) δ 2.06 (3H, s), 2.36 (3H, s), 5.31 (1H, s), 7.45 (2H, d), 7.48–7.58 (3H, m), 7.61 (1H, d), 7.88 (1H, t), 8.68 (1H, d), 11.66 (1H, br s); IR (solid) 1617, 1587, 1558, 1496, 14414, 1387, 1341, 1283, 1221, 1162, 1140; MS 348.1 (M+H)⁺

Example 15

[2-(2-Methoxyphenylsulfanyl)-quinazolin-4-yl-(5-methyl-2H-pyrazol-3-yl)-amine (IIa-15): Prepared in a manner similar to the above described Method E to afford a pale yellow solid, mp 237–239° C.; ¹H NMR (DMSO) δ 2.07 (3H, s), 3.71 (3H, s), 5.35 (1H, s), 7.12 (1H, t), 7.23 (1H, d), 7.55 (1H, t), 7.60–7.67 (3H, m), 7.87 (1H, t), 8.66 (1H, d), 11.20 (1H, br s); IR (solid) 1632, 1606, 1561, 1480, 1430, 1405, 1344, 1292, 1276, 1251, 1224; MS 364.1 (M+H)⁺

Example 16

[2-(2-Naphthalenylsulfanyl)-quinazolin-4-yl]-(5-methyl-2H-pyrazol-3-yl)-amine (IIa-16): Prepared in a manner similar to the above described Method E to afford a pale yellow solid, mp 267–270° C.; ¹H NMR (DMSO) δ 2.05 (3H, s), 5.09 (1H, s), 7.57 (1H, t), 7.62–7.75 (4H, m), 7.90 (1H, t), 8.07 (3H, t), 8.40 (1H, s), 8.66 (1H, d), 11.28 (1H, br s); IR (solid) 1624, 1606, 1550, 1487, 1435, 1407, 1341, 1285, 1216, 1158; MS 384.1.(M+H)⁺

Example 17

[2-(2,6-Dichlorophenylsulfanyl)-quinazolin-4-yl]-(5-methyl-2H-pyrazol-3-yl)-amine. (IIa-17): Prepared in a manner similar to the above described Method E to afford a pale brown solid, mp >300° C.; ¹H NMR (DMSO) δ 2.11 (3H, s), 5.49 (1H, s), 7.49 (1H, t), 7.59–7.67 (2H, m), 7.76 (2H, d), 7.81 (1H, d), 8.60 (1H, d), 10.60 (1H, s); IR (solid) 1618, 1599, 1565, 1533, 1486, 1424, 1401, 1361, 1344, 1285, 1246, 1216, 1188, 1172; MS 402.0 (M+H)⁺

Example 18

[2-(3,4-Dichlorophenylsulfanyl)-quinazolin-4-yl]-(5-methyl-2H-pyrazol-3-yl)-amine (IIa-18): Prepared in a manner similar to the above described Method E to afford a pale yellow solid, mp 268–272° C.; ¹H NMR (DMSO) δ 2.11 (3H, s), 5.47 (1H, s), 7.56 (1H, t), 7.68–7.72 (2H, m), 7.83 (2H, d), 7.88 (1H, t), 8.05 (1H, d), 8.66 (1H, d); IR (solid) 1628, 1607, 1556, 1488, 1436, 14412, 1399, 1367, 1341, 1288, 1216, 1166; MS 402.0 (M+H)⁺

Example 19

[2-(Benzimidazol-2-ylsulfanyl)-quinazolin-4-yl]-(5-methyl-2H-pyrazol-3-yl)-amine (IIa-19): Prepared in a manner similar to the above described Method E to afford a pale grey solid, mp 192–196° C.; ¹H NMR (DMSO) δ 1.60 (3H, s), 5.48 (1H, s), 7.44 (2H, m), 7.53 (1H, t), 7.69 (2H, d), 7.76 (2H, m), 7.85 (1H, t), 8.64 (1H, d), 10.79 (1H, s); IR (solid) 1618, 1606, 1569, 1537, 1487, 1411, 1395, 1369, 1343, 1288, 1273, 1170; MS 374.1 (M+H)⁺

Example 20

[2-(2-Aminophenylsulfanyl)-quinazolin-4-yl]-(5-methyl-2H-pyrazol-3-yl)-amino (IIa-20): Prepared in a manner similar to the above described Method E to afford a bright yellow solid, mp 257–259° C.; ¹H NMR (DMSO) δ 2.11–2.30 (3H, 2×br s), 6.10 (1H, br s), 7.10–7.80 (7H, m), 8.60 (1H, br s), 9.80 (1H, br s), 10.80 (1H, br s); IR (solid) 1623, 1591, 1567, 1538, 1496, 1483, 1410, 1351

Example 21

(5-Cyclopropyl-2H-pyrazol-3-yl)-(2-phenylsulfanyl-quinazolin-4-yl)-amine (IIa-21): Prepared in a manner similar to the above described Method E to afford a yellow solid, mp 233–236° C.; $^1$H NMR (DMSO) δ 0.89 (2H, d), 0.98 (2H, d), 1.67 (1H, m), 5.48 (1H, s), 7.54–7.73 (7H, m), 7.89 (1H, t), 8.68 (1H, d), 11.60 (1H, br s); IR (solid) 1629, 1606, 1577, 1546, 1509, 1484, 1438, 1413, 1370, 1291, 1219; MS 360.3 (M+H)$^+$ Example 22

(5-Cyclopropyl-2H-pyrazol-3-yl)-[2-(3-methoxycarbonylphenylsulfanyl)-quinazolin-4-yl]-amine (IIa-22): Prepared in a manner similar to the above described Method E to afford a white solid, mp 224–225° C.; $^1$H NMR (DMSO) δ 0.52 (2H, m), 0.86 (2H, m), 1.67 (1H, m), 3.86 (3H, s), 5.60 (1H, s), 7.45 (1H, t), 7.56 (1H, d), 7.66 (1H, t), 7.76 (1H, t), 7.93 (1H, d), 8.10 (1H, d), 8.18 (1H, s), 8.57 (1H, d), 10.48 (1H, br s), 12.01 (1H, br s); IR (solid) 1724, 1617, 1593, 1567, 1526, 1478, 1432, 1400, 1361, 1343, 1283, 1260, 1218, 1169, 1128; MS 418.3 (M+H)$^+$ Example 23

(5-Cyclopropyl-2H-pyrazol-3-yl)-[2-(3-methylphenylsulfanyl)-quinazolin-4-yl]-amine (IIa-23): Prepared in a manner similar to the above described Method E to afford a white solid, mp 241–243° C.; $^1$H NMR (DMSO) δ 0.55–0.63 (2H, m), 1.87–1.97 (1H, m), 1.67–1.79 (1H, m), 2.35 (3H, s), 5.72 (1H, s), 7.30–7.60 (6H, m), 7.68–7.78 (1H,m), 8.50–8.60 (1H, d), 10.38 (1H, s), 12.02 (1H, s); IR (solid) 1617, 1594, 1568, 1529, 1480, 1401, 1344, 1287, 1176, 758, 665,656; MS (M+H)$^+$ Example 24

(5-Cyclopropyl-2H-pyrazol-3-yl)-[2-(3-methoxyphenylsulfanyl)-quinazolin-4-yl]-amine (IIa-24): Prepared in a manner similar to the above described Method E to afford a white solid, mp 232–234° C.; $^1$H NMR (DMSO) δ 0.55–0.62 (2H, m), 0.88–0.97 (2H, m), 1.70–1.80 (1H, m), 3.79 (3H, s), 5.79 (1H, s), 7.08 (1H, d), 7.22–7.29 (2H, m), 7.40–7.50 (2H, m), 7.60 (1H, d), 7.79 (1H, t), 8.57 (1H, d), 10.40 (1H, s), 12.04 (1H, s); IR (solid) 3100, 1618, 1592, 1567, 1527, 1477, 1402, 1345, 1284, 1246, 1231, 1171, 1041, 1,001, 969, 826, 761, 692, 667; MS (M+H)$^+$ Example 25

(5-Cyclopropyl-2H-pyrazol-3-yl)-[2-(3,4-dimethoxyphenylsulfanyl)-quinazolin-4-yl]-amine (IIa-25): Prepared in a manner similar to the above described Method E to afford a white solid, mp 250–252° C.; $^1$H NMR (DMSO) δ 0.54–0.60 (2H, m), 0.83–0.91 (2H, m), 1.68–1.77 (1H, m), 3.79 (3H, s), 3.85 (3H, s), 5.79 (1H, s), 7.10 (1H, d), 7.20–7.26 (2H, m), 7.45 (1H, t), 7.57 (1H, d), 7.77 (1H, t), 8.55 (1H, d), 10.45 (1H, s),: 12.04 (1H, m); IR (solid) 1617, 1593, 1567, 1530, 1504, 1479, 1457, 1439, 1398, 1364, 1347, 1288, 1269, 1250, 1232, 1181, 1169, 1138, 1037, 1020, 997, 972, 882, 846, 804, 764, 750; MS (M+H)$^+$ Example 26

[2-(3-Carboxyphenylsulfanyl)-quinazolin-4-yl]-(5-cyclopropyl-2H-pyrazol-3-yl)-amine (IIa-26): Prepared from IIa-22 according to Method G to afford a yellow solid, mp >300° C.; $^1$H NMR (DMSO) δ 0.53 (2H, d), 0.86 (2H, d), 1.65 (1H, m), 5.37 (1H, s), 7.55 (1H, t), 7.68 (1H, t), 7.81 (1H, d), 7.88 (1H, t), 7.95 (1H, d), 8.15 (1H, d), 8.15 (1H, s), 8.71 (1H, d), 11.32 (1H, br s); IR (solid) 1702, 1626, 1609, 1559, 1490, 1412, 1355, 1293, 1222, 1170; MS 404.7 (M+H)$^+$ Example 27

(5-Cyclopropyl-2H-pyrazol-3-yl)-[2-(naphtalen-2-ylsulfanyl)-quinazolin-4-yl]-amine (IIa-27): Prepared in a manner similar to the above described Method E to afford an off white solid, mp 285–288° C.; $^1$H NMR (DMSO) δ 0.25 (2H, br s), 0.52 (2H, br s), 0.87 (1H, m), 5.54 (1H, br s), 7.42–7.77 (4H, m), 8.00 (3H, m), 8.30 (1H, br s), 8.56 (1H, br d), 10.42 and 11.88 (1H, 2×br s); IR (solid) 1615, 1592, 1562, 1527, 1476, 1398, 1366, 1287, 1240, 1216, 1167, 1158, 1142, 1128, 996, 965; MS 4 410.7 (M+H)$^+$ Example 28

(5-Cyclopropyl-2H-pyrazol-3-yl)-[2-(2,4-difluorophenylsulfanyl)-quinazolin-4-yl]-amine (IIa-28): Prepared in a manner similar to the above described Method E to afford an off-white solid, mp 250–253° C.; $^1$H NMR (DMSO) δ 0.61 (2H, m), 0.91 (2H, m), 1.74 (1H, m), 5.67 (1H, m), 7.24–7.28 (1H, m), 7.44–7.48 (3H, m), 7.53–7.81 (2H, brm), 8.55 (1H, m), 10.47 and 12.10 (1H, 2×br s); IR (solid) 1614, 1598, 1565, 1525, 1479, 1423, 1398, 1366, 1345, 1285, 1267, 1243, 1213, 1168, 1143, 1114, 1026, 995, 968; MS 396.6 (M+H)$^+$ Example 29

(5-Cyclopropyl-2H-pyrazol-3-yl)-[2-(naphthal n-2-ylsulfanyl)-5,6,7,8-tetrahydroquinazolin-4-yl]-amine (IIa-29) Prepared in a manner similar to the above described Method F to afford a white solid, mp 244° C.; $^1$H NMR (DMSO) δ 0.13 (2H,s), 0.45 (2H,s), 0.79 (1H, s), 1.73 (4H, s), 2.42 (2H, s), 2.58 (2H, s), 5.28 (1H, s), 7.58 (2H, d), 7.61 (2H, d), 7.97 (3H, d), 8.23 (1H, s), 8.56 (1H, s), 11.63 (1H, s); IR (solid) 1594, 1561, 1514, 1477, 1423, 1333, 1279, 1251, 990, 808, 744, 657, 651; MS 414.7 (M+H)$^+$ Example 30

(5-Cyclopropyl-2H-pyrazol-3-yl)-[2-(2,3-dichlorophenylsulfanyl)-quinazolin-4-yl]-amine (IIa-30): Prepared in a manner similar to the above described Method E to afford an off-white solid, mp 250–252° C.; $^1$H NMR (DMSO) δ 0.60. (2H, d), 0.93 (2H, d), 1.70 (1H, m), 5.54 (1H, s), 7.47 (2H, m), 7.57 (1H, d), 7.76 (1H, t), 7.86 (2H, d), 8.57 (1H, d), 10.48 (1H, s), 12.04 (1H, s); IR (solid) 1616, 1601, 1570, 1528, 1486, 1432, 1400, 1367, 1335, 1285, 1246, 1210, 1159, 1146, 1051, 1033, 1021, 997; MS 428.6(M+H)$^+$ Example 31

[2-(3-Chlorophenylsulfanyl)-quinazolin-4-yl]-(5-cyclopropyl-2H-pyrazol-3-yl)-amine (IIa-31): Prepared in a manner similar to the above described Method E to afford an off-white solid, mp 235–238° C.; $^1$H NMR (DMSO) δ 0.58 (2H, d), 0.92 (2H, d), 1.75 (1H, m), 5.71 (1H, s), 7.44 (1H, t), 7.50–7.63 (4H, m), 7.73 (1H, s), 7.75 (1H, t), 8.57 (1H, d), 10.46 (1H, s), 12.08 (1H, s); IR (solid) 1616, 1593, 1562, 1528, 1479, 1456, 1406, 1367, 1343, 1286, 1244, 1216, 1176, 1067, 1051, 997; MS 394.7(M+H)$^+$

Example 32

[2-(2-Chlorophenylsulfanyl)-quinazolin-4-yl]-(5-cyclopropyl-2H-pyrazol-3-yl)-amine (IIa-32): Prepared in a manner similar to the above described Method E to afford an off-white solid, mp 255–257° C.; $^1$H NMR (DMSO) δ 0.59 (2H, d), 0.91 (2H, d), 1.71 (1H, m), 5.62 (1H, s), 7.45 (2H, m), 7.57 (1H, m), 7.69 (1H, d), 7.75 (1H, t), 7.85 (1H, d), 8.56 (1H, d), 10.43 (1H, s), 12.03 (1H, s); IR (solid) 1619, 1596, 1564, 1529, 1480, 1446, 1398, 1370, 1343, 1289, 1246, 1218, 1165, 1148, 1089, 1054, 1030, 997; MS 394.7 (M+H)$^+$

Example 33

(5-Cyclopropyl-2H-pyrazol-3-yl)-[2-(3,4-dimethylphenylsulfanyl)-qinazolin-4-yl]-amine (IIa-33): Prepared in a manner similar to the above described Method E to afford an off-white solid, mp 255–256° C.; $^1$H NMR (DMSO) δ 0.56 (2H, m), 0.90 (2H, m), 1.67 (1H, m), 2.26 and 2.29 (6H, 2×s), 5.75 (1H, br s), 7.26 (1H, m), 7.35–7.55 (4H, m), 7.74 (1H, m), 8.54 (1H, br s), 10.44 and 12.06 (2H, 2×br s); IR (solid) 1617, 1596, 1569, 1526, 1479, 1459, 1404, 1366, 1343, 1287, 1243, 1218, 1167, 1145, 1017, 996, 966; MS 388.33(M+H)$^+$

Example 34

[2-(Benzimidazol-2-ylsulfanyl)-quinazolin-4-yl]-(5-cyclopropyl-2H-pyrazol-3-yl)-amine (IIa-34): Prepared in a manner similar to the above described Method E to afford an off-white solid, mp 201–203° C.; $^1$H NMR (DMSO) δ 0.44 (2H, m), 0.71 (2H, m), 1.17 (1H, m), 5.72 (1H, m), 7.23 (2H, m), 7.51–7.81 (5H, m), 85.9 (1H, m), 10.59, 12.06 and 13.17 (3H, 3×br s); IR (solid) 1617, 1601, 1572, 1532, 1485, 1402, 1374, 1341, 1290, 1273, 1209, 1168, 1024, 1010, 965; MS 400.2(M+H)$^+$

Example 35

(5-Cyclopropyl-2H-pyrazol-3-yl)-2-(4-methoxycarbonylphenylsulfanyl)-quinazolin-4-yl]-amine (IIa-35): Prepared in a manner similar to the above described Method E to afford an off-white solid, mp 245–246° C.; $^1$H NMR (DMSO) δ 0.47 (2H, br s), 0.80 (2H, br s), 1.62 (1H, m), 3.85 (3H, s), 5.69 (1H, br s), 7.46 (1H, m), 7.58 (1H, m), 7.76–7.81 (3H, m), 8.02–8.05 (2H, m), 8.57 (1H, m), 10.48 and 12.11 (2H, 2×br s); IR (solid) 1721, 1712, 1616, 1596, 1572, 1564, 1523, 1481, 1435, 1404, 1360, 1346, 1277, 1181, 1114, 1106, 996, 971; MS 418.2(M+H)$^+$

Example 36

[2-(4-Acetamido-phenylsulfanyl)-quinazolin-4-yl]-(5-cyclopropyl-2H-pyrazol-3-yl)-amine (IIa-36): Prepared in a manner similar to the above described Method E to afford an off-white solid, mp 239–241° C.; $^1$H NMR (DMSO) δ 0.57 (2H, m), 0.83 (2H, m), 1.69 (1H, m), 2.02 (3H, s), 5.73 (1H, br s), 7.41 (1H, m), 7.53–7.57 (3H, m), 7.73–7.75 (3H, m), 8.54 (1H, m), 10.18, 10.39 and 11.98 (3H, 3×br s); IR (solid) 1665, 1618, 1607, 1586, 1572, 1564, 1529, 1482, 1387, 1343, 1320, 1287, 1243, 1221, 1162, 1005, 968; MS 417.2 (M+H)$^+$

Example 37

(5-Cyclopropyl-2H-pyrazol-3-yl)-[2-(naphthalen-1-ylsulfanyl)-quinazolin-4-yl]-amine (IIa-37): Prepared in a manner similar to the above described Method E to afford an off-white solid, mp 271–273° C.; $^1$H NMR (DMSO) δ 0.46–0.47 (2H, m), 0.87–0.89 (2H, m), 1.57 (1H, m), 5.01 (1H, m), 7.42 (1H, m), 7.52–7.54 (3H, m), 7.64 (1H, m), 7.75 (1H, m), 7.98 (1H, m), 8.06 (1H, m), 8.17 (1H, m), 8.28 (1H, m), 8.50 (1H, m), 10.29 (1H, br s), 11.84 (1H, br s); IR (solid) 1615, 1592, 1567, 1528, 1483, 1401, 1362, 1343, 1285, 1242, 1219, 1173, 998, 963; MS 410.2(M+H)$^+$

Example 38

[2-(4-Acetamidophenylsulfanyl)-quinazolin-4-yl]-(5-methyl-2H-pyrazol-3-yl)-amine (IIa-38): Prepared in a manner similar to the above described Method E to afford an white solid, mp 268–271° C.; $^1$H NMR (DMSO) δ 2.02 (3H, s), 2.09 (3H, s), 5.56 (1H, s), 7.40 (1H, t), 7.55 (3H, m), 7.75 (3H, d), 8.55 (1H, d), 10.21 (1H, s), 10.40 (1H, s), 12.03 (1H, s); IR (solid) 1662, 1620, 1599, 1572, 1531, 1438, 1397, 1370, 1358, 1341, 1323, 1312, 1278, 1265, 1245, 1216, 1161, 1006, 966; MS 391.2(M+H)$^+$

Example 39

[2-(4-Methanesulfonylamino-phenylsulfanyl)-quinazolin-4-yl]-(5-methyl-2H-pyrazol-3-yl)-amine (IIa-39): Prepared in a manner similar to the above described Method E to afford an off-white solid, mp 219–222° C.; $^1$H NMR (DMSO) δ 2.15 (3H, s), 2.61 (3H, s), 5.84. (1H, s), 6.91 (2H, d), 7.22 (2H, d), 7.36 (1H, s), 7.52 (1H, d), 7.69 (1H, s), 8.53 (1H, d), 10.31 (1H, s), 11.96 (1H, s); IR (solid) 1621, 1602, 1584, 1567, 1528, 1486, 1351, 1287, 1253, 1207, 1179, 1102, 1091, 983; MS 427.0(M+H)$^+$

Example 40

[2-(4-Acetamidophenylsulfanyl)-7-methoxy-quinazolin-4-yl]-(5-methyl-2H-pyrazol-3-yl)-amine (IIa-40): Prepared in a manner similar to the above described Method E to afford a white solid, mp 291–293° C; $^1$H NMR (DMSO) δ 2.01 (3H, s), 2.09 (3H, s), 3.87 (3H, s), 5.55 (1H, s), 6.96 (1H, s), 6.99 (1H, d), 7.55 (2H, d), 7.73 (2H, d), 8.45 (1H, d), 10.21 (1H, s), 10.23 (1H, s), 11.99 (1H, s); IR (solid); MS 421.2(M+H)$^+$

Example 41

[2-(4-Acetamidophenylsulfanyl)-8-(3-morpholin-4-yl-propoxy)-quinazolin-4-yl]-(5-methyl-2H-pyrazol-3-yl)-amine (IIa-41): Prepared in a manner similar to the above described Method E to afford a white solid, mp 262–264° C.; $^1$H NMR (DMSO) δ 1.94 (2H, quint.), 2.03 (3H, s), 2.09 (3H, s), 2.38 (4H, s), 2.45 (2H, t), 3.58 (4H, s), 4.11 (2H, t), 5.60 (1H, s), 7.24 (1H, d), 7.30 (1H, t), 7.57 (2H, d), 7.73 (2H, d), 8.07 (1H, d) 10.20 (1H, s), 10.24 (1H, s), 12.02 (1H, br s); IR (solid) 3245, 3045, 2954, 2918, 2845, 1663, 1609, 1586, 1527, 1468, 1391, 1332, 1268, 1254, 1159, 1136, 1114, 1054, 995, 823; MS 534.4(M+H)$^+$

Example 42

[2-(4-Methoxycarbonylphenylsulfanyl)-quinazolin-4-yl]-(5-methyl-2H-pyrazol-3-yl)-amine (IIa-42): Prepared in a manner similar to the above described Method E to afford an off-white solid, mp 257–260° C.; $^1$H NMR (DMSO) δ 1.95 (3H, s), 3.89 (3H, s), 5.51 (1H, br s), 7.39 (1H, br s), 7.51

(1H, br s), 7.70 (1H, br s), 7.81 (2H, d), 8.04 (2H, d), 8.51 (1H, br s), 10.48 (1H, br s), 12.03 (1H, br s); IR (solid) 1718, 1618, 1599, 1568, 1531, 1481, 1434, 1395, 1362, 1342, 1286, 1247, 1216, 1156, 1116, 1018, 1003, 968; MS 392.2 $(M+H)^+$

Example 43

[2-(4-Carboxyphenylsulfanyl)-quinazolin-4-yl]-(5-methyl-2H-pyrazol-3-yl)-amine (IIa-43): Prepared in a manner similar to the above described Method E to afford an off-white solid, mp 263–265° C.; $^1$H NMR (DMSO) δ 1.98 (3H, s), 5.50 (1H, s), 7.46 (1H, t), 7.60 (1H, d), 7.78 (3H, m), 8.02 (2H, d), 8.58 (1H, d), 10.58 (1H, s), 12.50 (1H, br s); IR (solid) 1623, 1605, 1574, 1560, 1533, 1490, 1401, 1349, 1318, 1285, 1249, 1216, 1174, 1131, 1088, 1018; MS 378.2$(M+H)^+$

Example 44

[2-(4-Acetamidophenylsulfanyl)-8-methoxy-quinazolin-4-yl]-(5-methyl-2H-pyrazol-3-yl)-amine (IIa-44): Prepared in a manner similar to the above described Method E to afford an off-white solid, mp 247–249° C.; $^1$H NMR (DMSO) δ 1.99 (3H, s), 2.10 (3H, s), 3.93 (3H, s), 5.40 (1H, s), 7.31 (1H, d), 7.38 (1H, t), 7.57 (2H, d), 7.76 (2H, d), 8.11 (1H, d), 10.28 (1H, s), 10.61 (1H, s), 12.11 (1H, br s); IR (solid) 3234, 3052, 2938, 1673, 1618, 1591, 1536, 1481, 1459, 1390, 1372, 1345, 1317, 1267, 1249, 1158, 1058, 985, 830; MS 421.2$(M+H)^+$

Example 45

[2-(4-Acetamidophenylsulfanyl)-7-(3-morpholin-4-yl-propoxy)-quinazolin-4-yl]-(5-methyl-2H-pyrazol-3-yl)-amine (IIa-45): Prepared from IIa-74 according to Method I to afford an off-white solid, mp 153° C.(dec.); $^1$H NMR (DMSO) δ 2.02 (3H, s), 2.09 (3H, s), 2.29 (2H, quint.), 3.16 (2H, m), 3.36 (4H,m), 3.57 (4H, m), 4.11 (2H, m), 5.58 (1H, s), 7.22–7.29 (2H, m), 7.55 (2H, d), 7.76 (2H, d), 8.07 (1H, d), 10.26 (1H, br s), 10.35 (1H, s), 12.06 (1H, br s); IR (solid) 1673, 1614, 1591, 1532, 1486, 1391, 1336, 1254, 1109, 1063, 995; MS 534.2$(M+H)^+$

Example 46

[2-(4-Bromophenylsulfanyl)-quinazolin-4-yl]-(5-methyl-2H-pyrazol-3-yl)-amine (IIa-46): Prepared in a manner similar to the above described Method E to afford an off-white solid, mp >300° C.; $^1$H NMR (DMSO) δ 2.15 (3H, s), 5.63 (1H, br s), 7.44 (1H, m), 7.55–7.62 (3H, m), 7.69–7.77 (3H, m), 8.56 (1H, m), 10.47 and 12.12 (2H, 2×br s); IR (solid) 1615, 1597, 1565, 1525, 1478, 1396, 1362, 1339, 1285, 1218, 1158, 1034, 1009, 967; MS 412.1/414.1 $(M+H)^+$

Example 47

[2-(3-Bromophenylsulfanyl)-quinazolin-4-yl]-(5-methyl-2H-pyrazol-3-yl)-amine (IIa-47): Prepared in a manner similar to the above described Method E to afford an off-white solid, mp 280–281° C.; $^1$H NMR (DMSO) δ 2.12 (3H, s), 5.54 (1H, br s), 7.46 (1H, m), 7.55–7.68 (3H, m), 7.75–7.88 (3H, m), 8.81 (1H, m), 10.49 and 12.11 (2H, 2×br s); IR (solid) 1617, 1600, 1567, 1530, 1483, 1399, 1362, 1342, 1282, 1200, 1168, 1054, 1034, 1005, 967; MS 412.2/414.2$(M+H)^+$

Example 48

[2-(4-Isopropanesulfonylamino-phenylsulfanyl)-quinazolin-4-yl]-(5-methyl-2H-pyrazol-3-yl)-amine (IIa-48): Prepared in a manner similar to the above described Method E to afford a white-solid, mp 294–297° C.; $^1$H NMR (DMSO) δ 1.26 (6H, d), 2.13 (3H, s), 5.75 (1H, s), 7.34 (2H, d), 7.41 (1H, t), 7.54 (1H, d), 7.59 (2H, d), 7.73 (1H, t), 8.53 (1H, d), 10.16 (1H, s), 10.42 (1H, s), 12.07 (1H, br s); IR (solid) 1613, 1593, 1560, 1530, 1482, 1384, 1364, 1346, 1320, 1290, 1265, 1243, 1216, 1169, 1141, 1084, 1056, 1019, 999, 969, 916; MS 455.2$(M+H)^+$

Example 49

[2-(4-Isobutyrylamino-phenylsulfanyl)-quinazolin-4-yl]-(5-methyl-2H-pyrazol-3-yl)-amine (IIa-49): Prepared in a manner similar to the above described Method E to afford an off-white solid, mp 285–287° C.; $^1$H NMR (DMSO) δ 1.12–1.13 (6H, m), 1.99 (3H, s), 2.64. (1H, m), 5.52 (1H, br s), 7.41 (1H, m), 7.54–7.57 (3H, m), 7.72–7.77 (3H, m), 8.54 (1H, m), 10.12, 10.41 and 12.04 (3H, 3×br s); IR (solid) 1704, 1680, 1617, 1590, 1566, 1516, 1481, 1395, 1358, 1341, 1286, 1247, 1214, 1155, 1052, 1032, 1006, 969; MS 419.3$(M+H)^+$

Example 50

(5-Methyl-2H-pyrazol-3-yl)-[2-(4-propionylamino-phenylsulfanyl)-quinazolin-4-yl]-amine (IIa-50): Prepared in a manner similar to the above described Method E to afford an off-white solid, mp 281–282° C.; $^1$H NMR (DMSO) δ 1.11–1.13 (3H, m), 1.98 (3H, s), 2.33 (2H, m), 5.51 (1H, br s), 7.41 (1H, m), 7.55–7.57 (3H, m), 7.71–7.78 (3H, m), 8.54 (1H, m), 10.11, 10.41 and 12.04 (3H, 3×br s); IR (solid) 1654, 1621, 1599, 1571, 1527, 1476, 1398, 1358, 1341, 1286, 1244, 1216, 1155, 1006, 969; MS 405.3$(M+H)^+$

Example 51

[2-(4-cyclopropanecarbonylamino-phenylsulfanyl)-quinazolin-4-yl]-(5-methyl-2H-pyrazol-3-yl)-amine (IIa-51): Prepared in a manner similar to the above described Method E to afford an off-white solid, mp 300–303° C.; $^1$H NMR (DMSO) δ 0.82–0.84 (4H, m), 1.83 (1H, m), 2.01 (3H, s), 5.55 (1H, br s), 7.39–7.41 (2H, m), 7.53–7.57 (2H, m), 7.72–7.77 (2H, m), 8.53–8.55 (2H, m), 10.40, 10.46 and 12.03 (3H, 3×br s); IR (solid) 1664, 1614, 1591, 1560, 1526, 1480, 1432, 1390, 1344, 1288, 1240, 1194, 1177, 1152, 997; MS 417.2$(M+H)^+$

Example 52

[2-(4-Acetamido-phenylsulfanyl)-8-hydroxyquinazolin-4-yl]-(5-methyl-2H-pyrazol-3-yl)-amine (IIa-52): tan solid, mp 258–259° C.; $^1$H NMR (DMSO) δ 1.99 (3H, s), 2.09 (3H, s), 5.45 (1H, s), 7.10 (1H, d), 7.22 (1H, t), 7.57 (2H, d), 7.75 (2H, d), 7.95 (1H, d), 9.35 (1H, s), 10.22 (1H, s), 10.26 (1H, s), 12.00 (1H, br s); IR (solid) 3295, 3272, 3181, 3109, 1654, 1591, 1527, 1482, 1459, 1386, 1368, 1314, 1268, 1141, 1077, 991, 814; MS 407.2$(M+H)^+$

Example 53

[2-(4-Acetamido-phenylsulfanyl)-7-nitroquinazolin-4-yl]-(5-methyl-2H-pyrazol-3-yl)-amine (IIa-53): Prepared in a manner similar to the above described Method E to afford a yellow solid; ¹H NMR (DMSO) δ 2.02 (3H, s), 2.09 (3H, s), 5.54 (1H, s), 7.58 (2H, d), 7.75 (2H, d), 8.08 (1H, d), 8.22 (1H, s), 8.80 (1H, d), 10.24 (1H, s), 10.85 (1H, s), 12.15 (1H, s); IR (solid); MS 436.2(M+H)⁺

Example 54

(5-Methyl-2H-pyrazol-3-yl)-{2-[4-(propane-1-sulfonylamino)-phenylsulfanyl]-quinazolin-4-yl}-amine (IIa-54): Prepared in a manner similar to the above described Method E to afford a white solid, mp-272–273° C.; ¹H NMR (DMSO) δ 0.95 (3H, t), 1.71 (2H, m), 2.13 (3H,s), 3.18 (2H, t), 5.70 (1H, s), 7.31 (2H, d), 7.41 (1H, t), 7.52 (1H, d), 7.58 (1H, d), 7.73 (1H, t), 8.55 (1H, d), 10.16 (1H, s), 10.42 (1H, s), 12.07 (1H, s); IR (solid) 1615, 1594, 1563, 1530, 1481, 1389, 1362, 1346, 1325, 1291, 1245, 1147, 969; MS 455.2 (M+H)⁺

Example 55

[2-(4-Ethylsulfonylamino-phenylsulfanyl)-quinazolin-4-yl]-(5-methyl-2H-pyrazol-3-yl)-amine (IIa-55): Prepared in a manner similar to the above described Method E to afford an off-white solid, mp 279–280° C.; ¹H NMR (DMSO) δ 1.28 (3H, t), 2.19 (3H, m), 3.25 (1H, m), 5.76 (1H, s), 7.36 (2H, d), 7.48 (1H, t), 7.53 (1H, d), 7.65 (1H, d), 7.80 (1H, t), 8.61 (1H, d), 10.23 (1H, s), 10.49 (1H, s), 12.13 (1H, s); IR (solid) 1615, 1597, 1564, 1532, 1506, 1485, 1455, 1388, 1361, 1347, 1323, 1294, 1218, 1150, 1033, 1016, 998, 968, 918; MS 441.2(M+H)⁺

Example 56

[2-(4-Acetamido-phenylsulfanyl)-7-hydroxyamino-quinazolin-4-yl]-(5-methyl-2H-pyrazol-3-yl)-amine (IIa-56): Prepared from IIa-53 according to Method J to afford a yellow solid; ¹H NMR (DMSO) δ 1.97 (3H, s), 2.11 (3H, s), 5.19 (1H, s), 6.88–6.91 (2H, m), 7.65 (2H, d), 7.85 (2H, d), 8.44 (1H, d), 9.27 (1H, br s), 10.49 (1H, s), 11.38 (1H, s), 14.58 (1H, br s); IR (solid); MS 422.2(M+H)⁺

Example 57

[2-(4-Isobutanecarbonylamino-phenylsulfanyl)-quinazolin-4-yl]-(5-methyl-2H-pyrazol-3-yl)-amine (IIa-57): Prepared in a manner similar to the above described Method E to afford a white solid, mp 281–282° C.; ¹H NMR (DMSO) δ 0.95–0.97 (6H, m), 2.00 (3H, s), 2.12 (1H, m), 2.23–2.25 (2H, m), 5.56. (1H, s), 7.41 (1H, m), 7.54–7.57 (3H, m), 7.72–7.78 (3H, m), 8.54 (1H, m), 10.14, 10.41 and 12.03 (3H, 3×br s); IR (solid) 1737, 1658, 1618, 1599, 1566, 1530, 1483, 1432, 1394, 1364, 1343, 1313, 1287, 1242, 1216, 1167, 1151, 1003, 967; MS 433.2(M+H)⁺

Example 58

[2-(4-tert-Butoxycarbonylamino-phenylsulfanyl)-quinazolin-4-yl]-(5-methyl-2H-pyrazol-3-yl)-amine (IIa-58): Prepared in a manner similar to the above described Method E to afford a white solid, mp 243–246° C.; ¹H NMR (DMSO) δ 1.50 (9H, s), 1.97 (3H,s), 5.40 (1H, s), 7.07.(2H, br s), 7.36 (1H, br s), 7.47 (2H, d), 7.58 (2H, d), 8.12 (1H, br s), 9.58 (1H, s), 11.24 (1H, br s); IR (solid) 1701, 1593, 1559, 1515, 1482, 1396, 1365, 1346, 1308, 1288, 1237, 1154, 1051, 1020, 969; MS 449.2(M+H)⁺

Example 59

[2-(4-Acetamido-phenylsulfanyl)-7-aminoquinazolin-4-yl]-(5-methyl-2H-pyrazol-3-yl)-amine, (IIa-59): Prepared from IIa-53 according to Method K to afford an off-white solid, mp 264–265 ° C.; ¹H NMR (DMSO) δ 1.99 (3H, s), 2.09 (1H, s), 5.53 (1H, s), 5.97 (2H, s), 6.47 (1H, s), 6.68 (1H, d), 7.52 (2H, d), 7.71 (2H, d), 8.15 (1H, d), 9.83 (1H, br s), 10.19 (1H, s), 10.87 (1H, br s); IR (solid); MS 406.2(M+H)⁺

Example 60

(5-Methyl-2H-pyrazol-3-yl),-{2-[4-(2-morpholin-4-yl-acetylamino)-phenylsulfanyl]-quinazolin-4-yl}-amine (IIa-60): Prepared in a manner similar to the above described Method E to afford an off-white solid, mp 266–267° C.; ¹H NMR (DMSO) δ 2.03 (3H, s), 2.57 (4H, m), 3.23 (2H, s), 3.69 (4H, m), 5.58 (1 H, s), 7.40 (1H, t), 7.55–7.62 (3H, m), 7.75 (1H, t), 7.80 (2H, d), 8.54 (1H, d), 10.02 (1H, s), 10.41 (1H, s), 12.03 (1H, s); IR (solid) 1686, 1598, 1564, 1533, 1515, 1484, 1387, 1362, 1348, 1291, 1113, 868, 801, 773; MS 476.4(M+H)⁺

Example 61

(5-Cyclopropyl-2H-pyrazol-3-yl)-[2-(4-methylsulfonylamino-phenylsulfanyl)-quinazolin-4-yl]-amine (IIa-61): Prepared in a manner similar to the above described Method E to afford a white solid, mp 235–238° C.; ¹H NMR (DMSO) δ 0.61 (2H, s), 0.92 (2H, d), 1.82 (1H, br s), 2.98 (3H,s), 5.90 (1H, s), 7.23 (2H, d) 7.41 (1H, t), 7.54 (3H, m), 7.72 (1H, t), 8.55 (1H, d), 10.16 (1H, br s), 10.38 (1H, s), 11.99 (1H, s); IR (solid) 1621, 1605, 1573, 1532, 1494, 1455, 1375, 1342, 1316, 1290, 1232, 1143, 1113, 985, 972; MS 453.3(M+H)⁺

Example 62

[2-(4-Amino-phenylsulfanyl)-quinazolin-4-yl]-(5-methyl-2H-pyrazol-3-yl)-amine (IIa-62): Prepared in a manner similar to the above described Method E to afford an off-white solid, mp >300° C.; ¹H NMR (DMSO) δ 2.16 (3H, s), 5.58 (1H, s), 6.78 (2H, d), 7.36 (2H, d), 7.64 (2H, m), 7.94 (1H, t), 8.74 (1H, d), 11.82 (1H, br s); IR (solid) 1615, 1591, 1561, 1532, 1495, 1480, 1387, 1363, 1344, 1288, 1244, 1148, 966; MS 349.2(M+H)⁺

Example 63

[2-(4-Acetamido-phenylsulfanyl)-quinazolin-4-yl]-(2H-pyrazol-3-yl)-amine (IIa-63): Prepared in a manner similar to the above described Method E to afford a white solid, ¹H NMR (DMSO) δ 2.11 (3H, s), 5.93 (1H, s), 7.31–7.68 (8H, m), 8.54 (1H, s), 10.17.(1H, s), 10.54 (1H, s), 12.38 (1H, s); IR (solid); MS 377.4(M+H)⁺

Example 64

(5-Methyl-2H-pyrazol-3-yl)-{2-[4-(4-morpholin-4-yl-butyrylamino)-phenylsulfanyl]-quinazolin-4-yl}-amine (IIa-64): Prepared in a manner similar to the above described Method E to afford a white solid, mp-240–243° C.; ¹H NMR (DMSO) δ 1.77 (2H, m), 2.00 (3H, s), 2.31–2.38.(8H, m), 3.57 (4H, m), 5.54 (1H, s), 7.39–7.76 (7H, m), 8.53 (1H, br m), 10.15 (1H, s), 10.41 (1H, s), 12.00 (1H, br s); IR (solid); MS 504.3(M+H)⁺

Example 65

(5-Methyl-2H-pyrazol-3-yl)-{2-[4-(2-morpholin-4-yl-ethylcarbamoyl)-phenylsulfanyl]-quinazolin-4-yl}-amine (IIa-65): Prepared in a manner similar to the above described Method E to afford a white solid, mp 246–248° C.; $^1$H NMR (DMSO) δ 1.97 (3H, s), 2.43 (4H, br s), 3.30 (2H, s), 3.42 (2H, m), 3.58 (4H, br s), 5.52 (1H, s), 7.43 (1H, t), 7.55 (1H, d), 7.76 (3H, m), 7.97 (2H, d), 8.56 (2H, m), 10.45 (1H, s), 12.05 (1H, br s); IR (solid) 1637, 1618, 1596, 1568, 1530, 1484, 1396, 1362, 1343, 1286, 1247, 1216, 1159, 1116, 1006, 967; MS 4.90.3(M+H)$^+$

Example 66

[8-Methoxy-2-(4-methylsulfonylamino-phenylsulfanyl)-qinazolin-4-yl]-(5-methyl-2H-pyrazol-3-yl)-amine (IIa-66): Prepared in a manner similar to the above described Method E to afford an off-white solid, mp 275–277° C.; $^1$H NMR (DMSO) δ 2.10. (3H, s), 3.07 (3H, s), 3.89 (3H, s), 5.58 (1H, s), 7.24 (1H, d), 7.26–7.36 (3H, m), 7.60 (2H, d), 8.07 (1H, d), 10.13 (1H, s), 11.26 (1H, s), 12.03 (1H, s); IR (solid) 3379, 1622, 1595, 1531, 1481, 1467, 1344, 1326, 1271, 1248, 1143, 1061, 993, 975, 924, 829; MS 457.2(M+H)$^+$

Example 67

{2-[4-(2-Dimethylamino-ethylcarbamoyl)-phenylsulfanyl]-quinazolin-4-yl}-(5-methyl-2H-pyrazol-3-yl)-amine (IIa-67): Prepared in a manner similar to the above described Method E to afford a white solid, mp 192–193° C.; $^1$H NMR (DMSO) δ 1.99 (3H, s), 2.20 (6H, s), 2.42 (2H, t), 3.40 (2H, q), 5.56 (1H, s), 7.43 (1H, t), 7.57 (1H, d), 7.77 (3H, m), 7.92 (2H, d), 8.56 (2H, m), 10.44 (1H, s), 12.04 (1H, br s); IR (solid) 1650, 1618, 1593, 1561, 1525, 1481, 1419, 1395, 1361, 1337, 1287, 1247, 1214, 1165, 1004, 969; MS 448.3 (M+H)$^+$

Example 68

{2-[4-(2-Dimethylamino-acetylamino)-phenylsulfanyl]-quinazolin-4-yl}-(5-methyl-2H-pyrazol-3-yl)-amine (IIa-68): Prepared in a manner similar to the above described Method E to afford a white solid, mp 241–243° C.; $^1$H NMR (DMSO) δ 2.00 (3H, s), 2.33 (6H, s), 3.14 (2H, s), 5.60 (1H, s), 7.40 (1H, t), 7.58 (3H, m ), 7.77 (1H, t ), 7.76 (2H, d), 8.58 (1H, d), 10.04 (1H, s), 10.42 (1H, s), 11.99 (1H, s); IR (solid) 1707, 1617, 1601, 1571, 1509, 1485, 1420, 1397, 1365, 1304, 1290, 1243, 1215, 1161, 970, 847, 813, 765, 716, 683, 656; MS 434.3(M+H)$^+$

Example 69

[8-Hydroxy-2-(4-methylsulfonylamino-phenylsulfanyl)-quinazolin-4-yl]-(5-methyl-2H-pyrazol-3-yl)-amine (IIa-69): pale green solid, mp 291–293° C.; $^1$H NMR (DMSO) δ 2.10–3H, s), 3.09 (3H, s), 5.57 (1H, s), 7.11 (1H, d), 7.24 (1H, t), 7.31 (2H, d), 7.62 (2H, d), 7.96 (1H, d), 9.32 (1H, s), 10.16 (1H, s), 11.28 (1H, s), 12.02 (1H, s); IR (solid) 3256, 1596, 1531, 1460, 1392, 1317, 1334, 1296, 1267, 1146, 993, 968, 931, 824; MS 443.2(M+H)$^+$

Example 70

{2-[4-(3-Dimethylamino-propylcarbamoyl)-phenylsulfanyl]-quinazolin-4-yl}-(5-methyl-2H-pyrazol-3-yl)-amine (IIa-70): Prepared in a manner similar to the above described Method E to afford a pink solid, mp 210–213° C.; $^1$H NMR (DMSO) δ 1.48 (2H, m), 2.01 (3H, s), 2.24 (6H,s), 2.38 (2H, br s), 2.93 (2H, s), 5.57 (1H, 5), 7.48 (1H, t), 7.62 (1H, d), 7.80 (3H, m), 8.02 (2H, d), 8.61 (1H, d) 8.74 (1H, s), 10.50 (1H, s), 12.15 (1H, br s); IR (solid) 1682, 1618, 1595, 1567, 1528, 1484, 1400, 1361, 134, 1285, 1247, 1219, 1172, 1084, 1006, 969; MS 462.3(M+H)$^+$

Example 71

{2-[4-(3-Dimethylamino-propionylazino)-phenylsulfanyl]-quinazolin-4-yl-(5-methyl-2H-pyrazol-3-yl)-amine (IIa-71): Prepared in a manner similar to the above described Method E to afford an off-white solid, mp 280° C. (dec.); $^1$H NMR (DMSO) δ 2.09 (3H, s), 2.60 (6H, s), 2.93 (2H, m), 3.10 (2H, m), 5.64 (1H, s), 7.47 (1H, t), 7.59–7.70 (3H, m), 7.80–7.87 (3H, m), 8.61 (1H, d), 10.47 (1H, s), 10.48 (1H, s), 12.15 (1H, s) IR (solid) 1670, 1619, 1598, 1586, 1571, 1534, 1515, 1481, 1397, 1364, 1348, 1286, 1178, 1162, 764; MS 448.4(M+H)$^+$

Example 72

[2-(4-Acetamido-phenylsulfanyl)-8-methoxy-quinazolin-4-yl]-(5-cyclopropyl-2H-pyrazol-3-yl)-amine (IIa-72): Prepared in a manner similar to the above described Method E to afford an off-white solid, mp 265–268° C.; $^1$H NMR (DMSO) δ 0.49–0.56 (2H, m), 0.79–0.83 (2H, m), 1.55–1.70 (1H, m), 2.06 (3H, s), 3.89 (3H, s), 5.61 (1H, s), 7.25 (1H, d), 7.33 (1H, t), 7.5.6 (2H, d), 7.74 (2H, d), 8.07 (1H, d), 10.17 (1H, s), 10.26 (1H, s), 15 11.94 (1H, br s); IR (solid) 3250, 1671, 1617, 1595, 1536, 1480, 1460, 1396, 1373, 1335, 1254, 1160, 1131, 1071, 1011, 984, 869, 815; MS 447.4(M+H)$^+$

Example 73

[2-(4-Acetamidophenyl'sulfanyl)-8-(3-dimethylamino-propoxy)-quinazolin-4-yl]-(5-methyl-2H-pyrazol-3-yl)-amine (IIa-73): Prepared in a manner similar to the above described Method E to afford an off-white solid, mp 170–172° C.; $^1$H NMR (DMSO) δ 1.91 (2H, quint.), 2.03 (3H, s), 2.09 (3H, s), 2.17 (6H, s), 2.40 (2H, t), 4.10 (2H, t), 5.59 (1H, s), 7.23 (1H, d), 7.30 (1H, t), 7.57 (2H, d), 7.73 (2H, d), 8.06 (1H, d), 10.20 (1H, s), 10.24 (1H, s), 12.02 (1H, br s); IR (solid) 3234, 3108, 1675, 1614, 1592, 1531, 1484, 1395, 1371, 1338, 1316, 1253, 1161, 1137, 1062, 1038, 994, 958, 823; MS 492.4(M+H)$^+$

Example 74

[2-(4-Acetamidophenylsulfanyl)-7-hydroxy-quinazolin-4-yl]-(5-methyl-2H-pyrazol-3-yl)-amino (IIa-74): Prepared from IIa-40 according to Method H to afford an off-white solid, mp 246–248° C.; $^1$H NMR (DMSO) δ 2.00 (3H, s), 2.08 (3H, s), 5.52 (1H, s), 6.78 (1H, s), 6.87 (1H, d), 7.54 (2H, d), 7.72 (2H, d), 8.37 (1H, d), 10.06 (1H, s), 10.17 (1H, s), 10.37 (H, s), 11.95 :(1H, br s); IR (solid) 1661, 1633, 1594, 1572, 1539, 1492, 1420, 1389, 1359, 1298, 1223, 1176, 1148, 1087, 1026, 1010, 965; MS 407.4(M+H)$^+$

Example 75

[2-(4-Acetamidophenylsulfanyl)-7-(3-dimethylamino-propoxy)-quinazolin-4-yl]-(5-methyl-2H-pyrazol-3-yl)-amine (IIa-75): Prepared in a manner similar to the above described Method I to afford an off-white solid, mp 24.9–250° C.; ¹H NMR (DMSO) δ 1.90 (2H, quint.), 2.01 (3H, s), 2.09 (3H, s), 2.19 (6H, s), 2.42 (2H, m), 4.12 (2H, t), 5.55 (1H, s), 6.93 (1H, s), 6.98 (1H, d), 7.55 (2H, d), 7.73 (2H, d), 8.43. (1H, d), 10.21 (1H, s), 10.23 (1H, s), 11.98 (1H, br s); IR (solid) 3272, 1677, 1615, 1571, 1558, 1530, 1501, 1434, 1420, 1394, 1344, 1320, 1292, 1263, 1222, 1168, 1048, 1034, 1005, 967, 864, 844; MS 492.4(M+H)⁺

Example 76

(2-{4-[2-(tert-Butoxycarbonyl-methyl-amino)-acetylamino]phenylsulfanyl}-quinazolin-4-yl)-(5-methyl-2H-pyrazol-3-yl)-amine (IIa-76): Prepared in a manner similar to the above described Method E to afford a white solid, mp 228–229° C. (dec.); ¹H NMR (DMSO) δ 1.37 (3H, s), 1.40 (3H, s), 2.02+2.03 (3H, 2×s), 2.88+2.90-(3H, 2×s), 4.01+4.02 (2H, 2×s), 5.52+5.57 (1H, 2×s), 7.47 (1H, t), 7.55–7.63 (3H, m), 7.75–7.80 (3H, m), 8.60 (1H,d), 10.28+10.30 (1H, 2×s), 10.45 (1H, s), 12.08 (1H, s).; IR (solid) 1698, 1683, 1653, 1617, 1594, 1559, 1538, 1532, 1507, 1488, 1457, 1418, 1397, 1364, 1346, 1307, 1287, 1246, 1151, 842, 827, 759; MS 520.4 (M+H)⁺

Example 77

{2-[4-(2-Methylamino-acetylamino)-phenylsulfanyl]-quinazolin-4-yl}-(5-methyl-2H-pyrazol-3-yl)-amine (IIa-77): Prepared in a manner similar to the above described Method E to afford a white solid, mp 242–244° C.; ¹H NMR (DMSO) δ 2.01 (3H, s), 2.34 (3H, s), 3.32 (2H, s), 5.58 (1H, s), 7.45 (1H, t), 7.50–7.60 (3H, m), 7.75 (1H, t), 7.80 (2H, d), 8.55 (1H, d), 10.10 (1H, br s), 10.42 (1H, s), 12.02 (1H, s); IR (solid) 1674, 1619, 1598, 1570, 1525, 1483, 1417, 1363, 1345, 1298, 1285, 1247, 1160, 966, 827, 804, 784, 763, 712, 670, 653; MS 420.4 (M+H)⁺

Example 78

[2-(4-Acetamidophenylsulfanyl)-8-fluoro-quinazolin-4-yl]-(5-methyl-2H-pyrazol-3-yl)-amine (IIa-78): Prepared in a manner similar to the above described Method E to afford a white solid, mp 257–259° C.; ¹H NMR (DMSO) δ 2.01 (3H, s), 2.09 (3H, s), 5.49 (1H, s), 7.42 (1H, t), 7.57–7.68 (3H, m) 7.75 (2H, d), 8.40. (1H, d), 10.28 (1H, s), 10.75 (1H, s); ¹⁹F NMR (DMSO) δ−127.3; IR (solid) 1690, 1670, 1637, 1609, 1588, 1543, 1519, 1493, 1456, 1434, 1395, 1366, 1332, 1315, 1289, 1254, 1242, 1032, 838, 829, 808, 744; MS 409.4(M+H)⁺

Example 79

(1H-Indazol-3-yl)-(2-phenylsulfanyl-quinazolin-4-yl)-amine (IIa-79): Prepared in a manner similar to the above described Method E to afford a white solid. ¹H NMR (DMSO) δ 7.07 (m, 3H), 7.19 (t, 1H), 7.37 (d, 2H), 7.39 (t, 1H), 7.52 (dd, 1H), 7.54 (t, 1H), 7.55 (d, 1H), 7.56 (t, 1H), 7.83 (t, 1H), 8.53 (d, 1H), 10.71 (s, 1H), 12.85 (s, 1H); MS 370.1 (M+H)⁺

Example 80

{2-[(2-Hydroxyethyl)phenylamino]-quinazolin-4-yl}-(5-methyl-2H-pyrazol-3-yl)-amine (IIc-1): Prepared in a manner similar to the above described Method A to afford a brown solid, mp 217° C.; ¹H NMR (DMSO) δ 1.99 (3H, s), 3.69 (2H, t), 4.05 (2H, t), 5.00 (1H, br s), 5.53 (1H, br s), 7.09 (1H, m), 7.25–7.40 (4H, m), 7.40–7.48 (2H, m), 7.54 (1H, m), 8.34 (1H, m), 10.07 (1H, s), 11.67 (1H, br s); IR (solid) 3395, 3155, 3052, 2934, 1623, 1598, 1577, 1475, 1434, 1393; MS 361.2 (M+H)⁺

Example 81

[2-(Methylphenylamino)-quinazolin-4-yl]-(5-methyl-2H-pyrazol-3-yl)-amine (IIc-2): Prepared in a manner similar to the above described Method A to afford a white solid, mp 154–156° C.; ¹H NMR (DMSO) δ 2.03 (3H, s), 3.51(3H, s), 5.70(1H, s), 7.13(1H, m), 7.36–7.25(3H, m), 7.48–7.37 (3H, m), 7.58 (1H, m), 8.38, (1H, d), 9.98(1H, s), 11.91 (1H s); IR (solid) 1621, 1598, 1578, 1540, 1494, 1473, 1398, 1374; MS 331.0 (M+H)⁺

Example 82

(5-methyl-2H-pyrazol-3-yl)-{2-[N-methyl-N-(pyridin-3-ylmethyl)amino]-quinazolin-4-yl)-amine (IIc-3): Prepared in a manner similar to the above described Method A to afford a yellow solid, mp 177° C.; ¹H NMR(DMSO) δ 0.45 (2H, s), 0.84 (2H, s), 1.80 (1H, s), 3.16 (3H, s), 4.93 (2H, s), 6.18 (1H, br s), 7.10 (1H, t), 7.34 (2H, s), 7.55 (1H, t), 7.64 (1H, s), 8.36 (1H, d), 8.45 (1H, s), 8.52 (1H, s), 10.03 (1H, s), 12.17 (1H, s); IR (solid) 3104, 2995, 2936, 1618, 1591, 1559, 1541, 1518, 1477, 1409, 1386, 1350, 1300, 1018, 991, 873, 827; MS 372.3 (M+H)⁺

Example 83

(5-Methyl-2H-pyrazol-3-yl)-(2-phenylamino-quinazolin-4-yl)-amine (IIc-4): Prepared in a manner similar to the above described Method A to afford a white solid; ¹H NMR (DMSO @60° C.) δ 2.27(3H, s) 6.47(1H, br s), 6.92(1H, m), 7.31(3H, m), 7.53(1H, m), 7.70. (1H, m), 7.91 (2H, m), 8.37 (2Hi d), 9.16 (1H, br s), 10.05 (1H, br s), 12.15 (1H, br s); IR (solid) 1623, 1601, 1573, 1541, 1478; MS 317.0 (M+H)⁺

Example 84

(2-Benzylamino-quinazolin-4-yl)-(5-methyl-2H-pyrazol-3-yl)-amine (IIc-5): Prepared in a manner similar to the above described Method A to afford a white solid, mp 225–227° C.; ¹H NMR (DMSO) δ 2.20 (3H, s), 4.62(2H, d), 7.18 (1H, s), 7.43–7.60(8H, m), 8.22 (1H, s), 9.99 (1H, br s), 12.05 (1H, br s); IR (solid) 1630, 1609, 1578 1538, 1511; MS 331.0 (M+H)⁺

Example 85

(2-Cyclohexylamino-quinazolin-4-yl)-(5-methyl-2H-pyrazol-3-yl)-amine (IIc-6): Prepared in a manner similar to the above described Method A to afford an off-white solid, mp 280° C.(dec.); ¹H NMR (DMSO) δ 1.11–1.44(5H, m), 1.56 (1H, m), 1.71(2H, m), 1.92 (2H, m), 2.26(3H, s), 3.75(1H, s), 6.63 (1H, br s), 7.04 (1H, s), 7.28 (1H, s), 7.51(1H, m), 8.26(1H, s), 9.97(1H, br s), 12.08(1H, br s), 12.75(1H, br s); IR (solid) 2927, 2853, 1619, 1596, 1569, 1522, 1482; MS 323.0 (M+H)⁺

Example 86

[2-(2,3-Dihydrobenzo[1,4]dioxin-6-ylamino)-quinazolin-4-yl]-(5-methyl-2H-pyrazol-3-yl)-amine (IIc-7): Prepared in a manner similar to the above described Method A to afford an off-green solid, mp >250° C.; ¹H NMR (DMSO) δ 2.23 (3H, s), 4.15 (4H, m), 6.32 (1H, br s), 6.76 (1H, d), 7.16 (1H, t), 7.22 (1H, dd), 7.39 (1H, d), 7.57 (1H, t), 7.66 (1H, s), 8.34. (1H, d), 9.07 (1H, br s), 10.20 (1H, br s), 12.15 (1H, br s); IR (solid) 3445, 3045, 2968, 2927, 2868, 1618, 1595, 1577, 1559, 1509, 1441, 1377, 1073; MS 375.1 (M+H)$^+$ Example 87

(2-Cyclohexylmethylamino-quinazolin-4-yl)-(5-methyl-2H-pyrazol-3-yl)-amine (IIc-8): Prepared in a manner similar to the above described Method A to afford a white solid, mp 211° C.; $^1$H NMR (DMSO) δ 0.85–1.30 (5H, m), 1.50–1.85 (6H, m), 2.22 (3H, s), 3.19 (2H, s), 6.50–7.00 (1H, br s), 7.06 (1H, br s), 7.29 (1H, br s), 7.51 (1H, t), 8.26 (1H, br s), 9.97 (1H, br s), 12.04 (1H, br s), 12.75 (1H, br s); IR (solid) 3333, 2927, 2850, 2831, 1627, 1609, 1577, 1540, 1508, 1449, 1422, 1340, 988; MS 337.4 (M+H)$^+$ Example 88

[2-(1H-Indazol-6-ylamino)-quinazolin-4-yl]-(5-methyl-2H-pyrazol-3-yl)-amine (IIc-9): Prepared in a manner similar to the above described Method A to afford an off-white solid, mp >250° C.; $^1$H NMR (DMSO) δ 2.24 (3H, s), 5.93 and 6.89 (1H, 2×br s), 7.05–8.15 (6H, m), 8.25–8.90 (2H, m), 9.25 and 9.97 (1H, 2×br s), 10.11 and 10.57 (1H, 2×br s), 12.15 and 12.80 (2H, 2×br s); IR (solid) 3456, 3315, 2923, 1613, 1600, 1577, 1549, 1467; MS 357.1 (M+H)$^+$ Example 89

(5-Methyl-2H-pyrazol-3-yl)-[2-(pyridin-3-ylmethylamino)-quinazolin-4-yl3-amino (IIc-10): Prepared in a manner similar to the above described Method A to afford an off-white solid, mp 218° C.; $^1$H NMR (DMSO) δ 2.20 (3H, s), 4.59 (2H, s), 6.30 (1H, br s), 7.10 (1H, s), 7.33 (2H, s), 7.54 (1H, s), 7.78 (1H, s), 8.31 (1H, s), 8.43 (1H, s), 8.61 (1H, s), 10.0(1H, br s), 12.15 (1H, br s); IR (solid) 3308, 2945, 2919, 2858, 1623, 1593, 1577, 1552, 1501, 1475, 1449, 1383; MS 332.1 (M+H)$^+$ Example 90

[2-(3-Chlorophenylamino)-quinazolin-4-yl]-(5-methyl-2H-pyrazol-3-yl)-amine (IIc-11): Prepared in a manner similar to the above described Method A to afford an off-white solid, mp >250° C., $^1$H NMR (DMSO) δ 2.29 (3H, s), 5.30–6.98 (1H, m), 6.96 (1H, s), 7.28 (2H, s), 7.51 (1H, s), 7.67 (1H, s), 7.77 (1H, s), 8.23 (1H, s), 8.46 (1H, s), 9.35 and 10.00 (1H, 2×br s), 10.14. and 10.64 (1H, 2×br s), 12.20 and 12.82 (1H, 2×br s); IR (solid) 3447, 3078, 2945, 2914, 2863, 1618, 1600, 1572, 1549, 1472, 1440, 1403, 1372; MS 351.1 (M+H)$^+$ Example 91

[2-(4-Chlorophenylamino)-quinazolin-4-yl]-(5-methyl-2H-pyrazol-3-yl)-amine (IIc-12): Prepared in a manner similar-to the above described Method A to afford an off-white solid, mp >250° C.; $^1$H NMR (DMSO) δ 2.27 (3H, s), 5.20–6.80 (1H, m), 7.26 (1H, s), 7.33 (2H, s), 7.51 (1H, s), 7.66 (1H, s), 7.99 (2H, d), 8.42 (1H, s), 9.29 and 9.93 (1H, 2×br s), 10.13 and 10.55 (1H, 2×br s), 12.19 and 12.81 (1H, 2×br s); IR (solid) 3439, 3057, 2957, 1618, 1600, 1586, 1572, 1550, 1504, 1486, 1431, 1413, 1367; MS 351.1 (M+H)$^+$ Example 92

[2-(4-Fluorobenzylamino)-quinazolin-4-yl]-(5-methyl-2H-pyrazol-3-yl)-amine (IIc-13): Prepared in a manner similar to the above described Method A to afford a white solid, mp 216° C.; $^1$H NMR (DMSO) δ 2.20 (3H, s), 4.56 (2H, d), 6.30 (1H, br s), 7.05–7.20 (3H, m), 7.31 (1H, d), 7.42 (2H, s), 7.54 (1H, t), 8.32 (1H, s), 10.01 and 10.34 (1H, 2×br s), 12.09 and 12.75 (1H, 2×br s); IR (solid) 3333, 2854, 1632, 1609, 1577, 1536, 1508, 1367; MS:349.3 (M+H)$^+$ Example 93

{2-[2-(2-Hydroxyethyl)phenylamino]-quinazolin-4-yl}-(5-methyl-2H-pyrazol-3-yl)-amine (IIc-14): Prepared in a manner similar to the above described Method A to afford a white solid, mp 222° C.; $^1$H NMR (DMSO) δ 2.09 (3H, s), 2.80 (2H, t), 3.61 (2H, t), 4.87 (1H, br s), 5.85 (1H, br s), 7.30–7.53 (5H, m), 7.63 (1H, d), 7.86 (1H, t), 8.68 (1H, d), 10.11 (1H, br s), 11.55 (1H, br s), 12.49 (1H, br s), 13.50. (1H, br s); IR (solid) 3193, 3171, 3111, 3084, 1636, 1577, 1559, 1509, 1486, 1413, 1340, 1058; MS 361.3 (M+H)$^+$ Example 94

[2-(4-Cyanomethylphenylamino)-quinazolin-4-yl]-(5-methyl-2H-pyrazol-3-yl)-amine (IIc-15): Prepared in a manner similar to the above described Method A to afford an off-white solid, mp >250° C.; $^1$H NMR (DMSO) δ 2.23 (3H, s), 4.09 (2H, s), 6.28 (1H, br s), 7.41 (2H, d), 7.48 (1H, t), 7.57–7.63 (3H, m), 7.87 (1H, t), 10.70 (1H, s), 11.56 (1H, s), 12.63 (1H, br s), 13.25 (1H, br s); IR (solid) 3294, 3271, 3093, 1641, 1586, 1568, 1550, 1513, 1481, 1413, 1336, 1158, 999; MS 356.2 (M+H)$^+$ Example 95

[2-(3-Hydroxymethylphenylamino)-quinazolin4-yl]-(5-methyl-2H-pyrazol-3-yl)-amine (IIc-16): Prepared in a manner similar to the above described Method A to afford an off-white solid, mp >250° C.; $^1$H NMR (DMSO) δ 2.20 (3H, s), 4.53 (2H, s), 5.22 (1H, br s), 6.31 (1H, br s), 7.24 (1H, d), 7.33–7.53 (4H, m), 7.61 (1H, d), 7.86 (1H, t), 8.67 (1H, d), 10.61 (1H, br s), 11.52 (1H, br s), 12.59 (1H, br s), 13.10 (1H, br s); IR (solid) 3401, 3209, 3108, 3071, 2975, 2916, 1632, 1609, 1595, 1554, 1485, 1421, 1371, 1348, 1046, 1005, 813; MS 347.3 (M+H)$^+$ Example 96

[2-(3-Hydroxyphenylamino)-quinazolin-4-yl]-(5-methyl-2H-pyrazol-3-yl)-amine (IIc-17): Prepared in a manner similar to the above described Method A to afford a white solid, mp >250° C.; $^1$H NMR (DMSO) δ 2.22 (3H, s), 6.42 (1H, br s), 6.72 (1H, d), 6.97 (2H, s), 7.21 (1H, t), 7.47 (1H, t), 7.60 (1H, d), 7.85 (1H, t), 8.67 (1H, d), 9.76 (1H, s), 10.53 (1H, s), 11.53 (1H, s), 12.58 (1H, br s), 12.99 (1H, br s); IR (solid) 3354, 3027, 2893, 2817, 1654, 1588, 1541, 1490, 1436, 1418, 1332, 1154, 1004; MS 333.2 (M+H)$^+$ Example 97

(5-Cyclopropyl-2H-pyrazol-3-yl)-(2-phenylamino-quinazolin-4-yl)-amine (IIc-18): Prepared in a manner similar to the above described Method A to afford an off-white solid, mp 234° C.; $^1$H NMR (DMSO) δ 0.74 (1H, s), 0.92 (2H, s), 1.91 (1H, s), 5.83 and 6.54 (1H, 2×br s), 6.94 (1H, t), 7.30 (3H, m), 7.50 (1H, s), 7.65 (1H, s), 7.91 (2H, d), 8.27 (1H, s), 9.13 and 9.77 (1H, 2×br s), 10.07 and 10.52 (1H, 2×br s), 12.19 and 12.82 (1H, 2×br s); IR (solid) 3443, 1622, 1595, 1577, 1554, 1486, 1449, 1413, 1376, 1340, 1235, 1171, 988, 806; MS 343.2 (M+H)$^+$ Example 98

(5-Cyclopropyl-2H-pyrazol-3-yl)-[2-(3-methylphenylamino)-quinazolin-4-yl]-amine (IIc-19): Prepared in a manner similar to the above described Method A to afford an off-white solid, mp 117° C.; $^1$H NMR (DMSO) δ 0.72.(2H, s), 0.92 (2H, s), 1.90 (1H, m), 2.32 (3H, s), 6.20 (1H, br s), 6.80 (1H, d), 7.20 (1H, t), 7.27 (1H, br s), 7.51 (1H, br s), 7.55–7.85 (3H, m), 8.43 (1H, br s), 9.50 (1H, br s), 10.44, (1H, s), 12.55 (1H, br s); IR (solid) 3303, 1618, 1581, 1554, 1536, 1495, 1472, 1436, 1413, 1372, 1336, 1240, 990; MS 357.4 (M+H)$^+$ Example 99

(5-Cyclopropyl-2H-pyrazol-3-yl)-[2-(6-methoxypyridin-3-ylamino)-quinazolin-4-yl]-amine (IIc-20): Prepared in a manner similar to the above described Method A to afford a pink solid, mp 120° C.; $^1$H NMR (DMSO) δ 0.72 (2H, s), 0.91 (2H, s), 1.89 (1H, m), 3.85 (3H, s), 6.20 (1H, br s), 6.82 (1H, d), 7.25 (1H, s), 7.48 (1H, m), 7.66 (1H, t), 8.13 (1H, br s), 8.42 (1H, br s), 8.61 (1H, br s), 9.50 (1H, br s), 10.48(1H, br s), 12.55 (1H, br s); IR (solid) 3457, 3439, 1622, 1604, 1577, 1554, 1481, 1422, 1386, 1363, 1272, 1235, 1035, 985, 821; MS 374.2 (M+H)$^+$ Example 100

(5-Cyclopropyl-2H-pyrazol-3-yl)-[2-(indan-5-ylamino)-quinazolin-4-yl]-amine-(IIc-21): Prepared in a manner similar to the above described Method A to afford a pale brown solid, mp 199–204° C.; $^1$H NMR (DMSO) δ 0.69 (2H, br s), 0.91 (2H, br s) 1.90. (1H, m), 2.02 (2H, m), 2.68 (1H, m), 2.83 (3H, m), 6.46 (1H, br s), 7.18 (1H, d), 7.26 (1H, br s), 7.50 (1H, d), 7.67 (1H, t), 7.75 (1H, br s), 8.45 (1H, br s) 9.70 (1H, br s), 10.60 (1H, br s), 12.30 and 12.80 (1H, 2×br s); IR (solid) 1621, 1601, 1572, 1552, 1495, 1474, 1439, 1425, 1408, 1382, 1363, 1319, 1267; MS 383.3 (M+H)$^+$ Example 101

(5-Cyclopropyl-2H-pyrazol-3-yl)-[2-(1H-indol-6-ylamino)-quinazolin-4-yl]-amine (IIc-22): Prepared in a manner similar to the above described Method A to afford a dark brown solid, mp >300° C.; $^1$H NMR (DMSO) δ 0.69 (2H, br s), 0.89 (2H, br s), 1.88 (1H, m), 5.77 and 6.74 (1H, 2×br s), 6.35 (1H, s), 7.22 (3H, br s), 7.45 (2H, d), 7.65 (1H, s), 8.35 (2H, br s), 8.86, 9.70 and 10.01 (1H, 3×br s), 10.49, 12.12 and 12.84 (1H, 3×br s), 10.94 (s, 1H); IR (solid) 1623, 1603, 1571, 1549, 1495, 1477, 1460, 1419, 1383, 1336, 1264, 1250, 1238; MS 382.4 (M+H)$^+$ Example 102

[2-(4-Acetamido-3-methylphenylamino)-quinazolin-4-yl]-(5-cyclopropyl-2H-pyrazol-3-yl)-amine-(IIc-23): Prepared in a manner similar to the above described Method A to afford an off-white-solid, mp >188° C.(dec.); $^1$H NMR (DMSO) δ 0.72 (2H, br s), 0.94 (2H, br s), 1.92. (1H, m), 2.03 (3H, s), 2.19 (3H, s), 5.80 and 6.69 (1H, 2×br s), 7.22 (2H, br s), 7.49 (1H, br s), 7.70 (3H, m), 8.35 (1H, br s), 9.01, 9.59 and 10.01 (1H, 3×br s), 9.19 (1H, s), 10.53, 12.16 and 12.81 (1H, 3×br s); IR (solid) 1637, 1624, 1578, 1542, 1502, 1474, 1428, 1403, 1343, 1320, 1307, 1250; MS 414.4 (M+H)$^+$ Example 103

[2-(4-Chloro-3-methylphenylamino)-quinazolin-4-yl]-(5-cyclopropyl-2H-pyrazol-3-yl)-amine (IIc-24): Prepared in a manner similar to the above described Method A to afford a pale brown solid, mp 244–246° C.; $^1$H NMR (DMSO) δ 0.69 (2H, br s), 0.94 (2H, br s), 1.91 (1H, m), 2.32 (3H, s), 5.89 and 6.63 (1H, 2×br s), 7.28 (2H, m), 7.49 (1H, m), 7.65 (1H, m), 7.80 (1H, br s),7.86 (1H, s), 8.40 (1H, br s), 9.17, 9.81 and 10.06 (1H, 3×br s), 10.58, 12.19 and 12.78 (1H, 3×br s); IR (solid) 1615, 1578, 1549, 1475, 1419, 1397, 1365, 1331, 1296, 1261, 1238, 1187, 1139; MS 391.4 (M+H)$^+$ Example 104

(5-Cyclopropyl-2H-pyrazol-3-yl)-[2-(4-ethylphenylamino)-quinazolin-4-yl]-amine (IIc-25): Prepared in a manner similar to the above described Method A to afford a pale brown solid, mp 250–251° C.; $^1$H NMR (DMSO) δ 0.72 (2H, br s), 0.91 (2H, br s), 1.19 (3H, t), 1.91 (1H, m), 2.58 (2H, q), 5.81 and 6.64 (1H, 2×br s), 7.15 (2H, d), 7.22 (1H, s), 7.47 (1H, s), 7.64 (1H, s), 7.78 (2H, s), 8.36 (1H, br s), 9.03, 9.66 and 10.05 (1H, 3×br s), 10.49, 12.20 and 12.80 (1H, 3×br s); IR (solid) 1603, 1574, 1546, 1509, 1497, 1474, 1439, 1417, 1386; MS 371.5 (M+H)$^+$ Example 105

(5-Cyclopropyl-2H-pyrazol-3-yl)-[2-(4-propylphenylamino)-quinazolin-4-yl]-amine (IIc-26): Prepared in a manner similar to the above described Method A to afford an off-white solid, mp 255–256° C.; $^1$H NMR (DMSO) δ 0.72.(2H, br s), 0.91 (5H, t), 1.60 (2H, m), 1.90 (1H, m), 2.58 (2H, q), 5.81 and 6.63 (1H, 2×br s), 7.12 (2H, d), 7.21 (1H, s), 7.47 (1H, s), 7.63 (1H, s), 7.77 (2H, s), 8.36 (1H, br s), 9.01, 9.70 and 10.11 (1H, 3×br s), 10.51, 12.17 and 12.80 (1H, 3×br s); IR (solid) 1595, 1571, 1545, 1499, 1477, 1442, 1413, 1388; MS 385.6 (M+H)$^+$ Example 106

(5-Cyclopropyl-2H-pyrazol-3-yl)-{2-[4-(2-hydroxyethyl)phenylamino]-quinazolin-4-yl}-amine (IIc-27): Prepared in a manner similar to the above described Method A to afford a pale brown solid, mp 255–256° C.; $^1$H NMR (DMSO) δ 0.73 (2H, br s), 0.91 (5H, t), 1.90 (1H, m), 2.69.(2H, t), 3.60 (2H, q), 4.62 (1H, t), 5.81 and 6.65 (1H, 2×br s), 7.15 (2H, d), 7.22 (1H, s), 7.46 (1H, s), 7.63 (1H, s), 7.77 (2H, s), 8.36 (1H, br s), 9.05, 9.69 and 10.02 (1H, 3×br s), 10.52, 12.17 and 12.79 (1H, 3×br s); IR (solid) 1632, 1569, 1546, 1483, 1452, 1434, 1402, 1371, 1267, 1231; MS 387.4 (M+H)$^+$ Example 107

(5-Cyclopropyl-2H-pyrazol-3-yl)-(2-phenetylamino-quinazolin-4-yl)-amine (IIc-28): Prepared in a manner similar to the above described Method A to afford a white solid, mp >250° C.; $^1$H NMR (DMSO) δ 0.66 (2H, m), 0.84 (2H, m), 1.83 (1H, m), 2.90 (2H, t), 3.56 (2H, m), 6.29 (1H, br s), 7.01 (1H, t), 7.12–7.38 (6H, m), 7.48 (1H, t), 8.42 (1H, s), 10.91 (1H, br s), 13.11 (1H, br s); IR (solid) 2922, 1650, 1627, 1577, 1550, 1500, 1482, 1395, 1368, 1004, 832; MS 371.3 (M+H)$^+$

Example 108

[2-(2-Cyclohexylethylamino)-quinazolin-4-yl]-(5-cyclopropyl-2H-pyrazol-3-yl)-amine (IIc-29): Prepared in a manner similar to the above described Method A to afford a white solid, mp >250° C.; $^1$H NMR (DMSO) δ 0.70 (2H, s), 0.80–1.00 (4H, m), 1.05–1.30 (4H, m), 1.30–1.50 (3H, m), 1.55–1.80 (5H, m), 1.87 (1H, s), 5.40–6.70 (2H, br s), 7.04 (1H, s), 7.25 (1H, s), 7.49 (1H, s), 8.25 (1H, s), 10.06 (1H, br s), 11.93 (1H, br s); IR (solid) 3448, 2920, 2852, 1618, 1600, 1568, 1550, 1486, 1418, 1395, 1367, 1258, 1008, 985; MS 377.4 (M+H)$^+$

Example 109

[2-(4-Carboxymethoxyphenylamino)-quinazolin-4-yl]-(5-cyclopropyl-2H-pyrazol-3-yl)-amine (IIc-30): Prepared in a manner similar to the above described Method A to afford a yellow solid, mp >250° C.; $^1$H NMR (DMSO) δ 0.72 (2H, m), 0.91 (2H, m), 1.90 (1H, m), 4.62 (2H, s), 6.24 (1H, s), 6.88 (2H, s), 7.21 (1H, m), 7.45 (1H, m), 7.62 (1H, m), 7.78 (2H, m), 8.35 (1H, m), 9.31 (1H, s), 10.25 (1H, s), 11.70 (1H, br s); IR (solid) 1663, 1595, 1563, 1509, 1422, 1331, 1240, 1176, 1053, 999; MS 417.3 (M+H)$^+$

Example 110

[2-(4-Cyanomethylphenylamino)-quinazolin-4-yl]-(5-cyclopropyl-2H-pyrazol-3-yl)-amine (IIc-31): Prepared in a manner similar to the above described Method A to afford a white solid, mp 222° C.; $^1$H NMR (DMSO) δ 0.74 (2H, m), 0.93. (2H, m), 1.92 (1H, m), 3.97 (2H, s), 5.82 and 6.65 (1H, 2×br s),; 7.29 (3H, m), 7.50 (1H, m), 7.66 (1H, m), 7.92 (2H, m), 8.39 (1H, m), 9.21 and 9.85 (1H, 2×br s), 9.90 and 10.56 (1H, 2×s), 12.19 and 12.80 (1H, 2×br s); IR (solid) 1641, 1622, 1595, 1581, 1554, 1513, 1486, 1463, 1408, 1372, 985, 821; MS 382.3.(M+H)$^+$

Example 111

[2-(Benzothiazol-6-ylamino)-quinazolin-4-yl]-(5-cyclopropyl-2H-pyrazol-3-yl)-amine (IIc-32): Prepared in a manner similar to the above described Method A to afford an off-white solid, mp 255–256° C.; $^1$H NMR (DMSO) δ 0.73 (2H, m), 0.92 (2H, m), 1.92 (1H, m), 5.83 and 6.63 (1H, 2×br s), 7.27 (1H, br s), 7.59 (1H, br s), 7.68 (1H, br s), 7.79 (1H, br s), 7.98 (1H, br s), 8.41 (1H, br s), 8.97 (1H, br s), 9.19 (1H, s), 9.58 and 10.10 (1H, 2×br s), 10.57, 12.21 and 12.85 (1H, 3×br s); IR (solid) 1624, 1592, 1575, 1512, 1472, 1411, 1377, 1333, 1244; MS 400.3 (M+H)$^+$

Example 112

(5-Cyclopropyl-2H-pyrazol-3-yl)-[2-(3,4-dimethylphenylamino)-quinazolin-4-yl]-amine (IIc-33): Prepared in a manner similar to the above described Method A to afford a white solid, mp 245–246° C.; $^1$H NMR (DMSO) δ 0.72 (2H, br s), 0.90 (2H, br s), 1.90 (1H, m), 2.18 (3H, s), 2.23 (3H, s), 5.77 and 6.63 (1H, 2×br s), 7.09 (1H, d), 7.23 (1H, br s), 7.47 (1H, br s), 7.59 (1H, br s), 7.64 (1H, br s), 8.36 (1H, br s), 9.02, 9.55 and 10.07 (1H, 3×br s), 10.49, 12.31 and 12.80 (1H, 3×br s); IR (solid) 1620, 1600, 1574, 1552, 1497, 1474, 1436, 1416, 1385, 1262; MS 371.5 (M+H)$^+$

Example 113

(5-Cyclopropyl-2H-pyrazol-3-yl)-[2-(2-phenoxyethylamino)-quinazolin-4-yl]-amine (IIc-34): Prepared in a manner similar to the above described Method A to afford a white solid, mp 203° C.; $^1$H NMR (DMSO) δ 0.70 (2H, m), 0.88 (2H, m), 1.87 (1H, m), 3.73 (2H, d), 4.16 (2H, s), 5.75. and 6.70 (1H, 2×br s), 6.93 (1H, t), 6.90–7.20 (3H, m), 7.20–7.45 (3H, m), 7.55 (.1H, s), 7.76 (1H, br s), 8.32 (1H, s), 9.95 and 10.35 (1H, 2×s), 12.13 and 12.75 (1H, 2×br s); IR (solid) 3434, 1622, 1600, 1572, 1554, 1499, 1476, 1422, 1399, 1385, 1303, 1267, 1226, 1212, 1052, 829; MS 387.4 (M+H)$^+$

Example 114

(5-Cyclopropyl-2H-pyrazol-3-yl)-[2-(thiophen-2-methylamino)-quinazolin-4-yl]-amine (IIc-35): Prepared in a manner similar to the above described Method A to afford a white solid, mp 212° C.; $^1$H NMR (DMSO) δ 0.67 (2H, m), 0.90 (2H, m), 1.86 (1H, m), 4.74 (2H, d), 5.76 and 6.66 (1H, 2×br s), 6.95 (1H, s), 6.90–7.20 (2H, m), 7.20–8.45 (5H, m), 9.94 and 10.40 (1H, 2×s), 12.13 and 12.71 (1H, 2×br s); IR (solid) 3444, 2948, 2847, 1622, 1600, 1559, 1500, 1481, 1418, 1390, 1358, 1336, 1313, 1263, 1217, 1185, 1149, 990, 821; MS 363.4 (M+H)$^+$

Example 115

[2-(4-Carboxymethylphenylamino)-quinazolin-4-yl]-(5-cyclopropyl-2H-pyrazol-3-yl)-amine (IIc-36): Prepared in a manner similar to the above described Method A to afford a brown solid, mp >210° C.(dec.); $^1$H NMR (DMSO) δ 0.64 (2H, br s), 0.92 (2H, m), 1.92 (1H, m), 3.50 (2H, s), 5.76 and 6.54 (1H, 2×s), 7.19 (1H, s), 7.24 (1H, m), 7.49 (1H, d), 7.64 (1H, t), 7.84 (2H, d), 8.37 (1H, m), 10.27 and 12.25 (1H, 2×br s); IR (solid) 1648, 1591, 1555, 1512, 1489, 1428, 1411, 1374; MS 401.4 (M+H)$^+$

Example 116

(5-Cyclopropyl-2H-pyrazol-3-yl)-[2-(1H-indazol-5-ylamino)-quinazolin-4-yl]-amine (IIc-37): Prepared in a manner similar to the above described Method A to afford a purple solid, mp 268–271° C.; $^1$H NMR (DMSO) δ 0.69 (2H, br s), 0.90 (2H, m), 1.88 (1H, m), 5.86 and 6.58 (1H, 2×s), 7.22 (1H, s), 7.61 (1H, s), 7.71 (2H, m), 8.01 (1H, s), 8.37 (2H, s), 8.58, 9.05 and 9.58 (1H, 3×br s), 10.01, 10.68 and 12.38 (1H, 3×br s), 12.90 (1H, s); IR (solid) 1626, 1605, 1576, 1546, 1512, 1495, 1476, 1447, 1431, 1416, 1393, 1261, 1224; MS 383.3 (M+H)$^+$

Example 117

(5-Cyclopropyl-2H-pyrazol-3-yl)-[2-(pyridin-3-ylmethylamino)-quinazolin-4-yl]-amine (IIc-38): Prepared in a manner similar to the above described Method A to afford a yellow solid, mp 193° C.; $^1$H NMR (DMSO) δ 0.69 (2H, m), 0.89 (2H, m), 1.86 (1H, m), 4.60 (2H, s), 5.76, 6.22 and 6.66 (1H, 3×br s), 7.10 (1H, s), 7.33 (2H, s), 7.54 (1H, s), 7.78 (1H, s), 8.31 (1H, s), 8.44 (1H, s), 8.61 (1H, s), 10.00 and 10.32 (1H, 2×s), 12.15 and 12.63 (1H, 2×br s); IR (solid) 2927, 2850, 1623, 1600, 1577, 1536, 1477, 1418, 1332, 1254, 814; MS 358.3 (M+H)$^+$

Example 118

(5-Cyclopropyl-2H-pyrazol-3-yl)-[2-(3-methoxycarbonylphenylamino)-quinazolin-4-yl]-amino (IIc-39): Prepared in a manner similar to the above described Method A to afford a white solid, mp 228–231° C.; $^1$H NMR (DMSO) δ 0.73 (2H, br s), 0.91 (2H, m), 1.92 (1H, m), 3.88 (3H, s), 5.99 and 6.79 (1H, 2×s), 7.27 (1H, s), 7.46 (3H, m), 7.68 (1H, s), 8.36 (1H, d), 8.48 (2H, s), 9.36, 9.84 and 10.00 (1H, 3×br s), 10.63, 12.17 and 12.79 (1H, 3×br s); IR (solid) 1716, 1615, 1591, 1579, 1557, 1473, 1432, 1416, 1379, 1334, 1298, 1276, 1226, 1191, 1142, 1110, 1020, 985; MS 401.3 (M+H)$^+$ Example 119

[2-(3-Carboxyphenylamino)-quinazolin-4-yl]-(5-cyclopropyl-2H-pyrazol-3-yl)-amine (IIc-40): Prepared in a manner similar to the above described Method A to afford an off-white solid, mp 298–302° C.; $^1$H NMR (DMSO) δ 0.73 (2H, br s), 0.91 (2H, m), 1.90 (1H, m), 7.26 (1H, s), 7.35 (1H, t), 7.50 (2H, d), 7.66 (1H, t), 8.31 (2H, m), 8.41 (1H, d); IR (solid) 1661, 1597, 1578, 1558, 1517, 1486, 1424, 1385; MS 387.3 (M+H)$^+$ Example 120

(5-Cyclopropyl-2H-pyrazol-3-yl)-[2-(3-ethylphenylamino)-quinazolin-4-yl]-amine (IIc-41): Prepared in a manner similar to the above described Method A to afford an off-white solid, mp 186–188° C.; $^1$H NMR (DMSO) δ 0.73 (2H, br s), 0.91 (2H, br s), 1.22 (3H, t), 1.90 (1H, m), 2.62 (2H, d), 5.81 and 6.70 (1H, 2×br s), 6.78 (1H,d), 7.20 (2H, s), 7.48 (1H, s), 7.65 (1H, s), 7.69 (1H, s), 7.81 (1H, s), 8.38 (1H, br s), 9.03, 9.74 and 10.03 (1H, 3×br s), 10.55, 12.16 and 12.82 (1H, 3×br s); IR (solid) 1614, 1580, 1549, 1534, 1493, 1471, 1433, 1409, 1374, 1340, 1240, 1182, 1165, 1138; MS 371.3 (M+H)$^+$ Example 121

(5-Cyclopropyl-2H-pyrazol-3-yl)-[2-(2,3-dimethylphenylamino)-quinazolin-4-yl]-amine (IIc-42): Prepared in a manner similar to the above described Method A to afford an off-white solid, mp 241–242° C.; $^1$H NMR (DMSO) δ 0.58 (2H, br s), 0.86 (2H, d), 1.77 (1H, br s), 2.11 (3H, br s), 2.28 (3H, s), 5.77 and 6.14 (1H, 2×br s,), 7.01 (1H, s), 7.11 (1H, t), 7.22 (1H, br s), 7.29 (1H, d), 7.56 (1H, s), 8.36 (1H, br s), 8.49, 8.98 and 9.98 (1H, 3×br s), 10.48, 12.04 and 12.68 (1H, 3×br s); IR (solid) 1622, 1603, 1573, 1552, 1495, 1471, 1440, 1428, 1412, 1384, 1268; MS 371.4 (M+H)$^+$ Example 122

(5-Cyclopropyl-2-pyrazol-3-yl)-[2-(3,4-dimethoxyphenylamino)-quinazolin-4-yl]-amine (IIc-43): Prepared in a manner similar to the above described Method A to afford a grey, solid, mp 144° C.; $^1$H NMR (DMSO) δ 0.69 (2H, s), 0.86 (2H, d), 1.89 (1H, m), 3.61 (3H, s), 3.67 (3H, s), 5.76 (1H, br s), 6.12 (1H, d), 6.31 (1H, s), 6.66 (1H, d), 6.94 (1H, d), 7.27 (1H, t), 7.50 (1H, d), 7.68 (1H, t), 8.45 and 9.36 (1H, br s, rotamers), 9.42 and 10.54 (1H, s, rotamers), 12.29 and 12.82 (1H, br s, rotamers); IR (solid) 3331, 3000, 2959, 2931, 2836, 1627, 1604, 1577, 1536, 1509, 1463, 1441, 1418, 1336, 1259, 1232, 1200, 1027; MS 403.8 (M+H)$^+$ Example 123

(5-Cyclopropyl-2H-pyrazol-3-yl)-[2-(3-methoxyphenylamino)-quinazolin-4-yl]-amine (IIc-44): Prepared in a manner similar to the above described Method A to afford a grey solid, mp 207–211° C.; $^1$H NMR (DMSO) δ 0.73 (2H, br s), 0.91 (2H, br s), 1.91 (1H, m), 3.77 (3H, s), 5.81 and 6.71 (1H, 2×br s), 6.53 (1H, d), 7.19–7.85 (7H, m), 8.34 (1H, s), 9.08, 9.79 and 10.06 (1H, 3×br s), 10.56, 12.16 and 12.82 (1H, 3×br s); IR (solid) 1611, 1580, 1549, 1533, 1498, 1477, 1430, 1409, 1374, 1337, 1253, 1204, 1180, 1157, 1141, 1041, 1030, 992; MS 373.7 (M+H)$^+$ Example 124

(5-Methyl-2H-pyrazol-3-yl)-(2-phenylamino-5,6,7,8-tetrahydroquinazolinin-4-yl)-amine -(IIc-45): Prepared in a manner similar to the above described Method C.

Example 125

[2-(Biphenyl-3-ylamino)-quinazolin-4-yl]-(5-cyclopropyl-2H-pyrazol-3-yl)-amine+(IIc-46): Prepared in a manner similar to the above described Method A to afford a pale brown solid, mp 153° C.; $^1$H NMR (DMSO) δ 0.73 (2H, s), 0.90 (2H, d), 1.89 (1H, m), 5.83 and 6.70 (1H, br s, rotamers), 7.25 (2H, d), 7.32 (2H, m), 7.50 (3H, t), 7.68 (3H, m), 8.00 (1H, d), 8.22 (1H, br s), 8.40 (1H, br s), 9.20 and 9.89 (1H, br s, rotamers), 10.06 and 10.46 (1H, s, rotamers), 12.17 and 12.84 (1H, br s, rotamers); IR (solid) 3333, 1627, 1609, 1581, 1540, 1504, 1472, 1449, 1426, 1335, 1248, 1216, 1102, 988, 819; MS 419.3 (M+H)$^+$ Example 126

(5-Cyclopropyl-2H-pyrazol-3-yl)-[2-(3-phenylprop-1-ylamino)-quinazolin-4-yl]-amine -(IIc-47): Prepared in a manner similar to the above described Method A to afford a white solid, mp 189° C.; $^1$H NMR (DMSO) δ 0.71 (2H, s), 0.91 (2H, s), 1.89 (3H, s), 2.69 (2H, s), 3.37 (2H, s), 5.76 and 6.66 (1H, br s, rotamers), 6.95–7.60 (8H, m), 8.10–8.40 (1H, m), 9.89 and 10.30 (1H, br s, rotamers), 12.10 and 12.75 (1H, br s, rotamers); IR (solid) 1622, 1595, 1572, 1545, 1499, 1481, 1417, 1390, 1367, 1048, 997, 829; MS 385.4 (M+H)$^+$ Example 127

[2-(4-acetamido-3-methylphenylamino)-quinazolin-4-yl]-(5-methyl-2H-pyrazol-3-yl)-amine (IIc-48): Prepared in a manner similar to the above described Method A to afford a pale brown solid, mp 251° C.; $^1$H NMR (DMSO) δ 2.04 (3H, s), 2.19 (3H, s), 2.56 (3H, s), 5.92 and 6.80 (1H, br s, rotamers), 7.22 (2H, s), 7.48 (1H, s), 7.64 (1H, s), 7.73 (2H, s), 8.40 (1H, s), 9.05 and 9.74 (1H, br s, rotamers), 9.20 (1H, s), 10.05 and 10.54 (1H, br s, rotamers), 12.15 and 12.82 (1H, br s, rotamers); IR (solid) 3309, 2972, 2936, 1641, 1604, 1577, 1536, 1504, 1468, 1423, 1409, 1377, 1341, 1304, 1259, 1223, 1100, 1009, 864; MS 388.2 (M+H)$^+$ Example 128

(5-Cyclopropyl-2H-pyrazol-3-yl)-[2-(indan-2-ylamino)-quinazolin-4-yl]-amine (IIc-49): Prepared in a manner similar to the above described Method A to afford a brown solid, mp 233–234° C.; $^1$H NMR (DMSO) δ 0.65 (2H, s), 0.84 (2H, s), 1.83 (1H, s), 2.91 (2H, m), 3.33 (2H, s), 4.72 (1H, s), 6.07 (1H, br s), 7.00–7.60 (8H, m), 8.29. (1H, s), 10.30 (1H, br s), 12.24 (1H, br s); IR (solid) 3425, 2941, 2836, 1622, 1595, 1572, 1540, 1495, 1476, 1426, 1394, 1248, 1025, 1007, 870, 833; MS 383.3 (M+H)$^+$

Example 129

[2-(3-Methylphenylamino)-quinazolin-4-yl]-(5-methyl-2H-pyrazol-3-yl)-amine (IIc-50): Prepared in a manner similar to the above described Method A to afford an off-white solid, mp 240–242° C.; $^1$H NMR (DMSO) δ 2.25 (3H, s), 2.30 (3H, s), 5.95 (1H, br s), 6.76 (1H, d), 7.10–7.35 (2H, m), 7.48 (1H, s), 7.55–7.85 (3H, m), 8.40 (1H, s), 9.05 and 9.74 (1H, br s, rotamers), 10.01 and 10.55 (1H, br s, rotamers), 12.14 and 12.81 (1H, br s, rotamers); IR (solid) 3443, 2914, 2859, 1622, 1586, 1549, 1536, 1481, 1445, 1408, 1372, 1330, 1267, 1239, 1184, 1166, 1139, 993, 838, 806; MS 331.3 (M+H)$^+$

Example 130

[2-(2-Chloro-5-methylphenylamino)-quinazolin-4-yl]-(5-methyl-2H-pyrazol-3-yl)-amine (IIc-51): Prepared in a manner similar to the above described Method A to afford a grey solid, mp 246–247° C.; $^1$H NMR (DMSO) δ 2.19 (3H, s), 2.31 (3H, s), 6.37 (1H, br s), 6.94 (1H, d), 7.23 (1H, s), 7.37 (1H, d), 7.43 (1H, d), 7.64 (1H, t), 7.97 (1H, s), 8.42 (1H, br s), 10.17 (1H, br s), 12.19 (1H, br s); IR (solid) 3409, 2918, 2850, 1627, 1591, 1573, 1545, 1513, 1486, 1463, 1418, 1386, 1332, 1291, 1259, 1182, 1000, 827; MS 365.2 (M+H)$^+$

Example 131

(5-Cyclopropyl-2H-pyrazol-3-yl)-{2-[4-(morpholin-1-yl)phenylamino]-quinazolin-4-yl})-amine (IIc-52): Prepared in a manner similar to the above described Method A to afford a grey solid, mp 275–276° C.; $^1$H NMR (DMSO) δ 0.71, (2H, s), 0.90 (2H, s), 1.89 (1H, s), 3.05 (4H, 8), 3.75 (4H, s) 5.78 and 6.61 (1H, br s, rotamers), 6.93 (2H, s), 7.20 (1H, s), 7.43 (1H, s), 7.50–7.90 (3H, m), 8.39 (1H, s), 8.95 and 9.58 (1H, br s, rotamers), 10.07 and,10.47 (1H, br s, rotamers), 12.16 and 12.81 (1H, br s, rotamers); IR (solid) 3245, 2990, 2972, 2959, 2936, 2918, 1618, 1577, 1559, 1509, 1477, 1445, 1413, 1382, 1264, 1223, 1150, 1109, 1050, 923, 882, 823; MS 428.3 (M+H)$^+$

Example 132

[2-(Benzothiazol-6-ylamino)-quinazolin-4-yl]-(5-methyl-2H-pyrazol-3-yl)-amine (IIc-53): Prepared in a manner similar to the above described Method A to afford an off-white solid, mp 236–239° C.; $^1$H NMR (DMSO) δ 2.25 (3H, s), 6.35 (1H, br s), 7.22 (1H, t), 7.53 (1H, d), 7.62 (1H, t), 7.76 (1H, d), 7.98 (1H, d), 8.39 (1H, d), 9.05 (1H, s), 9.17 (1H, s), 9.59 (1H, br s), 10.30 (1H, br s), 12.35 (1H, br s); IR (solid) 1622, 1605, 1567, 1546, 1505, 1473, 1441, 1417, 1385, 1341, 1297, 1273, 1253, 1192, 1130; MS 374.1 (M+H)$^+$

Example 133

[2-(3,4-Dimethylphenylamino)-quinazolin-4-yl]-(5-methyl-2H-pyrazol-3-yl)-amine (IIc-54): Prepared in a manner similar to the above described Method A to afford an off-white solid, mp. 249–251° C.; $^1$H NMR (DMSO) δ 2.18 (3H, br s), 2.21. (3H, br s), 2.24 (3H, br s), 5.92 and 6.80 (1H, 2×br s), 7.05 (1H, br s), 7.21 (1H, br s), 7.46 (1H, br s), 7.64 (3H, br s), 8.37 (1H, br s), 9.00, 9.51 and 9.73 (1H, 3×br s), 10.12, 10.54 and 12.17 (1H, 3×br s); IR (solid) 1616, 1582, 1547, 1505, 1473, 1452, 1413, 1368, 1334, 1294, 1246, 1210, 1188, 1170, 1139; MS 345.3 (M+H)$^+$

Example 134

[2-(3-Ethylphenylamino)-quinazolin-4-yl]-(5-methyl-2H-pyrazol-3-yl)-amine (IIc-55): Prepared in a manner similar to the above described Method A to afford an off-white solid, mp 238–239° C.; $^1$H NMR (DMSO) δ 1.21 (3H, t), 2.25 (3H, br s), 2.61 (2H, q), 5.92 and 6.80 (1H, 2×br s), 6.78 (1H, d), 7.21 (2H, br s), 7.48 (1H, br s), 7.65 (1H, s), 7.72 (1H, s), 7.80 (1H, s), 8.40 (1H, br s), 9.09, 9.58 and 10.10 (1H, 3×br s), 10.54, 12.26. and 12.81 (1H, 3×br s); IR (solid) 1619, 1556, 1535, 1471, 1441, 1407, 1377, 1341, 1274, 1246, 1185, 1167, 1139, 995; MS 345.5 (M+H)$^+$

Example 135

[2-(3-Methoxyphenylamino)-quinazolin-4-yl]-(5-methyl-2H-pyrazol-3-yl)-amine (IIc-56): Prepared in a manner similar to the above described Method A to afford an off-white solid, mp 212–215° C.; $^1$H NMR (DMSO) δ 2.25 (3H, br s), 3.77 (3H, s), 5.92 and 6.84 (1H, 2×br s), 6.55 (1H, d), 7.13 (2H, m), 7.41–7.50 (2H, m), 7.65 (1H, s), 7.77 (1H, s), 8.41 (1H, br s), 9.10, 9.79 and 10.10 (1H, 3×br s), 10.55, 12.13 and 12.82 (1H, 3×br s); IR (solid) 1610, 1576, 1532, 1494, 1468, 1425, 1337, 1277, 1256, 1201, 1159; MS 347.4 (M+H)$^+$

Example 136

[2-(4-Acetamido-3-cyanophenylamino)-quinazolin-4-yl]-(5-methyl-2H-pyrazol-3-yl)-amine (IIc-57): Prepared in a manner similar to the above described Method A to afford an off-white solid, mp 294–296° C.; $^1$H NMR (DMSO) δ 2.08 (3H, s), 2.28 (3H, s), 6.67 (1H, br s), 7.27 (1H, s), 7.43 (1H, d), 7.53 (1H, s), 7.68 (1H, s), 8.04 (1H, d), 8.45 (2H, s), 9.41, 10.35 and 12.18 (2H, 3×br s), 10.00 (1H, s); IR (solid) 1620, 1583, 1558, 1237, 1508, 1477, 1446, 1413, 1373, 1341, 1292, 1259, 1241, 1180, 1162, 1142, 1105, 1030, 1000; MS 399.2 (M+H)$^+$

Example 137

[2-(2-Methoxybiphenyl-5-ylamino)-quinazolin-4-yl]-(5-methyl-2H-pyrazol-3-yl)-amine (IIc-58): Prepared in a manner similar to the above described Method A to afford a white solid, 222–223° C.; $^1$H NMR (DMSO) δ 2.22 (3H, s), 3.75 (3H, s), 6.82 (1H, br s), 7.05–7.11 (1H, m), 7.15–7.25 (1H, m), 7.30–7.36 (1H, m), 7.40–7.50 (3H, m), 7.49–7.55 (2H, m), 7.55–7.70 (1H, m), 7.70–7.82 (1H, m), 7.90–8.02 (1H, m), 8.30–8.50 (1H, m); IR (solid) 1625, 1604, 1574, 1556, 1496, 1473, 1444, 1403, 1384, 1258, 1234, 1182, 1018, 824, 806, 755, 698; MS 423.4 (M+H)$^+$

Example 138

[2-(4-Acetamidophenylamino)-quinazolin-4-yl]-(5-methyl-2H-pyrazol-3-yl)-amine (IIc-59): Prepared in a manner similar to the above described Method A to afford an off-white solid, mp 253–256° C.; $^1$H NMR (DMSO) δ 2.02 (3H, s), 2.25 (3H, br s), 5.92 and 6.77 (1H, 2×br s), 7.21 (1H, s), 7.49. (3H, s), 7.63 (1H, 8), 7.83 (2H, d), 8.38 (1H, br s), 9.03 and 10.05 (1H, 2×br s), 9.81 (1H, s), 12.13 and 12.80 (1H, 2×br s); IR (solid) 1669, 1635, 1617, 1574, 1535, 1512, 1486, 1422, 1394, 1366, 1316, 1268, 1231, 1184, 1119, 1101; MS 374.1 (M+H)$^+$

Example 139

[22-(4-tert-Butoxycarbonylamino-phenylamino)-quinazolin-4-yl]-(5-methyl-2H-pyrazol-3-yl)-amine (IIc-60): Prepared in a manner similar to the above described Method A to afford an off-white solid, mp 238–242° C.; $^1$H NMR (DMSO) δ 1.48 (9H, s), 2.24 (3H, s), 6.23 (1H, br s), 7.12 (1H, s), 7.36 (3H, s), 7.54 (1H, s), 7.67 (2H, d), 8.30 (1H, d), 9.14 (2H, br s), 10.24 and 12.19 (1H, 2×br s); IR (solid) 1698, 1620, 1555, 1520, 1475, 1443, 1405, 1371, 1310, 1241, 1167, 1055, 996; MS 432.1 (M+H)$^+$

Example 140

[2-(4-Cyanophenylamino)-quinazolin-4-yl]-(5-methyl-2H-pyrazol-3-yl)-amine (IIc-61): Prepared in a manner similar to the above described Method A to afford an off-white solid, mp 293–298° C.; $^1$H NMR (DMSO) δ 2.25 (3H, 5) 6.50 (1H, br s), 7.27 (1H, s), 7.51 (1H, s), 7.64 (1H, s), 7.71 (2H, d), 8.40 (1H, s), 9.76. (1H, br s), 10.34 (1H, br s), 12.33 (1H, br s); IR (solid) 1633, 1605, 1571, 1517, 1505, 1469, 1418, 1337, 1255, 1174, 1000; MS 342.1 (M+H)$^+$

Example 141

(5-Methyl-2H-pyrazol-3-yl)-[2-(6-oxo-6,10b-dihydro-4aH-benzo[c]chromen-2-ylamino)-quinazolin-4-yl]-amine (IIc-62): Prepared in a manner similar to the above described Method A to afford a pale yellow solid, mp 293–298° C.; $^1$H NMR (DMSO) δ 1.72 (3H, br s), 6.23 (1H, br s), 7.50 (1H, t), 7.66 (2H, t), 7.75 (1H, t), 7.87 (1H, t), 7.77 (1H, t), 8.26 (1H, d), 8.33 (1H, d), 8.58–8.72 (2H, m), 10.55 (1H, s), 11.55 (1H, s), 12.40 (1H, s); IR (solid) 1707, 1629, 1607, 1579, 1540, 1497, 1488, 1471, 1446, 1428, 1417, 1346, 1332, 1298, 1270, 1255, 1207, 1114, 998, 816, 793, 766, 758, 710, 685; MS 435.4 (M+H)$^+$

Example 142

[2-(Biphenyl-3-ylamino)-quinazolin-4-yl]-(5-methyl-2H-pyrazol-3-yl)-amine (IIc-63): Prepared in a manner similar to the above described Method A to afford a pale brown solid, mp 206–207° C.; 1H NMR (DMSO) δ 2.20 (3H,s), 6.80 (1H, br s), 7.24–7.27 (2H, m), 7.36–7.40 (2H, m), 7.48–7.52 (3H, m), 7.67–7.69 (3H, m), 7.94 (1H, m), 8.26 (1H, m), 8.42 (1H, m), 9.30. (1H, br s), 10.16 (1H, br s), 12.13 (1H, br s); IR (solid) 1593, 1578, 1544, 1498, 1479, 1414, 1384, 1251, 1209, 1003; MS 393.2 (M+H)$^+$

Example 143

[2-(4-Methoxycarbonylmethyl-3-methylphenylamino)-quinazolin-4-yl]-(5-methyl-2H-pyrazol-3-yl)-amine (IIc-64): Prepared in a manner similar to the above described Method A to afford a white solid, mp 245–246° C.; $^1$H NMR (DMSO) δ 2.23 (3H, s), 2.26 (3H, s), 3.63 (3H, s), 3.64 (2H, s), 5.99 (0.5H, br s), 6.80 (0.5 H, br s), 7.10 (1H, m), 7.25 (1H, m), 7.50 (1H, m), 7.61–7.80 (3H, m), 8.44 (1H, m), 9.10 (0.5H, br s), 9.78 (0.5H, br s), 10.11 (0.5H, br s), 10.56 (0.5H, br s), 12.18 (0.5H, br s), 12.90 (0.5H, br s); IR (solid) 1732, 1710, 1622, 1581, 1554, 1538, 1508, 1490, 1446, 1411, 1371, 1336, 1306, 1257, 1244, 1204, 1146, 1016, 998, 797, 754, 692; MS 403.4 (M+H)$^+$

Example 144

[2-(4-Carboxymethyl-3-methylphenylamino)-quinazolin-4-yl]-(5-methyl-2H-pyrazol-3-yl)-amine (IIc-65): A solution of [2-(4-methoxycarbonylmethyl-3-methylphenylamino)-quinazolin-4-yl]-(5-methyl-2H-pyrazol-3-yl)-amine (IIc-64, 200 mg, 0.5.mmol) in a mixture of methanol/water (3/1, 8 mL) was treated with 1M NaOH (2 mL, 2 mmol). The mixture was heated at 70° C. for 2 hours and then neutralised with 1M HCl (2 mL, 2 mmol). The solid that formed was collected by filtration to afford the title compound (185 mg, 95%) as a pale yellow solid, mp 245° C. (dec.); $^1$H NMR (DMSO) δ 2.27 (6H, 2×s), 3.55 (2H, s), 6.49.(1H, s), 7.13,(1H, d), 7.26 (1H, t), 7.50 (1H, d), 7.62–7.78 (3H, m), 8.42 (1H, d), 9.34 (1H,d), 10.26. (1H, s), 12.36 (1H, s); IR (solid) 1660, 1590, 1562, 1504, 1427, 1385, 810, 776, 751, 693; MS 389.4 (M+H)$^+$

Example 145

[2-(4-Aminophenylamino)-quinazolin-4-yl]-(5-methyl-2H-pyrazol-3-yl)-amine (IIc-66): A solution of [2-(4-tert-Butoxycarbonylamino-phenylamino)-quinazolin-4-yl]-(5-methyl-2H-pyrazol-3-yl)-amine (IIc-60, 100 mg, 0.232 mmol) in a mixture of DCM/TFA (5/1, 12 mL) was stirred for 2 hours at room temperature. The solvents were removed in vacuo and the residue triturated in aqueous $K_2CO_3$. The resulting solid was collected by filtration and washed with diethyl ether to afford IIc-66 (69 mg, 90%) as an off-white solid, mp 164–167° C.; $^1$H NMR (DMSO) δ 2.24 (3H, s), 6.33 (1H, br s), 7.12 (2H, d), 7.48 (3H, m), 7.58 (1H, d), 7.86 (1H, t), 8.64 (1H, d), 10.86 (1H, br s), 11.46 (1H, s); IR (solid) 1681, 1512, 1496, 1433, 1415, 1187, 1129; MS 332.4 (M+H)$^+$

Example 146

[2-(4-Bromophenylamino)-quinazolin-4-yl]-(5-methyl-2H-pyrazol-3-yl)-amine (IIc-67): Prepared in a manner similar to the above described Method A to afford an off-white solid, mp 290–293° C.; $^1$H NMR (DMSO) δ 2.27 (3H, s), 6.71 (1H, br s), 7.22 (1H, m), 7.46–7.50 (3H, m), 7.66 (1H, m), 7.92–7.94 (2H, m), 8.38 (1H, m), 9.28, 10.11 and 12.13 (3H, 3×br s); IR (solid) 1619, 1572, 1548, 1486, 1436, 1409, 1372, 1238, 1186, 1136, 1071, 997; MS 395.1/397.1 (M+H)$^+$

Example 147

[2-(4-Isobutyrylamino-phenylamino)-quinazolin-4-yl]-(5-methyl-2H-pyrazol-3-yl)-amine (IIc-68): Prepared in a manner similar to the above described Method A to afford a yellow solid, mp 176–179° C.; $^1$H NMR (DMSO) δ 1.11 (6H, d), 2.15 (3H, s), 2.62 (1H, m), 6.25 (1H, br s), 7.41 (1H, d), 7.46 (1H, t), 7.63 (1H, d), 7.71 (2H, d), 7.84 (1H, t), 8.64 (1H, d), 10.00 (1H, s), 10.34 (1H, br s), 11.47 (1H, br s), 12.47 (1H, br s); IR (solid) 1676, 1653, 1585, 1561, 1512, 1423, 1407, 1312, 1199, 1177, 1128; MS 402.3 (M+H)$^+$

Example 148

(5-Ethyl-2H-pyrazol-3-yl)-[2-(5-ethyl-2H-pyrazol-3-ylamino)-quinazolin-4-yl]-amine (IIc-69): To a solution of 2,4-dichloroquinazoline (0.5 g, 2.51 mmol) and 3-amino-5-ethylpyrazole (558 mg, 5.02 mmol) in ethanol (10 mL) was added triethylamine (0.35 mL, 2.51 mmol) and the resulting mixture was stirred for 3 hours at room temperature. The resulting pale yellow precipitate was collected by filtration, washed with cold ethanol and dried under vacuum to afford IIc-69 (306 mg, 35%) as an off-white solid, mp 248–252° C.; $^1$H NMR (DMSO) δ 1.30 (m, 6H), 2.72 (m, 4H), 6.12 (br.s, 1H), 6.54 and 6.90 (br. s, 1H), 7.58 (t, 1H), 7.74 (d, 1H), 7.90 (t, 1H), 8.78 (d, 1H); IR (solid) 1639, 1602, 1591, 1555, 1418; MS 349.2 (M+H)$^+$

Example 149

(1H-Indazol-3-yl)-(2-phenylamino-quinazolin-4-yl)-amine (IIc-70): Prepared in a manner similar to the above-described Method A to afford a white solid; $^1$H NMR (DMSO) δ 6.90 (m, 3H), 7.11 (t, 1H), 7.19 (m, 2H), 7.44 (t, 1H), 7.57 (m, 1H), 7.62 (d, 1H), 7.67 (d, 2H), 7.71 (d, 1H), 7.93 (t, 1H), 8.59 (d, 1H), 11.55 (br. s, 1H), 13.15 (s, 1H); MS 353.2 (M+H)$^+$

Example 150

(1-Indazol-3-yl)-[2-(3-trifluoromethylphenylamino)-quinazolin-4-yl]-amine (IIc-71): Prepared in a manner similar to the above described Method A to afford a pale yellow solid. $^1$H NMR (DMSO) δ 7.00 (t, 1H), 7.02 (d, 1H), 7.22 (d, 1H), 7.37 (td, 1H), 7.56 (m, 3H), 7.61 (d, 1H), 7.66(d, 2H), 7.92 (t, 1H), 8.60 (d, 1H), 10.61 (br. s, 1H), 11.42 (br. s, 1H), 13.12 (s, 1H); MS 421.2 (M+H)$^+$

Example 151

(1H-Indazol-3-yl) -[2-(4-trifluoromethylphenylamino)-quinazolin-4-yl]-amine (IIc-72): Prepared in a manner similar to the above described Method A to afford a pale yellow solid. $^1$H NMR (DMSO) δ 7.08 (t, 1H), 7.16 (d, 2H), 7.44 (m, 3H), 7.58 (t, 1H), 7.6 (t, 2H), 7.69 (d, 1H), 7.95 (t, 1H), 8.62 (d, 1H), 10.82 (br. s, 1H), 11.50 (br. s, 1H), 12.20 (s, 1H); MS 421.2 (M+H)$^+$

Example 152

[2-(Adamantan-2-ylamino)-quinazolin-4-yl]-(1H-indazol-3-yl)-amine (IIc-73): Prepared in a manner similar to the above described Method A to afford a white solid. $^1$H NMR (DMSO) δ 0.83 (br. s, 1H), 0.85 (br. s, 1H), 1.44 (m, 4H) 1.55 (m,3H); 1.63 (8, 2H), 1.73 (s, 1H), 1.82 (s, 1H), 1.84 (s, 1H), 3.56 (m, 1H), 7.10 (t, 1H), 7.41 (t, 1H), 7.51 (t, 1H), 7.54 (d, 1H), 7.57 (d, 1H), 7.69 (d, 1H), 7.90 (t, 1H), 8.45 (d, 1H), 8.58 (d, 1H), 11.60 (s, 1H), 13.10 (s, 1H); MS 411.3 (M+H)$^+$

Example 153

(1H-Indazol-3-yl)-(2-methyl-phenyl-amino-quinazolin-4-yl)-amine (IIc-74): Prepared in a manner similar to the above described Method A to afford a white solid; $^1$H NMR (DMSO) δ 3.27 (s, 1H), 6.88 (t, 1H), 6.93 (t, 2H), 7.04 (t, 1H), 7.14 (d, 2H), 7.22 (t, 1H), 7.36 (m, 2H), 7.48 (d, 1H), 7.54 (d, 1H), 7.62. (t, 1H), 8.37 (d, 1H), 10.11 (s, 1H), 12.71 (s, 1H); MS 367.2 (M+H)$^+$

Example 154

[2-(2-Chloro-phenyl)-amino-quinazolin-4-yl]-(1H-indazol-3-yl)-amine (IIc-75): Prepared in a manner similar to the above described Method A to afford a white solid. $^1$H NMR (DMSO) δ 6.81 (t, 1H), 6.87 (td, 1H), 7.07 (t, 1H), 7.34 (dd, 1H), 7.35 (t, 1H), 7.40 (t, 1H), 7.53 (d, 1H), 7.56 (d, 1H), 7;63 (d, 2H), 7.72.(t, 1H), 8.07 (d, 1H), 8.46 (d, 1H), 10.37 (s, 1H), 12.89 (s, 1H); MS 387.1 (M+H)$^+$

Example 155

(1H-Indazol-3-yl)-[2-(2-trifluoromethylphenylamino)-quinazolin-4-yl]-amine (IIc-76): Prepared in a manner similar to the above described Method A to afford a white solid; $^1$H NMR (DMSO) δ 7.01 (t, 1H), 7.20 (m, 1H), 7.32 (m, 1H), 7.36 (t, 1H), 7.43 (d, 1H), 7.49 (d, 1H), 7.55 (d, 1H), 7.61 (t, 1H), 7.64 (d, 1H), 7.69 (d, 1H), 7.95 (t, 2H), 8.62 (d, 1H), 10.15 (m, 1H), 11.62 (s, 1H), 13.03 (s, 1H); MS 421.2 (M+H)$^+$

Example 156

[2-(4-Cyanomethylphenylamino)-quinazolin-4-yl]-(1H-indazol-3-yl)-amine (IIc-77): Prepared in a manner similar to the above described Method A to afford a white solid; $^1$H NMR (DMSO) δ 13.16 (s, 1H), 11.49 (br. s, 1H), 10.38 (br. s, 1H), 8.58 (d, 1H), 7.92 (t, 1H), 7.67 (t, 2H), 7.61 (d, 1H), 7.56 (m, 1H), 7.44 (t, 1H), 7.22 (m, 2H), 7.08 (t, 1H), 6.86 (m, 2H), 3.87 (s, 2H); MS 392.2 (M+H)$^+$

Example 157

[2-(4-Chlorophenylamino)-5,6,7,8-tetrahydroquinazolinin-4-yl]-(5-methyl-2H-pyrazol-3-yl)-amine (IIc-78): Prepared in a manner similar to the above described Method C; MS 355.5 (M+H)$^+$

Example 158

(5-Methyl-2H-pyrazol-3-yl)-(2-phenylamino-6,7,8,9-tetrahydro-5H-cycloheptapyrimidin-4-yl)-amine (IIc-79): Prepared in a manner similar to the above described Method C; MS 335.3 (M+H)$^+$

Example 159

[2-(Benzimidazol-2-ylamino)-7-benzyl-5,6,7,8-tetrahydro-pyrido[3,4-d]pyrimidin-4-yl]-(5-methyl-2H-pyrazol-3-yl)-amine (IIc-80): Prepared in a manner similar to the above described Method C; MS 452.0 (M+H)$^+$

Example 160

(7-Benzyl-2-phenylamino-5,6,7,8-tetrahydro-pyrido[3,4-d]pyrimidin-4-yl)-(5-methyl-2H-pyrazol-3-yl)-amine (IIc-81): Prepared in a manner similar to the above described Method C; MS 412.1 (M+H)$^+$

Example 161

[6-Benzyl-2-(4-chlorophenylamino)-5,6,7,8-tetrahydro-pyrido[4,3-d]pyrimidin-4-yl]-(5-methyl-2H-pyrazol-3-yl)-amine (IIc-82): Prepared in a manner similar to the above described Method C; MS 446.3 (M+H)$^+$

Example 162

[2-(Benzimidazol-2-ylamino)-6-benzyl-5,6,7,8-tetrahydro-pyrido[4,3-d]pyrimidin-4-yl]-(5-methyl-2H-pyrazol-3-yl)-amine (IIc-83): Prepared in a manner similar to the above described Method C; MS 452.2 (M+H)$^+$

Example 163

(6-Benzyl-2-phenylamino-5,6,7,8-tetrahydro-pyrido[4,3-d]pyrimidin-4-yl)-(5-methyl-2H-pyrazol-3-yl)-amine (IIc- 84): Prepared in a manner similar to the above described Method C; MS 411.9 (M+H)+

Example 164

(5-Methyl-2H-pyrazol-3-yl)-(2-phenylamino-5,6,7,8-tetrahydro-pyrido[3,4-d]pyrimidin-4-yl)-amine (IIc-85): Prepared in a manner similar to the above described Method C; MS 322.3 (M+H)+

Example 165

[2-(4-Cyanomethylphenylamino)-quinazolin-4-yl]-(1-pyrazolo[3,4-b]pyridin-3-yl)-amine (IIc-86): Prepared in a manner similar to the above described Method A to afford an off-white solid; $^1$H NMR (DMSO) δ 13.65 (s, 1H), 12.82 (br. s, 1H), 11.69 (br. s, 1H), 8.55 (dd, 2H), 8.12 (d, 1H), 7.88 (m, 1H), 7.66 (m, 1H), 7.50 (m, 1H), 7.30 (m, 2H), 7.09 (m, 1H), 6.94 (m, 2H), 3.89 (s, 2H); MS 393.1 (M+H)+

Example 166

[2-(4-Cyanobenzylamino)-quinazolin-4-yl3-(1H-pyrazolo[3,4-b]pyridin-3-yl)-amine (IIc-87): Prepared in a manner similar to the above described Method A to afford an off-white solid; $^1$H NMR (DMSO) δ 13.68 (s, 1H), 12.82 (br. s, 1H), 11.70 (br. s, 1H), 8.55 (m, 3H), 8.00 (d, 1H), 7.92 (t, 1H), 7.59 (m, 4H), 6.96 (m, 2H), 6.86 (m, 2H), 4.23 (s, 2H); MS 393.1 (M+H)+

Example 167

[2-(4-Cyanomethylphenylamino)-quinazolin-4-yl]-(4-fluoro-1H-indazol-3-yl)-amine (IIc-88): Prepared in a manner similar to the above described Method A to afford a white solid; 1H NMR (DMSO) δ 13.49 (s, 1H), 11.61 (br. s, 1H), 10.64 (br. s, 1H), 8.56 (d, 1H), 7.95 (t, 1H), 7.67 (d, 1H), 7.58 (t, 1H), 7.46 (t, 1H), 7.43 (dd, 1H), 7.14 (m, 2H), 6.85 (dd, 3H), 3.88 (s, 2H); MS 410.1 (M+H)+

Example 168

[2-(4-Cyanophenylamino)-quinazolin-4-yl]-(1H-indazol-3-yl)-amine (IIc-89): Prepared in a manner similar to the above described Method A to afford a white solid; $^1$H NMR (DMSO) δ 13.14 (s, 1H), 11.31 (br. s, 1H), 10.51 (br. s, 1H), 8.59 (d, 1H), 7.91 (t, 1H), 7.65 (d, 3H), 7.56 (t, 1H), 7.50 (m, 2H), 7.45 (dd, 1H), 7.26 (d, 2H), 7.08 (t, 1H); MS 378.2 (M+H)+

Example 169

[2-(4-Cyanobenzylamino)-quinazolin-4-yl]-(1H-indazol-3-yl)-amine (IIc-90): Prepared in a manner similar to the above described Method A to afford a white solid; $^1$H NMR (DMSO) δ 13.12 (s, 1H), 12.91 (br. s, 1H), 11.60 (br. s, 1H), 8.57 (d, 1H), 7.91 (t, 1H), 7.63 (d, 1H), 7.55 (m,5H), 7.38 (t, 1H), 6.89 (t, 1H), 6.84 (br. d, 2H), 4.19 (s, 2H); MS 392.2 (M+H)+

Example 170

(5-Cyclopropyl-2H-pyrazol-3-yl)-[2-(naphthalen-2-yloxy)-quinazolin-4--yl]-amine (IIb-1): Prepared in a manner similar to the above described Method B to afford a white solid, mp 327–328° C.; $^1$H NMR (DMSO) δ –0.05–0.07 (2H, m), 0.50–0.68 (2H, m), 1.28–1.40 (1H, m), 5.68 (1H,s), 7.40–7.50 (2H, m), 7.50–7.64 (3H, m), 7.70–7.80 (2H, m), 7.82–8.08 (3H, m), 8.64 (1H,d), 10.58 (1H, s), 12.07 (1H, s); IR (solid) 1621, 1595, 1575, 1554, 1508, 1480, 1410, 1385, 1320, 1254, 1240, 1212, 1166, 830, 819, 758; MS 394.4 (M+H)+

Example 171

(5-Methyl-2H-pyrazol-3-yl)-[2-(naphthalen-2-yloxy)-quinazolin-4-yl]-amine (IIb-2): Prepared in a manner similar to the above described Method B to afford a pale brown-solid, mp >300° C.; $^1$H NMR (DMSO) δ 1.62 (3H, s), 5.65 (1H, s), 7.96 (2H, br s), 7.55 (3H, d), 7.76 (2H, m), 7.92 (1H, d), 8.00 (2H, m), 8.58 (1H, d), 10.56 (1H, s), 11.99 (1H, s); IR (solid) 1625, 1601, 1571, 1556, 1479, 1377, 1315, 1250, 1236, 1210, 1159; MS 368.7 (M+H)+

Example 172

(5-Methyl-2H-pyrazol-3-yl)-(2-phenoxy-quinazolin-4-yl)-amine (IIb-3): Prepared in a manner similar to the above described Method B to afford a tan solid, mp 287–290° C.; $^1$H NMR (DMSO) δ 2.10 (3H, s), 5.92 (1H, s), 7.23 (2H, d), 7.29 (1H, t), 7.38 (1H, t), 7.46–7.53 (3H, m), 7.85 (1H, t), 8.58 (1H, d), 10.55 (1H, s), 12.11 (1H, s); IR (solid) 1622, 1602, 1572, 1556, 1542, 1477, 1454, 1402, 1373, 1316, 1249, 1200, 1172, 1158; MS 318.3(M+H)+

Example 173

(5-Cyclopropyl-2H-pyrazol-3-yl)-[2-(5,6,7,8-tetrahydronaphthalen-2-yloxy)-quinazolin-4-yl]-amine (IIb-4): Prepared in a manner similar to the above described Method B to afford a solid, mp 277–279° C.; $^1$H NMR (DMSO) δ 0.40–0.50 (2H, m), 0.89–0.96 (2H, m), 1.71–1.87 (5H, m), 2.70–2.83 (4H, m), 5.88 (1H, s), 6.88–6.96 (2H, m), 7.12 (1H, d), 7.39 (1H,t), 7.58 (1H, d), 7.76 (1H, t), 8.58 (1H, d), 10.54 (1H, s), 12.20 (1H, s); IR (solid) 1731, 1641, 1614, 1570, 1506, 1495, 1464, 1424, 1362, 1340, 1240, 880, 831, 812, 776, 758; MS 398.4 (M+H)+

Example 174

(5-Cyclopropyl-2H-pyrazol-3-yl)-[2-(3-methylphenoxy)-quinazolin-4-yl]-amine (IIb-5): Prepared in a manner similar to the above described Method B to afford an off-white solid, mp 283–284° C.; $^1$H NMR (DMSO) δ 0.49–0.53 (2H, m), 0.89–0.96 (2H, m), 1.72–1.81 (1H, m), 2.40 (3H, s), 5.82 (1H, s), 7.03 (1H, d), 7.08 (1H, s), 7.15 (1H, d), 7.35–7.46 (2H, m), 7.58 (1H, d), 7.78 (1H, t), 8.62 (1H, d), 10.58 (1H, s), 12.25 (1H, s); IR (solid) 1622, 1604, 1576, 1557, 1483, 1419, 1381, 1319, 1253, 1189, 1158, 997, 842, 789, 763; MS 358.4 (M+H)+

Example 175

[2-(3-Methoxyphenoxy)-quinazolin-4-yl]-(5-methyl-2H-pyrazol-3-yl)-amine (IIb-6): Prepared in a manner similar to the above described Method B to afford a white solid, mp 277–278° C.; $^1$H NMR (DMSO) δ 2.15 (3H, s), 3.78 (3H, s), 6.00 (1H, s), 6.77–6.90 (3H, m), 7.30–7.41 (2H, m), 7.52 (1H, d), 7.70 (1H, t), 8.59 (1H, d), 10.57 (1H, s), 12.10 (1H, s); IR (solid) 1623, 1603, 1575, 1556, 1487, 1456, 1430, 1373, 1316, 1253, 1192, 1142, 1046, 1022, 833, 760; MS 348.4 (M+H)+

Example 176

[2-(3,4-Dimethoxyphenoxy)-quinazolin-4-yl]-(5-methyl-2H-pyrazol-3-yl)-amine (IIb-7): Prepared in a manner similar to the above described Method B to afford an off-white solid, mp 277–278° C.; $^1$H NMR (DMSO) δ 2.09 (3H, s), 3.70 (3H, s), 3.78 (3H, s), 5.98 (1H, s), 6.73–6.77 (1H, m), 6.90 (1H, s), 7.00 (1H, d), 7.35–7.45 (1H, m), 7.58 (1H, d), 7.70–7.78 (1H, m), 8.63 (1H, d), 10.55 (1H, s), 12.19 (1H, s); IR (solid) 1626, 1603, 1576, 1557, 1509, 1481, 1436, 1409, 1382, 1372, 1318, 1249, 1227, 1195, 1180, 1158, 1120, 1029, 965, 835, 803, 767,753; MS 378.4 (M+H)$^+$

Example 177

[2-(Benzo[1,3]dioxol-5-yloxy)-quinazolin-4-yl]-(5-methyl-2H-pyrazol-3-yl)-amine (IIb-8): Prepared in a manner similar to-the above described Method B to afford an off-white solid, mp 296–299° C. (dec.); $^1$H NMR (DMSO) δ 2.13 (3H, s), 6.05 (1H, s), 6.09 (2H, s), 6.69 (1H, s), 6.90 (1H, s), 6.98 (1H, d), 7.39 (1H, t), 7.53 (1H, d), 7.70 (1H,t), 8.58 (1H, d), 10.59 (1H, s); IR (solid) 1602, 1577, 1538, 1508, 1499, 1481, 1455, 1401, 1377, 1323, 1251, 1241, 1169, 1121, 1038, 1022, 951, 935, 863, 813, 752; MS 362.4 (M+H)$^+$

Example 178

[2-(3-Methoxycarbonylphenoxy)-quinazolin-4-yl]-(5-methyl-2H-pyrazol-3-yl)-amine (IIb-9): Prepared in a manner similar to the above described Method B to afford an off-white solid, mp 269–270° C.; $^1$H NMR (DMSO) δ 2.05 (3H, s), 3.90 (3H, s), 5.88 (1H, s), 7.00–7.90 (7H, m), 8.50–8.65 (1H, m), 10.65 (1H, s); IR (solid) 1722, 1626, 1605, 1578, 1559, 1507, 1429, 1378, 1317, 1282, 1272, 1255, 1204, 1185, 1096, 1021, 990, 869, 841, 758; MS 362.4 (M+H)$^+$

Example 179

(5-Cyclopropyl-2H-pyrazol-3-yl)-(2-phenoxymethyl-quinazolin-4-yl)-amine (IId-1): Prepared in a manner similar to the above described Method C to afford a pale yellow solid, mp 265–267° C.; $^1$H NMR (DMSO) δ 0.67 (2H, m), 0.93 (2H, m), 1.87 (1H, m), 5.19 (2H, s), 6.55 (1H, br s), 6.90–7.02 (3H, m), 7.26–7.30 (2H, m), 7.54 (1H, m), 7.74–7.83 (2H, m), 8.61. (1H, m), 10.45 (1H, br s), 12.18 (1H, br s); MS 358.4 (M+H)$^+$

Example 180

(2-Benzyloxymethyl-quinazolin-4-yl)-(5-cyclopropyl-2H-pyrazol-3-yl)-amine (IId-2): Prepared in a manner similar to the above described Method C to afford a white solid, mp 211–213° C.; $^1$H NMR-(DMSO) δ 0.65 (2H, m), 0.90 (2H, m), 1.86 (1H, m), 4.63 (2H, s), 4.68. (1H, s), 6.71 (1H, s), 7.28–7.54 (6H, m), 7.76–7.81 (2H, m), 8.61 (1H, m), 10.41 (1H, s), 12.19 (1H, s); MS 372.3 (M+H)$^+$

Example 181

(2-Benzyl-quinazolin-4-yl)-(5-cyclopropyl-2H-pyrazol-3-yl)-amine (IId-3): Prepared in a manner similar to the above described Method D to afford a white solid, mp 219–221° C.; $^1$H NMR (DMSO) δ0.66 (2H, m), 0.95 (2H, m), 1.87 (1H, m), 4.11 (2H, s), 6.31 (1H, s), 7.20–7.50 (6H, m), 7.71–7.79 (2H, m), 8.55 (1H, m), 10.27 (1H, m), 12.15 (1H, s); MS 342.7 (M+H)$^+$

Example 182

(5-Cyclopropyl-2H-pyrazol-3-yl)-(2-methyl-quinazolin-4-yl)-amine (IId-4): Prepared in a manner similar to the above described Method C to afford a white solid, mp 289–290° C.; $^1$H NMR (DMSO) δ 2.31 (3H, s), 2.71 (3H, s), 6.73 (1H, s), 7.75 (2H, q), 8.04 (1H, t), 8.82 (1H, s), 11.94 (1H, s), 12.65 (1H, s); IR (solid) 3266, 1636, 1607, 1579, 1479, 1407, 769, 668; MS 240.4 (M+H)$^+$

Example 183

[2-(4-Chlorophenoxymethyl)-6,7,8,9-tetrahydro-5-cyclo-heptapyrimidin-4-yl]-(5-methyl-2H-pyrazol-3-yl)-amine (IId-5): Prepared in a manner similar to the above described Method C to afford a white solid; $^1$H NMR (DMSO) δ1.58 (2H, m), 1.68 (2H, m), 1.85 (2H, m), 2.20 (3H, s), 2.90 (2H, m), 3.00 (2H, m), 5.26 (2H, s), 6.15 (1H, s), 7.15 (2H, d), 7.40 (2H, d), 10.25 (1H, br); MS 384.3 (M+H)$^+$

Example 184

[2-(4-Chlorophenoxymethyl)-5,6,7,8-tetrahydro-quinazolin-4-yl]-(5-methyl-2H-pyrazol-3-yl)-amine (IId-6): Prepared in a manner similar to the above described Method C to afford a white solid; $^1$H NMR (DMSO) δ1.80 (4H, m), 2.15 (3H, s), 2.55 (2H, m obscured), 2.75 (2H, m), 5.25 (2H, s), 6.12 (1H, s), 7.08 (2H, d), 7.35 (2H, d), 9.80 (1H, br); MS 370.2 (M+H)$^+$

Example 185

(5-Cyclopropyl-2H-pyrazol-3-yl)-[2-(naphtalen-2-ylsulfanyl)-6-phenylpyrimidin-4-yl]-amine (IIa-1): Prepared in a manner similar to the above described Method L to afford a white solid, mp 233–234° C.; $^1$H NMR (DMSO) δ 0.21 (2H, br s), 0.56 (2H, br s), 1.17 (1H, br m), 5.35 (1H, br s), 7.02 (1H, br s), 7.49 (3H, m), 7.59 (2H, m), 7.73 (1H, d), 7.88 (2H, m), 8.02 (3H, m), 8.30 (1H, m), 10.01 (1H, s), 11.75 (1H, br s); IR (solid); MS 436.7(M+H)$^+$

Example 186

(5-Cyclopropyl-2H-pyrazol-3-yl)-[2-(3-methoxycarbonyl-phenylylsulfanyl)-6-phenylpyrimidin-4-yl]-amine (IIIa-2): Prepared in a manner similar to the above described Method L to afford a white solid, mp 126–129° C.; $^1$H NMR (DMSO) δ 0.52 (2H, m), 0.87 (2H, m), 1.69 (1H, m), 3.87 (3H, s), 5.47 (1H, s), 7.03 (1H, br s), 7.49 (3H, m), 7.67 (1H, m), 7.87 (2H, m), 7.94 (1H, m), 8.09 (1H, m), 8.23 (1H, m), 10.07 (1H, s), 11.94 (1H, s); IR (solid); MS 444.7(M+H)$^+$

Example 187

(5-Cyclopropyl-2H-pyrazol-3-yl)-[2-(naphthalen-2-ylsulfanyl)-pyrimidin-4-yl]-amine (IIIa-3): Prepared in a manner similar to the above described Method L to afford a white solid, mp 248–250° c; $^1$H NMR (DMSO) δ 0.21, (2H, br s), 0.55 (2H, br s), 0.94 (1H, br m), 5.31 (1H, br s), 6.55 (1H, br s), 7.57–7.66 (3H, m), 7.99–8.03 (4H, m), 8.25 (1H, s), 9.94 (1H, s), 11.75 (1H, br s); IR (solid); MS 360.7(M+H)$^+$

Example 188

(5-Cyclopropyl-2H-pyrazol-3-yl)-[5,6-dimethyl-2-(naphthalen-2-ylsulfanyl)-pyrimidin-4-yl]-amine (IIIa-4): Prepared in a manner similar to the above described Method L

Example 189

(5-Cyclopropyl-2H-pyrazol-3-yl)-[5-methyl-2-(naphthalen-2-ylsulfanyl)-pyrimidin-4-yl]-amine (IIIa-5): Prepared in a manner similar to the above described Method L to afford a white solid, mp 197° C.; $^1$H NMR (DMSO) δ 0.21 (2H, d), 0.51 (2H, d), 0.78 (1H, s), 2.08 (3H, s), 5.40 (1H, s), 7.57 (2H, d), 7.62 (1H, d), 7.92 (1H, s), 7.97 (3H, d), 8.22 (1H, s), 8.88 (1H, s), 11.70 (1H, s); IR (solid) 1738, 1583, 1563, 1488, 1460, 1364, 1234,1216, 808, 656; MS 374.2 (M+H)$^+$

Example 190

(5-Cyclopropyl-2H-pyrazol-3-yl)-[6-methyl-2-(naphthalen-2-ylsulfanyl)-pyrimidin-4-yl]-amine (IIIa-6): Prepared in a manner similar to the above described Method L to afford a white solid, mp 232° C.; $^1$H NMR (DMSO) δ 0.15 (2H, s), 0.51 (2H, s), 0.92 (1H, s), 2.20 (3H, s), 5.22 (1H, s), 7.60 (2H, s), 7.67 (1H, d), 7.98 (3H, s), 8.24 (1H, s), 9.79 (1H s), 11.60 (1H, s); IR (solid) 1586, 1508.7, 1485, 1282, 1180, 815, 788, 744, 674, 666; MS 374.2(M+H)$^+$

Example 191

(5-Cyclopropyl-2H-pyrazol-3-yl)-[6-(morpholin-4-yl)-2-(naphthalen-2-ylsulfanyl)-pyrimidin-4-yl]-amine (IIIa-7): To a solution of 2,4,6-trichloropyrimidine (600 mg, 3.27 mmol) and 3-amino-5-cyclopropylpyrazole (403 mg, 3.27 mmol) in EtOH (10 mL) was added triethylamine (456 μL, 3.27 mmol) and the reaction mixture was stirred for 15 hours at room temperature. The solvent was evaporated and the residue was purified by flash chromatography (SiO$_2$, Hexane/AcOEt gradient) to afford (5-cyclopropyl-2H-pyrazol-3-yl-)-(2,6-dichloropyrimidin-4-yl)-amine (705 mg, 80%).

To a solution of (5-cyclopropyl-2H-pyrazol-3-yl)-(2,6-dichloropyrimidin-4-yl)-amine (211 mg, 0.781 mmol) and 2-naphthalenethiol (125 mg, 0.781 mmol) in tert-butanol (5 mL) was added triethylamine (174 μL, 1.25 mmol) and the resulting mixture was heated at reflux for 15 hours. The reaction mixture was cooled to room temperature and partitioned between ethyl acetate and aqueous NaHCO$_3$. The organic layer was washed with brine, dried over MgSO$_4$ and concentrated in vacuo. The residue was purified by flash chromatography (SiO$_2$, Hexane/AcOEt gradient) to afford [6-chloro-2-(naphthalen-2-ylsulfanyl)-pyrimidin-4-yl]-(5-cyclopropyl-2H-pyrazol-3-yl)-amine.

The above formed [6-chloro-2-(naphthalen-2-ylsulfanyl)-pyrimidin-4-yl]-(5-cyclopropyl-2H-pyrazol-3-yl)-amine (70 mg, 1.78.10$^{-4}$ mol) was dissolved in morpholine (3 mL) and the mixture heated at 120° C. for 15 hours. The solvent was evaporated and the residue was purified by flash chromatography to afford IIIa-7 (50 mg, 63%) as a white solid, mp 118–120° C.; $^1$H NMR (DMSO) δ 0.34–0.91 (4H, 4×m), 1.28 and 1.78 (1H, 2×m), 3.32m (2H, m), 3.60 (6H, m), 5.38–6.16 (2H, br m), 7.55–7.66 (3H, m), 7.95–8.02 (3H, m), 8.19 and 8.23 (1H, 2×s), 9.28 and 9.31 (1H, 2×br s), 11.71 and 11.84 (1H, 2×br s); IR (solid); MS 445.2(M+H)$^+$

Example 192

(5-Cyclopropyl-2H-pyrazol-3-yl)-[6-(1-methylpiperazin-4-yl)-2-(naphthalen-2-ylsulfanyl)-pyrimidin-4-yl]-amine (IIIa-8): Prepared in a manner substantially similar to the method describe above for compound IIIb-7 to afford a white solid, mp 113–115° C.; $^1$H NMR (DMSO) δ 0.35–0.91 (4H, 4×m), 1.31 and 1.78 (1H, 2×m), 2.17 and 2.19 (3H, 2×s), 2.29 (4H, m), 3.35 (2H, m), 3.61 (2H, m), 5.38–6.20 (2H, br m), 7.55–7.66 (3H, m), 7.95–8.02 (3H, m), 8.17 and 8.23 (1H, 2×s), 9.26 and 9.32 (1H, 2×br s), 11.71 and 11.85 (1H, 2×br s); IR (solid); MS 458.3 (M+H)$^+$

Example 193

[6-(2,6-Dimethylphenyl)-2-(naphthalen-2-ylsulfanyl)-pyrimidin-4-yl]-(5-methyl-2H-pyrazol-3-yl)-amine (IIIa-9): Prepared in a manner similar to the above described Method L to afford an off-white solid, mp 148–152° C.; $^1$H NMR (DMSO) δ 2.10 (6H, s), 2.26 (3H, d), 5.09 and 6.31 (1H, 2×br s), 7.03 (3H, s), 7.22 (1H, s), 7.59 (2H, t), 7.69 (1H, d), 7.99 (3H, d), 8.28 (1H, s), 9.93 (1H, s), 11.67 (1H, br s); IR (solid) 2970, 1739, 1436, 1365, 1229, 1217, 1205; MS 438.3(M+H)$^+$

Example 194

[6-(2-Methylphenyl)-2-(naphthalen-2-ylsulfanyl)-pyrimidin-4-yl]-(5-methyl-2H-pyrazol-3-yl)-amine (IIIa-10): Prepared in a manner similar to the above described Method L to afford a white solid, mp 211–214° C.; $^1$H NMR (DMSO) δ 1.41 (3H, s), 2.30 (3H, s), 5.26 and 6.55 (1H, 2×br s), 7.34 (5H, m), 7.62 (2H, t), 7.70 (1H, d), 7.99 (3H, t), 8.30 (1H, s), 9.97 (1H, s), 11.73 (1H, br s); IR (solid) 2356, 1615, 1582, 1483, 1265, 851, 822, 761; MS 424.0(M+H)$^+$

Example 195

[2-(4-Acetamido-phenylsulfanyl)-6-phenyl-pyrimidin-4-yl]-(5-methyl-2H-pyrazol-3-yl)-amine (III-11): Prepared in a manner similar to the above described Method L to afford a white solid, mp 153–155° C.; $^1$H NMR (DMSO) δ 2.01 (3H, s), 2.08 (3H, s), 5.43 (1H, s), 6.96 (1H, br s), 7.49–7.88 (9H, m), 10.00 (1H, br s), 10.23 (1H, s), 11.86 (1H, br s); MS 417.2(M+H)$^+$

Example 196

(5-Methyl-2H-pyrazol-3-yl)-[2-(naphthalen-2-ylsulfanyl)-6-phenyl-pyrimidin-4-yl]-amine (IIIa-12): Prepared in a manner similar to the above described Method L to afford a white solid, mp 237–239° C.; $^1$H NMR (DMSO) δ 1.39 (3H, br s), 5.12 (1H, br s), 6.98 (1H, br s), 7.50 (3H, m), 7.62–7.63 (2H, m), 7.72 (1H, d), 7.90 (2H, m), 8.03–8.05 (3H, m), 8.31 (1H, s), 10.00 (1H, s), 11.73 (1H, br s); IR (solid) ; MS 410.2(M+H)$^+$

Example 197

[2-(4-Isobutyrylylamino-phenylsulfanyl)-6-phenylpyrimidin-4-yl]-(5-methyl-2H-pyrazol-3-yl)-amino (IIIa-13): Prepared in a manner similar to the above described Method L to afford an off-white solid, mp 201–202° C.; $^1$H NMR (DMSO) δ 1.05–1.13 (6H, m), 1.97 (3H, s), 2.65 (1H, m), 5.37 (1H, br s), 6.93 (1H, br.s), 7.50–7.58 (5H, m), 7.78–7.90 (4H, m), 9.99, 10.12 and 11.84 (3H, 3×br s); IR (solid) 1676, 1614, 1586, 1573, 1514, 1483, 1395, 1299, 1262, 1242, 1214, 1168, 1089, 988; MS 445.3(M+H)$^+$

Example 198

[6-(4-Methylpiperazin-1-yl)-2-methylsulfanyl-pyrimdn-4-yl]-(5-methyl-2H -pyrazol-3-yl)-amine (IIIa-14): Prepared in a manner similar to the above described Method M to afford an off-white solid; $^1$H NMR (DMSO) δ 2.18 (3H, s), 2.20 (3H, s), 2.36 (4H, m), 2.41 (3H, s), 3.46 (4H, m), 5.91 (1H, s), 6.41 (1H, br s), 9.20 (1H, s) 11.87 (1H, s); IR (solid); MS 320.3(M+H)$^+$

Example 199

(5-Methyl-2H-pyrazol-3-yl)-[6-phenyl-2-(4-propionylamino-phenylsulfanyl)-pyrimidin-4-yl]-amine (IIIa-15): Prepared in a manner similar to the above described Method L to afford a pale pink solid, mp 204–206° C.; $^1$H NMR (DMSO) δ 1.09–1.13 (3H, m), 2.00 (3H, s), 2.33–2.37 (2H, m), 5.40 (1H, br s), 6.95 (1H, br s), 7.50 (3H, m), 7.56–7.58 (2H, m), 7.76–7.78 (2H, m), 7.88 (2H, m), 9.99, 10.15 and 11.85 (3H, 3×br s); IR (solid) 1678, 1623, 1580, 1534, 1496, 1453, 1398, 1307, 1245, 1203, 1119, 1049, 1030, 1004; MS 431.2(M+H)$^+$

Example 200

[2-(4-Cyclopropanecarbonylamino-phenylsulfanyl)-6-phenylpyrimidin-4-yl]-(5-methyl-2H-pyrazol-3-yl)-amine (IIIa-16): Prepared in a manner similar to the above described Method L to afford an off-white solid, mp 253–255° C.; $^1$H NMR (DMSO) δ 0.82–0.83 (4H, m), 1.83 (1H, m), 2.00 (3H, s), 5.41 (1H, br s), 6.88 (1H, br s), 7.42–7.50 (3H, m), 7.56–7.58 (2H, m), 7.76–7.78 (2H, m), 7.89 (2H, m), 9.99, 110.47 and 11.85 (3H, 3×br s); IR (solid) 1672, 1621, 1591, 1581, 1573, 1537, 1495, 1448, 1405, 1390, 1312, 1254, 1246, 1202, 1192, 1179, 1119.2, 1005, 959; MS 443.2(M+H)$^+$

Example 201

(5-Methyl-2H-pyrazol-3-yl)-{6-phenyl-2-[4-(propane-1-sulfonylamino)-phenylsulfanyl]-pyrimidin-4-yl}-amine (IIIa-17): Prepared in a manner similar to the above described Method L to afford an off-white solid, mp 232–235° C.; $^1$H NMR (DMSO) δ 0.94 (3H, t), 1.71 (2H, m), 2.12 (3H,s), 3.13 (2H, t), 5.59 (1H, s), 7.31 (2H, d), 7.49 (3H, s), 7.59 (2H, d), 7.85. (2H, s), 10.00 (1H, br s), 10.16 (1H, s), 12.05 (1H, br s); IR (solid) 1628, 1587, 1545, 1525, 1496, 1455, 1311, 1255, 1236, 1212, 1186, 1140, 1032, 1001, 934; MS 481.2(M+H)$^+$

Example 202

(2-(4-Ethanesulfonylamino-phenylsulfanyl)-6-phenyl-pyrimidin-4-yl]-(5-methyl-2H-pyrazol-3-yl)-amine (IIIa-18): Prepared in a manner similar to the above described Method L to afford a pale yellow solid, mp 251–254° C.; $^1$H NMR (DMSO) δ 1.21 (3H, t), 2.12 (3H,s),3.15 (2H, q), 5.59 (1H, s), 7.32 (2H, d), 7.49 (3H, s), 7.57 (2H, d), 7.85 (2H, s), 9.99 (1H, br s), 10.15 (1H, br s), 11.90 (1H, br s); IR (solid) 1621, 1585, 1542, 1523, 1495, 1455, 1315, 1257, 1208, 1142, 1049, 1033, 1002, 932; MS 467.2(M+H)$^+$

Example 203

[2-(4-Acetamidophenyl-sulfanyl)-6-(2-methylphenyl)-pyrimidin-4-yl]-(5-methyl-2H-pyrazol-3-yl)-amine (IIIa-19): Prepared in a manner similar to the above described Method L to afford a white solid, mp 212–214° C.; $^1$H NMR (DMSO) δ 2.01 (3H, s), 2.08 (3H, s), 2.24 (3H, s), 5.43 (1H, s), 6.56 (1H, br s), 7.49–7.88 (9H, m), 10.00 (1H, br s), 10.23 (1H, s), 11.86 (1H, br s); IR (solid1701, 1634, 1588, 1555, 1496, 1390, 1307, 1208, 1169, 823, 803; MS 431.4(M+H)$^+$

Example 204

[2-(4-Isobutanecarbonylamino-phenyl-sulfanyl)-6-phenyl-pyrimidin-4-yl]-(5-methyl-2H-pyrazol-3-yl)-amine (IIIa-20): Prepared in a manner similar to the above described Method L to afford an off-white solid, mp 241–243° C., $^1$H NMR (DMSO) δ 0.95–0.96 (6H, m), 2.00 (3H, s), 2.11 (1H, m), 2.23–2.25 (2H, m, 5.43 (1H, br s), 6.95 (1H, br s), 7.50–7.58 (5H, m), 7.77–7.89 (4H, m), 10.00, 10.13 and 11.84 (3H, 3×br s); IR (solid) 1660, 1628, 1589, 1575, 1543, 1525, 1496, 1451, 1398, 1357, 1314, 1301, 1251, 1206, 1108, 995; MS 459.2 (M+H)$^+$

Example 205

[2-(4-Acetamido-phenyl-sulfanyl)-5-methyl-6-phenyl-pyrimidin-4-yl]-(5-methyl-2H-pyrazol-3-yl)-amine (IIIa-21): Prepared in a manner similar to the above described Method L to afford a pale pink solid, mp 276–277° C.; $^1$H NMR (DMSO) δ 1.98 (3H, s) 2.08 (6H, s), 5.41 (1H, br s), 7.47–7.55 (7H, m), 7.72–7.74 (2H, m), 8.89, 10.20 and 11.87 (3H, 3×br s); IR (solid) 1676, 1591, 1555, 1540, 1519, 1493, 1393, 1375, 1303, 1260, 1230, 1176, 1148, 1045, 1011, 969; MS 431.2 (M+H)$^+$

Example 266

[2-(4-Acetamido-phenyl-sulfanyl)-6-(4-methoxyphenyl)-pyrimidin-4-yl]-(5-methyl-2H-pyrazol-3-yl)-amine (IIIa-22): Prepared in a manner similar to the above described Method L to afford an off white solid, mp 241–245° C.; $^1$H NMR (DMSO) δ 1.99 (3H,s), 2.06 (3H, s), 3.82 (3H, s), 5.44 (1H, s), 7.03 (2H, d), 7.53 (2H, d), 7.71 (2H, s), 7.83 (2H, s), 10.12 (1H, s), 10.23 (1H, s), 11.84 (1H, s); IR (solid) 1627, 1606, 1571, 1511, 1313, 1257, 1181, 830; MS 447.2 (M+H)$^+$

Example 207

[6-(3-Acetamidophenyl)-2-(4-acetamido-phenyl-sulfanyl)-pyrimidin-4-yl]-(5-methyl-2H-pyrazol-3-yl)-amine (IIIa-23): Prepared in a manner similar to the above described Method L to afford a brown solid, mp 227–230° C.; $^1$H NMR (DMSO) δ 2.01 (3H, s), 2.11 (6H, s), 5.34 (1H, s), 6.99 (1H, br s), 7.41. (1H, t), 7.49–7.62 (3H, m), 3.71–3.76 (3H, m), 8.19 (1H s), 10.09–10.18 (2H, br s), 10.23 (1H, s), 12.20 (1H, br s); IR (solid) 1635, 1573, 1533, 1488, 1372, 1318, 1297, 827, 798; MS 474.3 (M+H)$^+$

Example 208

[2-(4-Isopropanesulfonylamino-phenyl-sulfanyl)-6-phenyl-pyrimidin-4-yl]-(5-methyl-2H-pyrazol-3-yl)-amine (IIIa-24): Prepared in a manner similar to the above described Method L to afford a white solid, mp 255–257° C.; $^1$H NMR (DMSO) δ 1.28 (6H, d), 2.14 (3H,s), 3.32 (1H, s), 5.60 (1H, s), 7.36 (2H, d), 7.49 (3H, s), 7.60 (2H, d), 7.85 (2H, s), 10.00 (1H, br s), 10.11 (1H, s), 11.92 (1H, br s); IR (solid) 1625, 1587, 1574, 1545, 1525, 1495, 1313, 1295, 1257, 1234, 1136, 1000, 934; MS 481.2 (M+H)$^+$

Example 209

(2-[4-(2-Dimethylamino-acetylamino)-phenylsulfanyl]-6-phenyl-pyrimidin-4-yl}-(5-methyl-2H-pyrazol-3-yl)-amine (IIIa-25): Prepared in a manner similar to the above described Method L to afford an off-white solid, mp 213–215° C.; $^1$H NMR (DMSO) δ2.00 (3H, s), 2.31 (6H, s), 3.15 (2H, s), 5.45 (1H, s), 6.83 (1H, br s), 7.46–7.51 (3H, m), 7.59 (2H, d), 7.80–7.92 (5H, m), 9.98 (1H, s), 10.05 (1H, s); IR (solid) 1701, 1617, 1587, 1571, 1509, 1480, 1456, 1304, 1284, 1254, 1238, 1213, 1181, 1156, 987, 833, 782, 754, 695; MS 460.3(M+H)$^+$

Example 210

[2-(3-Chloro-benzylsulfanyl)-6-morpholin-4-yl-pyrimidin-4-yl]-(5-methyl-2H-pyrazol-3-yl)-amine (IIIa-26): Prepared in a manner similar to the above described Method M to afford a white solid, mp 224–225° C.; $^1$H NMR (DMSO) δ 2.17 (3H, s), 3.40–3.50 (4H, m), 3.60–3.71 (4H, m), 4.30 (2H, s), 5.95 (1H, brs), 6.41 (1H, brs), 7.23–7.55 (4H, m), 9.31 (1H; s), 11.89 (1H, brs); IR (solid) 1557, 1476, 1442, 1401, 1314, 1232, 1121, 1018; MS 417.4 (M+H)$^+$

Example 211

[2-(3-Chloro-benzylsulfanyl)-6-(2-methoxy-ethylamino)-pyrimidin-4-yl-(5-methyl-2H-pyrazol-3-yl)-amine (IIIa-27): Prepared in a manner similar to the above described Method M to afford a white solid, mp 101–102° C.; $^1$H NMR (DMSO) δ 2.15 (3H, s), 3.21 (3H, s), 3.28–3.41 (4H, m), 4.29 (2H, s), 5.78 (1H, brs), 6.20 (1H, brs), 7.10 (1H, brs), 7.21–7.50 (4H, m), 9.01 (1H, brs); IR (solid) 1598, 1555, 1527, 1336, 1293, 1117, 1079, 974, 783; MS 405.4 (M+H)$^+$

Example 212

[2-Benzylsulfanyl-6-(4-methylpiperazin-1-yl)-pyrimidin-4-yl]-(5-methyl-2H-pyrazol-3-yl)-amine (IIIa-28): Prepared in a manner similar to the above described Method M to afford a yellow gum; $^1$H NMR (CDCl$_3$) δ 2.23 (3H, s), 2.28 (3H, s), 2.31–2.64 (4H, m), 3.30–3.65 (4H, m), 4.38 (2H, s), 5.83 (1H, s), 6.23 (1H, br s), 7.17–7.49 (5H, m), 7.98–8.18 (1H, m); IR (solid) 1555, 1494, 1371, 1315, 1286, 1233, 999, 977, 801, 774, 709; MS 396.4 (M+H)$^+$

Example 213

[2-Benzylsulfanyl-6-morpholin-4-yl-pyrimidin-4-yl]-(5-methyl-2H-pyrazol-3-yl)-amine (IIIa-29): Prepared in a manner similar to the above described Method M to afford an off-white foam; $^1$H NMR (CDCl$_3$) δ 2.31 (3H, s), 3.39–3.80 (8H, m), 4.39 (2H, s), 5.84 (1H, s), 6.25 (1H, brs), 7.20–7.50 (5H, m), 8.10 (1H, s); IR (solid) 1557, 1486, 1442, 1314, 1229, 1213, 1121, 767, 698; MS 383.4 (M+H)$^+$

Example 214

[2-(3-Chloro-benzylsulfanyl)-6-(4-methylpiperazin-1-yl)-pyrimidin-4-yl]-(5-methyl-2H-pyrazol-3-yl)-amine (IIIa-30): Prepared in a manner similar to the above described Method M to afford a white foam; $^1$H NMR (CDCl$_3$) δ 2.31 (3H, s),2.35 (3H, s), 2.40–2.51 (4H, m), 3.56–3.69 (4H, m), 4.34 (2H, s), 5.85 (1H, s), 6.29 (1H, brs), 6.89 (1H, s), 7.18–7.50 (4H, m); IR (solid) 1553, 1514, 1484, 1446, 1277, 1228, 999, 799; MS 430.4(M+H)$^+$

Example 215

[2-(4-methoxy-benzylsulfanyl)-6-(4-methylpiperazin-1-yl)-pyrimidin-4-yl]-(5 methyl-2H-pyrazol-3-yl)-amine (IIIa-31): Prepared in a manner similar to the above described Method M to afford a yellow oil; $^1$H NMR (CDCl$_3$) δ 2.28 (3H, s), 2.33 (3H, s), 2.44–2.45 (4H, m), 3.62 (4H, m), 3.80 (3H, s), 4.34 (2H, s), 5.32 (1H, s), 6.26 (1H, br s), 6.93–6.85 (2 H, m), 7.34–7.36 (2H, m); IR (solid) 1659, 1554, 1508, 1485, 1449, 1366, 1318, 1302, 1277, 1230, 1166, 1146, 1030, 999, 973, 948; MS 443.4 (M+H)$^+$

Example 216

[2-(4-Acetamido-phenyl-sulfanyl)-6-tert-butyl-pyrimidin-4-yl-(5-methyl-2H-pyrazol-3-yl)-amine (IIIa-32): Prepared in a manner similar to the above described Method L to afford a white solid, mp 227–228° C.; $^1$H NMR (DMSO) δ 1.10 (3H, br s), 1.20 (9H, s), 2.00 (3H, s), 2.35 (2H, q), 5.35 (1H, br s), 6.55 (1H, br s), 7.55 (2H, d), 7.75 (2H, d), 10.1 (1H, br s), 1.15 (1H, s), 12.1 (1H, br s); IR (solid); MS (M+H)$^+$

Example 217

(5-Cyclopropyl-2-pyrazol-3-yl)-[6-phenyl-2-(4-propionylamino-phenyl-sulfanyl)-pyrimidin-4-yl]-amine (IIIa-33): Prepared in a manner similar to the above described Method L to afford an off-white solid, mp 208–209° C., $^1$H NMR (DMSO) δ 0.52 (2H, m) 0.80 (2H, m), 1.08–1.10 (3H, m), 1.65 (1H, br s), 2.33–2.37 (2H, m), 5.50 (1H, br s), 7.03 (1H, br s), 7.47 (3H, m), 7.50–7.58 (2H, m), 7.76–7.77 (2H, m), 7.88–7.98 (2H, m), 10.00, 10.11 and 11.86 (3H, 3×br s); IR (solid) 1676, 1617, 1575, 1539, 1520, 1485, 1459, 1418, 1395, 1304, 1255, 1243, 1215, 1161, 1071, 990; MS 457.4 (M+H)$^+$

Example 218

[2-(3-Chloro-benzylsulfanyl)-6-(piperidin-1-yl)-pyrimidin-4-yl]-(5-methyl-2H-pyrazol-3-yl)-amine (IIIa-34): Prepared in a manner similar to the above described Method M to afford a white solid, mp 234–235° C.; $^1$H NMR (DMSO) δ 1.40–1.64 (6H, m), 2.13 (3H, s), 3.42–3.51 (4H, m), 4.27 (2H, 9), 5.85 (1H, br s), 6.46 (1H, brs), 7.23–7.41 (3H, m), 7.48 (1H, s), 9.18 (1H, s), 11.83 (1H, s); IR (solid) 1598, 1546, 1483, 1398, 1317, 1227, 974, 798, 779; MS 415.4 (M+H)$^+$

Example 219

(5-Methyl-2H-pyrazol-3-yl)-(2-[4-(morpholinesulfonyl)-benzylsulfanyl]-6-morpholin-4-yl-pyrimidin-4-yl)-amine (IIIa-35): Prepared in a manner similar to the above described Method M to afford a white solid; $^1$H NMR (DMSO) δ 2.24.(3H, s), 2.90–3.01 (4H, m), 3.29–3.36 (4H, m), 3.48–3.57 (4H, m), 3.67–3.75 (4H, m), 4.43 (2H, s), 5.82–6.10 (2H, m), 7.50–7.70 (5H, m); IR (solid) 1550, 1483, 1441, 1346, 1308, 1255, 1160, 1112, 941, 726; MS 532.5 (M+H)$^+$

Example 220

{6-(2-Methoxy-ethylamino)-2-[4-(morpholinesulfonyl)-benzylsulfonyl]-pyrimidin-4-yl}-(5-methyl-2H-pyrazol-3-yl)-amine (IIIa-36): Prepared in a manner similar to the above described Method M to afford a white solid, mp 193–195° C.; ¹H NMR (DMSO) δ 2.15 (3H, s), 2.79–2.89 (4H, m), 3.34 (3H, s), 3.40–3.51 (4H, m), 3.59–3.67 (4H, m), 4.41 (2H, s), 5.76–5.72 (1H, m), 6.20 (1H, brs), 7.10 (1H, brs), 7.61–7.74 (4H, m), 9.03 (1H, brs), 11.81 (1H, brs); IR (solid) 1593, 1555, 1484, 1350, 1298, 1255, 1160, 1107, 936; MS 520.5 (M+H)⁺

Example 221

{6-(4-methylpiperazin-1-yl)-2-[4-(morpholinesulfonyl)-benzylsulfanyl]-pyrimidin-4-yl}-(5-methyl-2H-pyrazol-3-yl)-amine (IIIa-37): Prepared in a manner similar to the above described Method M to afford a white solid, mp 206–207° C.; ¹H NMR (DMSO) δ 2.09 (3H, s), 2.20 (3H, s), 2.26–2.40 (4H, m), 2.78–2.88 (4H, m), 3.38–3.49 (4H, m), 3.56–3.67 (4H, m), 4.41 (2H, s), 5.82.(1H, brs), 6.42 (1H, brs), 7.60–7.74 (4H, m), 9.26 (1H, s), 11.89 (1H, brs); IR (solid) 1583, 1558, 1479, 1346, 1231, 1160, 1112, 998, 969, 926; MS 545.5 (M+H)⁺

Example 222

[6-Methoxymethyl-2-(4-propionylamino-phenyl-sulfanyl)-pyrimidin-4-yl]-(5-methyl-2H-pyrazol-3-yl)-amine (IIIa-38): Prepared in a manner similar to the above described Method L to afford a white solid; ¹H NMR (DMSO) δ 1.03–1.14 (3H, m), 2.00. (3H, s), 2.29–2.40 (2H, m), OMe under DMSO, 4.22 (2H, m), 5.26.(1H, brs), 6.45 (1H, brs), 7.44–7.56 (2H, m), 7.68–7.80 (2H, m), 9.86 (1H, brs), 10.11 (1H, s), 11.79 (1H, brs); IR (solid) 1670, 1593, 1517, 1479, 1393, 1360, 1269, 1174, 1107; MS 399.4 (M+H)⁺

Example 223

[2-(4-Methoxycarbonyl-phenyl-sulfanyl)-6-methoxymethyl-pyrimidin-4-yl]-(5-methyl-2H-pyrazol-3-yl)-amine (IIIa-39): Prepared in a manner similar to the above described Method L to afford a white solid, mp 204–205° C.; ¹H NMR (DMSO) δ 1.89 (3H, brs), 3.85 (3H, s), OMe under DMSO, 4.23 (2H, s), 5.22 (1H, brs), 6.51 (1H, brs), 7.70–7.81 (2H, m), 7.96–8.06 (2H, m), 9.99 (1H, brs), 11.85 (1H, brs); IR (solid) 1721, 1621, 1583, 1519, 1484, 1289, 1271, 1178, 1119, 1109, 997, 841; MS 386.3 (M+H)⁺

Example 224

[2-(3,5-Dimethoxy-benzylsulfanyl)-6-morpholin-4-yl-pyrimidin-4-yl]-(5-methyl-2H-pyrazol-3-yl)-amine (IIIa-40): Prepared in a manner similar to the above described Method M to afford a white solid; ¹H NMR (DMSO) δ 2.15 (3H, s), 3.40–3.49 (4H, m), 3.60–3.74 (10H, m), 4.25 (2H, s), 5.88 (1H, brs), 6.31–6.61 (5H, m), 9.32 (1H, s), 11.86 (1H, s); IR (solid) 1581, 1556, 1470, 1439, 1315, 1232, 1205, 1159, 1144; MS 443.4 (M+H)⁺

Example 225

[2-(3,5-Dimethoxy-benzylsulfanyl)-6-pyrrolidin-4-yl-pyrimidin-4-yl]-(5-methyl-2H-pyrazol-3-yl)-amine (IIIa-41): Prepared in a manner similar to the above described Method M to afford a white solid; ¹H NMR (DMSO) δ 1.80–1.97 (4H, m), 2.15 (3H, s), 3.43–3.45 (4H, m), 3.69 (6H, s), 4.26 (2H, s), 5.85. (1H, brs), 6.18 (1H, brs), 6.35 (1H, brs), 6.60 (2H, s), 9.12 (1H, s), 11.88 (1H, s); IR (solid1598, 1560, 1474, 1470, 1346, 1303, 1207, 1136, 1050; MS 427.4 (M+H)⁺

Example 226

(5-Methyl-2H-pyrazol-3-yl)-[6-morpholin-4-yl-2-(naphthalene-2-ylmethylsulfanyl)-pyrimidin-4-yl]-amine (IIIa-42): Prepared in a manner similar to the above described Method M to afford an off-white solid; ¹H NMR (DMSO) δ 2.15 (3H, s), 3.37–3.50 (4H, m), 3.59–3.70 (4H, m), 4.48 (2H, s), 5.88 (1H, brs), 6.40 (1H, brs), 7.40–7.60 (3H, m), 7.78–7.95 (4H, m), 9.30 (1H, s), 11.89 (1H, brs); IR (solid) 1607, 1555, 1484, 1441, 1398, 1365, 1308, 1231, 1179, 1112; MS 433.4 (M+H)⁺

Example 227

{2-(4-Acetamido-phenyl-sulfanyl)-6-[4-(3-dimethylamino-propoxy)-phenyl]-pyrimidin-4-yl}-(5-methyl-2H-pyrazol-3-yl)-amine (IIIa-43): Prepared in a manner similar to the above described Method N to afford a white solid, mp 219–222° C.; ¹H NMR (CDCl₃) δ 1.97–2.07 (2H, m), 2.14 (3H, s), 2.18 (3H, s), 2.30 (6H, s), 2.52 (2H, t), 4.09 (2H, t), 5.56 (1H, s), 6.80 (1H, br s), 6.99 (2H, d), 7.60 (2H, d), 7.68–7.78 (3H, m), 7.85 (2H, d); IR (solid) 1606, 1590, 1512, 1482, 1309, 1250, 1238, 1210, 1178, 1151, 1055, 989, 824, 711, 690, 665, 656; MS 518.4 (M+H)⁺

Example 228

[2-(4-Acetamidophenylsulfanyl)-6-(morpholin-4-yl)-pyrimidin-4-yl]-(5-methyl-2H-pyrazol-3-yl)-amine (IIIa-44): Prepared in a manner similar to the above described Method P to afford a white solid; MS 426.4 (M+H)⁺

Example 229

[6-Hydroxymethyl-2-(4-propionylamino-phenyl-sulfanyl)-pyrimidin-4-yl]-(5-methyl-2H-pyrazol-3-yl)-amine (IIIa-45): Prepared from IIIa-48 according to Method O to afford a white solid; ¹H NMR (DMSO) δ 1.08–1.18 (3H, m), 1.96 (3H, brs), 2.29–2.40 (2H, m), 4.20–4.40 (3H, m), 5.20–5.46 (2H, m), 6.56 (1H, s), 7.50 (2H, d), 7.79 (2H, d), 9.90 (1H, brs), 10.13 (1H, s), 11.78 (1H, brs); MS 385.4 (M+H)⁺

Example 230

[2-(4-Acetamido-phenyl-sulfanyl)-pyrimidin-4-yl]-(5-methyl-2H-pyrazol-3-yl)-amine (IIIa-46): Prepared in a manner similar to the above described Method L to afford an off-white solid, mp 249–250° C.; ¹H NMR (DMSO) δ 1.99 (3H, s), 2.08 (3H, s), 5.38 (1H, br s), 6.45 (1H, br s), 7.50 (2H, d), 7.71 (2H, d), 7.98 (1H, d), 9.89 (1H, br s), 10.19 (1H, br s), 11.83 (1H, br s); IR (solid) 1657, 1609, 1584, 1515, 1494, 1468, 1395, 1372, 1355, 1330, 1316, 1201, 1175, 1157, 1027, 993; MS 341.4 (M+H)⁺

Example 231

[6-(1-Butoxycarbonyl)-2-(4-propionylamino-phenyl-sulfanyl)-pyrimidin-4-yl]-(5-methyl-2H-pyrazol-3-yl)-amine (IIIa-47): Prepared in a manner similar to the above described Method L to afford a yellow solid, ¹H NMR (DMSO) δ 0.90–0.98 (3H, m), 1.03–1.12 (3H, m), 1.31–1.45 (2H, m), 1.60–1.71 (2H, m), 1.94. (3H, brs), 2.29–2.40 (2H, m), 4.20–4.30 (2H, m), 5.25 (1H, brs), 7.08 (1H, brs), 7.49–7.55 (2H, m), 7.72–7.81 (2H, m), 10.15 (1H, brs), 10.32 (1H, brs), 11.89 (1H, brs); IR (solid) 1736, 1679, 1622, 1584, 1517, 1489, 1284, 1174; MS 455.4 (M+H)⁺

Example 232

[6-Methoxycarbonyl-2-(4-propionylamino-phenyl-sulfanyl)-pyrimidin-4-yl]-(5-methyl-2H-pyrazol-3-yl)-amine (IIIa-48): Prepared in a manner similar to the above described Method L to afford a yellow solid; $^1$H NMR (DMSO) δ 1.10 (3H, t), 1.94 (3H, brs), 2.35 (2H, q), 3.84 (3H, s), 5.22 (1H, brs), 7.05 (1H, s), 7.52 (2H, d), 7.79 (2H, d), 10.18 (1H, brs), 10.38 (1H, brs), 11.89 (1H, brs); IR (solid) 1741, 1679, 1617, 1589, 1512, 1484, 1374, 1284, 1250; MS 413.4 (M+H)$^+$

Example 233

(5-Methyl-2H-pyrazol-3-yl)-(6-phenyl-2-phenylamino-pyrimidin-4-yl)-amine (IIIc-1): white solid; MS 343.4 (M+H)$^+$

Example 234

(5-Cyclopropyl-2H-pyrazol-3-yl)-(6-phenyl-2-phenylamino-pyrimidin-4-yl)-amine (IIIc-2): white solid, mp 267–269° C.; $^1$H NMR (DMSO) δ 0.63 (2H, m), 0.96 (2H, m), 1.87 (1H, m), 6.07 (1H, s), 6.84 (1H, br s), 7.20 (1H, m), 7.33–8.05 (9H, m), 10.52 (1H, br s), 11.08 (1H, br s), 12.53 (1H, br s); IR (solid); MS 369.7 (M+H)$^+$

Example 235

(5-Cyclopropyl-2H-pyrazol-3-yl)-[2-(3-methylphenylamino)-6-phenyl-pyrimidin-4-yl]-amine (IIIc-3): white solid, mp 267–270° C.; $^1$H NMR (DMSO) δ 0.63 (2H, m), 0.94 (2H, m), 1.87 (1H,m), 2.36 (3H, s), 6.12 (1H, s), 6.81 (1H, br s), 7.03 (1H, m), 7.29–7.94 (8H, m), 10.43 (1H, br s), 11.12 (1H, br s), 12.47 (1H, br s); IR (solid); MS 383.7 (M+H)$^+$

Example 236

[2-(4-cyanomethylphenylamino)-6-phenyl-pyrimidin-4-yl]-(5-cyclopropyl-2H-pyrazol-3-yl)-amine (IIIc-4): pale yellow solid, mp 294–297° C.; $^1$H NMR (DMSO) δ 0.64 (2H, m), 097 (2H, m), 1.89 (1H, m), 4.06 (2H, s), 6.07 (1H, s), 6.87 (1H, br s), 7.40 (2H, m), 7.63–7.90 (5H, m), 7.95 (2H, m), 10.51 (1H, br s), 11.02 (1H, br s), 12.57 (1H, br s); IR (solid); MS 408.8 (M+H)$^+$

Example 237

(5-Cyclopropyl-2H-pyrazol-3-yl)-[6-phenyl-2-(pyridin-3-ylmethylamino)-pyrimidin-4-yl]-amine (IIIc-5): off-white solid, mp 191–193° C.; $^1$H NMR (DMSO) δ 0.65 (2H, m), 0.89 (2H, m), 1.83 (1H, m) 4.59. (2H, s), 6.04 (1H, br s), 6.76 (1H, br s), 7.32–7.56 (5H, m), 7.77 (1H, m), 7.88–7.97 (2H, m), 8.43 (1H, m), 8.61 (1H, s) 9.47 (1H, br s), 11.93.(1H, br s); IR (solid); MS 384.8 (M+H)$^+$

Example 238

[2-(3-Chlorophenyl)amino-6-(3-nitrophenyl)-pyrimidin-4-yl]-(5-methyl-2H-pyrazol-3-yl)-amine (IIIc-6): off-white solid; $^1$H NMR (CD$_3$OD) δ 5.95 (1H, s), 6.65 (1H, s), 6.90 (1H, d), 7.18 (1H, t), 7.32 (1H, d), 7.58 (1H, t), 7.82 (1H, s), 8.18 (1H, d), 8.25 (1H, d), 8.65 (1H, s) ; MS 422.1 (M+H)$^+$

Example 239

[2-(3-Chlorophenyl)amino-6-(3,4,5-trimethoxyphenyl)-pyrimidin-4-yl]-(5-methyl-2H-pyrazol-3-yl)-amine (IIIc-7): white solid; MS 467.7 (M+H)$^+$

Example 240

(5-Methyl-2H-pyrazol-3-yl)-[2-(4-sulfamoylphenylamino)-6-(3,4,5-trimethoxyphenyl)-pyrimidin-4-yl]-amine (IIIc-8): white solid; MS 512.6 (M+H)$^+$

Example 241

[2-(4-Chlorophenyl)amino-6-methyl-pyrimidin-4-yl]-[5-(furan-2-yl)-2H-pyrazol-3-yl]-amine (IIIc-9): white solid; MS 367.1 (M+H)$^+$

Example 242

[2-(Benzimidazol-2-ylamino-)6-ethyl-pyrimidin-4-yl]-(5-methyl-2H-pyrazol-3-yl)-amine (IIIc-10): MS 335.5 (M+H)$^+$

Example 243

[2-(4-Chlorophenyl)amino-6-methyl-pyrimidin-4-yl]-(5-phenyl-2H-pyrazol-3-yl)-amine (IIIc-11): MS 377.5 (M+H)$^+$

Example 244

[2-(4-Chlorophenyl)amino-6-ethyl-pyrimidin-4-yl]-(5-methyl-2H-pyrazol-3-yl)-amine (IIIc-12): MS 329.4 (M+H)$^+$

Example 245

(5-tert-Butyl-2H-pyrazol-3-yl)-[2-(3-chlorophenyl)amino-6-(3-nitrophenyl)-pyrimidin-4-yl]-amine (III-13): off-white solid; $^1$H NMR (CD$_3$OD) δ 1.32 (9H, s), 6.18 (1H, s), 7.04 (1H, s), 7.14 (1H, d), 7.35 (1H, t), 7.58 (1H, d), 7.82 (1H, t), 7.91 (1H, s), 8.35 (1H, d), 8.40 (1H, d), 8.90 (1H, s); MS 464.2 (M+H)$^+$

Example 246

[2-(3-Chlorophenyl)amino-6-(3-nitrophenyl)-pyrimidin-4-yl]-(5-phenyl-2H-pyrazol-3-yl)-amine (IIIc-14): δ off-white solid; $^1$H NMR (CD$_3$OD) δ 6.66 (1H, s), 7.12 (1H, d), 7.30–7.45 (5H, m), 7.50 (1H, d), 7.62 (2H, d), 7.78 (1H, t), 7.88 (1H, s), 8.35 (1H, d), 8.42 (1H, d), 8.85 (1H, s); MS 484.1 (M+H)$^+$

Example 247

[5-(Furan-2-yl)-2H-pyrazol-3-yl]-(6-phenyl-2-phenylamino-pyrimidin-4-yl)-amine (IIIc-15): MS 395.4 (M+H)$^+$

Example 248

[2-(Benzimidazol-2-ylamino)-6-methyl-pyrimidin-4-yl]-(5-phenyl-2H-pyrazol-3-yl)-amine (IIIc-16): MS 383.2 (M+H)$^+$

Example 249

[2-(Benzimidazol-2-ylamino)-6-methyl-pyrimidin-4-yl]-[5-(Furan-2-yl)-2H-pyrazol-3-yl]-amine (IIIc-17): MS 373.4 (M+H)$^+$

Example 250

[2-(4-Chlorophenylamino)-6-methyl-pyrimidin-4-yl]-(5-methyl-2H-pyrazol-3-yl)-amine (IIIc-18): MS 315.4 (M+H)$^+$

Example 251

[2-(4-Chlorophenyl)amino-5,6-dimethyl-pyrimidin-4-yl]-(5-methyl-2H-pyrazol-3-yl)-amine-(IIIc-19): MS 329.4 (M+H)$^+$

Example 252

(5,6-Dimethyl-2-phenylamino-pyrimidin-4-yl)-(5-methyl-2H-pyrazol-3-yl)-amine (IIIc-20): MS 295.5 (M+H)$^+$

Example 253

[2-(4-Chlorophenyl)amino-6-methoxymethyl-pyrimidin-4-yl]-(5-methyl-2H-pyrazol-3-yl)-amine (IIIc-21): MS 345.1 (M+H)$^+$

Example 254

[2-(Benzimidazol-2-ylamino)-6-methoxymethyl-pyrimidin-4-yl]-(5-methyl-2H-pyrazol-3-yl)-amine (IIIc-22): MS 35.1.2 (M+H)$^+$

Example 255

(6-Methoxymethyl-2-phenylamino-pyrimidin-4-yl)-(5-methyl-2H-pyrazol-3-yl)-amine (IIIc-23): MS 311.2 (M+H)$^+$

Example 256

(6-Methyl-2-phenylamino-pyrimidin-4-yl)-(5-methyl-2H-pyrazol-3-yl)-amine (IIIc-24): MS 2.81.1 (M+H)$^+$

Example 257

[2-5(2-Chlorophenoxymethyl)-6-methyl-pyrimidin-4-yl]-(5-phenyl-2H-pyrazol-3-yl)-amine (IIId-1): MS 392.1 (M+H)$^+$

Example 258

[2-(2-Chlorophenoxymethyl)-6-methyl-pyrimidin-4-yl]-[5-(furan-2-yl)-2H-pyrazol-3-yl]-amine (IIId-2): MS 382.1 (M+H)$^+$

Example 259

(6-methyl-2-phenoxymethyl-pyrimidin-4-yl)-(5-phenyl-2H-pyrazol-3-yl)-amine (IIId-3): MS 358.2 (M+H)$^+$

Example 260

[5-(Furan-2-yl)-2H-pyrazol-3-yl]-(6-methyl-2-phenoxymethyl-pyrimidin-4-yl)-amine (IIId-4): MS 348.2 (M+H)$^+$

Example 261

[5-(Furan-2-yl)-2H-pyrazol-3-yl]-(6-methyl-2-phenylsulfanylmethyl-pyrimidin-4-yl)-amine (IIId-5): MS 364.1 (M+H)$^+$

Example 262

[6-Methyl-2-(4-methyl-phenylsulfanylmethyl)-pyrimidin-4-yl]-(5-phenyl-2H-pyrazol-3-yl)-amine (IIId-6): MS 388.1 (M+H)$^+$

Example 263

[5-(Furan-2-yl)-2H-pyrazol-3-yl]-[6-Methyl-2-(4-methyl-phenylsulfanylmethyl)-pyrimidin-4-yl]-amine (IIId-7): MS 378.1 (M+H)$^+$

Example 264

(2-(4-Fluoro-phenoxymethyl)-6-methyl-pyrimidin-4-yl]-(5-phenyl-2H-pyrazol-3-yl)-amine (IIId-8): MS 376.2 (M+H)$^+$

Example 265

[2-(4-Fluoro-phenoxymethyl)-6-methyl-pyrimidin-4-yl]-[5-(furan-2-yl)-2H-pyrazol-3-yl]-amine (IIId-9): MS 366.2 (M+H)$^+$

Example 266

(6-Ethyl-2-phenylsulfanylmethyl-pyrimidin-4-yl)-(5-methyl-2H-pyrazol-3-yl)-amine (IIId-10): MS 326.2 (M+H)$^+$

Example 267

(6-Ethyl-2-phenoxymethyl-pyrimidin-4-yl)-(5-methyl-2H-pyrazol-3-yl)-amine (IIId-11): MS 310.2.(M+H)$^{30}$

Example 268

[6-Ethyl-2-(4-fluorophenoxymethyl)-pyrimidin-4-yl]-(5-methyl-2H-pyrazol-3-yl)-amine (IIId-12): MS 328.2 (M+H)$^+$

Example 269

[6-Ethyl-2-(1-methyl-1-phenyl-ethyl)-pyrimidin-4-yl]-(5-methyl-2H-pyrazol-3-yl)-amine (IIId-13): MS 322.2 (M+H)$^+$

Example 270

[2-(4-Chlororophenoxymethyl)-6-methyl-pyrimidin-4-yl]-(5-phenyl-2H-pyrazol-3-yl)-amine (IIId-14): MS392.2 (M+H)$^+$

Example 271

[2-(4-Chlororophenoxymethyl)-6-methyl-pyrimidin-4-yl-(-methyl-2H-pyrazol-3-yl)-amine (IIId-15): MS 330.2 (M+H)$^+$

Example 272

[2-(4-Chlororophenoxymethyl)-6-methoxymethyl-pyrimidin-4-yl]-(5-methyl-2H-pyrazol-3-yl)-amine (IIId-16): white solid; $^1$H NMR (DMSO) δ 2.20 (3H, s), 3.43 (3H, s), 4.49 (2H, s), 5.20 (2H, s), 6.05 (1H, br), 7.05 (2H, d), 7.33 (2H, d), 10.55 (1H, br) MS 360.2 (M+H)$^+$

Example 273

[2-(4-Chlorophenoxymethyl)-6-methyl-pyrimidin-4-yl]-5-(furan-2-yl)-2H-pyrazol-3-yl]-amine (IIId-17): MS 382.2 (M+H)$^+$

Example 274

(5-Methyl-2H-pyrazol-3-yl)-(2-phenylsulfanylmethyl-5,6,7,8-tetrahydro-quinazolin-4-yl)-amine (IId-7): MS 352.5 (M+H)$^+$

Example 275

[2-(4-Methylphenylsulfanylmethyl)-6,7,8,9-tetrahydro-5H-cycloheptapyrimidin-4-yl -(5-methyl-2H-pyrazol-3-yl)-amine (IId-8): MS 380.2 (M+H)$^+$

Example 276

[2-(1-Methyl-1-phenyl-ethyl)-6,7,8,9-tetrahydro-5H-cycloheptapyrimidin-4-yl]-(5-methyl-2H-pyrazol-3-yl)-amine (IId-9): MS 362.3 (M+H)$^+$

Example 277

[2-(2,6-Dichlorobenzyl)-5,6,7,8-tetrahydro-quinazolin-4-yl]-(5-methyl-2H-pyrazol-3-yl)-amine (IId-10): MS 388.1 (M+H)$^+$

Example 278

[7-Benzyl-2-(2,6-dichlorobenzyl)-5,6,7,8-tetrahydropyrido[3,4-d]pyrimidin-4-yl]-(5-methyl-2H-pyrazol-3-yl)-amine (IId-11): MS 479.5 (M+H)$^+$

Example 279

[6-Benzyl-2-(4-chlorophenoxymethyl)-5,6,7,8-tetrahydro-pyrido[4,3-d]pyrimidin-4-yl]-(5-methyl-2H-pyrazol-3-yl)-amine (IId-12): MS 461.2 (M+H)$^+$

Example 280

[2-(4-Chlorophenoxymethyl)-5,6,7,8-tetrahydro-pyrido[4,3-d]pyrimidin-4-yl]-(5-methyl-2H-pyrazol-3-yl)-amino (IId-13): MS 371.3 (M+H)$^+$

Example 281

[2-(2,6-Dichlorobenzyl)-6-methyl-pyrimidin-4-yl]-(5-methyl-2H-pyrazol-3-yl)-amine (IIId-18): MS 348.1 (M+H)$^+$

Example 282

[2-(2,6-Dichlorobenzyl -5,6-dimethyl-pyrimidin-4-yl]-(5-methyl-2H-pyrazol-3-yl)-amine (IIId-19): white solid; $^1$H NMR (DMSO) □ 8.50 (1H, s), 7.70. (1H, d), 7.3–7.1 (3H, m), 5.25 (1H, s), 4.10 (1H, s), 2.30 (3H, s), 2.10 (3H, s), 1.80 (3H, s); MS 362.1 (M+H)$^+$

Example 283

(1H-Indazol-3-yl)-[2-(2-phenyl-cyclopropyl)-quinazolin-4-yl]-amine (IId-16): $^1$H NMR (DMSO) 13.2(1H, s), 12.0 (1H, s), 8.76(1H, m), 8.10(1H, m), 7.85(2H, m), 7.75(1H, m), 7.61(1H, m) 7.41(1H, m), 7.30(2H, m), 7.20(2H, m), 7.12(2H, m), 2.35(2H, m), 1.60(1H, m), 1.35(1H, m); MS: m/z, 378.1 MH+; HPLC-R$_t$=3.21 min.

Example 284

(7-Fluoro-1H-indazol-3-yl)-[2-(2-phenyl-cyclopropyl)-quinazolin-4-yl]-amine (IId-17): $^1$H NMR (DMSO) 13.8 (1H, s), 12.05(1H, s), 8.75(1H, m), 8.10(1H, m), 7.85(2H, m), 7.60(1H, m), 7.35(3H, m) 7.25–7.10(4H, m), 2.35(2H, m), 1.60(1H, m), 1.35(1H, m); MS: m/z, 396.1 MH+; HPLC R$_t$=3.26 min.

Example 285

(5-Fluoro-1H-indazol-3-yl)-[2-(2-phenyl-cyclopropyl)-quinazolin-4-yl]-amine (IId-18): $^1$HNMR (DMSO) 13.3(1H, s), 12.0(1H, s), 8.75(1H, m), 8.10(1H, m), 7.85 (2H, m), 7.65(2H, m), 7.35(3H, m) 7.20(1H, m), 7.10(2H, m) 2.40.(2H, m), 1.65.(1H, m), 1.35(1H, m); MS: m/z, 396.1 MH+; HPLC R$_t$=3.26 min.

Example 286

(5-Methyl-1H-pyrazol-3-yl)-[2-(2-phenyl-cyclopropyl)-quinazolin-4-yl]-amine (IId-19): $^1$HNMR (DMSO) 12.8 (1H, s), 11.90(1H, s), 8.80(1H, m), 8.10(1H, m), 7.85(2H, m), 7.30–7.20(5H, m), 6.55 (1H, s) 2.80 (1H, m), 2.55(1H, m), 2.35 (3H,s) 2.00(2H, m); MS: m/z, 342.1 MH+; HPLC R$_t$=3.13 min.

Biological Testing

The activity of the compounds as protein kinase inhibitors may be assayed in vitro, in vivo or in a cell line. In vitro assays include assays that determine inhibition of either the phosphorylation activity or ATPase activity of the activated protein kinase. Alternate in vitro assays quantitate the ability of the inhibitor to bind to the protein kinase. Inhibitor binding may be measured by radiolabelling the inhibitor prior to binding, isolating the inhibitor/protein kinase complex and determining the amount of radiolabel bound. Alternatively, inhibitor binding may be determined by running a competition experiment where new inhibitors are incubated with the protein kinase bound to known radioligands.

Biological Testing Example 1

K$_i$ Determination for the Inhibition of GSK-3

Compounds were screened for their ability to inhibit GSK-3β (AA 1-420) activity using a standard coupled enzyme system (Fox et al. (1998) *Protein Sci.* 7, 2249). Reactions were carried out in a solution containing 100 mM HEPES (pH 7.5), 10 mM MgCl$_2$, 25 mM NaCl, 300 µM NADH, 1 mM DTT and 1.5% DMSO. Final substrate concentrations in the assay were 20 µM ATP (Sigma Chemicals, St Louis, Mo.) and 300 µM peptide (HSSPHQS (PO$_3$H$_2$)EDEEE, American Peptide, Sunnyvale, Calif.). Reactions were carried out at 30° C. and 20 nM GSK-3β. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above with the exception of ATP and the test compound of interest. The assay stock buffer solution (175 µl) was incubated in a 96 well plate with 5 µl of the test compound of interest at final concentrations spanning 0.002 μM to 30 μM at 30° C. for 10 min. Typically, a 12 point titration was conducted by preparing serial dilutions (from 10 mM compound stocks) with DMSO of the test compounds in daughter plates. The reaction was initiated by the addition of 20 μl of ATP (final concentration 20 μM). Rates of reaction were obtained using a Molecular Devices Spectramax plate reader (Sunnyvale, Calif.) over 10 min at 30° C. The $K_i$ values were determined from the rate data as a function of inhibitor concentration.

The following compounds were shown to have $K_i$ values less than 0.1 μM for GSK-3: IIa-2, IIa-3, IIa-8, IIa-9, IIa-11, IIa-12,-IIa-17, IIa-18, IIa-21 to IIa-24, IIa-26, IIa-28, IIa-30 through IIa-32, IIa-39, IIa-43, IIa-46, IIa-47, IIa-61, IIc-3, IIc-6, IIc-8, IIc-10 through IIc-12, IIc-15, IIc-18, IIc-20 through IIc-22, IIc-24, IIc-25, IIc-27, IIc-30 through IIc-32, IIc-35 to IIc-39, IIc-42, IIc-53, IIc-61, IIc-67, IIc-77, IIc-78, IIb-1, IIb-3, IIb-5, IIb-8, IId-1, IIIa-2, IIIa-3, IIIa-6, IIIa-17, IIIa-18, IIIa-24, IIIa-27, IIIc-2 through IIIc-5, IIIc-9, IIIc-11, IIIc-12, IIIc-15, IIIc-18, IIIc-19, IIIc-21, IIIc-24, IIIb-1 through IIIb-6, IIIb-8 through IIIb-10, IIIb-13, IIIb-14, IIId-20, IIId-21, IId-14, and IId-19.

The following compounds were shown to have $K_i$ values between 0.1 and 1.0 μM for GSK-3: IIa-1, IIa-4, IIa-5, IIa-7, IIa-14, IIa-15, IIa-20, IIa-29, IIa-34 through IIa-36, IIa-38, IIa-41, IIa-42, IIa-48, IIa-54, IIa-55, IIa-62, IIa-63, IIa-66, IIa-69, IIa-78, IIc-1, IIc-2, IIc-4, IIc-5, IIc-$7_1$ IIc-9, IIc-13, IIc-14, IIc-16, IIc-17, IIc-19, IIc-23, IIc-26, IIc-28, IIc-29, IIc-33, IIc-34, IIc-40, IIc-41, IIc-43 through IIc-45, IIc-47 through IIc-52, IIc-54 through IIc-57, IIc-59, IIc-63 through IIc-66, IIc-72, IIc-75, IIc-76, IIc-79, IIc-6, IIb-7, IIb-9, IId-2, IId-5, IId-6, IIIa-1, IIIa-4, IIIa-5, IIIa-7, IIIa-8, IIIa-10, IIIa-11, IIIa-19, IIIa-22, IIIa-23, IIIa-26, IIIa-29, IIIa-30, IIIa-31, IIIa-33, IIIa-34, IIIa-37, IIIa-42, III-1, IIIc-8, IIIc-20, IIIc-23, IIIb-7, IIIb-11, IIIb-12, IIIb-15, IIIb-16, IId-16, IId-17, and IId-18.

The following compounds were shown to have $K_i$ values between 1.0 and 7.0 μm for GSK-3: IIa-10, IIa-13, IIa-25, IIa-40, IIa-45, IIa-49, IIa-50 through IIa-52, IIa-64, IIa-65, IIa-67, IIa-68, IIa-71, IIa-72, IIa-74, IIa-76, IIa-77, IIa-81, IIc-58, IIc-60, IIc-62, IIc-68 through IIc-71, IIc-74, IId-3, IId-4, III-15, IIIa-16, IIIa-21, IIIa-28, IIIa-35, IIIa-36, IIIa-38, IIIa-41, IIIa-43, IIIa-45, IIIa-49, IIIc-10, IIIc-16, IIIc-17, and IIIc-22.

Biological Testing Example 2

$K_i$ Determination for the Inhibition of Aurora-2

Compounds were screened in the following manner for their ability to inhibit Aurora-2 using a standard coupled enzyme assay (Fox et al (1998) *Protein Sci* 7, 2249).

To an assay stock buffer solution containing 0.1M HEPES-7.5, 10 mM $MgCl_2$, 1 mM DTT, 25 mM NaCl, 2.5 mM phosphoenolpyruvate, 300 mM NADH, 30 mg/ml pyruvate kinase, 10 mg/ml lactate dehydrogenase, 40 mM ATP, and 800 μM peptide (LRRASLG, American Peptide, Sunnyvale, Calif.) was added a DMSO solution of a compound of the present invention to a final concentration of 30 μM. The resulting mixture was incubated at 30° C. for 10 min. The reaction was initiated by the addition of 10 μL of Aurora-2 stock solution to give a final concentration of 70 nM in the assay. The rates of reaction were obtained by monitoring absorbance at 340 nm over a 5 minute read time at 30° C. using a BioRad Ultramark plate reader (Hercules, Calif.). The $K_i$ values were determined from the rate data as a function of inhibitor concentration.

The following compounds were shown to have $K_i$ values less than 0.1 μM for Aurora-2: IIa-1 through IIa-18, IIa-21 through IIa-64, IIa-66, IIa-68, IIa-69, IIa-71 through IIa-78, IIa-81, IIc-1 through IIc-13, IIc-15 through IIc-44, IIc-46 through IIc-61, IIc-63 through IIc-65, IIc-67 through IIc-69, IIb-1 through IIb-9, IId-1 through IId-3, IIIa-1 through IIIa-8, IIIa-10 through IIIa-13, IIIa-15 through IIIa-32, IIIa-36 through IIIa-41, IIIa-44 through IIIa-49, IIIc-1 through IIIc-5, IIIc-12, and IIIc-15.

The following compounds were shown to have $K_i$ values between 0.1 and 1.0 μM for Aurora-2: IIa-20, IIa-65, IIa-67, IIa-70, IIa-80, IIc-14, IIc-66, IId-5, IId-6, IIIa-14, IIIa-33 through IIIa-35, IIIc-9, IIIc-11, IIIb-1, IIIb-2, IIIb-7, IIIb-10 through IIIb-13, IIIb-15, IIIb-16, and IIId-20.

The following compounds were shown to have $K_i$ values between 1.0 and 10.0 μM for Aurora-2: IIa-10, IIc-71, IIc-75, IIc-76, IId-4, IIIa-42, IIIa-43, IIIc-10, IIIb-3-6, IIIb-8, IIIb-9, and IIIb-14.

Biological Testing Example 3

CDK-2 Inhibition Assay

Compounds were screened in the following manner for their ability to inhibit CDK-2 using a standard coupled enzyme assay (Fox et al (1998) *Protein Sci* 7, 2249).

To an assay stock buffer solution containing 0.1M HEPES 7.5, 10 mM $MgCl_2$, 1 mM DTT, 25 mM NaCl, 2.5 mM phosphoenolpyruvate, 300 mM NADH, 30 mg/ml pyruvate kinase, 10 mg/ml lactate dehydrogenase, 100 mM ATP, and 100 μM peptide (MAHHHRSPRKRAKKK, American Peptide, Sunnyvale, Calif.) was added a DMSO solution of a compound of the present invention to a final concentration of 30 μM. The resulting mixture was incubated at 30° C. for 10 min.

The reaction was initiated by the addition of 10 μL of CDK-2/Cyclin A stock solution to give a final concentration of 25 nM in the assay. The rates of reaction were obtained by monitoring absorbance at 340 nm over a 5-minute read time at 30° C. using a BioRad Ultramark plate reader (Hercules, Calif.). The $K_i$ values were determined from the rate data as a function of inhibitor concentration.

The following compounds were shown to have $K_i$ values less than 1 μM for CDK-2: IIa-14, IIa-36, IIc-15, IIc-25, IIc-27, IIc-32, IIc-53, and IIIc-4.

The following compounds were shown to have $K_i$ values between 1.0 and 20.0 μM for CDK-2: IIa-38, IIa-40, IIa-44, IIa-52, and IIa-54.

Biological Testing Example 4

ERK Inhibition Assay

Compounds were assayed for the inhibition of ERK2 by a spectrophotometric coupled-enzyme assay (Fox et al (1998) *Protein Sci* 7, 2249). In this assay, a fixed concentration of activated ERK2 (10 nM) was incubated with various concentrations of the compound in DMSO (2.5%) for 10 min. at 30° C. in 0.1 M HEPES buffer, pH 7.5, containing 10 mM $MgCl_2$, 2.5 mM phosphoenolpyruvate, 200 μM NADH, 150 μg/mL pyruvate kinase, 50 μg/mL lactate dehydrogenase, and 200 μM erktide peptide. The reaction was initiated by the addition of 65 μM ATP. The rate of decrease of absorbance at 340 nM was monitored. The $IC_{50}$ was evaluated from the rate data as a function of inhibitor concentration.

The following compounds were shown to have $K_i$ values less than 1 μM for ERK-2: IIc-15, IIc-27, IIc-32, IIc-53, and IIIc-4.

The following compounds were shown to have $K_i$ values between 1.0 and 20.0 μM for ERK-2: IIc-18, IIc-25, and IIa-36.

Biological Testing Example 5

AKT Inhibition Assay

Compounds were screened for their ability to inhibit AKT using a standard coupled enzyme assay (Fox et al., Protein Sci., (1998) 7, 2249). Assays were carried out in a mixture of 100 mM HEPES 7.5, 10 mM MgCl2, 25 mM NaCl, 1 mM DTT and 1.5% DMSO. Final substrate concentrations in the assay were 170 μM ATP (Sigma Chemicals) and 200 μM peptide (RPRAATF, American Peptide, Sunnyvale, Calif.). Assays were carried out at 30° C. and 45 nM AKT. Final concentrations of the components of the coupled enzyme system were 2.5 mM phosphoenolpyruvate, 300 μM NADH, 30 μg/ML pyruvate kinase and 10 μg/ml lactate dehydrogenase.

An assay stock buffer solution was prepared containing all of the reagents listed above, with the exception of AKT, DTT, and the test compound of interest. 56 μl of the stock solution was placed in a 384 well plate followed by addition of 1 μl of 2 mM DMSO stock containing the test compound (final compound concentration 30 μM). The plate was pre-incubated for about 10 minutes at 30° C. and the reaction initiated by addition of 10 μl of enzyme (final concentration 45 nM) and 1 mM DTT. Rates of reaction were obtained using a BioRad Ultramark plate reader (Hercules, Calif.) over a 5 minute read time at 30° C. Compounds showing greater than 50% inhibition versus standard wells containing the assay mixture and DMSO without test compound were titrated to determine $IC_{50}$ values.

The following compounds were shown to have $K_i$ values between 1.0 and 20.0 μM for AKT-3: IIc-18, IIc-22, IIc-25, IIc-27, IIc-31, IIc-32, IIc-37, IIc-39, IIc-42, and IIc-53.

Biological Testing Example 6

SRC Inhibition Assay

The compounds were evaluated as inhibitors of human Src kinase using either a radioactivity-based assay or spectrophotometric assay.

Src Inhibition Assay A: Radioactivity-based Assay

The compounds were assayed as inhibitors of full length recombinant human Src kinase (from-Upstate Biotechnology, cat. no. 14-117) expressed and purified from baculo viral cells. Src kinase activity was monitored by following the incorporation of $^{33}P$ from ATP into the tyrosine of a random poly Glu-Tyr polymer substrate of composition, Glu:Tyr=4:1 (Sigma, cat. no. P-0275). The following were the final concentrations of the assay components: 0.05 M HEPES, pH 7.6, 10 mM MgCl$_2$, 2 mM DTT, 0.25 mg/ml BSA, 10 μM ATP (1–2 μCi $^{33}$P-ATP per reaction), 5 mg/ml poly Glu-Tyr, and 1–2 units of recombinant human Src kinase. In a typical assay, all the reaction components with the exception of ATP were pre-mixed and aliquoted into assay plate wells. Inhibitors dissolved in DMSO were added to the wells to give a final DMSO concentration of 2.5%. The assay plate was incubated at 30° C. for 10 min before initiating the reaction with $^{33}$P-ATP. After 20 min of reaction, the reactions were quenched with 150 μl of 10% trichloroacetic acid (TCA) containing 20 mM Na$_3$PO$_4$. The quenched samples were then transferred to a 96-well filter plate (Whatman, UNI-Filter GF/F Glass Fiber Filter, cat no. 7700-3310) installed on a filter plate vacuum manifold. Filter plates were washed four times with 10% TCA containing 20 mM Na$_3$PO$_4$ and then 4 times with methanol. 200 μl of scintillation fluid was then added to each well. The plates were sealed and the amount of radioactivity associated with the filters was quantified on a TopCount scintillation counter. The radioactivity incorporated was plotted as a function of the inhibitor concentration. The data was fitted to a competitive inhibition kinetics model to get the $K_i$ for the compound.

Src Inhibition Assay B: Spectrophotometric Assay

The ADP produced from ATP by the human recombinant Src kinase-catalyzed phosphorylation of poly Glu-Tyr substrate was quantified using a coupled enzyme assay (Fox et al (1998) *Protein Sci* 7, 2249). In this assay one molecule of NADH is oxidised to NAD for every molecule of ADP produced in the kinase reaction. The disappearance of NADH can be conveniently followed at 340 nm.

The following were the final concentrations of the assay components: 0.025 M HEPES, pH 7.6, 10 mM MgCl2, 2 mM DTT, 0.25 mg/ml poly Glu-Tyr, and 25 nM of recombinant human Src kinase. Final concentrations of the components of the coupled enzyme system were 2.5 mM phosphoenolpyruvate, 200 μM NADH, 30 μg/ml pyruvate kinase and 10 μg/ml lactate dehydrogenase.

In a typical assay, all the reaction components with the exception of ATP were pre-mixed and aliquoted into assay plate wells. Inhibitors dissolved in DMSO were added to the wells to give a final DMSO concentration of 2.5%. The assay plate was incubated at 30° C. for 10 min before initiating the reaction with 100 μM ATP. The absorbance change at 340 nm with time, the rate of the reaction, was monitored on a molecular devices plate reader. The data of rate as a function of the inhibitor concentration was fitted to competitive inhibition kinetics model to get the $K_i$ for the compound.

The following compounds were shown to have a $K_i$ value of <100 nM on SRC: IIa-8, IIa-21, IIa-23, IIa-24, IIa-27, IIa-28, IIa-30 through IIa-33, IIb-1, IIb-4, IIb-5, IIc-3, IIc-8, IIc-10, IIc-13, IIc-15, IIc-18, IIc-19, IIc-21 through IIc-24, IIc-31 through IIc-35, IIc-37 through IIc-39, IIc-41 through IIc-44, IIc-51, IId-1, IId-2, IIIa-1, IIIa-6 through IIIa-8, IIIa-26 through IIIa-30, and IIIc-1 through IIIc-5.

The following compounds were shown to have a $K_i$ value of between 100 nM and 1 μM for SRC: IIa-1, IIa-2, IIa-7, IIa-9, IIa-12, IIa-14, IIa-22, IIa-25, IIa-26, IIa-29, IIa-34 through IIa-42, IIa-46, IIa-47, IIa-49 through IIa-52, IIa-56, IIa-57, IIa-59, IIa-61, IIa-62, IIa-66, IIa-67, IIa-69, IIa-72, IIa-73, IIa-75, IIb-6, IIb-8, IIc-4 through IIc-7, IIc-9, IIc-11, IIc-12 IIc-14, IIc-16, IIc-17, IIc-20, IIc-25 through IIc-30, IIc-36, IIc-40, IIc-46 through IIc-50, IIc-52 through IIc-61, IIc-63 through IIc-65, IIc-67, IIc-69, IId-3, IIIa-2 through IIIa-5, IIIa-11, IIIa-14 through-IIIa-18, IIIa-22 is through IIIa-24, IIIa-31, IIIa-33, IIIa-35, IIIa-38 through IIIa-43, and IIIa-47.

The following compounds were shown to have a $K_i$ value of between 1 μM and 6 μM for SRC: IIa-13, IIa-20, IIa-44, IIa-45, IIa-48, IIa-54, IIa-55, IIa-63, IIa-65, IIa-68, IIa-70, IIa-71, IIa-74, IIa-77, IIa-78, IIa-81, IIb-3, IIb-9, IIc-1, IIc-2,-IIc-66, IIc-68, IIIa-13, IIIa-21, IIIa-25, IIIa-34, IIIa-36, IIIa-37, and IIIa-44.

While we have presented a number of embodiments of this invention, it is apparent that our basic construction can be altered to provide other embodiments which utilize the compounds and methods of this invention. Therefore, it will be appreciated that the scope of this invention is to be defined by the appended claims rather than by the specific embodiments which have been represented by way of example.

We claim:
1. A compound of formula IV:

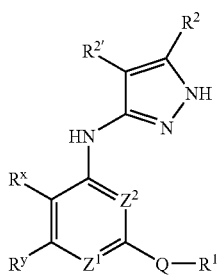

IV or a pharmaceutically acceptable derivative thereof, wherein:

$Z^1$ is nitrogen or C—$R^8$ and $Z^2$ is nitrogen or CH, wherein one and only one of $Z^1$ or $Z^2$ is nitrogen;

Q is selected from —N($R^4$)—, —O—, —S—, —C($R^6$)$_2$—, 1,2-cyclopropanediyl, 1,2-cyclobutanediyl, or 1,3-cyclobutanediyl;

$R^x$ and $R^y$ are independently selected from T—$R^3$ or L—Z—$R^3$, or $R^x$ and $R^y$ are taken together with their intervening atoms to form a fused, unsaturated or partially unsaturated, 5–7 membered ring having 0–3 ring heteroatoms selected from oxygen, sulfur, or nitrogen, wherein each substitutable ring carbon of said fused ring formed by $R^x$ and $R^y$ is independently substituted by oxo, T—$R^3$, or L—Z—$R^3$, and each substitutable ring nitrogen of said ring formed by $R^x$ and $R^y$ is independently substituted by $R^4$;

$R^1$ is T-(Ring D);

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein each substitutable ring carbon of Ring D is independently substituted by oxo, T—$R^5$, or V—Z—$R^5$, and each substitutable ring nitrogen of Ring D is independently substituted by —$R^4$;

T is a valence bond or a $C_{1-4}$ alkylidene chain, wherein when Q is —CH($R^6$)—, a methylene unit of said $C_{1-4}$ alkylidene chain is optionally replaced by —O—, —S—, —N($R^4$)—, —CO—, —CONH—, —NHCO—, —SO$_2$—, —SO$_2$NH—, —NHSO$_2$—, —CO$_2$—, —OC(O)—, —OC(O)NH—, or —NHCO$_2$—;

Z is a $C_{1-4}$ alkylidene chain;

L is —O—, —S—, —SO—, —SO$_2$—, —N($R^6$)SO$_2$—, —SO$_2$N($R^6$)—, —N($R^6$)—, —CO—, —CO$_2$—, —N($R^6$)CO—, —N($R^6$)C(O)O—, —N($R^6$)CON($R^6$)—, —N($R^6$)SO$_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)SO$_2$N($R^6$)—, or —C($R^6$)$_2$N($R^6$)CON($R^6$)—;

$R^2$ and $R^{2'}$ are independently selected from —R, —T—W—$R^6$, or $R^2$ and $R^{2'}$ are taken together with their intervening atoms to form a fused, 5–8 membered, unsaturated or partially unsaturated, ring having 0–3 ring heteroatoms selected from nitrogen, oxygen, or sulfur, wherein each substitutable ring carbon of said fused ring formed by $R^2$ and $R^{2'}$ is independently substituted by halo, oxo, —CN, —NO$_2$, —$R^7$, or —V—$R^6$, and each substitutable ring nitrogen of said ring formed by $R^2$ and $R^{2'}$ is independently substituted by $R^4$;

$R^3$ is selected from —R, -halo, —OR, —C(=O)R, —CO$_2$R, —COCOR, —COCH$_2$COR, —NO$_2$, —CN, —S(O)R, —S(O)$_2$R, —SR, —N($R^4$)$_2$, —CON($R^7$)$_2$, —SO$_2$N($R^7$)$_2$, —OC(=O)R, —N($R^7$)COR, —N($R^7$)CO$_2$($C_{1-6}$ aliphatic), —N($R^4$)N($R^4$)$_2$, —C=NN($R^4$)$_2$, —C=N—OR, —N($R^7$)CON($R^7$)$_2$, —N($R^7$)SO$_2$N($R^7$)$_2$, —N($R^4$)SO$_2$R, or —OC(=O)N($R^7$)$_2$;

each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;

each $R^4$ is independently selected from —$R^7$, —COR$^7$, —CO$_2$(optionally substituted $C_{1-6}$ aliphatic), —CON($R^7$)$_2$, or —SO$_2$R$^7$;

each $R^5$ independently selected from —R, halo, —OR, —C(=O)R, —CO$_2$R, —COCOR, —NO$_2$, —CN, —S(O)R, —SO$_2$R, —SR, —N($R^4$)$_2$, —CON($R^4$)$_2$, —SO$_2$N($R^4$)$_2$, —OC(=O)R, —N($R^4$)COR, —N($R^4$)CO$_2$(optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)SO$_2$N($R^4$)$_2$, —N($R^4$)SO$_2$R, or —OC(=O)N($R^4$)$_2$;

V is —O—, —S—, —SO—, —SO$_2$—, —N($R^6$)SO$_2$—, —SO$_2$N($R^6$)—, —N($R^6$)—, —CO—, —CO$_2$—, —N($R^6$)CO—, —N($R^6$)C(O)O—, —N($R^6$)CON($R^6$)—, —N($R^6$)SO$_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)SO$_2$N($R^6$)—, or —C($R^6$)$_2$N($R^6$)CON($R^6$)—;

W is —C($R^6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N($R^6$)—, —CO—, —CO$_2$—, —C($R^6$)OC(O)—, —C($R^6$)OC(O)N($R^6$)—, —C($R^6$)$_2$N($R^6$)CO—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)SO$_2$N($R^6$)—, —C($R^6$)$_2$N($R^6$)CON($R^6$)—, or —CON($R^6$)—;

each $R^6$ is independently selected from hydrogen or an optionally substituted $C_{1-4}$ aliphatic group, or two $R^6$ groups on the same nitrogen atom are taken together with the nitrogen atom to form a 5–6 membered heterocyclyl or heteroaryl ring;

each $R^{6'}$ is independently selected from hydrogen or a $C_{1-4}$ aliphatic group, or two $R^{6'}$ on the same carbon atom are taken together to form a 3–6 membered carbocyclic ring;

each $R^7$ is independently selected from hydrogen or an optionally substituted $C_{1-6}$ aliphatic group, or two $R^7$ on the same nitrogen are taken together with the nitrogen to form a 5–8 membered heterocyclyl or heteroaryl ring; and $R^8$ is selected from —R, halo, —OR, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$(optionally substituted $C_{1-6}$ aliphatic), —N(R$^4$)N(R$^4$)$_2$, $R^1$ is T-(Ring D), wherein T is a valence bond or a methylene unit;

(c) Ring D is a 5–7 membered monocyclic or an 8–10 membered bicyclic aryl or heteroaryl ring; and (d) $R^2$ is —R or —T—W—R$^6$ and $R^{2'}$ is hydrogen, or $R^2$ and $R^{2'}$ are taken together to form an optionally substituted benzo ring.

3. The compound according to claim 2, wherein:

(a) $R^x$ is hydrogen, alkyl- or dialkylamino, acetamido, or a $C_{1-4}$ aliphatic group and $R^y$ is T—R$^3$ or L—Z—R$^3$, wherein T is a valence bond or a methylene and $R^3$ is —R, —N(R$^4$)$_2$, or —OR; or $R^x$ and $R^y$ are taken together with their intervening atoms to form a fused, unsaturated or partially unsaturated, 5–6 membered ring having 0–2 heteroatoms selected from oxygen, sulfur, or nitrogen, wherein each substitutable ring carbon of said fused ring formed by $R^x$ and $R^y$ is independently substituted by oxo, T—R$^3$, or L—Z—R$^3$, and each substitutable ring nitrogen of said ring formed by $R^x$ and $R^y$ is independently substituted by R$^4$;

(b) $R^1$ is T-(Ring D), wherein T is a valence bond or a methylene unit;

(c) Ring D is a 5–7 membered monocyclic or an 8–10 membered bicyclic aryl or heteroaryl ring; and (d) $R^2$ is —R or —T—W—R$^6$ and $R^2$ is hydrogen, or $R^{2'}$ and $R^{2'}$ are taken together to form an optionally substituted benzo ring.

4. The compound according to claim 2, wherein said compound has one or more features selected from the group consisting of:

(a) $R^y$ is T—R$^3$ or L—Z—R$^3$ wherein T is a valence bond or a methylene and $R^3$ is selected from —R, —OR, or —N(R$^4$)$_2$, wherein R is selected from hydrogen $C_{1-6}$ aliphatic, or 5–6 membered heterocyclyl, phenyl, or 5–6 membered heteroaryl; or $R^x$ and $R^y$ are taken together with their intervening atoms to form a benzo, pyrido, cyclopento, cyclohexo, cyclohepto, thieno, piperidino, or imidazo ring, wherein each substitutable ring carbon of said fused ring formed by $R^x$ and $R^y$ is independently substituted by oxo, T—R$^3$, or L—Z—R$^3$, and each substitutable ring nitrogen of said ring formed by $R^x$ and $R^y$ is independently substituted by R$^4$;

(b) $R^1$ is T-(Ring D), wherein T is a valence bond, and Ring D is a 5–6 membered monocyclic or an 8–10 membered bicyclic aryl or heteroaryl ring;

(c) $R^2$ is —R and $R^{2'}$ is hydrogen, wherein R is selected from hydrogen, $C_{1-6}$ aliphatic, phenyl, a 5–6 membered heteroaryl ring, or a 5–6 membered heterocyclic ring; and (d) $R^3$ is selected from —R, -halo, —OR, or —N(R$^4$)$_2$, wherein R is selected from hydrogen, $C_{1-6}$ aliphatic, or 5–6 membered heterocyclyl, phenyl, or 5–6 membered heteroaryl, and L is —O—, —S—, or —N(R$^4$)—.

5. The compound according to claim 4, wherein:

(a) $R^y$ is T—R$^3$ or L—Z—R$^3$ wherein T is a valence bond or a methylene and $R^3$ is selected from —R, —OR, or —N(R$^4$)$_2$, wherein R is selected from hydrogen, $C_{1-6}$ aliphatic, or 5–6 membered heterocyclyl, phenyl, or 5–6 membered heteroaryl; or $R^x$ and $R^y$ are taken together with their intervening atoms to form a benzo, pyrido, cyclopento, cyclohexo, cyclohepto, thieno, piperidino, or imidazo ring, wherein each substitutable ring carbon of said fused ring formed by $R^x$ and $R^y$ is independently substituted by oxo, T—R$^3$, or L—Z—R$^3$, and each substitutable ring nitrogen of said ring formed by $R^x$ and $R^y$ is independently substituted by R$^4$;

(b) $R^1$ is T-(Ring D), wherein T is a valence bond, and Ring D is a 5–6 membered monocyclic or an 8–10 membered bicyclic aryl or heteroaryl ring;

(c) $R^2$ is —R and $R^{2'}$ is hydrogen, wherein R is selected from hydrogen, $C_{1-6}$ aliphatic, phenyl, a 5–6 membered heteroaryl ring, or a 5–6 membered heterocyclic ring; and (d) $R^3$ is selected from —R, -halo, —OR, or —N(R$^4$)$_2$, wherein R is selected from hydrogen, $C_{1-6}$ aliphatic, or 5–6 membered heterocyclyl, phenyl, or 5–6 membered heteroaryl, and L is —O—, —S—, or —N(R$^4$)—.

6. The compound according to claim 4, wherein said compound has one or more features selected from the group consisting of:

(a) $R^x$ is hydrogen methyl, ethyl, propyl, cyclopropyl, isopropyl, methylamino or acetamido and $R^y$ is selected from 2-pyridyl, 4-pyridyl, pyrrolidinyl, piperidinyl, morpholinyl, piperazinyl, methyl, ethyl, cyclopropyl, isopropyl, t-butyl, alkoxyalkylamino, alkoxyalkyl, alkyl- or dialkylamino, alkyl- or dialkylaminoalkoxy, acetamido, optionally substituted phenyl, or methoxymethyl; or $R^x$ and $R^y$ are taken together with their intervening atoms to form a benzo, pyrido, piperidino, or cyclohexo ring, wherein said ring is optionally substituted with -halo, —R, —OR, —COR, —CO$_2$R, —CON(R$^4$)$_2$, —CN, —O(CH$_2$)$_{2-4}$—N(R$^4$)$_2$, —O(CH$_2$)$_{2-4}$—R, —NO$_2$, —N(R$^4$)$_2$, —NR$^4$COR, —NR$^4$SO$_2$R, or —SO$_2$N(R$^4$)$_2$, wherein R is hydrogen or an optionally substituted $C_{1-6}$ aliphatic group;

(b) $R^1$ is T-(Ring D), wherein T is a valence bond and Ring D is a 5–6 membered aryl or heteroaryl ring optionally substituted with one or two groups selected from -halo, —CN, —NO$_2$, —N(R$^4$)$_2$, optionally substituted $C_{1-6}$ aliphatic, —OR, —C(O)R, —CO$_2$R, —CONH(R$^4$), —N(R$^4$)COR, —N(R$^4$)CO$_2$R, —SO$_2$N(R$^4$)$_2$, —N(R$^4$)SO$_2$R, —N(R$^6$)COCH$_2$N(R$^4$)$_2$, —N(R$^6$)COCH$_2$CH$_2$N(R$^4$)$_2$, or —N(R$^6$)COCH$_2$CH$_2$CH$_2$N(R$^4$)$_2$;

(c) $R^2$ is hydrogen or a substituted or unsubstituted group selected from aryl, heteroaryl, or a $C_{1-6}$ aliphatic group, and $R^{2'}$ is hydrogen; and (d) $R^3$ is selected from —R, —OR, or —N(R$^4$)$_2$, wherein R is selected from hydrogen, $C_{1-6}$ aliphatic, 5–6 membered heterocyclyl, phenyl, or 5–6 membered heteroaryl, and L is —O—, —S—, or —NH—; and (e) Ring D is substituted by up to three substituents selected from -halo, —CN, —NO$_2$, —N(R$^4$)$_2$, optionally substituted $C_{1-6}$ aliphatic group, —OR, —C(O)R, —CO$_2$R, —CONH(R$^4$), —N(R$^4$)COR, —N(R$^4$)CO$_2$R, —SO$_2$N(R$^4$)$_2$, —N(R$^4$)SO$_2$R, —N(R$^6$)COCH$_2$N(R$^4$)$_2$, —N(R$^6$)COCH$_2$CH$_2$N(R$^4$)$_2$, or —N(R$^6$)COCH$_2$CH$_2$CH$_2$N(R$^4$)$_2$, wherein R is selected from hydrogen, C$_{1-6}$ aliphatic, phenyl, a 5–6 membered heteroaryl ring, or a 5–6 membered heterocyclic ring.

7. The compound according to claim 1, wherein Q is —C(R$^{6'}$)$_2$—, 1,2-cyclopropanediyl, 1,2-cyclobutanediyl, or 1,3-cyclobutanediyl; and said compound has one or more features selected from the group consisting of:

(a) R$^x$ is hydrogen, alkyl- or dialkylamino, acetamido, or a C$_{1-4}$ aliphatic group and R$^y$ is T—R$^3$ or L—Z—R$^3$ wherein T is a valence bond or a methylene and R$^3$ is —R, —N(R$^4$)$_2$, or —OR; or R$^x$ and R$^y$ are taken together with their intervening atoms to form a fused, unsaturated or partially unsaturated, 5–6 membered ring having 0–2 heteroatoms selected from oxygen, sulfur, or nitrogen, wherein each substitutable ring carbon of said fused ring formed by R$^x$ and R$^y$ is independently substituted by oxo, T—R$^3$, or L—Z—R$^3$, and each substitutable ring nitrogen of said ring formed by R$^x$ and R$^y$ is independently substituted by R$^4$;

(b) R$^1$ is T-(Ring D), wherein T is a valence bond or a methylene unit and wherein said methylene unit is optionally replaced by —O—, —NH—, or —S—;

(c) Ring D is a 5–7 membered monocyclic or an 8–10 membered bicyclic aryl or heteroaryl ring; and (d) R$^2$ is —R or —T—W—R$^6$ and R$^{2'}$ is hydrogen, or R$^2$ and R$^{2'}$ are taken together to form an optionally substituted benzo ring.

8. The compound according to claim 7, wherein:

(a) R$^x$ is hydrogen, alkyl- or dialkylamino, acetamido, or a C$_{1-4}$ aliphatic group, and R$^y$ is T—R$^3$ or L—Z—R$^3$, wherein T is a valence bond or a methylene and R$^3$ is —R, —N(R$^4$)$_2$, or —OR; or R$^x$ and R$^y$ are taken together with their intervening atoms to form a fused, unsaturated or partially unsaturated, 5–6 membered ring having 0–2 heteroatoms selected from oxygen, sulfur, or nitrogen, wherein each substitutable ring carbon of said fused ring formed by R$^x$ and R$^y$ is independently substituted by oxo, T—R$^3$, or L—Z—R$^3$, and each substitutable ring nitrogen of said ring formed by R$^x$ and R$^y$ is independently substituted by R$^4$;

(b) R$^1$ is T-(Ring D), wherein T is a valence bond or a methylene unit and wherein said methylene unit is optionally replaced by —O—, —NH—, or —S—;

(c) Ring D is a 5–7 membered monocyclic or an 8–10 membered bicyclic aryl or heteroaryl ring; and (d) R$^2$ is —R or —T—W—R$^6$ and R$^{2'}$ is hydrogen, or R$^2$ and R$^{2'}$ are taken together to form an optionally substituted benzo ring.

9. The compound according to claim 7, wherein Q is —C(R$^{6'}$)$_2$— or 1,2-cyclopropanediyl, and said compound has one or more features selected from the group consisting of:

(a) R$^y$ is T—R$^3$ or L—Z—R$^3$ wherein T is a valence bond or a methylene and R$^3$ is selected from —R, —OR, or —N(R$^4$)$_2$, wherein R is selected from hydrogen, C$_{1-6}$ aliphatic, or 5–6 membered heterocyclyl, phenyl, or 5–6 membered heteroaryl; or R$^x$ and R$^y$ are taken together with their intervening atoms to form a benzo, pyrido, cyclopento, cyclohexo, cyclohepto, thieno, piperidino, or imidazo ring, wherein each substitutable ring carbon of said fused ring formed by R$^x$ and R$^y$ is independently substituted by oxo, T—R$^3$, or L—Z—R$^3$, and each substitutable ring nitrogen of said ring formed by R$^x$ and R$^y$ is independently substituted by R$^4$;

(b) R$^1$ is T-(Ring D), wherein T is a valence bond, and Ring D is a 5–6 membered monocyclic or an 8–10 membered bicyclic aryl or heteroaryl ring;

(c) R$^2$ is —R and R$^{2'}$ is hydrogen, wherein R is selected from hydrogen, C$_{1-6}$ aliphatic, phenyl, a 5–6 membered heteroaryl ring, or a 5–6 membered heterocyclic ring; and (d) R$^3$ is selected from —R, -halo, —OR, or —N(R$^4$)$_2$, wherein R is selected from hydrogen, C$_{1-6}$ aliphatic, or 5–6 membered heterocyclyl, phenyl, or 5–6 membered heteroaryl, and L is —O—, —S—, or —N(R$^4$)—.

10. The compound according to claim 9, wherein:

(a) R$^y$ is T—R$^3$ or L—Z—R$^3$ wherein T is a valence bond or a methylene and R$^3$ is selected from —R, —OR, or —N(R$^4$)$_2$, wherein R is selected from hydrogen, C$_{1-6}$ aliphatic, or 5–6 membered heterocyclyl, phenyl, or 5–6 membered heteroaryl; or R$^x$ and R$^y$ are taken together with their intervening atoms to form a benzo, pyrido, cyclopento, cyclohexo, cyclohepto, thieno, piperidino, or imidazo ring, wherein each substitutable ring carbon of said fused ring formed by R$^x$ and R$^y$ is independently substituted by oxo, T—R$^3$, or L—Z—R$^3$, and each substitutable ring nitrogen of said ring formed by R$^x$ and R$^y$ is independently substituted by R$^4$;

(b) R$^1$ is T-(Ring D), wherein T is a valence bond, and Ring D is a 5–6 membered monocyclic or an 8–10 membered bicyclic aryl or heteroaryl ring;

(c) R$^2$ is —R and R$^{2'}$ is hydrogen, wherein R is selected from hydrogen, C$_{1-6}$ aliphatic, phenyl, a 5–6 membered heteroaryl ring, or a 5–6 membered heterocyclic ring; and (d) R$^3$ is selected from —R, -halo, —OR, or —N(R$^4$)$_2$, wherein R is selected from hydrogen, C$_{1-6}$ aliphatic, or 5–6 membered heterocyclyl, phenyl, or 5–6 membered heteroaryl, and L is —O—, —S—, or —N(R$^4$)—.

11. The compound according to claim 9, wherein Q is —CH$_2$— and said compound has one or more features selected from the group consisting of:

(a) R$^x$ is hydrogen methyl, ethyl, propyl, cyclopropyl, isopropyl, methylamino or acetamido and R$^y$ is selected from 2-pyridyl, 4-pyridyl, pyrrolidinyl, piperidinyl, morpholinyl, piperazinyl, methyl, ethyl, cyclopropyl, isopropyl, t-butyl, alkoxyalkylamino, alkoxyalkyl, alkyl- or dialkylamino, alkyl- or dialkylaminoalkoxy, acetamido, optionally substituted phenyl, or methoxymethyl; or R$^x$ and R$^y$ are taken together with their intervening atoms to form a benzo, pyrido, piperidino, or cyclohexo ring, wherein said ring is optionally substituted with -halo, —R, —OR, —COR, —CO$_2$R, —CON(R$^4$)$_2$, —CN, —O(CH$_2$)$_{2-4}$—N(R$^4$)$_2$, —O(CH$_2$)$_{2-4}$—R, —NO$_2$ —N(R$^4$)$_2$, —NR$^4$COR, —NR$^4$SO$_2$R, or —SO$_2$N(R$^4$)$_2$, wherein R is hydrogen or an optionally substituted C$_{1-6}$ aliphatic group;

(b) R$^1$ is T-(Ring D), wherein T is a valence bond and Ring D is a 5–6 membered aryl or heteroaryl ring optionally substituted with one or two groups selected from -halo, —CN, —NO$_2$, —N(R$^4$)$_2$, optionally substituted C$_{1-6}$ aliphatic, —OR, —C(O)R, —CO$_2$R, —CONH(R$^4$), —N(R$^4$)COR, —N(R$^4$)CO$_2$R, —SO$_2$N(R$^4$)$_2$, —N(R$^4$)SO$_2$R, —N(R$^6$)COCH$_2$N(R$^4$)$_2$, —N(R$^6$)COCH$_2$CH$_2$N(R$^4$)$_2$, or —N(R$^6$)COCH$_2$CH$_2$CH$_2$N(R$^4$)$_2$;

(c) R² is hydrogen or a substituted or unsubstituted group selected from aryl, heteroaryl, or a C₁₋₆ aliphatic group, and R²' is hydrogen; and (d) R³ is selected from —R, —OR, or —N(R⁴)₂, wherein R is selected from hydrogen, C₁₋₆ aliphatic, 5–6 membered heterocyclyl, phenyl, or 5–6 membered heteroaryl, and L is —O—, —S—, or —NH—; and (e) Ring D is substituted by up to three substituents selected from -halo, —CN, —NO₂, —N(R⁴)₂, optionally substituted C₁₋₆ aliphatic group, —OR, —C(O)R, —CO₂R, —CONH(R⁴), —N(R⁴)COR, —N(R⁴)CO₂R, —SO₂N(R⁴)₂, —N(R⁴)SO₂R, —N(R⁶)COCH₂N(R⁴)₂, —N(R⁶)COCH₂CH₂N(R⁴)₂, or —N(R⁶)COCH₂CH₂CH₂N(R⁴)₂, wherein R is selected from hydrogen, C₁₋₆ aliphatic, phenyl, a 5–6 membered heteroaryl ring, or a 5–6 membered heterocyclic ring.

12. The compound according to claim 11, wherein:

(a) Rˣ is hydrogen methyl, ethyl, propyl, cyclopropyl, isopropyl, methylamino or acetamido and Rʸ is selected from 2-pyridyl, 4-pyridyl, pyrrolidinyl, piperidinyl, morpholinyl, piperazinyl, methyl, ethyl, cyclopropyl, isopropyl, t-butyl, alkoxyalkylamino, alkoxyalkyl, alkyl- or dialkylamino, alkyl- or dialkylaminoalkoxy, acetamido, optionally substituted phenyl, or methoxymethyl; or Rˣ and Rʸ are taken together with their intervening atoms to form a benzo, pyrido, piperidino, or cyclohexo ring, wherein said ring is optionally substituted with -halo, —R, —OR, —COR, —CO₂R, —CON(R⁴)₂, —CN, —O(CH₂)₂₋₄—N(R⁴)₂, —O(CH₂)₂₋₄—R, —NO₂, —N(R⁴)₂, —NR⁴COR, —NR⁴SO₂R, or —SO₂N(R⁴)₂, wherein R is hydrogen or an optionally substituted C₁₋₆ aliphatic group;

(b) R¹ is T-(Ring D), wherein T is a valence bond and Ring D is a 5–6 membered aryl or heteroaryl ring optionally substituted with one or two groups selected from -halo, —CN, —NO₂, —N(R⁴)₂, optionally substituted C₁₋₆ aliphatic, —OR, —C(O)R, —CO₂R, —CONH(R⁴), —N(R⁴)COR, —N(R⁴)CO₂R, —SO₂N(R⁴)₂, —N(R⁴)SO₂R, —N(R⁶)COCH₂N(R⁴)₂, —N(R⁶)COCH₂CH₂N(R⁴)₂, or —N(R⁶)COCH₂CH₂CH₂N(R⁴)₂;

(c) R² is hydrogen or a substituted or unsubstituted group selected from aryl, heteroaryl, or a C₁₋₆ aliphatic group, and R²' is hydrogen; and (d) R³ is selected from —R, —OR, or —N(R⁴)₂, wherein R is selected from hydrogen, C₁₋₆ aliphatic, 5–6 membered heterocyclyl, phenyl, or 5–6 membered heteroaryl, and L is —O—, —S—, or —NH—;

(e) Ring D is substituted by up to three substituents selected from -halo, —CN, —NO₂, —N(R⁴)₂, optionally substituted C₁₋₆ aliphatic group, —OR, —C(O)R, —CO₂R, —CONH(R⁴), —N(R⁴)COR, —N(R⁴)CO₂R, —SO₂N(R⁴)₂, —N(R⁴)SO₂R, —N(R⁶)COCH₂N(R⁴)₂, —N(R⁶)COCH₂CH₂N(R⁴)₂, or —N(R⁶)COCH₂CH₂CH₂N(R⁴)₂, wherein R is selected from hydrogen, C₁₋₆ aliphatic, phenyl, a 5–6 membered heteroaryl ring, or a 5–6 membered heterocyclic ring.

13. A composition comprising a compound according to any one of claims 1–12, and a pharmaceutically acceptable carrier.

14. The composition according to claim 1, wherein the compound is:

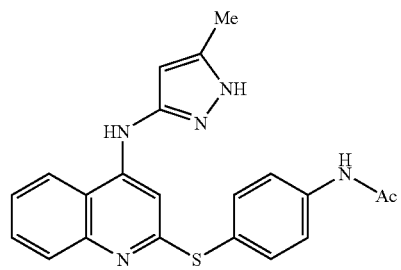

IVa-1

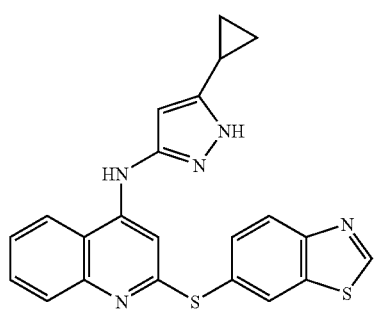

IVa-2

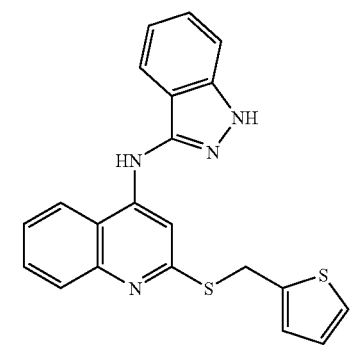

IVa-3

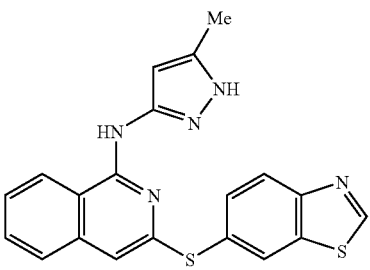

IVa-4

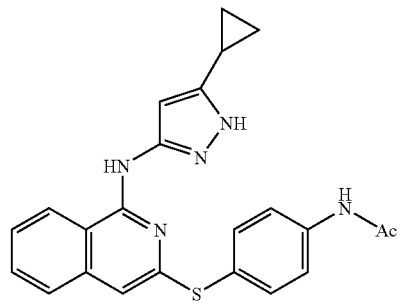

IVa-5

-continued
IVa-6
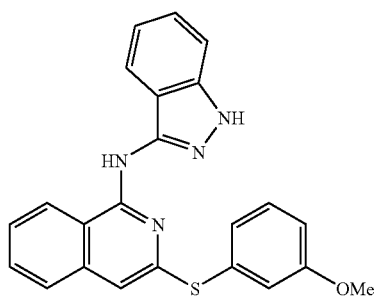
IVa-7
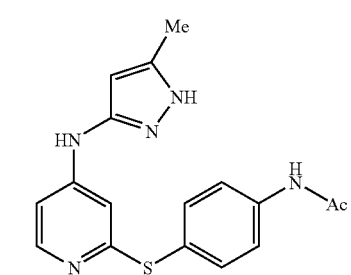
IVa-8
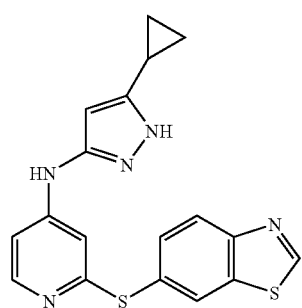
IVa-9
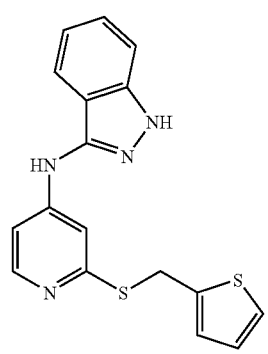
IVa-10
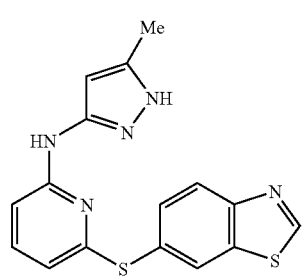
-continued
IVa-11
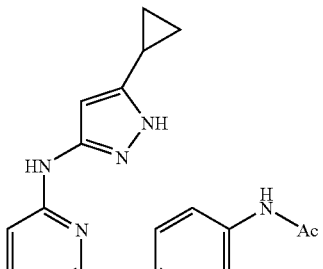
IVa-12
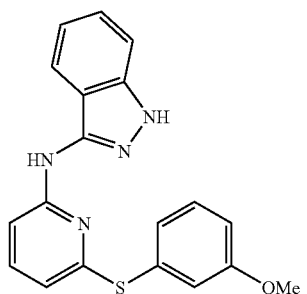
IVb-1
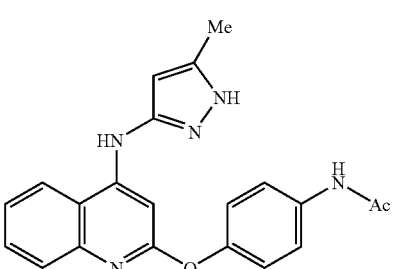
IVb-2
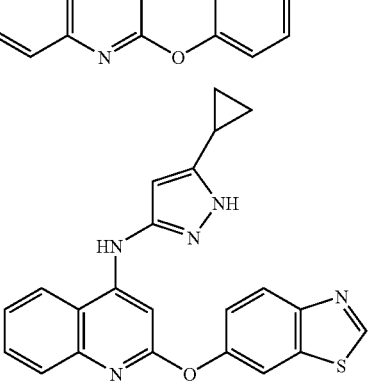
IVb-3
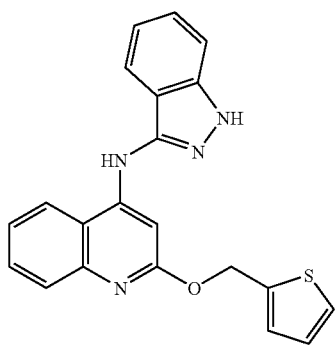

IVb-4
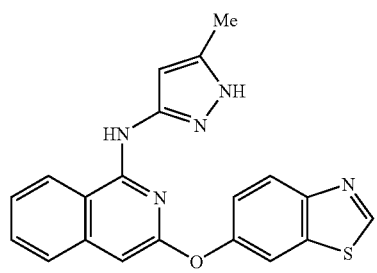
IVb-5
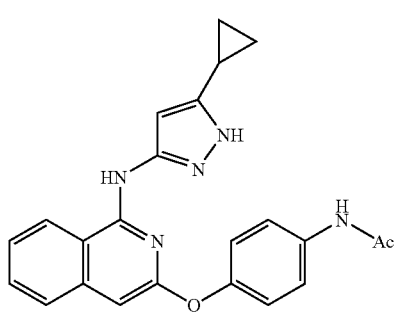
IVb-6
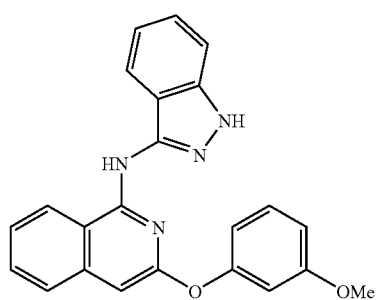
IVb-7
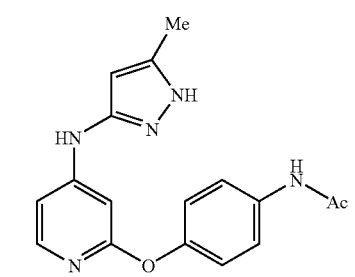
IVb-8
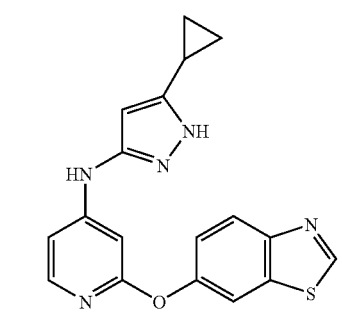
IVb-9
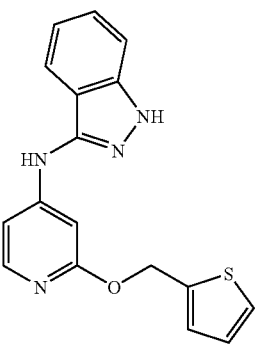
IVb-10
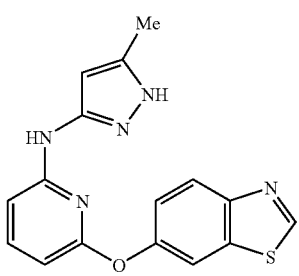
IVb-11
IVb-12
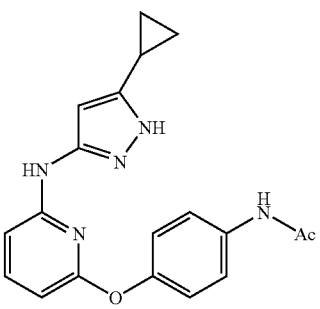
IVb-13
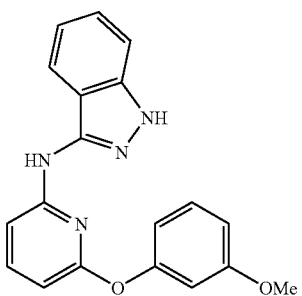

IVb-14
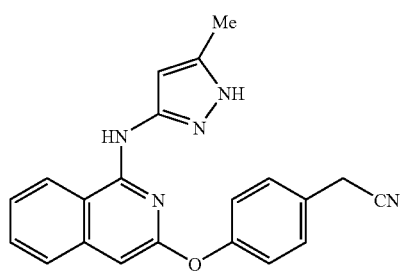
IVb-15
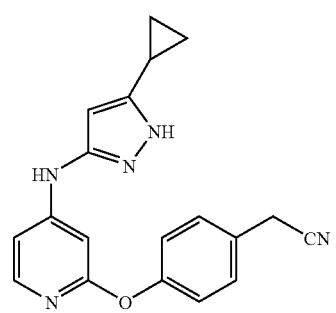
IVb-16
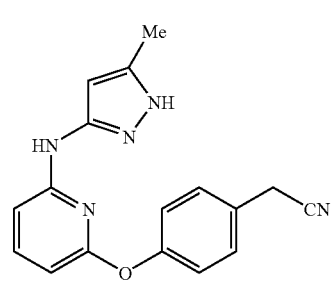
IVc-1
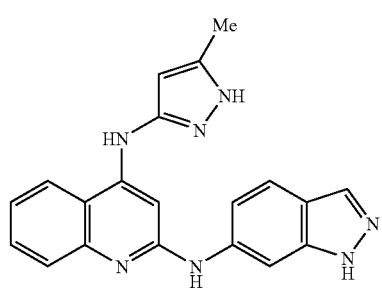
IVc-2
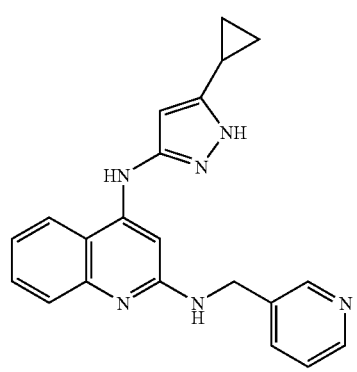
IVc-3
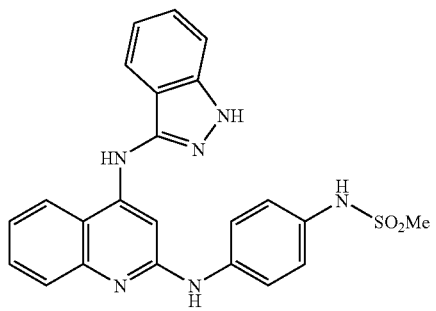
IVc-4
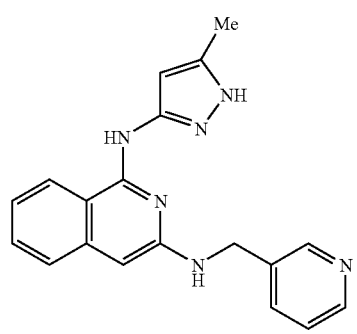
IVc-5
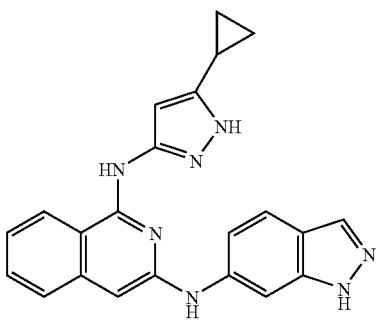
IVc-6
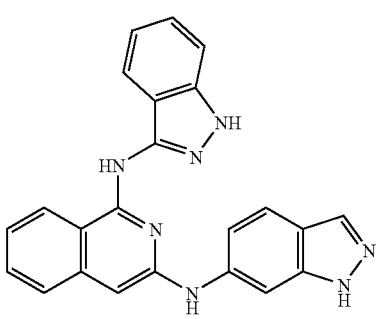

IVc-7
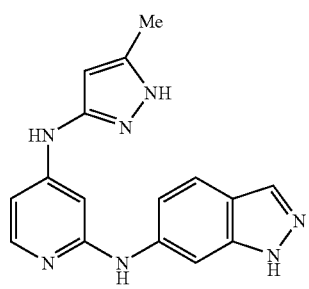
IVc-8
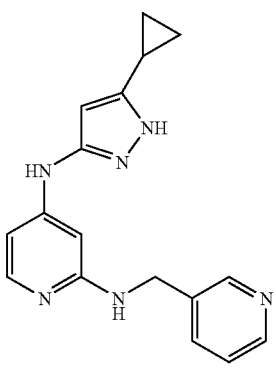
IVc-9
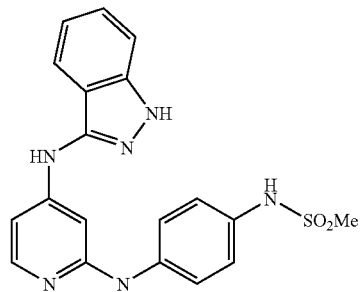
IVc-10
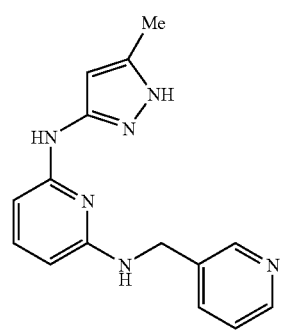
IVc-11
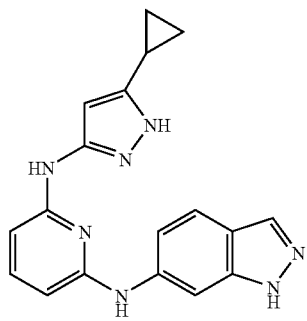
IVc-12
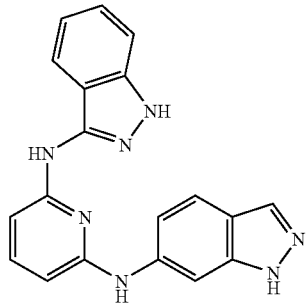
IVd-1
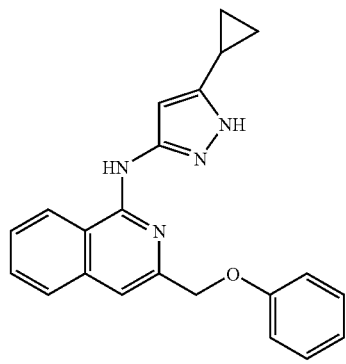
IVd-2

-continued
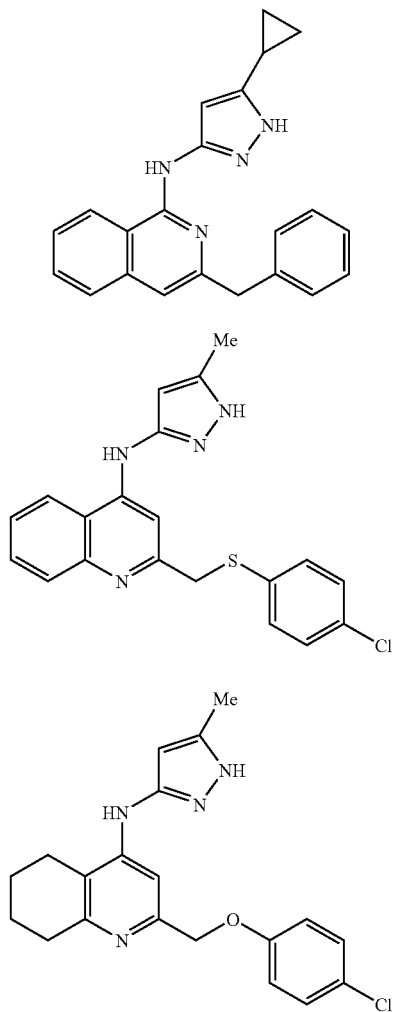
IVd-3
IVd-4
IVd-5
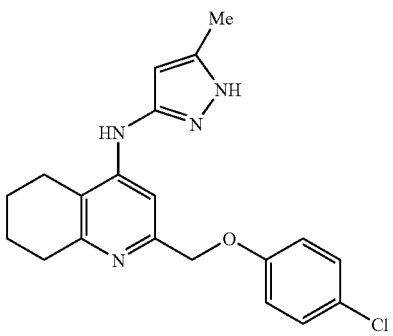
IVd-6
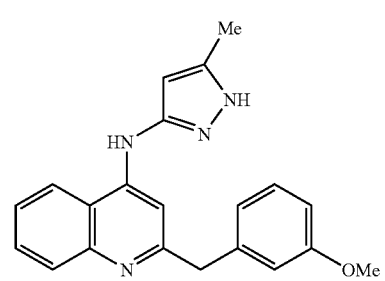
IVd-7
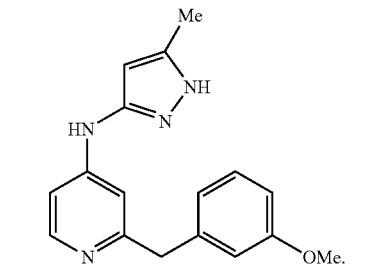
IVd-8
* * * * *